US012767635B2

(12) United States Patent
Jong et al.

(10) Patent No.: US 12,767,635 B2
(45) Date of Patent: Oct. 20, 2026

(54) LIPOXYGENASE INHIBITORS

(71) Applicant: SRI International, Menlo Park, CA (US)

(72) Inventors: Ling Jong, Sunnyvale, CA (US); Raymond Ng, Pleasant Hill, CA (US); Nathan Collins, San Mateo, CA (US)

(73) Assignee: SRI International, Menlo Park, CA (US)

( * ) Notice: Subject to any disclaimer, the term of this patent is extended or adjusted under 35 U.S.C. 154(b) by 899 days.

(21) Appl. No.: 17/906,885

(22) PCT Filed: Mar. 25, 2021

(86) PCT No.: PCT/US2021/024103
§ 371 (c)(1),
(2) Date: Sep. 21, 2022

(87) PCT Pub. No.: WO2021/195346
PCT Pub. Date: Sep. 30, 2021

(65) Prior Publication Data

US 2023/0174485 A1 Jun. 8, 2023

Related U.S. Application Data

(60) Provisional application No. 62/994,550, filed on Mar. 25, 2020.

(51) Int. Cl.
*C07D 209/88* (2006.01)
*C07D 209/86* (2006.01)
(Continued)

(52) U.S. Cl.
CPC ......... *C07D 209/88* (2013.01); *C07D 209/86* (2013.01); *C07D 223/28* (2013.01); (Continued)

(58) Field of Classification Search
CPC .. C07D 401/12; C07D 215/38; C07D 209/88; C07D 209/86; C07C 217/86; C07C 211/49
See application file for complete search history.

(56) References Cited

U.S. PATENT DOCUMENTS

| | | |
|---|---|---|
| 3,743,663 A | 7/1973 | Baschang et al. |
| 3,743,667 A | 7/1973 | Wagner et al. |

(Continued)

FOREIGN PATENT DOCUMENTS

| | | | | |
|---|---|---|---|---|
| CN | 104250254 A | | 12/2014 | |
| CN | 105523991 A | * | 4/2016 | ........... C07D 401/10 |

(Continued)

OTHER PUBLICATIONS

Ackermann et al., "The double-edged role of 12/15-lipoxygenase during inflammation and immunity", Biochimica et Biophysica Acta, 1862:371-381 (2017).

(Continued)

*Primary Examiner* — Kyle A Purdy
(74) *Attorney, Agent, or Firm* — Dicke, Billig & Czaja, PLLC

(57) ABSTRACT

Various embodiments of the present disclosure are directed to compounds having Formula (I), Formula (IA), Formula (IB), Formula (IC), Formula (ID), Formula (IE), and/or pharmaceutically acceptable salts thereof. The compounds can be suitable for inhibiting lipoxygenases, and/or treating associated diseases, such as Alzheimer's disease. In some embodiments, the compounds may be administered to a patient as part of a pharmaceutical formulation.

(I)

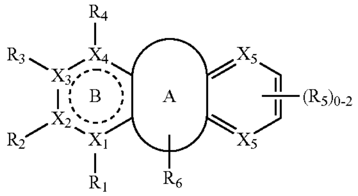

(IA)

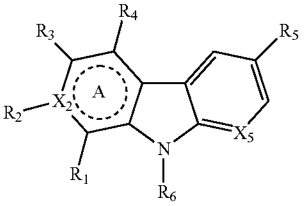

(IB)

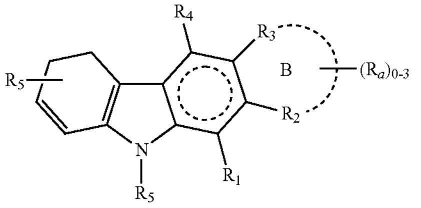

(IC)

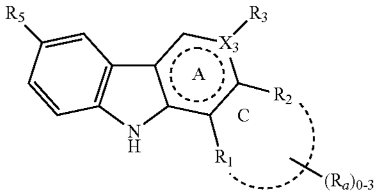

(ID)

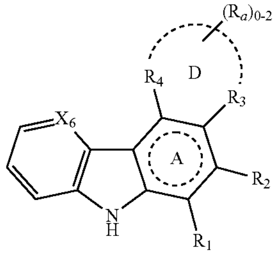

(Continued)

-continued

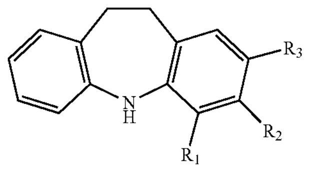

7 Claims, No Drawings

(51) Int. Cl.

| | |
|---|---|
| ***C07D 223/28*** | (2006.01) |
| ***C07D 401/12*** | (2006.01) |
| ***C07D 403/02*** | (2006.01) |
| ***C07D 403/04*** | (2006.01) |
| ***C07D 403/12*** | (2006.01) |
| ***C07D 405/14*** | (2006.01) |
| ***C07D 471/04*** | (2006.01) |
| ***C07D 471/22*** | (2006.01) |
| ***C07D 487/04*** | (2006.01) |
| ***C07D 495/04*** | (2006.01) |

(52) U.S. Cl.

CPC ......... *C07D 401/12* (2013.01); *C07D 403/04* (2013.01); *C07D 403/12* (2013.01); *C07D 405/14* (2013.01); *C07D 471/04* (2013.01); *C07D 471/22* (2013.01); *C07D 487/04* (2013.01); *C07D 495/04* (2013.01)

(56) References Cited

U.S. PATENT DOCUMENTS

| | | | |
|---|---|---|---|
| 4,731,258 | A | 3/1988 | Liberman |
| 4,731,358 | A | 3/1988 | Huth et al. |
| 4,822,811 | A | 4/1989 | Summers |
| 4,906,662 | A | 3/1990 | Hashimoto et al. |
| 5,420,289 | A | 5/1995 | Musser et al. |
| 6,399,631 | B1 | 6/2002 | Elliott et al. |
| 6,800,655 | B2 | 10/2004 | Jong et al. |
| 7,462,628 | B2 | 12/2008 | Ishihara et al. |
| 8,207,214 | B2 | 6/2012 | Alisi et al. |
| 10,646,471 | B2 | 5/2020 | Jong |
| 10,961,277 | B2 | 3/2021 | Lutz et al. |
| 11,382,893 | B2 | 7/2022 | Maccecchini |
| 11,447,486 | B2 | 9/2022 | Kim et al. |
| 2004/0067999 | A1 | 4/2004 | Block et al. |
| 2008/0280899 | A1 | 11/2008 | Bilodeau et al. |
| 2010/0069355 | A1 | 3/2010 | Jong et al. |
| 2010/0240726 | A1 | 9/2010 | Gazit et al. |
| 2011/0013263 | A1 | 1/2011 | Miteva et al. |
| 2013/0041238 | A1 | 2/2013 | Joseph et al. |
| 2013/0345214 | A1 | 12/2013 | Jong |
| 2018/0092919 | A1 | 4/2018 | Shiba et al. |
| 2018/0222861 | A1 | 8/2018 | Tang et al. |
| 2018/0265777 | A1 | 9/2018 | Ambrosek et al. |

FOREIGN PATENT DOCUMENTS

| | | | |
|---|---|---|---|
| CN | 106879256 | A | 6/2017 |
| EP | 0234708 | A1 | 9/1987 |
| EP | 1382598 | A1 | 1/2004 |
| EP | 2720727 | A1 | 4/2014 |
| JP | S 59-044386 | A | 3/1984 |
| JP | S 59-089678 | A | 5/1984 |
| JP | H 10-511663 | A | 11/1998 |
| JP | 2014510753 | A | 5/2014 |
| KR | 2016-0020616 | A | 2/2016 |
| WO | 198903818 | A1 | 5/1989 |
| (IE) WO | 1991/06537 | A1 | 5/1991 |
| WO | 1998/050033 | A | 11/1998 |
| WO | 1999032433 | A1 | 7/1999 |
| WO | 2001/007409 | A1 | 2/2001 |
| WO | 2001/096299 | A2 | 12/2001 |
| WO | 2002/051806 | A1 | 4/2002 |
| WO | 2006/083458 | A2 | 8/2006 |
| WO | 2006/105196 | A2 | 10/2006 |
| WO | 2010008864 | A2 | 1/2010 |
| WO | 2010029300 | A1 | 3/2010 |
| WO | 2010/118339 | A2 | 10/2010 |
| WO | 2010/129622 | A1 | 11/2010 |
| WO | 2012/135133 | A1 | 10/2012 |
| WO | 2012/177807 | A1 | 12/2012 |

OTHER PUBLICATIONS

Ash et al., Handbook of Pharmaceutical Additives, Hampshire, England, Gower Pub (1995) (copy unavailable).

Banwell et al., "Exploitation of Cyclopropane Ring-Cleavage Reactions for the Rapid Assembly of Tetracyclic Framework Related to Gibberellins", Organic Letters, 8(23):5341-5344 abstract, compound 5 (2006).

Berge et al., "Pharmaceuticals Salts", J. Pharma. Sci., 66(1):1-19 (Jan. 1977).

Cannon, Chapter 19 in "Burger's Medicinal Chemistry and Drug Discovery", Fifth Ed, Principles and Practice, Wiley-Interscience, vol. 1(19):783-802, (1995).

Chao et al., "Computer-Aided Rational Drug Design: A Novel Agent (SR13668) Designed to Mimic the Unique Anticancer Mechanisms of Dietary Indole-3-Carbinol to Block Akt Signaling", J. Med. Chem., 50:3412-3415 (Jan. 11, 2007).

Chu et al., "5-lipoxygenase as an endogenous modulator of amyloid beta formation in vivo", Ann Neurol., 69(1):34-46 (Jan. 2011).

Crowell et al., "Targeting the AKT protein kinase for cancer chemoprevention", Mol. Cancer. Ther., 6(8), 23 pgs (Aug. 2007).

European Office Action (Art 94(3) for related EP Patent Appl No. 12763995.3 (5 pg) (May 23, 2018).

Forest, Forest Laboratories (2003) (copy unavailable).

Foster, "Deuterium isotope effects in studies of drug metabolism", Trends Pharmacol. Sci., 5(12):524-527 (1984). (Abstract).

Greene et al. "Protective Groups in Organic Synthesis", 3rd Ed, New York: Wiley-Interscience (1999) (copy unavailable).

Haeggström et al., "Lipoxygenase and Leukotriene Pathways: Biochemistry, Biology, and Roles in Disease", Chem. Rev., 111(10):5866-5898 (Oct. 12, 2011) (Table of contents in lieu of abstract.).

International Search Report and Written Opinion for related PCT Application PCT/US2020/066191 mailed Jun. 29, 2021.

International Search Report and Written Opinion for related PCT Application PCT/US2021/024103 mailed Jul. 26, 2021.

Kuhn et al., "Mammalian lipoxygenases and their biological relevance", Biochimica et Biophysica Acta, 1851(4):308-330 (Apr. 2015).

Listi, et al., "Role of Cyclooxygenase-2 and 5-Lipoxygenase Polymorphisms in Alzheimer's Disease in a Population from Northern Italy: Implication for Pharmacogenomics", J. Alzheimers. Dis., 19(2):551-557 (Jan. 7, 2010).

Manev et al., "Cyclooxygenases and 5-lipoxygenase in Alzheimer's disease", Prog. Neuropsychopharmacol Biol. Psychiatry, 35(2):315-319 (Mar. 30, 2011). (Abstract).

Manev et al., "5-Lipoxygenase in the Central Nervous System: Therapeutic Implications", Curr. Med. Chem—Anti-Inflammatory & Anti-Allergy Agents, 1(2):115-121 (2002).

March, "Advanced Organic Chemistry: Reactions, Mechanisms and Structure", 5th Ed. (New York: Wiley-Interscience (2001) (copy unavailable).

Mashima et al., "The role of lipoxygenases in pathophysiology; new insights and future perspectives", Redox Biology, 6:297-310 (2015).

PubChem-SID: 104787593 Deposit Date Feb. 22, 2011 pp. 1-6.

PubChem-SID 315864309 Deposit Date Aug. 2, 2016 pp. 1-5.

PubChem-SID: 399039609 Deposit Date Dec. 7, 2019 pp. 1-5.

(56) References Cited

OTHER PUBLICATIONS

Pufahl et al., "Development of a fluorescence-based enzyme assay of human 5-lipoxygenase", Anal. Biochem., 364(2):204-212 (May 15, 2007) (Abstract).
Remington, The Science and Practice of Pharmacy, R. Hendrickson, ed., 21st edition, Lippincott, Williams & Wilkins, Philadelphia, Pa., (2005), at p. 732, Table 38-5.
Waslidge et al., "A Colorimetric Method for the Determination of Lipoxygenase Activity Suitable for Use in a High Throughput Assay Format", Anal. Biochem., 231(2):354-358 (Nov. 1995) (Abstract).
Wisastra et al., "Inflammation, Cancer and Oxidative Lipoxygenase Activity are Intimately Linked", Cancers, 6:1500-1521 (2014).
Kenyon, et al. "Novel Human Lipoxygenase Inhibitors Discovered Using Virtual Screening with Homology Models" Journal of Medicinal Chemistry, vol. 49, No. 4, Jan. 31, 2006, pp. 1356-1363.
Extended European Search Report for related EP Appl No. 20904761.2, pp. 11, Dec. 14, 2023.
Pawar Py, et al., "Synthesis and in vitro screening of some 1,3,4-oxadiazole derivatives as lipoxygenase inhibitors", Biosciences Biotechnology Research Asia, vol. 4, No. 2, Jan. 1, 2007 (Jan. 1, 2007), pp. 609-614, XP00913985.
Asselin, et al., "Cycloalkanoindles. 2. 1-Alkyl-1,2,3,4-Tetrahydrocarbaxole-1-ethanamines and Related Compounds, Potential Antidepressants", Journal of Medicinal Chemistry, 1976, 19(6), p. 792-797.
Kleks, et al., "Orthoscuticellines A-E, P-Carboline Alkaloids from the Bryozoan *Orthoscuticella ventricosa* Collected in Australia", Journal of Natural Products, 2020, 83, 422-428.
Pouilhes, et al., "6',7'-Dihydrokeramamine C and Analogues: synthesis and Biological Evaluation", Tetrahedron Letters, 42, 2001, 8297-8299.
Database Registry Online, Retrieved from STN Registry, May 19, 2019, pp. 1-25.
Database Registry Online, Retrieved from STN Registry, Jan. 17, 2015, pp. 1-5.
Bedford et al., "Intramolecular Direct Arylation in the Synthesis of Fluorinated Carbazoles", Tetrahedron, 64(26):6038-6050 (Mar. 4, 2008).
Gritsenko et al., "Synthesis of 3,5-Disubstituted 10, 11-Dihydro-5H-Dibenz [b,f] Azepines", Pharmaceutical Chemistry Journal, 32(9):500-503 (Sep. 1, 1998).
Gu et al., "Facile One-Pot Synthesis of Novel 6-Monosubstituted 5, 11-Dihydroindolo [3,2-b] carbazoles and Preparation of Different Derivatives", Synlett, 2006(10):1535-1538 (Jun. 12, 2006).
Ishii et al., "Polymerisation of Indole. Part 3. Two Indolylquinolines, an Indole Tetramer, and the Dihydro Derivative of the Indole Dimer", Journal of the Chemical Society Perkin Transactions 1, 1988(8):2387-2396 (Aug. 1, 1988).
Li et al., "Direct Access to Substituted Benzo [b] Carbazoles through Cascade Annulation of 2-Vinylbenzaldehyde with Indoles", Chemical Communications, 55(23):3339-3342 (Feb. 14, 2019).
PubChem-CID: 21901897, "2,3,8,8a-Tetrahydropyrrolo[2,3-b]indole" Compound Summary (Dec. 5, 2007).
Mascio et al., "Singlet Molecular Oxygen Reactions with Nucleic Acids, and Proteins", Chemical Reviews, 119(3):A-AR (Feb. 5, 2019).
Roy et al., "Hexahydropyrrolo[2,3-b]indole alkaloids of biological relevance: proposed biosynthesis and synthetic approaches", Arkivoc, Part i:437-471 (Oct. 22, 2020).
Shagako et al., "Synthesis in the Phenothiazine Series. XX. 2-Alkylaminoacylamino- and 2-alkylaminoalkylamino-Substituted Phenothiazine and 10-Methyl-Phenothiazine", Chemistry of Heterocyclic Compounds, 3(2):213-215 (Jul. 1, 1967).
Chinese First Office Action from CN202080097156.X, mailed Mar. 27, 2024.
Extended European Search Report from EP21774060.4, mailed Apr. 4, 2024.
International Search Report from PCT/US2023/082278, mailed Apr. 17, 2024.

* cited by examiner

LIPOXYGENASE INHIBITORS

CROSS-REFERENCE TO RELATED APPLICATIONS

This application is a U.S. National Stage Application under 35 U.S.C. § 371 of PCT/US2021/024103, filed Mar. 25, 2021, which claims benefit to U.S. Provisional Patent Application No. 62/994,550, filed Mar. 25, 2020, which are each incorporated herein by reference in their entireties.

BACKGROUND

Lipoxygenases (LOXs) and their catalyzed products, such as inflammatory leukotrienes (LTs) and hydroxyeicosatetraenoic acids (HETEs) have been implicated in the pathogenesis of a variety of human diseases, including inflammatory disease, cancer and neurodegenerative diseases. Lipoxygenase inhibitors are known to be useful for the treatment of all kinds of LOXs-related inflammatory diseases, including neurodegenerative diseases, such as Alzheimer's disease; See, e.g., Haeggstrom, Chem. Rev. 2011, 111, 5866-589; Manev, H., et al., Prog Neuropsychopharmacol Biol Psychiatry, 2010; Listi, F., et al., J Alzheimers Dis, 2010. 19(2): p. 551-7; Chu, J. and D. Pratico, Ann Neurol, 2010.

SUMMARY

The present invention is directed to overcoming the above-mentioned challenges and others related to compounds, such as compounds that are LOX inhibitors. Some aspects are directed to classes of LOX inhibitors that exhibit inhibitory activity against 5-, 12- and/or 15-LOX.

Various embodiments of the present disclosure are directed to a compound having Formula I:

Formula I

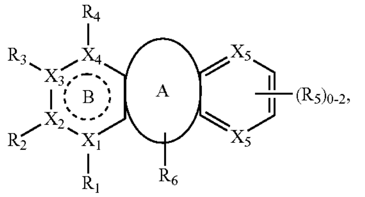

wherein: A is a 5-7 membered cycloalkyl ring or a 5-7 membered heterocyclic ring; B is a 6 membered cycloalkyl, 6 membered heterocycle, a 6 membered aryl, or a 6 membered heteroaryl; $X_1$, $X_2$, $X_3$, $X_4$, and $X_5$ are each independently C, N, or S; $R_1$ is a —H, a halo, a $C_{1-3}$ alkyl, a $C_{1-3}$ alkoxy, or a 5-6 membered aryl, wherein the $C_{1-5}$ alkyl, the $C_{1-3}$ alkoxy, or the 5-6 membered aryl is optionally further independently substituted with one to three $R_a$; $R_2$ is a —H, a halo, an oxo, a hydroxyl, a $C_{1-3}$ alkyl, $C_{1-3}$ alkenyl, a $C_{1-3}$ alkoxy, a $C_{1-3}$ haloalkyl, a —$NR_aR_b$, or a 5-6 membered aryl, wherein the $C_{1-3}$ alkyl, the $C_{1-3}$ alkenyl, the $C_{1-3}$ alkoxy, the $C_{1-3}$ haloalkyl, the —$NR_aR_b$, or the 5-6 membered aryl is optionally further independently substituted with one to three $R_a$; $R_3$ is a —H, a halo, an oxo, a $C_{1-3}$ alkyl, a $C_{1-3}$ alkenyl, a $C_{1-3}$ alkoxy, a —$NR_aR_b$, a —$NH(CH_2)_{1-3}R_aR_b$, a 3-6 membered cycloalkyl, or a 5-6 membered aryl, wherein the $C_{1-3}$ alkyl, the $C_{1-3}$ alkenyl, the $C_{1-3}$ alkoxy, the —$NR_aR_b$, the —$NH(CH_2)_{1-3}R_aR_b$, the 3-6 membered cycloalkyl, or the 5-6 membered aryl is optionally further independently substituted with one to three $R_a$; $R_4$ is a —H, a halo, a $C_{1-3}$ alkyl, or a $C_{1-3}$ alkoxy, wherein the $C_{1-3}$ alkyl or the $C_{1-3}$ alkoxy is optionally further independently substituted with one to three $R_a$; $R_5$ is a halo; $R_6$ is an oxo, or a $C_{1-4}$ alkyl, wherein the $C_{1-4}$ alkyl is optionally further independently substituted with one to three $R_a$; $R_1$ and $R_2$ optionally come together to form a 5-6 membered heterocycle or a 5-6 membered aryl, wherein the 5-6 membered heterocycle or the 5-6 membered aryl is optionally further independently substituted with one to three $R_a$; $R_2$ and $R_3$ optionally come together to form a 5-6 membered heterocycle, 5-6 membered aryl, or a 5-6 membered heteroaryl, wherein the 5-6 membered heterocycle, 5-6 membered aryl, or the 5-6 membered heteroaryl is optionally further independently substituted with one to three $R_a$; $R_3$ and $R_4$ optionally come together to form a 5-6 membered heterocycl, wherein the 5-6 membered heterocycl is optionally further independently substituted with one to three $R_a$; wherein when two $R_5$ are adjacent to each other, the two $R_5$ optionally come together to form a 5-6 membered aryl, wherein the 5-6 membered aryl is optionally further independently substituted with one to three $R_a$; each $R_a$ and $R_b$ are independently a —H, a halo, an oxo, a hydroxy, a $C_{1-2}$ carboxyl, a $C_{1-3}$ alkyl, a $C_{1-3}$ alkoxy, a —$NH_2$, a —$NO_2$, a —$NR_xR_y$, a —$NR_x$, a 4-6 membered heterocycle, a 4-6 heterocycle, a 5-6 membered aryl, or a 5-6 membered heteroaryl, wherein the $C_{1-2}$ carboxyl, the $C_{1-3}$ alkyl, the $C_{1-3}$ alkoxy, the —$NH_2$, the —$NR_xR_y$, the —$NR_x$, the 4-6 membered heterocycle, the 4-6 heterocycle, the 5-6 membered aryl, and/or the 5-6 membered heteroaryl are optionally further independently substituted with one to three Rx; wherein adjacent $R_a$ and $R_b$ optionally further come together to form a 5-6 membered aryl or a 5-6 membered heteroaryl, wherein the 5-6 membered aryl and/or the 5-6 membered heteroaryl are optionally independently substituted with one to three Rx; each $R_x$ and $R_y$ is independently a —H, a halo, a hydroxyl, an oxo, a $C_{1-3}$ alkyl, a —$NR_{x1}R_{x2}$, a —$CH_2NR_{x1}R_{x2}$, a 4-6 membered heterocycle, a 5-6 membered aryl, or a 5-6 membered heteroaryl, wherein the $C_{1-3}$ alkyl, the —$NR_{x1}R_{x2}$, the —$CH_2NR_{x1}R_{x2}$, the 4-6 membered heterocycle, the 5-6 membered aryl, and/or the 5-6 membered heteroaryl are optionally further independently substituted with one to three $R_{x1}$; wherein when two $R_x$ are bonded to the same atom, the two $R_x$ groups optionally come together to form a 4-6 membered heterocycle, wherein the 4-6 membered heterocycle is optionally further independently substituted with one to three $R_{x1}$; each $R_{x1}$ and $R_{x2}$ is independently a —H, a halo, a $C_{1-2}$ alkyl, a $C_{1-3}$ alkoxy, or a 5-6 membered heteroaryl; and a pharmaceutically acceptable salt thereof.

In some embodiments, $R_1$ is selected from:

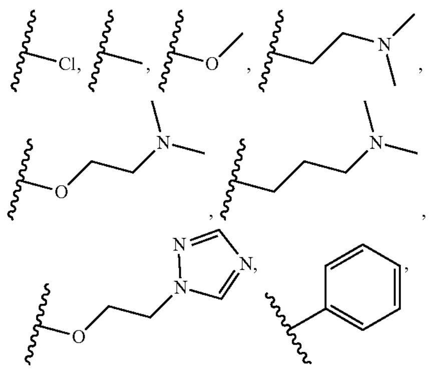

-continued
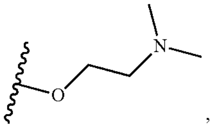,
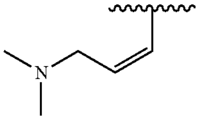,
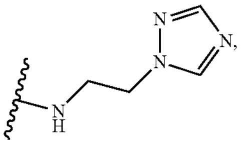 and 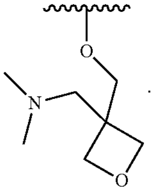.
In some embodiments, $R_2$ is selected from:
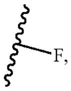 —OH, 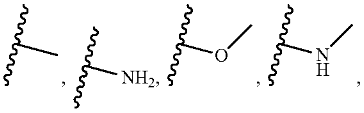,
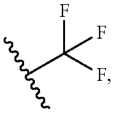, 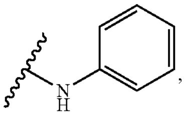,
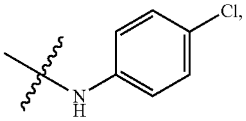, 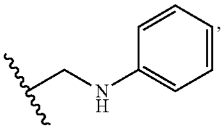,
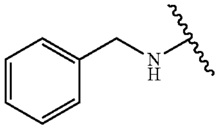, 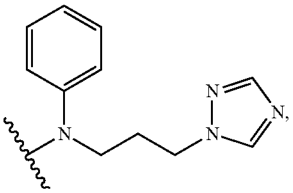,
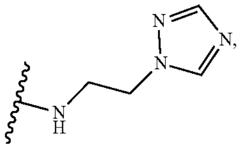, 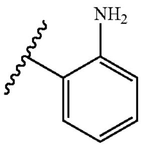, 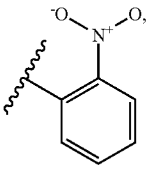,
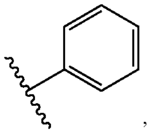, 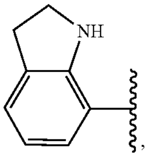, 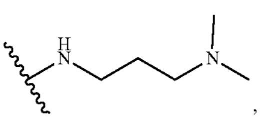,
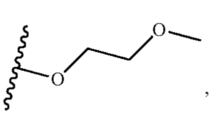, and 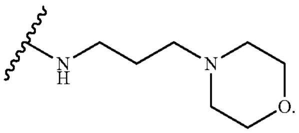.
In some embodiments, $R_3$ is selected from:
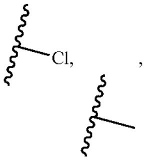, 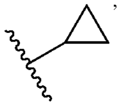, 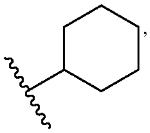, 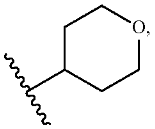,
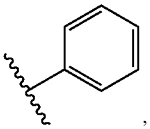, 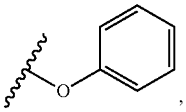, 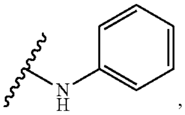,
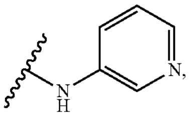, 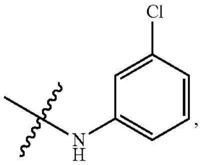,
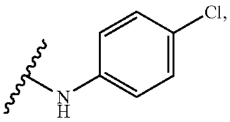, 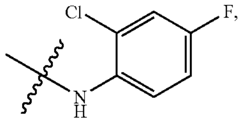,
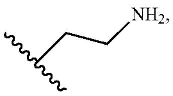, 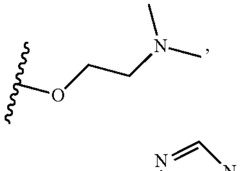,
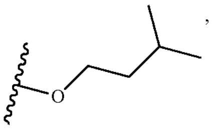, 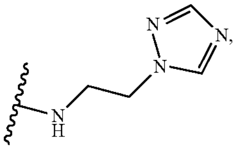,
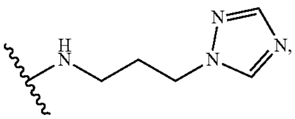, 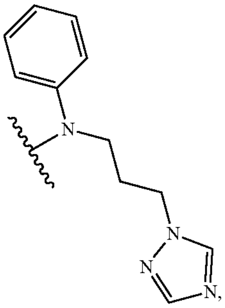,
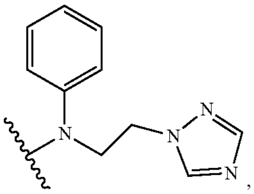, 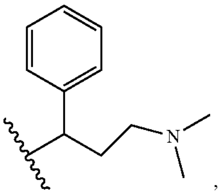,
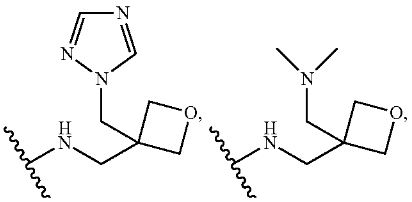, -continued

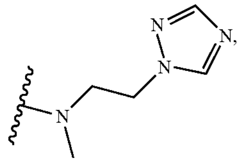
and
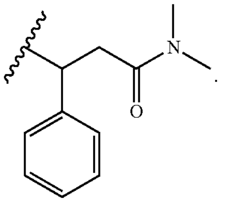
.

In some embodiments, $R_4$ is selected from:

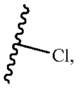
,
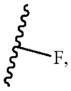
,
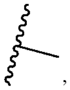
,
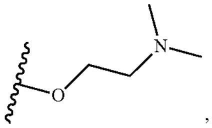
, and
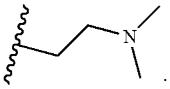
.

In some embodiments, $R_5$ is selected from:

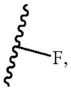
,
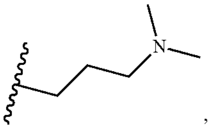
, and
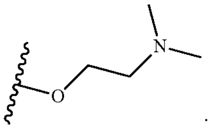
.

In some embodiments, $R_6$ is selected from: —H,

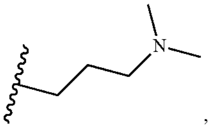
, and
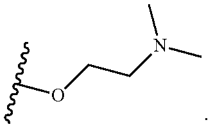
.

In some embodiments, $R_1$ and $R_2$ come together to form a structure selected from:

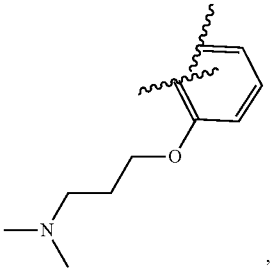
,
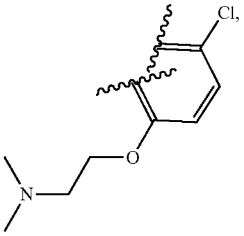

-continued

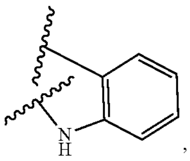
, and
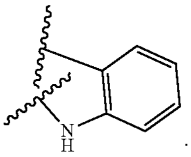
.

In some embodiments, $R_2$ and $R_3$ come together to form a structure selected from:

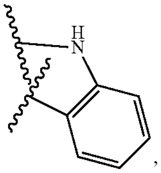
,
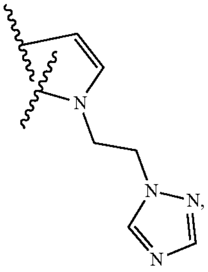
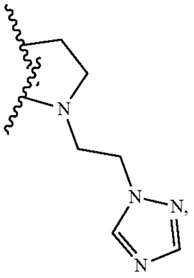
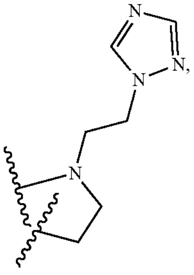
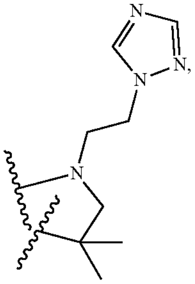
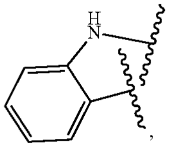
,
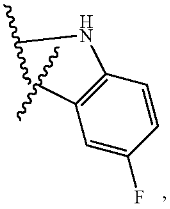
,
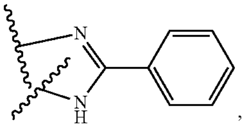
, and
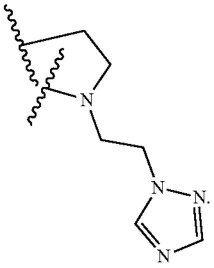

In some embodiments, $R_3$ and $R_4$ come together to form a structure selected from:

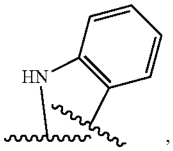, 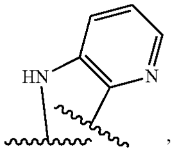, and 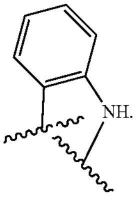
In some embodiments, the compound (of Formula I) is selected from:
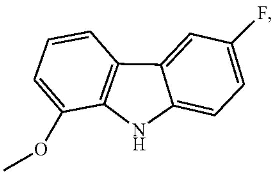
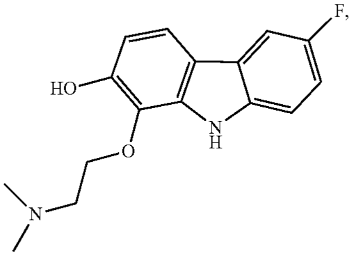
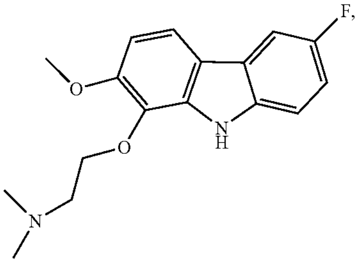
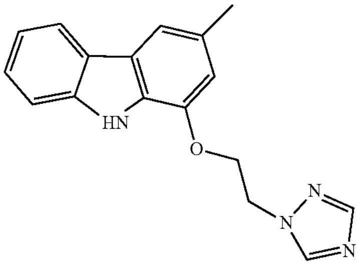,
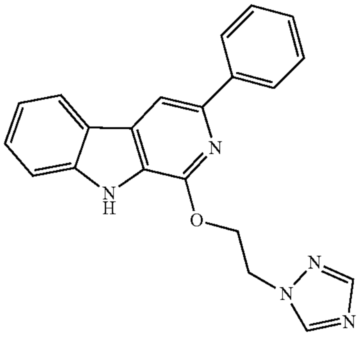,
-continued
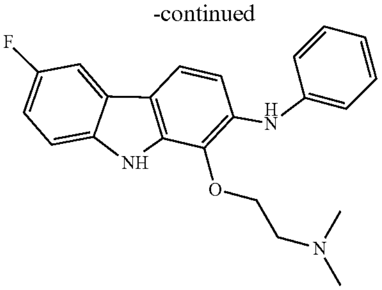,
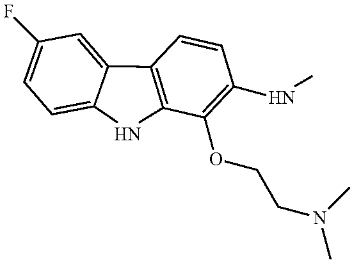,
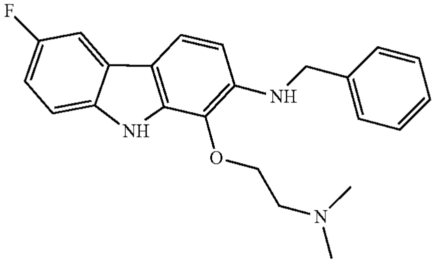,
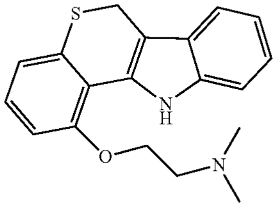,
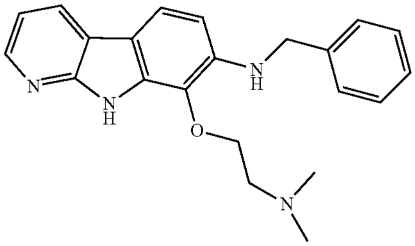,
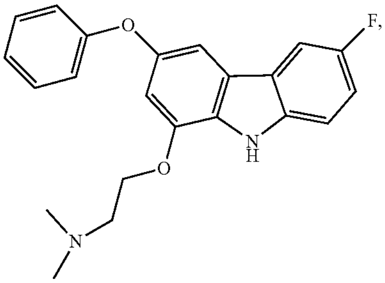

-continued
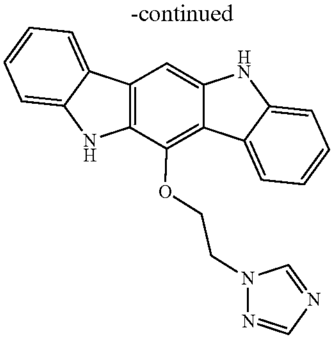
,
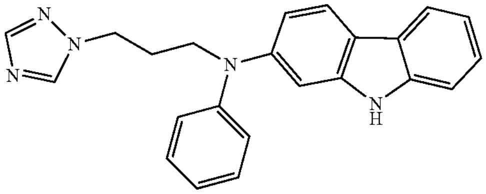
,
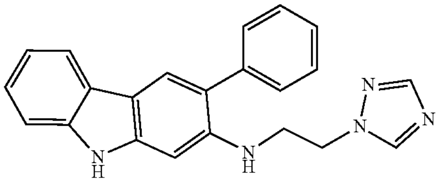
,
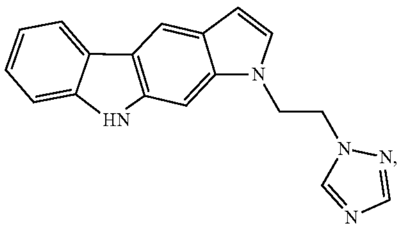
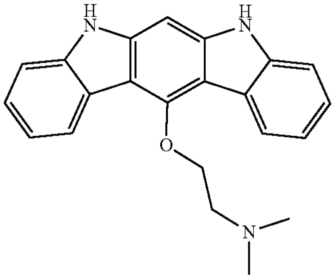
,
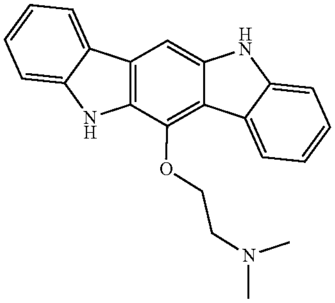
,
-continued
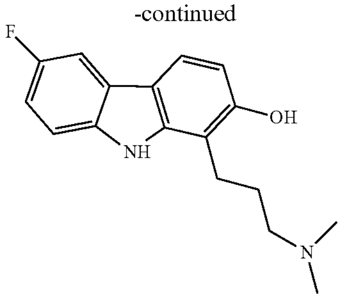
,
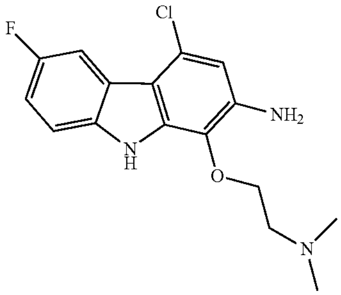
,
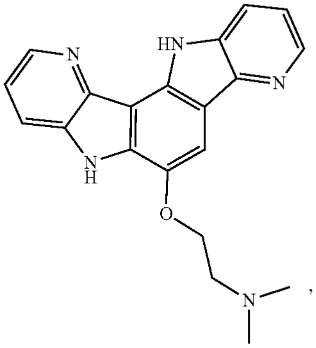
,
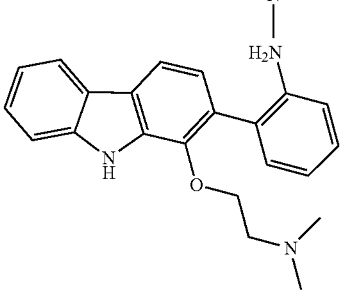
,
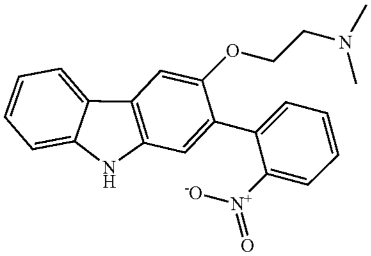
,
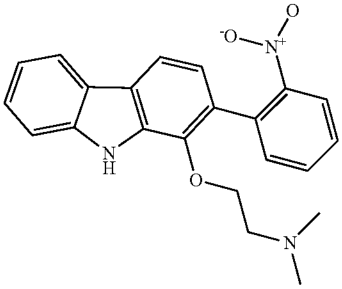
, -continued
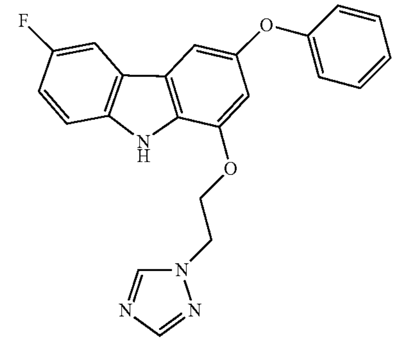
,
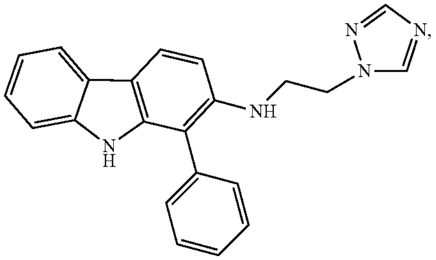
,
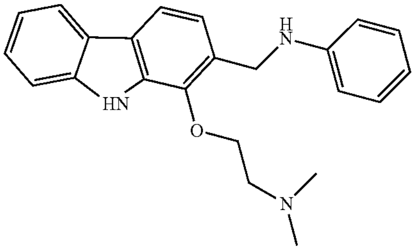
,
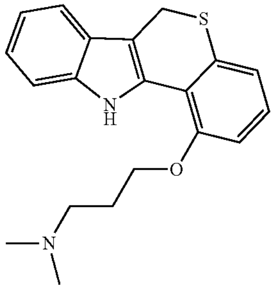
,
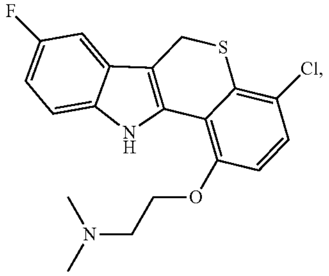
,
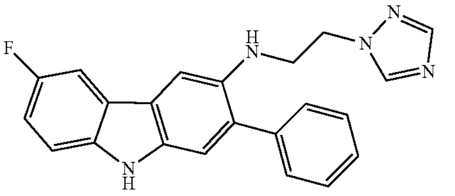
,
-continued
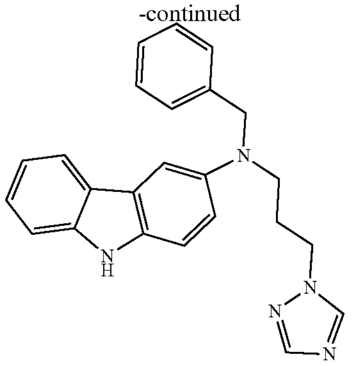
,
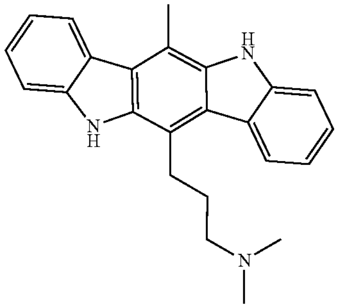
,
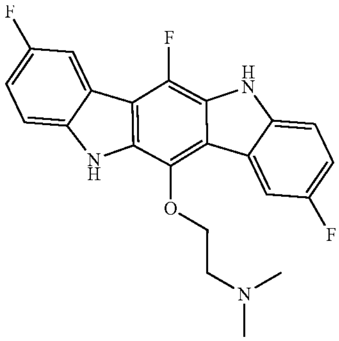
,
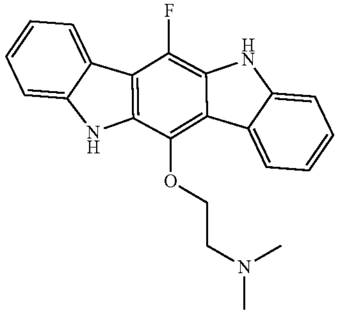
,
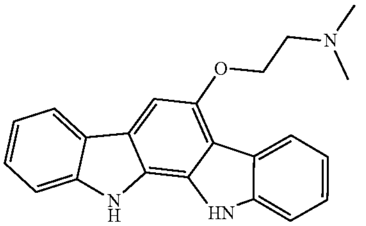

-continued
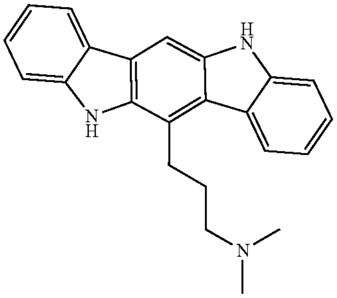
,
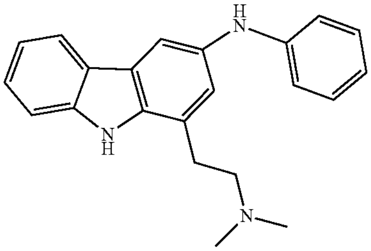
,
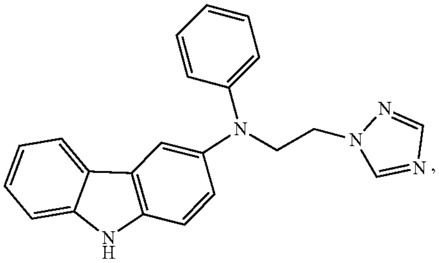
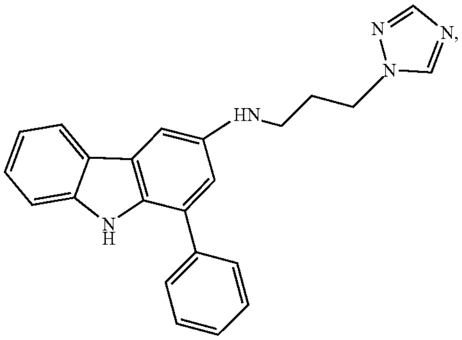
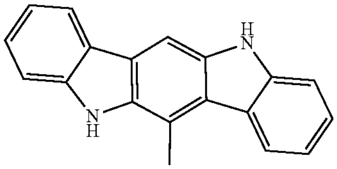
,
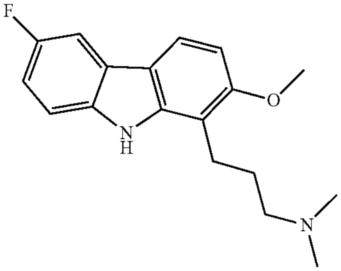
,
-continued
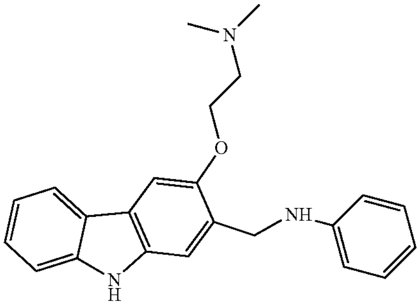
,
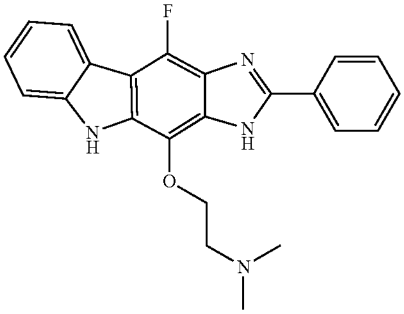
,
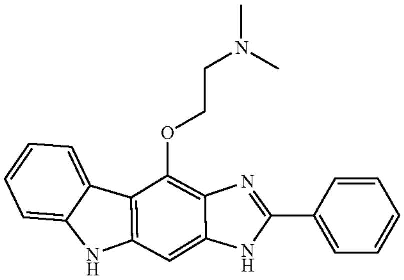
,
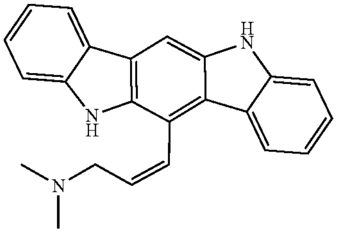
,
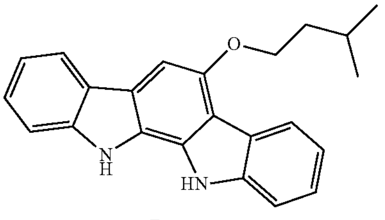
,
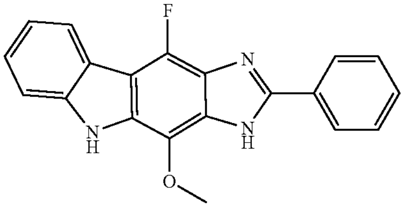
, -continued
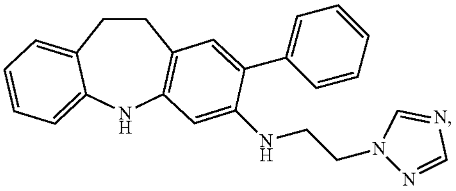
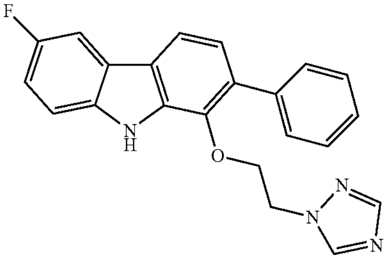
,
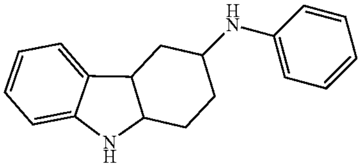
,
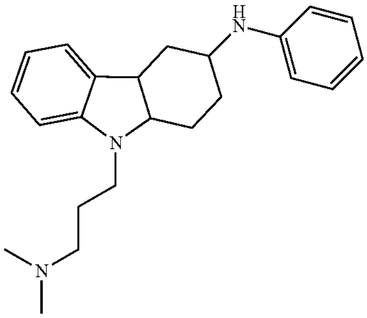
,
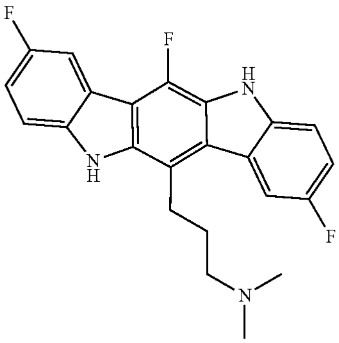
,
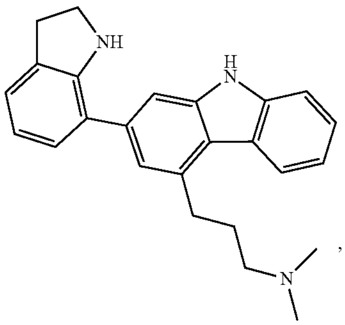
,
-continued
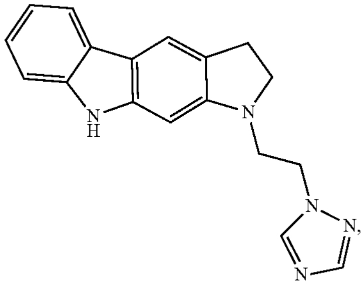
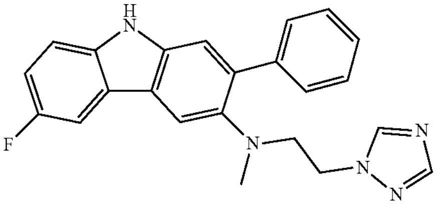
,
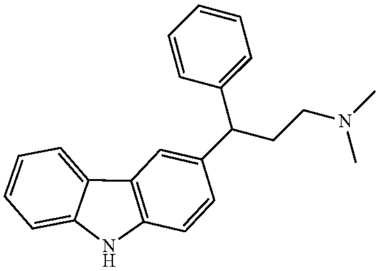
,
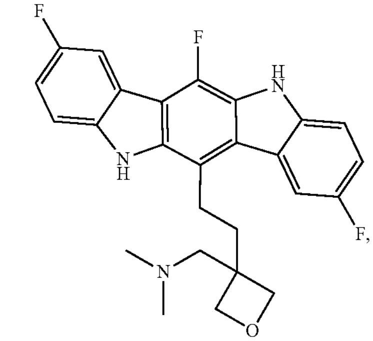
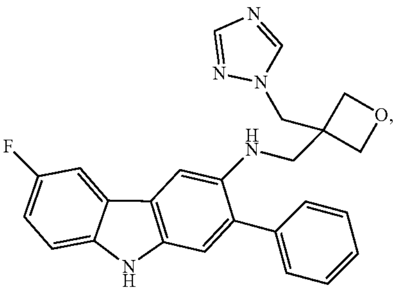
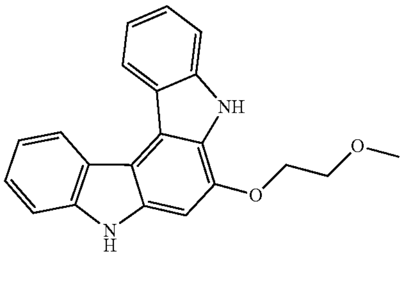
, -continued
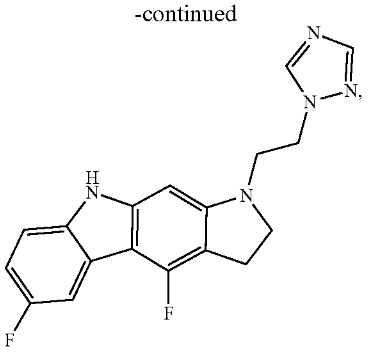
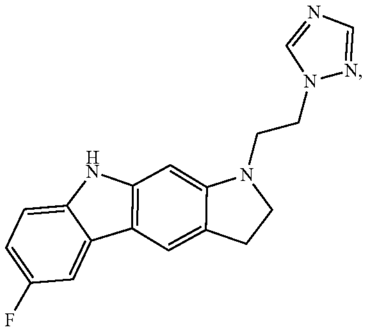
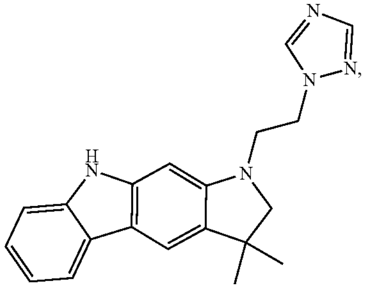
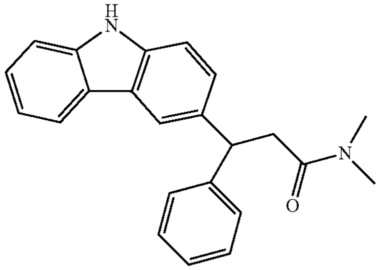
,
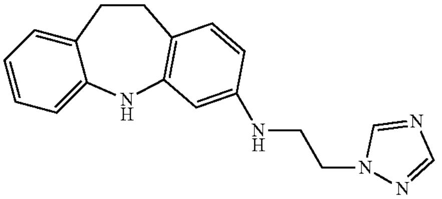
,
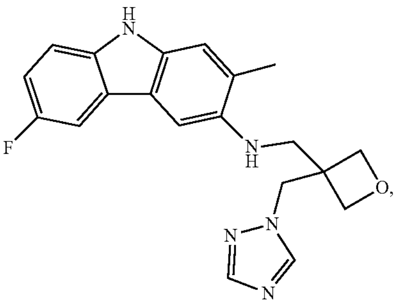
-continued
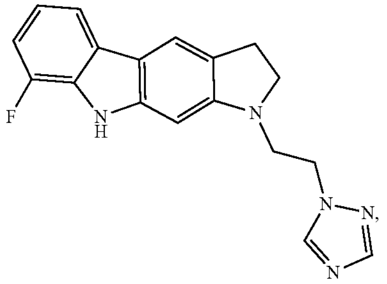
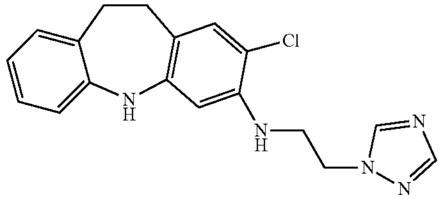
,
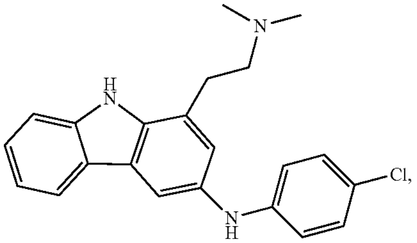
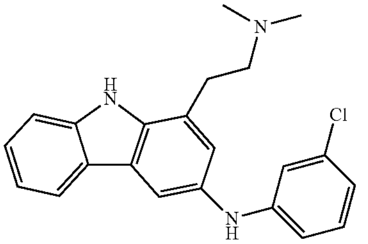
,
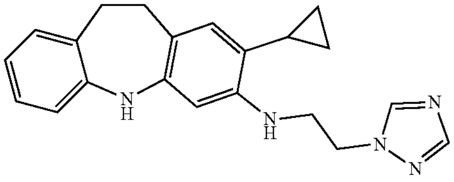
,
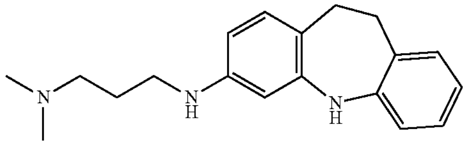
,
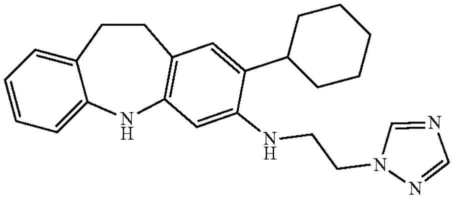
,
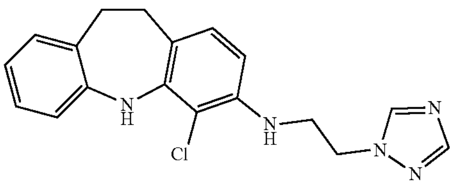
, -continued

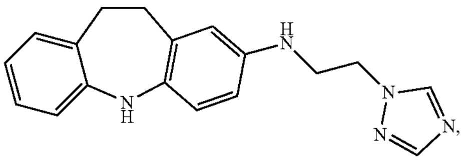

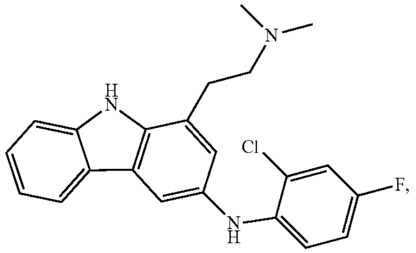

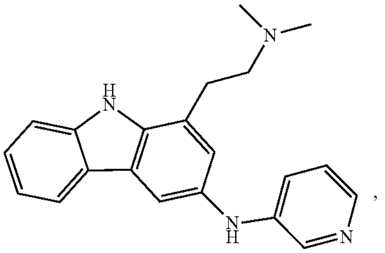

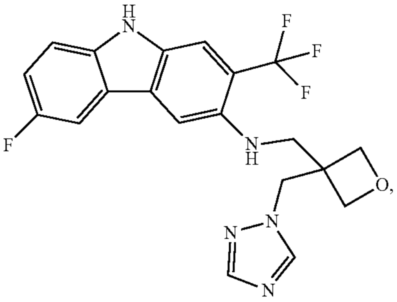

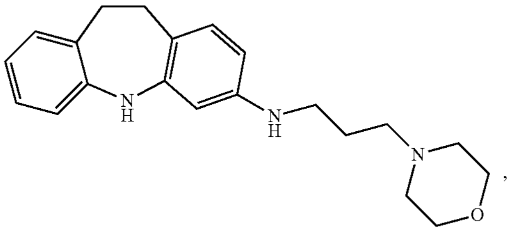

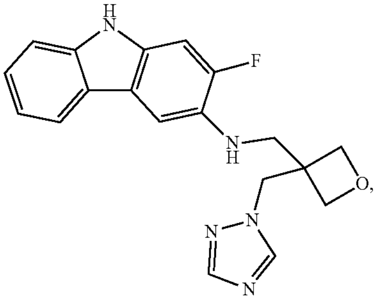

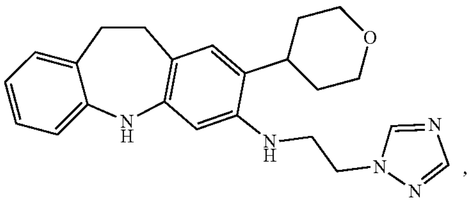

-continued

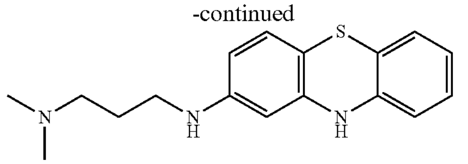

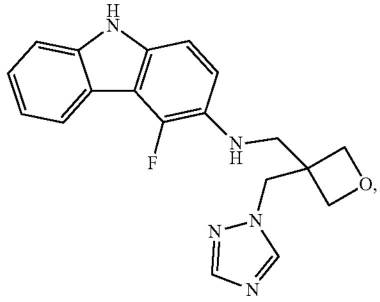

and pharmaceutically acceptable salts thereof.

Various embodiments are directed to a compound having Formula IA:

Formula IA

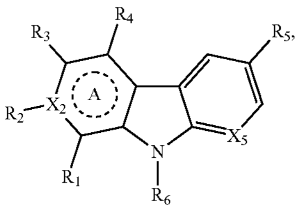

wherein: A is an aromatic ring or a cycloalkyl; $X_2$ and $X_5$ are each independently C or N; $R_1$ is a —H, a $C_{1-3}$ alkyl, a $C_{1-3}$ alkoxy, or a 5-6 membered aryl, wherein the $C_{1-5}$ alkyl, the $C_{1-3}$ alkoxy, or the 5-6 membered aryl is optionally further independently substituted with one to three $R_a$; $R_2$ is a —H, a halo, an oxo, a hydroxyl, a $C_{1-3}$ alkyl, a $C_{1-3}$ alkoxy, a $C_{1-3}$ haloalkyl, a —$NR_aR_b$, a 5-6 membered aryl, or a 5-10 heterocycl aryl, wherein the $C_{1-3}$ alkyl, the $C_{1-3}$ alkoxy, the $C_{1-3}$ haloalkyl, the —$NR_aR_b$, the 5-6 membered aryl, or the 5-10 heterocycl aryl is optionally further independently substituted with one to three $R_x$ and/or $R_y$; $R_3$ is a —H, an oxo, a $C_{1-3}$ alkyl, a $C_{1-3}$ alkoxy, a —$NR_aR_b$, a —$NH(CH_2)_{1-3}R_aR_b$, a 3-6 membered cycloalkyl, or a 5-6 membered aryl, wherein the $C_{1-3}$ alkyl, the $C_{1-3}$ alkoxy, the —$NR_aR_b$, the —$NH(CH_2)_{1-3}R_aR_b$, the 3-6 membered cycloalkyl, or the 5-6 membered aryl is optionally further independently substituted with one to three $R_x$ and/or $R_y$; $R_4$ is a —H or a halo; $R_5$ is a —H or a halo; $R_6$ is a —H, or a $C_{1-4}$ alkyl, wherein the $C_{1-4}$ alkyl is optionally further independently substituted with one to three $R_a$; each $R_a$ and $R_b$ is independently a —H, a $C_{1-3}$ alkyl, a $C_{1-3}$ alkoxy, a —$NH_2$, a —$NR_xR_y$, a 4-6 membered heterocycle, a 5-6 membered aryl, or a 5-6 membered heteroaryl, wherein the $C_{1-3}$ alkyl, the $C_{1-3}$ alkoxy, the —$NR_xR_y$, the 4-6 membered heterocycle, the 5-6 membered aryl, and/or the 5-6 membered heteroaryl are optionally further independently substituted with one to three $R_x$; each $R_x$ and $R_y$ is independently a —H, a halo, an oxo, a $C_{1-3}$ alkyl, or a 5-6 membered heteroaryl, wherein the $C_{1-3}$ alkyl and/or the 5-6 membered heteroaryl are optionally further independently substituted with one to three $R_{x1}$; each $R_{x1}$ is independently a —H, a halo, a $C_{1-2}$ alkyl, a $C_{1-3}$ alkoxy, or a 5-6 membered heteroaryl; and a pharmaceutically acceptable salt thereof.

In some embodiments, $R_1$ is selected from:
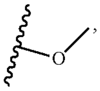, 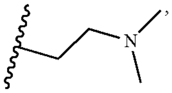, 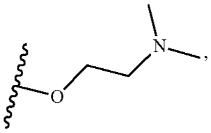,
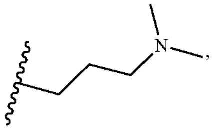, 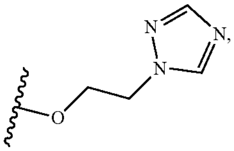
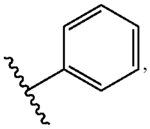, and 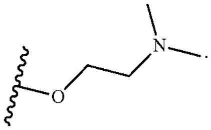.
In some embodiments, $R_2$ is selected from:
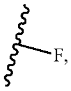 —OH, 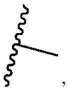, 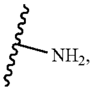 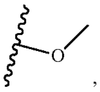, 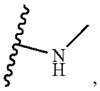,
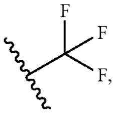 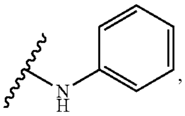, 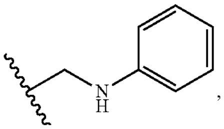,
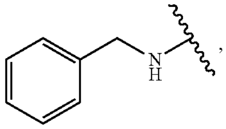, 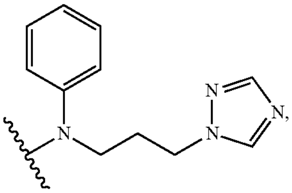
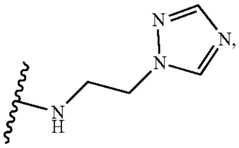 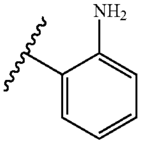, 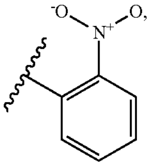 and
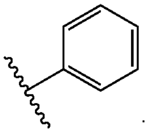.
-continued
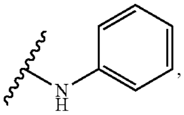, 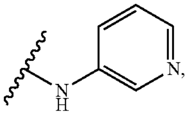 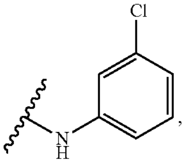,
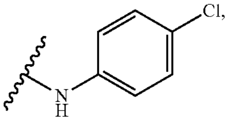 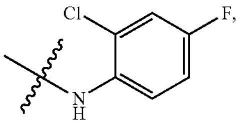
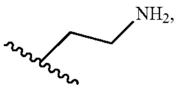 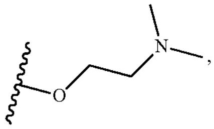,
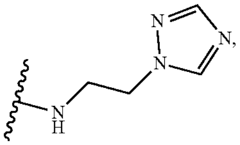 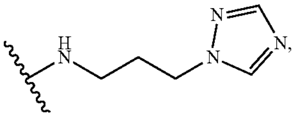
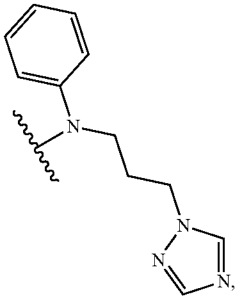 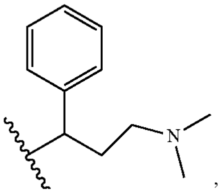,
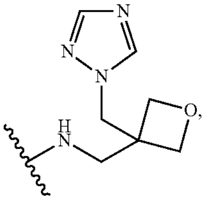 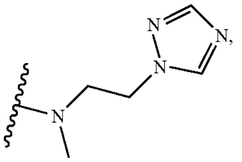 and
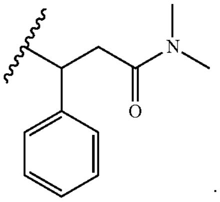.
In some embodiments $R_3$ is selected from:
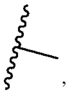, 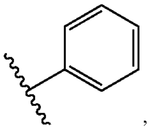, 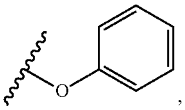,
In some embodiments, $R_4$ is
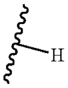 or 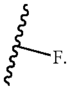

In some embodiments, $R_5$ is
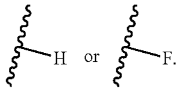
In some embodiments, $R_6$ is a —H or
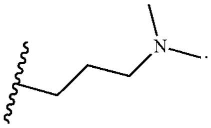 [SMILES: *CCCN(C)C]
In some embodiments, the compound (of Formula IA) is selected from:
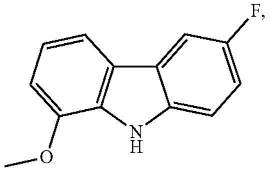
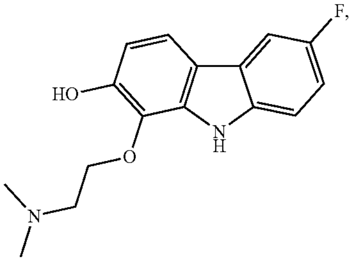
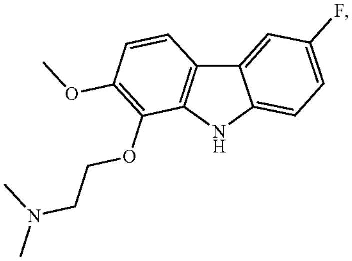
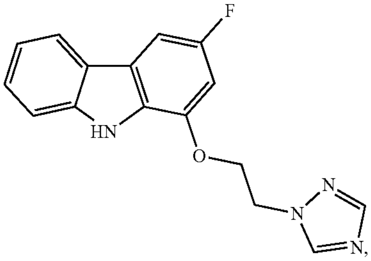
-continued
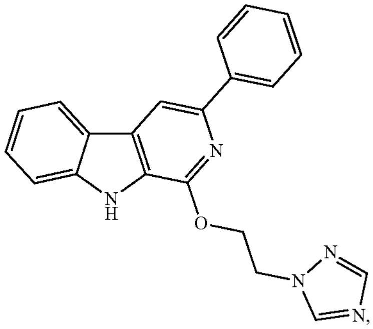
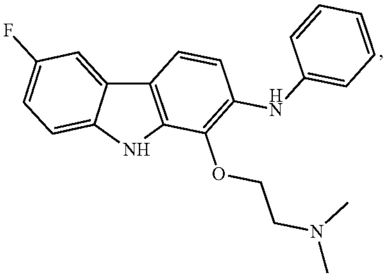
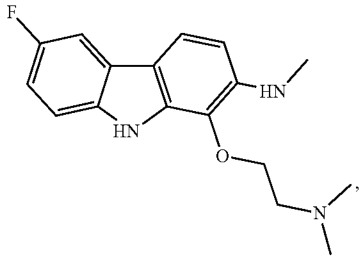
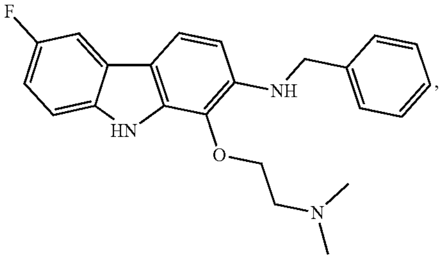
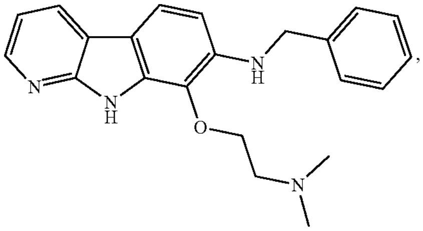
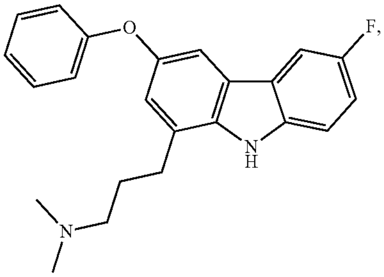

-continued
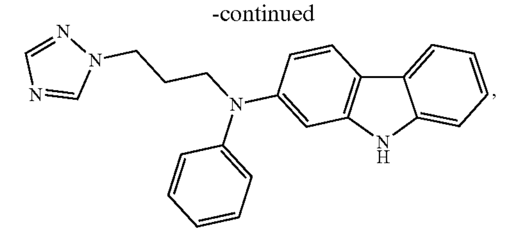
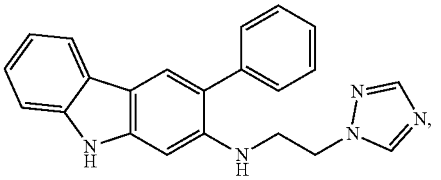
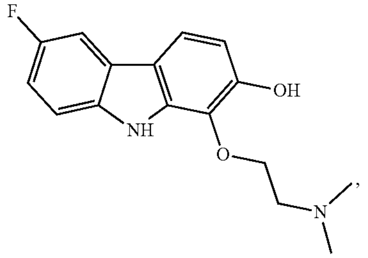
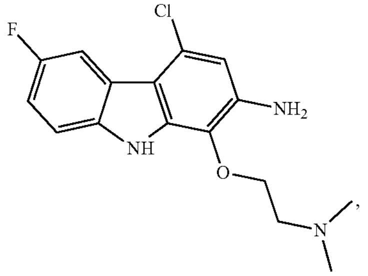
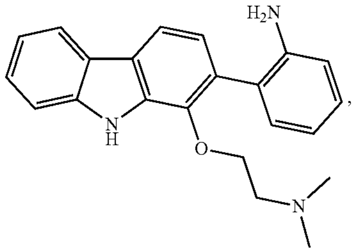
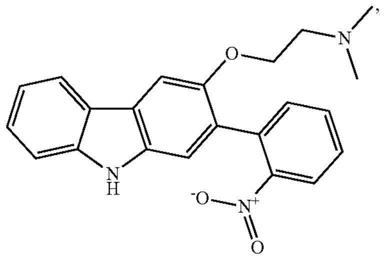
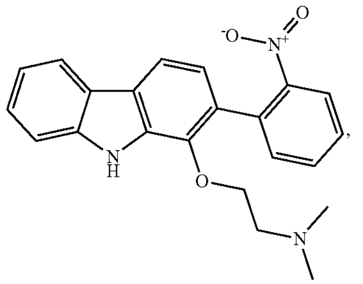
-continued
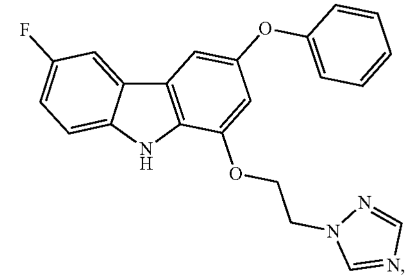
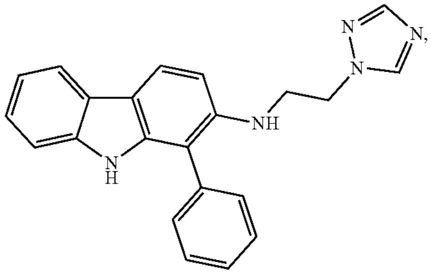
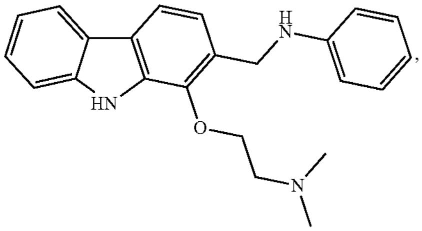
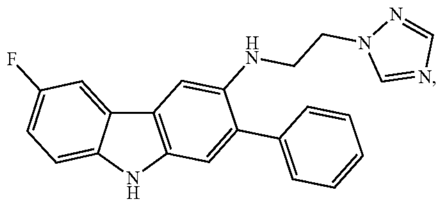
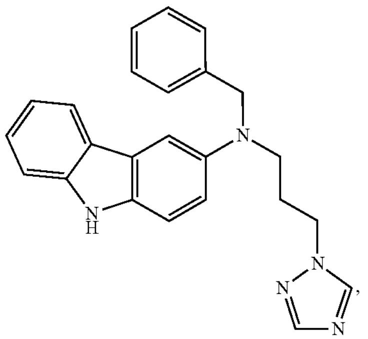
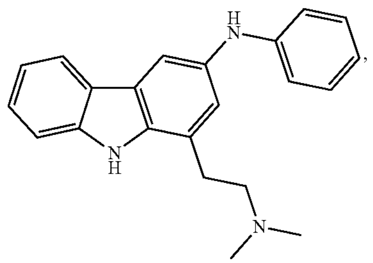

-continued
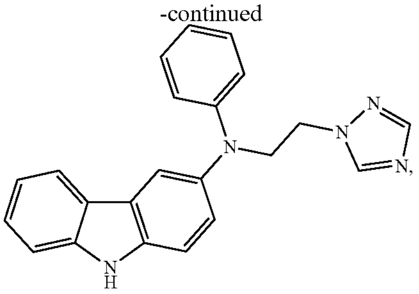
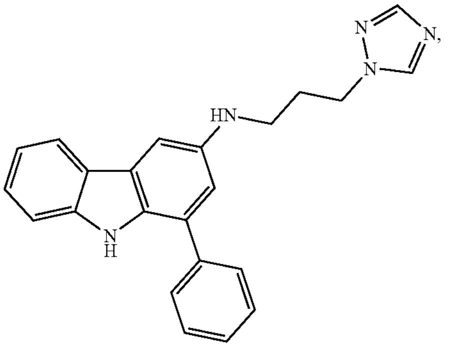
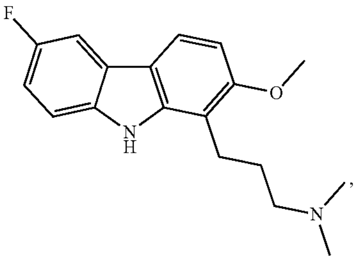
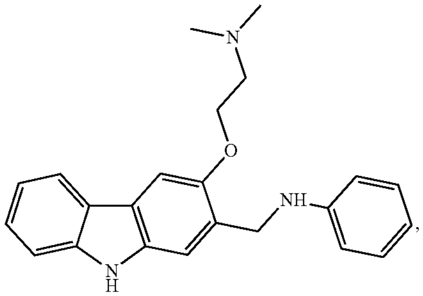
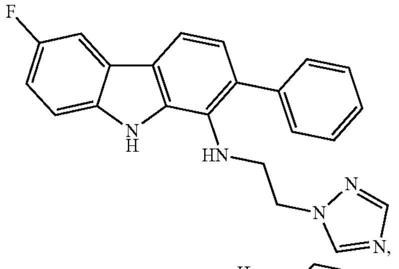
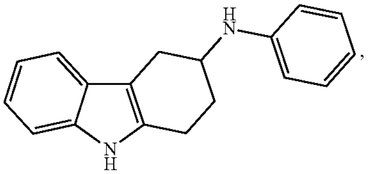
-continued
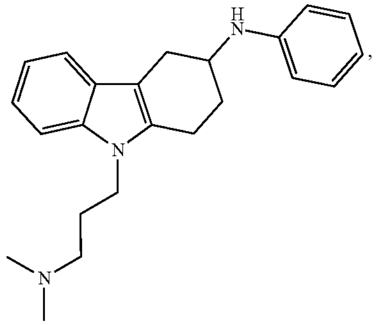
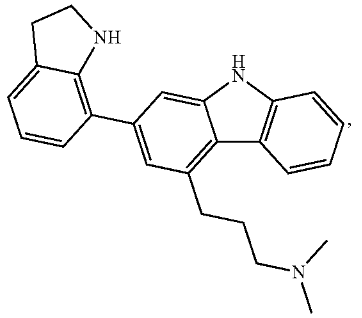
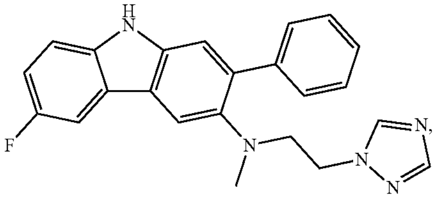
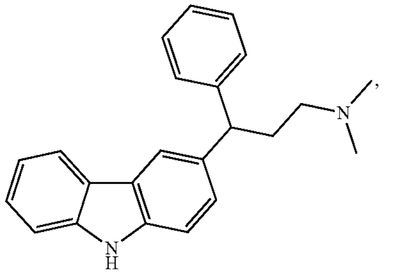
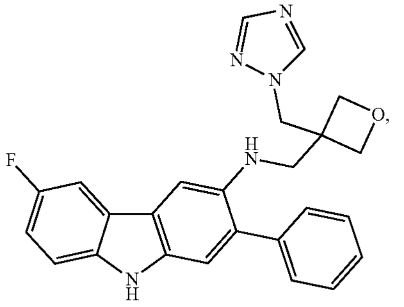
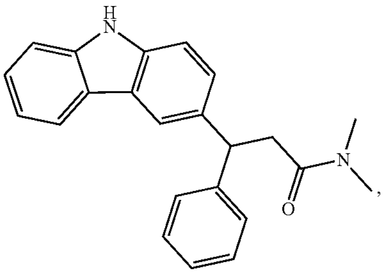

-continued

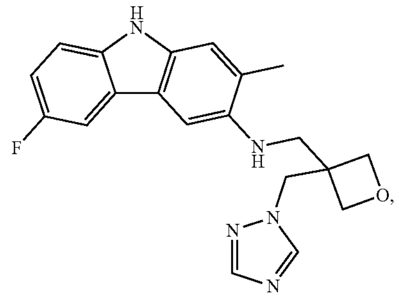

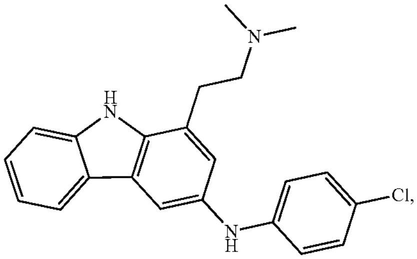

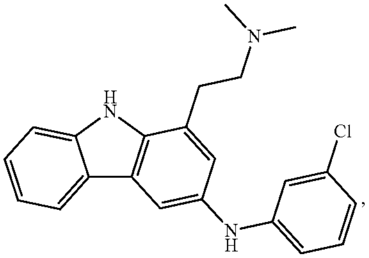

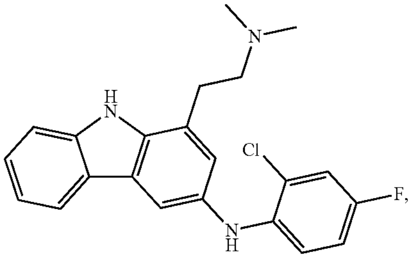

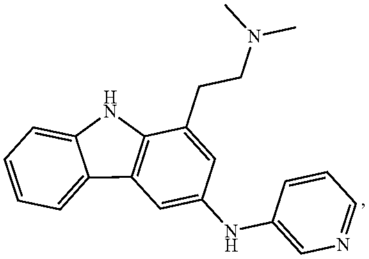

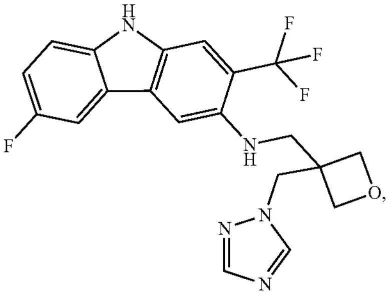

-continued

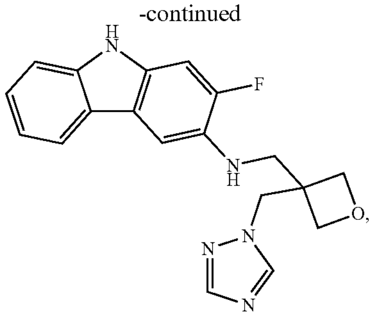

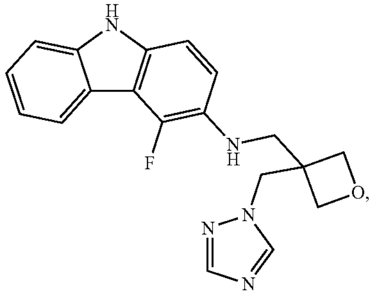

and pharmaceutically acceptable salts thereof.

Some embodiments are directed to a compound of Formula IB:

Formula IB

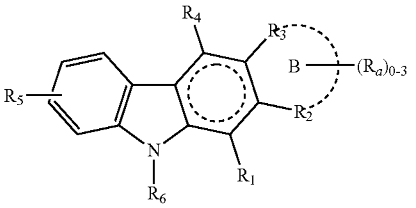

wherein: $R_1$ is a —H, a $C_{1-3}$ alkyl, or a $C_{1-3}$ alkoxy, wherein the $C_{1-5}$ alkyl or the $C_{1-3}$ alkoxy is optionally further independently substituted with one to three $R_a$; $R_2$ and $R_3$ come together to form B, wherein B is a 5-6 membered heterocycle or a 7-10 membered cycloalkyl aryl, wherein the 5-6 membered heterocycle or the 7-10 membered cycloalkyl aryl is optionally further independently substituted with one to three $R_a$; $R_4$ is a —H, a halo, a $C_{1-3}$ alkyl, or a $C_{1-3}$ alkoxy, wherein the $C_{1-3}$ alkyl or the $C_{1-3}$ alkoxy is optionally further independently substituted with one to three $R_a$; $R_5$ is a —H or a halo; $R_6$ is an oxo or a $C_{1-4}$ alkyl, wherein the $C_{1-4}$ alkyl is optionally further independently substituted with one to three $R_a$; each $R_a$ is independently a —H, a $C_{1-3}$ alkyl, a $C_{1-3}$ alkenyl, a —$NR_xR_y$, a —$NR_x$, a 4-6 membered heterocycle, a 5-6 membered aryl, or a 5-6 membered heteroaryl, wherein the $C_{1-3}$ alkyl, the $C_{1-3}$ alkenyl, the —$NR_xR_y$, the 4-6 membered heterocycle, the 5-6 membered aryl, and/or the 5-6 membered heteroaryl are optionally further independently substituted with one to three $R_x$; wherein two adjacent $R_a$ optionally further come together to form a 4-6 membered heterocycle or a 5-6 membered aryl, wherein the 4-6 membered heterocycle or the 5-6 membered aryl is optionally further independently substituted with one to three $R_x$; each $R_x$ and $R_y$ is independently a —H, a halo, a $C_{1-3}$ alkyl, or a 5-6 membered heteroaryl, wherein the $C_{1-3}$ alkyl and/or the 5-6 membered heteroaryl are optionally further independently substituted with one to three $R_{x1}$; wherein when two $R_x$ are bonded to the same atom, the two $R_x$ optionally come together to form a 4-6 membered heterocycle, wherein the 4-6 membered heterocycle is optionally further independently substituted with one to three $R_{x1}$; each $R_{x1}$ is independently a —H, a halo, a $C_{1-2}$ alkyl, a $C_{1-3}$ alkoxy, or a 5-6 membered heteroaryl; and a pharmaceutically acceptable salt thereof.

In some embodiments, $R_1$ is selected from:

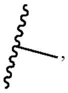,
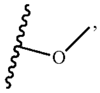,
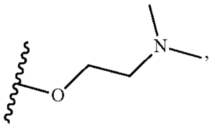,
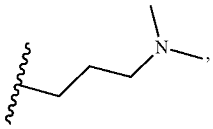,
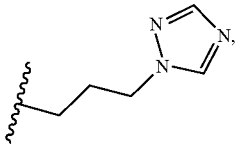
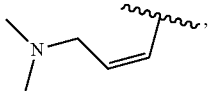, and
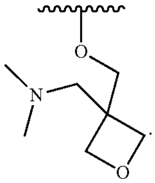.

In some embodiments, $R_2$ and $R_3$ come together to form B, wherein B is a structure selected from:

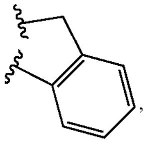,
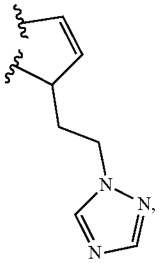
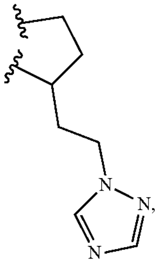
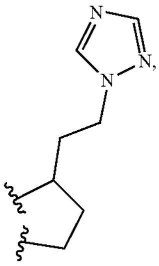
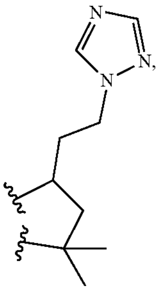
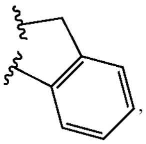, and
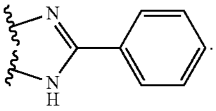.

In some embodiments, $R_4$ is selected from:

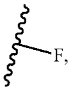,
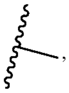, and
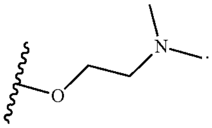.

In some embodiments, $R_5$ is —H or —F.

In some embodiments, $R_6$ is —H or

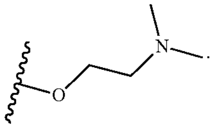.

In some embodiments, the compound (of Formula IB) is selected from:

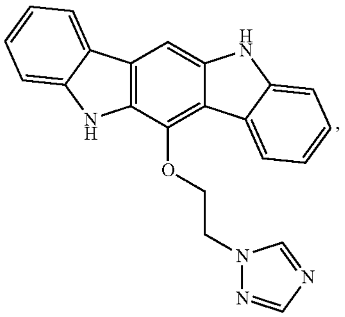,
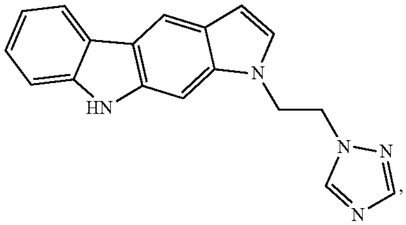
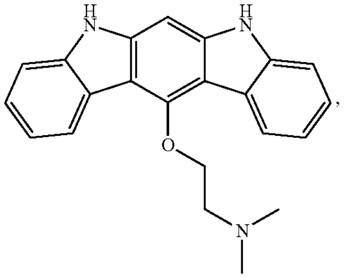,
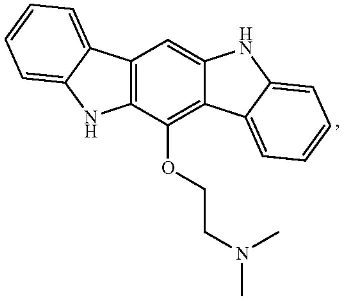,

-continued
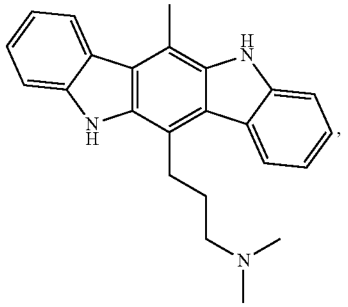,
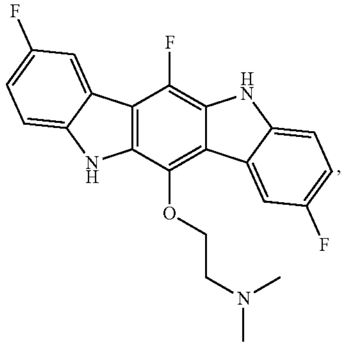,
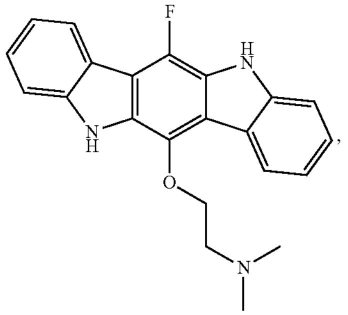,
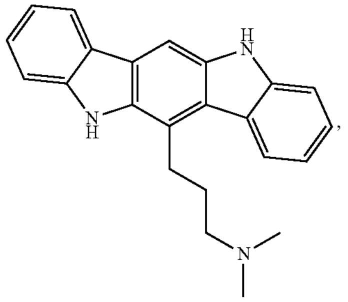,
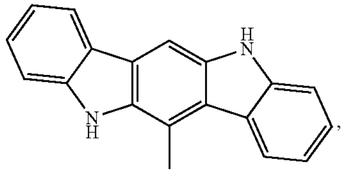,
-continued
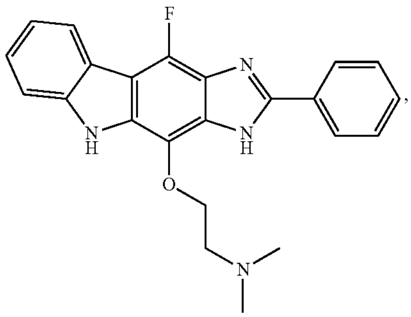,
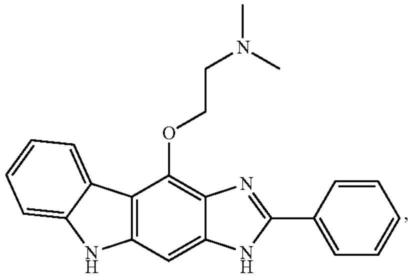,
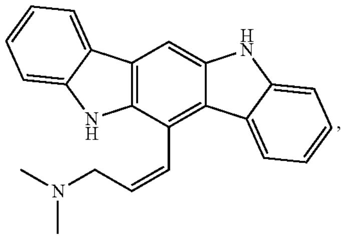,
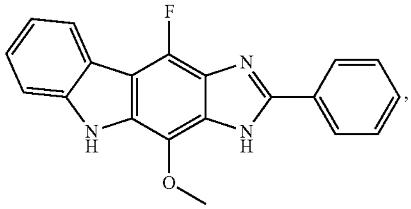,
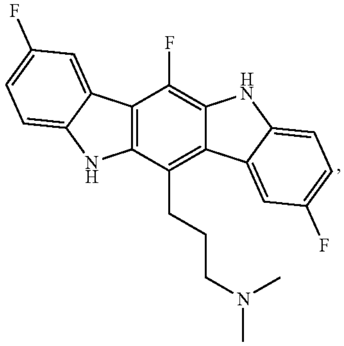,
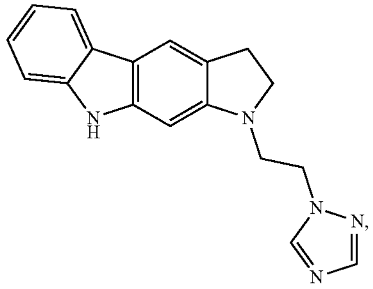, -continued

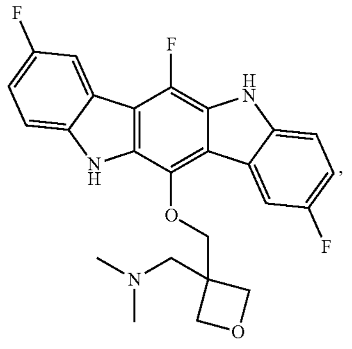

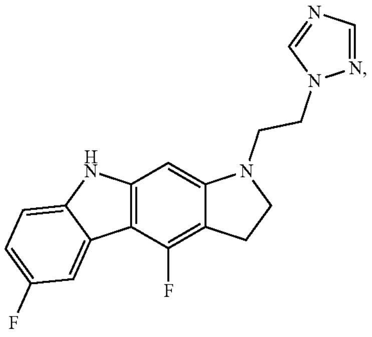

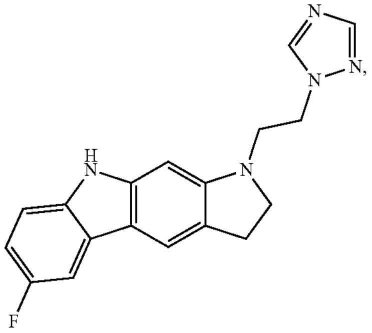

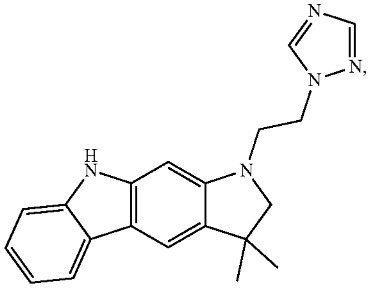

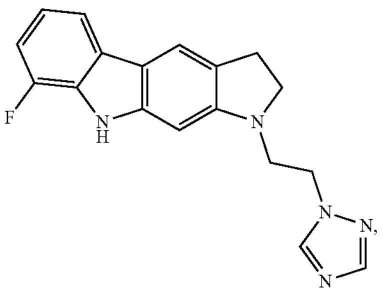

and pharmaceutically acceptable salts thereof.

Some embodiments are directed to a compound of Formula IC:

Formula IC

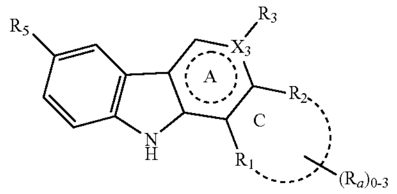

wherein: A is a 6 membered heterocycle or a 6 membered aryl; $X_3$ is C or S; $R_1$ and $R_2$ come together to form C, wherein C is a 5-6 membered aryl or a 5-6 membered heterocycle, and wherein the 5-6 membered aryl or the 5-6 membered heterocycle is optionally further independently substituted with one to three $R_a$; $R_3$ is a —H or a $C_{1-3}$ alkoxy, wherein the $C_{1-3}$ alkoxy is optionally further independently substituted with one to three $R_a$; $R_5$ is a —H or a halo; $R_a$ is a —H or a $C_{1-3}$ alkoxy, wherein the $C_{1-3}$ alkoxy is optionally further substituted with $R_x$ or two $R_a$ bonded to adjacent atoms optionally further come together to form a 5-6 membered aryl; $R_x$ is independently a —H or a —$NR_{x1}R_{x2}$; each $R_{x1}$ and $R_{x2}$ is independently a —H or a $C_{1-2}$ alkyl, and a pharmaceutically acceptable salt thereof.

In some embodiments, the ring formed by $R_1$ and $R_2$ is selected from:

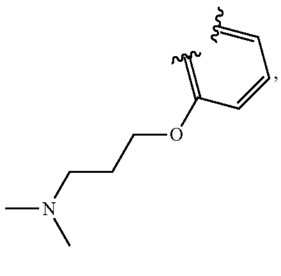,

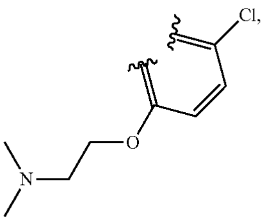

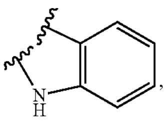, and 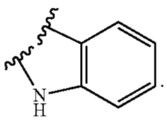.

In some embodiments, $R_3$ is:

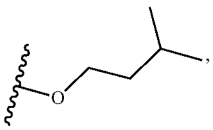, or 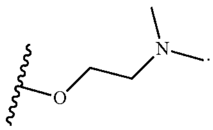 [SMILES: *OCCN(C)C].

In some embodiments, $R_5$ is —H or —F.

In some embodiments, the compound (of Formula IC) is selected from:

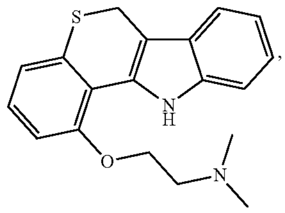
,
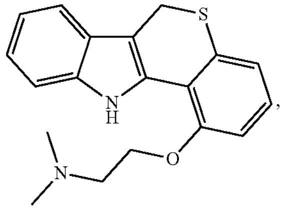
,
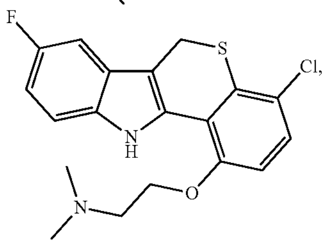

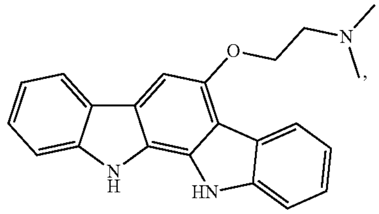

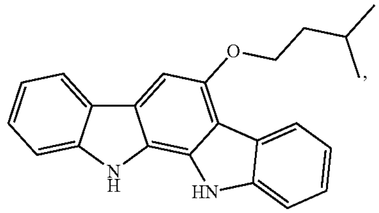

and pharmaceutically acceptable salts thereof.

Some embodiments are directed to a compound of Formula ID:

Formula ID

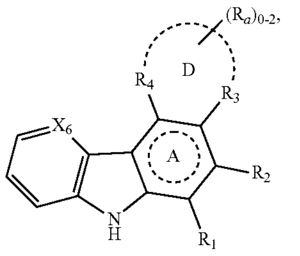

wherein: A is a 6 membered heterocycle or a 6 membered aryl; $X_6$ is a C or N; $R_1$ is a H or a $C_{1-3}$ alkoxy, wherein the $C_{1-3}$ alkoxy is optionally further substituted with $R_a$; $R_2$ is a H or a $C_{1-3}$ alkoxy, wherein the $C_{1-3}$ alkoxy is optionally further substituted with $R_a$; $R_3$ and $R_4$ optionally come together to form D, wherein D is a 5 membered heterocycle, wherein D is optionally further independently substituted with up to two $R_a$; each $R_a$ is independently a $C_{1-3}$ alkyl, $C_{1-3}$ alkenyl, or a —$NR_xR_y$, wherein the $C_{1-3}$ alkyl and/or the $C_{1-3}$ alkenyl are optionally further substituted with up to two $R_x$, or two $R_a$ bonded to adjacent atoms optionally come together to form a 5-6 membered aryl or a 5-6 membered heteroaryl; each Rx and $R_y$ is independently a —H or a $C_{1-3}$ alkyl; and a pharmaceutically acceptable salt thereof.

In some embodiments, a ring formed by $R_3$ and $R_4$ is:

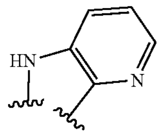
or
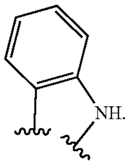

In some embodiments, $R_1$ is

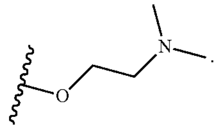 [SMILES: *OCCN(C)C]

In some embodiments, $R_2$ is

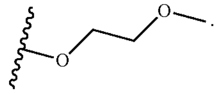 [SMILES: *OCCOC]

In some embodiments, the compound (of Formula ID) is selected from:

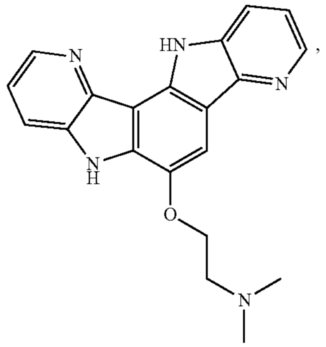
,
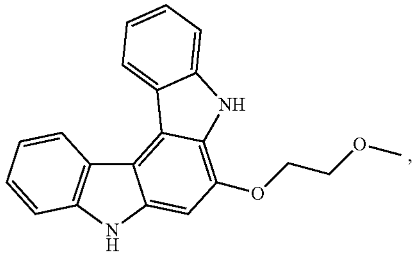

and pharmaceutically acceptable salts thereof.

Some embodiments are directed to a compound of Formula IE:

Formula IE

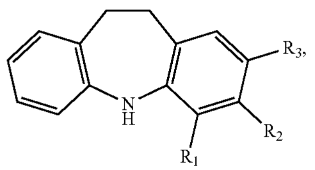

wherein: $R_1$ is a —H or a halo; $R_2$ is a —H or a —$NR_aR_b$, wherein the —$NR_aR_b$ is optionally further substituted with up to two Rx; $R_3$ is a —H, a 5-6 membered aryl, a 3-6 membered cycloalkyl, or a 5-6 membered heterocycle, wherein the 5-6 membered aryl, the 3-6 membered cycloalkyl, or the 5-6 membered heterocycle is optionally further substituted with up to two $R_a$; each $R_a$ and $R_b$ is independently —H or $C_{1-3}$ alkyl; each Rx is independently —$NR_{x1}R_{x2}$ or a 5-6 membered heteroaryl; each $R_{x1}$ and $R_{x2}$ is independently $C_{1-3}$ alkyl; and a pharmaceutically acceptable salt thereof.

In some embodiments, $R_1$ is —H or —Cl.

In some embodiments, $R_2$ is —H,

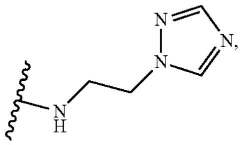 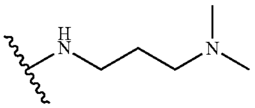, or

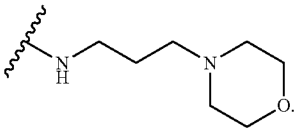

In some embodiments, $R_3$ is —H, —Cl,

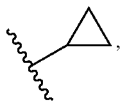, 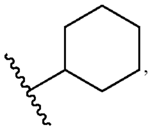, 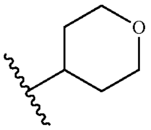,

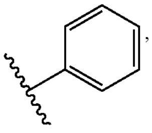, or 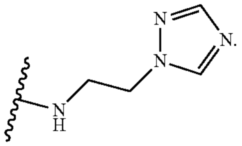

In some embodiments, the compound (of Formula IE) is selected from:

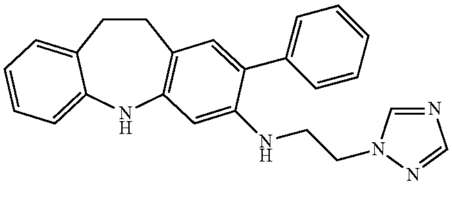,

-continued

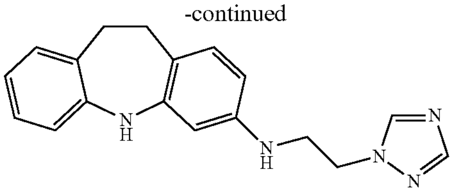,

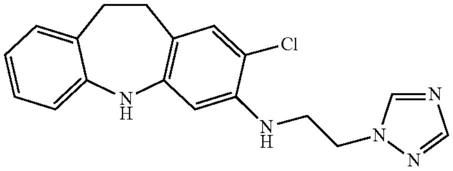,

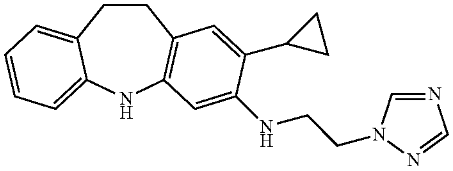,

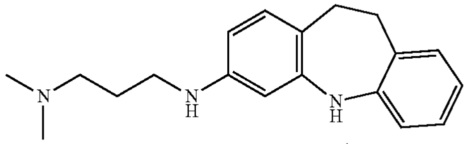,

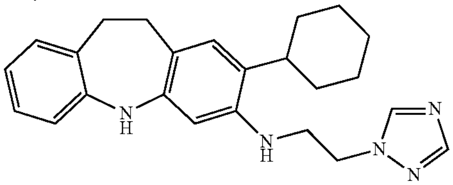,

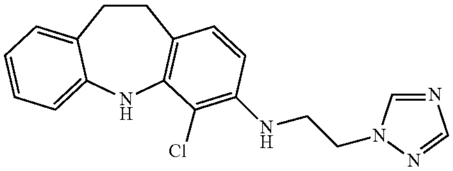,

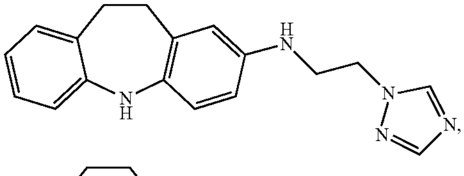

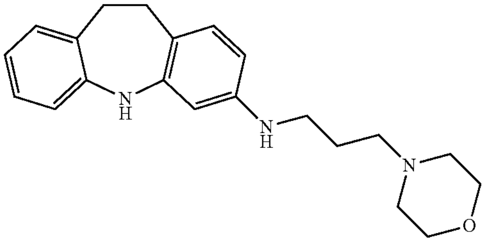,

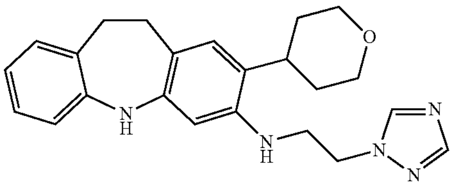, and pharmaceutically acceptable salts thereof.

Some embodiments are directed to compositions and methods to inhibit lipoxygenases in cells in vitro and in situ. Some embodiments are directed to a method of inhibiting a lipoxygenase in cells determined to be in need thereof, comprising contacting the cells with a compound having a structure disclosed in any of the above claims, such as Formula I in claim 1, which cells may be isolated in vitro, or as part of a body, in situ. In some embodiments, the cells are part of person determined to be in need of lipoxygenase inhibition or suffering from disease associated with pathogenic lipoxygenase activity, particularly a disease other than bacterial or viral infections, cancer or estrogen-dependent disorders, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, amyloid beta (Aβ)-associated disease, Alzheimer's Disease, ischemia-related disorder, Creutzfeldt-Jakob disease/prion peptide toxicity, ALS, dementia and Parkinson Disease.

Some embodiments are directed to a method for inhibiting amyloid-beta formation in neuronal cells determined to be in need thereof, comprising contacting the neuronal cells with a formula (I), which cells may be isolated in vitro, or as part of a body, in situ.

In some embodiments, a method comprises treating a person with a disease associated with pathogenic lipoxygenase activity, other than a bacterial or viral infection, cancer or estrogen-dependent disorder, particularly wherein the disease is an acute or chronic inflammatory disease or a neurodegenerative disease, comprising administering to the person a composition as described herein.

In some embodiments, the compound inhibits a lipoxygenase selected from 5-LOX, 12-LOX, 15-LOX, and combinations thereof, and/or decrease the levels of leukotrienes (LTs) and their corresponding HETE).

In some embodiments, a method comprises (i) measuring a lipoxygenase activity in a sample of the person; (ii) determining a level of a lipoxygenase metabolite in a sample of the person; and/or (iii) determining the person has the disease.

In some embodiments, the disease is: (i) an acute or chronic inflammatory disease that is asthma, rheumatoid arthritis, inflammatory bowel disease, psoriasis, hereditary ichthyosis, dermatitis, nephritis, atherosclerosis, or cardiovascular disease, or (ii) a neurodegenerative disease that is age-related neurodegeneration, neuroinflammation-associated disease, Alzheimer's Disease, ischemia-related disorder, Creutzfeldt-jakob disease/prion peptide toxicity, ALS, dementia or Parkinson Disease.

Some embodiments are directed to the compounds of Table 1, and salts, hydrates and pharmaceutical compositions, formulations and unit dosage forms thereof.

Various embodiments are directed to compositions comprising a subject LOX inhibitors, and a different, second drug active against a disease associated with pathogenic lipoxygenase activity, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, neuroinflammation-associated disease, Alzheimer's Disease, ischemia-related disorder, creutzfeldt-jakob disease/prion peptide toxicity, ALS, dementia and Parkinson Disease. In a particular embodiment, the second drug is an anti-neurodegenerative disease drug, such as acetylcholinesterase inhibitors, NMDA receptor antagonists, hyperzine A, latrepirdine, and hypothalamic proline-rich peptide 1.

Some embodiments are directed to a method for identifying a lipoxygenase inhibitor, comprising the step of screening for lipoxygenase inhibitory activity of a subject.

Embodiments in accordance with the present disclosure include all combinations of the recited particular embodiments. Further embodiments and the full scope of applicability of the invention will become apparent from the detailed description provided hereinafter. However, it should be understood that the detailed description and specific embodiments, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

DETAILED DESCRIPTION

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A wavy line drawn through a line in a chemical structure or a dashed line drawn through a line in a chemical structure indicates a point of attachment of a group. A dashed line within a chemical structure indicates an optional bond. A prefix such as "Cu-V" or (Cu-Cv) indicates that the following group has from u to v carbon atoms. For example, "C1-6alkyl or $C_{1-6}$ alkyl" indicates that the alkyl group has from 1 to 6 carbon atoms.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

The prefix "Cx-y" indicates that the following group has from x (e.g., 1) to y (e.g., 6) carbon atoms, one or more of which, in certain groups (e.g., heteroalkyl, heteroaryl, heteroarylalkyl, etc.), may be replaced with one or more heteroatoms or heteroatomic groups. For example, "C1-6 alkyl" indicates that the alkyl group has from 1 to 6 carbon atoms. Likewise, the term "x-y membered" rings, wherein x and y are numerical ranges, such as "3-12 membered heterocyclyl", refers to a ring containing x-y atoms (e.g., 3-12), of which up to half may be heteroatoms, such as N, O, S, P, and the remaining atoms are carbon. Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl ($-CH{\equiv}CH$), propargyl ($-CH2C{\equiv}CH$), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH2. Amino groups may also be substituted as described herein, such as with alkyl, carbonyl or other amino groups. The term "alkylamino" refers to an amino group substituted with one or two alkyl substituents (e.g. dimethylamino or propylamino).

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like.

"Arylalkyl" (also "aralkyl") refers to any combination aryl group and an alkyl group. Arylalkyl groups include, but are not limited to, those groups derived from benzyl, tolyl, dimethylphenyl, 2-phenylethan-1-yl, 2-naphthylmethyl, and the like. An arylalkyl group comprises from 6 to 30 carbon atoms, for example the alkyl group can comprise from 1 to 10 carbon atoms and the aryl group can comprise from 5 to 20 carbon atoms.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

"Cycloalkyl" refers to a cyclic alkyl and alkenyl groups. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcycloproyl (cyclopropylmethyl), ethylcyclopropyl, cyclohexenyl and the like. Another example includes C5-7 cycloakenyl.

"Cycloalkyl-aryl" refers to a cycloalkyl ring bonded to an aryl ring. Cycloalkyl is defined above as is the term 'Aryl'. Examples include but are not limited to 2,3-dihydro-1H-indene and 1,2,3,4-tetrahydronaphthalene.

"Halo" and "halogen" refer to fluoro, chloro, bromo and iodo.

"Haloalkyl" refers to an alkyl wherein one or more hydrogen atoms are each replaced by a halogen. Examples include, but are not limited to, $-CH_2Cl$, $-CH_2F$, $-CH_2Br$, $-CFClBr$, $-CH_2CH_2Cl$, $-CH_2CH_2F$, $-CF_3$, $-CH_2CF_3$, $-CH_2CCl_3$, and the like, as well as alkyl groups such as perfluoroalkyl in which all hydrogen atoms are replaced by fluorine atoms.

"Hydroxyalkyl" refers to an alkyl wherein one or more hydrogen atoms are each replaced by a hydroxyl group. Examples include, but are not limited to, —CH2OH, $-CH_2CH_2OH$, —C(CH3)2OH, and the like.

"Halo 3-6 membered heterocyclyl" refers to a heterocyclyl group substituted at a carbon atom with at least one halogen atom, and may include multiple halogen atoms, such as 3,3-difluoroazetidinyl.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, $-P(O)_2-$, —S(O)—, $-S(O)_2-$, and the like, where R is H, alkyl, aryl, cycloalkyl, heteroalkyl, heteroaryl or cycloheteroalkyl. Heteroalkyl groups include, but are not limited to, $-OCH_3$, $-CH_2OCH_3$, $-SCH_3$, $-CH_2SCH_3$, $-NRCH_3$, $-CH_2NRCH_3$, $-CH_2OH$ and the like, where R is hydrogen, alkyl, aryl, arylalkyl, heteroalkyl, or heteroaryl, each of which may be optionally substituted. A heteroalkyl group comprises from 1 to 10 carbon and up to three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-14 members, 5-10 members, or 5-6 members.

"Heterocycle," "heterocyclic," and "heterocyclyl" refer to a saturated or partially unsaturated non-aromatic ring or a partially non-aromatic multiple-ring system with at least one heteroatom or heteroatomic group, as defined above. Heterocycles include, but are not limited to, groups derived from azetidine, aziridine, imidazolidine, morpholine, thiomorpholine, tetrahydro-2H-thiopyran, 1-iminotetrahydro-2H-thiopyran 1-oxide, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like. Heterocyclyl groups also include partially unsaturated ring systems containing one or more double bonds, including fused ring systems with one aromatic ring and one non-aromatic ring, but not fully aromatic ring systems. Examples include dihydroquinolines, e.g., 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Heterocycle groups may have 3-12 members, or 3-10 members, or 3-7 members, or 5-6 members. Other examples include cyclopente-type rings.

"Hydroxyl" and "hydroxy" are used interchangeably and refer to —OH. "Oxo" refers to =O, or oxide where N-oxide or S-oxide exist. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g. $CH_3CH_2NHC(O)$—) $C_{1-6}$ alkoxycarbonyl (e.g. $CH_3O$—C(O)—), 5-7 membered heterocyclyl-$C_{1-6}$ alkyl (e.g. piperazinyl-$CH_2$—), $C_{1-6}$ alkylsulfonyl-5-7 membered heterocyclyl (e.g. $CH_3S(O)_2$-morpholinyl-), 5-7 membered heterocyclyl $C_{1-6}$ alkoxy (e.g. pyrrolidinyl-O—), 5-7 membered heterocyclyloxy, (4-7 membered heterocyclyl)-4-7 membered heterocyclyl (e.g. oxetanyl-pyrrolidinyl-), $C_{3-6}$ cycloalkylaminocarbonyl (e.g. cyclopropyl-NH—C(O)—), 5-7 membered heterocyclyl-$C_{2-6}$ alkynyl (e.g. N-piperazinyl-$CH_2C{\equiv}CCH_2$—), and $C_{6-10}$ arylaminocarbonyl (e.g. phenyl-NH—C(O)—).

The present disclosure includes both racemic mixtures of a compound of the disclosed formulas and isolated isomers or any variation thereof. Where more than one chiral center is present in a compound of the present disclosure, some, none, or all of the chiral centers may be enantiomerically enriched. Thus, mixtures of a compound of the disclosed formulas may be racemic with respect to one or more chiral centers and/or enantiomerically enriched with respect to one or more chiral centers.

Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

As used herein and in the claims, "hydrogen" and "H", "oxygen" and "O", "carbon" and "C", and "nitrogen" and "N" are interchangeably used, and each respectively refer to a hydrogen atom, an oxygen atom, a carbon atom, and/or a nitrogen atom. As used herein and in the claims, the rings of various compounds are sometimes interchangeably referred to as "ring A" or "A" and "ring B" or "B", both of which respectively refer to the specifically referenced ring. Similarly, as used herein and in the claims, the various groups of the compounds are sometimes interchangeably referred with or without "atom" or "group" at the end, such as "$R_1$" and $R_1$ group", both of which respectively refer to the specifically referenced atom or chemical group.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

"Treating" and "treatment" of a disease include the following:

(1) preventing or reducing the risk of developing the disease, i.e., causing the clinical symptoms of the disease not to develop in a subject that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"Effective amount" refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated. The effective amount can include a range of amounts.

The compounds of the invention include solvates, hydrates, tautomers, stereoisomers and salt forms thereof.

Provided are also compounds in which from 1 to n hydrogen atoms attached to a carbon atom may be replaced by a deuterium atom, or tritiated with a tritium atom, in which n is the number of hydrogen atoms in the molecule. As known in the art, the deuterium atom is a non-radioactive isotope of the hydrogen atom and tritium is a radioactive isotope. Such compounds, particularly deuterated compounds, may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

The pharmaceutical compositions of compounds of the disclosed formulas may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In some embodiments, the compounds described herein may be administered orally. Oral administration may be via, for example, capsule or enteric coated tablets. In making the pharmaceutical compositions that include at least one compound of Formula I, or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propyl hydroxy-benzoates; sweetening agents; and flavoring agents.

In some embodiments, compounds of Formula I have the following structures:

Formula I

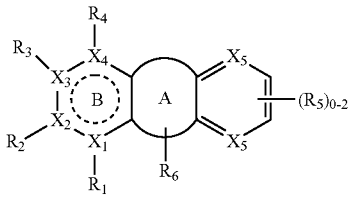

In some embodiments, A is a 5-7 membered cycloalkyl ring or a 5-7 membered heterocyclic ring. In some embodiments, A is a pyrrolidinyl. In some embodiments, A is an azepanyl.

In some embodiments, B is either a 6 membered cycloalkyl, 6 membered heterocycle, a 6 membered aryl, or a 6 membered heteroaryl. In some embodiments, B is cyclohexyl. In some embodiments, B is a phenyl. In some embodiments, B is a thiopyranyl.

In some embodiments, $X_1$, $X_2$, $X_3$, $X_4$, and $X_5$ are each independently C, N, or S.

In some embodiments, $R_1$ is a —H, a halo, a $C_{1-3}$ alkyl, $C_{1-3}$ alkenyl, a $C_{1-3}$ alkoxy, a 5-6 membered aryl, wherein the $C_{1-5}$ alkyl, the $C_{1-3}$ alkoxy, and/or the 5-6 membered aryl can be further independently substituted with one to three $R_a$. In some embodiments, $R_1$ is chloro. In some embodiments, $R_1$ is methyl, ethyl or propyl. In some embodiments, $R_1$ is methoxy. In some embodiments, $R_1$ is methoxypropanyl that can be further substituted with 5 membered heteroaryl. In some embodiments, $R_1$ is methoxypropanyl that can be further substituted with triazoyl. In some embodiments, $R_1$ is methoxy or methoxypropanyl that can be further substituted with dimethylamino. In some embodiments, $R_1$ is methoxy or methoxypropanyl that can be further substituted with oxetanyl. In some embodiments, $R_1$ is methoxymethyloxetanyl that can be further substituted with dimethylmethanamino. In some embodiments, $R_1$ is aminopropyl that can be further substituted with a five membered heteroaryl. In some embodiments, $R_1$ is aminopropyl that can be further substituted with triazoyl. In some embodiments, $R_1$ is butenyl that can be further substituted with amino. In some embodiments, $R_1$ is butenyl that can be further substituted with dimethylamino.

In some specific embodiments, $R_1$ is one of the following structures:

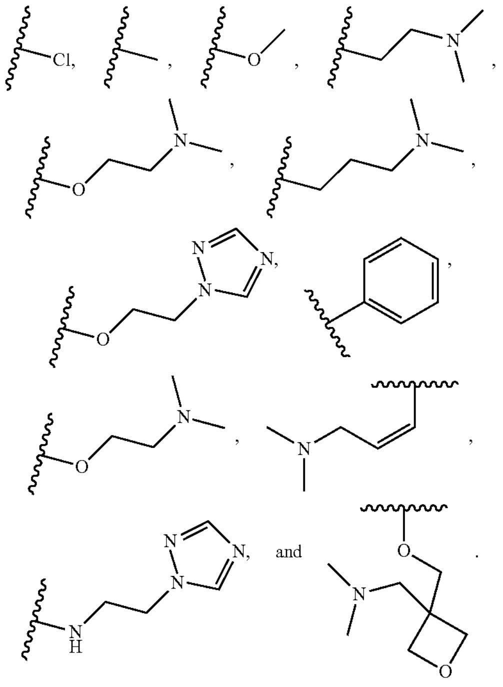

In some embodiments, $R_2$ is a —H, a halo, an oxo, a hydroxyl, a $C_{1-3}$ alkyl, $C_{1-3}$ alkenyl, a $C_{1-3}$ alkoxy, a $C_{1-3}$ haloalkyl, a —$NR_aR_b$, or a 5-6 membered aryl, wherein the $C_{1-3}$ alkyl, the $C_{1-3}$ alkenyl, the $C_{1-3}$ alkoxy, the $C_{1-3}$ haloalkyl, the —$NR_aR_b$, or the 5-6 membered aryl can be further independently substituted with one to three $R_a$. In some embodiments, $R_2$ is fluoro. In some embodiments, $R_2$ is methyl. In some embodiments, $R_2$ is amino. In some embodiments, $R_2$ is methoxy. In some embodiments, $R_2$ is amino —C1-3 alkyl. In some embodiments, $R_2$ is amino methyl. In some embodiments, $R_2$ is amino that can be further substituted with aryl. In some embodiments, $R_2$ is amino that can be further substituted with halo-aryl. In some embodiments, $R_2$ is methylamine that can be further substituted with aryl. In some embodiments, $R_2$ is methylaniline. In some embodiments, $R_2$ is ethyl amine that can be further substituted with five membered heteroaryl. In some embodiments, $R_2$ is ethyl amine that can be further substituted with triazoyl. In some embodiments, $R_2$ is propyl amine that can be further substituted with five or six membered, heterocycle, aryl, or heteroaryl or dimethyl amine. In some embodiments, $R_2$ is phenyl substituted with nitro group or an amino group. In some embodiments, $R_2$ is indolinyl. In some embodiments, $R_2$ is ethoxy that can be further substituted with methoxy. In some embodiments, $R_2$ is trifluoromethyl.

In some specific embodiments, $R_2$ is one of the following structures:

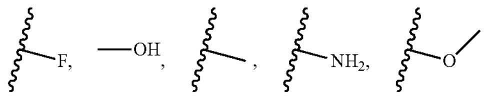

-continued

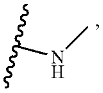, 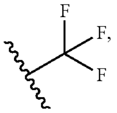 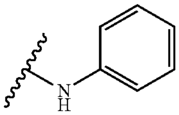,

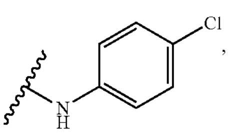, 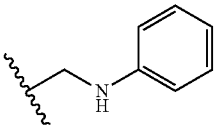,

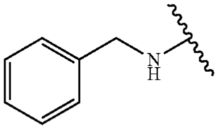, 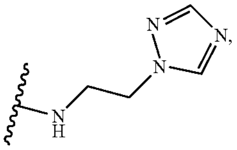

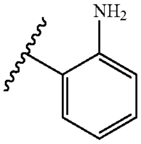, 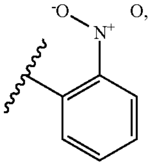 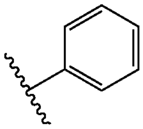,

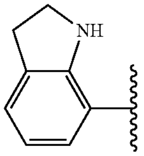, 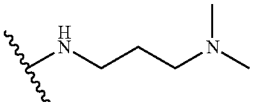,

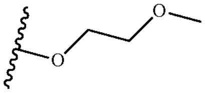, and

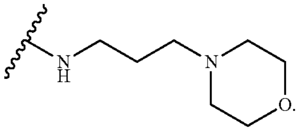

In some embodiments, $R_3$ is a —H, a halo, an oxo, a $C_{1-3}$ alkyl, a $C_{1-3}$ alkenyl, a $C_{1-3}$ alkoxy, a —$NR_aR_b$, a —$NH(CH_2)_{1-3}R_aR_b$, a 3-6 membered cycloalkyl, or a 5-6 membered aryl, wherein the $C_{1-3}$ alkyl, the $C_{1-3}$ alkenyl, the $C_{1-3}$ alkoxy, the —$NR_aR_b$, the —$NH(CH_2)_{1-3}R_aR_b$, the 3-6 membered cycloalkyl, or the 5-6 membered aryl can be further independently substituted with one to three $R_a$.

In some embodiments, $R_3$ is chloro. In some embodiments, $R_3$ is methyl. In some embodiments, $R_3$ is cyclopropanyl or cyclohexyl. In some embodiments, $R_3$ is tetrahydropyranyl. In some embodiments, $R_3$ is phenyl. In some embodiments, $R_3$ is oxy-phenyl. In some embodiments, $R_3$ is aminophenyl or aminopyridinyl. In some embodiments, $R_2$ is aminophenyl that can be further substituted with chloro and/or fluoro. In some embodiments, $R_3$ is ethylamine. In some embodiments, $R_3$ is ethoxyamino. In some embodiments, $R_3$ is butoxymethyl. In some embodiments, $R_3$ is aminoethyl or aminopropyl that can be further substituted with a five membered heteroaryl. In some embodiments, $R_3$ is aminoethyl or aminopropyl that can be further substituted with a trizoyl. In some embodiments, $R_3$ is aminoethyl or aminopropyl that can be further substituted with a methyl, a phenyl, dimethylamino, and/or triazoyl.

In some embodiments, $R_3$ is an aminomethyloxetanyl that can be further substituted with methyltriazoyl or dimethylethanamino. In some embodiments, $R_3$ is an aminoethyloxetanyl that can be further substituted with methyl and/or triazoyl. In some embodiments, $R_3$ is dimethyl-phenylpropanamidyl.

In some specific embodiments, $R_3$ is one of the following structures:

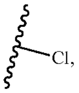 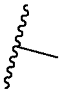, 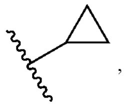, 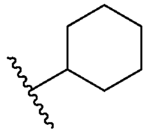,

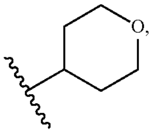 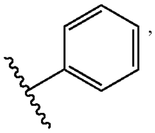, 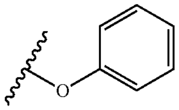,

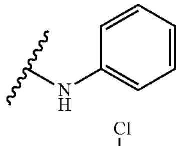, 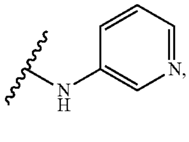

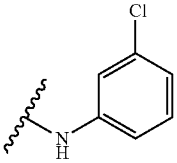, 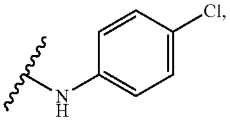

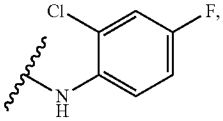 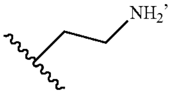

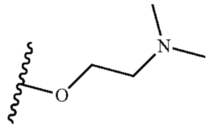, 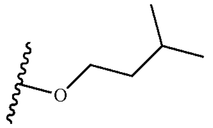,

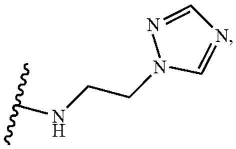 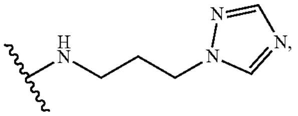

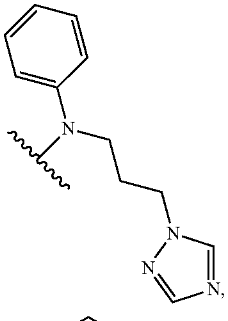 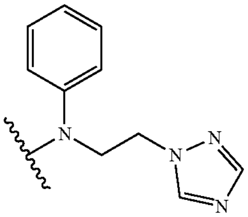,

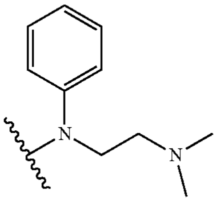, 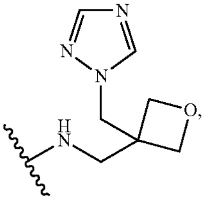

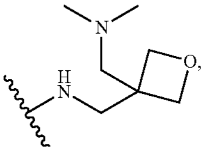, 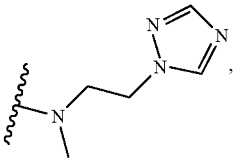, and

-continued

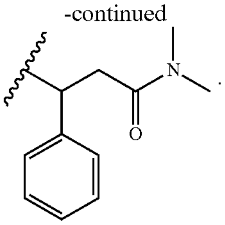

In some embodiments, $R_4$ is a —H, a halo, a $C_{1-3}$ alkyl, or a $C_{1-3}$ alkoxy, wherein the $C_{1-3}$ alkyl and the $C_{1-3}$ alkoxy can be further independently substituted with one to three $R_a$. In some embodiments, $R_4$ is fluoro or chloro. In some embodiments, $R_4$ is methyl. In some embodiments, $R_4$ is dimethylaminoethyl. In some embodiments, $R_4$ is dimethylaminoethoxy. In some embodiments, $R_4$ is selected from:

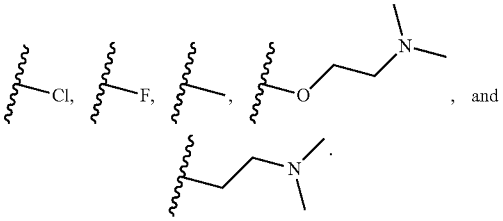

In some embodiments, $R_5$ is a —H or a halo. In some embodiments, $R_5$ is a halo. In some embodiments, $R_5$ is selected from:

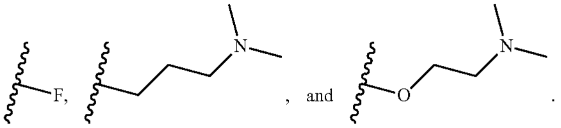

In some embodiments, $R_5$ is H or

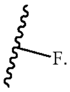

In some embodiments, $R_6$ is an oxo or a $C_{1-4}$ alkyl, where the $C_{1-4}$ alkyl can be further independently substituted with one to three $R_a$.

In some specific embodiments, $R_6$ is selected from:

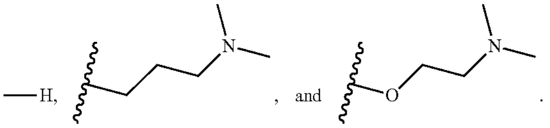

In some embodiments, $R_1$ and $R_2$ can come together to form a 5-6 membered heterocycle or a 5-6 membered aryl, wherein the 5-6 membered heterocycle and the 5-6 membered aryl can further be independently substituted with one to three $R_a$.

In some embodiments, $R_1$ and $R_2$ can come together to form one of:

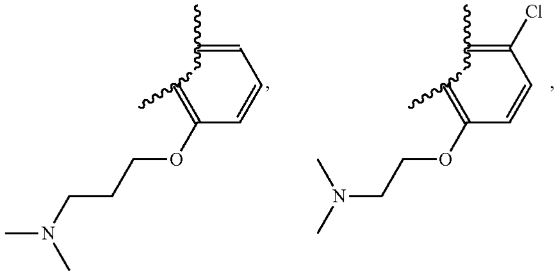

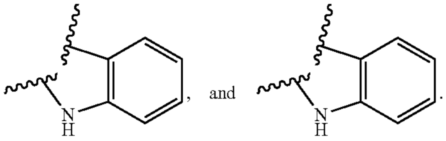

In some embodiments, $R_3$ and $R_4$ can come together to form a 5-6 membered heterocycl, wherein the 5-6 membered heterocycl can further be independently substituted with one to three $R_a$.

In some embodiments, $R_2$ and $R_3$ can come together to form one of:

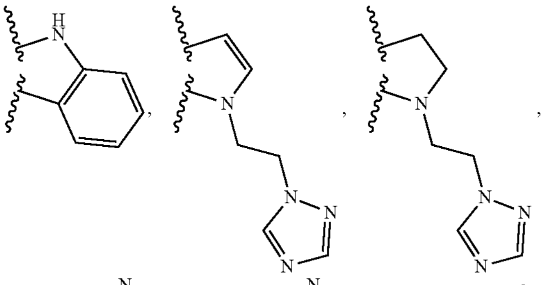

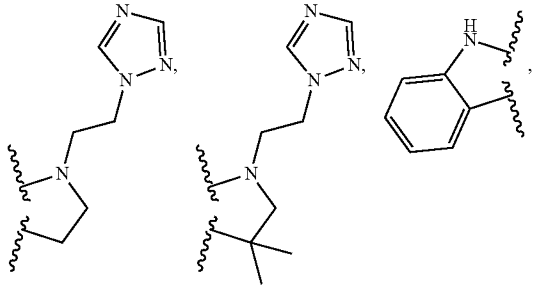

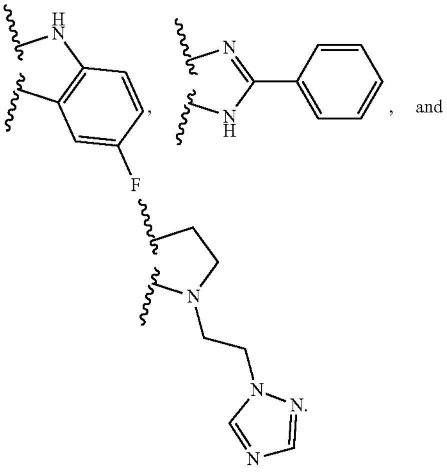

In some embodiments, $R_3$ and $R_4$ can come together to form:

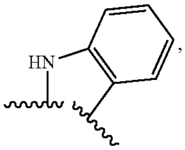,
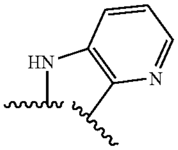
or
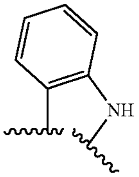.

In some embodiments, two $R_5$ are adjacent to each other, and the two $R_5$ can come together to form a 5-6 membered aryl, wherein the 5-6 membered aryl can further be independently substituted with one to three $R_a$.

In some embodiments, each $R_a$ and $R_b$ is independently a —H, a halo, an oxo, a hydroxy, a $C_{1-2}$ carboxyl, a $C_{1-3}$ alkyl, a $C_{1-3}$ alkoxy, a —$NH_2$, a —$NO_2$, a —$NR_xR_y$, a —$NR_x$, a 4-6 membered heterocycle, a 4-6 heterocycle, a 5-6 membered aryl, or a 5-6 membered heteroaryl, wherein the $C_{1-2}$ carboxyl, the $C_{1-3}$ alkyl, the $C_{1-3}$ alkoxy, the —$NH_2$, the —$NR_xR_y$, the —$NR_x$, the 4-6 membered heterocycle, the 4-6 heterocycle, the 5-6 membered aryl, and/or the 5-6 membered heteroaryl can further be independently substituted with one to three Rx.

In some embodiments, adjacent $R_a$ and/or $R_a$/$R_b$ groups can further come together to form a 5-6 membered aryl or a 5-6 membered heteroaryl, wherein the 5-6 membered aryl and/or the 5-6 membered heteroaryl can be independently substituted with one to three $R_x$ groups.

In some embodiments, each $R_x$ and/or $R_y$ is independently a —H, a halo, a hydroxyl, an oxo, a $C_{1-3}$ alkyl, a —$NR_{x1}R_{x2}$, a —$CH_2NR_{x1}R_{x2}$, a 4-6 membered heterocycle, a 5-6 membered aryl, or a 5-6 membered heteroaryl, wherein the $C_{1-3}$ alkyl, the —$NR_{x2}R_{x2}$, the —$CH_2NR_{x1}R_{x2}$, the 4-6 membered heterocycle, the 5-6 membered aryl, and/or the 5-6 membered heteroaryl can further be independently substituted with one to three $R_{x1}$.

In some embodiments, wherein when two $R_x$ are bonded to the same atom, the two $R_x$ can come together to form a 4-6 membered heterocycle, where the 4-6 membered heterocycle can be further independently substituted with one to three $R_{x1}$.

In some embodiments, each $R_{x1}$ and $R_{x2}$ is independently a —H, a halo, a $C_{1-2}$ alkyl, a $C_{1-3}$ alkoxy, or a 5-6 membered heteroaryl. In some embodiments, each $R_{x1}$ and $R_{x2}$ is independently a —H or a $C_{1-3}$ alky. In some embodiments, each $R_{x1}$ and $R_{x2}$ is independently a $C_{1-3}$ alky. In some embodiments, each $R_{x1}$ and $R_{x2}$ is independently a $C_{1-2}$ alky.

In some embodiments of Formula I, the compounds are selected from:

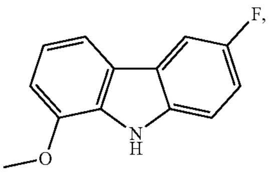

-continued

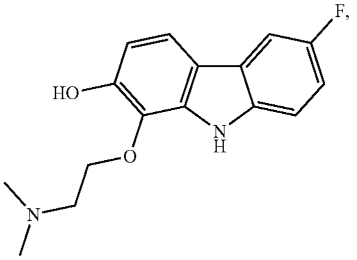

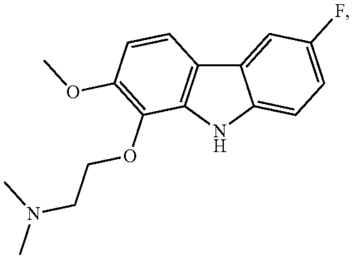

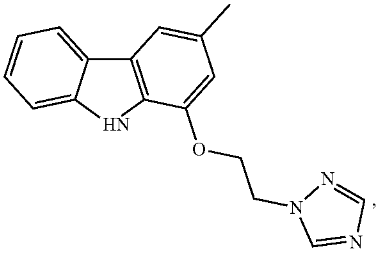

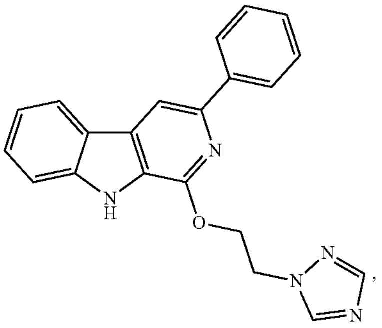

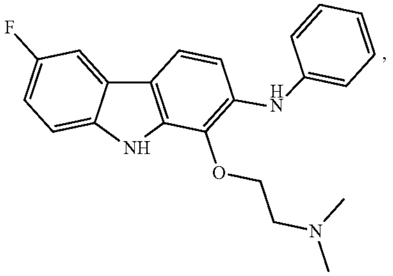

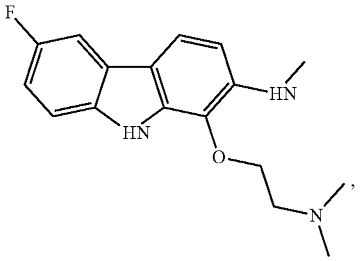

-continued
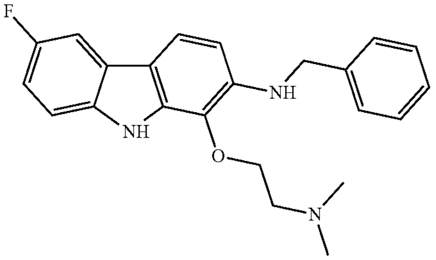,
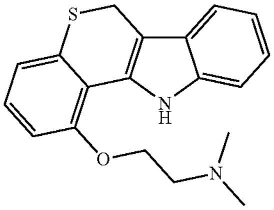,
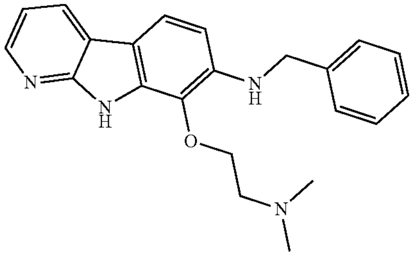,
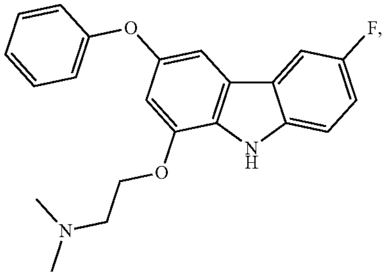
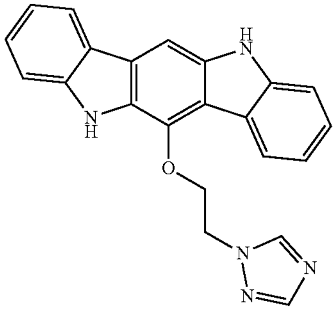,
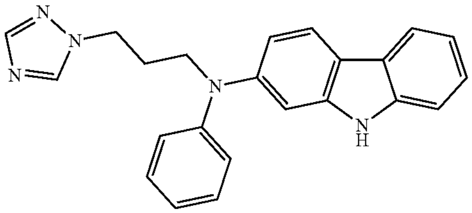,
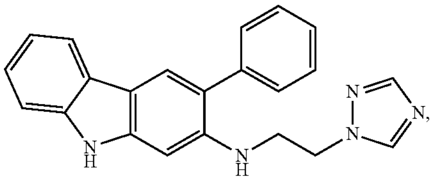
-continued
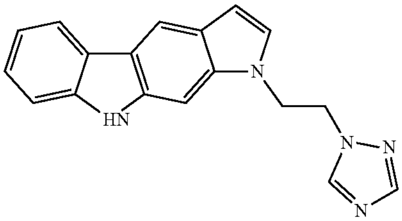,
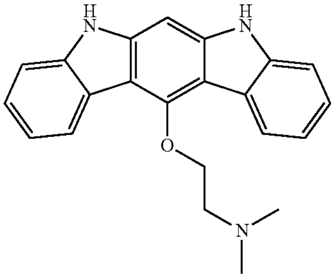,
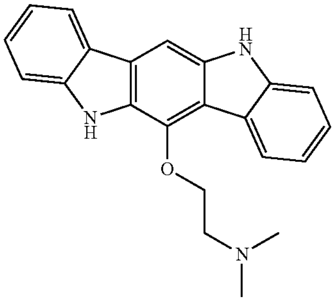,
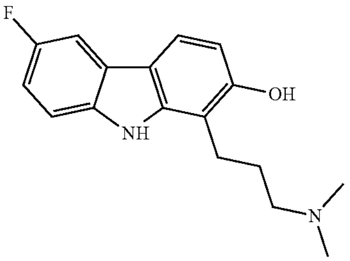,
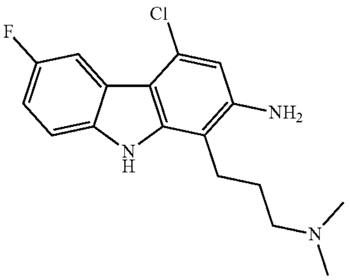,
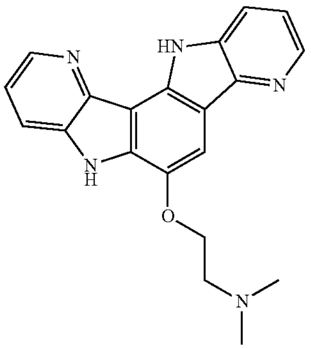,

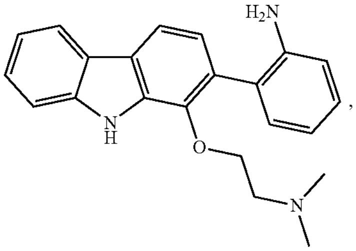
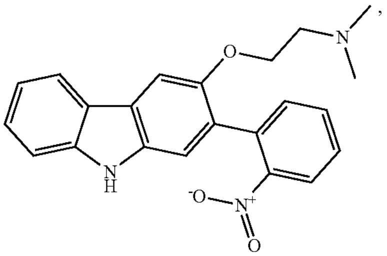
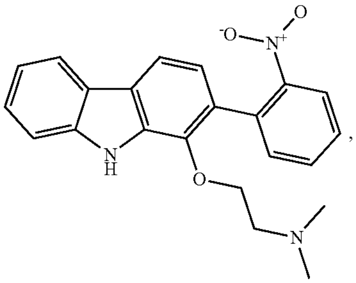
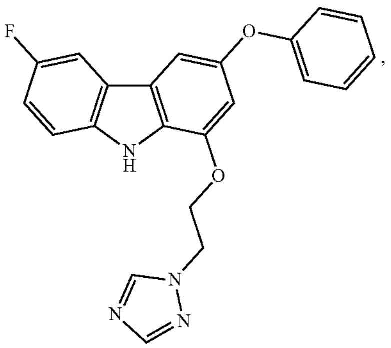
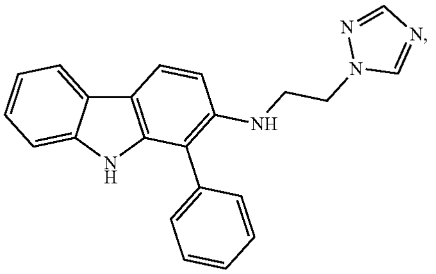
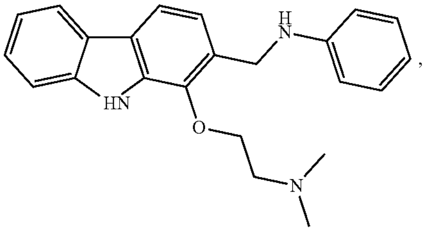
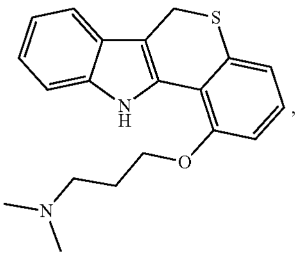
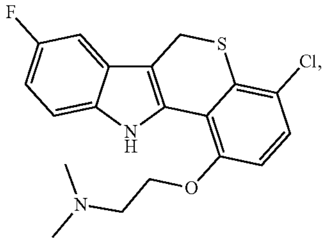
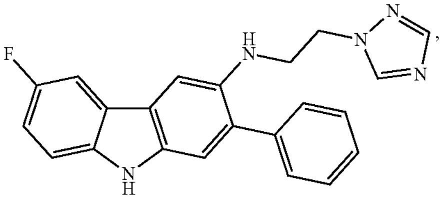
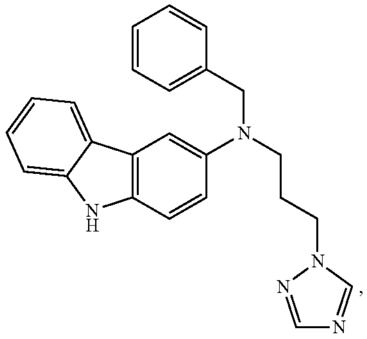
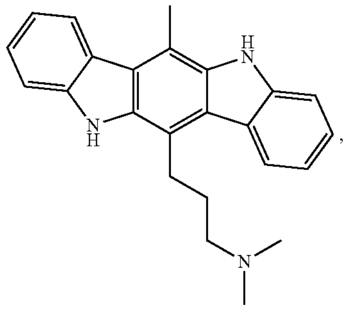
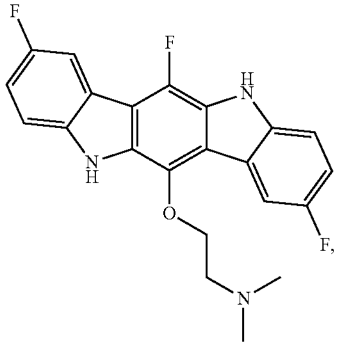

-continued
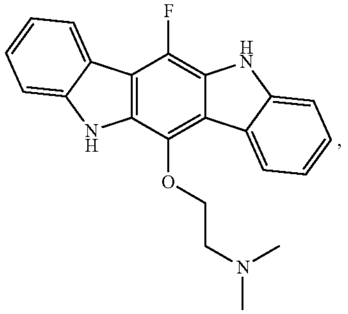
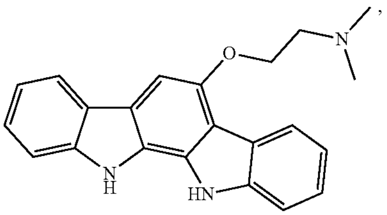
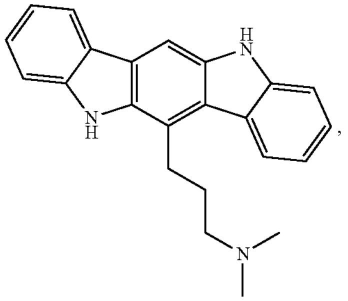
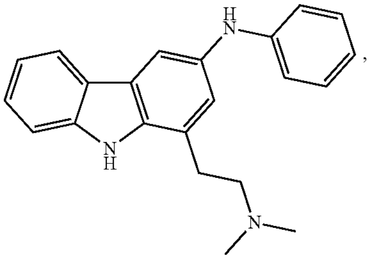
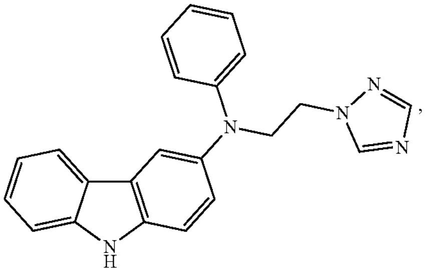
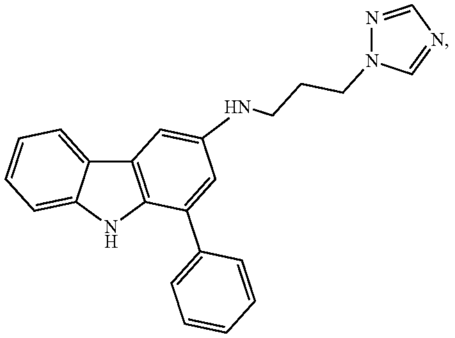
-continued
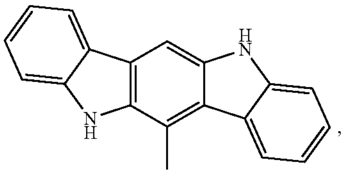
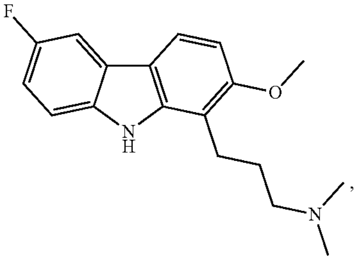
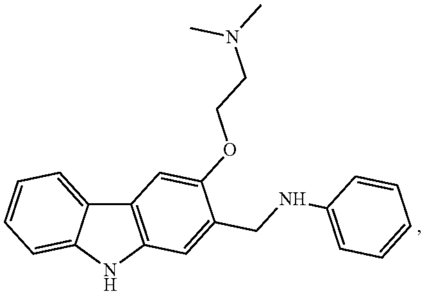
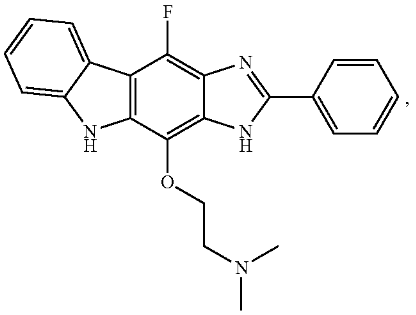
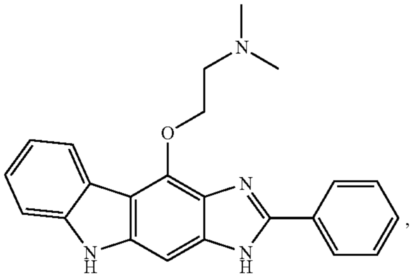
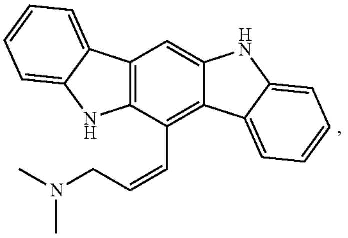

-continued
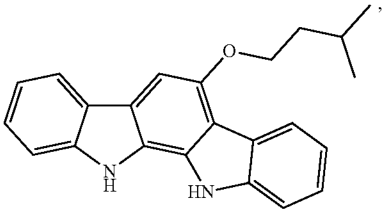
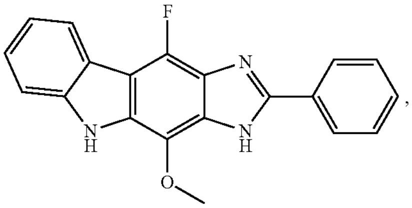
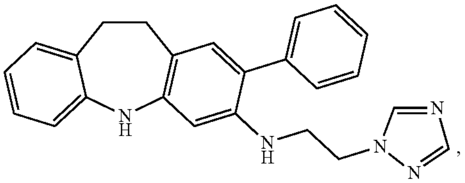
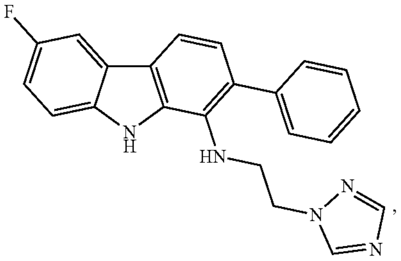
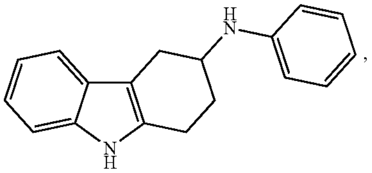
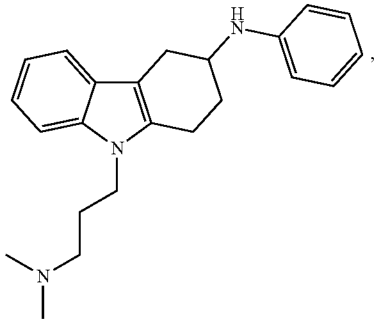
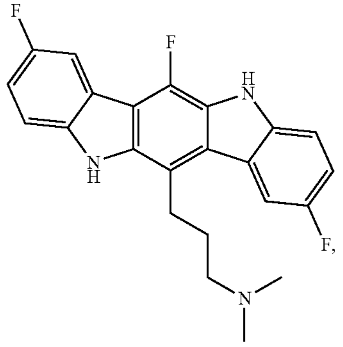
-continued
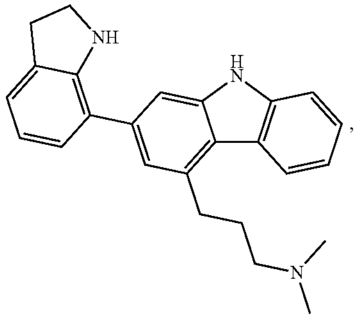
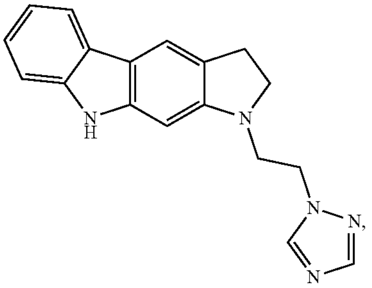
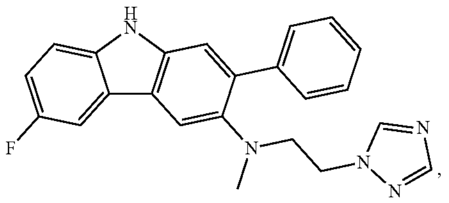
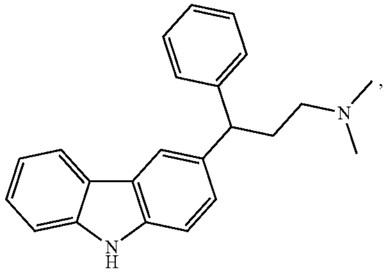
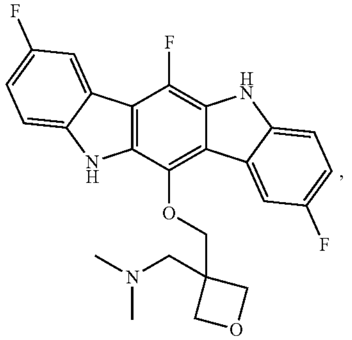
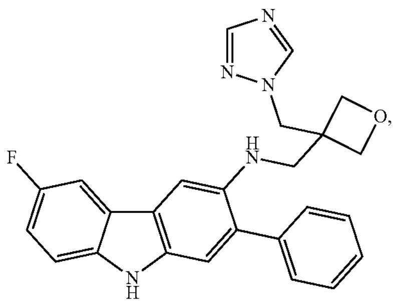

-continued
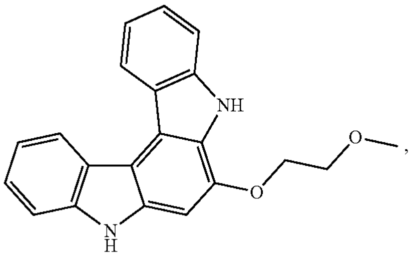
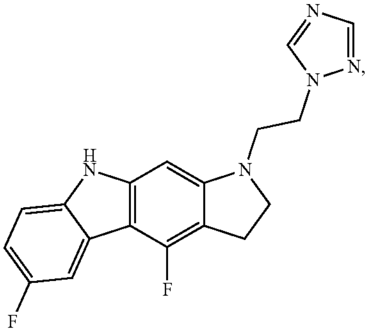
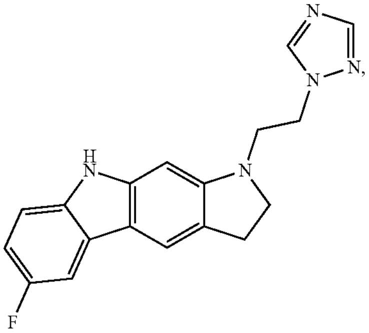
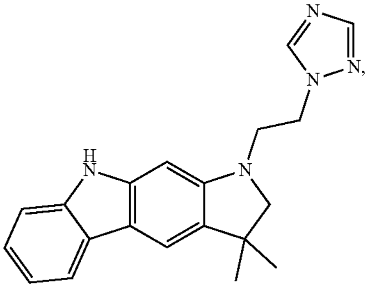
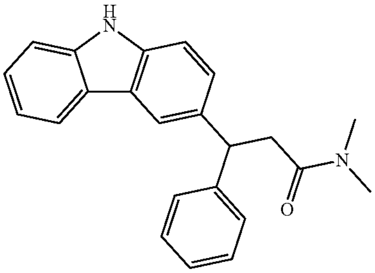
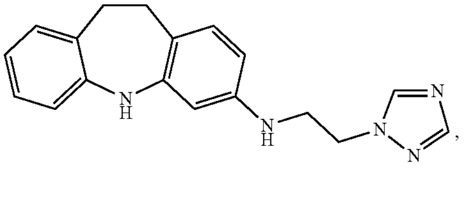
-continued
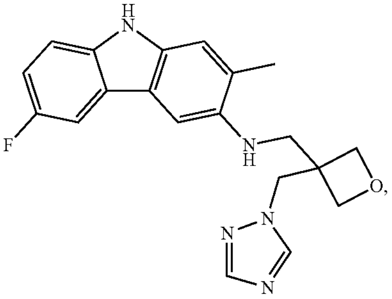
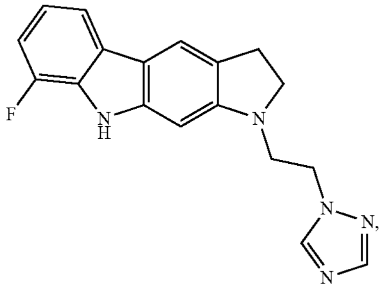
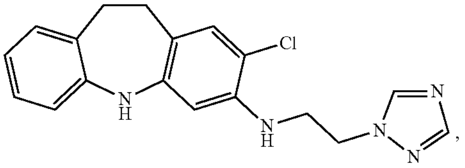
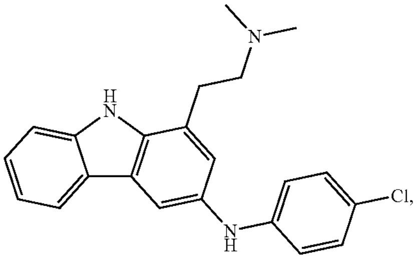
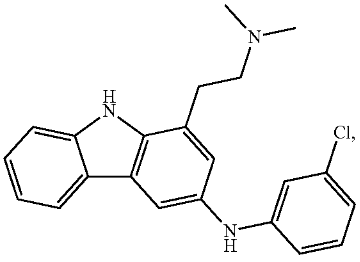
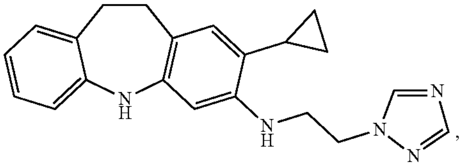
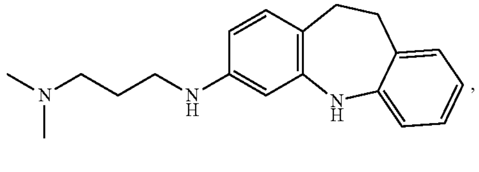

-continued

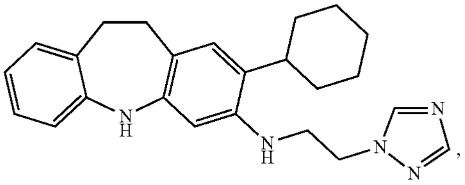

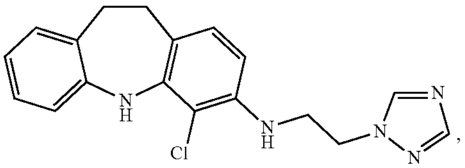

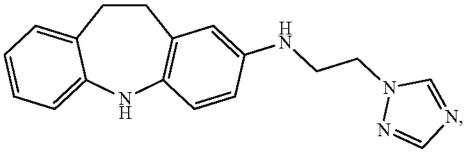

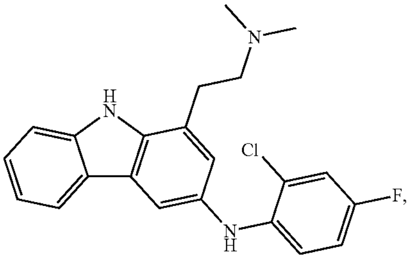

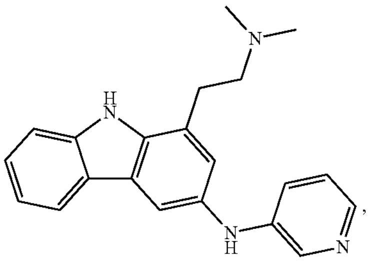

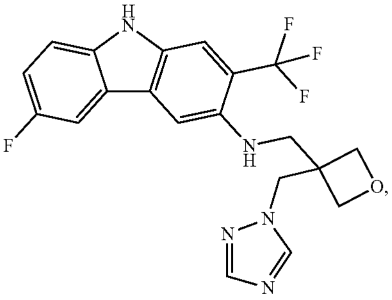

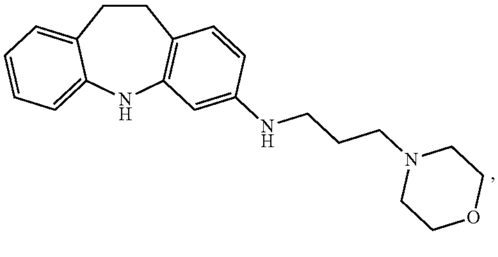

-continued

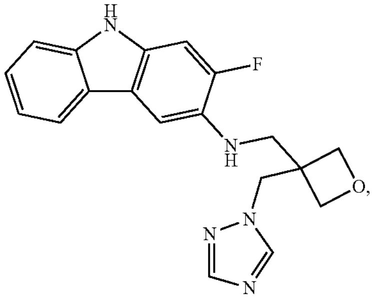

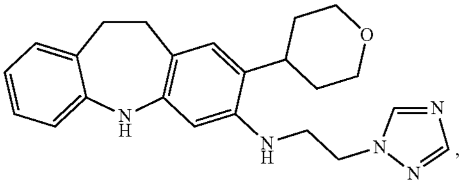

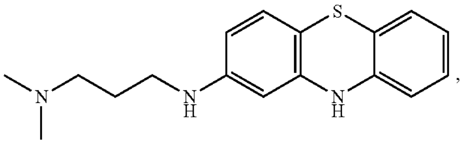

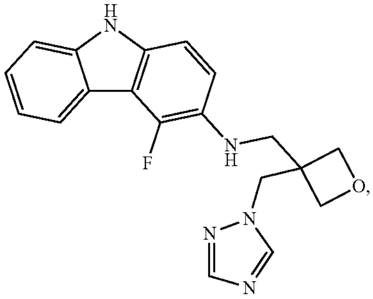

and pharmaceutically acceptable salts thereof.

In some embodiments, the compounds disclosed herein have the structure of Formula IA, wherein Formula IA is:

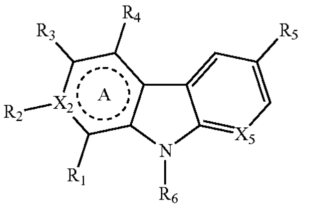

In some embodiments, A is an aromatic ring or a cycloalkyl. In some embodiments, A is a phenyl. In some embodiments, A can be cyclohexyl. In some embodiments, A can be a pyridinyl. In some embodiments, A can be a piperidinyl.

In some embodiments, $X_2$ and $X_5$ are each independently C or N.

In some embodiments, $R_1$ is a —H, a $C_{1-3}$ alkyl, a $C_{1-3}$ alkoxy, or a 5-6 membered aryl, wherein the $C_{1-5}$ alkyl, the $C_{1-3}$ alkoxy, or the 5-6 membered aryl can be further independently substituted with one to three $R_a$.

In some embodiments, $R_1$ is selected from:

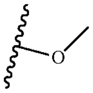,
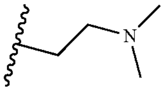,
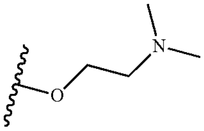,
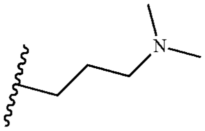,
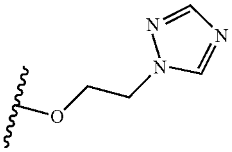,
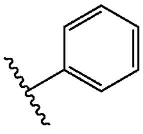, and
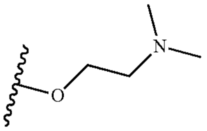.

In some embodiments, $R_2$ is a —H, a halo, an oxo, a hydroxyl, a $C_{1-3}$ alkyl, a $C_{1-3}$ alkoxy, a $C_{1-3}$ haloalkyl, a —$NR_aR_b$, a 5-6 membered aryl, or a 5-10 heterocycl aryl, wherein the $C_{1-3}$ alkyl, the $C_{1-3}$ alkoxy, the $C_{1-3}$haloalkyl, the —$NR_aR_b$, the 5-6 membered aryl, or the 5-10 heterocycl aryl can be further independently substituted with one to three $R_x$ and/or $R_y$.

In some specific embodiments, $R_2$ is selected from:

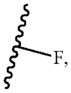, —OH, 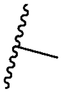, 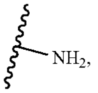, 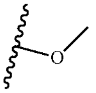,
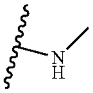, 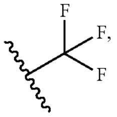, 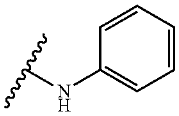,
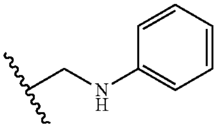, 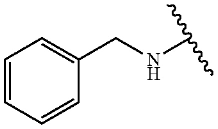,
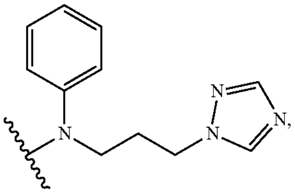 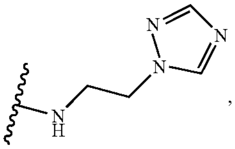,
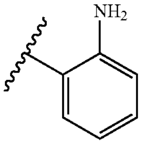, 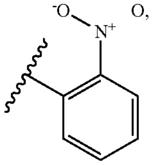, and 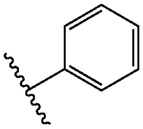.

In some embodiments, $R_3$ is a —H, an oxo, a $C_{1-3}$ alkyl, a $C_{1-3}$ alkoxy, a —$NR_aR_b$, a —$NH(CH_2)_{1-3}R_aR_b$, a 3-6 membered cycloalkyl, or a 5-6 membered aryl, wherein the $C_{1-3}$ alkyl, the $C_{1-3}$ alkoxy, the —$NR_aR_b$, the —$NH(CH_2)_{1-3}R_aR_b$, the 3-6 membered cycloalkyl, or the 5-6 membered aryl can be further independently substituted with one to three $R_x$ and/or $R_y$.

In some specific embodiments, $R_3$ is selected from:

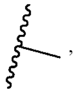, 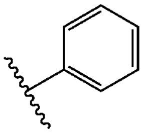, 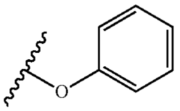,
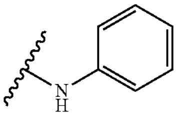, 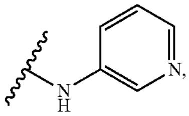
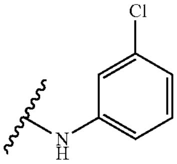, 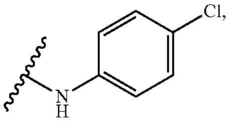
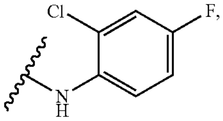 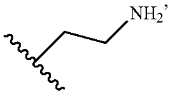
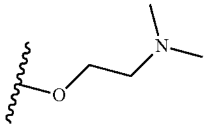, 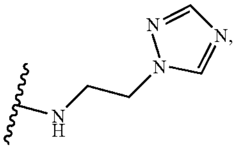
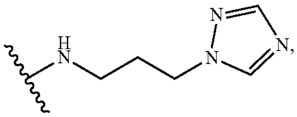 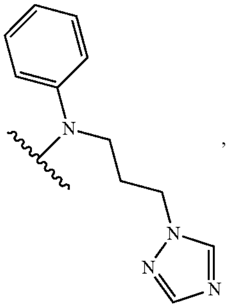,
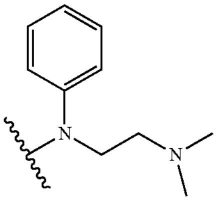, 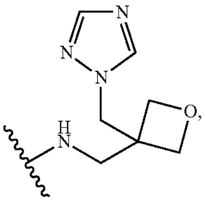
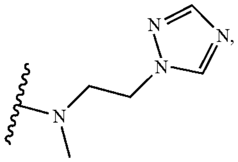 and 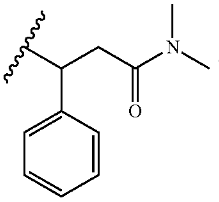.

In some embodiments, $R_4$ is a —H or a halo. In some embodiments, $R_4$ is a hydrogen. In some embodiments, $R_4$ is fluoro.

In some embodiments, $R_5$ is a —H or a halo. In some embodiments, $R_5$ is a hydrogen. In some embodiments, $R_5$ is fluoro.

In some embodiments, $R_6$ is a —H, or a $C_{1-4}$ alkyl, where the $C_{1-4}$ alkyl is further independently substituted with one to three $R_a$.

In some specific embodiments, $R_6$ is dimethylaminopropyl.

In some embodiments, each $R_a$ and $R_b$ is independently a —H, a $C_{1-3}$ alkyl, a —$NH_2$, a —$NR_xR_y$, a 5-6 membered aryl, or a 5-6 membered heteroaryl, wherein the $C_{1-3}$ alkyl, the —$NR_xR_y$, the 5-6 membered aryl, and/or the 5-6 membered heteroaryl can further be independently substituted with one to three $R_x$.

In some embodiments, each $R_x$ and and $R_y$ is independently a —H, a halo, an oxo, $C_{1-3}$ alkyl, dimethylamino, —$NO_2$, or a five-six membered heteroaryl. In some embodiments, the $C_{1-3}$ alkyl and/or the 5-6 membered heteroaryl can be further independently substituted with one to three $R_{x1}$. In some embodiments, each $R_{x1}$ is independently a —H, a halo, a $C_{1-2}$ alkyl, a $C_{1-3}$ alkoxy, or a 5-6 membered heteroaryl.

In some embodiments of Formula IA, the compounds are:

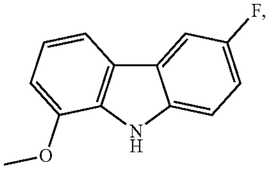

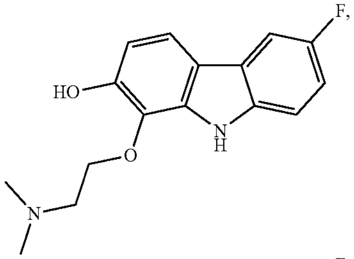

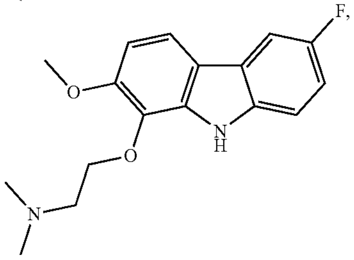

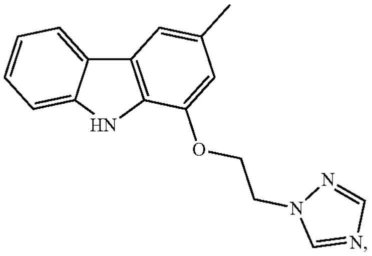

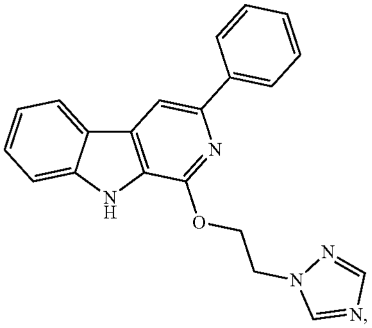

-continued

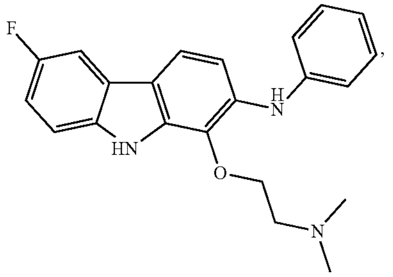

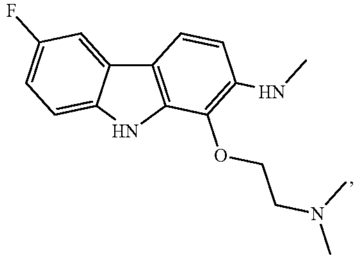

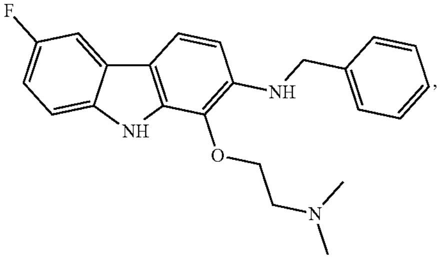

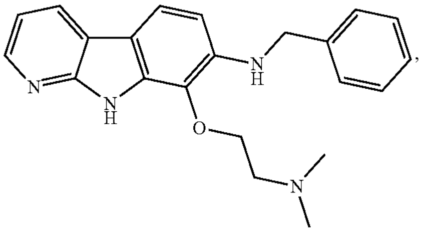

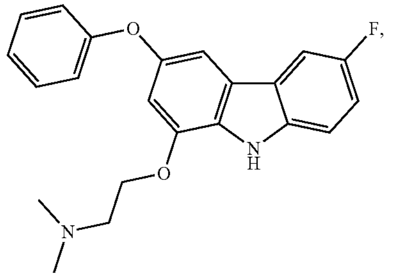

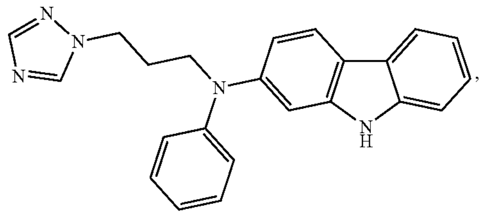

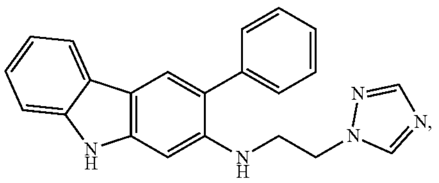

-continued
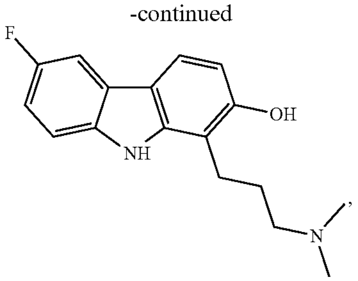
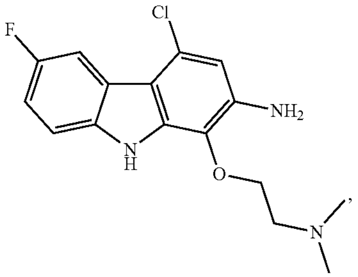
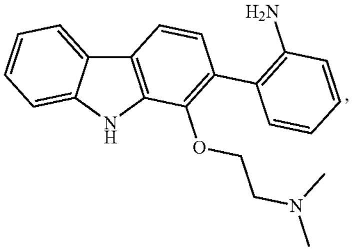
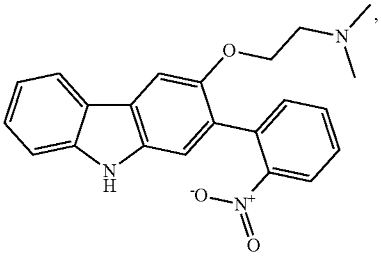
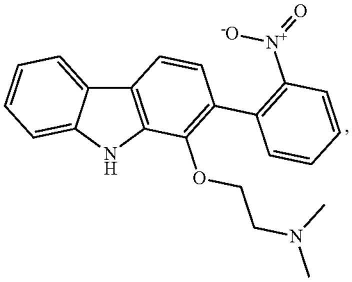
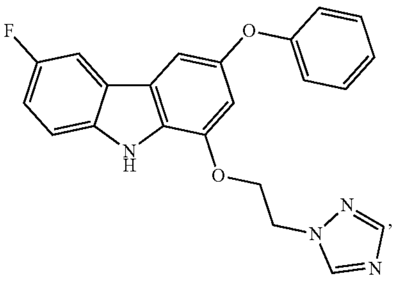
-continued
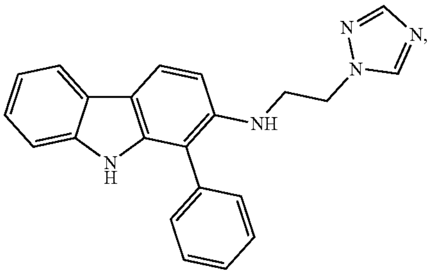
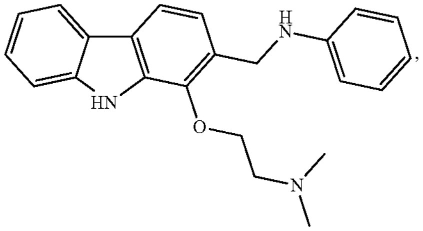
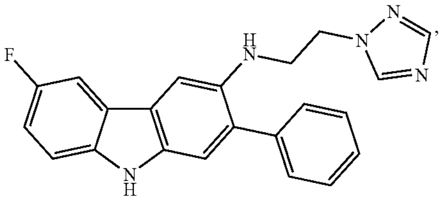
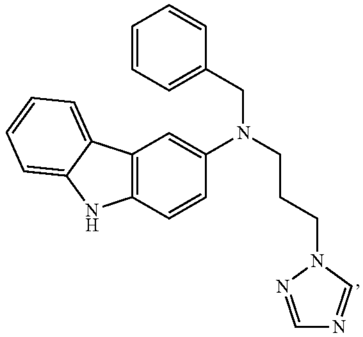
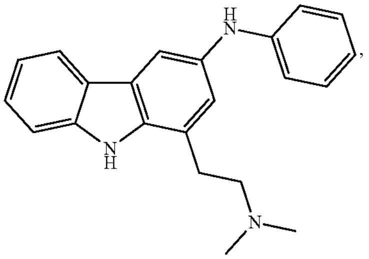
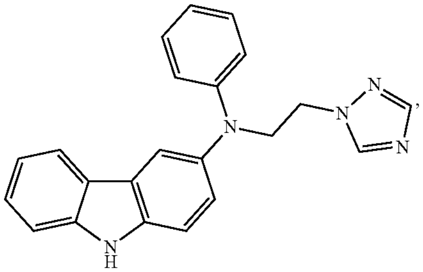

-continued
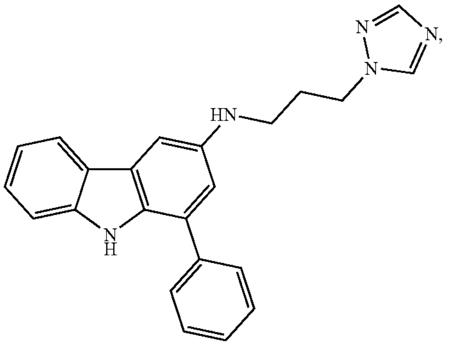
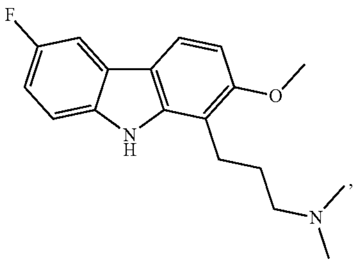
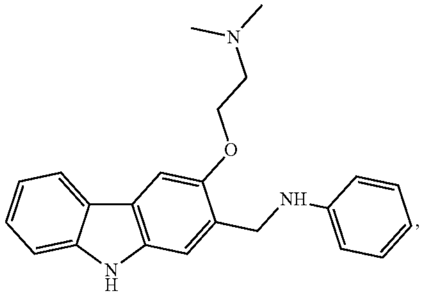
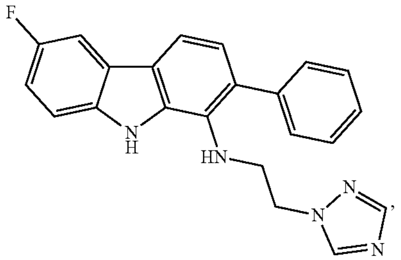
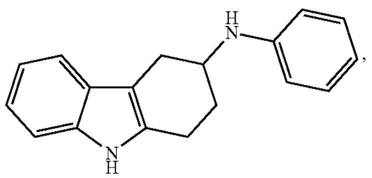
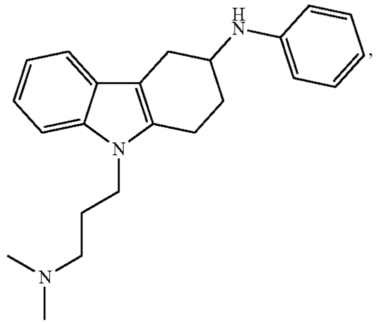
-continued
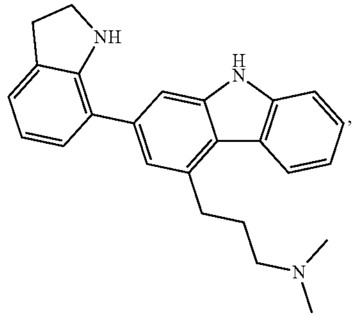
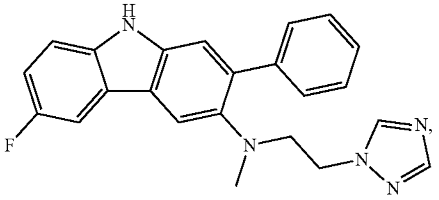
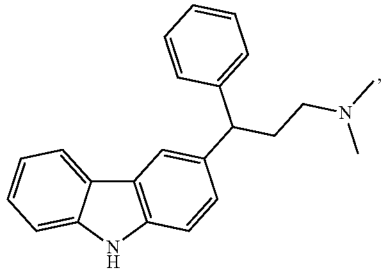
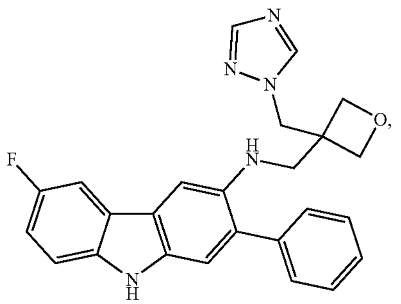
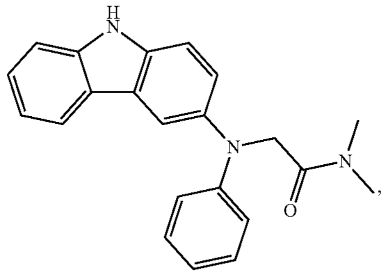
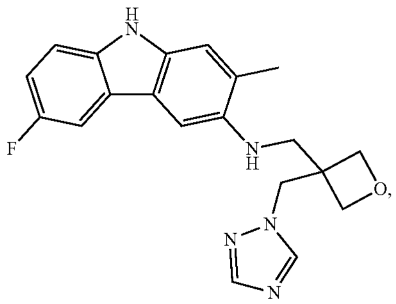

-continued

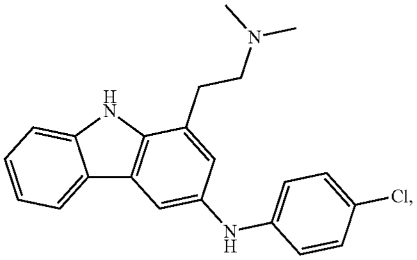

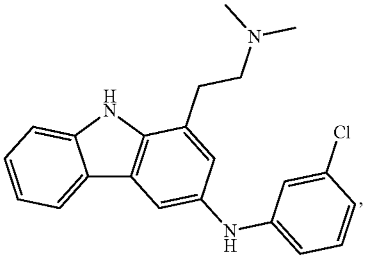

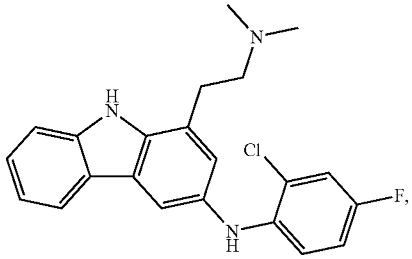

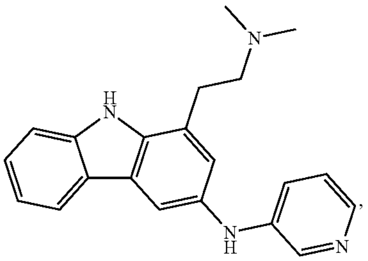

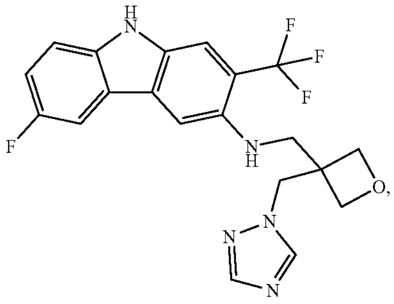

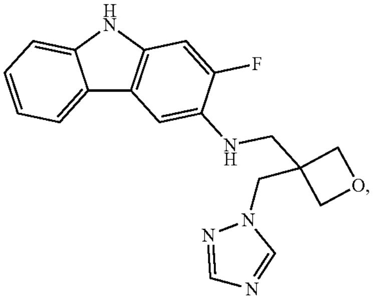

-continued

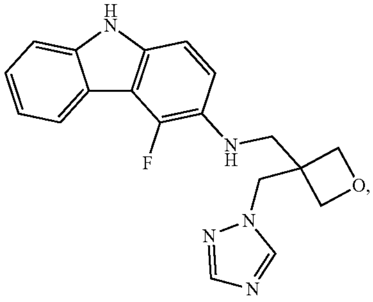

and pharmaceutically acceptable salts thereof.

In some embodiments, the compounds disclosed herein have the structure of Formula IB, wherein Formula IB is:

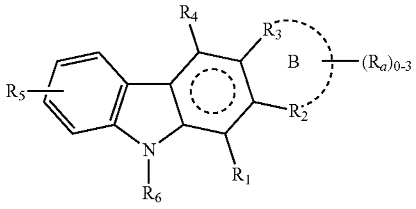

In some embodiments of Formula IB, $R_1$ is a —H, a $C_{1-3}$ alkyl, or a $C_{1-3}$ alkoxy, wherein the $C_{1-5}$ alkyl, or the $C_{1-3}$ alkoxy can be further independently substituted with one to three $R_a$.

In some embodiments, $R_1$ is selected from:

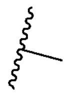
,
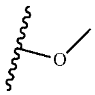
,
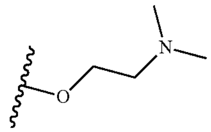
,
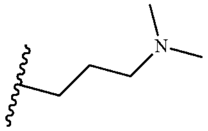
,
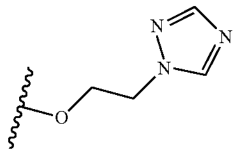
,
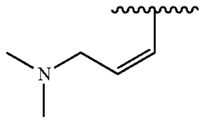
, and
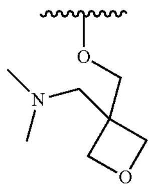
.

In some embodiments, $R_2$ and $R_3$ come together to form B, wherein B is a 5-6 membered heterocycle or a 7-10 membered cycloalkyl aryl, wherein the 5-6 membered heterocycle, or the 7-10 membered cycloalkyl aryl can further be independently substituted with one to three $R_a$.

In some embodiments, $R_2$ and $R_3$ can come together to form B, where B has one of the following structures:

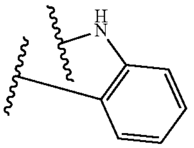,
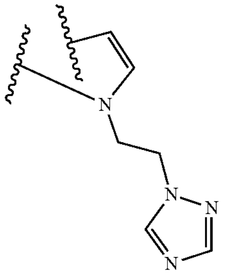,
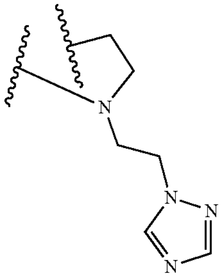,
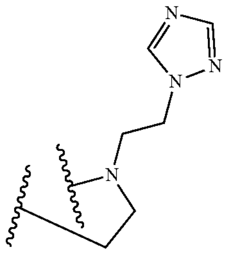,
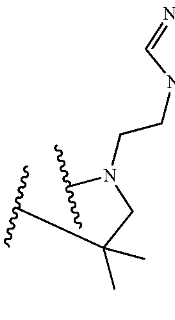,
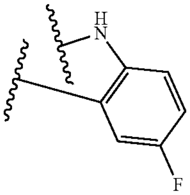, or
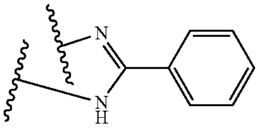.

In some embodiments, $R_4$ is a —H, a halo, a $C_{1-3}$ alkyl, or a $C_{1-3}$ alkoxy, wherein the $C_{1-3}$ alkyl or the $C_{1-3}$ alkoxy can be further independently substituted with one to three $R_a$.

In some embodiments, $R_4$ is selected from:

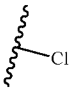,
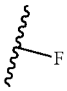,
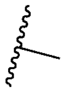,
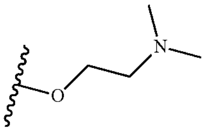, and
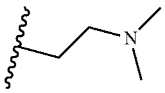.

In some embodiments, $R_5$ is a —H or a halo. In some embodiments, $R_5$ is fluoro.

In some embodiments, $R_6$ is an oxo or a $C_{1-4}$ alkyl, where the $C_{1-4}$ alkyl can be further independently substituted with one to three $R_a$.

In some embodiments, $R_6$ is selected from: —H and

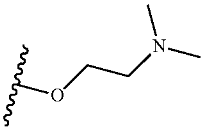.

In some embodiments of Formula IB, each $R_a$ is independently a $C_{1-3}$ alkyl, a $C_{1-3}$ alkenyl, a $—NR_xR_y$, a 4-6 membered heterocycle, a 5-6 membered aryl, or a 5-6 membered heteroaryl, wherein the $C_{1-3}$ alkyl, the $C_{1-3}$ alkenyl, the $—NR_xR_y$, the 4-6 membered heterocycle, the 5-6 membered aryl, and/or the 5-6 membered heteroaryl can further be independently substituted with one to three $R_x$.

In some embodiments, where there are two adjacent and independent $R_a$ groups, the $R_a$ groups can further come together to form a 4-6 membered heterocycle and/or a 5-6 membered aryl, wherein the 4-6 membered heterocycle and/or the 5-6 membered aryl can be independently substituted with one to three $R_x$ groups.

In some embodiments, each $R_x$ and $R_y$ is independently a —H, a halo, a $C_{1-3}$ alkyl, or a 5-6 membered heteroaryl, wherein the $C_{1-3}$ alkyl and/or the 5-6 membered heteroaryl can further be independently substituted with one to three $R_{x1}$.

In some embodiments, wherein when two $R_x$ are bonded to the same atom, the two $R_x$ groups can come together to form a 4-6 membered heterocycle where the 4-6 membered heterocycle can be further independently substituted with one to three $R_{x1}$.

In some embodiments of Formula IB, each $R_{x1}$ is independently a —H, a halo, a $C_{1-2}$ alkyl, a $C_{1-3}$ alkoxy, or a 5-6 membered heteroaryl.

In some embodiments of Formula IB, $R_1$ is selected from:

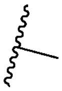,
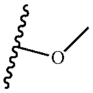,
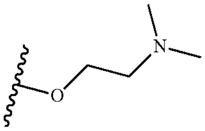,
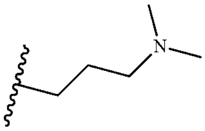,
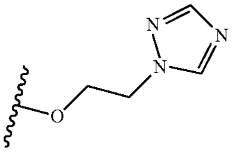,
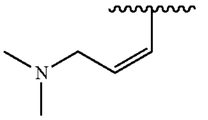, and
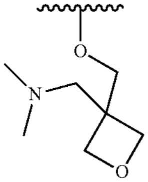.

In some embodiments, where $R_2$ and $R_3$ come together to form B, B is selected from one of the following structures:

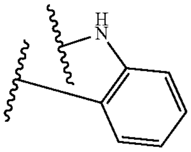,
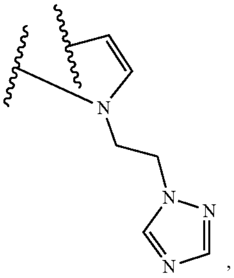,
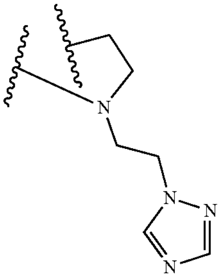,
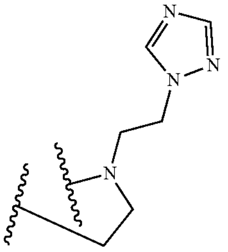,
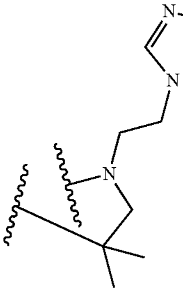,
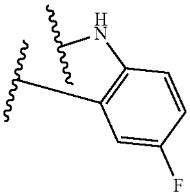, and
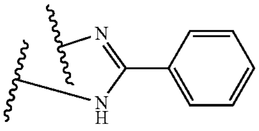.
In some embodiments, $R_4$ is selected from:
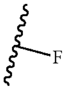, 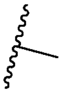, and 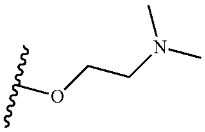,
In some embodiments, $R_5$ is —H or —F. In some embodiments, $R_5$ is a hydrogen atom. In some embodiments, $R_5$ is fluoro.
In some embodiment, $R_6$ is —H, or
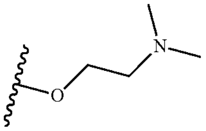.
In some embodiments, $R_6$ is a hydrogen. In some embodiments, $R_6$ is
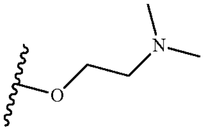.
In some embodiments, compounds having the structure of Formula IB are:
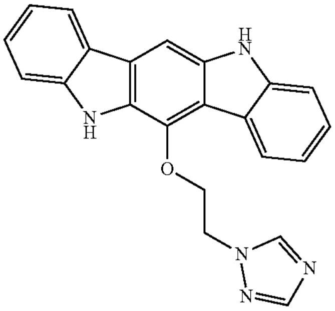,
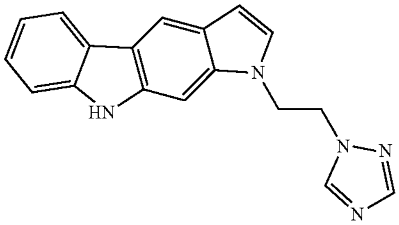,
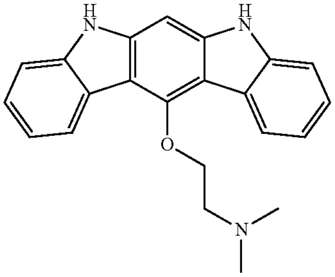,
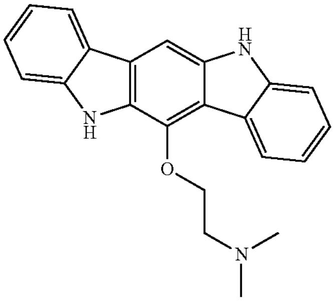,
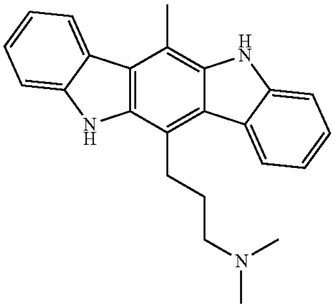, -continued
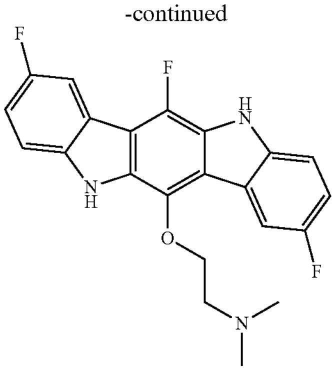
,
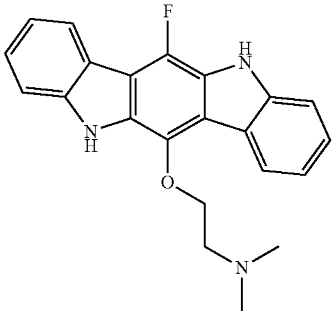
,
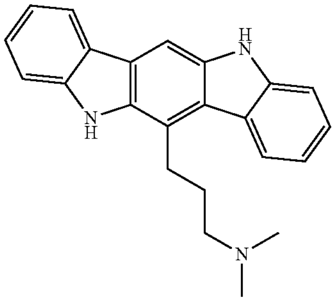
,
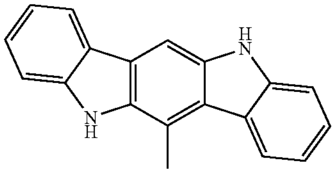
,
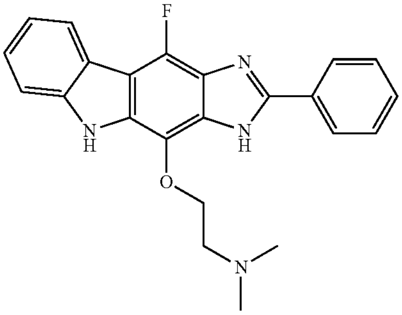
,
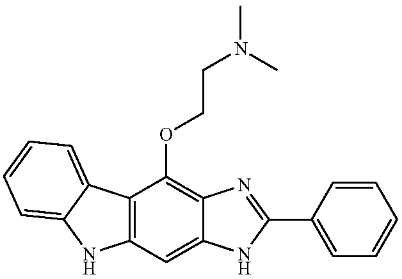
,
-continued
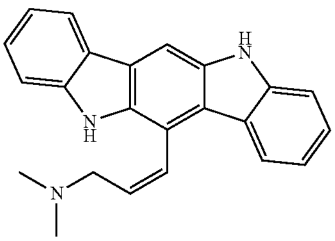
,
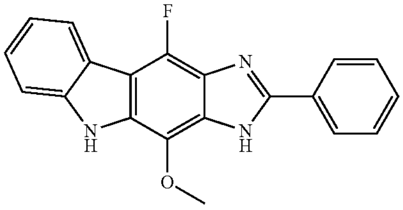
,
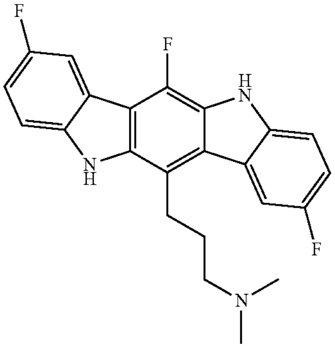
,
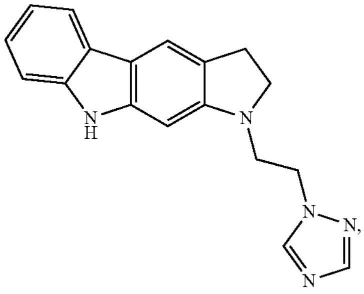
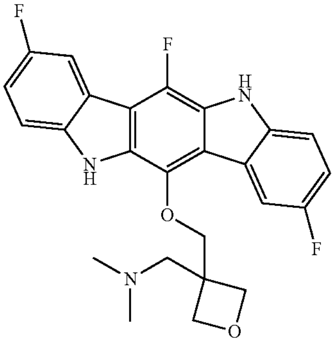
, -continued

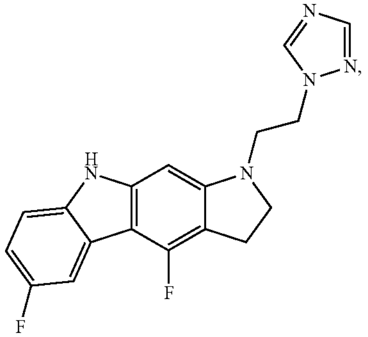

,

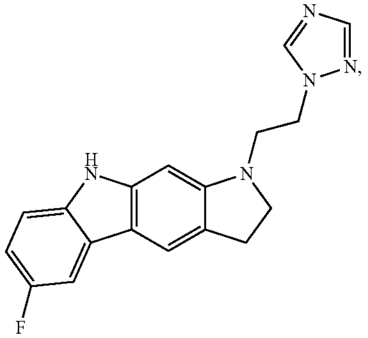

,

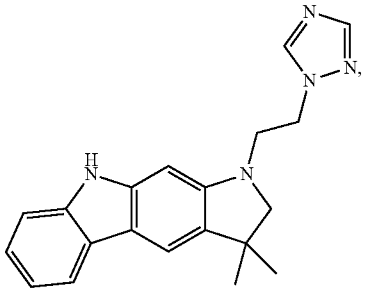

,

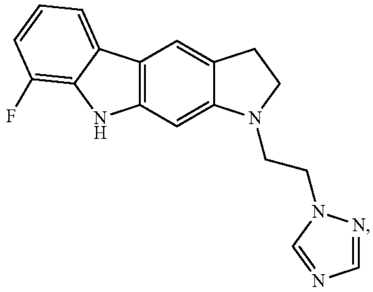

, and pharmaceutically acceptable salts thereof.

In some embodiments, the compounds disclosed herein have the structure of Formula IC, wherein Formula IC is:

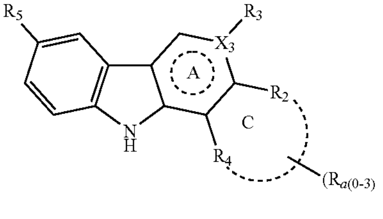

In some embodiments, A is a 6 membered heterocycle or a 6 membered aryl. In some embodiments, A is a tetrahydrothiopyranyl. In some embodiments, A is a dihydrothiopyranyl. In some embodiments, A is a phenyl.

In some embodiments, $X_3$ can be C or S.

In some embodiments, $R_1$ and $R_2$ come together to form C, wherein C can be a 5-6 membered aryl or a 5-6 membered heterocycle and wherein the 5-6 membered aryl or the 5-6 membered heterocycle can be further independently substituted with one to three Ra groups. In some embodiments, C is a phenyl. In some specific embodiments, C is pyrrolidinyl.

In some embodiments, $R_3$ is a —H or a $C_{1-3}$ alkoxy, wherein the $C_{1-3}$ alkoxy can be further independently substituted with one to three $R_a$.

In some embodiments, $R_3$ is

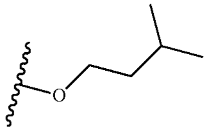

.

In some embodiments, $R_3$ is

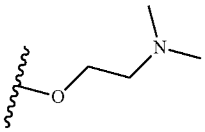

.

In some embodiments, $R_5$ is a —H or a halo. In some embodiments, $R_5$ is fluoro.

In some embodiments of Formula IC, $R_a$ is a —H or a $C_{1-3}$ alkoxy, wherein the $C_{1-3}$ alkoxy can be further substituted with an $R_x$ group, or two $R_a$ groups bonded to adjacent atoms can further come together to form a 5-6 membered aryl. In some embodiments, two $R_a$ groups bonded to adjacent atoms can further come together to form a phenyl.

In some embodiments, each $R_x$ is independently a —H or a —$NR_{x1}R_{x2}$. In some embodiments, each $R_{x1}$ and $R_{x2}$ is independently a —H or a $C_{1-2}$ alkyl. In some embodiments, each $R_{x1}$ and $R_{x2}$ is independently a dimethylamino.

In some embodiments, the ring formed by $R_1$ and $R_2$ (e.g., C) is:

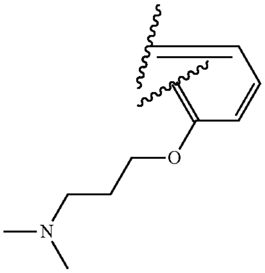

,

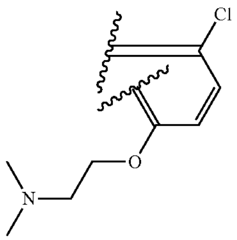

,

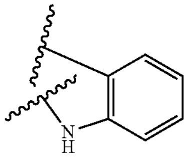

, or

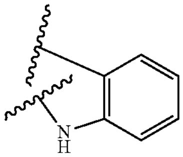

.

In some embodiments, $R_3$ is:

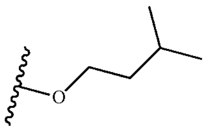

or

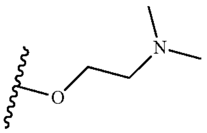

.

In some embodiments, $R_5$ is —H or —F.

In some embodiments, compounds having the structure of Formula IC are:

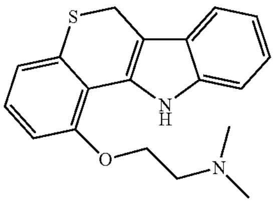

,

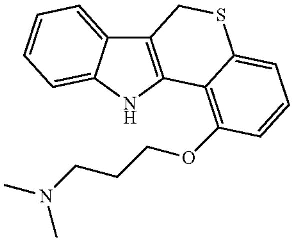

,

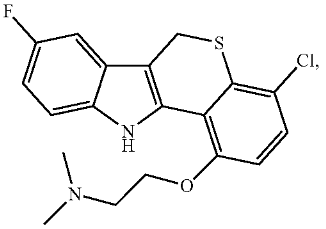

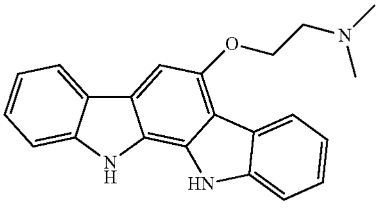

,

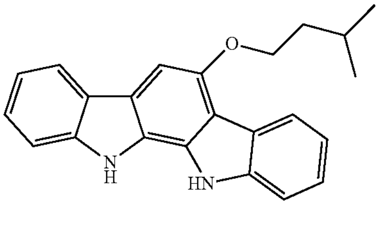

, and pharmaceutically acceptable salts thereof.

In some embodiments, the compounds disclosed herein have the structure of Formula ID, wherein Formula ID is:

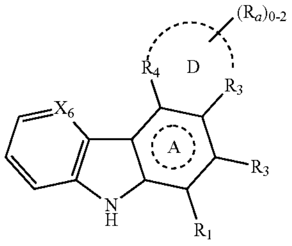

In some embodiments, A is a 6 membered heterocycle or a 6 membered aryl.

In some embodiments, $X_6$ can be C or N.

In some embodiments, $R_1$ is a H or a $C_{1-3}$ alkoxy, wherein the $C_{1-3}$ alkoxy can further be substituted with $R_a$.

In some embodiments, $R_2$ is a H or a $C_{1-3}$ alkoxy, wherein the $C_{1-3}$ alkoxy can further be substituted with $R_a$.

In some embodiments, $R_4$ and $R_3$ can come together to form D, where D is a 5 membered heterocycle, and wherein D can further be independently substituted with up to two $R_a$.

In some embodiments, each $R_a$ is independently a $C_{1-3}$ alkyl, $C_{1-3}$ alkenyl, or a —$NR_xR_y$, wherein the $C_{1-3}$ alkyl and/or the $C_{1-3}$ alkenyl can be further substituted with up to two $R_x$. In some embodiments, two $R_a$ groups bonded to adjacent atoms can further come together to form a 5-6 membered aryl or a 5-6 membered heteroaryl.

In some embodiments, each $R_x$ and $R_y$ is independently a —H or a $C_{1-3}$ alkyl.

In some embodiments, the ring formed by $R_3$ and $R_4$ (e.g., ring D) is

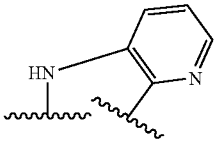

or

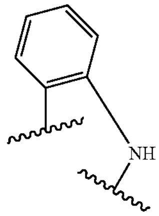

.

In some embodiments, $R_1$ is

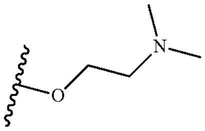

.

In some embodiments, $R_2$ is

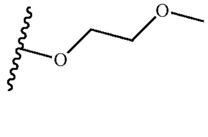

.

In some embodiments, the compound of Formula ID has the structure:

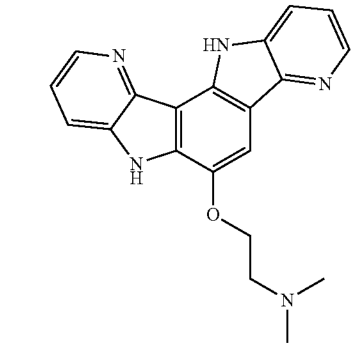,

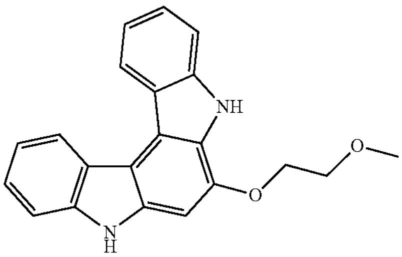, and pharmaceutically acceptable salts thereof.

In some embodiments, the compounds disclosed herein have the structure of Formula IE, wherein Formula IE is:

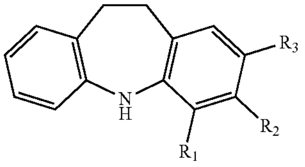

In some embodiments, $R_1$ is a —H or a halo. In some embodiments, $R_1$ is a —H or —Cl.

In some embodiments, $R_2$ is a —H or a —$NR_aR_b$, wherein the —$NR_aR_b$ can be further substituted with up to two $R_x$ groups. In some embodiments, $R_2$ is —H,

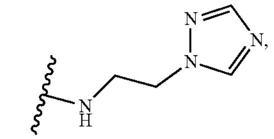

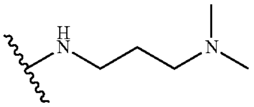, or

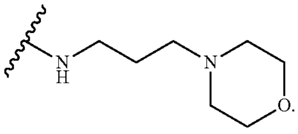

In some embodiments, $R_3$ is a —H, a 5-6 membered aryl, a 3-6 membered cycloalkyl, or a 5-6 membered heterocycle, wherein the 5-6 membered aryl, the 3-6 membered cycloalkyl, or the 5-6 membered heterocycle can be substituted with up to two $R_a$ groups. In some embodiments, $R_3$ is —H, —Cl,

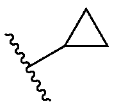, 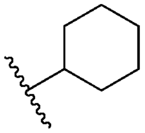, 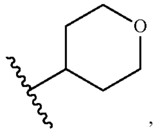,

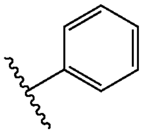, or 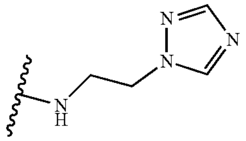,

In some embodiments, each $R_a$ and $R_b$ is independently —H or $C_{1-3}$ alkyl.

In some embodiments, each $R_x$ is independently —$NR_{x1}R_{x2}$ or a 5-6 membered heteroaryl.

In some embodiments, each $R_{x1}$ and $R_{x2}$ is independently $C_{1-3}$ alkyl.

In some embodiments of Formula IE, the compound has the structure:

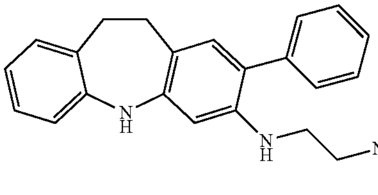,

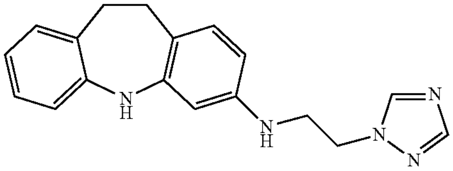,

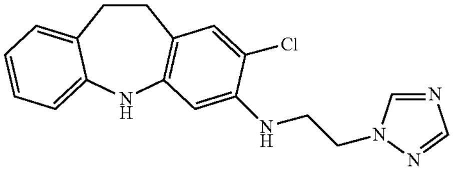,

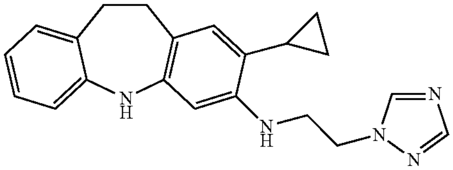,

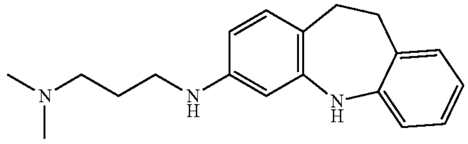,

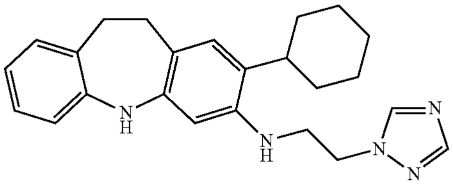,

-continued

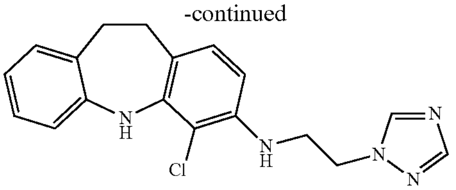

,

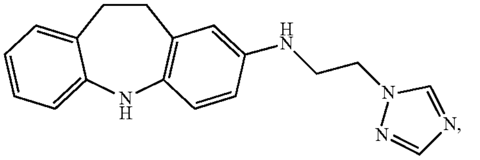

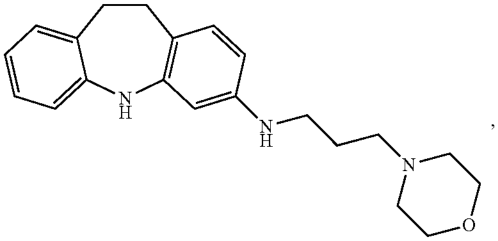

,

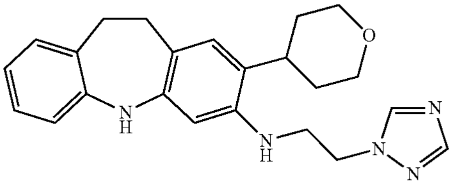

, and pharmaceutically acceptable salts thereof.

Some embodiments are methods of inhibiting a lipoxygenase in cells determined to be in need thereof, comprising contacting the cells with (or administering to the cells) a compound having structure disclosed in any of the compounds above, where the cells are human cells that are either in vivo or isolated in vitro. In some embodiments, the cells are in situ as part of a person determined to be in need of lipoxygenase inhibition or suffering from a disease associated with pathogenic lipoxygenase activity, wherein the disease is selected from an acute or chronic inflammatory disease or a neurodegenerative disease. Some of the methods further comprising: (i) measuring a lipoxygenase activity in a sample of the person; (ii) determining a level of a lipoxygenase metabolite in a sample of the person; or (iii) determining the person has the disease. In some of the methods, the disease is: (i) an acute or chronic inflammatory disease that is asthma, rheumatoid arthritis, inflammatory bowel disease, psoriasis, hereditary ichthyosis, dermatitis, nephritis, atherosclerosis, or cardiovascular disease, or (ii) a neurodegenerative disease that is age-related neurodegeneration, amyloid beta-associated disease, Alzheimer's Disease, ischemia-related disorder, creutzfeldt-jakob disease/prion peptide toxicity, ALS, dementia or Parkinson Disease.

Further conceived are pharmaceutical compositions comprising a compound disclosed above for inhibiting lipoxygenase activity, or a pharmaceutically acceptable salt thereof, and a pharmaceutically acceptable carrier. Further conceived of are pharmaceutical compositions comprising compounds disclosed above for inhibiting lipoxygenase activity, or a pharmaceutically acceptable salt thereof, and a pharmaceutically acceptable carrier. Further conceived are compositions comprising a compound of Formula I, supra, and a second anti-neurodegenerative disease drug. Further conceived of are methods for identifying a lipoxygenase inhibitor, comprising the step of screening for lipoxygenase inhibitory activity of one or more of the above compounds.

As described herein in more detail, subject compounds can be used in pharmaceutically acceptable alternative forms, such as pharmaceutically acceptable salts, prodrugs (e.g., sulfamates, phosphates, esters, ethers, amides, etc.), and the like. Unless otherwise specified, all references herein to compounds according to the formulas are intended to include such alternative forms. Pharmaceutically acceptable and pharmaceutically active combinations of such forms, such as salts of prodrugs, are possible and within the scope of the disclosure as well. Some examples of salts and prodrugs are provided herein.

In some embodiments, subject compounds are used to prepare a composition that is effective in treating neurodegenerative diseases (also referred to herein as "neurodegenerative conditions"). Examples of neurodegenerative diseases include neuroinflammation-associated neurodegeneration, Alzheimer's Disease, ischemia-related disorder, creutzfeldt-jakob disease/prion peptide toxicity, ALS, dementia, and Parkinson Disease. In some embodiments, treatment of a neurodegenerative disease involves administering a formulation containing a subject compound. As described in more detail herein, the composition may comprise one or more active agents and one or more pharmaceutically acceptable additives. Furthermore, the compositions may be formulated into any suitable dosage form.

In some embodiments, the subject compositions contain a compound according to Formula (I) as the sole active agent; such formulations may include pharmaceutically inactive components such as carriers and the like.

In some embodiments, subject compounds are administered in combination with one or more additional anti-neurodegenerative disease drug(s). The additional drug may be present along with a subject compound in a single formulation, and therefore administered at the same time. Alternatively, the additional drug may be in a separate formulation, and may be administered according to a regimen that is separate from the regimen for administration of the formulation containing a subject compounds. In such embodiments the two regimens may be related; for example the second formulation is administered along with, or immediately before, or immediately after administration of the first formulation. Examples of additional anti-neurodegenerative disease drugs include acetylcholinesterase inhibitors (e.g., tacrine, rivastigmine, galantamine, donepezil, etc.), N-methyl-D-aspartate (NMDA) receptor antagonists (e.g., memantine), hyperzine A, latrepirdine, hypothalamic proline-rich peptide 1 (PRP-1), and the like.

Subject compounds may be administered as a free base, or in the form of a salt, ester, amide, prodrug, active metabolite, analog, or the like, provided that the salt, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 5th Ed. (New York: Wiley-Interscience, 2001), and Green, *Protective Groups in Organic Synthesis,* 3rd Ed. (New York: Wiley-Interscience, 1999).

A pharmaceutically acceptable salt may be prepared from any pharmaceutically acceptable organic acid or base, any pharmaceutically acceptable inorganic acid or base, or combinations thereof.

Suitable organic acids for preparing acid addition salts include, e.g., $C_1$-$C_6$ alkyl and $C_6$-$C_{12}$ aryl carboxylic acids, di-carboxylic acids, and tri-carboxylic acids such as acetic acid, propionic acid, succinic acid, maleic acid, fumaric acid, tartaric acid, glycolic acid, citric acid, pyruvic acid, oxalic acid, malic acid, malonic acid, benzoic acid, cinnamic acid, mandelic acid, salicylic acid, phthalic acid, and terephthalic acid, and aryl and alkyl sulfonic acids such as methanesulfonic acid, ethanesulfonic acid, and p-toluenesulfonic acid, and the like. Suitable inorganic acids for preparing acid addition salts include, e.g., hydrochloric acid, hydrobromic acid, hydroiodic acid, sulfuric acid, nitric acid, and phosphoric acid, and the like. An acid addition salt may be reconverted to the free base by treatment with a suitable base.

Suitable organic bases for preparing basic addition salts include, e.g., primary, secondary and tertiary amines, such as trimethylamine, triethylamine, tripropylamine, N,N-dibenzylethylenediamine, 2-dimethylaminoethanol, ethanolamine, ethylenediamine, glucamine, glucosamine, histidine, and polyamine resins, cyclic amines such as caffeine, N-ethylmorpholine, N-ethylpiperidine, and purine, and salts of amines such as betaine, choline, and procaine, and the like. Suitable inorganic bases for preparing basic addition salts include, e.g., salts derived from sodium, potassium, ammonium, calcium, ferric, ferrous, aluminum, lithium, magnesium, or zinc such as sodium hydroxide, potassium hydroxide, calcium carbonate, sodium carbonate, and potassium carbonate, and the like. A basic addition salt may be reconverted to the free acid by treatment with a suitable acid.

Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system. For example, a compound according to Formula I may be in the form of a pharmaceutically acceptable prodrug such as the sulfamate prodrug.

Other derivatives and analogs of the active agents may be prepared using standard techniques known to those skilled in the art of synthetic organic chemistry, or may be deduced by reference to the pertinent literature.

Any of the compounds of the disclosure may be the active agent in a subject formulation. Formulations containing the compounds of the disclosure may include 1, 2, 3 or more of the subject compounds, and may also include one or more additional active agents such as analgesics and other antibiotics. By "any of the compounds of the disclosure" is meant any compound selected from a subject compound per se (i.e. as a free base) and salts, prodrugs, etc. thereof.

The amount of active agent in the formulation typically ranges from about 0.05 wt % to about 95 wt % based on the total weight of the formulation. For example, the amount of active agent may range from about 0.05 wt % to about 50 wt %, or from about 0.1 wt % to about 25 wt %. Alternatively, the amount of active agent in the formulation may be measured so as to achieve a desired dose.

Formulations containing a subject compound may be presented in unit dose form or in multi-dose containers with an optional preservative to increase shelf life.

The compositions of the disclosure may be administered to the patient by any appropriate method. In general, both systemic and localized methods of administration are acceptable. It will be obvious to those skilled in the art that the selection of a method of administration will be influenced by a number of factors, such as the condition being treated, frequency of administration, dosage level, and the wants and needs of the patient. For example, certain methods may be better suited for rapid delivery of high doses of active agent, while other methods may be better suited for slow, steady delivery of active agent. Examples of methods of administration that are suitable for delivery of the compounds of the disclosure include parental and transmembrane absorption (including delivery via the digestive and respiratory tracts). Formulations suitable for delivery via these methods are well known in the art.

For example, formulations containing the compounds of the disclosure may be administered parenterally, such as via intravenous, subcutaneous, intraperitoneal, or intramuscular injection, using bolus injection and/or continuous infusion. Generally, parenteral administration employs liquid formulations.

The compositions may also be administered via the digestive tract, including orally and rectally. Examples of formulations that are appropriate for administration via the digestive tract include tablets, capsules, pastilles, chewing gum, aqueous solutions, and suppositories.

The formulations may also be administered via transmucosal administration. Transmucosal delivery includes delivery via the oral (including buccal and sublingual), nasal, vaginal, and rectal mucosal membranes. Formulations suitable for transmucosal deliver are well known in the art and include tablets, chewing gums, mouthwashes, lozenges, suppositories, gels, creams, liquids, and pastes.

The formulations may also be administered transdermally. Transdermal delivery may be accomplished using, for example, topically applied creams, liquids, pastes, gels and the like as well as what is often referred to as transdermal "patches."

The formulations may also be administered via the respiratory tract. Pulmonary delivery may be accomplished via oral or nasal inhalation, using aerosols, dry powders, liquid formulations, or the like. Aerosol inhalers and imitation cigarettes are examples of pulmonary dosage forms.

Liquid formulations include solutions, suspensions, and emulsions. For example, solutions may be aqueous solutions of the active agent and may include one or more of propylene glycol, polyethylene glycol, and the like. Aqueous suspensions can be made by dispersing the finely divided active agent in water with viscous material, such as natural or synthetic gums, resins, methylcellulose, sodium carboxymethylcellulose, or other well known suspending agents. Also included are formulations of solid form which are intended to be converted, shortly before use, to liquid form.

Tablets and lozenges may comprise, for example, a flavored base such as compressed lactose, sucrose and acacia or tragacanth and an effective amount of an active agent. Pastilles generally comprise the active agent in an inert base such as gelatin and glycerine or sucrose and acacia.

The subject compounds may inhibit one or more lipoxygenases, e.g. by at least 50%, or by at least 75%, or by at least 85%, or by at least 95%, or by at least 98%. In some embodiments, the compounds are selective inhibitors, and are inhibitors of a subsection of the LOX family of enzymes. In some embodiments, the subject compounds may inhibit 5-LOX, 12-LOX, or 15-LOX. In some embodiments, the subject compounds may inhibit various combinations of 5-LOX, 12-LOX, and 15-LOX, such as inhibiting 5-LOX and 12-LOX, inhibiting 5-LOX and 15-LOX, inhibiting 12-LOX and 15-LOX, and/or inhibiting 5-LOX, 12-LOX, and 15-LOX.

Subject compounds are useful in therapies for treating diseases associated with pathogenic lipoxygenase activity, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, neuroinflammation-associated disease, Alzheimer's Disease, ischemia-related disorder, creutzfeldt-jakob disease/prion peptide toxicity, ALS, dementia and Parkinson Disease.

For example, the methods may involve administering a subject compound to a patient in need thereof (e.g. a patient suffering from a neurodegenerative disease such as Alzheimer's Disease, or a patient at risk for such conditions, or a patient exhibiting symptoms of such conditions, etc.). In some embodiments, subject compounds are used in a method for reducing or eliminating the severity of symptoms associated with a subject disease. For example, the method may involve contacting nervous system cells or cells located in a nervous system, or contacting tissue associated with a nervous system, and such contacting results in one or more of the following: the inhibition of further neurodegeneration; the inhibition of abnormal cell growth and development; the inhibition of growth of non-cell objects in a nervous system; the reduction of neuroinflammation; the reduction in severity of symptoms associated with a neurodegenerative disease, and the like.

In some embodiments, subject compounds are used to prepare a composition that is effective in treating a subject disease. As described in more detail herein, the composition may comprise one or more active agents and one or more pharmaceutically acceptable additives. Furthermore, the compositions may be formulated into any suitable dosage form.

In some embodiments, treatment of a subject disease involves administering a formulation containing a subject compound. As described in more detail herein, such formulations may include any of a number of additives and/or additional active agents, and such formulations may be prepared in any of a variety of dosage forms. In some embodiments, treatment of a subject disease using a compound involves determining that the person has a subject disease associated with pathogenic lipoxygenase activity. Such determination may be made by any means appropriate for the particular condition, including blood tests and imaging tests.

In some embodiments, the methods involve measuring a lipoxygenase activity (such as 5-LOX, 12-LOX, or 15-LOX, and/or various combinations thereof) in a patient prior to treatment with a subject compound, after treatment with a subject compound, or both prior to and after treatment. In some embodiments, the methods involve measuring a level of a lipoxygenase metabolite in a patient. An example metabolite is 5-HETE. In these methods, measuring enzyme activity or measuring metabolite levels may be carried out using any appropriate sample from the person, such as a body fluid (e.g., blood, urine, etc.).

Various embodiments are implemented in accordance with the underlying Provisional Application (Ser. No. 62/994,550), entitled "Lipoxygenase Inhibitors," filed Mar. 25, 2020, to which benefit is claimed and which is fully incorporated herein by reference for their general and specific teachings. For instance, embodiments herein and/or in the provisional application can be combined in varying degrees (including wholly). Reference can also be made to the experimental teachings and underlying references provided in the underlying Provisional Application. Embodiments discussed in the Provisional Application are not intended, in any way, to be limiting to the overall technical disclosure, or to any part of the claimed disclosure unless specifically noted.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXPERIMENTAL EMBODIMENTS

The compounds disclosed herein were found to inhibit Akt and ERK activation by inhibiting 12-LOX mediated metabolism of arachidonic acid.

5-LOX FI assay Fluorescent Assay

The enzyme assay (100 μL) contained 50 mM Tris, pH 7.5, 0.1 mM EDTA, 0.3 mM $CaCl_2$, 20 μM AA, 100 μM ATP, 1 μM DHR123, and recombinant 5-LOX cell lysate (0.5 μL/100 μL). Inhibitors (dissolved in DMSO) were plated at 1 μL into 96-well assay microplates followed by a 40 μL addition of a solution containing 5-LOX enzyme. Enzyme was pre-incubated with compounds for 15 mins. The assay was initiated by the addition of a 40 μL substrate solution containing AA and ATP, and 20 μL addition of a solution containing DHR123. Enzymatic reaction proceeded for 30 min with kinetic reading at 500 nm excitation & 536 nm emission in SpectraMax Paradigm (MolecularDevice). Percent inhibition was calculated for each compound dose for $IC_{50}$ curve fitting using 4 Parameter Logistic Model or Sigmoidal Dose-Response Model.

12-LOX/15-LOX Fluorescent Assay

The enzyme assay (100 ul) contained 50 mM Tris, pH 7.5, 0.05% Tween-20, 20 μM AA/LA, 1 μM DHR123, and 100 nM recombinant 12-LOX enzyme/50 nM recombinant 15-LOX enzyme. Inhibitors (dissolved in DMSO) were plated at 1 μL into 96-well assay microplates followed by a 40 μL addition of a solution containing 12-LOX/15-LOX enzyme. Enzyme was pre-incubated with compounds for 15 mins. The assay was initiated by the addition of a 40 μL substrate solution containing AA/LA, and 20 μL addition of a solution containing DHR123. Enzymatic reaction proceeded for 30 min with kinetic reading at 500 nm excitation & 536 nm emission in SpectraMax Paradigm (MolecularDevice). Percent inhibition was calculated for each compound dose for $IC_{50}$ curve fitting using 4 Parameter Logistic Model or Sigmoidal Dose-Response Model.

The compounds disclosure herein were found to inhibit lipoxygenases. In some experiments, the inhibitory activity of the compounds against a panel of lipoxygenases was demonstrated in cell-based assays, e.g., for 5-LOX, a fluorescence-based enzyme assay of human 5-LOX (Anal. Biochem., 364:204.) was used, and for 12-LOX, a colorimetric method to determine platelet 12-LOX activity (Anal. biochem., 231:354) was used. Table 1 provides results to exemplary compounds on 5-LOX, 12-LOX, and 15-LOX.

TABLE 1

IC50 (μM) values for in vitro lipoxygenase inhibition

| Compound Structure | Smiles | SRI ID | 5-LOX | 12-LOX | 15-LOX | MW |
|---|---|---|---|---|---|---|
| 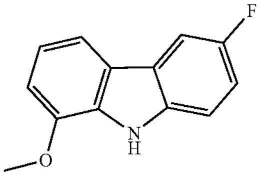 [SMILES: COc1cccc2c1[nH]c1ccc(F)cc12] | COC1=CC=CC2=C1NC1=CC=C(F)C=C21 | SS20308-0002-01 | 20.82 | 8.04 | 4.33 | 215.22 |
| 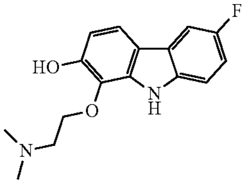 [SMILES: CN(C)CCOc1c(O)ccc2c1[nH]c1ccc(F)cc12] | CN(C)CCOC1=C(O)C=CC2=C1NC1=CC=C(F)C=C21 | SS20308-0004-01 | | 3.19 | 2.55 | 288.13 |
| 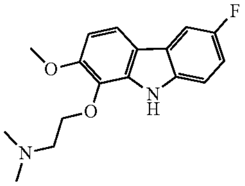 [SMILES: COc1ccc2c([nH]c3ccc(F)cc32)c1OCCN(C)C] | COC1=C(OCCN(C)C)C2=C(C=C1)C1=CC(F)=CC=C1N2 | SS20308-0007-01 | 32.25 | 22.02 | 8.64 | 302.34 |
| 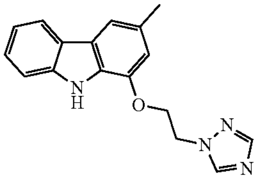 [SMILES: Cc1cc(OCCn2cncn2)c2[nH]c3ccccc3c2c1] | CC1=CC2=C(NC3=CC=CC=C23)C(OCCN2C=NC=N2)=C1 | SS20308-0017-01 | 6.06 | 2.85 | 3.49 | 350.37 |
| 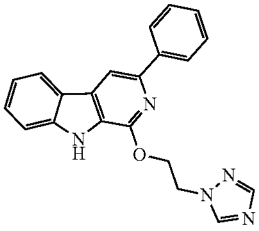 [SMILES: c1ccc(-c2cc3c([nH]c4ccccc43)c(OCCn3cncn3)n2)cc1] | C(CN1C=NC=N1)OC1=NC(=CC2=C1NC1=CC=CC=C21)C1=CC=CC=C1 | SS20308-0018-01 | 46.99 | 4.07 | 1.39 | 292.34 |
| 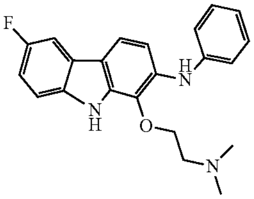 [SMILES: CN(C)CCOc1c(Nc2ccccc2)ccc2c1[nH]c1ccc(F)cc12] | CN(C)CCOC1=C(NC2=CC=CC=C2)C=CC2=C1NC1=CC=C(F)C=C21 | SS20308-0032-01 | 0.27 | 0.21 | 15.9 | 363.44 |
| 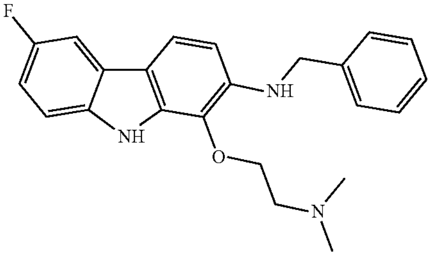 [SMILES: CN(C)CCOc1c(NCc2ccccc2)ccc2c1[nH]c1ccc(F)cc12] | CN(C)CCOC1=C(NCC2=CC=CC=C2)C=CC2=C1NC1=CC=C(F)C=C21 | SS20308-0036-01 | 0.35 | 0.4 | 0.8 | 377.45 |

TABLE 1-continued

IC50 (μM) values for in vitro lipoxygenase inhibition

| Compound Structure | Smiles | SRI ID | 5-LOX | 12-LOX | 15-LOX | MW |
|---|---|---|---|---|---|---|
| 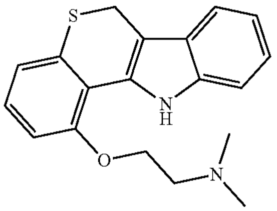 [SMILES: CN(C)CCOc1cccc2c1-c1[nH]c3ccccc3c1CS2] | CN(C)CCOC1═C2C3═C(CSC2═CC═C1)C1═CC═CC═C1N3 | SS20308-0046-01 | 0.63 | 0.62 | 0.97 | 324.44 |
| 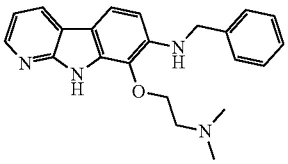 [SMILES: CN(C)CCOc1c(NCc2ccccc2)ccc2c1[nH]c1ncccc12] | CN(C)CCOC1═C(NCC2═CC═CC═C2)C═CC2═C1NC1═NC═CC═C21 | SS20308-0047-01 | 0.36; 0.82 | 0.36; 0.49 | 1.13; 1.93 | 360.45 |
| 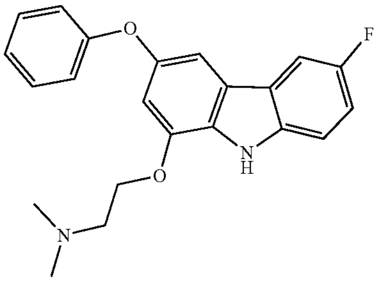 [SMILES: CN(C)CCOc1cc(Oc2ccccc2)cc2c1[nH]c1ccc(F)cc12] | CN(C)CCOC1═CC(OC2═CC═CC═C2)═CC2═C1NC1═CC═C(F)C═C21 | SS20308-0054-01 | 6.83 | 7.6 | 1.82 | 364.41 |
| 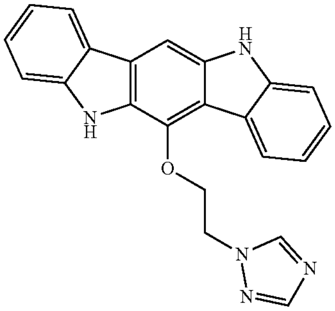 [SMILES: c1ccc2c(c1)[nH]c1c(OCCn3cncn3)c3c(cc12)[nH]c1ccccc13] | C(CN1C═NC═N1)OC1═C2C(NC3═CC═CC═C23)═CC2═C1NC1═CC═CC═C21 | SS20308-0059-01 | 0.04; 0.03 | 0.03; 0.02 | 0.03; 0.02 | 367.4 |
| 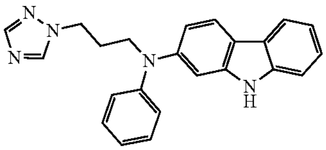 [SMILES: c1ccc(N(CCCn2cncn2)c2ccc3c(c2)[nH]c2ccccc23)cc1] | C(CN(C1═CC═CC═C1)C1═CC2═C(C═C1)C1═CC═CC═C1N2)CN1C═NC═N1 | SS20308-0060-01 | 0.62 | 0.99 | 2.19 | 367.45 |
| 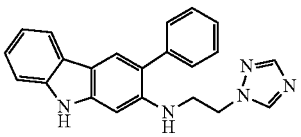 [SMILES: c1ccc(-c2cc3c(cc2NCCn2cncn2)[nH]c2ccccc23)cc1] | C(CN1C═NC═N1)NC1═CC2═C(C═C1C1═CC═CC═C1)C1═CC═CC═C1N2 | SS20308-0061-01 | 0.36; 0.79 | 0.19; 0.29 | 0.94; 1.33 | 353.42 |
| 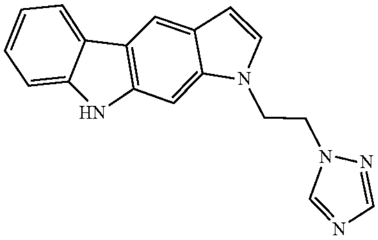 [SMILES: c1ccc2c(c1)[nH]c1cc3c(ccn3CCn3cncn3)cc12] | C(CN1C═CC2═CC3═C(NC4═CC═CC═C34)C═C12)N1C═NC═N1 | SS20308-0062-01 | 0.53; 0.42 | 0.19; 0.24 | 0.94; 1.68 | 301.35 |

TABLE 1-continued
| Compound Structure | Smiles | SRI ID | 5-LOX | 12-LOX | 15-LOX | MW |
|---|---|---|---|---|---|---|
| IC50 (μM) values for in vitro lipoxygenase inhibition | | | | | | |
| 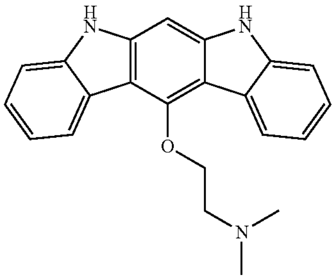 [SMILES: CN(C)CCOc1c2c(cc3[nH]c4ccccc4c13)[nH]c1ccccc12] | CN(C)CCOC1=C2C(NC3=CC=CC=C23)=CC2=C1C1=CC=CC=C1N2 | SS20308-0063-01 | 0.53; 0.69 | 0.46; 0.56 | 0.29; 0.90 | 301.35 |
| 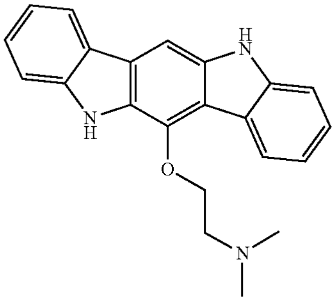 [SMILES: CN(C)CCOc1c2[nH]c3ccccc3c2cc2[nH]c3ccccc3c12] | CN(C)CCOC1=C2C(NC3=CC=CC=C23)=CC2=C1NC1=CC=CC=C21 | SS20308-0065-01 | 0.01; 0.04 | 0.02; 0.06 | 0.03; 0.03 | 359.42 |
| 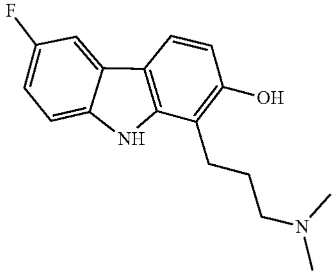 [SMILES: CN(C)CCCc1c(O)ccc2c1[nH]c1ccc(F)cc12] | CN(C)CCCC1=C(O)C=CC2=C1NC1=CC=C(F)C=C21 | SS20308-0068-01 | 5.63 | 0.77 | 1.76 | 286.34 |
| 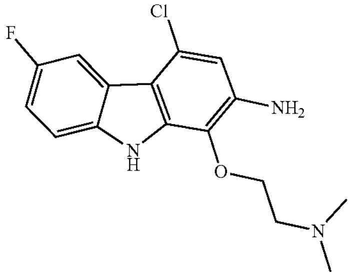 [SMILES: CN(C)CCOc1c(N)cc(Cl)c2c1[nH]c1ccc(F)cc12] | CN(C)CCOC1=C(N)C=C(C1)C2=C1NC1=CC=C(F)C=C21 | SS20308-0069-01 | 14.77 | 7.93 | 8.34 | 321.78 |
| 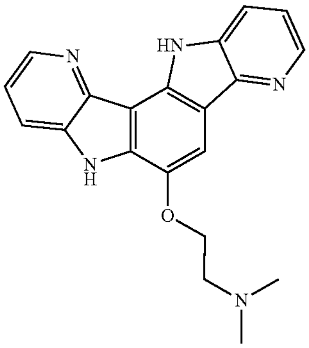 [SMILES: CN(C)CCOc1cc2c3ncccc3[nH]c2c2c1[nH]c1cccnc12] | CN(C)CCOC1=CC2=C(NC3=CC=CN=C23)C2=C1NC1=CC=CN=C21 | SS20308-0070-01 | 9.17 | 6.32 | 4.53 | 345.4 |

TABLE 1-continued

| IC50 (μM) values for in vitro lipoxygenase inhibition | | | | | | |
|---|---|---|---|---|---|---|
| Compound Structure | Smiles | SRI ID | 5-LOX | 12-LOX | 15-LOX | MW |
| 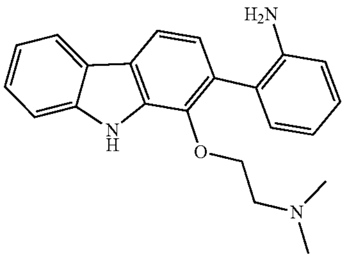 [SMILES: CN(C)CCOc1c(-c2ccccc2N)ccc2c1[nH]c1ccccc12] | CN(C)CCOC1=C(C=CC2=C1NC1=CC=CC=C21)C1=C(N)C=CC=C1 | SS20308-0073-01 | 14.44 | 49.19 | 26.13 | 345.45 (fb); 418.36 (2HCl) |
| 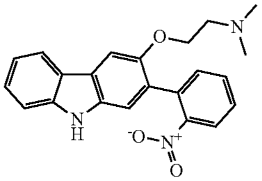 | CN(C)CCOC1=CC2=C(NC3=CC=CC=C23)C=C1C1=CC=CC=C1[N+]([O-])=O | SS20308-0076-01 | 4.54 | 3.59 | 5.7 | 375.42 |
| 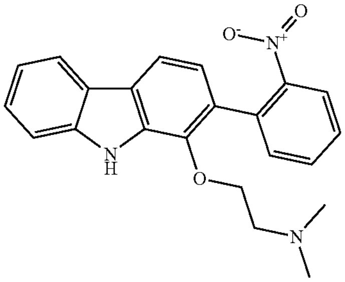 [SMILES: CN(C)CCOc1c(-c2ccccc2[N+](=O)[O-])ccc2c1[nH]c1ccccc12] | CN(C)CCOC1=C(C=CC2=C1NC1=CC=CC=C21)C1=C(C=CC=C1)[N+]([O-])=O | SS20308-0077-01 | 2.66 | 2.32 | 2.15 | 375.42 |
| 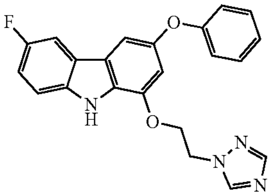 [SMILES: Fc1ccc2[nH]c3c(OCCn4cncn4)cc(Oc4ccccc4)cc3c2c1] | FC1=CC=C2NC3=C(C=C(OC4=CC=CC=C4)C=C3OCCN3C=NC=N3)C2=C1 | SS20308-0084-01 | 6.79 | 5.42 | 3.36 | 388.39 |
| 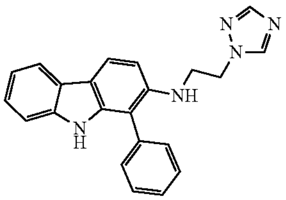 [SMILES: c1ccc(-c2c(NCCn3cncn3)ccc3c2[nH]c2ccccc23)cc1] | C(CN1C=NC=N1)NC1=C(C2=C(C=C1)C1=CC=CC=C1N2)C1=CC=CC=C1 | SS20308-0085-01 | 0.57; 1.60 | 0.32; 0.92 | 1.19; 2.23 | 353.42 |
| 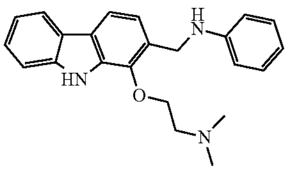 [SMILES: CN(C)CCOc1c(CNc2ccccc2)ccc2c1[nH]c1ccccc12] | CN(C)CCOC1=C(CNC2=CC=CC=C2)C=CC2=C1NC1=CC=CC=C21 | SS20308-0086-01 | 0.62 | 0.87 | 0.42 | 359.46 |

TABLE 1-continued
IC50 (μM) values for in vitro lipoxygenase inhibition
| Compound Structure | Smiles | SRI ID | 5-LOX | 12-LOX | 15-LOX | MW |
|---|---|---|---|---|---|---|
| 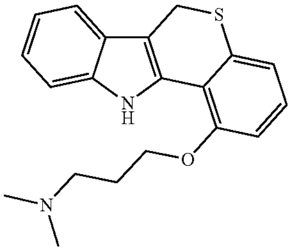 [SMILES: CN(C)CCCOc1cccc2c1-c1[nH]c3ccccc3c1CS2] | CN(C)CCCOC1=C2C3=C(CSC2=CC=C1)C1=CC=CC=C1N3 | SS20308-0090-01 | 0.47 | 0.43 | 0.69 | 338.47 |
| 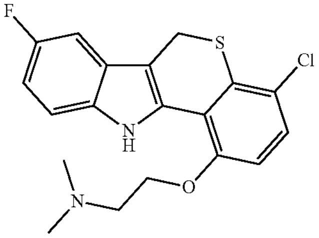 [SMILES: CN(C)CCOc1ccc(Cl)c2c1-c1[nH]c3ccc(F)cc3c1CS2] | CN(C)CCOC1=C2C3=C(CSC2=C(C1)C=C1)C1=CC(F)=CC=C1N3 | SS20308-0093-01 | 1.46 | 1.69 | 2.37 | 376.88 |
| 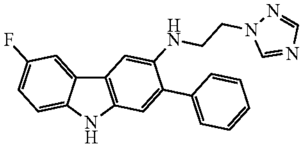 [SMILES: Fc1ccc2[nH]c3cc(-c4ccccc4)c(NCCn4cncn4)cc3c2c1] | FC1=CC=C2NC3=C(C=C(NCCN4C=NC=N4)C(=C3)C3=CC=CC=C3)C2=C1 | SS20308-0094-01 | 17.59; 0.05; 44.76; 0.07 | 0.03; 0.04; 0.04; 0.04 | 0.04; 0.06; 0.08; 57.99; 0.07 | 371.41 |
| 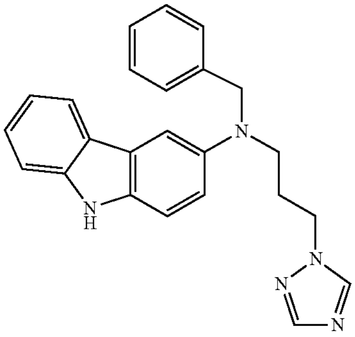 [SMILES: c1ccc(CN(CCCn2cncn2)c2ccc3[nH]c4ccccc4c3c2)cc1] | C(CN(CC1=CC=CC=C1)C1=CC2=C(NC3=CC=CC=C23)C=C1)CN1C=NC=N1 | SS20308-0097-01 | 32.99; >1 | 62.16; 0.03 | >83.2; 0.05 | 381.47 |
| 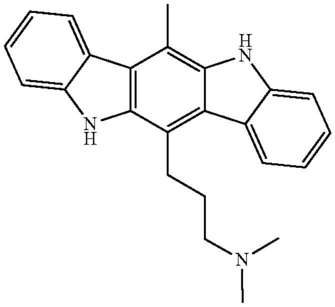 [SMILES: Cc1c2[nH]c3ccccc3c2c(CCCN(C)C)c2[nH]c3ccccc3c12] | CN(C)CCCC1=C2C(NC3=CC=CC=C23)=C(C)C2=C1NC1=CC=CC=C21 | SS20308-0100-01 | >100 | >100 | >100 | 355.48 |

TABLE 1-continued
IC50 (μM) values for in vitro lipoxygenase inhibition
| Compound Structure | Smiles | SRI ID | 5-LOX | 12-LOX | 15-LOX | MW |
|---|---|---|---|---|---|---|
| 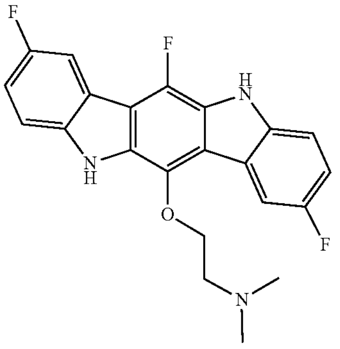 [SMILES: CN(C)CCOc1c2[nH]c3ccc(F)cc3c2c(F)c2[nH]c3ccc(F)cc3c12] | CN(C)CCOC1=C2C(NC3=CC=C(F)C=C23)=C(F)C2=C1NC1=CC=C(F)C=C21 | SS20308-0101-01 | 0.07; 0.05; 0.04 | 0.08; 0.10; 0.12 | 0.04; 0.07; 0.04 | 397.39 |
| 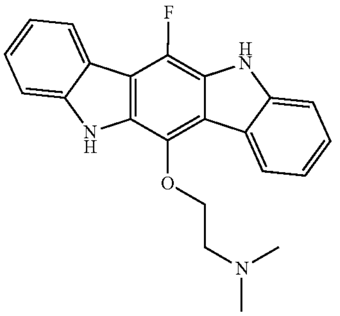 [SMILES: CN(C)CCOc1c2[nH]c3ccccc3c2c(F)c2[nH]c3ccccc3c12] | CN(C)CCOC1=C2C(NC3=CC=CC=C23)=C(F)C2=C1NC1=CC=CC=C21 | SS20308-0102-01 | <0.005; 0.06 | 0.05; 0.11 | 0.02; 0.04 | 397.39 |
| 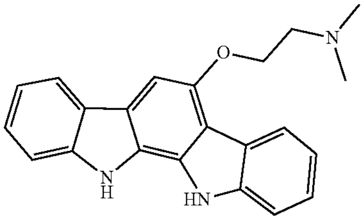 [SMILES: CN(C)CCOc1cc2c3ccccc3[nH]c2c2[nH]c3ccccc3c12] | CN(C)CCOC1=C2C(NC3=CC=CC=C23)=C2NC3=CC=CC=C3C2=C1 | SS20308-0103-01 | 0.02 | 2.23 | 0.06 | 361.41 |
| 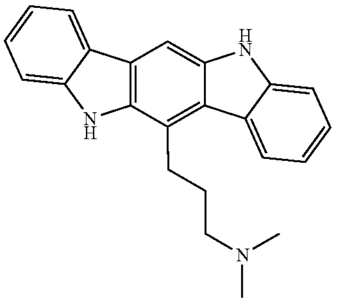 [SMILES: CN(C)CCCc1c2[nH]c3ccccc3c2cc2[nH]c3ccccc3c12] | CN(C)CCCC1=C2C(NC3=CC=CC=C23)=CC2=C1NC1=CC=CC=C21 | SS20308-0104-01 | 0.01; 73.07; 0.02 | 0.01; >100; 0.03 | 0.02; 0.02; 0.02 | 343.42 |
| 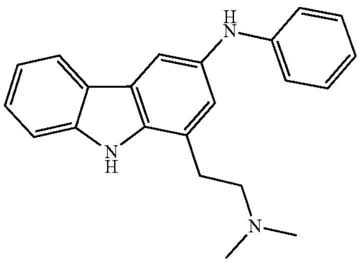 [SMILES: CN(C)CCc1cc(Nc2ccccc2)cc2c1[nH]c1ccccc12] | CN(C)CCC1=CC(NC2=CC=CC=C2)=CC2=C1NC1=CC=CC=C21 | SS20308-0106-01 | 0.04; 6.44; 0.01; 0.14; 0.06 | 0.02; 0.06; 0.03; 5.93; 0.02 | 0.04; 5.22; 0.01; 4.10; 12.86 | 329.44 |

TABLE 1-continued

IC50 (μM) values for in vitro lipoxygenase inhibition

| Compound Structure | Smiles | SRI ID | 5-LOX | 12-LOX | 15-LOX | MW |
|---|---|---|---|---|---|---|
| 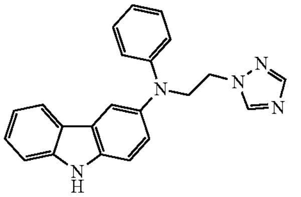 [SMILES: c1ccc(N(CCn2cncn2)c2ccc3[nH]c4ccccc4c3c2)cc1] | C(CN1C=NC=N 1)N(C1=CC=CC =C1)C1=CC2=C (NC3=CC=CC= C23)C=C1 | SS2030 8-0108- 01 | 0.55; 0.26; 0.35 | 0.24; 8.91; 0.46 | 1; 0.41; 0.86 | 353.42 |
| 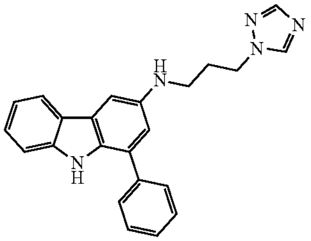 [SMILES: c1ccc(-c2cc(NCCCn3cncn3)cc3c2[nH]c2ccccc23)cc1] | C(CNC1=CC2= C(NC3=CC=CC =C23)C(=C1)C1 =CC=CC=C1)C N1C=NC=N1 | SS2030 8-0111- 01 | 20.29 | 44.95 | 0.09 | 367.45 |
| 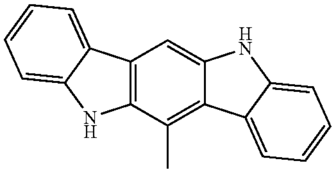 [SMILES: Cc1c2[nH]c3ccccc3c2cc2[nH]c3ccccc3c12] | CC1=C2C(NC3= CC=CC=C23)=C C2=C1NC1=CC =CC=C21 | SS2030 8-0112- 01 | >100 | >100 | >100 | 270.12 |
| 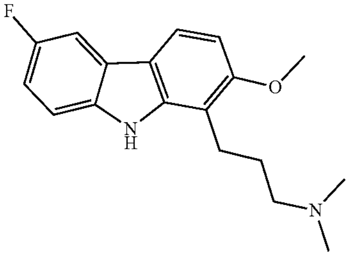 [SMILES: COc1ccc2c([nH]c3ccc(F)cc32)c1CCCN(C)C] | COC1=C(CCCN (C)C)C2=C(C=C 1)C1=CC(F)=CC =C1N2 | SS2030 8-0118- 01 | 23.17 | 24.18 | 26.92 | 300.37 |
| 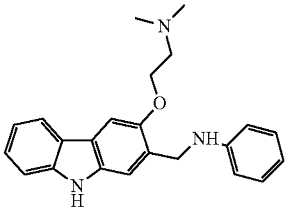 [SMILES: CN(C)CCOc1cc2c(cc1CNc1ccccc1)[nH]c1ccccc12] | CN(C)CCOC1= CC2=C(NC3=C C=CC=C23)C=C 1CNC1=CC=CC =C1 | SS2030 8-0119- 01 | 1.04 | 0.83 | 0.71 | 359.46 |
| 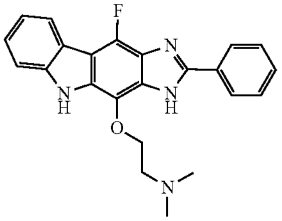 [SMILES: CN(C)CCOc1c2[nH]c(-c3ccccc3)nc2c(F)c2c1[nH]c1ccccc12] | CN(C)CCOC1= C2NC(=NC2=C( F)C2=ClNCl=C C=CC=C21)C1= CC=CC=C1 | SS2030 8-0121- 01 | 0.53 | 1.16 | 0.86 | 388.44 |
| 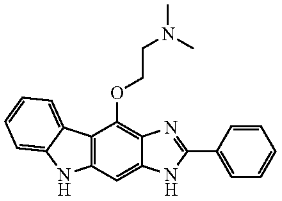 [SMILES: CN(C)CCOc1c2nc(-c3ccccc3)[nH]c2cc2[nH]c3ccccc3c12] | CN(C)CCOC1= C2N=C(NC2=C C2=C1C1=CC= CC=C1N2)C1=C C=CC=C1 | SS2030 8-0122- 01 | 1.02 | 0.87 | 1.38 | 370.45 |

TABLE 1-continued

IC50 (μM) values for in vitro lipoxygenase inhibition

| Compound Structure | Smiles | SRI ID | 5-LOX | 12-LOX | 15-LOX | MW |
|---|---|---|---|---|---|---|
| 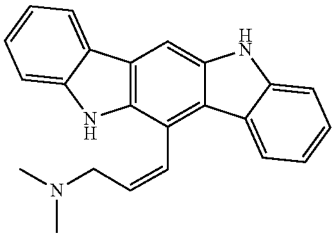 [SMILES: CN(C)C/C=C\c1c2[nH]c3ccccc3c2cc2[nH]c3ccccc3c12] | CN(C)C\C=C/C1=C2C(NC3=CC=CC=C23)=CC2=C1NC1=CC=CC=C21 | SS20308-0126-01 | 0.04 | 0.04 | 0.04 | 339.43 |
| 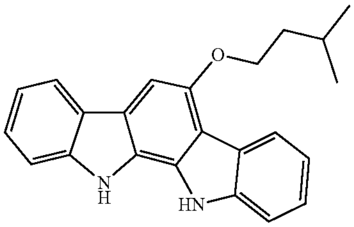 [SMILES: CC(C)CCOc1cc2c3ccccc3[nH]c2c2[nH]c3ccccc3c12] | CC(C)CCOC1=C2C(NC3=CC=CC=C23)=C2NC3=CC=CC=C3C2=C1 | SS20308-0127-01 | 0.62; 3.95; 0.18 | 0.09; 0.04; 0.14 | 0.12; 0.08; 0.17 | 342.43 |
| 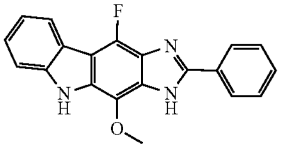 [SMILES: COc1c2[nH]c(-c3ccccc3)nc2c(F)c2c1[nH]c1ccccc12] | COC1=C2NC(=NC2=C(F)C2=C1NC1=CC=CC=C21)C1=CC=CC=C1 | SS20308-0137-01 | 0.72 | 0.53 | 0.5 | 331.34 |
| 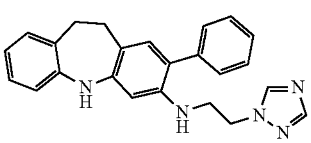 [SMILES: c1ccc(-c2cc3c(cc2NCCn2cncn2)Nc2ccccc2CC3)cc1] | C(CN1C=NC=N1)NC1=CC2=C(CCC3=CC=CC=C3N2)C=C1C1=CC=CC=C1 | SS20308-0152-01 | 0.01; 0.12 | 0.05; 0.08 | 0.08; 0.2 | 381.47 |
| 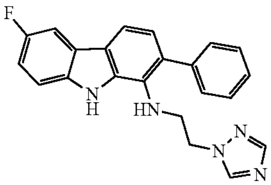 [SMILES: Fc1ccc2[nH]c3c(NCCn4cncn4)c(-c4ccccc4)ccc3c2c1] | FC1=CC=C2NC3=C(C=CC(C4=CC=CC=C4)=C3NCCN3C=NC=N3)C2=C1 | SS20308-0154-01 | 1.06 | 0.35 | 0.44 | 371.41 |
| 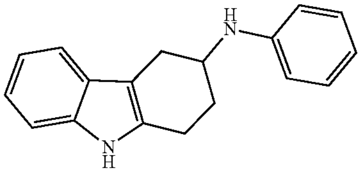 [SMILES: c1ccc(NC2CCc3[nH]c4ccccc4c3C2)cc1] | C12=CC=CC=C1C3=C(CCC(NC4=CC=CC=C4)C3)N2 | SS20308-0158-01 | 3.75 | 3.16 | 1.55 | 262.35 |
| 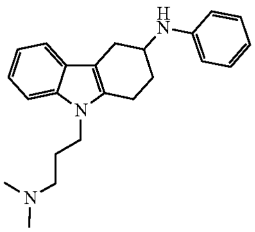 [SMILES: CN(C)CCCn1c2c(c3ccccc31)CC(Nc1ccccc1)CC2] | CN(C)CCCN1C2=CC=CC=C2C3=C1CCC(NC4=CC=CC=C4)C3 | SS20308-0159-01 | 1.85 | 2.75 | 1.59 | 347.5 |

TABLE 1-continued
| IC50 (μM) values for in vitro lipoxygenase inhibition | | | | | | |
|---|---|---|---|---|---|---|
| Compound Structure | Smiles | SRI ID | 5-LOX | 12-LOX | 15-LOX | MW |
| 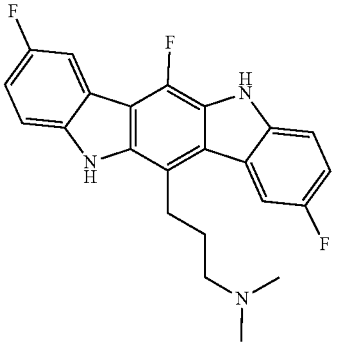 [SMILES: CN(C)CCCc1c2[nH]c3ccc(F)cc3c2c(F)c2[nH]c3ccc(F)cc3c12] | CN(C)CCCC1=C 2C(NC3=CC=C( F)C=C23)=C(F) C2=C1NC1=CC =C(F)C=C21 | SS2030 8-0163- 01 | 0.02; 0.04; 0.05; 0.01; 0.02 | 0.0003; 0.05; 0.04; 0.03; 0.04 | 0.0002; 0.02; 0.02; 0.01; 0.01 | 395.42 |
| 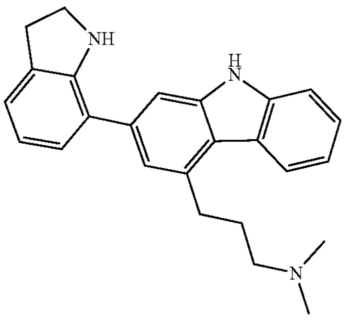 [SMILES: CN(C)CCCc1cc(-c2cccc3c2NCC3)cc2[nH]c3ccccc3c12] | CN(C)CCCC1=C 2C(NC3=C2C=C C=C3)=CC(=C1) C1=C2NCCC2= CC=C1 | SS2030 8-0170- 01 | 4.38 | 2.17 | 1.53 | 369.5 |
| 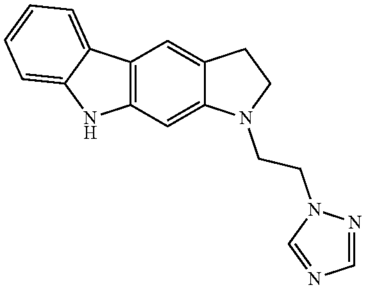 [SMILES: c1ccc2c(c1)[nH]c1cc3c(cc12)CCN3CCn1cncn1] | C(CN1CCC2=C C3=C(NC4=CC= CC=C34)C=C12) N1C=NC=N1 | SS2030 8-0180- 01 | 0.44; 0.81 | 0.03; 0.08 | 0.39; 0.51 | 303.36 |
| 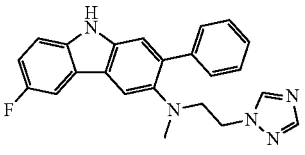 [SMILES: CN(CCn1cncn1)c1cc2c(cc1-c1ccccc1)[nH]c1ccc(F)cc12] | CN(CCN1C=NC =N1)C1=CC2=C (NC3=CC=C(F) C=C23)C=C1C1 =CC=CC=C1 | SS2030 8-0182- 01 | 0.77 | 0.31 | 1.4 | 385.44 |
| 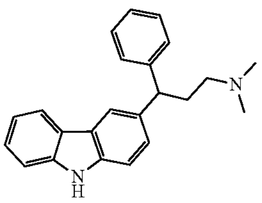 [SMILES: CN(C)CCC(c1ccccc1)c1ccc2[nH]c3ccccc3c2c1] | CN(C)CCC(C1= CC=CC=C1)C1= CC2=C(NC3=C C=CC=C23)C=C 1 | SS2030 8-0183- 01 | 5.01 | 50.93 | 13.08 | 328.45 |

TABLE 1-continued

IC50 (μM) values for in vitro lipoxygenase inhibition

| Compound Structure | Smiles | SRI ID | 5-LOX | 12-LOX | 15-LOX | MW |
|---|---|---|---|---|---|---|
| 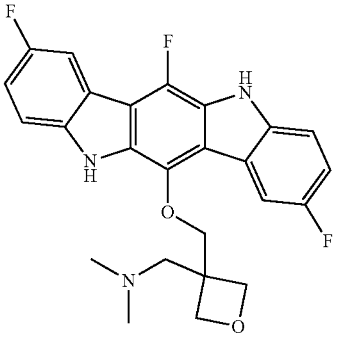 [SMILES: CN(C)CC1(COc2c3[nH]c4ccc(F)cc4c3c(F)c3[nH]c4ccc(F)cc4c23)COC1] | CN(C)CC1(COC2=C3C(NC4=CC=C(F)C=C34)=C(F)C3=C2NC2=CC=C(F)C=C32)COC1 | SS20308-0185-01 | 0.08 | 0.1 | 0.05 | 453.46 |
| 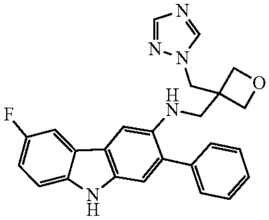 [SMILES: Fc1ccc2[nH]c3cc(-c4ccccc4)c(NCC4(Cn5cncn5)COC4)cc3c2c1] | FC1=CC=C2NC3=C(C=C(NCC4(CN5C=NC=N5)COC4)C(=C3)C3=CC=CC=C3)C2=C1 | SS20308-0186-01 | 0.04; 0.01 | 0.03; 0.01 | 0.05; 0.02 | 427.47 |
| 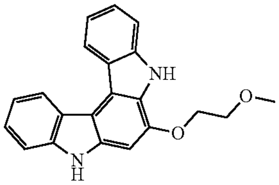 [SMILES: COCCOc1cc2[nH]c3ccccc3c2c2c1[nH]c1ccccc12] | COCCOC1=C2NC3=CC=CC=C3C2=C2C(NC3=C2C=CC=C3)=C1 | SS20308-0196-01 | >100; 0.03; 0.07 | >100; 0.03; 0.06 | >100; 0.09; 0.13 | 330.38 |
| 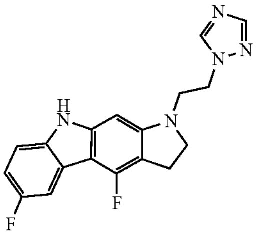 [SMILES: Fc1ccc2[nH]c3cc4c(c(F)c3c2c1)CCN4CCn1cncn1] | FC1=CC=C2NC3=C(C2=C1)C(F)=C1CCN(CCN2C=NC=N2)C1=C3 | SS20308-0207-01 | 0.59 | 0.1 | 1.15 | 339.34 |
| 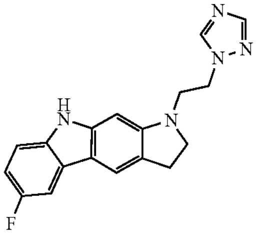 [SMILES: Fc1ccc2[nH]c3cc4c(cc3c2c1)CCN4CCn1cncn1] | FC1=CC=C2NC3=C(C=C4CCN(CCN5C=NC=N5)C4=C3)C2=C1 | SS20308-0208-01 | 0.2 | 0.01 | 0.18 | 321.35 |
| 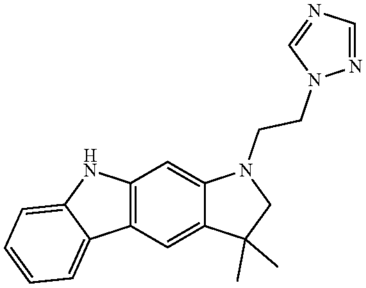 [SMILES: CC1(C)CN(CCn2cncn2)c2cc3[nH]c4ccccc4c3cc21] | CC1(C)CN(CCN2C=NC=N2)C2=CC3=C(C=C12)C1=CC=CC=C1N3 | SS20308-0209-01 | 0.92 | 0.03 | 1.12 | 331.41 |

TABLE 1-continued

IC50 (μM) values for in vitro lipoxygenase inhibition

| Compound Structure | Smiles | SRI ID | 5-LOX | 12-LOX | 15-LOX | MW |
|---|---|---|---|---|---|---|
| 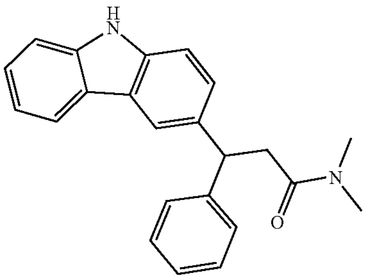 [SMILES: CN(C)C(=O)CC(c1ccccc1)c1ccc2[nH]c3ccccc3c2c1] | CN(C)C(CC(C1=CC=CC=C1)C2=CC3=C(C=C2)NC4=CC=CC=C43)=O | SS20308-0222-01 | 10.86 | 14.02 | 4.53 | 342.43 |
| 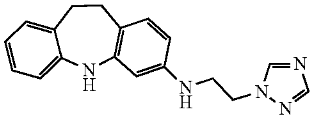 [SMILES: c1ccc2c(c1)CCc1ccc(NCCn3cncn3)cc1N2] | C(CN1C=NC=N1)NC1=CC2=C(CCC3=CC=CC=C3N2)C=C1 | SS20308-0224-01 | 0.22 | 0.11 | 1.12 | 305.38 |
| 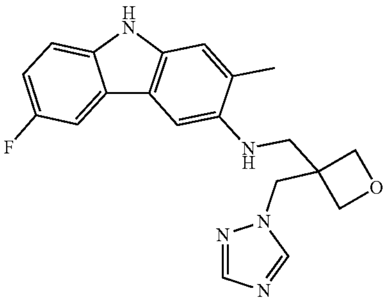 [SMILES: Cc1cc2[nH]c3ccc(F)cc3c2cc1NCC1(Cn2cncn2)COC1] | CC1=CC2=C(C=C1NCC1(CN3C=NC=N3)COC1)C1=CC(F)=CC=C1N2 | SS20308-0233-01 | 0.19 | 0.03 | 0.2 | 365.4 |
| 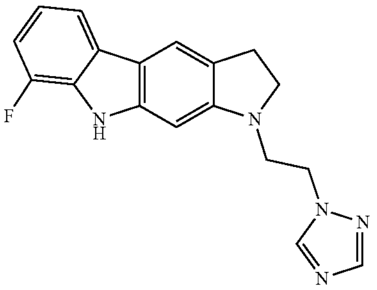 [SMILES: Fc1cccc2c1[nH]c1cc3c(cc12)CCN3CCn1cncn1] | FC1=C2NC3=C(C=C4CCN(CCN5C=NC=N5)C4=C3)C2=CC=C1 | SS20308-0243-01 | 0.2 | 0.03 | 1.13 | 321.35 |
| 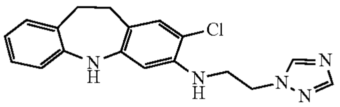 [SMILES: Clc1cc2c(cc1NCCn1cncn1)Nc1ccccc1CC2] | ClC1=CC2=C(NC3=CC=CC=C3CC2)C=C1NCCN1C=NC=N1 | SS20308-0251-01 | 0.45; 0.56 | 0.05; 0.22 | 0.75; 0.73 | 339.82 |
| 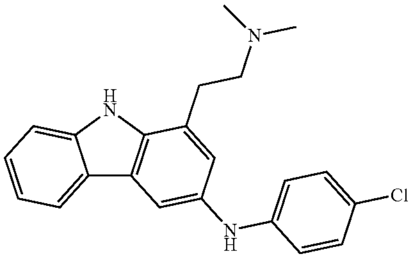 [SMILES: CN(C)CCc1cc(Nc2ccc(Cl)cc2)cc2c1[nH]c1ccccc12] | CN(C)CCC1=CC(NC2=CC=C(Cl)C=C2)=CC2=C1NC1=CC=CC=C21 | SS20308-0257-01 | 0.01; 0.04 | 50.14; 0.09 | 7.99; 0.04 | 363.88 |

TABLE 1-continued

| IC50 (μM) values for in vitro lipoxygenase inhibition | | | | | | |
|---|---|---|---|---|---|---|
| Compound Structure | Smiles | SRI ID | 5-LOX | 12-LOX | 15-LOX | MW |
| 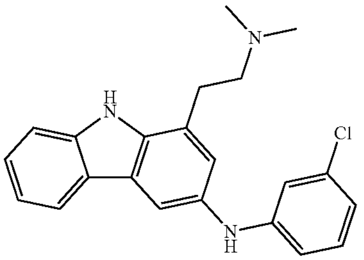 [SMILES: CN(C)CCc1cc(Nc2cccc(Cl)c2)cc2c1[nH]c1ccccc12] | CN(C)CCC1=CC(NC2=CC=CC(C1)=C2)=CC2=C1NC1=CC=CC=C21 | SS20308-0258-01 | 0.06; 0.08 | 0.16 | 0.09; 0.55 | 363.88 |
| 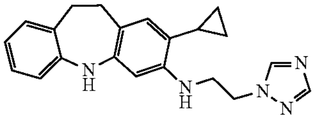 [SMILES: c1ccc2c(c1)CCc1cc(C3CC3)c(NCCn3cncn3)cc1N2] | C(CN1C=NC=N1)NC1=CC2=C(CCC3=CC=CC=C3N2)C=C1C1CC1 | SS20308-0269-01 | 0.55 | 0.11 | 0.55 | 345.2 |
| 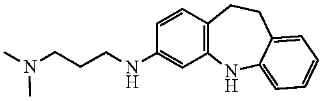 [SMILES: CN(C)CCCNc1ccc2c(c1)Nc1ccccc1CC2] | CN(C)CCCNC1=CC2=C(CCC3=CC=CC=C3N2)C=C1 | SS20308-0270-01 | 0.15; 0.15 | 0.1; 0.1 | 1.08; 0.9 | 295.42 |
| 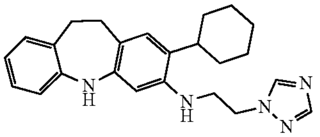 [SMILES: c1ccc2c(c1)CCc1cc(C3CCCCC3)c(NCCn3cncn3)cc1N2] | C(CN1C=NC=N1)NC1=CC2=C(CCC3=CC=CC=C3N2)C=C1C1CCCCC1 | SS20308-0271-01 | 0.15; 0.17 | 0.11; 0.12 | 0.28; 0.32 | 387.52 |
| 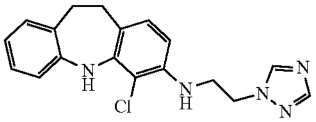 [SMILES: Clc1c(NCCn2cncn2)ccc2c1Nc1ccccc1CC2] | ClC1=C(NCCN2C=NC=N2)C=CC2=C1NC1=CC=CC=C1CC2 | SS20308-0273-01 | 5.6 | 2.66 | 9.82 | 339.82 |
| 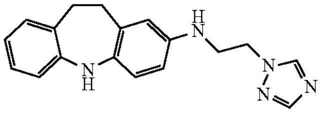 [SMILES: c1ccc2c(c1)CCc1cc(NCCn3cncn3)ccc1N2] | C(CN1C=NC=N1)NC1=CC2=C(NC3=CC=CC=C3CC2)C=C1 | SS20308-0276-01 | 0.13; 0.06 | 0.03; 0.02 | 0.28; 0.1 | 305.38 |
| 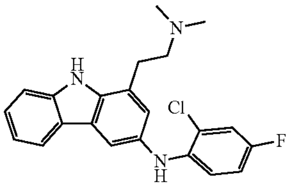 [SMILES: CN(C)CCc1cc(Nc2ccc(F)cc2Cl)cc2c1[nH]c1ccccc12] | CN(C)CCC1=CC(NC2=CC=C(F)C=C2C1)=CC2=C1NC1=CC=CC=C21 | SS20308-0277-01 | 0.32 | 0.04 | 0.57 | 381.87 |
| 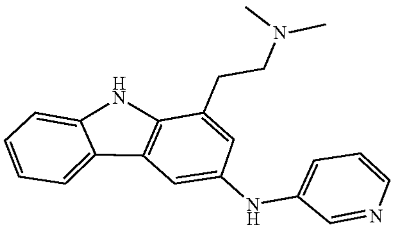 [SMILES: CN(C)CCc1cc(Nc2cccnc2)cc2c1[nH]c1ccccc12] | CN(C)CCC1=CC(NC2=CC=CN=C2)=CC2=C1NC1=CC=CC=C21 | SS20308-0291-01 | 0.06; 0.12 | 0.05; 0.06 | 0.02; 0.16 | 330.43 |

TABLE 1-continued

IC50 (μM) values for in vitro lipoxygenase inhibition

| Compound Structure | Smiles | SRI ID | 5-LOX | 12-LOX | 15-LOX | MW |
|---|---|---|---|---|---|---|
| 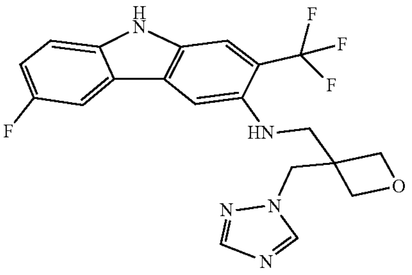 [SMILES: Fc1ccc2[nH]c3cc(C(F)(F)F)c(NCC4(Cn5cncn5)COC4)cc3c2c1] | FC1=CC=C2NC3=C(C=C(NCC4(CN5C=NC=N5)COC4)C(=C3)C(F)(F)F)C2=C1 | SS20308-0295-01 | 0.66 | 0.22 | 0.49 | 419.38 |
| 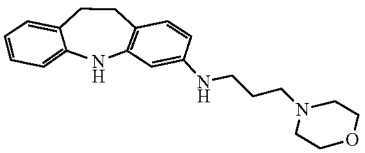 [SMILES: c1ccc2c(c1)CCc1ccc(NCCCN3CCOCC3)cc1N2] | C(CNC1=CC2=C(CCC3=CC=CC=C3N2)C=C1)CN1CCOCC1 | SS20308-0303-01 | 0.12 | 0.09 | 0.9 | 337.46 |
| 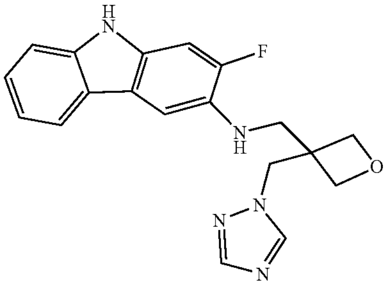 [SMILES: Fc1cc2[nH]c3ccccc3c2cc1NCC1(Cn2cncn2)COC1] | FC1=CC2=C(C=C1NCC1(CN3C=NC=N3)COC1)C1=CC=CC=C1N2 | SS20308-0304-01 | 0.2 | 0.09 | 0.4 | 351.38 |
| 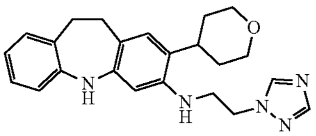 [SMILES: c1ccc2c(c1)CCc1cc(C3CCOCC3)c(NCCn3cncn3)cc1N2] | C(CN1C=NC=N1)NC1=CC2=C(CCC3=CC=CC=C3N2)C=C1C1CCOCC1 | SS20308-0305-01 | 0.2 | 0.14 | 0.58 | 389.4 |
| 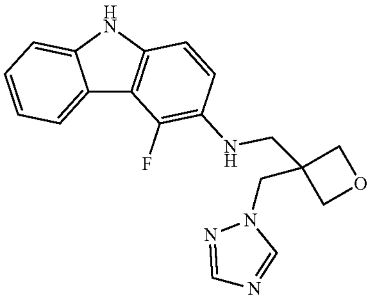 [SMILES: Fc1c(NCC2(Cn3cncn3)COC2)ccc2[nH]c3ccccc3c12] | FC1=C(NCC2(CN3C=NC=N3)COC2)C=CC2=C1C1=CC=CC=C1N2 | SS20308-0312-01 | 0.09 | 0.03 | 0.15 | 351.38 |

General information Examples: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

Example 1

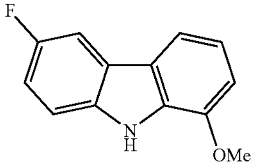

SS20308-0002-01
Chemical Formula: $C_{13}H_{10}FNO$
Molecular Weight: 215.23

Example Route for Example 1 (SS20308-0002-01):

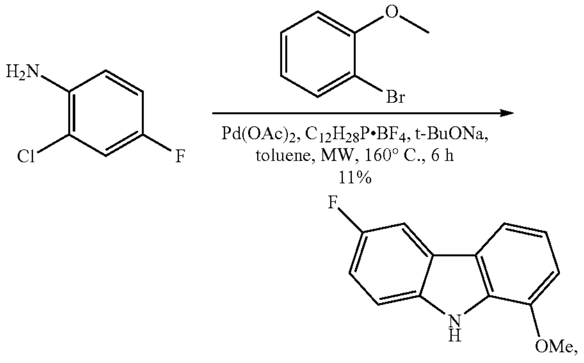

SS20308-0002-01

The synthesis of 6-fluoro-1-methoxy-9H-carbazole (SS20308-0002-01):

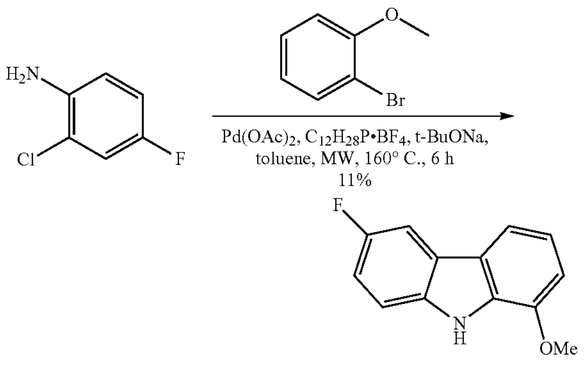

SS20308-0002-01

A mixture of 2-chloro-4-fluoroaniline (200 mg, 1.37 mmol), 1-bromo-2-methoxybenzene (322 mg, 1.64 mmol) and $Pd(OAc)_2$ (16 mg, 0.07 mmol), tri-n-butylphosphonium tetrafluoroborate (41 mg, 0.14 mmol) and t-BuONa (263 mg, 2.74 mmol), in toluene (5 mL) was stirred at 160° C. under nitrogen atmosphere overnight. After the reaction was complete, the insoluble material was removed by filtration. The filtrate was poured into water (20 mL) and extracted with EtOAc (20 mL×3). The combined layers were dried over $Na_2SO_4$, and concentrated under vacuum. The residue was purified by Prep-HPLC to give SS20308-0002-01 (32 mg, about 11% yield) as a solid. MS Calcd.: 215.1; MS Found: 216.1 $[M+H]^+$.

$^1$H NMR (400 MHz, $CDCl_3$) δ 8.23 (s, 1H), 7.90 (dd, J=9.0, 2.8 Hz, 1H), 7.61 (d, J=8.0 Hz, 1H), 7.37 (dd, J=8.8, 4.0 Hz, 1H), 7.17-6.92 (m, 2H), 6.91 (d, J=7.6 Hz, 1H), 4.01 (s, 3H).

Example 2

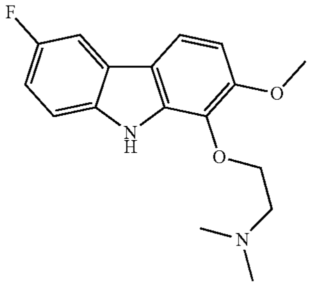

SS20308-0007-01
Chemical Formula: $C_{17}H_{19}FN_2O_2$
Molecular Weight: 302.35

Example Route for Example 2 (SS20308-0007-01):

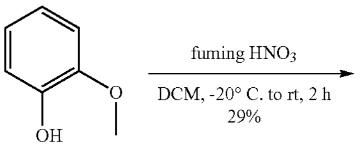

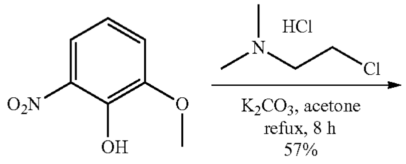

7-1

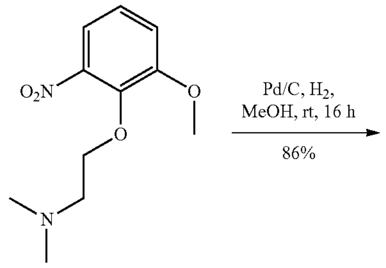

7-2

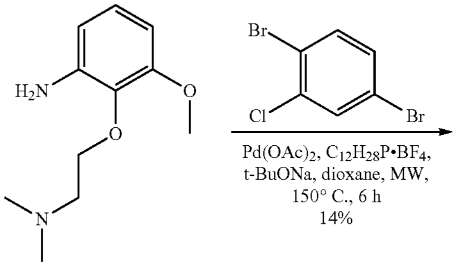

7-3

-continued

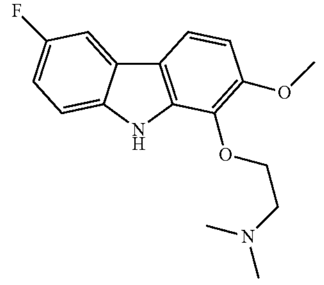

SS20308-0007-01

The synthesis of 2-methoxy-6-nitrophenol (7-1):

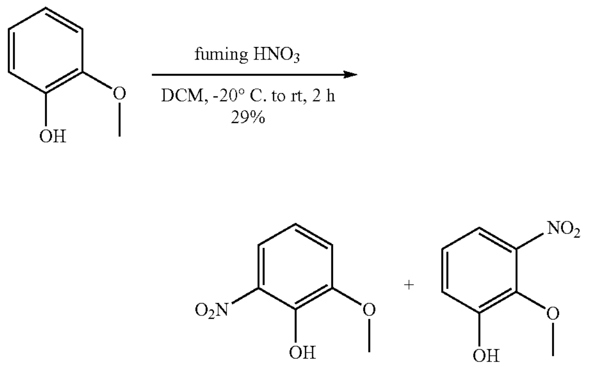

7-1

To a solution of 2-methoxyphenol (5.0 g, 40.3 mmol) in DCM (50 mL) was added fuming $HNO_3$ (1.7 mL, 40.3 mmol, d=1.5) at −20° C. and then the reaction mixture was stirred at room temperature for 5 h. After the reaction was complete, the reaction mixture was quenched with water (100 mL) and extracted with EtOAc (100 mL×3). The combined layers were dried over $Na_2SO_4$ and concentrated under vacuum. The residue was purified by column chromatography on silica gel (EtOAc/petroleum ether=1/10) to give 7-1 (2.0 g, about 29% yield) as a solid.

$^1$H NMR (400 MHz, $CDCl_3$) δ 10.78 (s, 1H), 7.71 (dd, J=8.8, 1.6 Hz, 1H), 7.71 (dd, J=8.0, 1.2 Hz, 1H), 6.92 (dd, J=8.4, 8.4 Hz, 1H), 3.96 (s, 3H).

The synthesis of 2-(2-methoxy-6-nitrophenoxy)-N,N-dimethylethanamine (7-2).

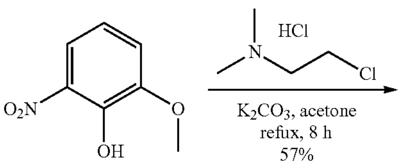

7-1

-continued

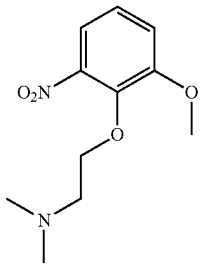

7-2

A mixture of the 7-1 (1.5 g, 8.88 mmol), 2-chloro-N,N-dimethylethanamine hydrochloride (1.9 g, 13.3 mmol) and $K_2CO_3$ (3.7 g, 26.6 mmol) in acetone (30 mL) was stirred at 70° C. overnight. After the reaction was complete, the reaction mixture was quenched with water (10 mL), extracted with EtOAc (30 mL×3). The combined layers were dried over $Na_2SO_4$ and concentrated under vacuum. The residue was purified by column chromatography on silica gel (petroleum ether/EtOAc=10/1) to give 7-2 (1.2 g, about 57% yield) as a solid. MS Calcd.: 240.1; MS Found: 241.4 $[M+H]^+$.

The synthesis of 2-(2-(dimethylamino)ethoxy)-3-methoxyaniline (7-3):

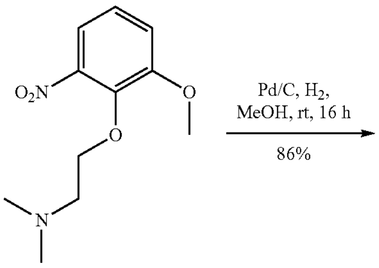

7-2

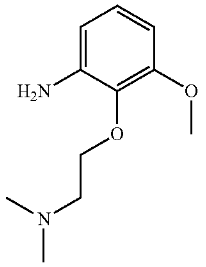

7-3

A mixture of 7-2 (1.2 g, 5.0 mmol) and Pd/C (0.2 g, 10%) in MeOH (10 mL) was stirred at room temperature overnight under hydrogen gas (balloon). After the reaction was complete, the insoluble material was removed by filtration. The filtrate was concentrated under vacuum. The residue was purified by column chromatography on silica gel (petroleum ether/EtOAc=10/1) to give 7-3 (900 mg, about 86% yield) as a solid. MS Calcd.: 210.1; MS Found: 211.4 $[M+H]^+$.

The synthesis of 2-(6-fluoro-2-methoxy-9H-carbazol-1-yloxy)-N,N-dimethylethanamine (SS20308-0007-01):

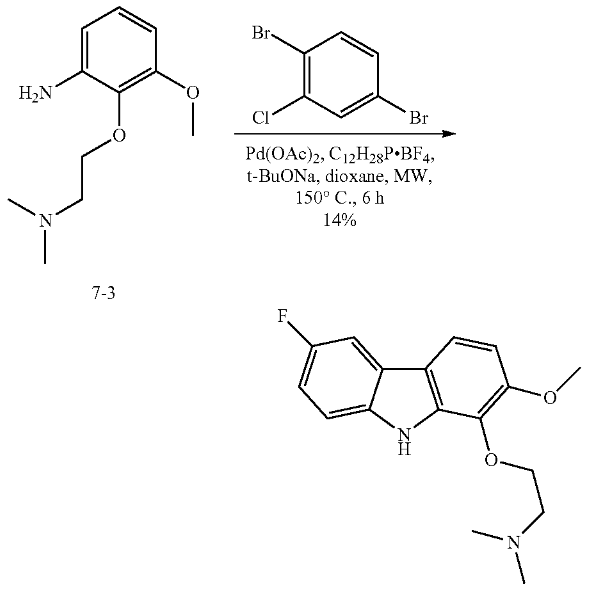

7-3

SS20308-0007-01

A mixture of 7-3 (600 mg, 2.86 mmol), 1-bromo-2-chloro-4-fluorobenzene (714 mg, 3.43 mmol) and $Pd(OAc)_2$ (32 mg, 0.14 mmol), tri-n-butylphosphonium tetrafluoroborate (84 mg, 0.29 mmol) and t-BuONa (686 mg, 7.15 mmol), in dioxane (10 mL) was stirred at 150° C. under nitrogen atmosphere overnight. After the reaction was complete, the insoluble material was removed by filtration. The filtrate was poured into water (30 mL) and extracted with EtOAc (30 mL×3). The combined layers were dried over $Na_2SO_4$, and concentrated under vacuum. The residue was purified by Prep-HPLC to give SS20308-0007-01 (120 mg, about 14% yield) as a solid. MS Calcd.: 302.1; MS Found: 303.2 $[M+H]^+$.

$^1$H NMR (400 MHz, DMSO-$d_6$) δ 11.28 (s, 1H), 7.83 (dd, J=9.4, 2.8 Hz, 1H), 7.78 (d, J=8.4 Hz, 1H), 7.44 (dd, J=8.8, 4.4 Hz, 1H), 7.17-7.12 (m, 1H), 6.94 (d, J=8.8 Hz, 1H), 4.14 (t, J=6.0 Hz, 2H), 3.89 (s, 3H), 2.65 (t, J=6.0 Hz, 2H), 2.27 (s, 6H).

Example 3

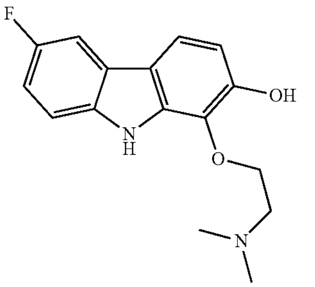

SS20308-0004-01

Chemical Formula: $C_{16}H_{17}FN_2O_2$

Molecular Weight: 288.32

Example Route for Example 3 (SS20308-0004-01):

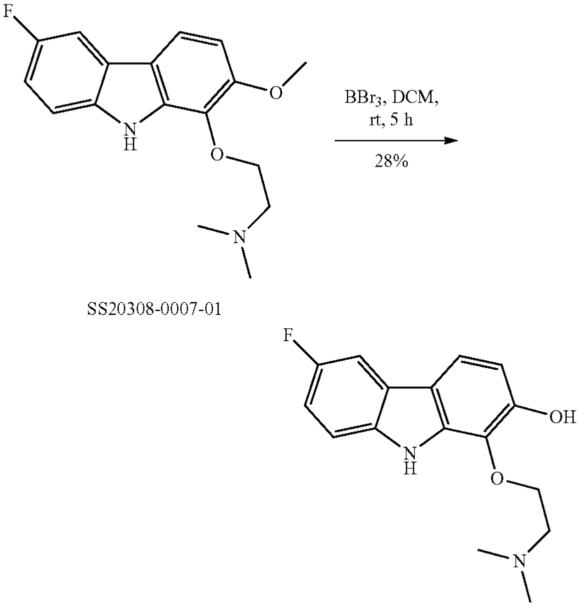

SS20308-0007-01

SS20308-0004-01

The synthesis of 1-(2-(dimethylamino)ethoxy)-6-fluoro-9H-carbazol-2-ol (SS20308-0004-01):

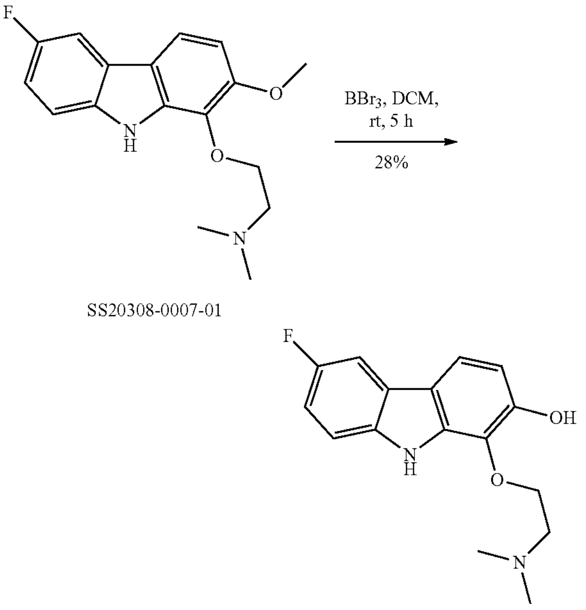

SS20308-0007-01

SS20308-0004-01

A mixture of SS20308-0007-01 (80 mg, 0.26 mmol) and $BBr_3$ (1 M in DCM, 0.52 mL, 0.52 mmol) in DCM (3 mL) was stirred at room temperature for 5 h. After the reaction was complete, the mixture was poured into water (10 mL) and extracted with EtOAc (10 mL×3). The combined layers were dried over $Na_2SO_4$, and concentrated under vacuum. The residue was purified by Prep-HPLC to give SS20308-0004-01 (21 mg, about 28% yield) as a solid. MS Calcd.: 288.1; MS Found: 289.2 $[M+H]^+$.

$^{1}H$ NMR (400 MHz, $CDCl_3$) δ 8.11 (s, 1H), 7.60 (d, J=8.4 Hz, 1H), 7.57 (dd, J=9.2, 2.8 Hz, 1H), 7.30-7.27 (m, 1H), 7.06-7.01 (m, 1H), 6.83 (d, J=8.4 Hz, 1H), 4.24 (t, J=5.2 Hz, 2H), 2.69 (t, J=5.2 Hz, 2H), 2.47 (s, 6H).

Example 4

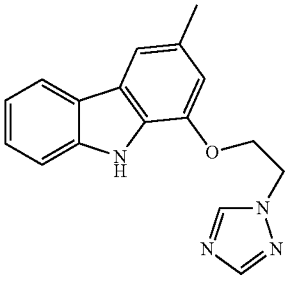

SS20308-0017-01
Chemical Formula: $C_{17}H_{16}N_4O$
Molecular Weight: 292.34

Example Route for Example 4 (SS20308-0017-01):

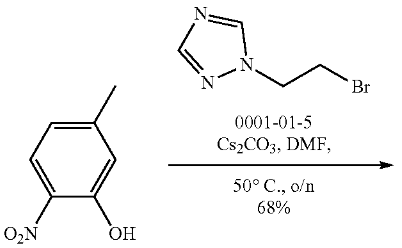

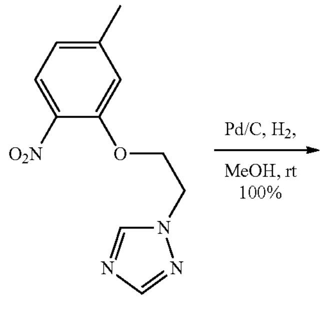

17-1

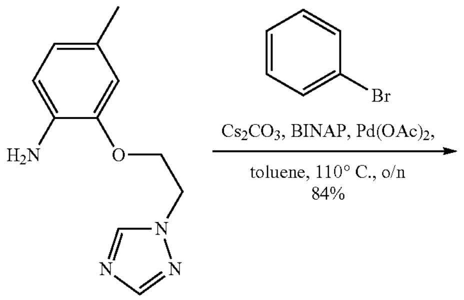

17-2

-continued

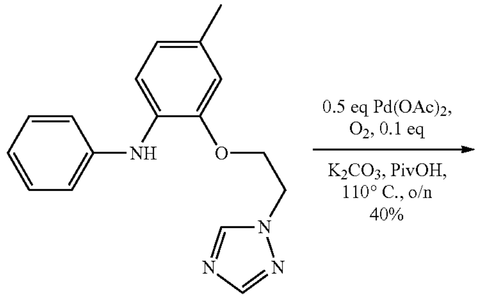

17-3

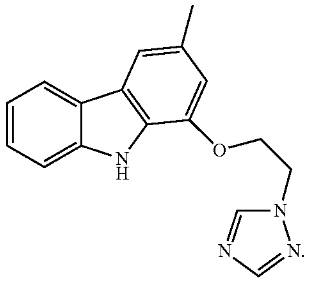

SS20308-0017-01

The synthesis of 1-(2-(5-methyl-2-nitrophenoxy)ethyl)-1H-1,2,4-triazole (17-1):

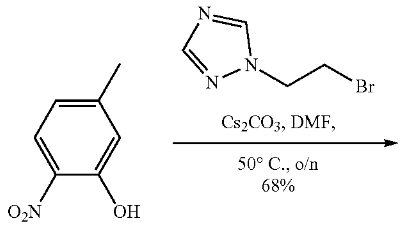

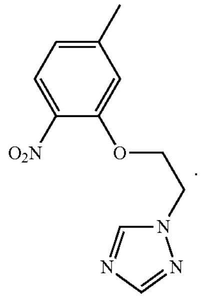

17-1

A mixture of 5-methyl-2-nitrophenol (1.0 g, 6.53 mmol), 1-(2-bromoethyl)-1H-1,2,4-triazole (2.6 g, 15.02 mmol) and anhydrous cesium carbonate (11.9 g, 36.57 mmol) in DMF (40 mL) was stirred at 50° C. overnight. Then the reaction mixture was quenched with water (200 mL), and extracted with EtOAc (50 mL×3). The organic layers were washed with water and brine, dried over $MgSO_4$ and concentrated. The residue was purified by column chromatography on silica gel (petroleum ether/EtOAc=3/1 to 1/1 to 1/3) to give 17-1 (1.1 g, about 68% yield) as a solid. MS Calcd.: 248.1; MS Found: 249.4 $[M+H]^+$.

The synthesis of 2-(2-(1H-1,2,4-triazol-1-yl)ethoxy)-4-methylaniline (17-2):

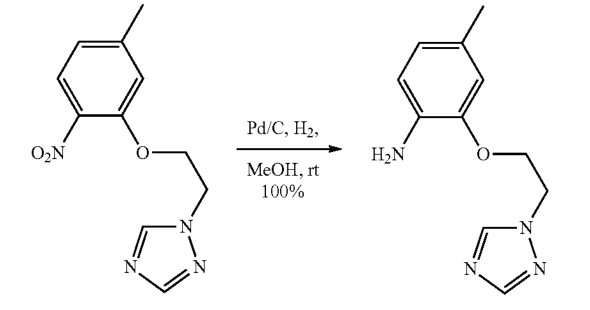

17-1 17-2

A suspension of 17-1 (1.1 g, 4.4 mmol) in MeOH (30 mL) was added 110 mg of 10% palladium on carbon and stirred vigorously under hydrogen gas (balloon) overnight at room temperature. The solid was removed by filtration through a pad of celite and the filtrate was concentrated. The residue was purified by column chromatography on silica gel (petroleum ether/EtOAc=1/1 to 1/3) to (DCM/MeOH=30/1) to give 17-2 (0.97 g, about 100% yield) as a solid. MS Calcd.: 218.1; MS Found: 219.4 $[M+H]^+$.

The synthesis of 2-(2-(1H-1,2,4-triazol-1-yl)ethoxy)-4-methyl-N-phenylaniline (17-3):

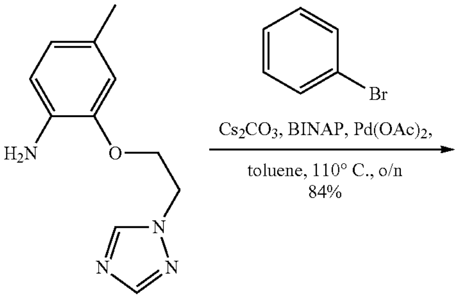

17-2

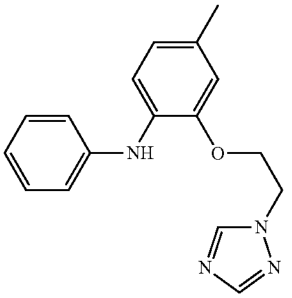

17-3

A solution of 17-2 (532 mg, 2.44 mmol), bromobenzene (575 mg, 3.66 mmol), BINAP (152 mg, 0.24 mmol), palladium (II) acetate (28 mg, 0.12 mmol), and anhydrous cesium carbonate (1.2 g, 3.66 mmol,) were suspended in toluene (20 mL). The reaction mixture was heated overnight at reflux under nitrogen and then filtered, followed by rinsing with EtOAc. The filtrate was concentrated and purified by column chromatography on silica gel (petroleum ether/EtOAc=3/1 to 1/1) to give 17-3 (0.6 g, about 84% yield) as an oil. MS Calcd.: 294.2; MS Found: 295.4 $[M+H]^+$.

The synthesis of 1-(2-(1H-1,2,4-triazol-1-yl)ethoxy)-3-methyl-9H-carbazole (SS20308-0017-01):

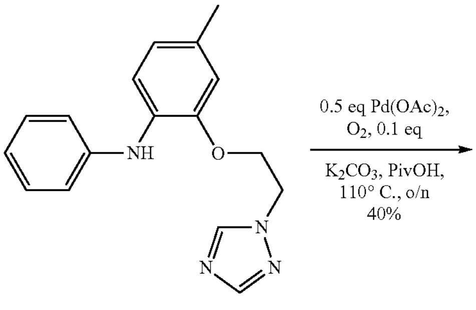

17-3

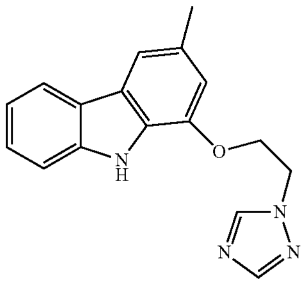

SS20308-0017-01

A mixture of 17-3 (50 mg, 0.17 mmol), pivalic acid (500 mg), palladium (II) acetate (20 mg, 0.089 mmol), and anhydrous potassium carbonate (2.4 mg, 0.017 mmol,) were heated overnight at 110° C. under oxygen gas (balloon) and then cooled to room temperature. The solid was dissolved in ACN and basicified with NaOH (10%) to pH=11. After stirring for 2 h, the mixture was extracted with EtOAc (20 mL×3). The organic layers were washed with water and brine, dried over $MgSO_4$ and concentrated. The residue was purified by Prep-TLC (DCM/MeOH=30/1) to give SS20308-0017-01 (20 mg, about 40% yield) as a solid. MS Calcd.: 292.1; MS Found: 293.3 $[M+H]^+$.

$^1H$ NMR (400 MHz, $CDCl_3$) δ 8.28-8.21 (m, 2H), 8.03 (s, 1H), 7.99 (d, J=4.0 Hz, 1H), 7.52 (s, 1H), 7.46-7.37 (m, 2H), 7.23-7.17 (m, 1H), 6.72 (s, 1H), 4.66 (t, J=4.8 Hz, 2H), 4.58 (t, J=4.8 Hz, 2H), 2.50 (s, 3H).

Example 5

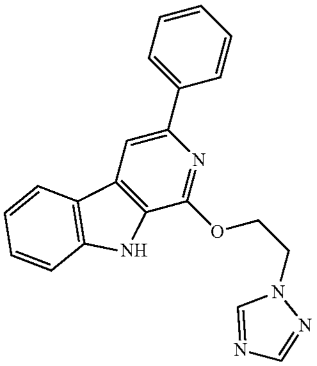

SS20308-0018-01
Chemical Formula: $C_{21}H_{17}N_5O$
Molecular Weight: 355.40

Example Route for Example 5 (SS20308-0018-01):

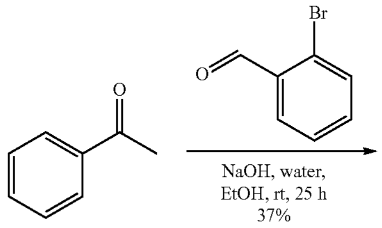

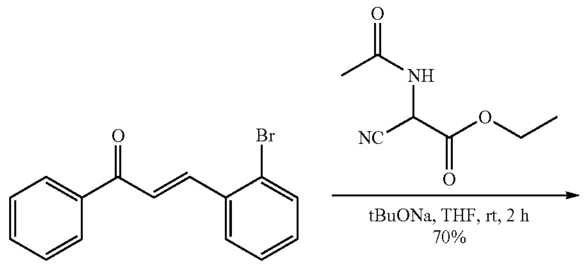

18-1

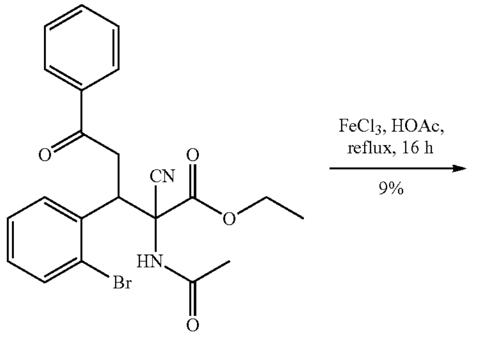

18-2

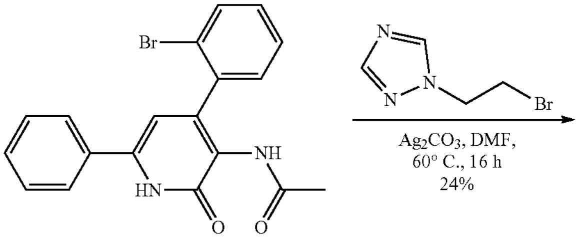

18-3

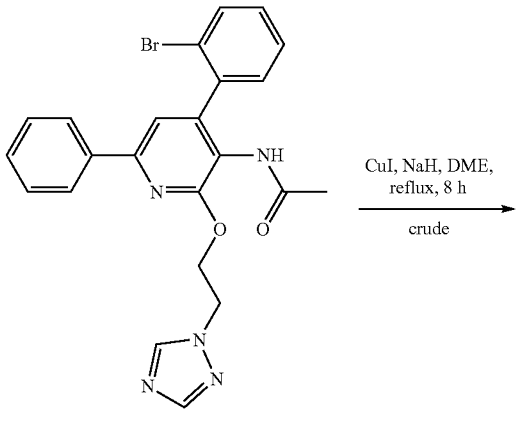

18-4

-continued

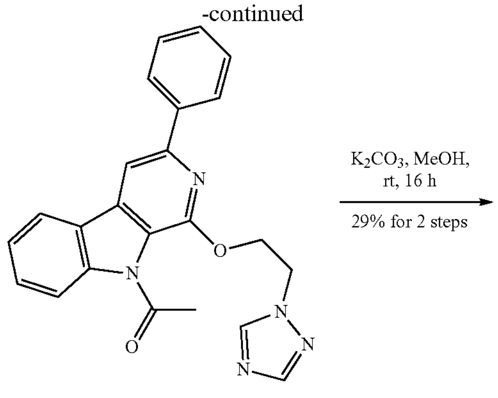

18-5

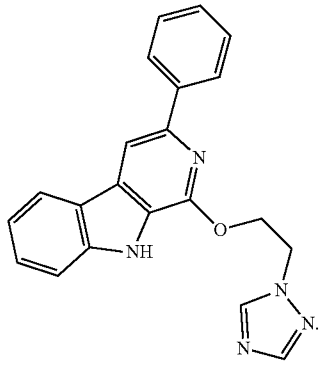

SS20308-0018-01

The synthesis of (E)-3-(2-bromophenyl)-1-phenylprop-2-en-1-one (18-1):

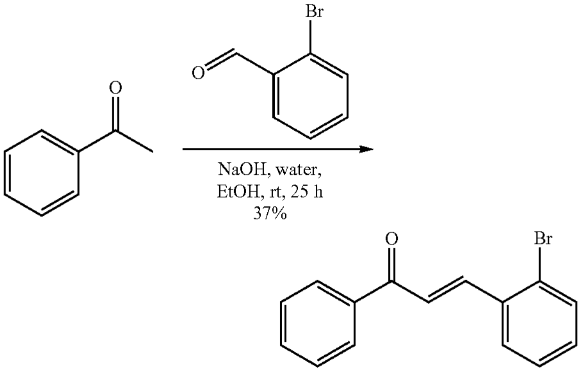

18-1

A mixture of acetophenone (2.5 g, 20.8 mmol) and 2-bromobenzaldehyde (3.8 g, 20.8 mmol) was added to the solution of NaOH (1.1 g, 27.1 mmol) in water (10 mL) and EtOH (10 mL) dropwise at 0° C. When the addition was complete, the mixture was stirred at room temperature for 25 h. The mixture was diluted with EtOAc (100 mL). The organic layer was successively washed with water (100 mL) and saturated brine (100 mL). The organic layer was then dried with $MgSO_4$ and concentrated under reduced pressure. The crude product was purified by column chromatography on silica gel (petroleum ether/EtOAc=1/10) to give 18-1 (2.2 g, about 37% yield) as an oil. MS Calcd.: 286.0; MS Found: 287.1 $[M+H]^+$.

The synthesis of ethyl 2-acetamido-3-(2-bromophenyl)-2-cyano-5-oxo-5-phenylpentanoate (18-2)"

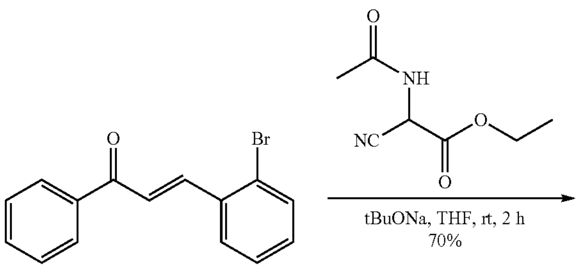

18-1

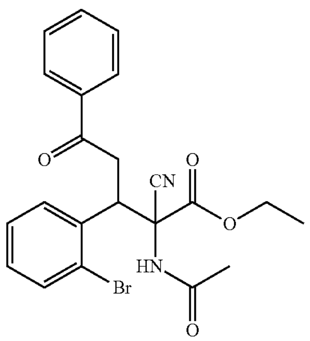

18-2

To a mixture of 18-1 (2.0 g, 7.0 mmol) and ethyl 2-acetamido-2-cyanoacetate (2.4 g, 14.0 mmol) in THF (40 mL) was added t-BuONa (67 mg, 0.7 mmol) at 0° C. Then the mixture was stirred at room temperature for 2 h under nitrogen. The reaction mixture was cooled to room temperature, filtered and washed with EtOAc (50 mL). The mixture was diluted with DCM (100 mL). The organic layer was successively washed with sat $Na_2CO_3$ (70 mL) and saturated brine solution (100 mL). The organic layer was then dried with $MgSO_4$ and concentrated under reduced pressure. The crude product was purified by column chromatography on silica gel (petroleum ether/EtOAc=1/1) to give 18-2 (2.2 g, about 70% yield) as a solid. MS Calcd.: 456.1; MS Found: 457.1 [M+H]$^+$.

The synthesis of N-(4-(2-bromophenyl)-2-oxo-6-phenyl-1,2-dihydropyridin-3-yl)acetamide (18-3):

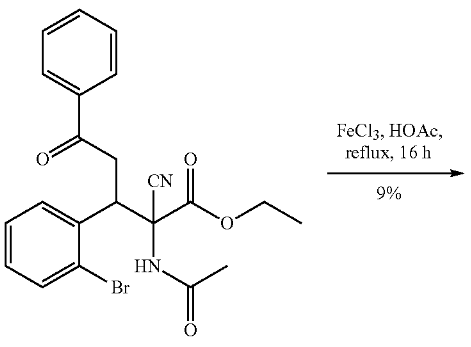

18-2

-continued

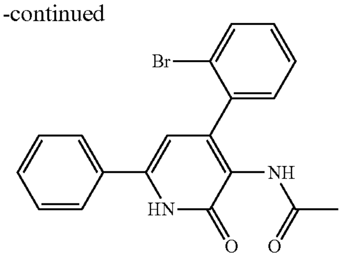

18-3

To a mixture of 18-2 (2.1 g, 4.6 mmol) in HOAc (30 mL) was added $FeCl_3$ (1.5 g, 9.2 mmol) at room temperature, then the mixture was heated to reflux for 16 h. The reaction mixture was cooled to room temperature, and diluted with DCM (100 mL). The organic layer was successively washed with sat. $Na_2CO_3$ (70 mL) and brine (100 mL). The organic layer was then dried with $MgSO_4$ and concentrated under reduced pressure. The crude product was purified by column chromatography on silica gel (MeOH/DCM=1/10) to give 18-3 (150 mg, about 9% yield) as a solid. MS Calcd.: 382.0; MS Found: 383.2 [M+H]$^+$.

The synthesis of N-(2-(2-(1H-1,2,4-triazol-1-yl)ethoxy)-4-(2-bromophenyl)-6-phenylpyridin-3-yl)acetamide (18-4):

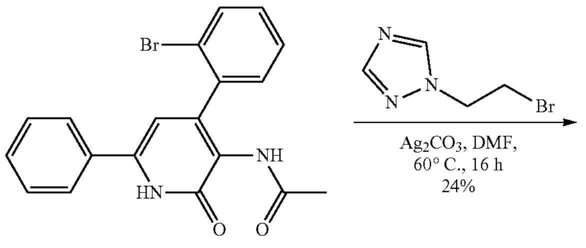

18-3

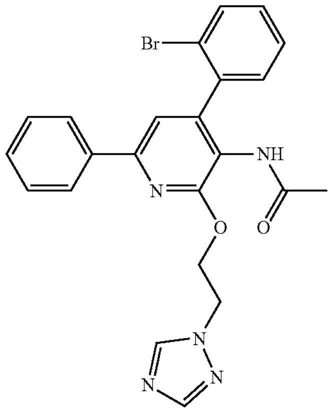

18-4

To a mixture of 18-3 (500 mg, 1.3 mmol) in DMF (10 mL) was added 1-(2-bromoethyl)-1H-1,2,4-triazole (229 mg, 1.3 mmol) and $Ag_2CO_3$ (713 mg, 2.6 mmol) at room temperature, then the mixture was heated to 60° C. for 16 h. The reaction mixture was cooled to room temperature and diluted with EtOAc (50 mL). The organic layer was successively washed with brine (100 mL). The organic layer was then dried with $MgSO_4$ and concentrated under reduced pressure. The crude product was purified by reverse phase column chromatography to give 18-4 (140 mg, about 24% yield) as a solid. MS Calcd.: 477.1; MS Found: 478.2 $[M+H]^+$.

The synthesis of 1-(1-(2-(1H-1,2,4-triazol-1-yl)ethoxy)-3-phenyl-9H-pyrido[3,4-b]indol-9-yl)ethanone (18-5):

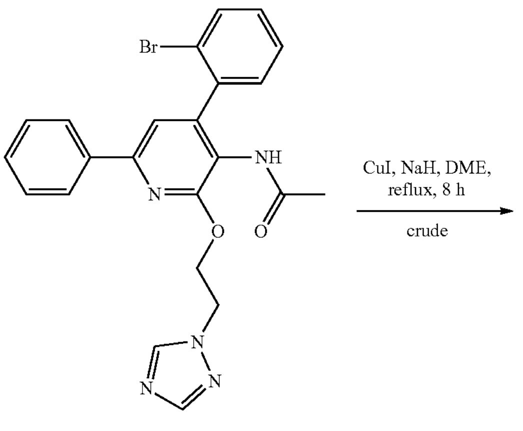

18-4

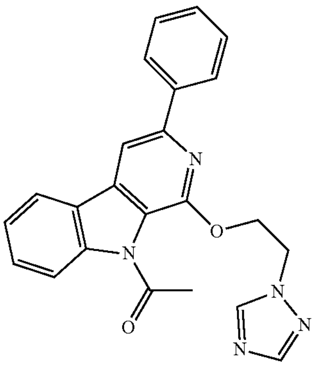

18-5

To a mixture of 18-4 (140 mg, 0.3 mmol) in DME (5 mL) was added CuI (171 mg, 0.9 mmol) and NaH (20 mg, 0.5 mmol) at room temperature, then the mixture was heated to reflux for 8 h. The reaction mixture was cooled to room temperature and the crude solution 18-5 was used for next step directly. MS Calcd.: 397.2; MS Found: 398.4 $[M+H]^+$.

The synthesis of 1-(1-(2-(1H-1,2,4-triazol-1-yl)ethoxy)-3-phenyl-9H-pyrido[3,4-b]indol-9-yl)ethanone (SS20308-0018-01):

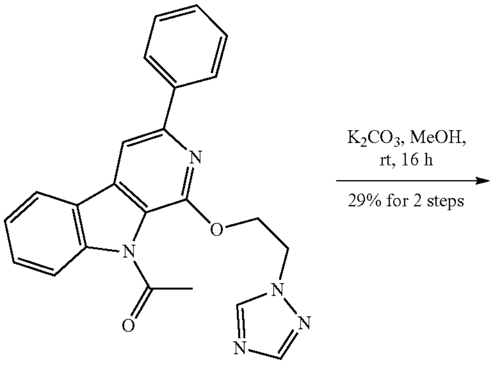

18-5

-continued

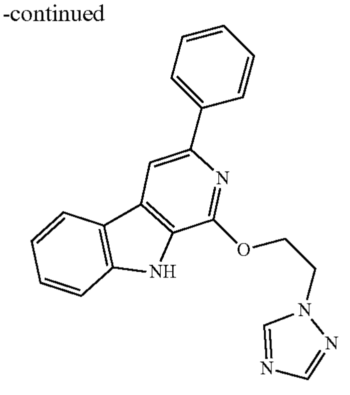

SS20308-0018-01

To a mixture of crude 18-5 was added $K_2CO_3$ (359 mg, 2.6 mmol) and MeOH (5 mL) at room temperature. The mixture was then stirred at room temperature for 16 h. The reaction mixture was filtered and washed by MeOH. The filtrate was concentrated to an oil, which was purified by Prep-HPLC to give SS20308-0018-01 (30 mg, about 29% yield for 2 steps) as a solid. MS Calcd.: 355.1; MS Found: 356.3 $[M+H]^+$.

$^1$H NMR (400 MHz, DMSO-$d_6$) δ 11.67 (s, 1H), 8.70 (s, 1H), 8.40 (s, 1H), 8.25 (d, J=8.0, 1H), 8.19 (dd, J=8.4, 1.2 Hz, 2H), 8.00 (s, 1H), 7.58 (d, J=8.4 Hz, 1H), 7.54-7.46 (m, 3H), 7.35 (dd, J=7.6, 7.2 Hz, 1H), 7.25 (dd, J=7.6, 7.2 Hz, 1H), 4.99 (t, J=5.0 Hz, 2H), 4.79 (t, J=4.8 Hz, 2H).

Example 6

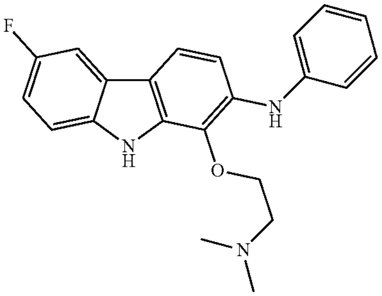

SS20308-0032-01
Chemical Formula: $C_{22}H_{22}FN_3O$
Molecular Weight: 363.43

Example Route for Example 6 (SS20308-0032-01):

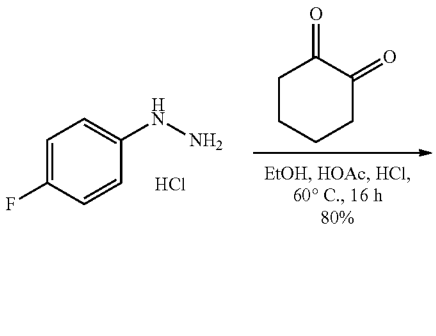

-continued

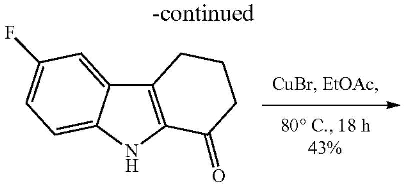

32-1

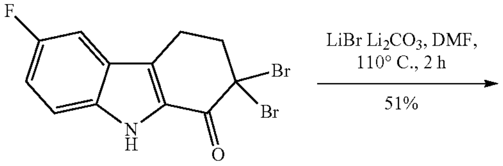

32-2

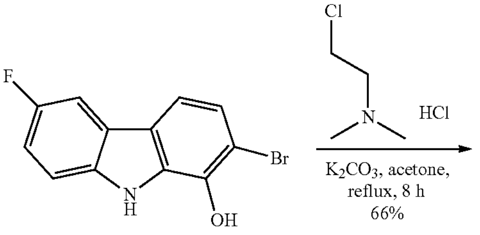

32-3

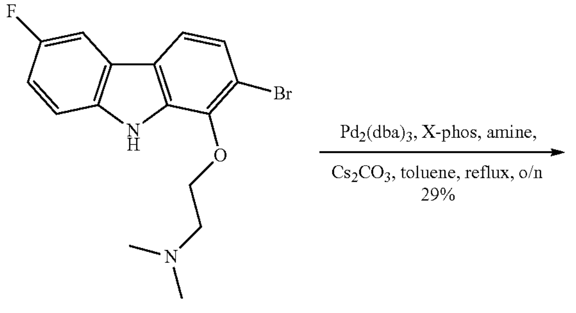

32-3

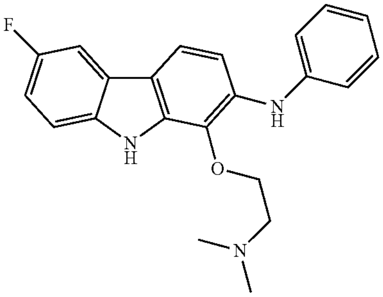

SS20308-0032-01

The synthesis of 6-fluoro-2,3,4,9-tetrahydro-1H-carbazol-1-one (32-1):

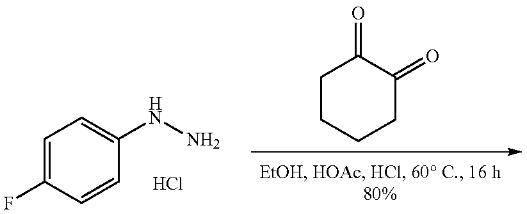

-continued

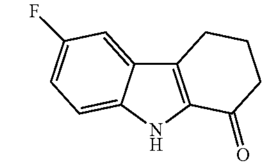

32-1

To a solution of 4-fluoro-phenyl hydrazine hydrochloride (2.0 g, 12.3 mmol) in EtOH (20 mL), heated to 60° C., was added cyclohexane-1,2-dione (1.5 g, 12.9 mmol) in AcOH (21 mL) and conc. HCl (9 mL). The reaction mixture was stirred at 60° C. for 16 h, then neutralized with saturated $NaHCO_3$ (20 mL) and extracted with EtOAc (2×20 mL). The organic layer was washed with brine and evaporated, the residue crude product was purified by column chromatography on silica gel (petroleum ether/EtOAc=5/1) to give 32-1 (2.0 g, about 80% yield) as a solid. MS Calcd.: 203.1; MS Found: 204.3 $[M+H]^+$.

The synthesis of 2,2-dibromo-6-fluoro-2,3,4,9-tetrahydro-1H-carbazol-1-one (32-2):

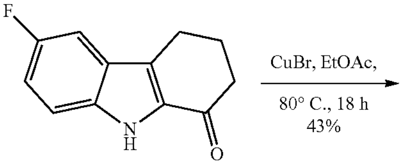

32-1

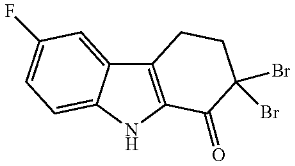

32-2

To a solution of 32-1 (2.0 g, 9.85 mmol) in EtOAc (20 mL) was added CuBr (1.5 g, 68.95 mmol,) the reaction mixture was heated to 80° C. for 18 h and filtered, the combined organic extracts were concentrated under reduced pressure to give a crude solid, which was purified by column chromatography on silica gel (petroleum ether/EtOAc=5/1) to give 32-2 (1.5 g, about 43% yield) as a solid. MS Calcd.: 358.9; MS Found: 360.2 $[M+H]^{30}$.

The synthesis of 2-bromo-6-fluoro-9H-carbazol-1-ol (32-3):

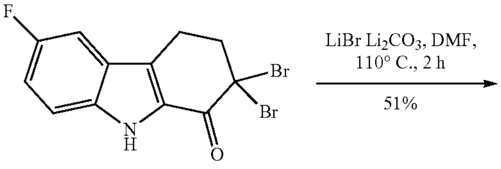

32-2

-continued

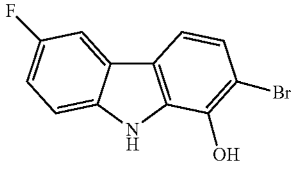

32-3

Compound 32-2 (1.5 g, 4.2 mmol) was dissolved in DMF (20 mL) and LiBr (397 mg, 4.6 mmol) followed by $Li_2CO_3$ (340 g, 4.6 mmol) were added. The reaction mixture was heated to 110° C. for 2 h, cooled to room temperature and quenched with saturated $NH_4Cl$ (50 mL), extracted with EtOAc (2×30 mL) and the combined organic extracts were concentrated in vacuo to give the crude compound which was purified by column chromatography on silica gel (EtOAc) to give 32-3 (600 mg, about 51% yield) as a solid. MS Calcd.: 279.0; MS Found: 280.1 $[M+H]^+$.

The synthesis of 2-(2-bromo-6-fluoro-9H-carbazol-1-yloxy)-N,N-dimethylethanamine (32-4):

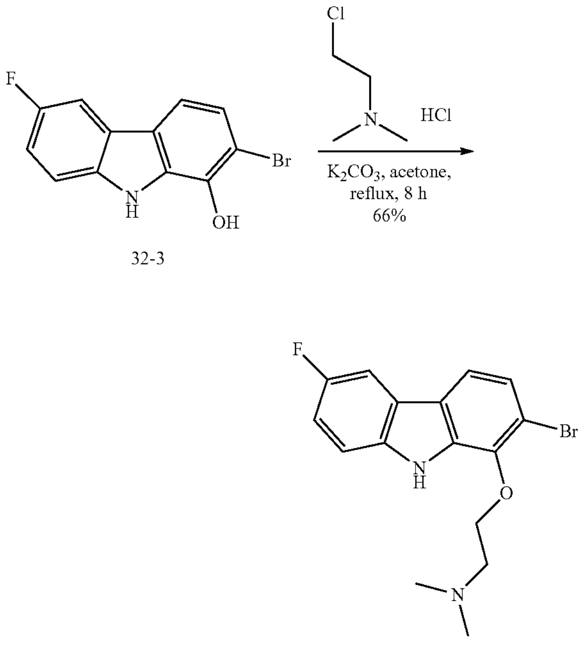

32-3

32-4

A mixture of 32-3 (600 mg, 2.15 mmol), 2-chloro-N,N-dimethylethanamine hydrochloride (465 mg, 3.23 mmol) and $K_2CO_3$ (593 mg, 4.30 mmol) in acetone (10 mL) was stirred at 70° C. overnight. The reaction mixture was cooled to room temperature and poured into water (100 mL) and extracted with EtOAc (60 mL×3). The organic layer was washed with brine and evaporated, the residue crude product was purified by column chromatography on silica gel (petroleum ether/EtOAc=4/1) to give 32-4 (500 mg, about 66% yield) as a solid. MS Calcd.: 350.0; MS Found: 351.0 $[M+H]^+$.

The synthesis of 1-(2-(dimethylamino)ethoxy)-6-fluoro-N-phenyl-9H-carbazol-2-amine (SS20308-0032-01):

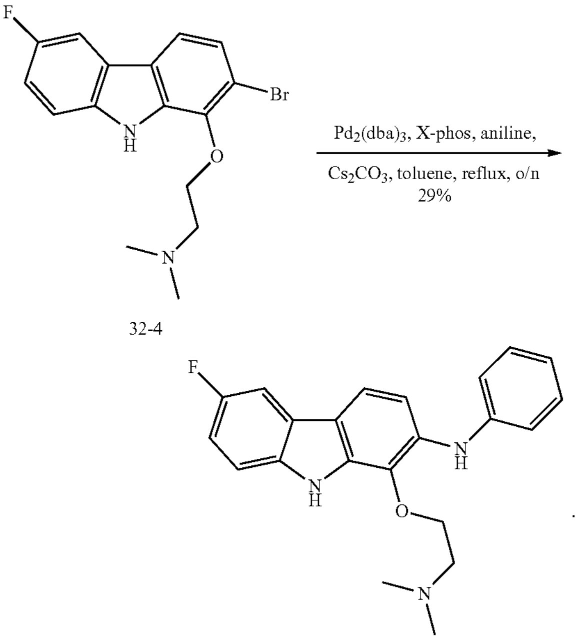

32-4

SS20308-0032-01

A mixture of 32-4 (100 mg, 0.29 mmol), aniline (54 mg, 0.58 mmol), $Pd_2(dba)_3$ (11 mg, 0.02 mmol), X-Phos (14 mg, 0.03 mmol) and $Cs_2CO_3$ (188 mg, 0.58 mmol) in toluene (3 mL) was stirred at reflux overnight. The reaction mixture was cooled to room temperature and poured into water (5 mL) and extracted with EtOAc (5 mL×3). The organic layer was washed with brine and evaporated, the residue crude product was purified by Prep-TLC (DCM/MeOH=20/1) to give SS20308-0032-01 (31 mg, about 29% yield) as a solid. MS Calcd.: 363.2; MS Found: 364.3 $[M+H]^+$.

$^1H$ NMR (400 MHz, $CDCl_3$) δ 11.09 (s, 1H), 7.58 (d, J=8.4 Hz, 1H), 7.58 (dd, J=9.2, 2.4 Hz, 1H), 7.33-7.29 (m, 1H), 7.23-7.22 (m, 2H), 7.10-7.06 (m, 3H), 7.04 (dt, J=9.2, 2.8 Hz, 1H), 6.86 (t, J=7.2 Hz, 1H), 6.51 (s, 1H), 4.22-4.20 (m, 2H), 2.80 (t, J=6.4 Hz, 2H), 2.52 (s, 6H).

Example 7

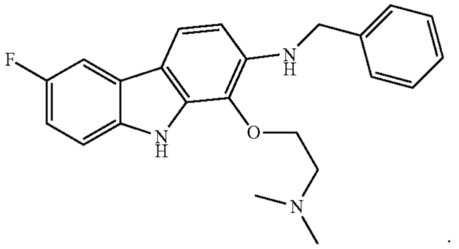

SS20308-0036-01
Chemical Formula: $C_{23}H_{24}FN_3O$
Molecular Weight: 377.45

The synthesis of N-benzyl-1-(2-(dimethylamino)ethoxy)-6-fluoro-9H-carbazol-2-amine (SS20308-0036-01):

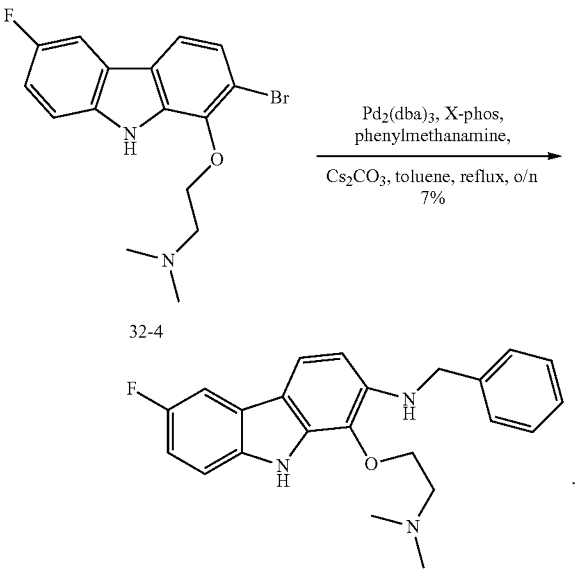

32-4

SS20308-0036-01

A mixture of 32-4 (100 mg, 0.29 mmol), phenylmethanamine (62 mg, 0.58 mmol), $Pd_2(dba)_3$ (11 mg, 0.02 mmol), X-Phos (14 mg, 0.03 mmol) and $Cs_2CO_3$ (188 mg, 0.58 mmol) in toluene (3 mL) was stirred at reflux overnight. The reaction mixture was cooled to room temperature and poured into water (5 mL) and extracted with EtOAc (5 mL×3). The organic layer was washed with brine and concentrated. The residue crude product was purified by Prep-TLC (DCM/MeOH=20/1) to give SS20308-0036-01 (8 mg, about 7% yield) as a solid. MS Calcd.: 377.2; MS Found: 378.0 $[M+H]^+$.

$^1H$ NMR (400 MHz, $CDCl_3$) δ 11.02 (s, 1H), 7.52 (d, J=8.4 Hz, 1H), 7.58 (dd, J=9.4, 2.4 Hz, 1H), 7.35-7.32 (m, 2H), 7.30-7.26 (m, 3H), 7.23-7.20 (m, 2H), 6.93 (dt, J=9.2, 2.4 Hz, 1H), 6.55 (d, J=8.8 Hz, 1H), 6.39 (s, 2H), 4.20-4.10 (m, 2H), 2.77-2.73 (m, 2H), 2.51 (s, 6H).

Example 8

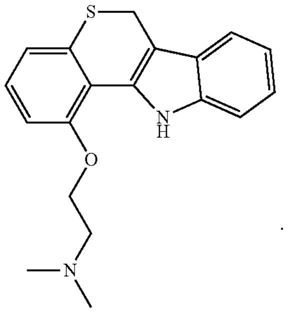

SS20308-0046-01

Chemical Formula: $C_{19}H_{20}N_2OS$

Molecular Weight: 324.44

Route for SS20308-0046-01:

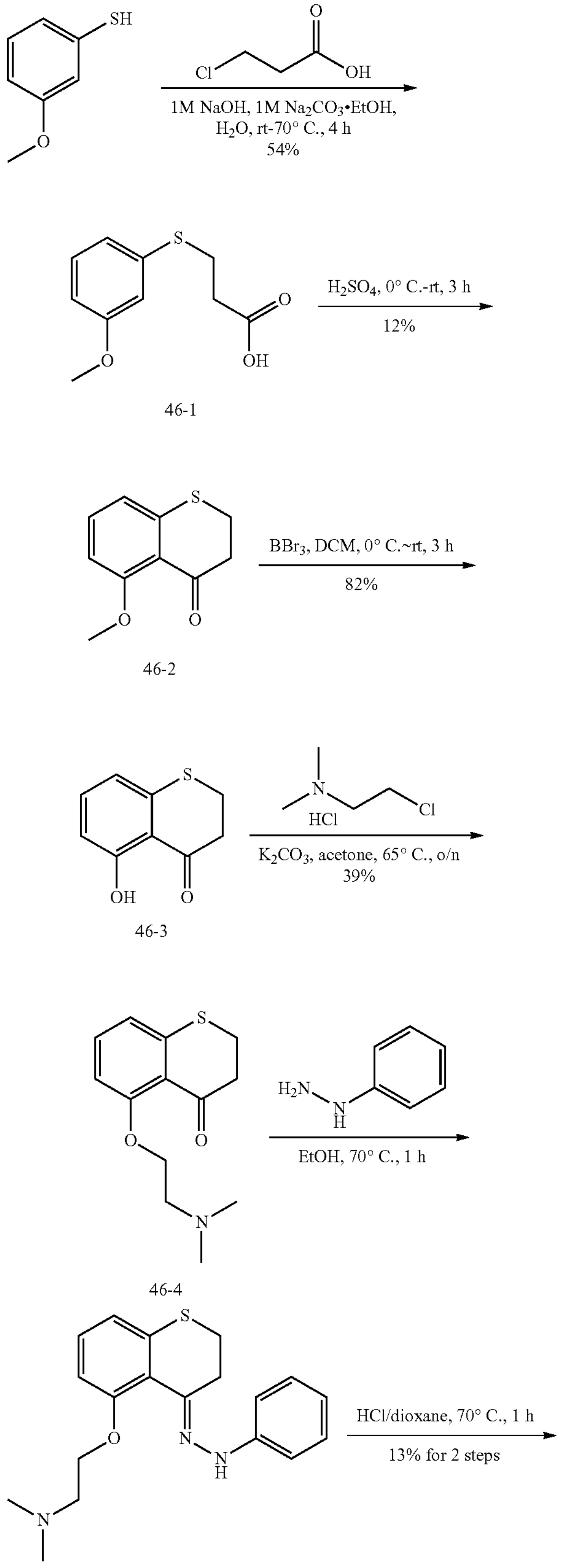

46-1

46-2

46-3

46-4

46-5

-continued

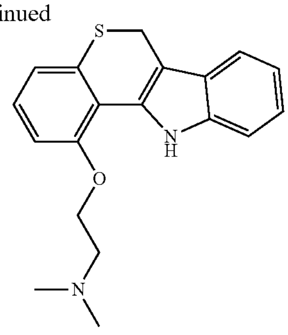

SS20308-0046-01

The synthesis of 3-(3-methoxyphenylthio)propanoic acid (46-1):

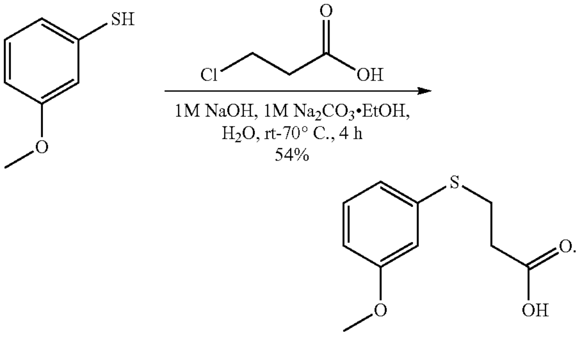

46-1

To a mixture of 1 M NaOH (10 mL) and 1 M $Na_2CO_3$ (10 mL) was added a solution of 3-methoxythiophenol (2.80 g, 20.00 mmol) in EtOH (12 mL) and 3-chloropropionic acid (2.07 g, 20.00 mmol) in water (8 mL) respectively. The mixture was heated to reflux for 4 h. After being cooled to room temperature, the mixture was washed with petroleum ether (10 mL×2). Then the aqueous phase was acidified with 1 N HCl to pH 1 and extracted with EtOAc (20 mL×3). The organic layers were washed with brine, dried over $MgSO_4$ and concentrated to give 46-1 (2.30 g, about 54% yield) as an oil. MS Calcd.: 212.1; MS Found: 213.3 $[M+H]^+$.

The synthesis of 5-methoxythiochroman-4-one (46-2):

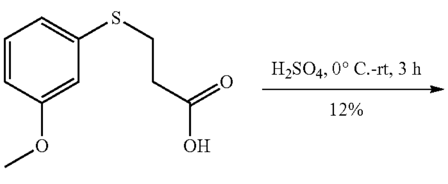

46-1

46-2

To 46-1 (2.30 g, 10.84 mmol) stirred at 0° C. was added conc. $H_2SO_4$ (6 mL) slowly. Then the mixture was allowed to warm to room temperature and stirred for 3 h. Then mixture was poured onto ice carefully. The resulting mixture was extracted with EtOAc (30 mL×3) and the organic layers were washed with brine, dried over $MgSO_4$ and concentrated. The residue was purified by column chromatography on silica gel (petroleum ether/EtOAc=5/1) to give 46-2 (250 mg, about 12% yield) as an oil. MS Calcd.: 194.0; MS Found: 195.1 $[M+H]^+$.

$^1H$ NMR (400 MHz, $CDCl_3$) δ 7.27 (t, J=8.0 Hz, 1H), 6.86 (dd, J=8.0, 0.8 Hz, 1H), 6.70 (d, J=8.0 Hz, 1H), 3.20-3.15 (m, 2H), 3.00-2.95 (m, 2H).

The synthesis of 5-hydroxythiochroman-4-one (46-3):

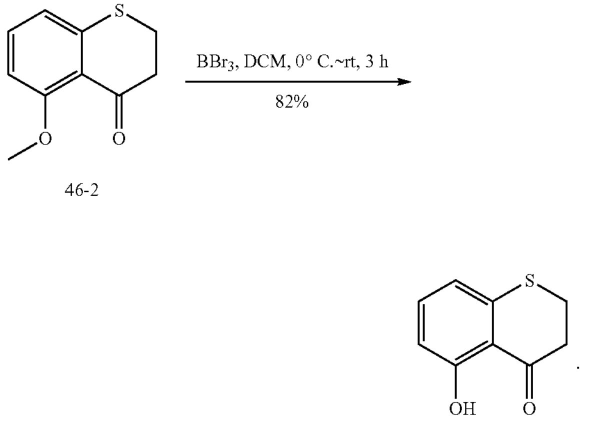

46-2

46-3

To a mixture of 46-2 (660 mg, 3.40 mmol) in $CH_2Cl_2$ (15 mL) stirred at 0° C. was added $BBr_3$ (10.2 mL, 1 M in DCM) dropwise. After the addition, the mixture was allowed to warm to room temperature and stirred for 3 h. Then the mixture was poured into water and extracted with DCM (3×30 mL). The combined organic layers were washed with water and brine, dried over $Na_2SO_4$ and concentrated. The residue was purified by column chromatography on silica gel (petroleum ether/EtOAc=3/1) to give 46-3 (500 mg, about 82% yield) as a solid.

$^1H$ NMR (400 MHz, $CDCl_3$) δ 12.66 (s, 1H), 7.20 (t, J=8.0 Hz, 1H), 6.70 (dd, J=8.0, 0.8 Hz, 1H), 6.61 (dd, J=8.0, 0.8 Hz, 1H), 3.16-3.09 (m, 2H), 2.99-2.93 (m, 2H).

The synthesis of 5-(2-(dimethylamino)ethoxy)thiochroman-4-one (46-4):

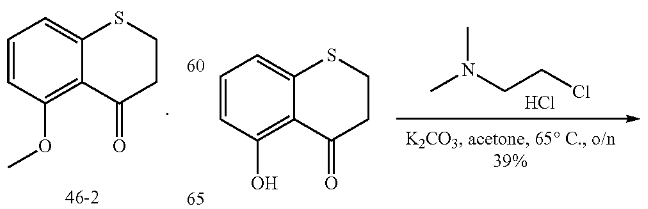

46-3

-continued

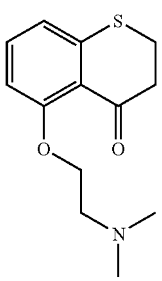

46-4

A mixture of 46-3 (275 mg, 1.53 mmol), 2-(dimethylamino) ethyl chloride hydrochloride (330 mg, 2.29 mmol) and $K_2CO_3$ (634 mg, 4.59 mmol) in acetone (30 mL) was stirred at 65° C. overnight. Then the reaction mixture was filtered and concentrated. The residue was purified by Prep-TLC (DCM/MeOH=20/1) to give 46-4 (150 mg, about 39% yield) as an oil. MS Calcd.: 251.1; MS Found: 252.1 $[M+H]^+$.

The synthesis of (E)-N,N-dimethyl-2-(4-(2-phenylhydrazono)thiochroman-5-yloxy)ethanamine (46-5):

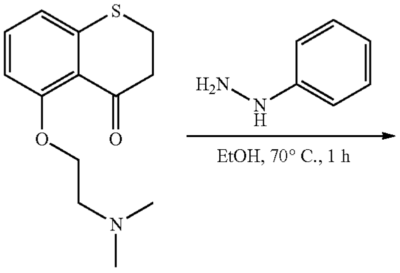

46-4

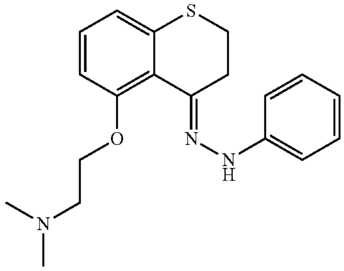

46-5

A mixture of 46-4 (120 mg, 0.48 mmol) and phenylhydrazine (52 mg, 0.48 mmol) in EtOH (15 mL) was stirred at 70° C. for 1 h. Then the reaction mixture was used for next step directly. MS Calcd.: 341.2; MS Found: 342.1 $[M+H]^+$.

The synthesis of 2-(6,11-dihydrothiochromeno[4,3-b]indol-1-yloxy)-N,N-dimethylethanamine (SS20308-0046-01):

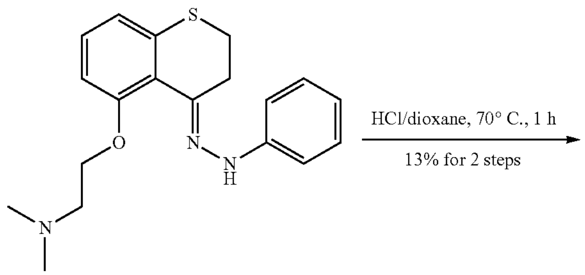

46-5

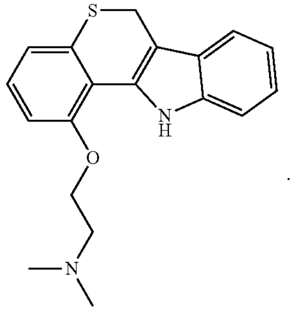

SS20308-0046-01

To a reaction mixture of 46-5 was added HCl (2 mL, 4 M in dioxane). The mixture was stirred at 70° C. for 1 h. After being cooled to room temperature, the mixture was concentrated. The residue was basicified with 1 N NaOH to pH 10. The resulting mixture was extracted with EtOAc (30 mL×3) and the organic layers were washed with brine, dried over $Na_2SO_4$ and concentrated. The residue was purified by Prep-TLC (petroleum ether/EtOAc=1/1) to give SS20308-0046-01 (20 mg, about 13% yield for 2 steps) as a solid. MS Calcd.: 324.1; MS Found: 325.3 $[M+H]^+$.

$^1H$ NMR (400 MHz, DMSO-$d_6$) δ 12.03 (s, 1H), 7.56 (d, J=8.0 Hz, 1H), 7.34 (d, J=8.0 Hz, 1H), 7.17-7.12 (m, 2H), 7.06-7.01 (m, 1H), 7.02-6.99 (m, 1H), 7.00-6.97 (m, 1H), 4.30 (t, J=5.2 Hz, 2H), 4.26 (s, 2H), 2.78 (t, J=5.2 Hz, 2H), 2.42 (s, 6H).

Example 9

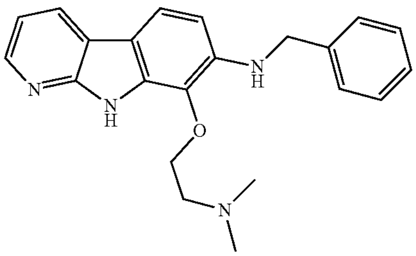

SS20308-0047-01
Chemical Formula: $C_{22}H_{24}N_4O$
Molecular Weight: 360.45

Example Route for Example 9 (SS20308-0047-01):

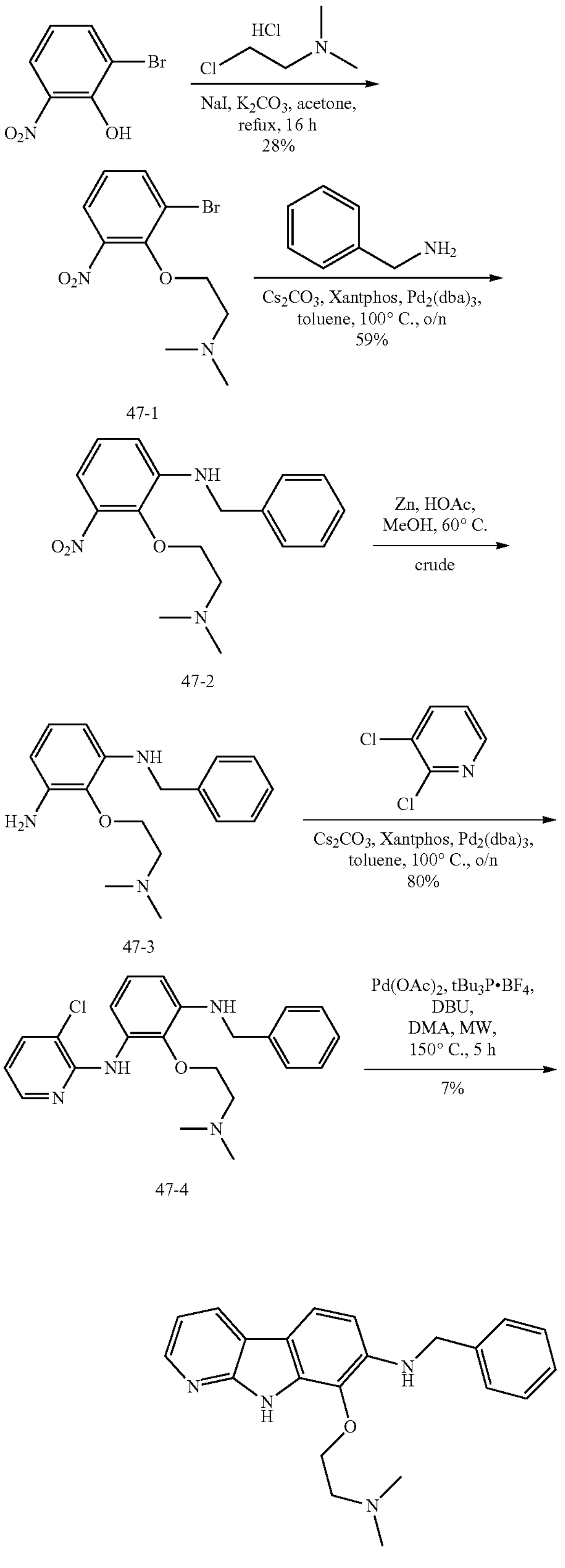

47-1

47-2

47-3

47-4

SS20308-0047-01

The synthesis of 2-(2-bromo-6-nitrophenoxy)-N,N-dimethylethanamine (47-1):

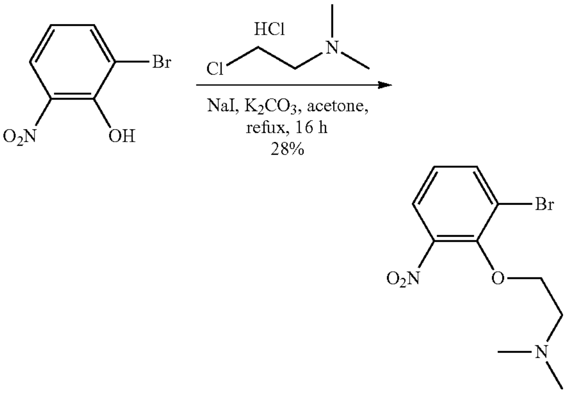

47-1

The mixture of 2-bromo-6-nitrophenol (3.0 g, 13.6 mmol), 2-chloro-N,N-dimethylethanamine hydrochloride (2.2 g, 15.0 mmol), $K_2CO_3$ (3.8 g, 27.3 mmol) and NaI (1.0 g, 6.8 mmol) in acetone (25 mL) was stirred at 60° C. for 16 h. The reaction mixture was cooled to room temperature and filtered through celite. The filtrate was diluted with water (50 mL) and then extracted with EtOAc (30 mL×5). The organic layer was washed with brine and concentrated to dryness to give 47-1 (1.1 g, about 28% yield) as an oil. MS Calcd.: 288.0; MS Found: 289.1 $[M+H]^+$.

The synthesis of N-benzyl-2-(2-(dimethylamino)ethoxy)-3-nitroaniline (47-2):

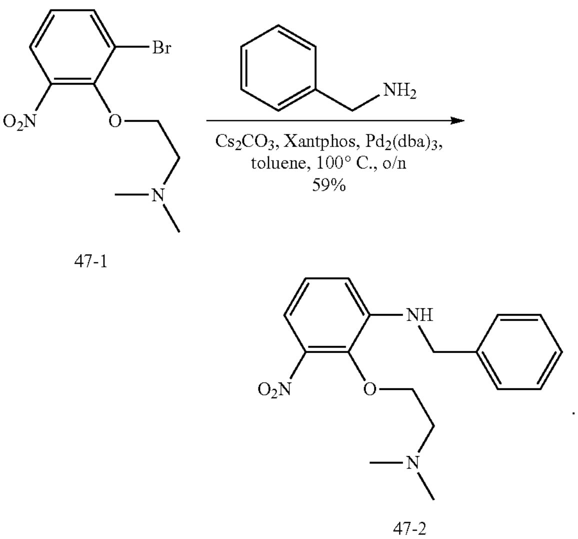

47-1

47-2

To a solution of 47-1 (300 mg, 1.0 mmol) in toluene (3 mL) was added phenylmethanamine (111 mg, 1.0 mmol), $Cs_2CO_3$ (696 mg, 2.0 mmol), Xantpshos (62 mg, 0.1 mmol) and $Pd_2(dba)_3$ (98 mg, 0.1 mmol), then the reaction mixture was stirred at 100° C. under nitrogen atmosphere overnight. The reaction mixture was cooled to room temperature and filtered through celite then washed with EtOAc (20 mL). The organic layer was washed with brine and concentrated to dryness. The residue was purified by column chromatography on silica gel (EtOAc/petroleum ether=1/1 to 1/O) to give 47-2 (200 mg, about 59% yield) as an oil. MS Calcd.: 315.2; MS Found: 316.3 $[M+H]^+$.

The synthesis of $N^1$-benzyl-2-(2-(dimethylamino)ethoxy)benzene-1,3-diamine (47-3):

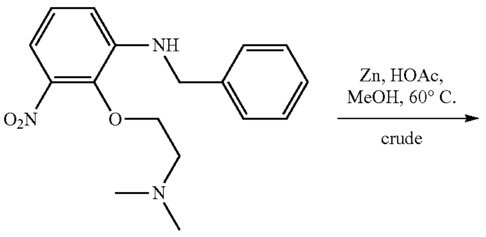

47-2

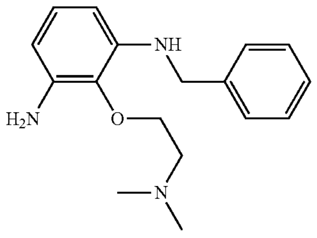

47-3

To a solution of 47-2 (200 mg, 0.63 mmol) in MeOH (6 mL) was added Zn powder (166 mg, 2.5 mmol), and HOAc (152 mg, 2.5 mmol). Then the reaction mixture was stirred at 60° C. for 4 h. The mixture was diluted with water and extracted with EtOAc (150 mL). The organic layer was washed with brine and concentrated to dryness to give 47-3 (200 mg, crude) as an oil. MS Calcd.: 285.2; MS Found: 286.2 $[M+H]^+$.

The synthesis of $N^1$-benzyl-$N^3$-(3-chloropyridin-2-yl)-2-(2-(dimethylamino)ethoxy)benzene-1,3-diamine (47-4):

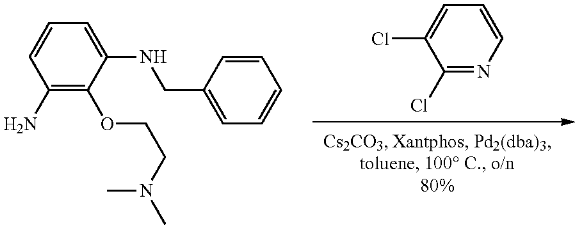

47-3

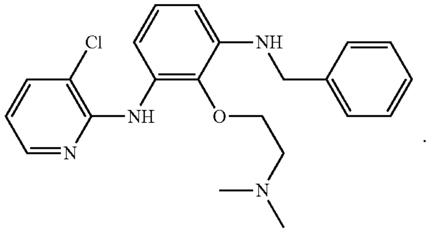

47-4

To a solution of 47-3 (380 mg, 1.33 mmol) in toluene (15 mL) was added 2,3-dichloropyridine (237 mg, 1.60 mmol), $Cs_2CO_3$ (868 mg, 2.66 mmol), Xantphos (77 mg, 0.1 mmol) and $Pd_2(dba)_3$ (61 mg, 0.13 mmol). Then the reaction mixture was stirred at 100° C. under nitrogen atmosphere overnight. The reaction mixture was cooled to room temperature, diluted with water and extracted with EtOAc (10 mL×3). The organic layer was washed with brine and concentrated to dryness. The residue was purified by Prep-TLC (EtOAc) to give 47-4 (420 mg, about 80% yield) as an oil. MS Calcd.: 396.2; MS Found: 397.3 $[M+H]^+$.

$^1H$ NMR (400 MHz, $CDCl_3$) δ 8.08 (dd, J=4.8, 1.6 Hz, 1H), 7.69-7.67 (m, 2H), 7.49 (dd, J=7.6, 1.6 Hz, 1H), 7.34-7.32 (m, 2H), 7.28-7.24 (m, 2H), 7.20-7.19 (m, 1H), 6.90 (dd, J=8.4, 8.0 Hz, 1H), 6.61 (dd, J=8.0, 6.4 Hz, 1H), 6.26 (dd, J=8.0, 1.2 Hz, 1H), 5.93 (t, J=5.2 Hz, 1H), 4.28 (d, J=5.6 Hz, 2H), 3.94 (d, J=4.4 Hz, 2H), 2.56 (br, 2H), 2.09 (s, 6H).

The synthesis of N-benzyl-8-(2-(dimethylamino)ethoxy)-9H-pyrido[2,3-b]indol-7-amine (SS20308-0047-01):

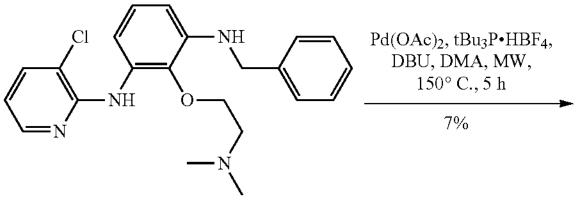

47-4

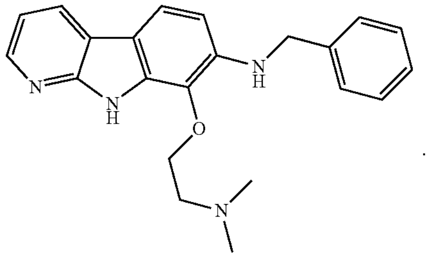

SS20308-0047-01

To a mixture of 47-4 (100 mg, 0.25 mmol), $(t\text{-}Bu)_3P—HBF_4$ (15 mg, 0.05 mmol) and DBU (38 mg, 0.25 mmol) in DMA (4 mL) was added $Pd(OAc)_2$ (6 mg, 0.03 mmol). The reaction mixture was stirred in a microwave reactor at 150° C. for 5 h under nitrogen atmosphere. The mixture was poured into water and extracted with EtOAc (10 mL×2). The organic layer was washed with brine (10 mL×2), dried over $Na_2SO_4$, and concentrated in vacuo. The residue was purified by Prep-TLC to give SS20308-0047-01 (6 mg, about 7% yield) as a solid. MS Calcd.: 360.2; MS Found: 361.3 $[M+H]^+$.

$^1H$ NMR (400 MHz, DMSO-$d_6$) δ11.73 (s, 1H), 8.21-8.16 (m, 2H), 7.60 (d, J=8.4 Hz, 1H), 7.42-7.40 (m, 2H), 7.36-7.32 (m, 2H), 7.26-7.22 (m, 1H), 7.05 (dd, J=7.6, 4.8 Hz, 1H), 6.65 (t, J=6.0 Hz, 1H), 6.53 (d, J=8.4 Hz, 1H), 4.41 (d, J=6.0 Hz, 2H), 4.11 (t, J=5.2 Hz, 2H), 2.58 (t, J=4.8 Hz, 2H), 2.17 (s, 6H).

Example 10
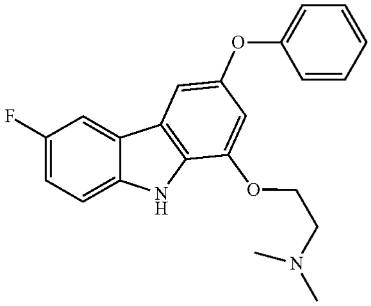
SS20308-0054-01
Chemical Formula: $C_{22}H_{21}FN_2O_2$
Molecular Weight: 364.41
Example Route for Example 10 (SS20308-0054-01):
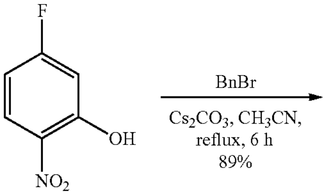
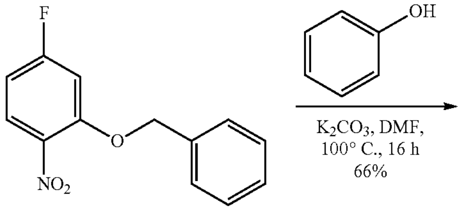
54-1
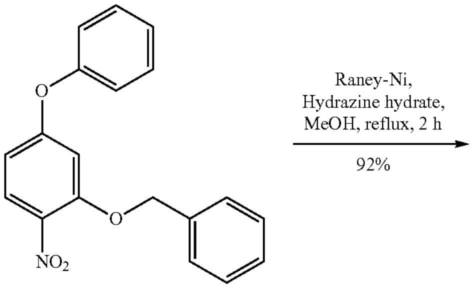
54-2
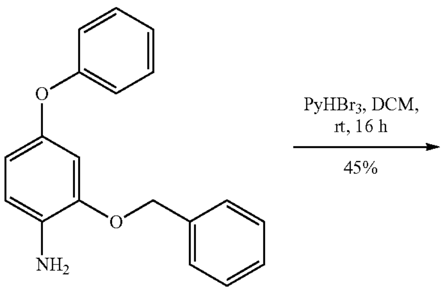
54-3
-continued
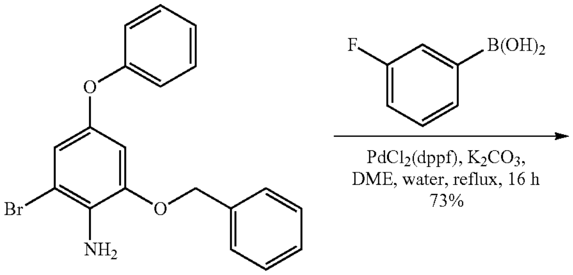
54-4
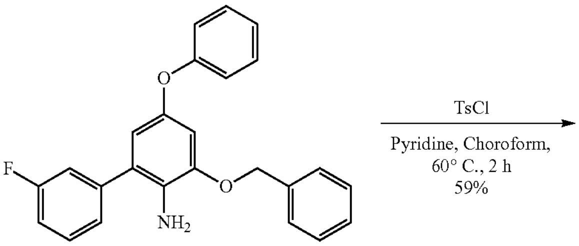
54-5
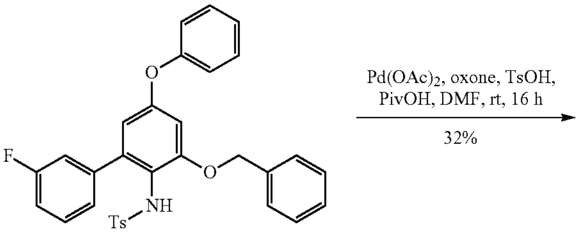
54-6
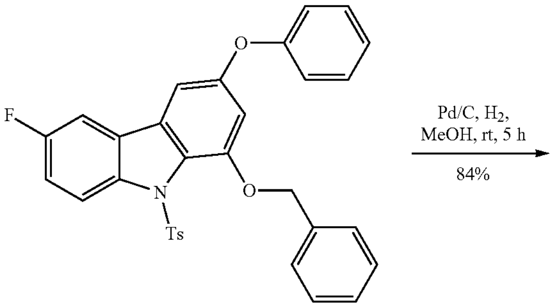
54-7
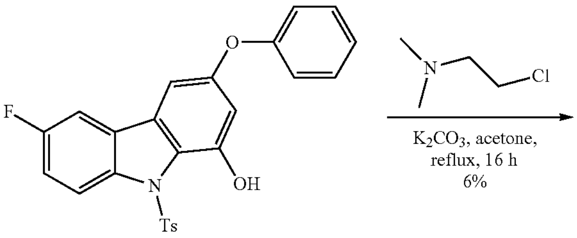
54-8

-continued

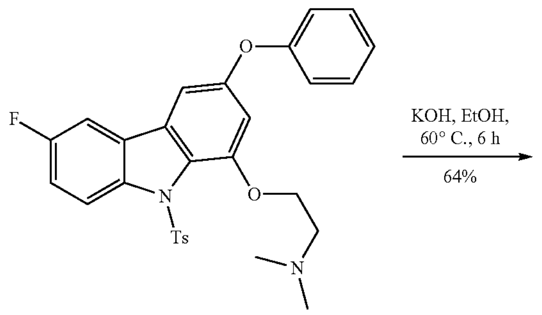

54-9

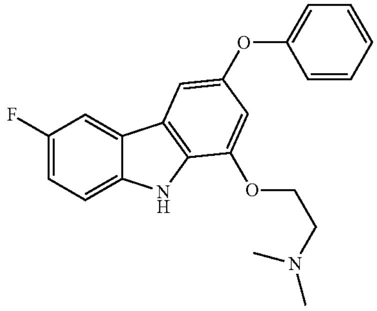

SS20308-0054-01

The synthesis of 2-(benzyloxy)-4-fluoro-1-nitrobenzene (54-1):

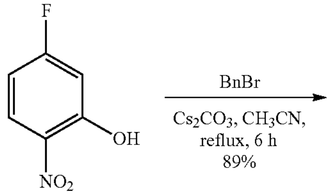

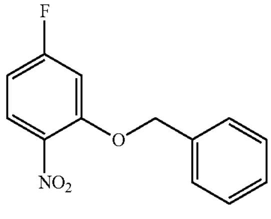

54-1

To a mixture of 5-fluoro-2-nitrophenol (10.0 g, 63.7 mmol) in $CH_3CN$ (100 mL) was added $Cs_2CO_3$ (41.5 g, 127.4 mmol). Then benzyl bromide (12.0 g, 70.1 mmol) was added dropwise at room temperature. When the addition was complete, the mixture was heated to reflux for 6 h. The mixture was diluted with EtOAc (200 mL). The organic layer was successively washed with water (100 mL) and brine (100 mL). The organic layer was then dried with $MgSO_4$ and concentrated under reduced pressure. The crude product was purified by column chromatography on silica gel (petroleum ether/EtOAc=1/20) to give 54-1 (14.0 g, about 89% yield) as a solid. MS Calcd.: 247.1; MS Found: 270.2 $[M+Na]^+$.

The synthesis of 2-(benzyloxy)-1-nitro-4-phenoxybenzene (54-2):

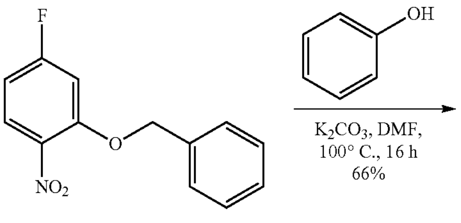

54-1

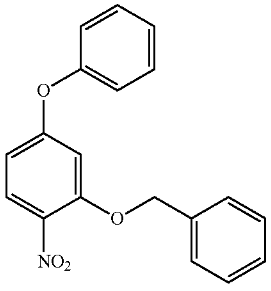

54-2

To a mixture of 54-1 (14.0 g, 56.7 mmol) and $K_2CO_3$ (15.6 g, 113.4 mmol) in DMF (100 mL) was added phenol (6.4 g, 68.0 mmol) at room temperature. Then the mixture was heated to 100° C. for 16 h under nitrogen. The reaction mixture was cooled to room temperature, and diluted with EtOAc (200 mL). The mixture was successively washed with water (100 mL) and brine (100 mL). The organic layer was then dried with $MgSO_4$ and concentrated under reduced pressure. The crude product was purified by column chromatography on silica gel (petroleum ether/EtOAc=1/6) to give 54-2 (12 g, about 66% yield) as a solid. MS Calcd.: 321.1; MS Found: 344.1 $[M+Na]^+$.

The synthesis of 2-(benzyloxy)-4-phenoxyaniline (54-3):

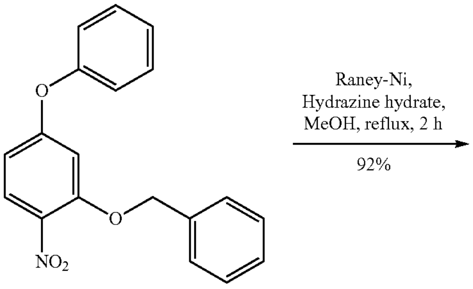

54-2

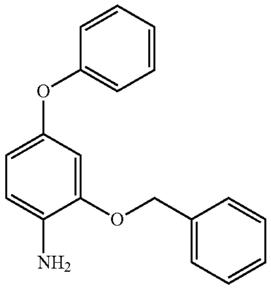

54-3

To a mixture of 54-2 (12 g, 37.4 mmol) in MeOH (80 mL) was added hydrazine hydrate (5 mL) at room temperature, then Raney-Ni (0.5 g) was added. The mixture was heated to reflux for 2 h. After being cooled to room temperature, the mixture was filtered through celite, and washed with MeOH (50 mL). The filtrate was concentrated to give 54-3 (10.0 g, about 92% yield) as an oil. MS Calcd.: 291.1; MS Found: 292.2 [M+H]$^+$.

The synthesis of 2-(benzyloxy)-6-bromo-4-phenoxyaniline (54-4):

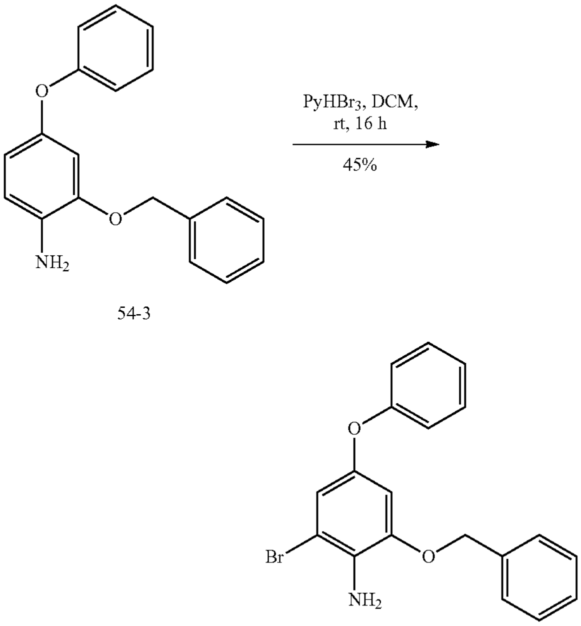

54-3

54-4

To a mixture of 54-3 (10.0 g, 34.4 mmol) in DCM (50 mL) was added pyridinium tribromide (11.0 g, 34.4 mmol) at room temperature. Then the mixture was stirred at room temperature for 16 h. The mixture was diluted with DCM (200 mL). The mixture was successively washed with saturated $NaHCO_3$ (100 mL) and brine (100 mL). The organic layer was then dried with $MgSO_4$ and concentrated under reduced pressure. The crude product was purified by column chromatography on silica gel (petroleum ether/EtOAc=1/5) to give 54-4 (5.7 g, about 45% yield) as an oil. MS Calcd.: 369.0; MS Found: 370.1 [M+H]$^+$.

The synthesis of 3-(benzyloxy)-3'-fluoro-5-phenoxybiphenyl-2-amine (54-5):

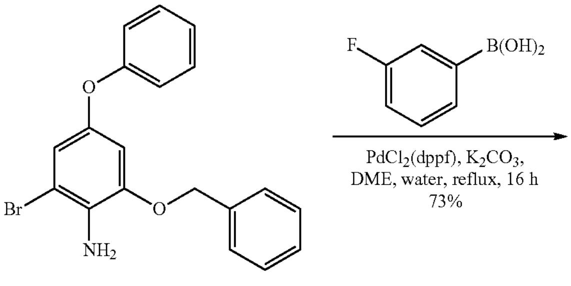

54-4

-continued

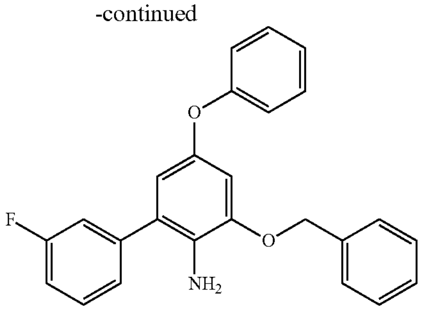

54-5

To a mixture of 54-4 (3.0 g, 8.1 mmol) in DME (50 mL) and water (5 mL) was added 3-fluorophenylboronic acid (1.2 g, 8.1 mmol), $K_2CO_3$ (2.8 g, 20.3 mmol) and $PdCl_2$(dppf) (586 mg, 0.8 mmol) at room temperature, and then the mixture was heated to reflux for 16 h under nitrogen. The reaction mixture was cooled to room temperature. The mixture was filtered, and washed with EtOAc (80 mL). The filtrate was successively washed with water (100 mL) and brine (100 mL). The organic layer was then dried with $MgSO_4$ and concentrated under reduced pressure. The crude product was purified by column chromatography on silica gel (petroleum ether/EtOAc=1/6 to 1/1) to give 54-5 (2.3 g, about 73% yield) as an oil. MS Calcd.: 385.2; MS Found: 386.2 [M+H]$^+$.

The synthesis of N-(3-(benzyloxy)-3'-fluoro-5-phenoxybiphenyl-2-yl)-4-methylbenzenesulfonamide (54-6):

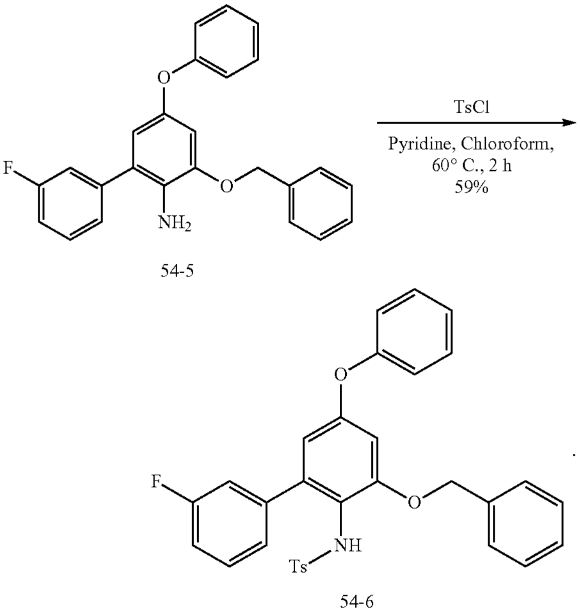

54-5

54-6

To a mixture of 54-5 (2.3 g, 6.0 mmol) in $CHCl_3$ (30 mL) was added pyridine (2.4 g, 30.0 mmol) and TsCl (1.3 g, 7.0 mmol) at room temperature. Then the mixture was heated to 60° C. for 2 h. The reaction mixture was cooled to room temperature. The mixture was diluted with DCM (50 mL). The organic layer was washed with brine (100 mL). The organic layer was then dried with $MgSO_4$ and concentrated to oil to give 54-6 (2.8 g, about 59% yield) as an oil. MS Calcd.: 539.2; MS Found: 540.2 [M+H]$^+$.

The synthesis of 1-(benzyloxy)-6-fluoro-3-phenoxy-9-tosyl-9H-carbazole (54-7):

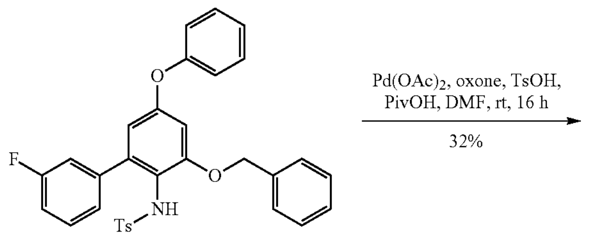

54-6

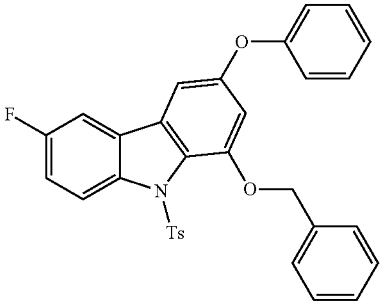

54-7

*n*.

To a mixture of 54-6 (2.8 g, 5.2 mmol) in PivOH (5 mL) and DMF (15 mL) was added TsOH (298 mg, 5.2 mmol), oxone (6.4 g, 10.4 mmol) and $Pd(OAc)_2$ (582 mg, 2.6 mmol) at room temperature. Then the mixture was stirred at room temperature for 16 h. The mixture was diluted with EtOAc (100 mL), then was successively washed with water (100 mL) and brine (100 mL). The organic layer was then dried with $MgSO_4$ and concentrated under reduced pressure. The crude product was purified by column chromatography on silica gel (petroleum ether/EtOAc=1/5 to 2/1) to give 54-7 (0.9 g, about 32% yield) as an oil. MS Calcd.: 537.1; MS Found: 538.3 $[M+H]^+$.

The synthesis of 6-fluoro-3-phenoxy-9-tosyl-9H-carbazol-1-ol (54-8):

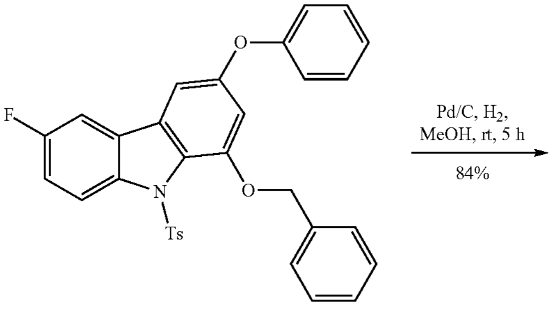

54-7

-continued

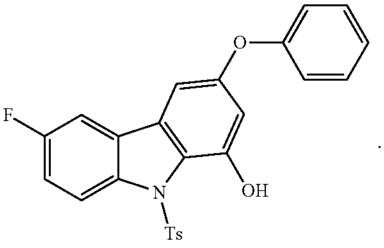

54-8

To a solution of 54-7 (900 mg, 1.7 mmol) in MeOH (5 mL) was added Pd/C (5%, 100 mg) at room temperature, then the mixture was stirred at room temperature under hydrogen gas (balloon) for 5 h. The reaction mixture was filtered through celite and washed with MeOH. The filtrate was concentrated to give 54-8 (630 mg, about 84% yield) as a solid. MS Calcd.: 447.1; MS Found: 448.2 $[M+H]^+$.

The synthesis of 2-(6-fluoro-3-phenoxy-9-tosyl-9H-carbazol-1-yloxy)-N,N-dimethylethanamine (54-9):

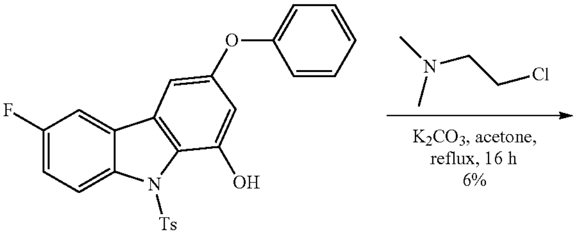

54-8

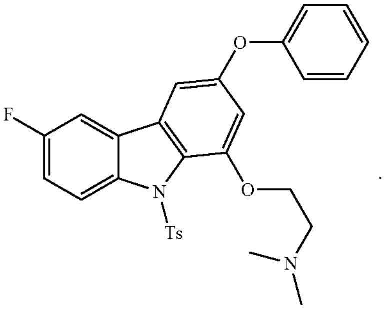

54-9

To a solution of 54-8 (284 mg, 0.6 mmol) in acetone (8 mL) was added $K_2CO_3$ (166 mg, 1.2 mmol) and 2-chloro-N,N-dimethylethanamine hydrochloride (91 mg, 0.6 mmol) at room temperature. Then the mixture was heated to reflux for 16 h. The mixture was diluted with EtOAc (20 mL), successively washed with water (20 mL) and brine (20 mL). The organic layer was then dried with $MgSO_4$ and concentrated under reduced pressure. The crude product was purified by Prep-TLC (MeOH/EtOAc=1/100) to give 54-9 (20 mg, about 6% yield) as an oil. MS Calcd.: 518.2; MS Found: 519.2 $[M+H]^+$.

The synthesis of 2-(6-fluoro-3-phenoxy-9-tosyl-9H-carbazol-1-yloxy)-N,N-dimethylethanamine (SS20308-0054-01):

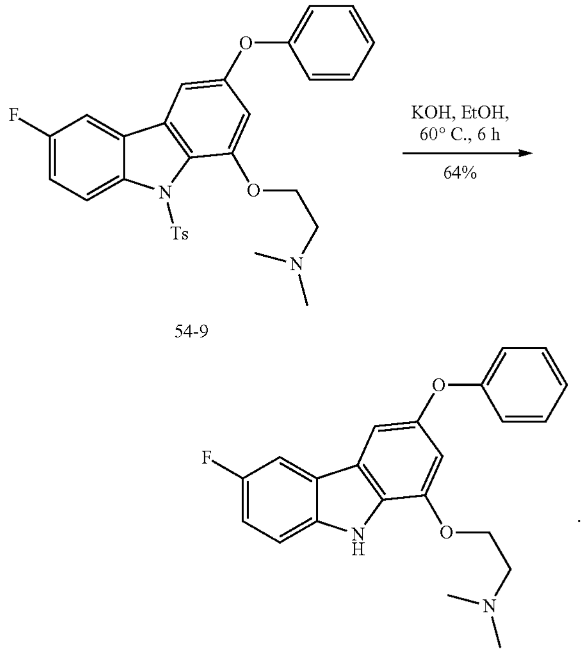

54-9

SS20308-0054-01

To a solution of 54-9 (20 mg, 0.04 mmol) in EtOH (3 mL) was added KOH (11 mg, 0.2 mmol) at room temperature. Then the mixture was heated to 60° C. and stirred for 6 h. After cooling to room temperature, the mixture was diluted with EtOAc (10 mL), then successively washed with water (10 mL) and brine (10 mL). The organic layer was then dried with $MgSO_4$ and concentrated under reduced pressure. The crude product was purified by Prep-HPLC to give SS20308-0054-01 (9 mg, about 64% yield) as a solid. MS Calcd.: 364.2; MS Found: 365.3 $[M+H]^+$. $^1H$ NMR (400 MHz, $CDCl_3$) δ 10.04 (s, 1H), 7.50 (dd, J=9.2, 2.4 Hz, 1H), 7.31-7.21 (m, 4H), 7.06 (ddd, J=9.0, 8.8, 1.2 Hz, 1H), 6.98 (t, J=7.4 Hz, 1H), 6.93 (d, J=7.6 Hz, 2H), 6.65 (d, J=2.0 Hz, 1H), 4.13 (t, J=5.4 Hz, 2H), 2.74 (t, J=5.2 Hz, 2H), 2.31 (s, 6H).

Example 11

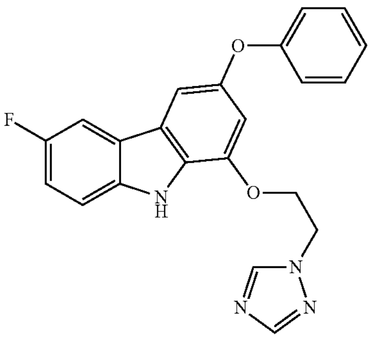

SS20308-0084-01
Chemical Formula: $C_{22}H_{17}FN_4O_2$
Molecular Weight: 388.39

Example Route for Example 11 (SS20308-0084-01):

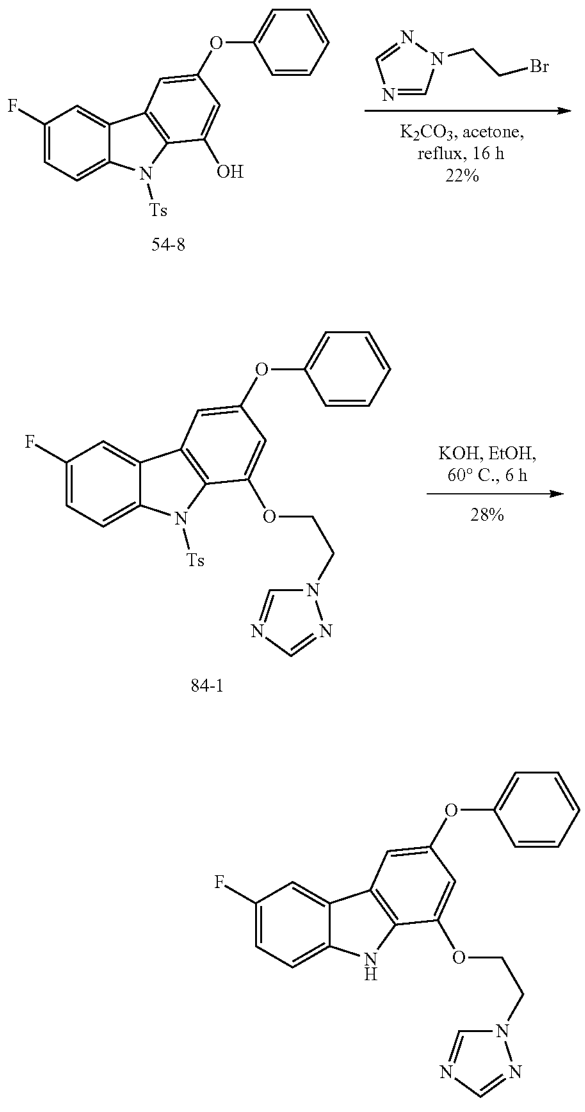

54-8

84-1

SS20308-0084-01

The synthesis of 1-(2-(1H-1,2,4-triazol-1-yl)ethoxy)-6-fluoro-3-phenoxy-9-tosyl-9H-carbazole (84-1):

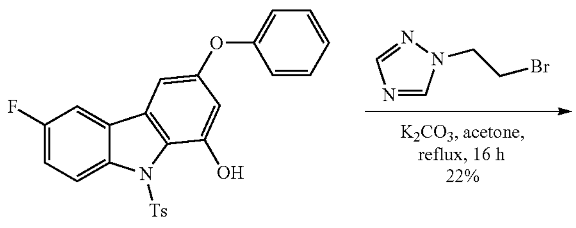

54-8

-continued

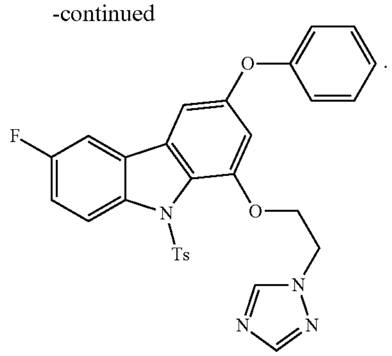

84-1

To a solution of 54-8 (200 mg, 0.5 mmol) in acetone (8 mL) was added $K_2CO_3$ (207 mg, 1.5 mmol) and 1-(2-bromoethyl)-1H-1,2,4-triazole (175 mg, 1.0 mmol) at room temperature. Then the mixture was heated to reflux for 16 h. The mixture was diluted with EtOAc (20 mL), and then successively washed with water (20 mL) and brine (20 mL). The organic layer was then dried with $MgSO_4$ and concentrated under reduced pressure. The crude product was purified by Prep-TLC (MeOH/EtOAc=1/100) to give 84-1 (60 mg, about 22% yield) as an oil. MS Calcd.: 542.1; MS Found: 543.3 $[M+H]^+$.

The synthesis of 1-(2-(1H-1,2,4-triazol-1-yl)ethoxy)-6-fluoro-3-phenoxy-9H-carbazole (SS20308-0084-01):

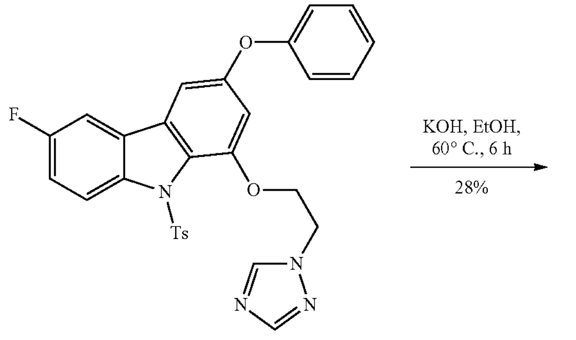

84-1

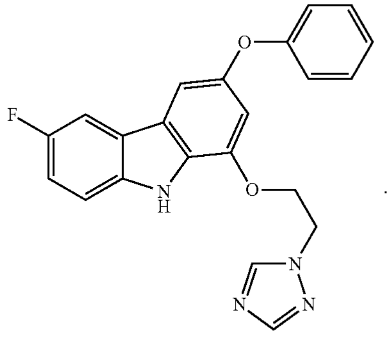

SS20308-0084-01

To a solution of 84-1 (45 mg, 0.04 mmol) in EtOH (3 mL) was added KOH (11 mg, 0.2 mmol) at room temperature. Then the mixture was heated to 60° C. and stirred for 6 h. The mixture was diluted with EtOAc (10 mL), and successively washed with water (10 mL) and brine (10 mL). The organic layer was then dried with $MgSO_4$ and concentrated under reduced pressure. The crude product was purified by Prep-HPLC to give SS20308-0084-01 (9 mg, about 28% yield) as a solid. MS Calcd.: 388.1; MS Found: 389.1 $[M+H]^+$.

$^1H$ NMR (400 MHz, $CDCl_3$) δ 8.44 (s, 1H), 8.22 (s, 1H), 7.95 (s, 1H), 7.50 (dd, J=9.0, 2.6 Hz, 1H), 7.32 (dd, J=8.8, 4.4 Hz, 1H), 7.28-7.22 (m, 3H), 7.09 (ddd, J=9.2, 9.0, 2.4 Hz, 1H), 7.01 (t, J=7.2 Hz, 1H), 6.95-6.90 (m, 2H), 6.63 (d, J=2.0 Hz, 1H), 4.59 (t, J=5.0 Hz, 2H), 4.46 (t, J=5.0 Hz, 2H).

Example 12

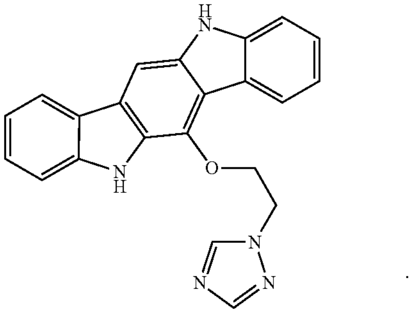

SS20308-0059-01
Chemical Formula: $C_{22}H_{17}N_5O$
Molecular Weight: 367.40

Example Route for Example 12 (SS20308-0059-01):

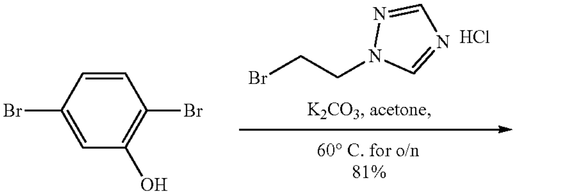

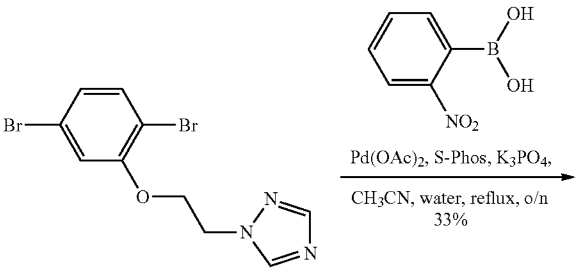

59-1

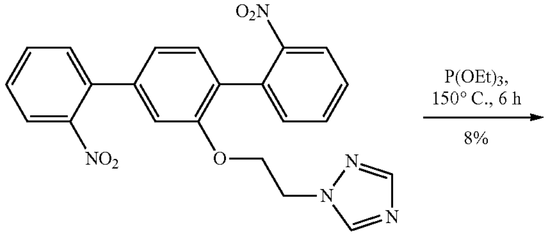

59-2

-continued

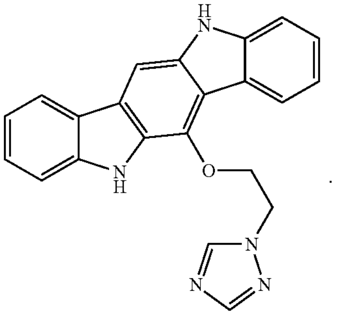

SS20308-0059-01

The synthesis of 1-(2-(2,5-dibromophenoxy)ethyl)-1H-1,2,4-triazole (59-1):

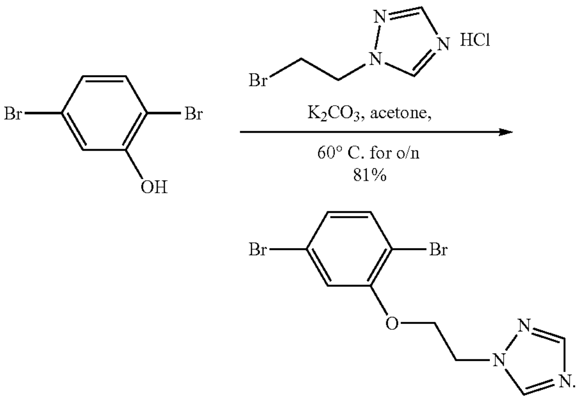

59-1

A mixture of 2,5-dibromophenol (0.5 g, 1.98 mmol), 1-(2-bromoethyl)-1H-1,2,4-triazole hydrochloride (1.27 g, 5.95 mmol) and $K_2CO_3$ (1.65 g, 11.91 mmol) in acetone (40 mL) was stirred at 60° C. for overnight. Then the reaction mixture was cooled down to room temperature and filtered. The filtrate was concentrated and purified by column chromatography on silica gel (EtOAc/petroleum ether=5/1, 1/1) to give 59-1 (0.56 g, about 81% yield) as a solid. MS Calcd.: 344.9; MS Found: 345.6 $[M+H]^+$.

The synthesis of 1-(2-((2,2"-dintro-[1,1',4',1"-terphenyl]-2'-yl)oxy)ethyl)-1H-1,2,4-triazole (59-2):

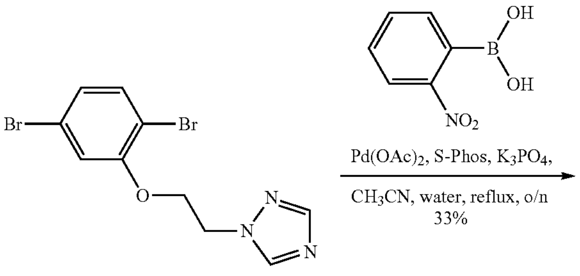

59-1

-continued

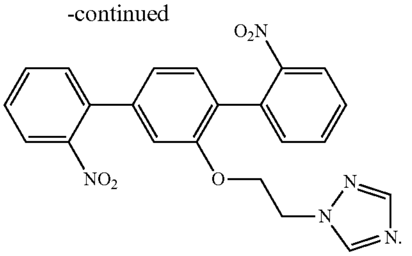

59-2

A solution of 59-1 (560 mg, 1.61 mmol), 2-nitrophenylboronic acid (809 mg, 4.85 mmol), S-Phos (67 mg, 0.16 mmol), palladium (II) acetate (19 mg, 0.085 mmol), and potassium phosphate (1.71 g, 8.07 mmol,) were suspended in $CH_3CN$ (30 mL) and water (10 mL). The reaction mixture was heated at reflux for overnight. The mixture was filtered through celite and rinsed with EtOAc. The filtrate was concentrated and the residue was purified by column chromatography on silica gel (petroleum ether/EtOAc=1/1 to DCM/MeOH=20/1) to give 59-2 (230 mg, about 33% yield) as solid. MS Calcd.:431.1; MS Found: 431.7 $[M+H]^+$.

The synthesis of 6-(2-(1H-1,2,4-triazol-1-yl)ethoxy)-5,11-dihydroindolo[3,2-b]carbazole (SS20308-0059-01):

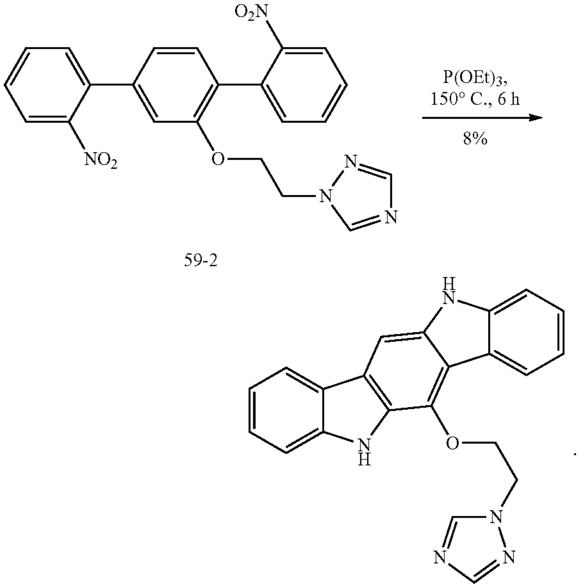

59-2

SS20308-0059-01

A solution of 59-2 (230 mg, 0.53 mmol) in $P(OEt)_3$ (4 mL) was stirred at 150° C. for 6 h. After the reaction was completed, the reaction was concentrated to a crude mixture, which was purified by reverse phase column chromatography and Prep-TLC to give SS20308-0059-01 (15 mg, about 8% yield) as a solid. MS Calcd.: 367.1; MS Found: 367.8 $[M+H]^+$.

$^1H$ NMR (400 MHz, DMSO-$d_6$) δ 11.08 (s, 1H), 11.07 (s, 1H), 8.78 (s, 1H), 8.21-8.17 (m, 2H), 7.89 (s, 1H), 7.53 (d, J=8.0 Hz, 1H), 7.44-7.38 (m, 2H), 7.36-7.29 (m, 2H), 7.18-7.11 (m, 1H), 6.97-6.90 (m, 1H), 4.86 (t, J=5.0 Hz, 2H), 4.65 (t, J=5.0 Hz, 2H).

Example 13

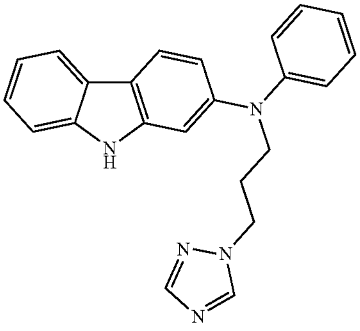

SS20308-0060-01
Chemical Formula: $C_{23}H_{21}N_5$
Molecular Weight: 367.45

Example Route for Example 13 (SS20308-0060-01):

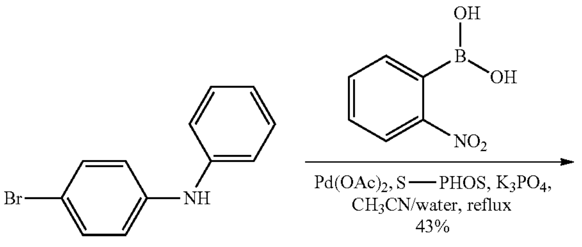

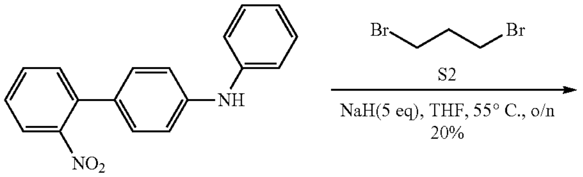

60-1

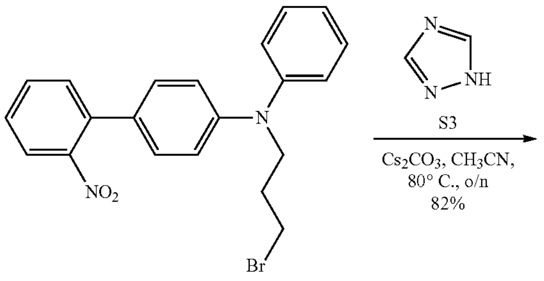

60-2

-continued

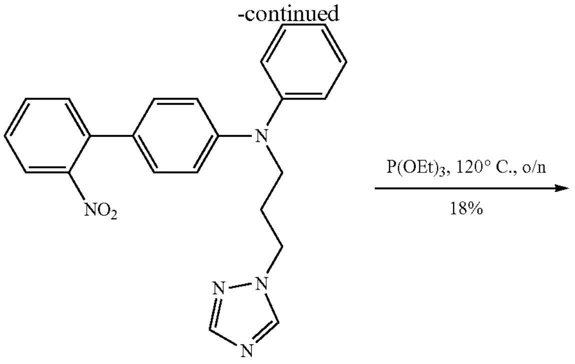

60-3

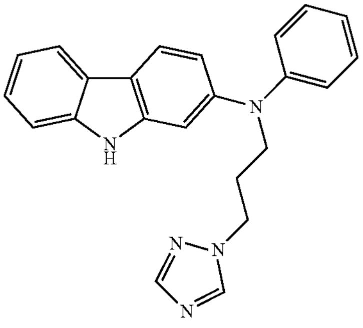

SS20308-0060-01

The synthesis of 2'-nitro-N-phenylbiphenyl-4-amine (60-1):

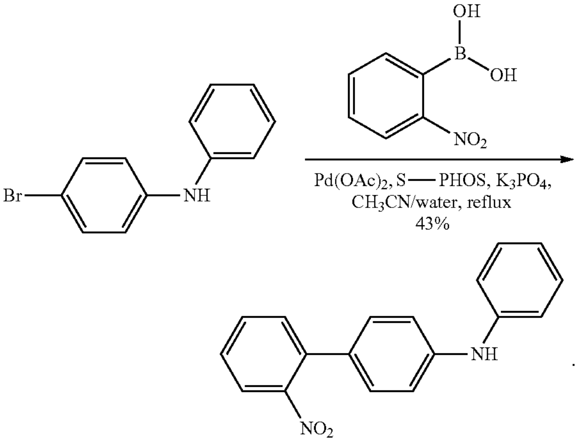

60-1

A mixture of 4-bromo-N-phenylbenzenamine (2.0 g, 8.06 mmol), 2-nitro-phenyl boronic acid (1.6 g, 9.67 mmol), $Pd(OAc)_2$ (90 mg, 0.40 mmol), S-Phos (33 mg, 0.08 mmol) and $K_3PO_4$ (3.4 g, 16.12 mmol) in $CH_3CN$/water (50/10 mL) was stirred at reflux under nitrogen overnight. The reaction mixture was cooled to room temperature and poured into water (100 mL) and extracted with EtOAc (60 mL×3). The organic layer was washed with brine and concentrated. The residue was purified by column chromatography on silica gel (petroleum ether/EtOAc=30/1~5/1) to give 60-1 (1.0 g, about 43% yield) as a solid. MS Calcd.: 290.1; MS Found: 291.2 $[M+H]^+$.

The synthesis of N-(3-bromopropyl)-2'-nitro-N-phenylbiphenyl-4-amine (60-2)

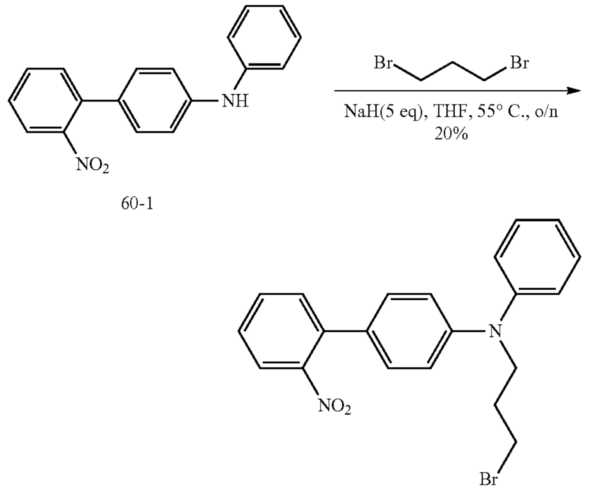

60-1

60-2

To a solution of 60-1 (700 mg, 2.41 mmol) in THF (20 mL) was added NaH (482 mg, 12.06 mmol, 60% in mineral oil) and the resulting mixture was stirred at room temperature for 0.5 h. 1,3-Dibromopropane (730 mg, 3.62 mmol) was added, and the reaction mixture was stirred at 55° C. overnight. Then the reaction was poured into water (50 mL) and extracted with EtOAc (30 mL×3). The organic layer was washed with water (20 mL), brine (2×20 mL), dried over $Na_2SO_4$, filtered and evaporated to give a crude solid, which was purified by column chromatography on silica gel (petroleum ether/EtOAc=30/1 to 5/1) to give 60-2 (200 mg, about 20% yield) as an oil. MS Calcd.: 410.0; MS Found: 411.2 $[M+H]^+$.

The synthesis of N-(3-(1H-1,2,4-triazol-1-yl)propyl)-2'-nitro-N-phenylbiphenyl-4-amine (60-3):

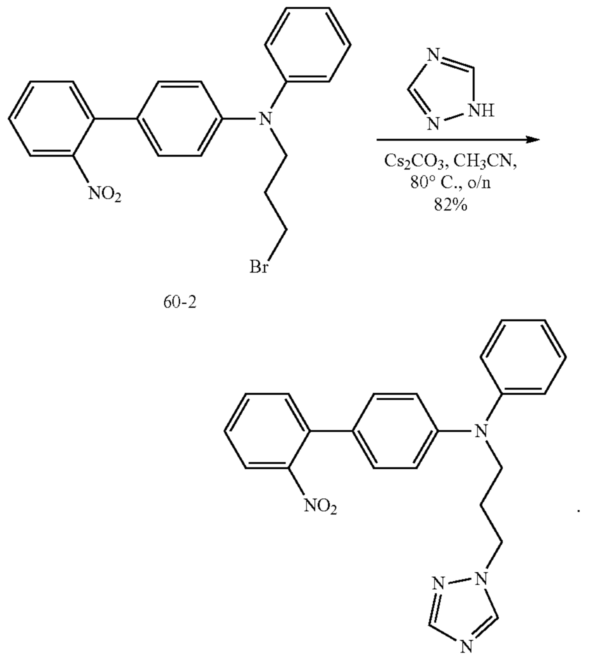

60-2

60-3

A mixture of 60-2 (250 mg, 0.61 mmol), 1,2,4-triazole (63 mg, 0.91 mmol) and $Cs_2CO_3$ (297 mg, 0.91 mmol) in $CH_3CN$ (50/10 mL) was stirred at 80° C. overnight. The reaction mixture was cooled to room temperature and poured into water (100 mL) and extracted with EtOAc (60 mL×3). The organic layer was washed with brine and evaporated. The residue was purified by column chromatography on silica gel (petroleum ether/EtOAc=30/1 to 4/1) to give 60-3 (200 mg, about 82% yield) as an oil. MS Calcd.: 399.2; MS Found: 400.2 $[M+H]^+$.

The synthesis of N-(3-(1H-1,2,4-triazol-1-yl)propyl)-N-phenyl-9H-carbazol-2-amine (SS20308-0060-01):

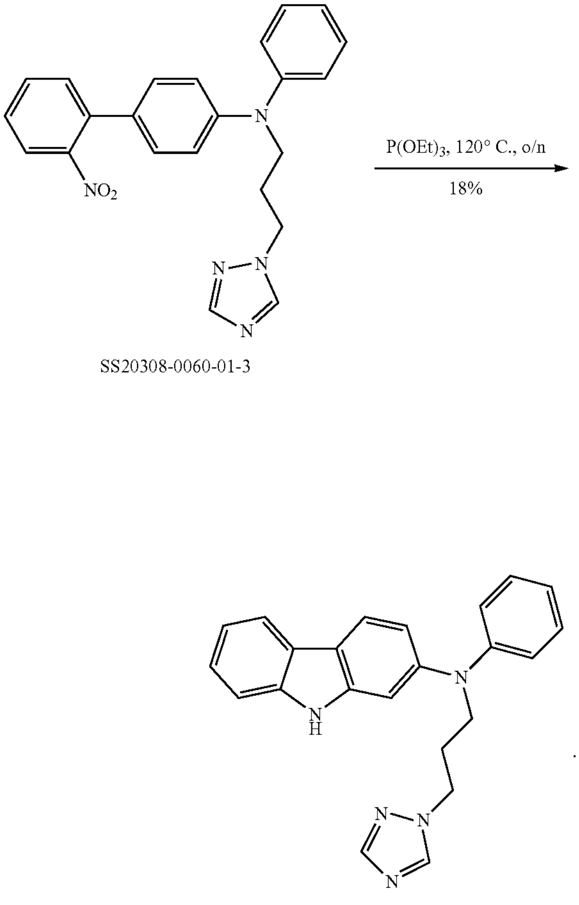

SS20308-0060-01-3

SS20308-0060-01

A solution of 60-3 (200 mg, 0.50 mmol) in $P(OEt)_3$ (6 mL) was stirred at 120° C. overnight. Then the reaction was concentrated to a crude mixture, which was purified by Prep-HPLC twice to give SS20308-0060-01 (34 mg, about 18% yield) as a solid. MS Calcd.: 367.2; MS Found: 368.2 $[M+H]^+$.

$^1H$ NMR (400 MHz, $CDCl_3$) δ 7.93-7.88 (m, 4H), 7.78 (s, 1H), 7.33-7.27 (m, 2H), 7.21-7.13 (m, 2H), 6.93-6.91 (m, 1H), 6.89-6.83 (m, 4H), 4.20 (t, J=6.8 Hz, 2H), 3.76 (t, J=6.8 Hz, 2H), 2.30-2.23 (m, 2H).

Example 14
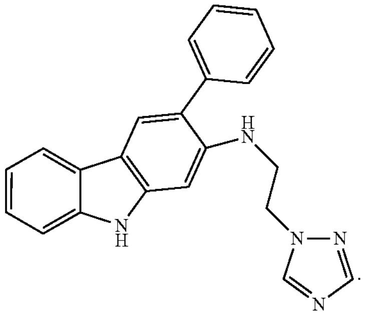
SS20308-0061-01
Chemical Formula: $C_{22}H_{19}N_5$
Molecular Weight: 353.42
Example 15
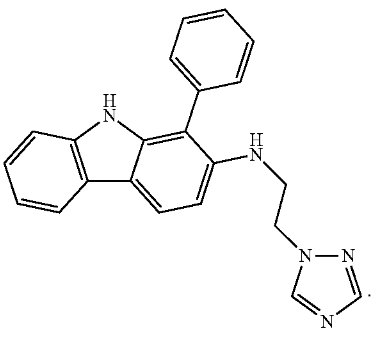
SS20308-0085-01
Chemical Formula: $C_{22}H_{19}N_5$
Molecular Weight: 353.42
Example Route for Examples 14 and 15 (SS20308-0061-01 and SS20308-0085-01):
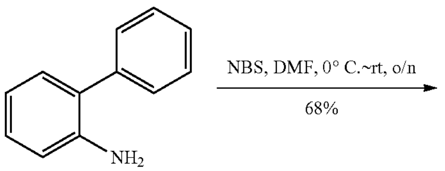
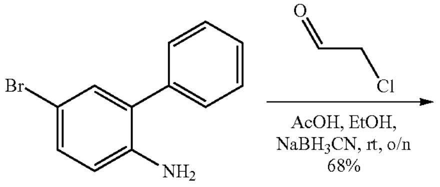
61-1
-continued
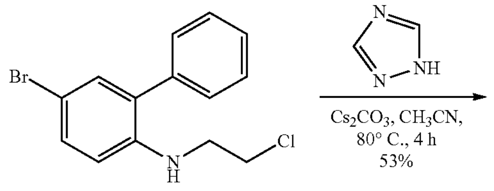
61-2
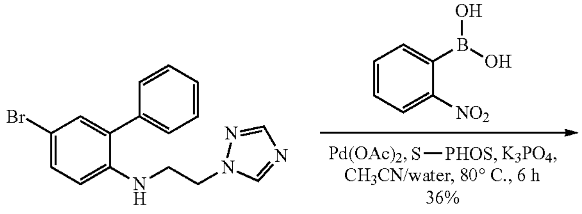
61-3
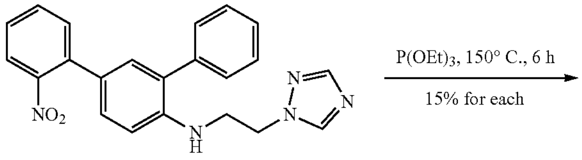
61-4
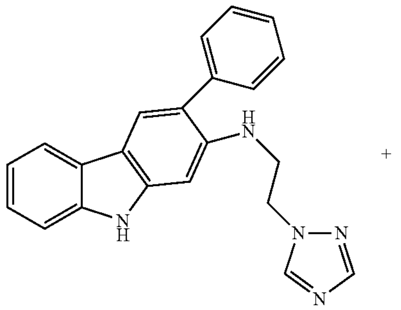
SS20308-0061-01
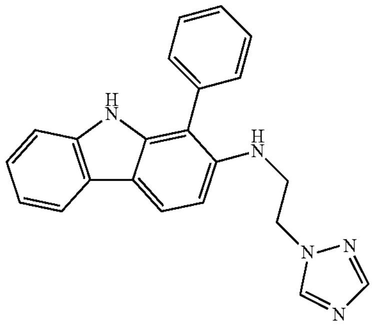
SS20308-0085-01
The synthesis of 5-bromobiphenyl-2-amine (61-1):
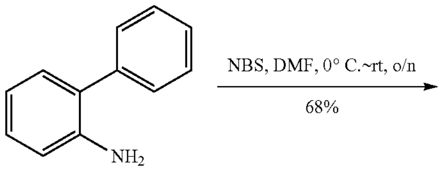

-continued

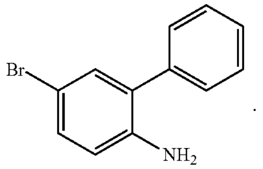

61-1

The mixture of 2-aminobiphenyl (5.0 g, 29.6 mmol) in DMF (30 mL) was stirred at 0° C., NBS (5.3 g, 29.6 mmol) was added, then the mixture was stirred at room temperature overnight. After being poured into water (60 mL), the mixture was extracted with EtOAc (30 mL×4). The organic layer was washed with brine and concentrated to dryness to give 61-1 (5.0 g, about 68% yield) as an oil. MS Calcd.: 247.0; MS Found: 250.1 $[M+H]^+$.

The synthesis of 5-bromo-N-(2-chloroethyl)biphenyl-2-amine (61-2):

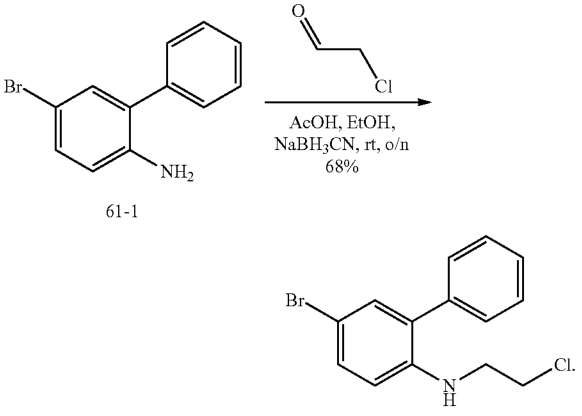

61-1

61-2

To a solution of 61-1 (2.0 g, 8.1 mmol) in EtOH (20 mL) was added 2-chloroacetaldehyde (950 mg, 12.1 mmol), AcOH (970 mg, 16.1 mmol), and $NaBH_3CN$ (507 mg, 8.1 mmol). Then the reaction mixture was stirred at room temperature overnight. The reaction mixture was poured into cool water (50 mL), basicified with saturated $Na_2CO_3$ solution to pH 9, and then extracted with EtOAc (150 mL). The organic layer was washed with brine and concentrated to dryness to give 61-2 (1.7 g, about 68% yield) as an oil. MS Calcd.: 309.0; MS Found: 310.0 $[M+H]^+$.

The synthesis of N-(2-(1H-1,2,4-triazol-1-yl)ethyl)-5-bromobiphenyl-2-amine (61-3):

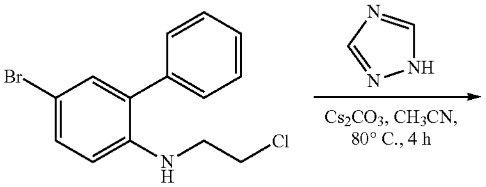

61-2

-continued

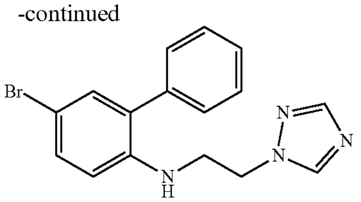

61-3

To a solution of 61-2 (1.7 g, 5.5 mmol) in $CH_3CN$ (10 mL) was added 1,2,4-triazole (756 mg, 11.0 mmol) and $Cs_2CO_3$ (3.6 g, 11.0 mmol), then the reaction mixture was stirred at 80° C. for 4 hours. The reaction mixture was cooled to room temperature and filtered through celite. The filtrate was concentrated to dryness. The residue was purified by column chromatography on silica gel (EtOAc/petroleum ether=1/5) to give 61-3 (1.0 g, about 53% yield) as an oil. MS Calcd.: 343.2; MS Found: 345.2 $[M+H]^+$.

The synthesis of 61-4:

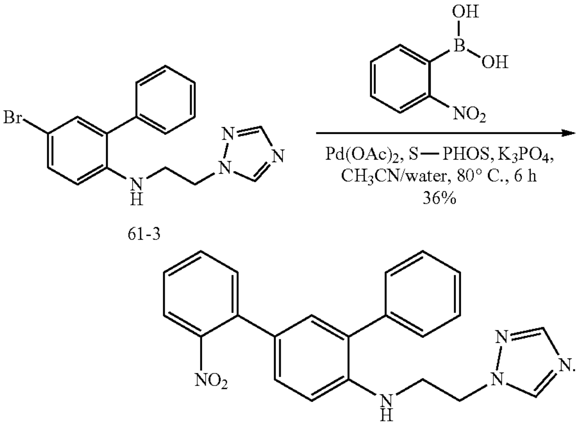

61-3

61-4

To a solution of 61-3 (1.0 g, 2.9 mmol) in $CH_3CN$/water (3/1, 20 mL) was added 2-nitrophenylboronic acid (684 mg, 4.1 mmol), S-Phos (119 mg, 0.3 mmol), $Pd(OAc)_2$ (67 mg, 0.3 mmol) and $K_3PO_4$ (1.8 g, 8.7 mmol), then the reaction mixture was stirred at 80° C. under nitrogen atmosphere for 6 hours. The reaction mixture was cooled to room temperature and filtered through celite. The filtrate was diluted with water (10 mL) and then extracted with EtOAc (20 mL×3). The organic layer was washed with brine and concentrated to dryness. The residue was purified by Prep-HPLC to give 61-4 (400 g, about 36% yield) as an oil. MS Calcd.: 385.2; MS Found: 386.4 $[M+H]^+$.

The synthesis of N-(2-(1H-1,2,4-triazol-1-yl)ethyl)-3-phenyl-9H-carbazol-2-amine (SS20308-0061-01) and N-(2-(1H-1,2,4-triazol-1-yl)ethyl)-1-phenyl-9H-carbazol-2-amine (SS20308-0085-01).

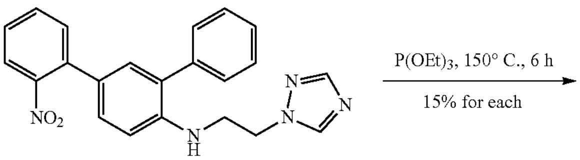

61-4

-continued

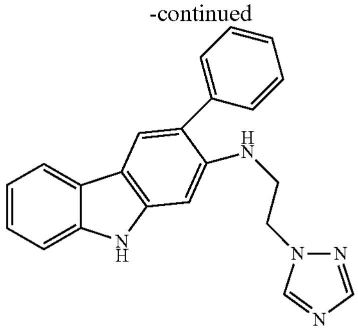

SS20308-0061-01

+

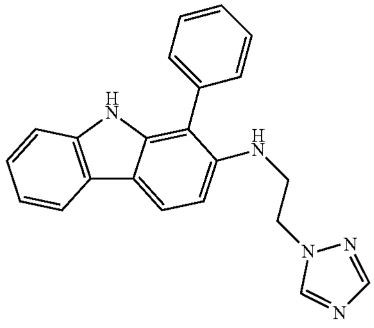

SS20308-0085-01

.

A solution of 61-4 (100 mg, 0.26 mmol) in $P(OEt)_3$ (1.5 mL) was stirred at 150° C. for 6 hours. Then the residue was purified by Prep-HPLC to give SS20308-0085-01 (14 mg, 15% yield) as a solid and 25 mg of SS20308-0061-01 (impure), which was further purified by Prep-TLC (EtOAc) to give SS20308-0061-01 (14 mg, 15% yield) as a solid.

SS20308-0061-01:MS Calcd.: 353.2; MS Found: 354.2 $[M+H]^+$. $^1H$ NMR (400 MHz, DMSO-$d_6$) δ 10.91 (s, 1H), 8.47 (s, 1H), 7.98 (s, 1H), 7.88 (d, J=7.6 Hz, 1H), 7.68 (s, 1H), 7.45-7.43 (m, 2H), 7.38-7.32 (m, 4H), 7.22-7.18 (m, 1H), 7.05-7.01 (m, 1H), 6.67 (s, 1H), 4.78 (t, J=6.0 Hz, 1H), 4.44 (t, J=6.0 Hz, 2H), 3.57 (td, J=6.0, 5.6 Hz, 2H).

SS20308-0085-01: MS Calcd.: 353.2; MS Found: 354.2 $[M+H]^+$. $^1H$ NMR (400 MHz, DMSO-$d_6$) δ 10.13 (s, 1H), 8.43 (s, 1H), 7.94 (s, 1H), 7.91-7.87 (m, 2H), 7.57-7.48 (m, 2H), 7.48-7.46 (m, 1H), 7.32-7.29 (m, 3H), 7.18-7.14 (m, 1H), 7.05-7.01 (m, 1H), 6.68 (d, J=8.8 Hz, 1H), 4.48 (t, J=6.0 Hz, 1H), 4.35 (t, J=6.0 Hz, 2H), 3.57 (td, J=6.0, 6.0 Hz, 2H).

Example 16

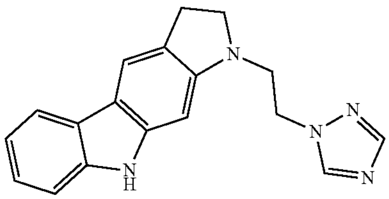

SS20308-0180-01
Chemical Formula: $C_{18}H_{17}N_5$
Molecular Weight: 303.36

Example Route for Example 16 (SS20308-0180-01):

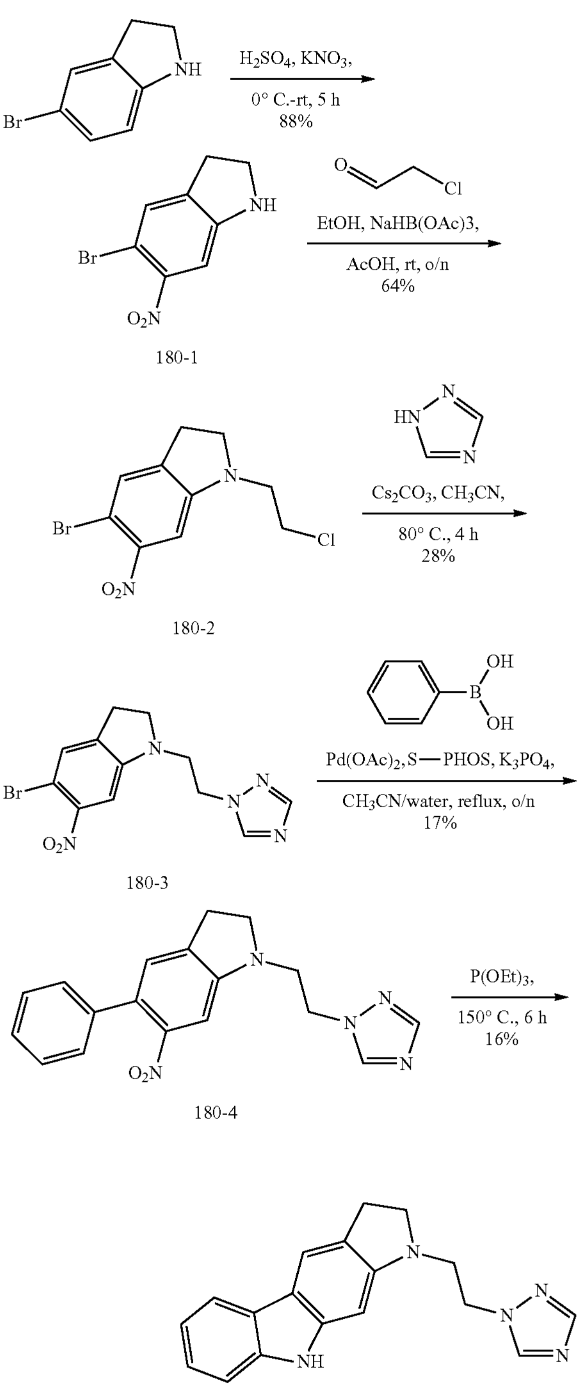

SS20308-0180-01

The synthesis of 5-bromo-6-nitroindoline (180-1):

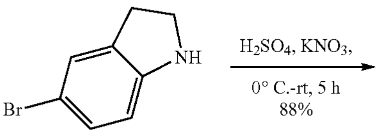

-continued

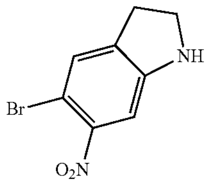

180-1

To the mixture of 5-bromoindoline (2.50 g, 12.62 mmol) in $H_2SO_4$ (10 mL) stirred at 0° C. was added $KNO_3$ (1.29 g, 12.74 mmol). The mixture was then allowed to warm to room temperature and stirred for 5 h. Then the mixture was poured onto ice slowly and basicified with sat. $Na_2CO_3$ to pH 8. The resulting mixture was extracted with EtOAc (50 mL×3). The organic layers were washed with brine, dried over $Na_2SO_4$ and concentrated. The residue was purified by column chromatography on silica gel (petroleum ether/EtOAc=8/1) to give 180-1 (2.70 g, about 88% yield) as a solid. MS Calcd.: 242.0; MS Found: 243.1 $[M+H]^+$.

The synthesis of 5-bromo-1-(2-chloroethyl)-6-nitroindoline (180-2):

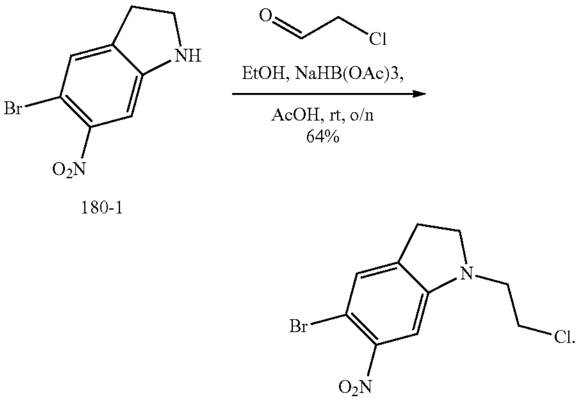

180-1

180-2

A solution of 180-1 (2.0 g, 8.23 mmol), 2-chloroacetaldehyde (6.46 g, 32.91 mmol, 40% in water), $NaBH_3CN$ (1.55 g, 24.69 mmol), in EtOH (40 mL) was stirred at room temperature for overnight and then basicified with $NaHCO_3$ solution. The resulting solid was filtered and dissolved in EtOAc, washed with brine, dried, concentrated. The residue was washed with $Et_2O$ to give 180-2 (1.6 g, about 64% yield) as a solid. MS Calcd.:304.0; MS Found: 304.9 $[M+H]^+$.

The synthesis of 1-(2-(1H-1,2,4-triazol-1-yl)ethyl)-5-bromo-6-nitroindoline (180-3):

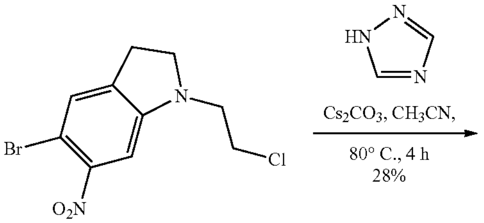

180-2

-continued

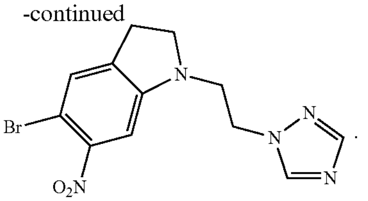

180-3

A mixture of 180-2 (1.6 g, 5.24 mmol), 1H-1,2,4-triazole (543 mg, 7.86 mmol) and $Cs_2CO_3$ (2.56 g, 7.85 mmol) in $CH_3CN$ (40 mL) was stirred at 80° C. for 4 h. Then the reaction mixture was cooled down to room temperature and filtered. The filtrate was concentrated and purified by column chromatography on silica gel (EtOAc/petroleum ether=1/1 to DCM/MeOH=20/1) to give 180-3 (0.5 g, about 28% yield) as a solid. MS Calcd.:337.0; MS Found: 337.8 $[M+H]^+$.

The synthesis of 1-(2-(1H-1,2,4-triazol-1-yl)ethyl)-6-nitro-5-phenylindoline (180-4):

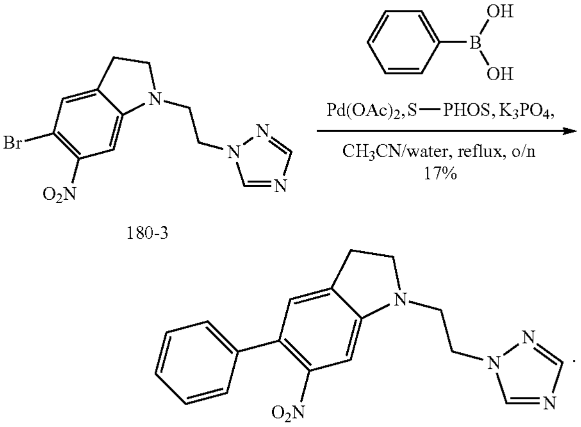

180-3

180-4

A solution of 180-3 (610 mg, 1.81 mmol), phenylboronic acid (332 mg, 2.72 mmol,), S-Phos (149 mg, 0.36 mmol), palladium (II) acetate (41 mg, 0.18 mmol), and potassium phosphate (0.96 g, 4.54 mmol,) were suspended in $CH_3CN$ (30 mL) and water (10 mL). The reaction mixture was heated at reflux for overnight and then filtered; rinsing with EtOAc. The filtrate was concentrated and the residue was purified by column chromatography on silica gel (petroleum ether/EtOAc=1/1, 1/2, 1/3) to give 180-4 (100 mg, about 17% yield) as a pale oil. MS Calcd.: 335.1; MS Found: 335.8 $[M+H]^+$.

The synthesis of 1-(2-(1H-1,2,4-triazol-1-yl)ethyl)-1,2,3,9-tetrahydropyrrolo[2,3-b]carbazole (SS20308-0180-01):

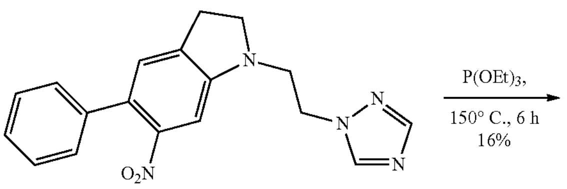

180-4

-continued

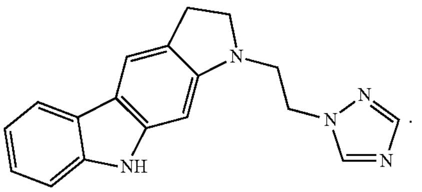

SS20308-0180-01

A solution of 180-4 (95 mg, 0.28 mmol) in $P(OEt)_3$ (2 mL) was stirred at 150° C. for 6 h. After the reaction was completed, the reaction was purified by reverse phase flash column chromatography and Prep-TLC to give SS20308-0180-01 (14 mg, about 16% yield) as a solid. MS Calcd.: 303.2; MS Found: 304.1 $[M+H]^+$.

$^1H$ NMR (400 MHz, DMSO-$d_6$) δ 10.78 (brs, 1H), 8.55 (s, 1H), 8.00 (s, 1H), 7.82 (d, J=7.6 Hz, 1H), 7.65 (s, 1H), 7.30 (d, J=8.0 Hz, 1H), 7.14 (dd, J=7.2, 7.2 Hz, 1H), 7.00 (dd, J=7.6, 7.2 Hz, 1H), 6.35 (s, 1H), 4.47 (t, J=6.0 Hz, 2H), 3.58 (t, J=6.0 Hz, 2H), 3.39 (t, J=8.2 Hz, 2H), 2.98 (t, J=8.2 Hz, 2H).

Example 17

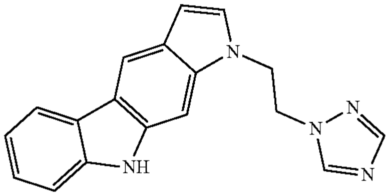

SS20308-0062-01
Chemical Formula: $C_{18}H_{15}N_5$
Molecular Weight: 301.35

Example Route for Example 17 (SS20308-0062-01_:

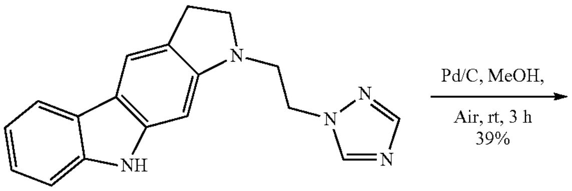

SS20308-0180-01

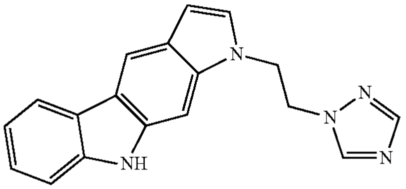

SS20308-0062-01

The synthesis of 1-(2-(1H-1,2,4-triazol-1-yl)ethyl)-1,9-dihydropyrrolo[2,3-b]carbazole (SS20308-0062-01):

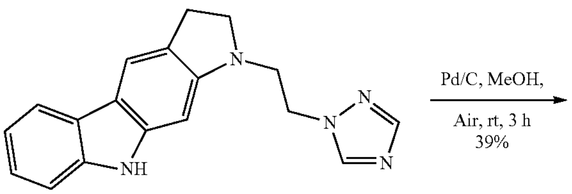

SS20308-0180-01

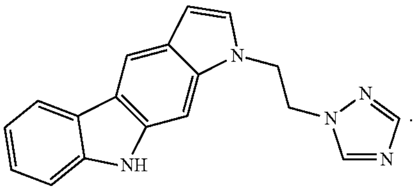

SS20308-0062-01

A solution of SS20308-0180-01 (12 mg, 0.039 mmol) and 10% Pd/C (2 mg) in MeOH (2 mL) was stirred at room temperature for 3 h under air. After the reaction was completed, the reaction was purified by reverse flash column chromatography and Prep-TLC to give SS20308-0062-01 (4.7 mg, about 39% yield) as a solid. MS Calcd.: 301.1; MS Found: 302.2 $[M+H]^+$.

$^1H$ NMR (400 MHz, $CDCl_3$) δ 8.18 (s, 1H), 8.01 (d, J=7.6 Hz, 1H), 7.94 (s, 1H), 7.81 (brs, 1H), 7.41 (s, 1H), 7.32-7.29 (m, 2H), 7.17-7.11 (m, 1H), 7.02 (s, 1H), 6.63 (d, J=3.2 Hz, 1H), 6.50 (d, J=3.2 Hz, 1H), 4.58-4.46 (m, 4H).

Example 18

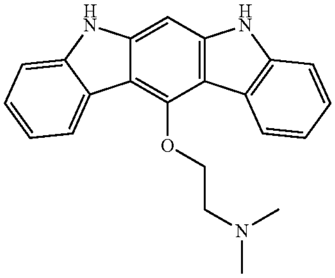

SS20308-0063-01
Chemical Formula: $C_{22}H_{21}N_3O$
Molecular Weight: 343.42

Example Route for Example 18 (SS20308-0063-01):

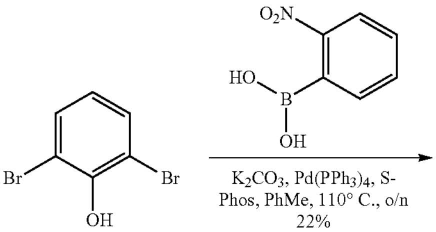

-continued

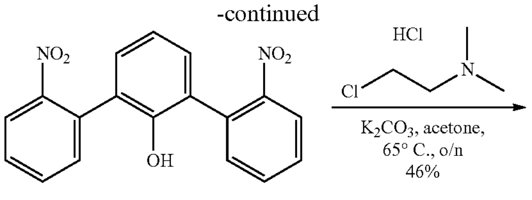

63-1

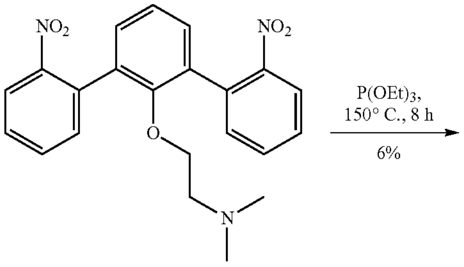

63-2

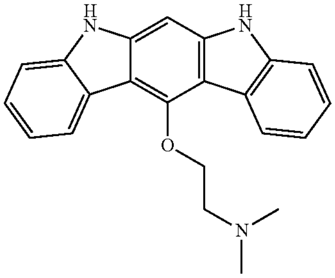

SS20308-0063-01

The synthesis of 2,2"-dinitro-[1,1',3',1"-terphenyl]-2'-ol (63-1):

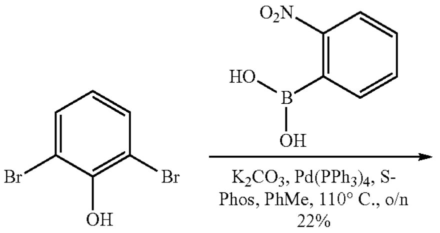

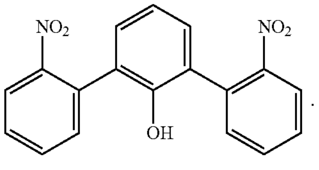

63-1

A mixture of 2,6-dibromophenol (50 mg, 0.20 mmol), 2-nitrophenylboronic acid (33 mg, 0.20 mmol), $Pd(PPh_3)_4$ (10 mg, 0.01 mmol), S-Phos (8 mg, 0.02 mmol), $K_2CO_3$ (55 mg, 0.40 mmol) in PhMe (5 ml) was stirred at 110° C. under nitrogen atmosphere overnight. After the reaction was completed, the mixture was quenched with water and the insoluble material was removed by filtration. The filtrate was extracted with EtOAc (20 mL×3). The organic layer was separated, dried over $MgSO_4$, and concentrated under vacuum. The residue was purified by Prep-TLC (EtOAc/petroleum ether=1/3) to give 63-1 (15 mg, about 22% yield) as a solid. MS Calcd.: 336.1; MS Found: 354.2 $[M+NH_4]^+$.

The synthesis of 2-((2,2"-dinitro-[1,1':3',1"-terphenyl]-2'-yl)oxy)-N,N-dimethylethan-1-amine (63-2):

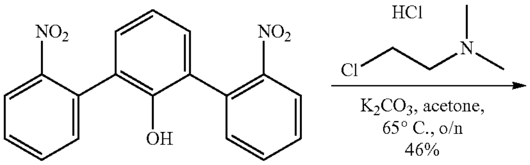

63-1

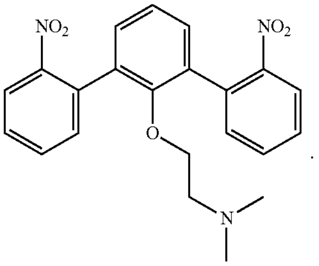

63-2

A mixture of 63-1 (320 mg, 0.95 mmol), 2-chloro-N,N-dimethylethanamine hydrochloride (205 mg, 1.43 mmol) and $K_2CO_3$ (263 mg, 1.90 mmol) in acetone (10 mL) was stirred at 65° C. overnight. Then the reaction mixture was quenched with water, and extracted with EtOAc (20 mL×3). The residue was purified by Prep-TLC (EtOAc/petroleum ether=1/1) to give 63-2 (180 mg, about 46% yield) as a solid. MS Calcd.:407.2; MS Found: 408.3 $[M+H]^+$.

The synthesis of 2-(5,7-dihydroindolo[2,3-b]carbazol-12-yloxy)-N,N-dimethylethanamine (63-3):

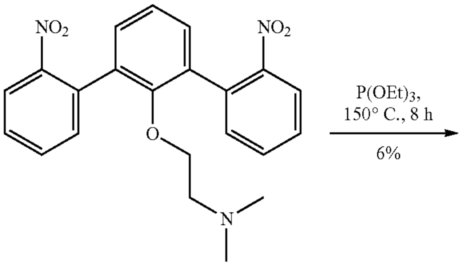

63-2

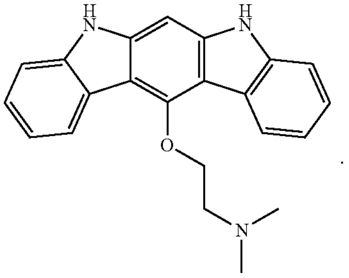

SS20308-0063-01

A solution of 63-2 (160 mg, 0.39 mmol) in $P(OEt)_3$ (1 mL) was stirred at 150° C. overnight. After the reaction was completed, the reaction concentrated to a crude mixture, which was purified by Prep-HPLC three times to give SS20308-0063-01 (8 mg, about 6% yield) as a solid. MS Calcd.: 343.2; MS Found: 344.2 $[M+H]^+$.

$^1H$ NMR (400 MHz, $CDCl_3$) δ 8.30 (d, J=7.6 Hz, 2H), 7.99 (s, 2H), 7.34-7.39 (m, 4H), 7.23-7.19 (m, 2H), 7.05 (s, 1H), 4.41 (t, J=6.0 Hz, 2H), 3.04 (t, J=5.2 Hz, 2H), 2.43 (s, 6H).

Example 19

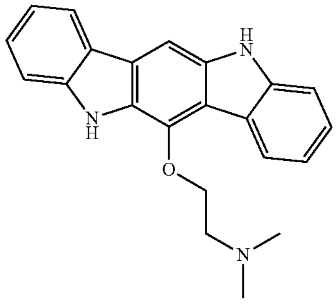

SS20308-0065-01
Chemical Formula: $C_{22}H_{21}N_3O$
Molecular Weight: 343.42

Example Route for Example 19 (SS20308-0065-01):

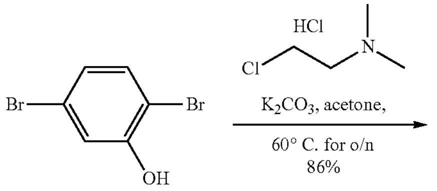

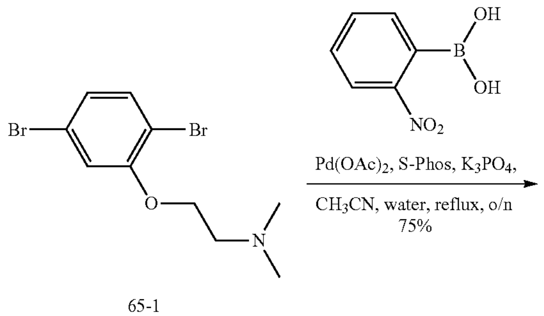

65-1

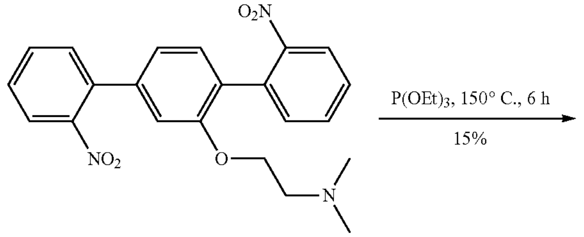

65-2

-continued

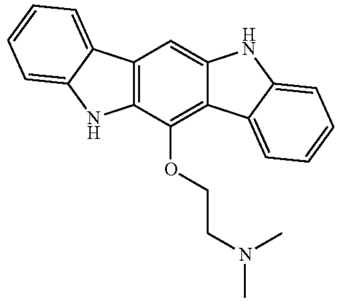

SS20308-0065-01

The synthesis of 2-(2,5-dibromophenoxy)-N,N-dimethylethanamine (65-1):

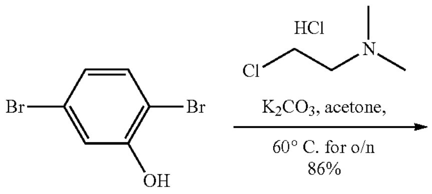

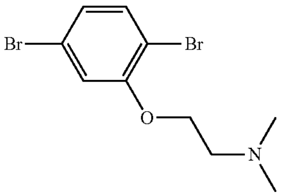

65-1

A mixture of 2,5-dibromophenol (1.0 g, 3.97 mmol), 2-chloro-N,N-dimethylethanamine hydrochloride (858 mg, 5.96 mmol) and $K_2CO_3$ (1.65 g, 11.91 mmol) in acetone (20 mL) was stirred at 60° C. for overnight. Then the reaction mixture was cooled down to room temperature and filtered. The filtrate was concentrated and purified by column chromatography on silica gel (EtOAc/petroleum ether=1/1) to give 65-1 (1.1 g, about 86% yield) as a pale oil. MS Calcd.: 320.9; MS Found: 322.2 $[M+H]^+$.

The synthesis of 2-((2,2"-dinitro-[1,1':4',1"-terphenyl]-2'-yl)oxy)-N,N-dimethylethan-1-amine (65-2):

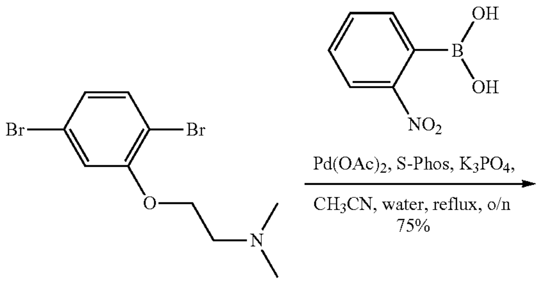

65-1

-continued

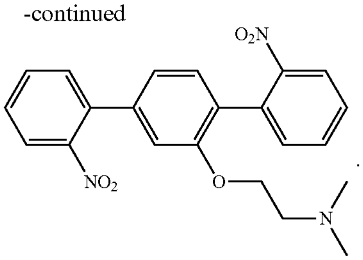

65-2

A solution of 65-1 (500 mg, 1.55 mmol), 2-nitrophenylboronic acid (776 mg, 4.65 mmol,), S-Phos (64 mg, 0.16 mmol), palladium (II) acetate (18 mg, 0.08 mmol), and potassium phosphate (1.64 g, 7.74 mmol,) were suspended in $CH_3CN$ (9 mL) and water (3 mL). The reaction mixture was heated at reflux under nitrogen overnight and then filtered, rinsing with EtOAc. The filtrate was concentrated and the residue was purified by column chromatography on silica gel (petroleum ether/EtOAc=1/1) to give 65-2 (470 mg, about 75% yield) as an oil. MS Calcd.:407.2; MS Found: 408.3 $[M+H]^+$.

The synthesis of 2-(5,11-dihydroindolo[3,2-b]carbazol-6-yloxy)-N,N-dimethylethanamine (SS20308-0065-01):

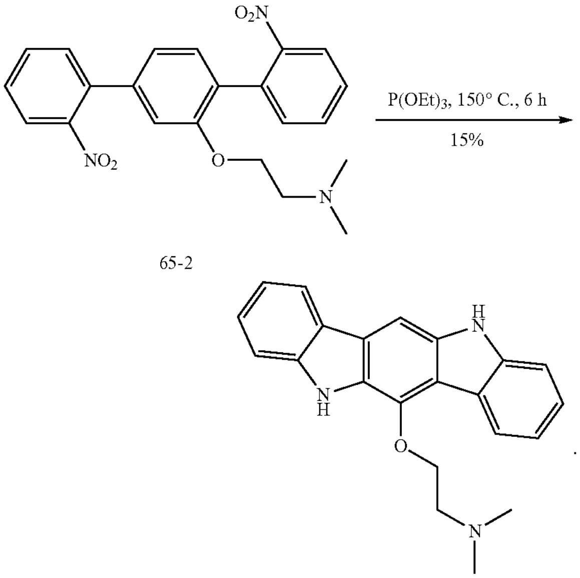

65-2

SS20308-0065-01

A solution of 65-2 (100 mg, 0.25 mmol) in $P(OEt)_3$ (2 mL) was stirred at 150° C. for 6 h. After the reaction was completed, the reaction was purified by reverse phase flash column chromatography and Prep-TLC twice, followed by Prep-HPLC, to give SS20308-0065-01 (13 mg, about 15% yield) as a solid. MS Calcd.: 343.2; MS Found: 344.2 $[M+H]^+$.

$^1$H NMR (400 MHz, DMSO-$d_6$) δ 11.28 (s, 1H), 11.09 (s, 1H), 8.34 (d, J=7.6 Hz, 1H), 8.18 (d, J=8.0 Hz, 1H), 7.88 (s, 1H), 7.51 (d, J=8.0 Hz, 1H), 7.45 (d, J=8.0 Hz, 1H), 7.42-7.34 (m, 2H), 7.18-7.09 (m, 2H), 4.42 (t, J=5.8 Hz, 2H), 2.83 (t, J=5.8 Hz, 2H), 2.35 (s, 6H).

Example 20

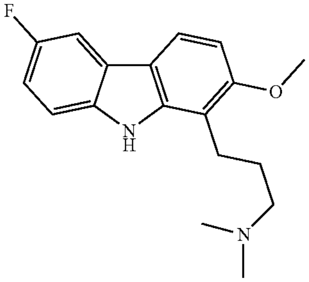

SS20308-0118-01

Chemical Formula: $C_{18}H_{21}FN_2O$

Molecular Weight: 300.4

Example Route for Example 20 (SS20308-0118-01):

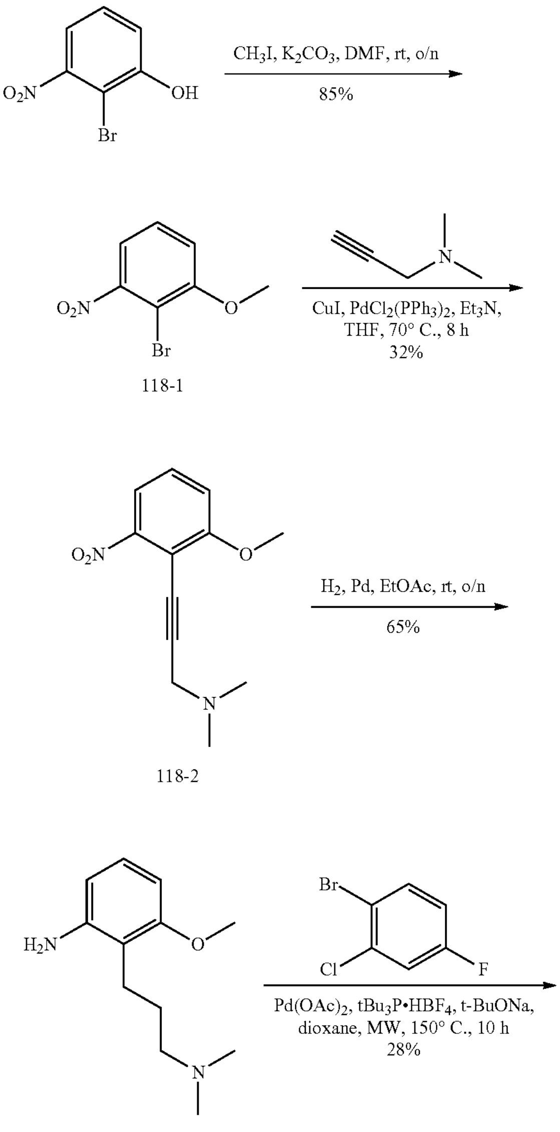

118-1

118-2

118-3

-continued

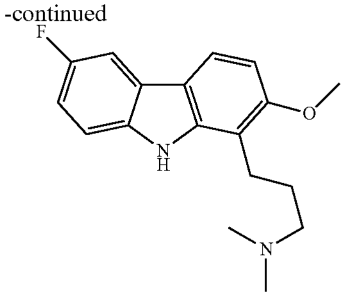

SS20308-0118-01

The synthesis of 2-bromo-1-methoxy-3-nitrobenzene (118-1):

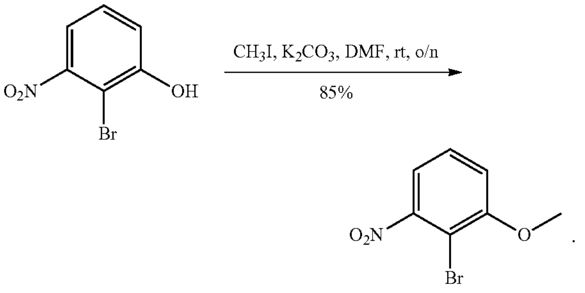

118-1

To a mixture of 2-bromo-1-hydroxy-3-nitrobenzene (1.1 g, 5.05 mmol) and $K_2CO_3$ (1.4 g, 10.09 mmol) in DMF (25 mL) was added $CH_3I$ (859 mg, 6.05 mmol), and then stirred at room temperature overnight. The reaction mixture was diluted with water and then extracted with EtOAc (3×50 mL). The organic layer was washed with brine and concentrated to dryness to give crude, which was purified by column chromatography on silica gel (petroleum ether/EtOAc=10/1 to 5/1) to give 118-1 (1.0 g, about 85% yield) as a solid.

The synthesis of 3-(2-methoxy-6-nitrophenyl)-N,N-dimethylprop-2-yn-1-amine (118-2):

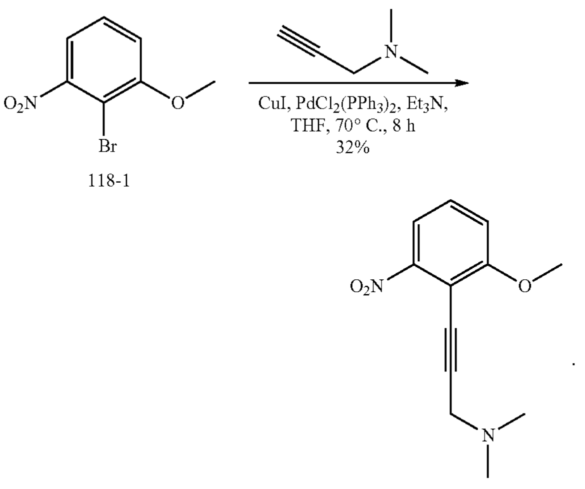

118-2

To a solution of 118-1 (3.7 g, 15.86 mmol) in THF (80 mL) was added N,N-dimethylpropargylamine (4.6 g, 55.51 mmol), $PdCl_2(PPh_3)_2$ (2.23 g, 3.17 mmol), CuI (302 mg, 1.59 mmol) and $Et_3N$ (8.0 g, 79.30 mmol). Then the reaction mixture was stirred at 70° C. for 8 h. After the reaction mixture was cooled to room temperature, it was diluted with water and extracted with EtOAc (3×100 mL). The organic layer was washed with brine and concentrated to dryness. The residue was purified by column chromatography on silica gel (petroleum ether/EtOAc=1/5) and then Prep-TLC (petroleum ether/EtOAc=1/1) to give 118-2 (1.2 g, about 32% yield) as an oil. MS Calcd.: 234.1; MS Found: 235.4 $[M+H]^+$.

The synthesis of 2-(3-(dimethylamino)propyl)-3-methoxyaniline (118-3):

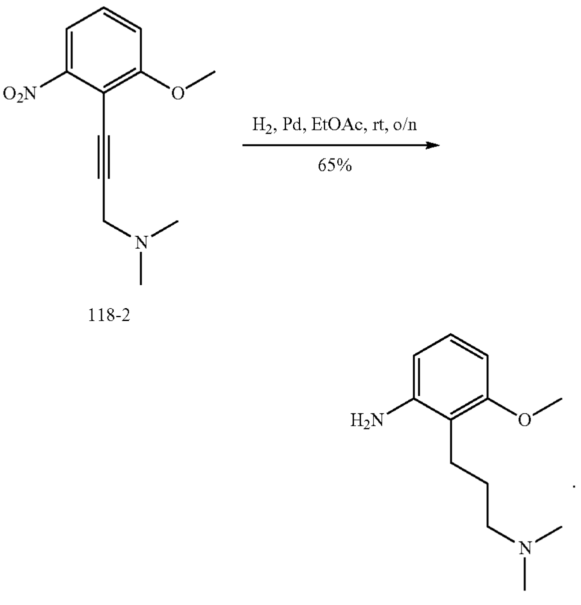

118-3

To a solution of 118-2 (400 mg, 1.71 mmol) in EtOAc (20 mL) was added Pd on carbon (40 mg, 10%). Then the reaction mixture was stirred at room temperature overnight under hydrogen gas (balloon). The reaction mixture was filtered through celite and then concentrated to dryness. The residue was purified by Prep-HPLC to give 118-3 (230 mg, about 65% yield) as an oil. MS Calcd.: 208.2; MS Found: 345.2 $[M+H]^+$.

The synthesis of 3-(6-fluoro-2-methoxy-9H-carbazol-1-yl)-N,N-dimethylpropan-1-amine (SS20308-0118-01):

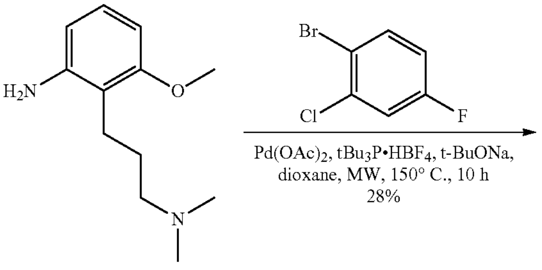

118-3

-continued

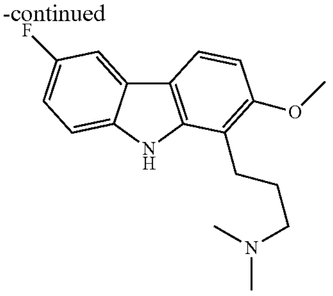

SS20308-0118-01

To a solution of 118-3 (150 mg, 0.72 mmol) in dioxane (5 mL) was added 1-bromo-2-chloro-4-fluorobenzene (181 mg, 0.86 mmol), $Pd(OAc)_2$ (16 mg, 0.07 mmol), $tBu_3P.HBF_4$ (01 mg, 0.07 mmol) and t-BuONa (173 mg, 1.8 mmol). Then the reaction mixture was stirred at 150° C. for 10 h under microwave. The reaction mixture was cooled to room temperature and filtered through celite and then extracted with EtOAc (3×30 mL). The organic layer was washed with brine and concentrated to dryness. The residue was purified by column chromatography on silica gel (DCM/MeOH=5/1) twice to give SS20308-0118-01 (60 mg, about 28% yield) as a solid. MS Calcd.: 300.2; MS Found: 301.1 $[M+H]^+$.\

$^1H$ NMR (400 MHz, $CDCl_3$) δ 10.99 (s, 1H), 7.74 (d, J=8.4 Hz, 1H), 7.54 (dd, J=5.2, 2.4 Hz, 1H), 7.26 (dd, J=8.8, 4.4 Hz, 1H), 6.98 (td, J=9.2, 2.8 Hz, 1H), 6.76 (d, J=8.8 Hz, 1H), 3.85 (s, 3H), 3.00 (t, J=6.4 Hz, 2H), 2.37 (s, 6H), 2.33-2.26 (m, 2H), 1.94-1.84 (m, 2H).

Example 21

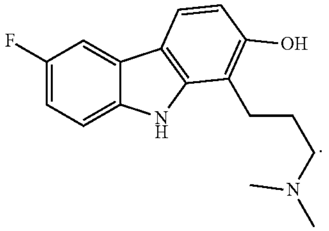

SS20308-0068-01
Chemical Formula: $C_{17}H_{19}FN_2O$
Molecular Weight: 286.3

Example Route for Example 21 (SS20308-0068-01):

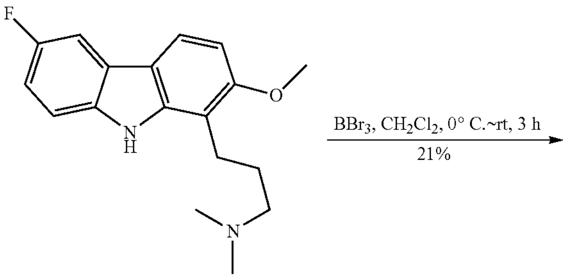

SS20308-0118-01

-continued

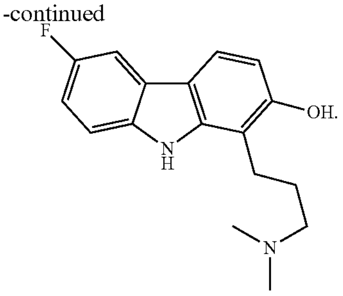

SS20308-0068-01

The synthesis of 1-(3-(dimethylamino)propyl)-6-fluoro-9H-carbazol-2-ol (SS20308-0068-01):

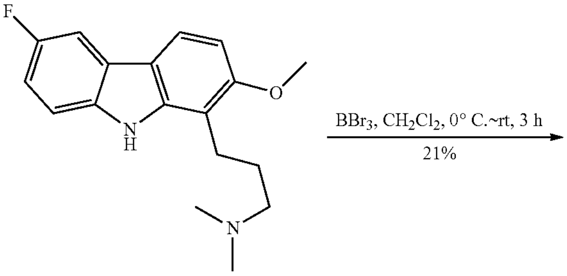

SS20308-0118-01

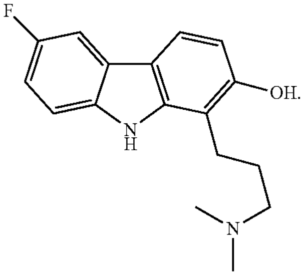

SS20308-0068-01

To a solution of SS20308-0118-01 (60 mg, 0.20 mmol) in DCM (10 mL) was added $BBr_3$ (0.5 mL, 1N in DCM) and stirred at 0° C. to room temperature for 3 h. Then the solution was adjusted to pH 8 with $NaHCO_3$, diluted with water and extracted with DCM (3×20 mL). The organic layer was washed with brine and concentrated to dryness. The residue was purified by Prep-HPLC to give SS20308-0068-01 (12 mg, about 21% yield) as a solid. MS Calcd.: 286.1; MS Found: 287.0 $[M+H]^+$.

$^1H$ NMR (400 MHz, DMSO-$d_6$) δ 10.97 (s, 1H), 10.16 (br, 1H), 7.74-7.71 (m, 2H), 7.37 (dd, J=8.8, 4.4 Hz, 1H), 7.06 (td, J=9.2, 2.8 Hz, 1H), 6.68 (d, J=8.4 Hz, 1H), 2.84 (t, J=6.8 Hz, 2H), 2.33-2.22 (m, 8H), 1.82 (t, J=6.8 Hz, 2H).

Example 22

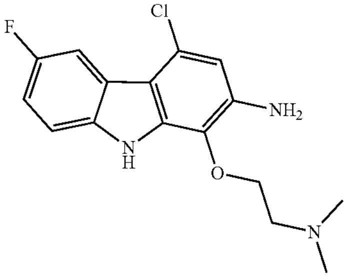

SS20308-0069-01
Chemical Formula: $C_{16}H_{17}ClFN_3O$
Molecular Weight: 321.78

Example Route for Example 22 (SS20308-0069-01):

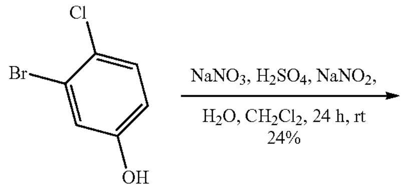

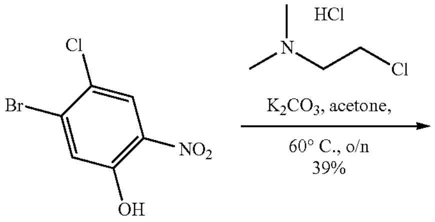

69-1

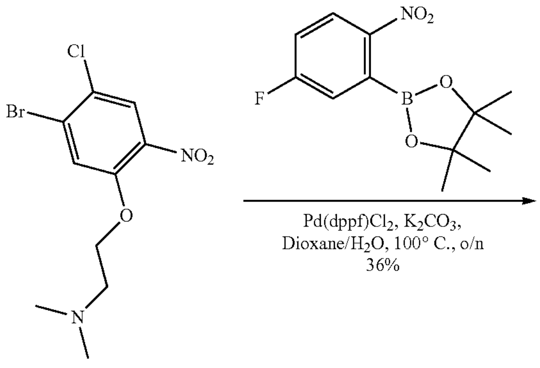

69-2

-continued

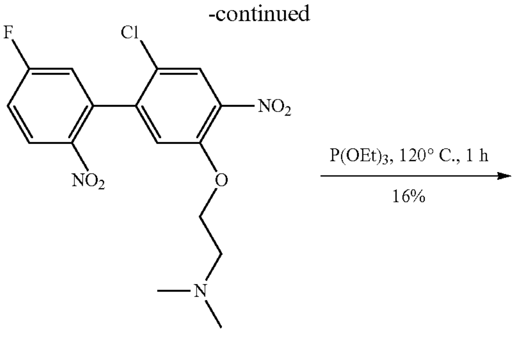

69-3

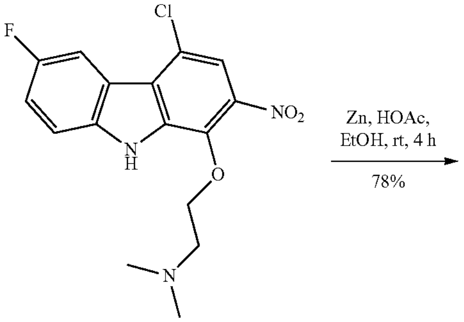

69-4

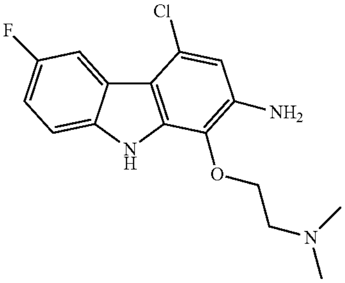

SS20308-0069-01

The synthesis of 5-bromo-4-chloro-2-nitrophenol (69-1):

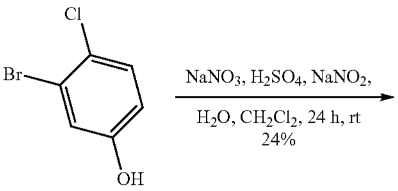

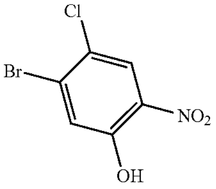

69-1

To a solution of 3-bromo-4-chlorophenol (10 g, 49 mmol) in DCM (200 mL) was added $NaNO_3$ (3.7 g, 53 mmol), $H_2SO_4$ (60 mL, 3 M) and $NaNO_2$ (50 mg, catalytic amount), then the reaction mixture was stirred at room temperature for 24 h. After the reaction was complete, the reaction mixture was quenched with water (100 mL), and extracted with EtOAc (100 mL×3). The combined organic layers were dried over $Na_2SO_4$ and concentrated under vacuum. The residue was purified by Prep-TLC (DCM/MeOH=20/1) to give 69-1 (3.0 g, about 24% yield) as a solid.

$^1H$ NMR (400 MHz, $CDCl_3$) δ 10.36 (s, 1H), 8.14 (s, 1H), 7.46 (s, 1H).

The synthesis of 2-(5-bromo-4-chloro-2-nitrophenoxy)-N,N-dimethylethanamine (69-2):

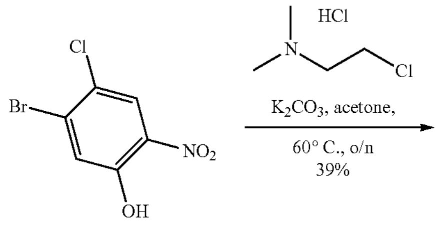

69-1

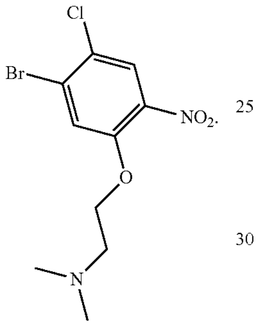

69-2

A mixture of the 69-1 (2.0 g, 8.0 mmol), 2-chloro-N,N-dimethylethanamine hydrochloride (2.3 g, 16.0 mmol) and $K_2CO_3$ (3.3 g, 24.0 mmol) in acetone (100 mL) was stirred at 70° C. overnight. After the reaction was complete, the reaction mixture was quenched with water (10 mL), and extracted with EtOAc (30 mL×3). The combined layers were dried over $Na_2SO_4$ and concentrated under vacuum. The residue was purified by reverse phase column chromatography to give 69-2 (1.0 g, about 39% yield) as a solid. MS Calcd.: 322.0; MS Found: 323.0 [M+H]$^+$.

The synthesis of 2-(6-chloro-5'-fluoro-2',4-dinitrobiphenyl-3-yloxy)-N,N-dimethylethanamine (69-3)

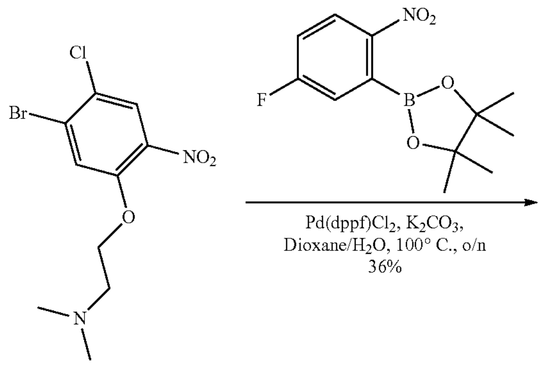

69-2

-continued

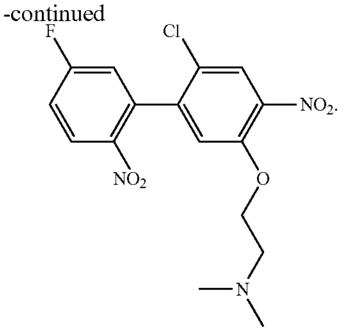

69-3

A mixture of 69-2 (700 mg, 2.17 mmol), 2-(5-fluoro-2-nitrophenyl)-4,4,5,5-tetramethyl-1,3,2-dioxaborolane (578 mg, 2.17 mmol), $Pd(dppf)Cl_2$ (158 mg, 0.22 mmol), and $K_2CO_3$ (599 mg, 4.34 mmol) in dioxane/$H_2O$ (10/2 mL) was stirred at reflux overnight. The reaction mixture was cooled to room temperature and poured into water (10 mL) and extracted with EtOAc (30 mL×3). The organic layer was washed with brine and evaporated, the residue crude product was purified by column chromatography on silica gel (DCM/MeOH=20/1) to give 69-3 (300 mg, about 36% yield) as a solid. MS Calcd.: 384.2; MS Found: 383.1 [M+H]$^+$.

The synthesis of 2-(4-chloro-6-fluoro-2-nitro-9H-carbazol-1-yloxy)-N,N-dimethylethanamine (69-4):

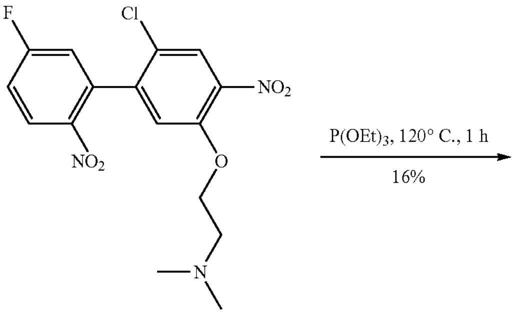

69-3

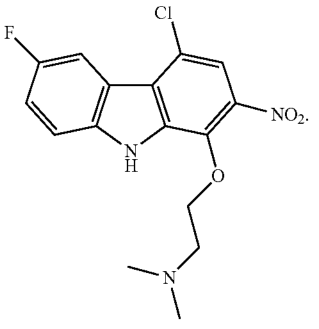

69-4

To a solution of 69-3 (100 mg, 0.26 mmol) in $P(OEt)_3$ (1 mL) was stirred at 120° C. for 1 h. Then the reaction was concentrated to a crude mixture, which was purified by Prep-HPLC twice to give 69-4 (15 mg, about 16% yield) as a solid. MS Calcd.: 351.1; MS Found: 352.2 [M+H]$^+$.

The synthesis of 4-chloro-1-(2-(dimethylamino)ethoxy)-6-fluoro-9H-carbazol-2-amine (SS20308-0069-01):

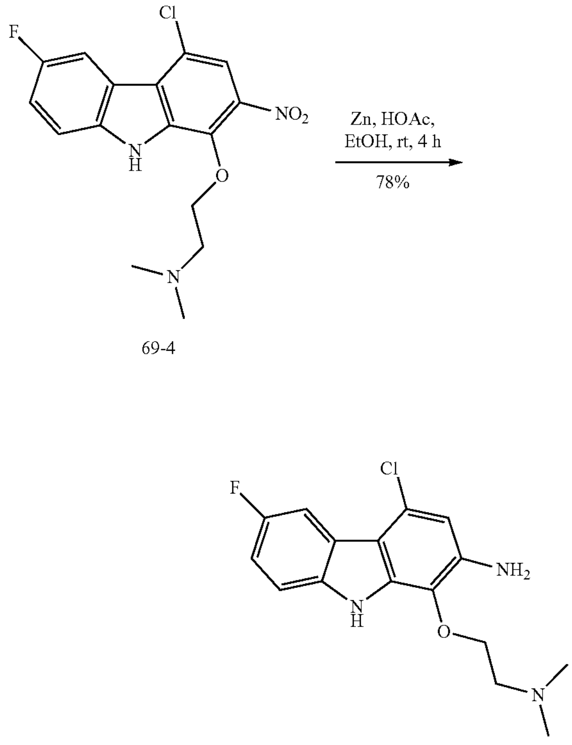

69-4

SS20308-0069-01

A mixture of 69-4 (15 mg, 0.04 mmol), zinc powder (13 mg, 0.2 mmol) and acetic acid (12 mg, 0.2 mmol) was suspended in EtOH (1 mL) and the mixture was stirred at room temperature for 4 h. The mixture was filtered through a pad of celite, washed with hot MeOH, concentrated, and purified by Prep-HPLC to give SS20308-0069-01 (10 mg, about 78% yield) as a solid. MS Calcd.: 321.1; MS Found: 322.2 $[M+H]^+$.

$^1$H NMR (400 MHz, $CD_3OD$) δ 7.95 (dd, J=10.0, 2.4 Hz, 1H), 7.41 (q, J=8.8 Hz, 1H), 7.11 (ddd, J=9.0, 9.0, 2.4 Hz, 1H), 6.76 (s, 1H), 4.38 (t, J=4.8 Hz, 2H), 3.66 (t, J=4.8 Hz, 2H), 3.10 (s, 6H).

Example 23

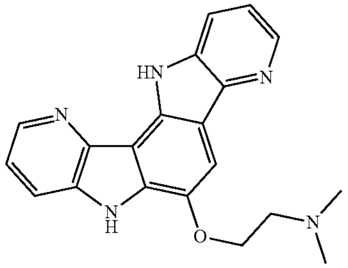

SS20308-0070-01
Chemical Formula: $C_{20}H_{19}N_5O$
Molecular Weight: 345.40

Example Route for Example 23 (SS20308-0070-01):

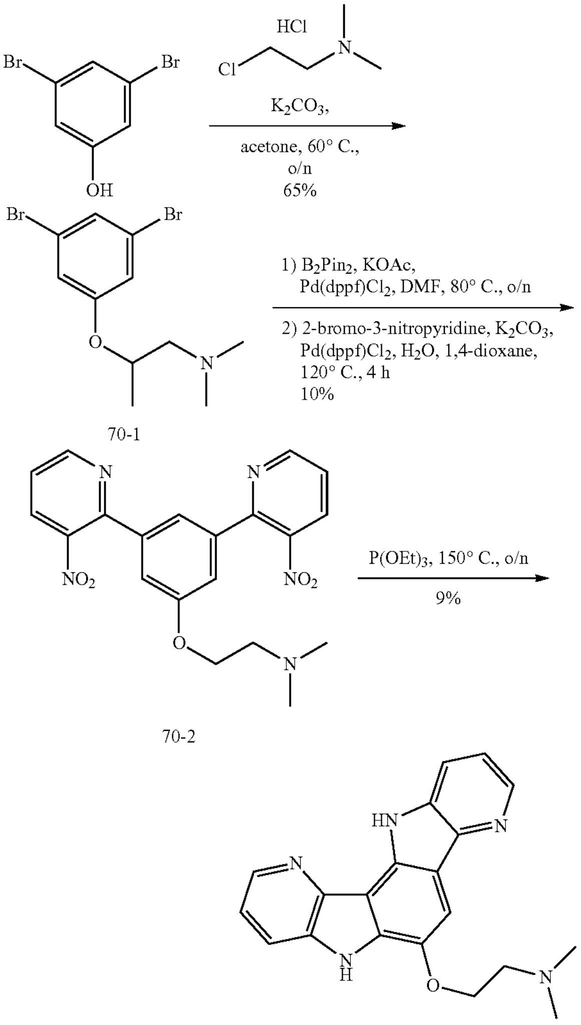

70-1

70-2

SS20308-0070-01

The synthesis of 2-(3,5-dibromophenoxy)-N,N-dimethylethanamine (70-1):

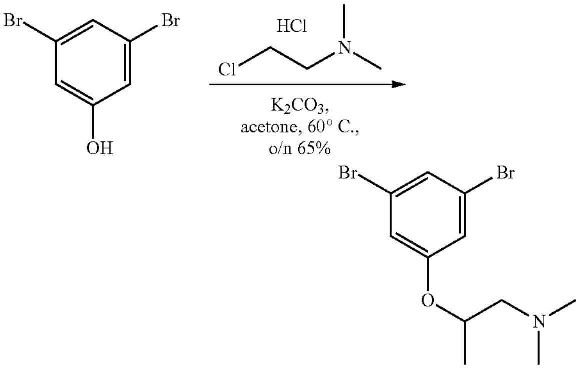

70-1

A mixture of 3,5-dibromophenol (100 mg, 0.40 mmol), 2-chloro-N,N-dimethylethanamine hydrochloride (86 mg, 0.60 mmol) and $K_2CO_3$ (110 mg, 0.79 mmol) in acetone (10 mL) was stirred at 60° C. overnight. Then the reaction mixture was quenched with water, and extracted with EtOAc (20 mL×3). The organic layers were washed with brine, dried over $MgSO_4$ and concentrated. The residue 70-1 (80 mg, 65% yield) was used in the next step without further purification. MS Calcd.: 320.9; MS Found: 322.3 $[M+H]^+$.

The synthesis of 2-(3,5-bis(3-nitropyridin-2-yl)phenoxy)-N,N-dimethylethanamine (70-2):

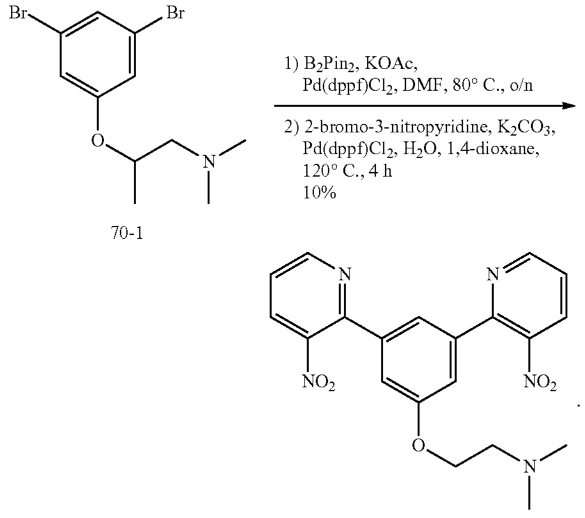

70-1

70-2

A mixture of 70-1 (80 mg, 0.25 mmol), $B_2Pin_2$ (189 mg, 0.74 mmol), $Pd(dppf)Cl_2$ (10 mg, 0.01 mmol), KOAc (97 mg, 0.99 mmol) in DMF (5 mL) was stirred at 80° C. under nitrogen atmosphere overnight. After the reaction was completed, the mixture was quenched with water. The insoluble material was removed by filtration, and the filtrate was extracted with EtOAc (20 mL×3). The organic layer was separated, dried over $MgSO_4$, and concentrated under vacuum. The residue was used for the next step directly. A mixture of the residue (80 mg, crude), 2-bromo-3-nitropyridine (101 mg, 0.50 mmol), $Pd(dppf)Cl_2$ (10 mg, 0.01 mmol), potassium carbonate (103 mg, 0.74 mmol) in 1,4-dioxane (10 mL) and water (1 mL) was stirred at 120° C. under nitrogen atmosphere for 4 h. After the reaction was completed, the mixture was quenched with water. The insoluble material was removed by filtration, and the filtrate was extracted with EtOAc (20 mL×3). The organic layer was separated, dried over $MgSO_4$, and concentrated under vacuum. The residue was purified by Prep-TLC (EtOAc/petroleum ether=1/1) to give 70-2 (10 mg, about 10% yield) as a solid. MS Calcd.: 409.1; MS Found: 410.1 $[M+H]^+$.

The synthesis of SS20308-0070-01:

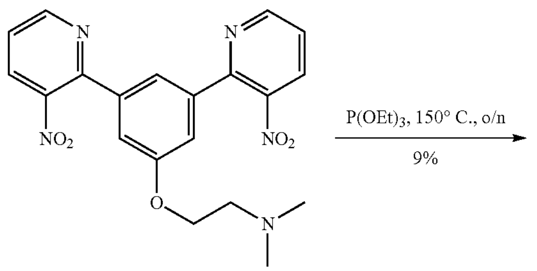

70-2

-continued

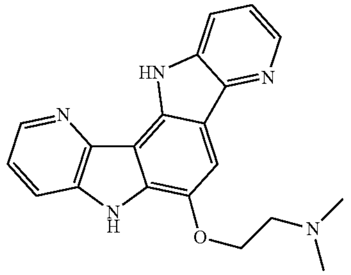

SS20308-0070-01

A solution of 70-2 (100 mg, 0.24 mmol) in $P(OEt)_3$ (1 mL) was stirred at 150° C. overnight. After the reaction was completed, the solution was concentrated to a crude mixture, which was purified by Prep-HPLC twice to give SS20308-0070-01 (8 mg, about 9% yield) as a solid. MS Calcd.: 345.2; MS Found: 346.1 $[M+H]^+$.

$^1H$ NMR (400 MHz, $CDCl_3$) δ 11.60 (s, 1H), 10.50 (s, 1H), 8.57-8.53 (m, 2H), 7.96 (s, 1H), 7.89-7.83 (m, 2H), 7.35 (dd, J=8.4, 4.8 Hz, 1H), 7.27 (dd, J=8.4, 4.8 Hz, 1H), 4.39 (t, J=4.8 Hz, 2H), 2.94 (t, J=4.8 Hz, 2H), 2.50 (s, 6H).

Example 24 and Example 25

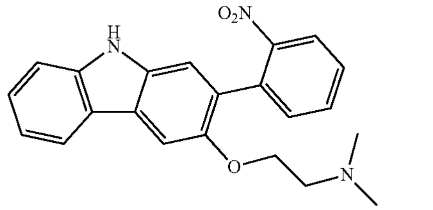

SS20308-0076-01
Chemical Formula: $C_{22}H_{21}N_3O_3$
Molecular Weight: 375-42

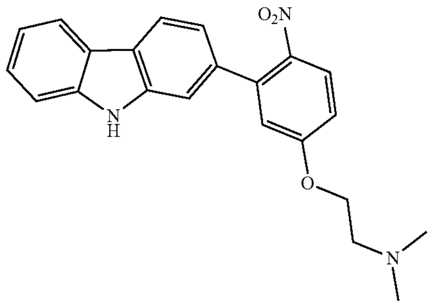

SS20308-0077-01
Chemical Formula: $C_{22}H_{21}N_3O_3$
Molecular Weight: 375.42

Example Route for Example 24 (SS20308-0076-01) and Example 25 (SS20308-0077-01):

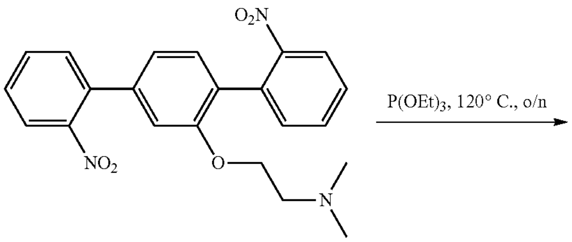

65-2

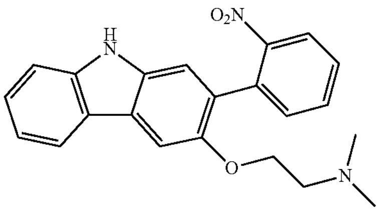

SS20308-0076-01

+

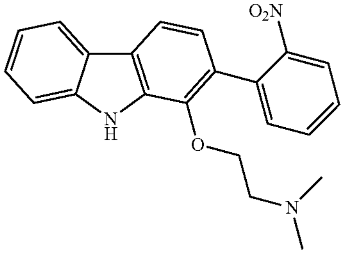

SS20308-0077-01

The synthesis of N,N-dimethyl-2-(2-(2-nitrophenyl)-9H-carbazol-3-yloxy)ethanamine (SS20308-0076-01-1) & N,N-dimethyl-2-(2-(2-nitrophenyl)-9H-carbazol-1-yloxy) ethanamine (SS20308-0077-01-1):

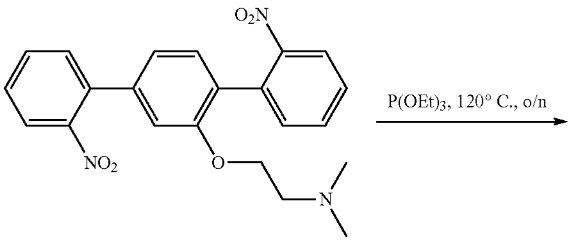

65-2

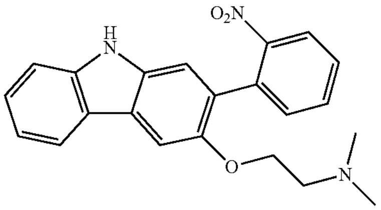

SS20308-0076-01

+

-continued

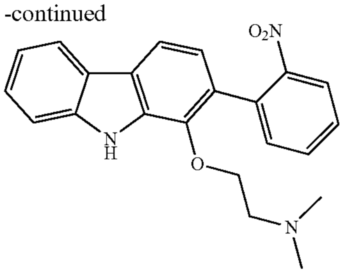

SS20308-0077-01

A solution of 65-2 (100 mg, 0.25 mmol) in $P(OEt)_3$ (2 mL) was stirred at 120° C. for overnight. After the reaction was completed, the reaction was purified by reverse phase flash column chromatography and Prep-TLC twice to give SS20308-0076-01 (5 mg, about 5% yield) as a solid, and SS20308-0077-01 (2.6 mg, about 3% yield) as a solid.

SS20308-0076-01:MS Calcd.: 375.2; MS Found: 376.3 $[M+H]^+$. $^1H$ NMR (400 MHz, DMSO-$d_6$) δ 11.19 (s, 1H), 8.13 (d, J=8.0 Hz, 1H), 8.02 (dd, J=8.0, 0.8 Hz, 1H), 7.82-7.76 (m, 2H), 7.64-7.58 (m, 2H), 7.49 (d, J=8.0 Hz, 1H), 7.42 (s, 1H), 7.40-7.35 (m, 1H), 7.15 (dd, J=7.6, 7.2 Hz, 1H), 4.05-3.94 (m, 2H), 2.49-2.44 (m, 2H), 2.08 (s, 6H).

SS20308-0077-01: MS Calcd.: 375.2; MS Found: 376.3 $[M+H]^+$. $^1H$ NMR (400 MHz, DMSO-$d_6$) δ 11.72 (s, 1H), 8.14 (d, J=8.0 Hz, 1H), 8.06 (dd, J=8.0, 0.8 Hz, 1H), 7.97 (d, J=8.0 Hz, 1H), 7.82 (ddd, J=7.8, 7.2, 1.2 Hz, 1H), 7.69-7.62 (m, 2H), 7.55 (d, J=8.0 Hz, 1H), 7.46-7.40 (m, 1H), 7.22-7.17 (m, 1H), 7.10 (d, J=8.0 Hz, 1H), 3.85-3.70 (m, 2H), 2.39-2.34 (m, 2H), 2.06 (s, 6H).

Example 26

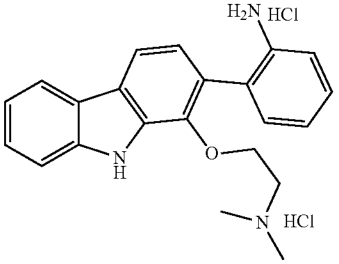

SS20308-0073-01

Chemical Formula: $C_{22}H_{25}Cl_2N_3O$

Molecular Weight: 418.36

Example Route for Example 26 (SS20308-0073-01):

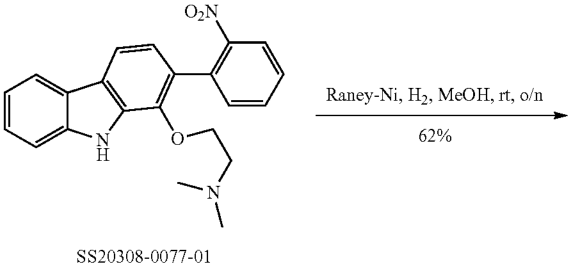

SS20308-0077-01

-continued

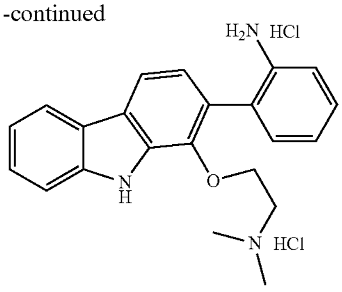

SS20308-0073-01

The synthesis of 2-(1-(2-(dimethylamino)ethoxy)-9H-carbazol-2-yl)aniline dihydrochloride (SS20308-0073-01):

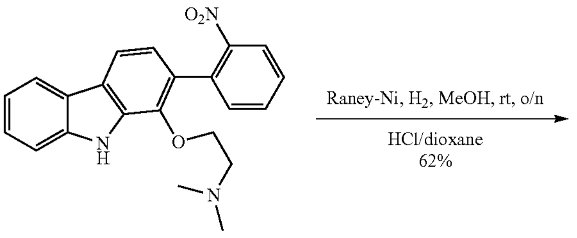

SS20308-0077-01

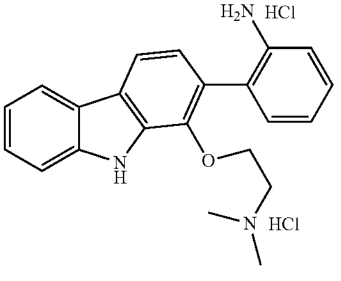

SS20308-0073-01

A suspension of SS20308-0077-01 (16 mg, 0.043 mmol) and Raney-Ni (3 drop) in 2 ml of methanol is stirred vigorously under hydrogen gas (balloon) for overnight at room temperature. The solid is removed by filtration through celite. The filtrate was acidified with 4M HCl/dioxane and concentrated to give SS20308-0073-01 (11 mg, 62% yield) as a solid. MS Calcd.: 345.2; MS Found: 346.3 $[M+H]^+$.

$^1$H NMR (400 MHz, DMSO-$d_6$) δ 11.92 (s, 1H), 8.15 (d, J=8.0 Hz, 1H), 7.99 (d, J=8.0, Hz, 1H), 7.59 (d, J=8.0 Hz, 1H), 7.41-7.46 (m, 1H), 7.37-7.26 (m, 2H), 7.23-6.99 (m, 4H), 4.15-3.87 (m, 2H), 3.35-3.23 (m, 2H), 2.62 (s, 6H).

Example 27

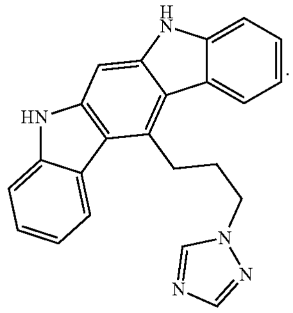

SS20308-0082-01
Chemical Formula: $C_{22}H_{17}N_5O$
Molecular Weight: 367.40

Example Route for Example 27 (SS20308-0082-01):

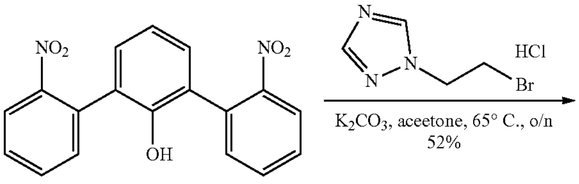

63-1

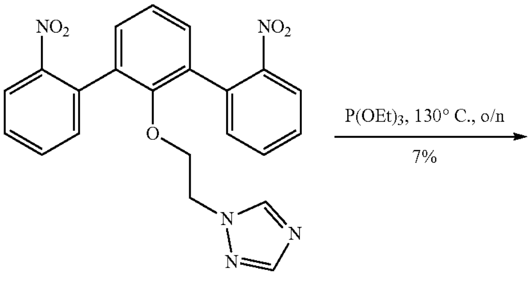

82-1

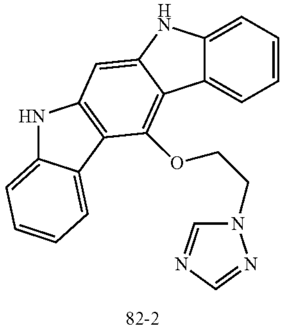

82-2

The synthesis of (82-1):

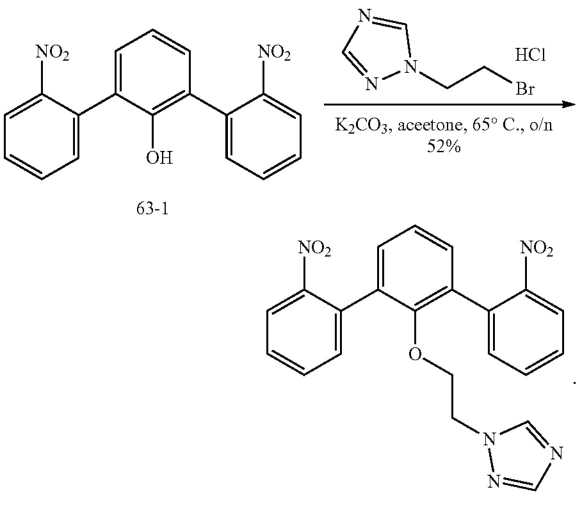

63-1

82-1

To a solution of 63-1 (134 mg, 0.40 mmol) in acetone (20 mL) was added $K_2CO_3$ (330 mg, 2.40 mmol) and 1-(2-bromoethyl)-1H-1,2,4-triazole hydrochloride (2.0 g, 8.1 mmol) then the reaction mixture was stirred at 65° C. overnight. The mixture was diluted with water (30 mL), extracted with water EtOAc (20 mL×3), dried over $Na_2SO_4$, filtered, and concentrated. The residue was purified by Prep-TLC (EtOAc) to give 82-1 (90 mg, about 52% yield) as a solid. MS Calcd.: 431.1; MS Found: 432.3 $[M+H]^+$.

The synthesis of 12-(2-(1H-1,2,4-triazol-1-yl)ethoxy)-5,7-dihydroindolo[2,3-b]carbazole (SS20308-0082-01):

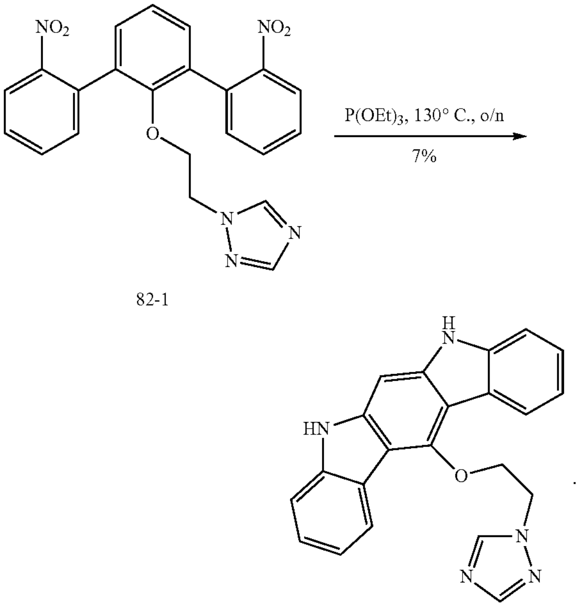

82-1

SS20308-0082-01

A solution of 82-1 (90 mg, 0.21 mmol) in $P(OEt)_3$ (2 mL) was stirred at 130° C. overnight. The reaction mixture was purified by reverse phase column chromatography, then purified by Prep-HPLC, and washed with hexanes to give 0082-01 (5 mg, about 7% yield) as a solid. MS Calcd.: 367.1; MS Found: 368.3 $[M+H]^+$.

$^1H$ NMR (400 MHz, $CDCl_3$) δ 8.43 (s, 1H), 8.17 (s, 1H), 8.09 (br, 2H), 7.72 (d, J=8.0 Hz, 2H), 7.54-7.36 (m, 4H), 7.25-7.19 (m, 2H), 7.18 (s, 1H), 4.89 (t, J=5.0 Hz, 2H), 4.73 (t, J=5.2 Hz, 2H).

Example 28

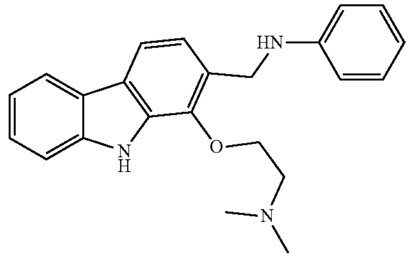

SS20308-0086-01
Chemical Formula: $C_{23}H_{25}N_3O$
Molecular Weight: 359.46

Example Route for Example 28 (SS20308-0086-01):

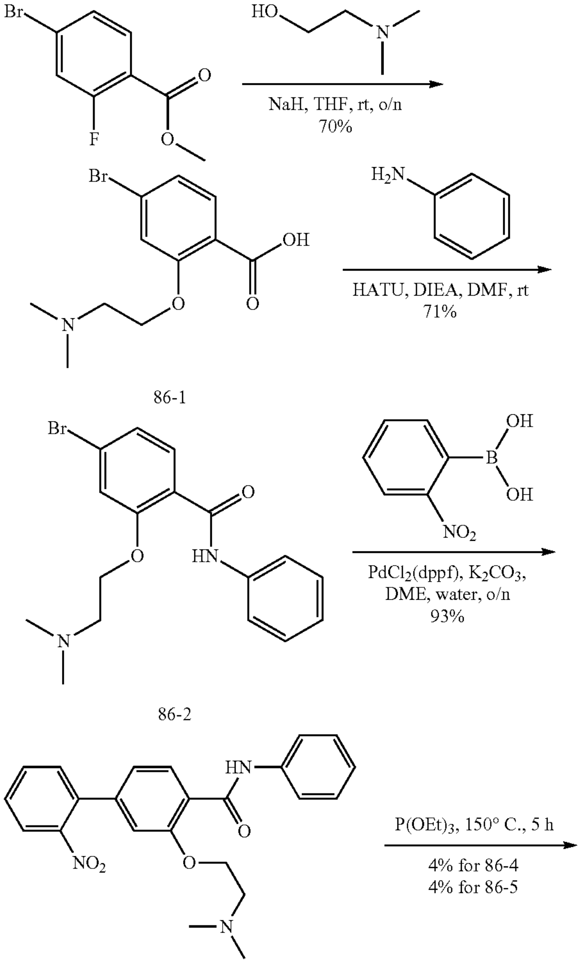

86-1

86-2

86-3

-continued

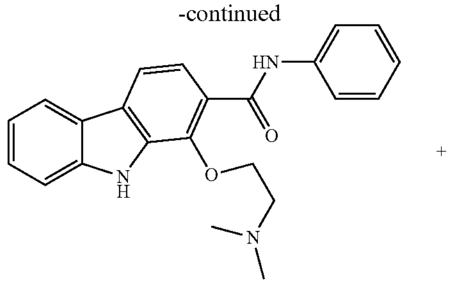

86-4

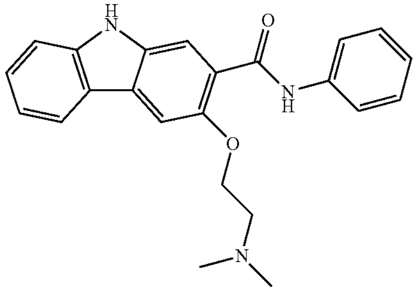

86-5

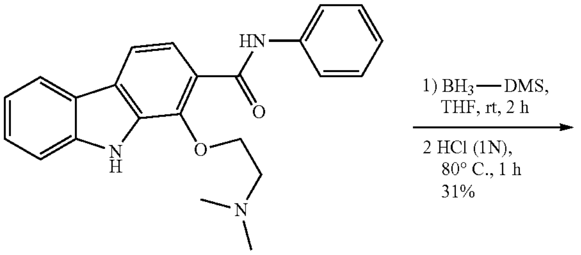

86-4

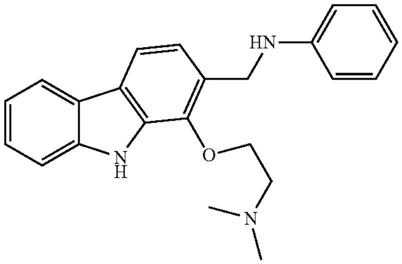

SS20308-0086-01

The synthesis of 4-bromo-2-(2-(dimethylamino)ethoxy) benzoic acid (86-1):

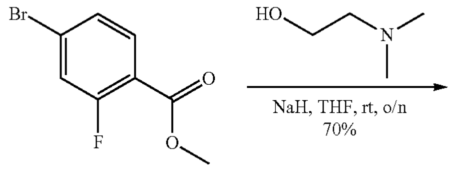

-continued

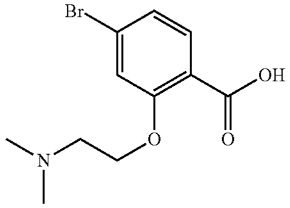

86-1

To a solution of 2-(dimethylamino)ethanol (1.2 g, 12.87 mmol) in THF (80 mL) was added NaH (772 mg, 19.31 mmol, 60%) slowly and the mixture was stirred at room temperature for 0.5 h. Then methyl 4-bromo-2-fluorobenzoate (3.0 g, 12.87 mmol) was added and the reaction mixture was stirred at room temperature overnight. The reaction mixture was poured into water (150 mL), adjust to pH 5-6 with 10% HCl (aq) and washed with EtOAc (100 mL×5). The water layer was concentrated and purified by Prep-HPLC to give 86-1 (2.2 g, about 70% yield) as an oil. MS Calcd.: 287.0; MS Found: 286.0 $[M-H]^+$.

The synthesis of 4-bromo-2-(2-(dimethylamino)ethoxy)-N-phenylbenzamide (86-2):

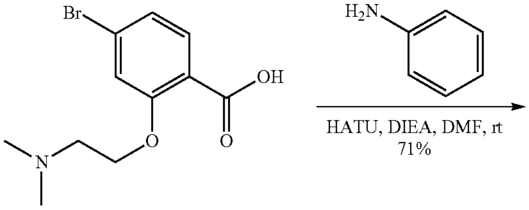

86-1

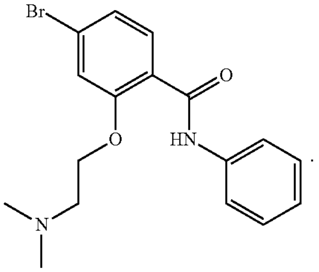

86-2

A solution of 86-1 (1.0 g, 3.47 mmol), aniline (485 mg, 5.21 mmol), HATU (2.0 g, 5.21 mmol) and DIEA (0.9 g, 6.94 mmol) in DMF (30 mL) was stirred at room temperature overnight. Then the reaction was poured into water (50 mL) and extracted with EtOAc (30 mL×4). The organic layer was washed with water (50 mL), and brine (2×50 mL). The solvent was evaporated to give a solid, which was purified by column chromatography on silica gel (petroleum ether/EtOAc=50/1 to 3/1) to give 86-2 (0.9 g, about 71% yield) as an oil. MS Calcd.: 362.1; MS Found: 363.2 $[M+H]^+$.

The synthesis of 3-(2-(dimethylamino)ethoxy)-2'-nitro-N-phenylbiphenyl-4-carboxamide (86-3):

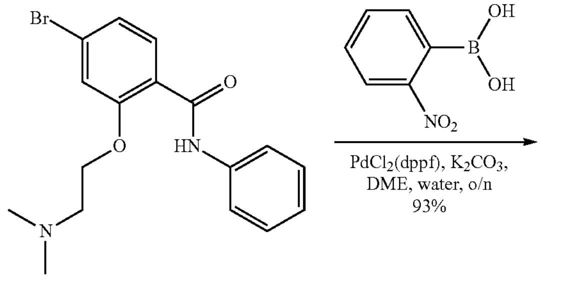

86-2

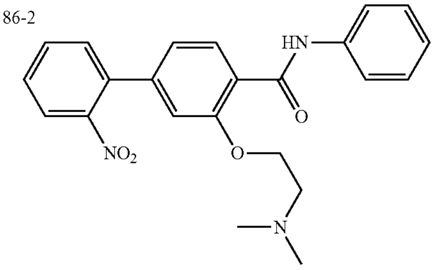

86-3

A solution of 86-2 (650 mg, 1.79 mmol), 2-nitrophenylboronic acid (358 mg, 2.15 mmol), $PdCl_2(dppf)$ (131 mg, 0.18 mmol) and $K_2CO_3$ (495 mg, 3.58 mmol) in DME (30 mL) and water (3 mL) was stirred at 120° C. under nitrogen atmosphere overnight. After the reaction was complete, the mixture was quenched with water, and the insoluble material was removed by filtration. The filtrate was extracted with EtOAc (50 mL×3). The organic layer was separated, dried over $MgSO_4$, and concentrated under vacuum. The residue was purified by column chromatography on silica gel (petroleum ether/EtOAc=10/1 to 3/1) to give 86-3 (675 mg, about 93% yield) as a solid. MS Calcd.: 405.2; MS Found: 406.2 $[M+H]^+$.

The synthesis of 1-(2-(dimethylamino)ethoxy)-N-phenyl-9H-carbazole-2-carboxamide (86-4), 3-(2-(dimethylamino)ethoxy)-N-phenyl-9H-carbazole-2-carboxamide (86-5):

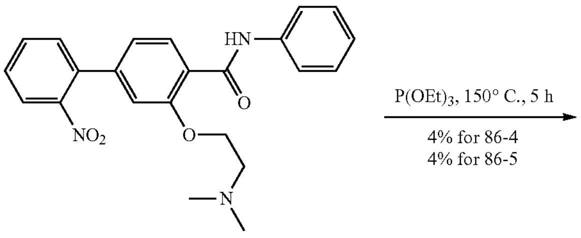

86-3

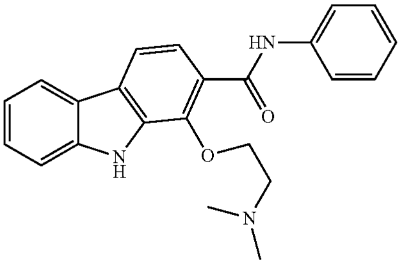

86-4

+

-continued

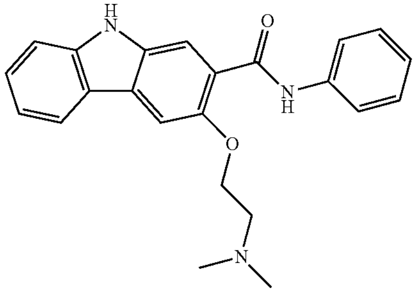

86-5

+.

A solution of 86-3 (300 mg, 0.74 mmol) in $P(OEt)_3$ (2 mL) was stirred at 150° C. for 5 h. After the reaction was complete, the solution was concentrated to a crude mixture, which was purified by Prep-HPLC twice to give 86-4 (12 mg, about 4% yield) as a solid, MS Calcd.: 373.2; MS Found: 374.0 $[M+H]^+$; and 86-5 (12 mg, about 4% yield) as a solid, MS Calcd.: 373.2; MS Found: 374.0 $[M+H]^+$.

86-4: $^1H$ NMR (400 MHz, DMSO-$d_6$) δ 11.85 (s, 1H), 10.51 (s, 1H), 8.17 (d, J=8.0 Hz, 1H), 7.98 (d, J=8.4 Hz, 1H), 7.79-7.77 (m, 2H), 7.61-7.56 (m, 2H), 7.47 (ddd, J=8.0, 7.2, 1.2 Hz, 1H), 7.39-7.35 (m, 2H), 7.23-7.19 (m, 1H), 7.11 (dd, J=7.2 Hz, 1H), 4.34 (t, J=5.2 Hz, 2H), 2.73 (t, J=5.2 Hz, 2H), 2.20 (s, 6H).

86-5: $^1H$ NMR (400 MHz, DMSO-$d_6$) δ 11.29 (s, 1H), 10.67 (s, 1H), 8.18 (d, J=8.0 Hz, 1H), 8.13 (s, 1H), 8.01 (s, 1H), 7.80-7.78 (m, 2H), 7.50 (d, J=7.6 Hz, 1H), 7.43 (dd, J=8.0, 7.2 Hz, 1H), 7.40-7.36 (m, 2H), 7.17 (dd, J=8.0, 7.2 Hz, 1H), 7.11 (dd, J=7.6, 7.2 Hz, 1H), 4.42 (t, J=5.2 Hz, 2H), 2.80 (t, J=5.6 Hz, 2H), 2.26 (s, 6H).

The synthesis of N-((1-(2-(dimethylamino)ethoxy)-9H-carbazol-2-yl)methyl)aniline (SS20308-0086-01):

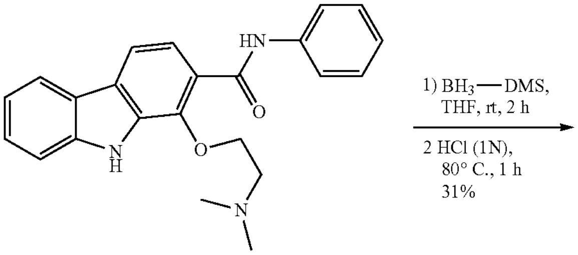

86-4

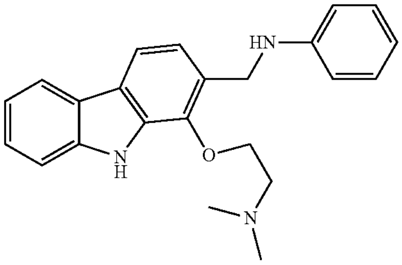

SS20308-0086-01

A solution of 86-4 (40 mg, 0.11 mmol) in $BH_3$-DMS (5 mL, 1N in THF) was stirred at room temperature for 2 h. After the reaction was complete, HCl (1N, 10 mL) was added, and then the reaction was stirred at 80° C. for 1 h. After completion, the mixture was poured into water (10 mL) and adjusted to pH 8 with $Na_2CO_3$ (aq.), and extracted with EtOAc (50 mL×4). The organic layer was washed with brine (2×50 mL) and the solvent evaporated to give a solid, which was purified by Prep-HPLC to give SS20308-0086-01 (12 mg, about 31% yield) as a solid. MS Calcd.: 359.2; MS Found: 359.9 $[M+H]^+$.

$^1H$ NMR (400 MHz, $CDCl_3$) δ 12.12 (s, 1H), 8.05 (d, J=8.0 Hz, 1H), 7.80 (d, J=8.0 Hz, 1H), 7.41-7.40 (m, 2H), 7.22-7.15 (m, 4H), 6.74-6.70 (m, 3H), 4.51 (s, 2H), 4.21 (t, J=4.8 Hz, 2H), 4.02 (s, 1H), 2.74 (t, J=4.4 Hz, 2H), 2.51 (s, 6H).

Example 29

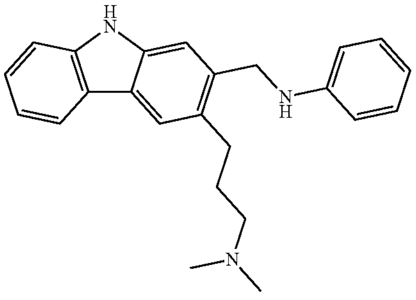

SS20308-0119-01
Chemical Formula: $C_{23}H_{25}N_3O$
Molecular Weight: 359.46

Example Route for Example 29 (SS20308-0119-01):

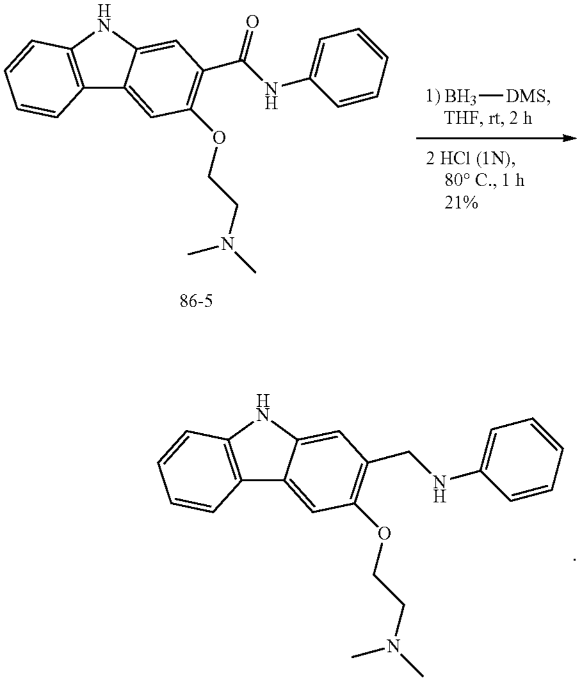

86-5

SS20308-0119-01

The synthesis of N-((3-(2-(dimethylamino)ethoxy)-9H-carbazol-2-yl)methyl)aniline (SS20308-0119-01):

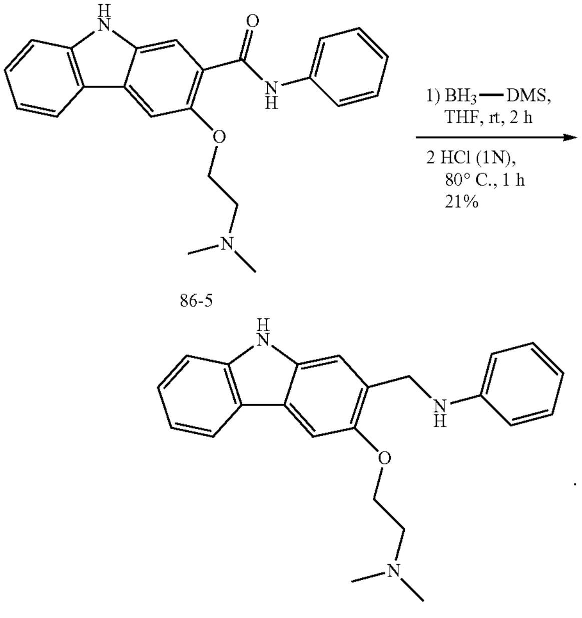

86-5

SS20308-0119-01

A solution of 86-5 (40 mg, 0.11 mmol) in $BH_3$-DMS (5 mL, 1N in THF) was stirred at room temperature for 2 h. After the reaction was complete, the HCl (1N, 10 mL) was added, and then the reaction was stirred at 80° C. for 1 h. The mixture was then poured into water (10 mL) and adjusted to pH 8 with $Na_2CO_3$ (aq.), and extracted with EtOAc (50 mL×4). The organic layer was washed with brine (2×50 mL) and the solvent evaporated to give a solid, which was purified by Prep-HPLC to give SS20308-0119-01 (8 mg, about 21% yield) as a solid. MS Calcd.: 359.2; MS Found: 360.1 $[M+H]^+$.

$^1H$ NMR (400 MHz, $CDCl_3$) δ 7.93 (d, J=8.0 Hz, 1H), 7.85 (s, 1H), 7.47 (s, 1H), 7.34-7.31 (m, 3H), 7.15-7.07 (m, 3H), 6.64-6.60 (m, 3H), 4.41 (s, 2H), 4.29 (s, 2H), 2.91 (s, 2H), 2.44 (s, 6H).

Example 30

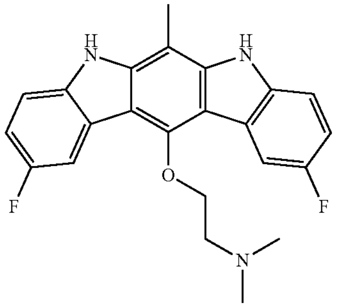

Chemical Formula: $C_{23}H_{21}F_2N_3O$
Molecular Weight: 393.43

Example Route for Example 30 (SS20308-0089-01):

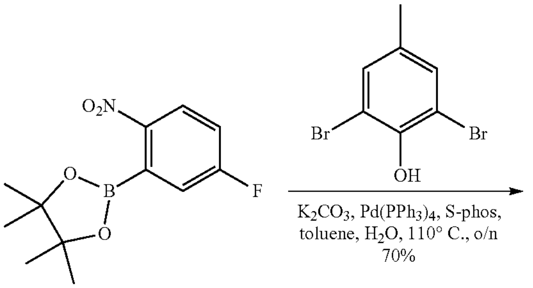

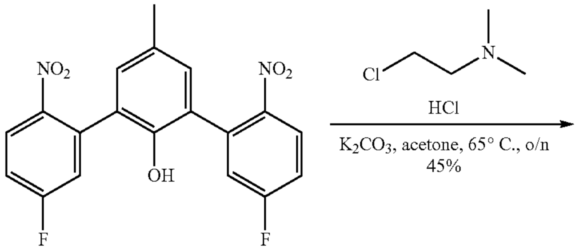

89-1

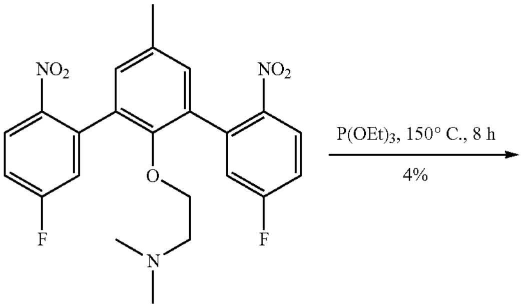

89-2

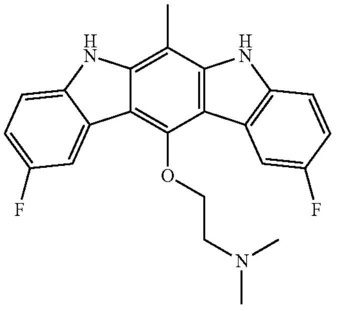

SS20308-0089-01

The synthesis of 5,5"-difluoro-5'-methyl-2,2"-dinitro-[1,1':3',1"-terphenyl]-2'-ol (89-1):

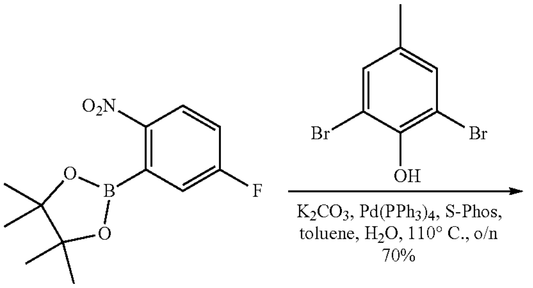

-continued

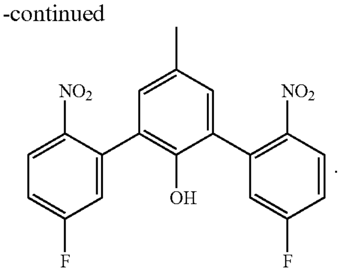

89-1

To a mixture of 2-(5-fluoro-2-nitrophenyl)-4,4,5,5-tetramethyl-1,3,2-dioxaborolane (650 mg, 2.43 mmol), $K_2CO_3$ (611 mg, 4.43 mmol), 2,6-dibromo-4-methylphenol (294 mg, 1.11 mmol) and S-Phos (92 mg, 0.22 mmol) in toluene/$H_2O$ (30/3 mL) was added $Pd(PPh_3)_4$ (128 mg, 0.11 mmol). This mixture was then stirred at room temperature overnight. The reaction mixture was concentrated, diluted with water and extracted with EtOAc (3×50 mL). The organic layer was washed with brine and concentrated to dryness to give crude compound, which was purified by Prep-TLC (petroleum ether/EtOAc=5/1) to give 89-1 (300 mg, about 70% yield) as an oil. MS Calcd.: 386.1; MS Found: 385.0 $[M-H]^-$.

The synthesis of 2-((5,5"-difluoro-5'-methyl-2,2"-dinitro-[1,1':3',1"-terphenyl]-2'-yl)oxy)-N,N-dimethylethanamine (89-2):

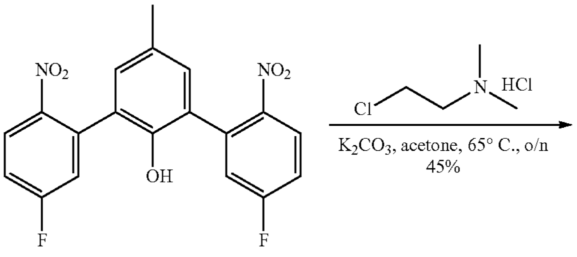

89-1

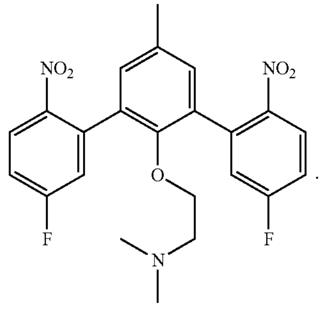

89-2

To a mixture of 89-1 (300 mg, 0.78 mmol) and $K_2CO_3$ (429 mg, 3.11 mmol) in acetone (15 mL) was added 2-chloro-N,N-dimethylethanamine hydrochloride (168 mg, 1.16 mmol), and then stirred at 65° C. overnight. The reaction mixture was concentrated, diluted with water then extracted with EtOAc (3×20 mL). The organic layer was washed with brine and concentrated to dryness to give crude compound, which was purified by Prep-TLC (petroleum ether/EtOAc=5/1) to give 89-2 (160 mg, about 45% yield) as a solid. MS Calcd.: 457.1; MS Found: 458.2 $[M+H]^+$.

The synthesis of 2-(2,10-difluoro-6-methyl-5,7-dihydroindolo[2,3-b]carbazol-12-yloxy)-N,N-dimethylethanamine (SS20308-0089-01):

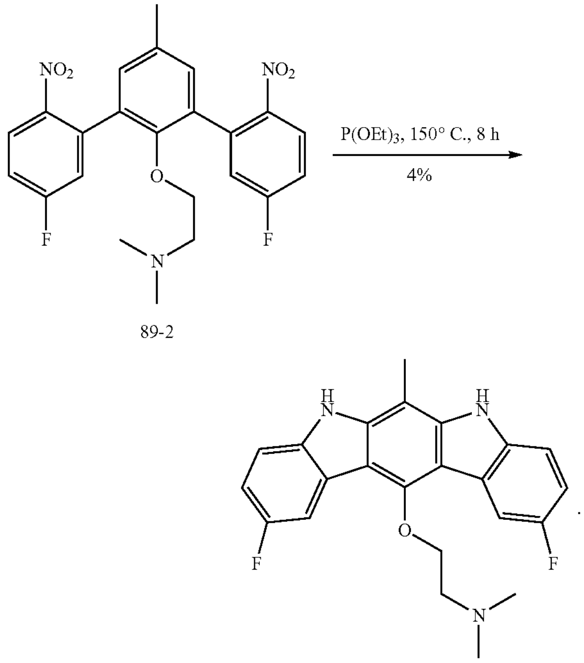

89-2

SS20308-0089-01

A solution of 89-2 (90 mg, 0.20 mmol) in $P(OEt)_3$ (1.5 mL) was stirred at 150° C. for 8 hours. The solution was concentrated under vacuum to afford the crude product, which was purified by Prep-TLC (EtOAc) then Prep-HPLC to give SS20308-0089-01 (3 mg, about 4% yield) as a solid. MS Calcd.: 393.2; MS Found: 394.0 $[M+H]^+$.

$^1H$ NMR (400 MHz, DMSO-$d_6$) δ 11.15 (s, 2H), 8.07 (dd, J=5.6 Hz, 2.4 Hz, 2H), 7.43 (dd, J=8.8 Hz, 4.4 Hz, 2H), 7.18 (td, J=9.2 Hz, 2.4 Hz, 2H), 4.25 (t, J=5.2 Hz, 2H), 2.87 (t, J=5.2 Hz, 2H), 2.65 (s, 3H), 2.36 (s, 6H).

Example 31

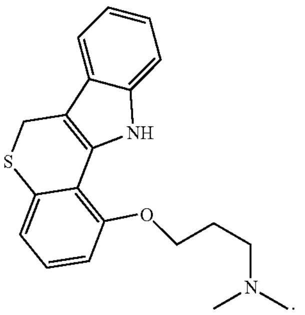

SS20308-0090-01
Chemical Formula: $C_{20}H_{22}N_2OS$
Molecular Weight: 338.47

Example Route for Example 31 (SS20308-0090-01):

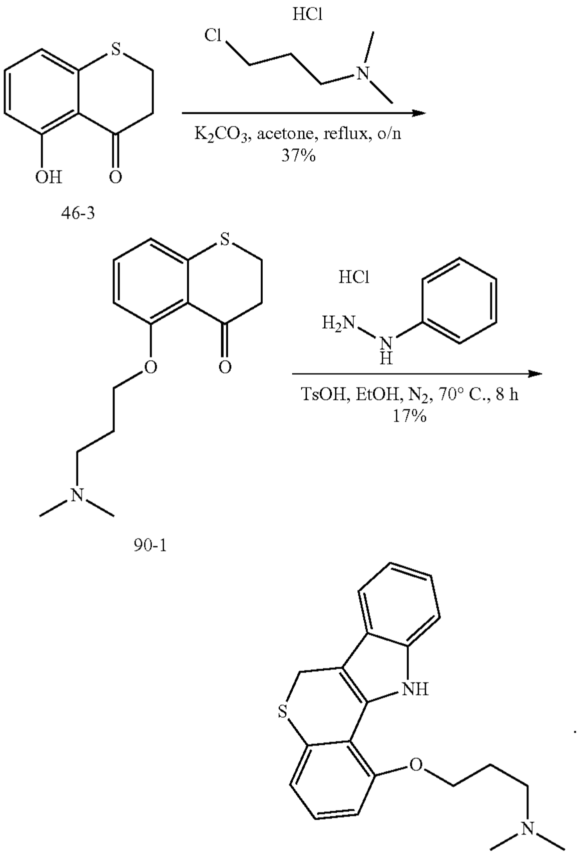

46-3

90-1

SS20308-0090-01

The synthesis of 5-(3-(dimethylamino)propoxy)thiochroman-4-one (90-1):

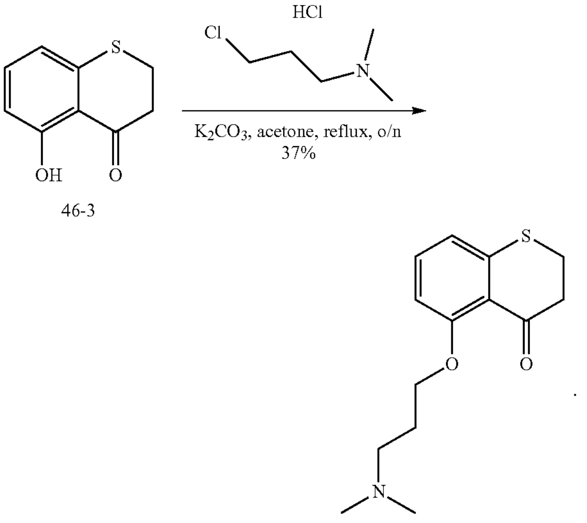

46-3

SS20308-0090-01

A mixture of 46-3 (220 mg, 1.22 mmol), 3-(dimethylamino)propyl chloride hydrochloride (579 mg, 3.66 mmol) and $K_2CO_3$ (843 mg, 6.10 mmol) in acetone (30 mL) was stirred at reflux overnight. Then the reaction mixture was filtered and concentrated. The residue was purified by Prep-TLC ($CH_2Cl_2$/MeOH=10/1) to give 90-1 (100 mg, about 37% yield) as an oil. MS Calcd.: 265.1; MS Found: 266.2 $[M+H]^+$.

The synthesis of 3-(6,11-dihydrothiochromeno[4,3-b]indol-1-yloxy)-N,N-dimethylpropan-1-amine (SS20308-0090-01):

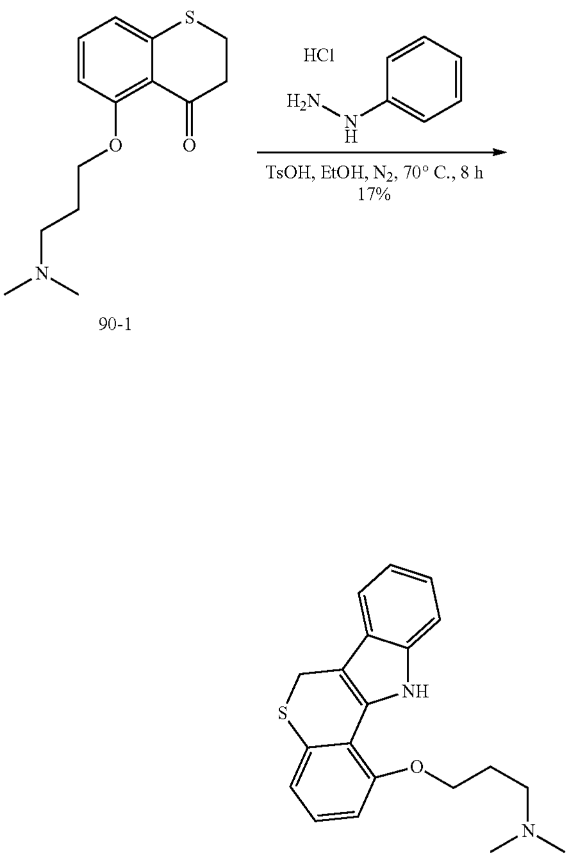

90-1

SS20308-0090-01

A mixture of 90-1 (120 mg, 0.45 mmol), phenylhydrazine hydrochloride (65 mg, 0.45 mmol) and TsOH (387 mg, 2.25 mmol) in EtOH (15 mL) was stirred at 70° C. under nitrogen atmosphere for 8 h. After being cooled to room temperature, the mixture was concentrated. The residue was basicified with 1 N NaOH till pH 10. The resulting mixture was extracted with EtOAc (30 mL×3) and the organic layers were washed with brine, dried over $Na_2SO_4$ and concentrated. The residue was purified by Prep-TLC (DCM/MeOH=10/1) to give SS20308-0090-01 (26.6 mg, about 17% yield) as a solid. MS Calcd.: 338.2; MS Found: 339.2 $[M+H]^+$.

$^1$H NMR (400 MHz, $CDCl_3$) δ 10.39 (s, 1H), 7.52 (d, J=8.0 Hz, 1H), 7.37 (d, J=8.0 Hz, 1H), 7.19 (dd, J=7.6, 7.2 Hz, 2H), 7.12 (dd, J=7.6, 7.2 Hz, 2H), 7.10-7.00 (m, 2H), 6.77 (d, J=8.0 Hz, 1H), 4.28-4.19 (m, 4H), 2.56 (t, J=6.4 Hz, 2H), 2.34 (s, 6H), 2.13-2.05 (m, 2H).

Example 32

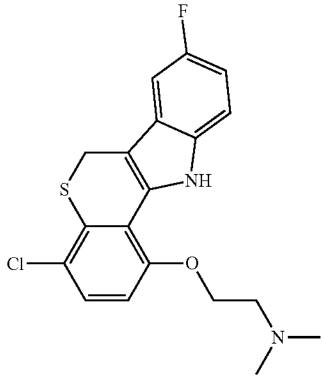

SS20308-0093-01
Chemical Formula: $C_{19}H_{18}ClFN_2OS$
Molecular Weight: 376.88

Example Route for Example 32 (SS20308-0093-01):

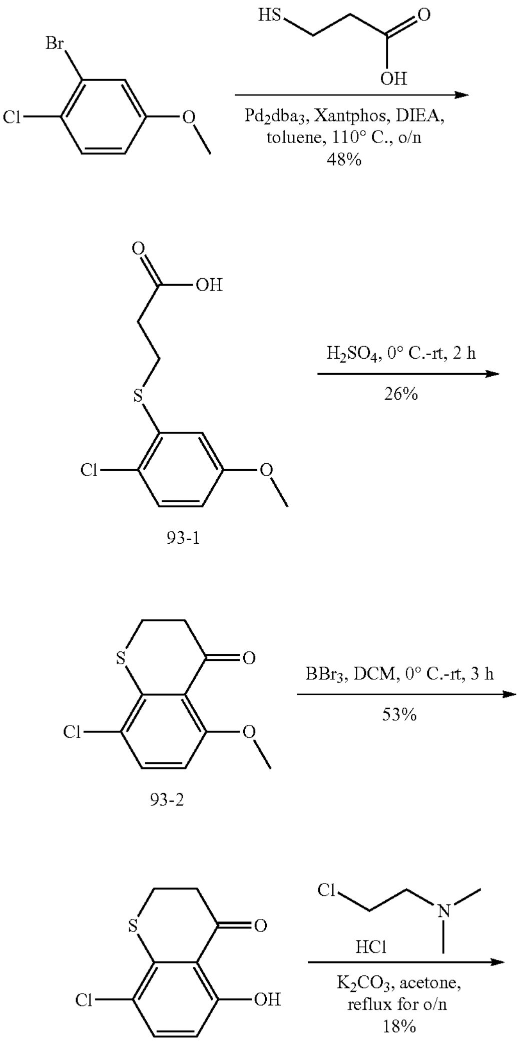

93-1

93-2

93-3

-continued

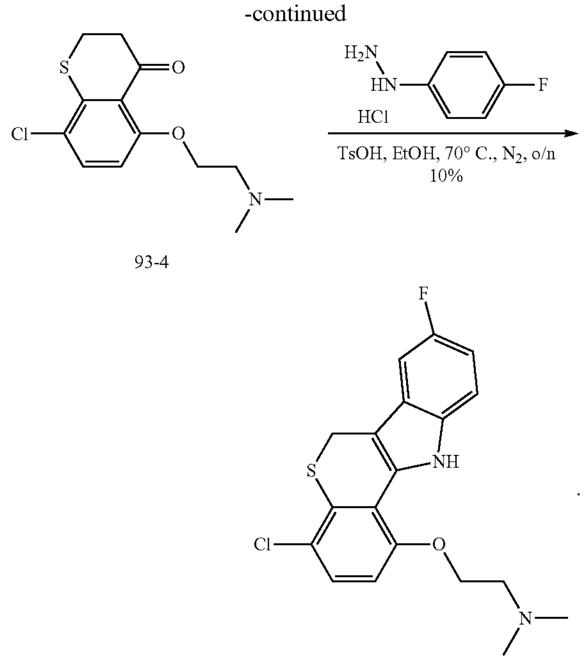

93-4

SS20308-0093-01

The synthesis of 3-(3-methoxyphenylthio)propanoic acid (93-1):

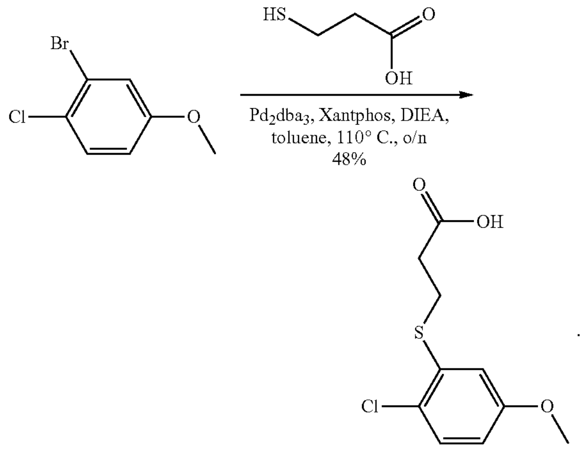

93-1

The mixture of 3-bromo-4-chloroanisole (5.00 g, 22.58 mmol), 3-mercaptopropionic acid (2.40 g, 22.58 mmol), $Pd_2dba_3$ (1.00 g, 1.13 mmol), Xantphos (1.30 g, 2.26 mmol) and DIPEA (5.80 g, 45.16 mmol) in toluene (30 mL) was stirred at 110° C. overnight under $N_2$ atmosphere. The reaction mixture was then cooled to room temperature and concentrated. The residue was poured into water and basicified with 40% NaOH solution to pH 10. Then the mixture was extracted with EtOAc (50 mL×2). The water layer was acidified with 1N HCl till pH 1 and extracted with EtOAc (50 mL×3). The combined organic layers were washed with brine, dried over $Na_2SO_4$ and concentrated to give 93-1 (2.70 g, about 48% yield) as an oil. MS Calcd.: 246.0; MS Found: 247.1 $[M+H]^+$.

The synthesis of 8-chloro-5-methoxythiochroman-4-one (93-2):

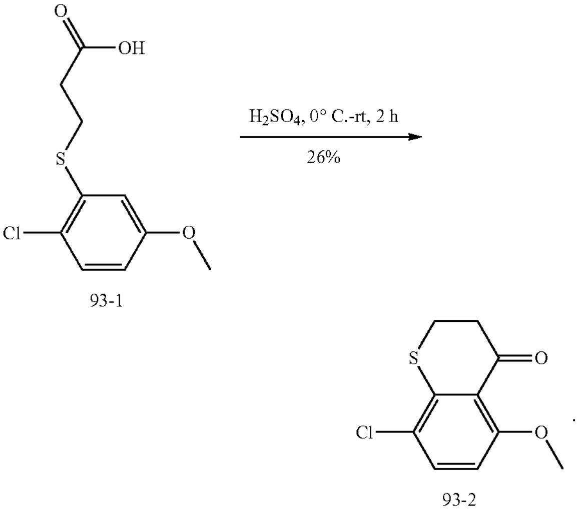

93-1

93-2

To 93-1 (2.70 g, 10.94 mmol) stirred at 0° C. was added $H_2SO_4$ (10 mL) slowly. Then the mixture was allowed to warm to room temperature and stirred for 2 h. Then mixture was poured onto ice carefully. The resulting mixture was extracted with EtOAc (30 mL×3) and the organic layers were washed with brine, dried over $MgSO_4$ and concentrated. The residue was purified by column chromatography on silica gel (petroleum ether/EtOAc=20/1) to give 93-2 (660 mg, about 26% yield) as an oil. MS Calcd.: 228.0; MS Found: 229.1 $[M+H]^+$.

The synthesis of 8-chloro-5-hydroxythiochroman-4-one (93-3):

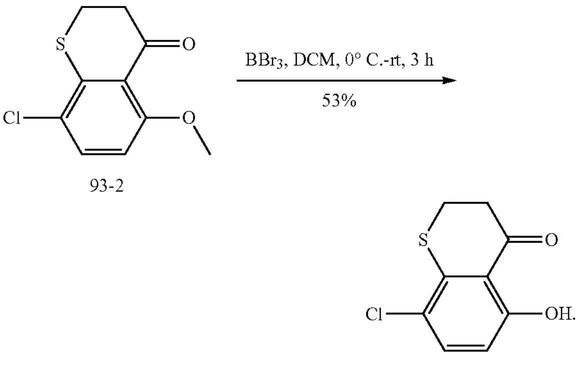

93-2

93-3

To the mixture of 93-2 (660 mg, 2.89 mmol) in $CH_2Cl_2$ (15 mL) stirred at 0° C. was added $BBr_3$ (8.7 mL, 1M in $CH_2Cl_2$) dropwise. After addition, the mixture was allowed to warm to room temperature and stirred for 3 h. Then the mixture was poured into water and extracted with DCM (3×30 mL). The combined organic layers were washed with water and brine, dried over $Na_2SO_4$ and concentrated. The residue was purified by column chromatography on silica gel (petroleum ether/EtOAc=20/1) to give 93-3 (330 mg, about 53% yield) as a solid.

The synthesis of 8-chloro-5-(2-(dimethylamino)ethoxy)thiochroman-4-one (93-4):

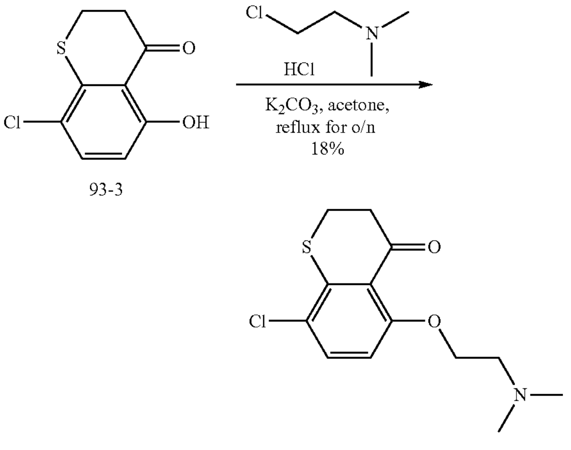

93-3

93-4

A mixture of 93-3 (330 mg, 1.54 mmol), dimethylaminoethyl chloride hydrochloride (332 mg, 2.31 mmol) and $K_2CO_3$ (639 mg, 4.62 mmol) in acetone (30 mL) was stirred at 65° C. overnight. Then the reaction mixture was filtered and concentrated. The residue was purified by Prep-TLC (DCM/MeOH=10/1) to give 93-4 (80 mg, about 18% yield) as an oil. MS Calcd.: 285.1; MS Found: 286.0 $[M+H]^+$.

The synthesis of 2-(4-chloro-8-fluoro-6,11-dihydrothiochromeno[4,3-b]indol-1-yloxy)-N,N-dimethylethanamine (SS20308-0093-01):

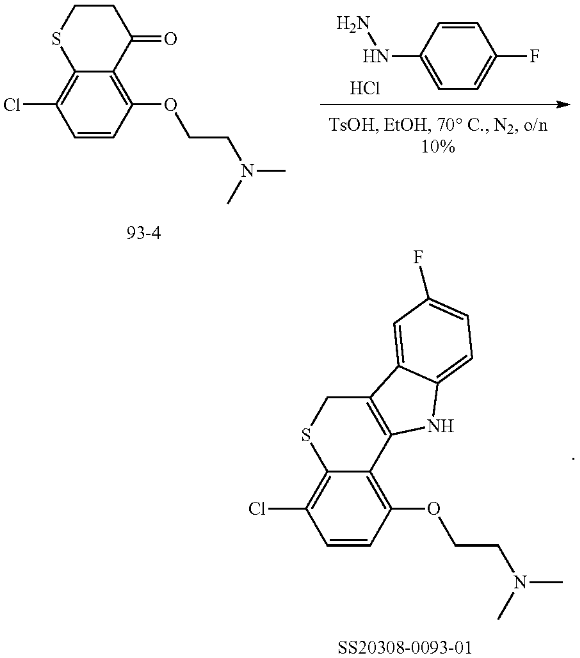

93-4

SS20308-0093-01

A mixture of 93-4 (80 mg, 0.28 mmol), 4-fluorophenylhydrazine hydrochloride (46 mg, 0.28 mmol) and TsOH (241 mg, 1.40 mmol) in EtOH (15 mL) was stirred at 70° C. under $N_2$ gas overnight. After cooling to room temperature, the mixture was concentrated. The residue was basicified with 1N NaOH till pH 10. The resulting mixture was extracted with EtOAc (30 mL×3) and the organic layers were washed with brine, dried over $Na_2SO_4$ and concentrated. The residue was purified by Prep-HPLC to give SS20308-0093-01 (10.7 mg, about 10% yield) as a solid. MS Calcd.: 376.1; MS Found: 377.0 $[M+H]^+$.

$^1$H NMR (400 MHz, $CDCl_3$) δ 11.94 (s, 1H), 7.23-7.18 (m, 1H), 7.18-7.12 (m, 2H), 6.93 (td, J=9.2 Hz, 2.4 Hz, 1H), 6.72 (d, J=8.8 Hz, 1H), 4.25-4.20 (m, 4H), 2.83 (t, J=5.6 Hz, 2H), 2.48 (s, 6H).

Example 33

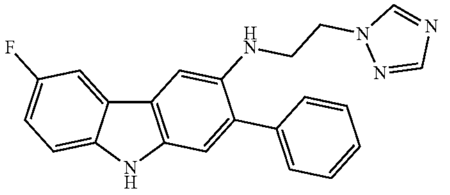

SS20308-0094-01
Chemical Formula: $C_{22}H_{18}FN_5$
Molecular Weight: 371.41

Example Route for Example 33 (SS20308-094-01):

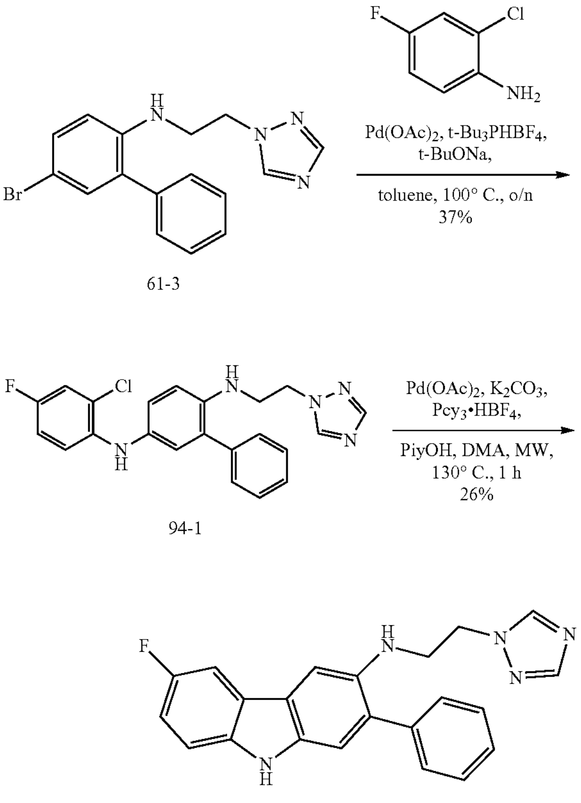

61-3

94-1

SS20308-0094-01

The synthesis of $N^2$-(2-(1H-1,2,4-triazol-1-yl)ethyl)-$N^5$-(2-chloro-4-fluorophenyl)biphenyl-2,5-diamine (94-1):

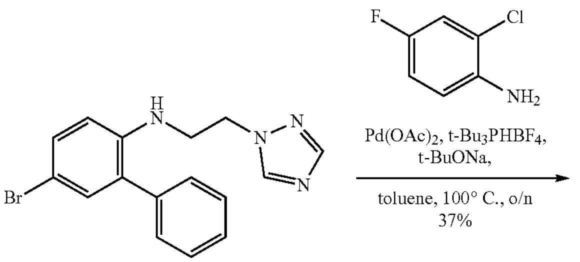

61-3

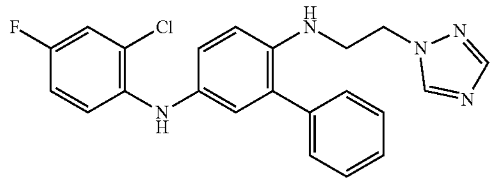

94-1

A solution of 61-3 1.0 g, 2.91 mmol), 2-chloro-4-fluoroaniline (637 mg, 4.38 mmol), $(t\text{-}Bu)_3PHBF_4$ (169 mg, 0.583 mmol), $Pd(OAc)_2$ (66 mg, 0.294 mmol), and t-BuONa (840 mg, 8.74 mmol) were suspended in toluene (20 mL). The reaction mixture was heated at reflux overnight under $N_2$ and then filtered, rinsing with EtOAc. The filtrate was concentrated and purified by column chromatography on silica gel (petroleum ether/EtOAc=5/1 to 3/1 to 1/1) to give 94-1 (440 mg, about 37% yield) as an oil. MS Calcd.:407.1; MS Found: 408.0 $[M+H]^+$.

$^1H$ NMR (400 MHz, DMSO-$d_6$) δ 8.46 (s, 1H), 7.96 (s, 1H), 7.45-7.39 (m, 2H), 7.37-7.30 (m, 2H), 7.29-7.26 (m, 2H), 7.14 (s, 1H), 7.03-6.93 (m, 3H), 6.79 (d, J=2.8 Hz, 1H), 6.71 (d, J=8.8 Hz, 1H), 4.59 (t, J=6.0 Hz, 1H), 4.35 (t, J=5.8 Hz, 2H), 3.50-3.44 (m, 2H).

The synthesis of N-(2-(1H-1,2,4-triazol-1-yl)ethyl)-6-fluoro-2-phenyl-9H-carbazol-3-amine (SS20308-0094-01):

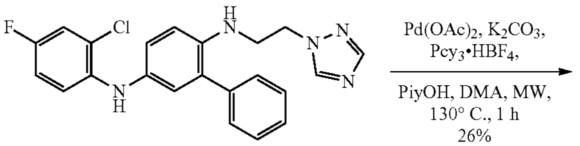

94-1

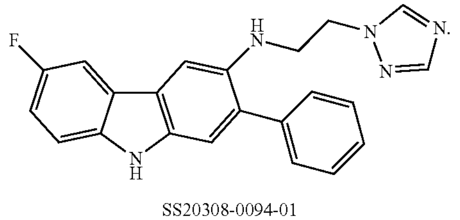

SS20308-0094-01

A mixture of 94-1 (100 mg, 0.25 mmol), $P(Cy)_3HBF_4$ (91 mg, 0.25 mmol), $Pd(OAc)_2$ (28 mg, 0.12 mmol), pivalic acid (38 mg, 0.37 mmol) and $K_2CO_3$ (68 mg, 0.49 mmol) under $N_2$ gas was stirred and heated to 130° C. for 1 h under microwave irradiation. The reaction mixture was poured into water, and extracted with EtOAc (10 mL×3). The combined organic layers were washed with brine (10 mL×2), dried over sodium sulfate, and concentrated to dryness. The residue was purified by Prep-TLC (petroleum ether/EtOAc=1/3) to give SS20308-0094-01 (24 mg, about 26% yield) as a solid. MS Calcd.:371.2; MS Found: 372.0 $[M+H]^+$.

$^1H$ NMR (400 MHz, DMSO-$d_6$) δ 10.87 (brs, 1H), 8.46 (s, 1H), 7.97 (s, 1H), 7.89 (dd, J=9.4, 2.6 Hz, 1H), 7.48-7.42 (m, 3H), 7.41-7.37 (m, 2H), 7.35-7.31 (m, 2H), 7.19-7.12 (m, 2H), 4.44 (t, J=5.8 Hz, 1H), 4.33 (t, J=6.0 Hz, 2H), 3.61-3.54 (m, 2H).

Example 34

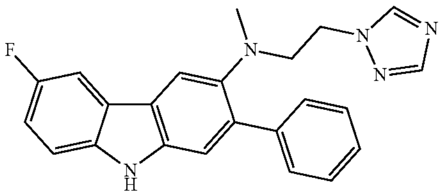

SS20308-0182-01
Chemical Formula: $C_{23}H_{20}FN_5$
Molecular Weight: 385.44

Example Route for Example 34 (SS20308-0182-01):

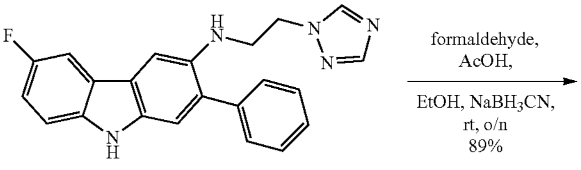

SS20308-0094-01

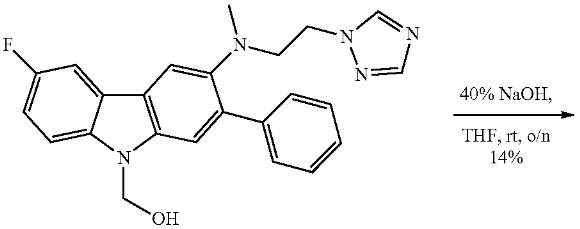

182-1

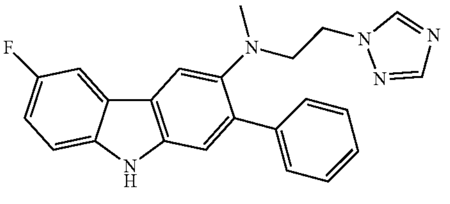

SS20308-0182-01

The synthesis of (3-((2-(1H-1,2,4-triazol-1-yl)ethyl)(methyl)amino)-6-fluoro-2-phenyl-9H-carbazol-9-yl)methanol (182-1):

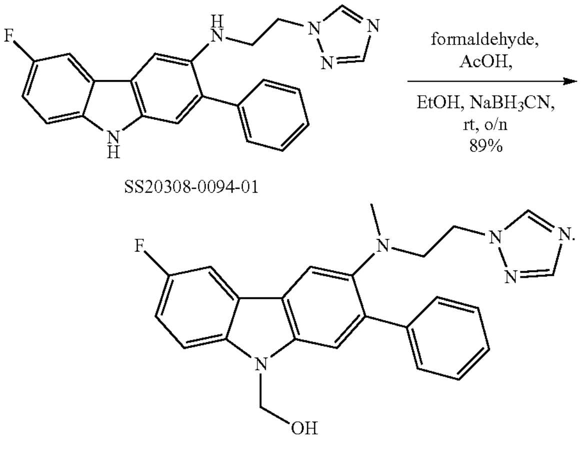

SS20308-0094-01

182-1

To a solution of SS20308-0094-01 (20 mg, 0.054 mmol) in EtOH (2 mL) and AcOH (0.2 mL) was added formaldehyde (44 mg, 0.54 mmol) and $NaBH_3CN$ (5 mg, 0.08 mmol). Then the reaction mixture was stirred at room temperature for overnight. The reaction mixture was poured into cool water (10 mL), basified with saturated $Na_2CO_3$ solution until pH 9. The mixture then extracted with EtOAc (10 mL×3). The combined organic layers were washed with brine (10 mL×2), dried over sodium sulfate, and concentrated to dryness. The residue was purified by Prep-TLC (petroleum ether/acetone=3/1) to give 182-1 (20 mg, about 89% yield) as an oil. MS Calcd.:415.2; MS Found: 416.3 $[M+H]^+$.

The synthesis of N-(2-(1H-1,2,4-triazol-1-yl)ethyl)-6-fluoro-N-methyl-2-phenyl-9H-carbazol-3-amine (182-1):

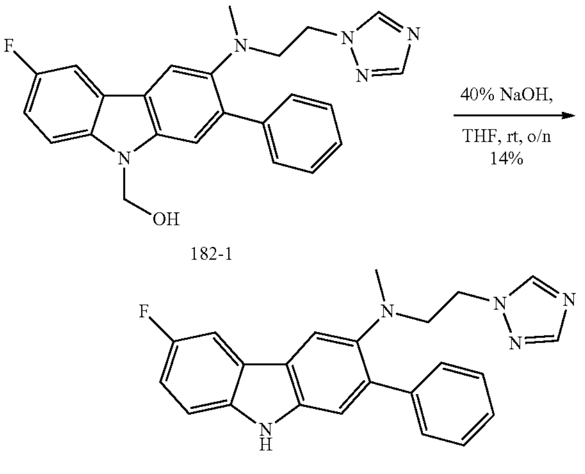

182-1

SS20308-0182-01

A solution of 182-01 (20 mg, 0.048 mmol) and 40% NaOH (aq) (2 mL) in THF (10 mL) was stirred at room temperature for overnight. The reaction mixture was poured into water, and extracted with EtOAc (10 mL×3). The combined organic layers were washed with brine (10 mL×2), dried over sodium sulfate, and concentrated to dryness. The residue was purified by Prep-TLC (petroleum ether/EtOAc=1/3) to give SS20308-0182-01 (2.6 mg, about 14% yield) as a solid. MS Calcd.: 385.2; MS Found: 386.3 $[M+H]^+$.

$^1H$ NMR (400 MHz, DMSO-$d_6$) δ 11.14 (brs, 1H), 8.32 (s, 1H), 7.99-7.94 (m, 3H), 7.45 (dd, J=8.8, 4.4 Hz, 1H), 7.31-7.29 (m, 3H), 7.28-7.24 (m, 3H), 7.23-7.17 (m, 1H), 4.22 (t, J=6.2 Hz, 2H), 3.36 (t, J=6.4 Hz, 2H), 2.46 (s, 3H).

Example 35

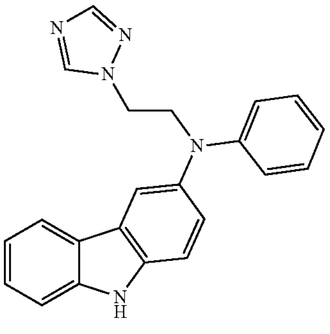

SS20308-108-01
Chemical Formula: $C_{22}H_{19}N_5$
Molecular Weight: 353.42

Example Route for Example 35 (SS20308-0108-01):

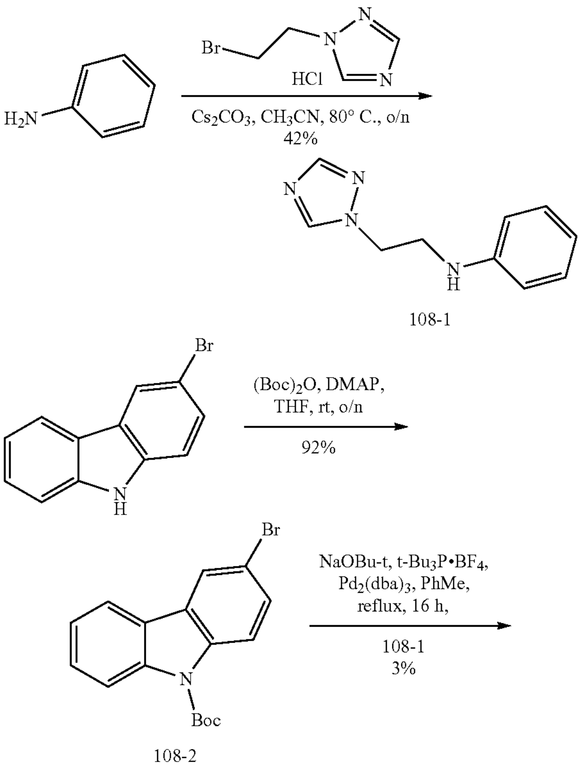

-continued

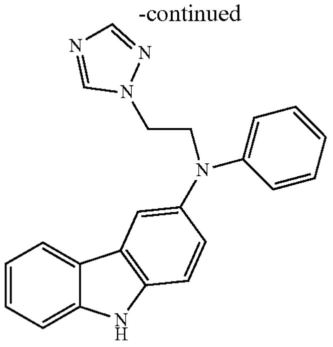

+

SS20308-108-01

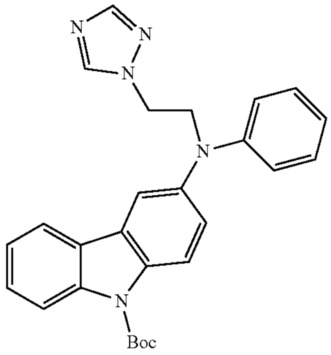

108-3

The synthesis of N-(2-(1H-1,2,4-triazol-1-yl)ethyl)aniline (108-1):

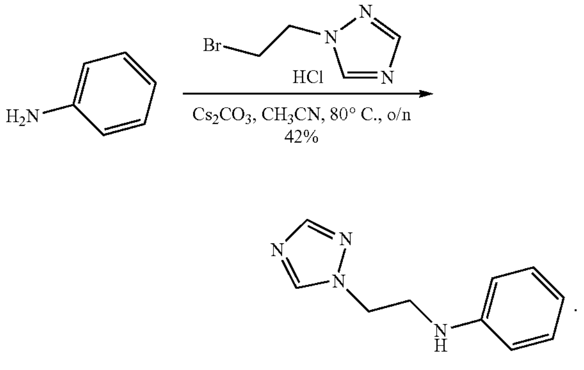

108-1

A mixture of aniline (5.26 g, 56.48 mmol), 1-(2-bromoethyl)-1H-1,2,4-triazole hydrochloride (4.0 g, 18.83 mmol) and $Cs_2CO_3$ (12.27 g, 37.65 mmol) in $CH_3CN$ (80 mL) was stirred at 80° C. overnight. After the reaction was complete, the insoluble material was removed by filtration, and the filtrate was diluted with water (80 mL) and extracted with EtOAc (100 mL×3). The organic layer was separated, dried over $MgSO_4$, and concentrated under vacuum. The residue was purified by column chromatography (petroleum ether/EtOAc=1/1) to give 108-1 (1.5 g, about 42% yield) as a solid. MS Calcd.: 188.1; MS Found: 189.3 $[M+H]^+$.

The synthesis of tert-butyl 3-bromo-9H-carbazole-9-carboxylate (108-2):

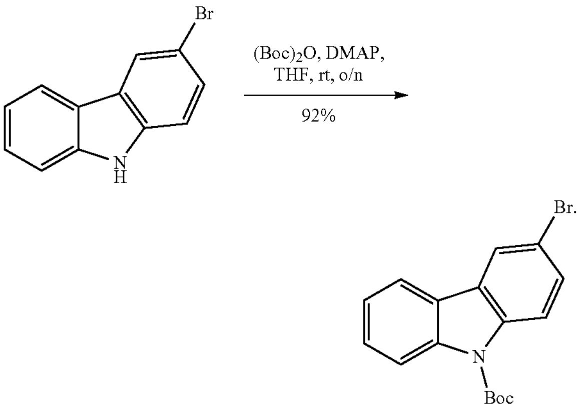

108-2

A solution of 3-bromocarbazole (500 mg, 2.03 mmol), $(Boc)_2O$ (665 mg, 3.05 mmol) and DMAP (25 mg, 0.20 mmol) in THF (20 mL) was stirred at room temperature overnight. After the reaction was complete, the reaction was poured into water (50 mL) and extracted with EtOAc (30 mL×4). The organic layer was washed with water (50 mL), brine (2×50 mL) and the solvent evaporated to give a crude solid. The crude was purified by column chromatography on silica gel (petroleum ether/EtOAc=20/1) to give 108-2 (650 mg, about 92% yield) as a solid.

The synthesis of N-(2-(1H-1,2,4-triazol-1-yl)ethyl)-N-phenyl-9H-carbazol-3-amine (SS20308-0108-01):

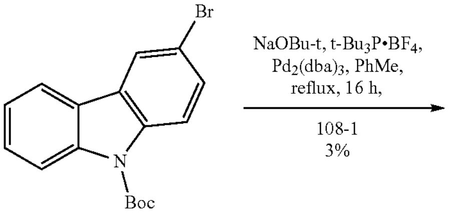

108-2

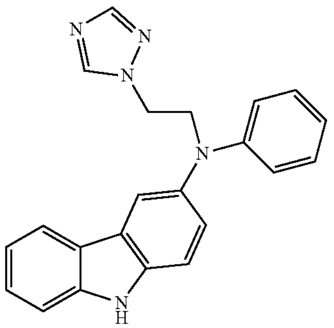

+

SS20308-108-01

-continued

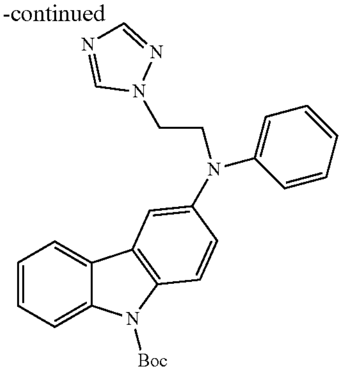

108-3

A mixture of 108-2 (400 mg, 1.16 mmol), 108-1 (217 mg, 1.16 mmol), $Pd_2(dba)_3$ (106 mg, 0.12 mmol), t-$Bu_3P$—$BF_4$ (67 mg, 0.23 mmol) and t-BuONa (222 mg, 2.31 mmol) in PhMe (20 mL) was stirred at 110° C. under nitrogen atmosphere overnight. After the reaction was complete, the mixture was quenched with water, and the insoluble material was removed by filtration. The filtrate was extracted with EtOAc (50 mL×3). The organic layer was separated, dried over $MgSO_4$, and concentrated under vacuum. The residue was purified by Prep-HPLC to give SS20308-0108-01 (14 mg, about 3% yield) as a solid. MS Calcd.: 353.2; MS Found: 354.0 $[M+H]^+$.

$^1H$ NMR (400 MHz, DMSO-$d_6$) δ 11.30 (s, 1H), 8.53 (s, 1H), 8.06 (d, J=8.0 Hz, 1H), 7.99 (s, 1H), 7.78 (d, J=2.0 Hz, 1H), 7.50-7.48 (m, 2H), 7.41-7.37 (m, 1H), 7.16-7.07 (m, 4H), 6.68-6.64 (m, 1H), 6.58-6.56 (m, 2H), 4.46 (t, J=6.4 Hz, 2H), 4.7 (t, J=6.4 Hz, 2H).

Example 36

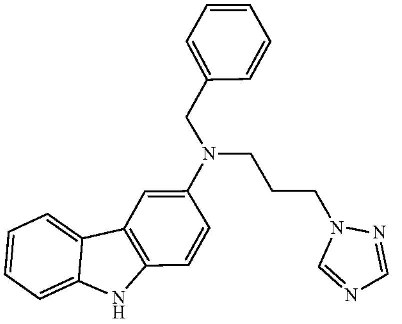

SS20308-0097-01
Chemical Formula: $C_{24}H_{23}N_5$
Molecular Weight: 381.47

Example Route for Example 36 (SS20308-0097-01):

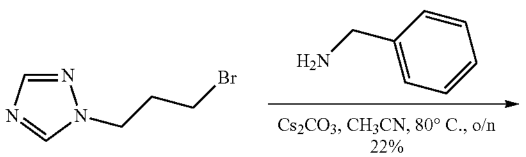

-continued

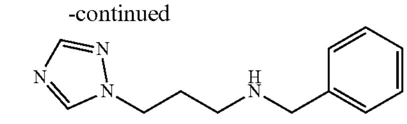

97-1

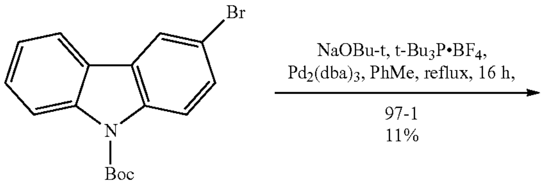

108-2

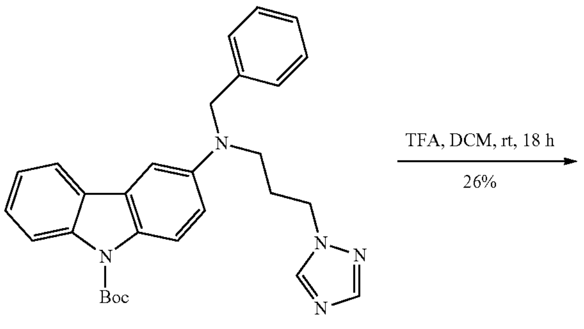

97-2

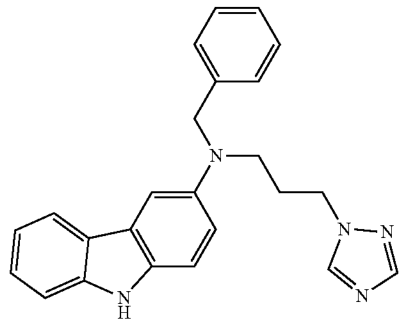

SS20308-0097-01

The synthesis of N-benzyl-3-(1H-1,2,4-triazol-1-yl)propan-1-amine (97-1):

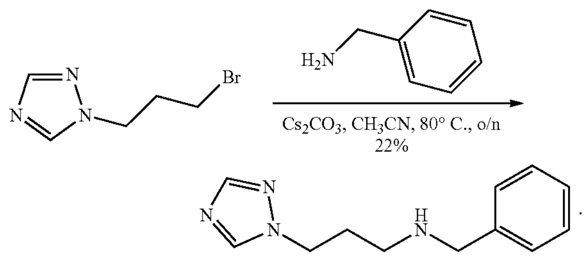

97-1

A mixture of 1-(3-bromopropyl)-1H-1,2,4-triazole (3.8 g, 16.9 mmol), phenylmethanamine (2.2 g, 20.33 mmol) and $Cs_2CO_3$ (11.0 g, 33.8 mmol) in $CH_3CN$ (50 mL) was stirred at 80° C. overnight. After the reaction was complete, the insoluble material was removed by filtration. The filtrate was diluted with water (80 mL) and extracted with EtOAc (100 mL×3). The organic layer was separated, dried over $MgSO_4$, and concentrated under vacuum. The residue was purified by column chromatography on silica gel (petroleum ether/EtOAc=5/1) to give 97-1 (800 mg, about 22% yield) as an oil. MS Calcd.: 216.1; MS Found: 217.3 [M+H]$^+$.

The synthesis of tert-butyl 3-((3-(1H-1,2,4-triazol-1-yl)propyl)(benzyl)amino)-9H-carbazole-9-carboxylate (0097-01-3):

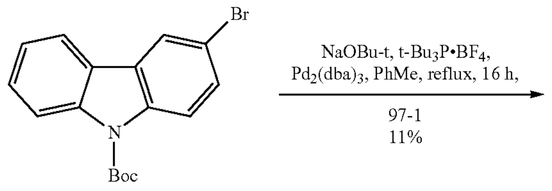

108-2

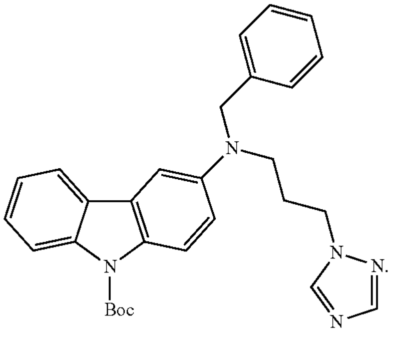

97-2

A mixture of 108-2 (200 mg, 0.58 mmol), 97-1 (150 mg, 0.70 mmol), $Pd_2(dba)_3$ (27 mg, 0.03 mmol), $(t\text{-}Bu)_3P—BF_4$ (17 mg, 0.06 mmol) and t-BuONa (167 mg, 1.74 mmol) in PhMe (10 mL) was stirred at 110° C. under nitrogen atmosphere overnight. After the reaction was complete, the mixture was quenched with water, and the insoluble material was removed by filtration. The filtrate was extracted with EtOAc (50 mL×3). The organic layer was separated, dried over $MgSO_4$, and concentrated under vacuum. The residue was purified by Prep-TLC to give 97-2 (30 mg, about 11% yield) as a solid. MS Calcd.: 481.3; MS Found: 482.3 [M+H]$^+$.

The synthesis of N-(3-(1H-1,2,4-triazol-1-yl)propyl)-N-benzyl-9H-carbazol-3-amine (SS20308-0097-01

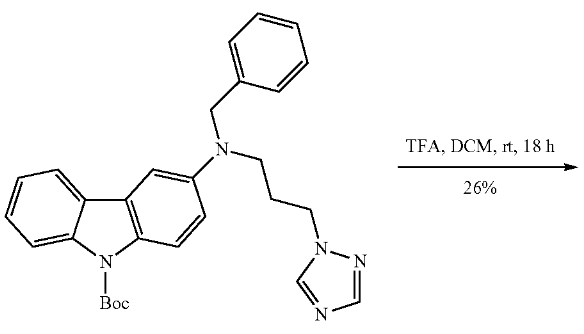

97-2

-continued

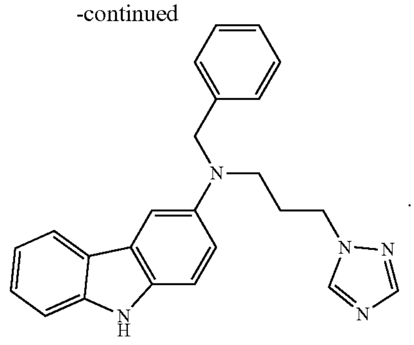

SS20308-0097-01

A solution of 97-2 (30 mg, 0.06 mmol) and TFA (0.3 mL) in DCM (5 mL) was stirred at room temperature overnight. After the reaction was complete, the reaction was poured into water (50 mL) and extracted with EtOAc (30 mL×4). The organic layer was washed with water (50 mL), brine (2×50 mL) and the solvent evaporated. The crude solid was purified by Prep-HPLC to give SS20308-0097-01 (6.0 mg, about 26% yield) as a solid. MS Calcd.: 381.2; MS Found: 382.0 [M+H]$^+$.

$^1$H NMR (400 MHz, MeOD-$d_4$) δ 10.84 (s, 1H), 8.50 (s, 1H), 8.00 (s, 1H), 7.96 (d, J=7.6 Hz, 1H), 7.43-7.37 (m, 2H), 7.32-7.27 (m, 6H), 7.22-7.19 (m, 1H), 7.08-7.05 (m, 1H), 6.95-6.93 (m, 1H), 4.60-4.50 (m, 2H), 4.27 (t, J=6.8 Hz, 2H), 3.60-3.50 (m, 2H), 2.11 (t, J=6.8 Hz, 2H).

Example 37

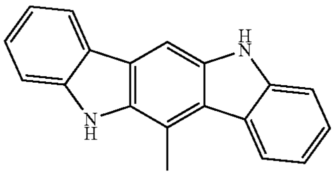

SS20308-0112-01
Chemical Formula: $C_{19}H_{14}N_2$
Molecular Weight: 270.33

Example Route for Example 37 (SS20308-0112-01):

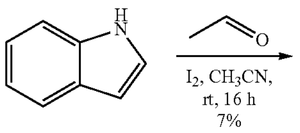

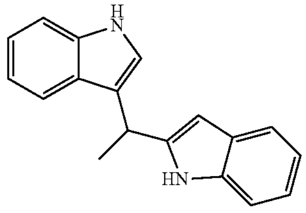

112-1

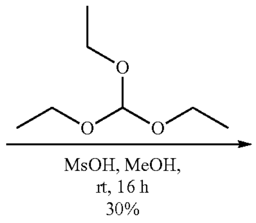

-continued

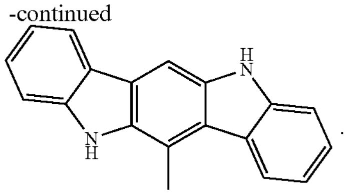

SS20308-0112-01

The synthesis of 3-(1-(1H-indol-2-yl)ethyl)-1H-indole (112-1):

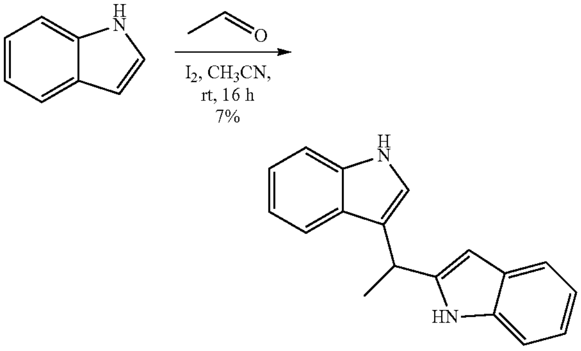

112-1

To a solution of indole (5.00 g, 42.7 mmol) and acetaldehyde (0.94 g, 21.4 mmol) in $CH_3CN$ (60 mL), $I_2$ (1.08 g, 4.27 mmol) was added. The reaction mixture was stirred at room temperature for 16 h. $Na_2SO_3$ (aq, saturated) was added, and the solution was extracted with EtOAc (50 mL×3). The organic layer was then dried with $MgSO_4$ and concentrated under reduced pressure. The crude product was purified by column chromatography on silica gel (petroleum ether/EtOAc=1/10) to give 112-1 (0.83 g, about 7% yield) as an oil. MS Calcd.: 260.1; MS Found: 259.2 $[M-H]^-$.

The synthesis of 6-methyl-5,11-dihydroindolo[3,2-b]carbazole (SS20308-0112-01):

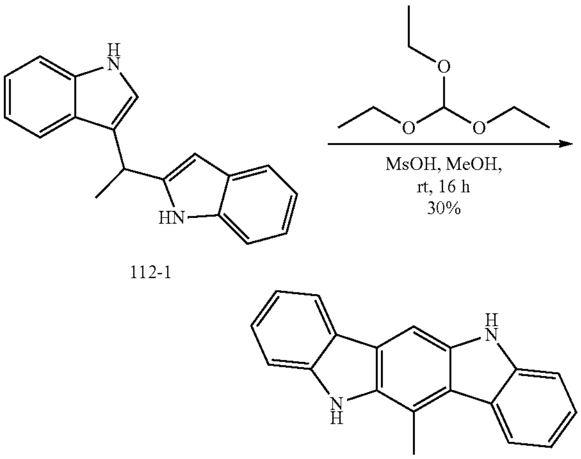

112-1

SS20308-0112-01

To a solution of 112-1 (1.03 g, 4.0 mmol) in MeOH (20 mL) was added triethoxymethane (296 mg, 2.0 mmol), methanesulfonic acid (38 mg, 0.4 mmol), and the reaction mixture was stirred at room temperature for 16 h. The formed precipitate was filtered off, washed by MeOH, dried under vacuum to give SS20308-0112-01 (0.32 g, about 30% yield) as a solid. MS Calcd.: 270.1; MS Found: 271.1 $[M+H]^+$.

$^1$H NMR (400 MHz, DMSO-$d_6$) δ 11.05 (s, 1H), 11.95 (s, 1H), 8.24 (d, J=8.0, 1H), 8.17 (d, J=8.0 Hz, 1H), 7.96 (s, 1H), 7.50-7.45 (m, 2H), 7.37 (dd, J=7.6, 7.2 Hz, 2H), 7.17-7.09 (m, 2H), 3.04 (s, 3H).

Example 38

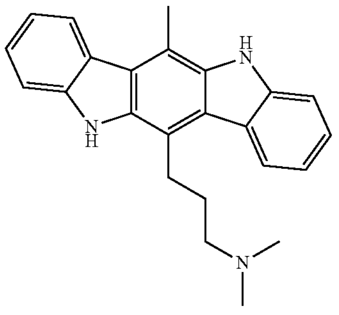

SS20308-0100-01
Chemical Formula: $C_{24}H_{25}N_3$
Molecular Weight: 355.48

Example Route for Example 38 (SS20308-0100-01):

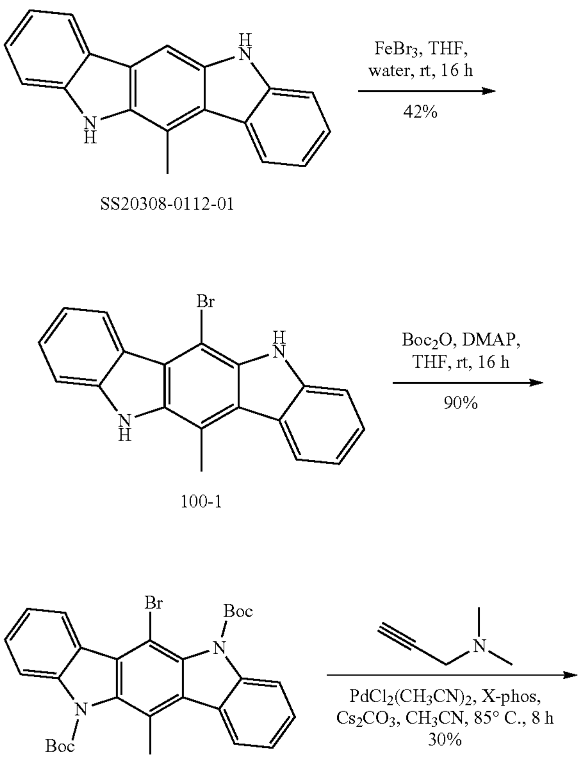

SS20308-0112-01

100-1

100-2

-continued

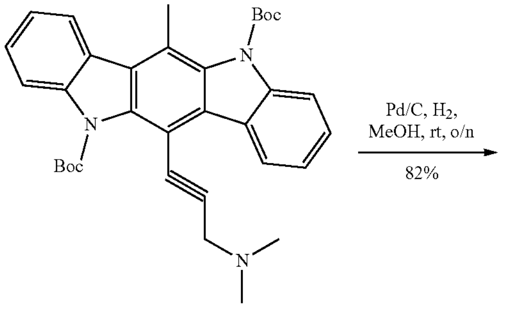

100-3

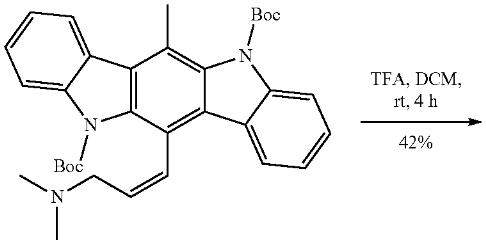

100-4

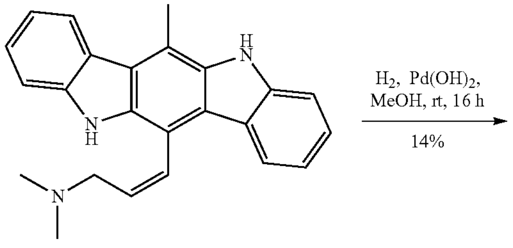

100-5

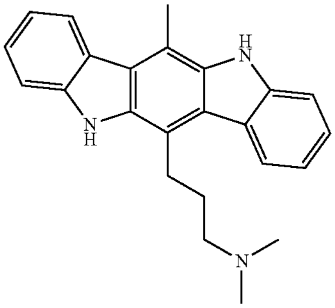

SS20308-0100-01

The synthesis of 6-bromo-12-methyl-5,11-dihydroindolo[3,2-b]carbazole (100-3):

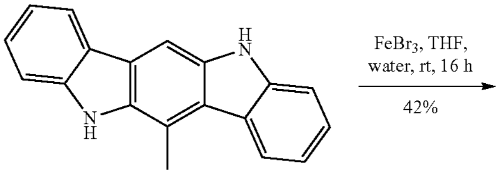

SS20308-0112-01

-continued

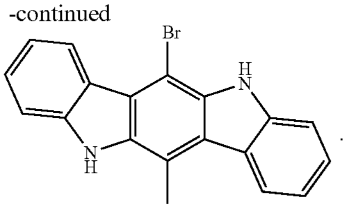

100-3

To a solution of SS20308-0112-01 (800 mg, 3.0 mmol) in THF (10 mL) and water (4 mL) was added $FeBr_3$ (2.66 g, 9.0 mmol) at room temperature. The mixture was stirred at room temperature for 16 h under nitrogen. The mixture was filtered, and the filtrate was diluted with EtOAc (50 mL). The mixture was washed by brine (30 mL×2) and the organic layer was then dried with $MgSO_4$ and concentrated under reduced pressure. The crude product was purified by column chromatography on silica gel (petroleum ether/EtOAc=1/8) to give 100-3 (430 mg, about 42% yield) as a solid. MS Calcd.:348.0; MS Found: 346.9 $[M-H]^-$.

The synthesis of di-tert-butyl 6-bromoindolo[3,2-b]carbazole-5,11-dicarboxylate (100-4):

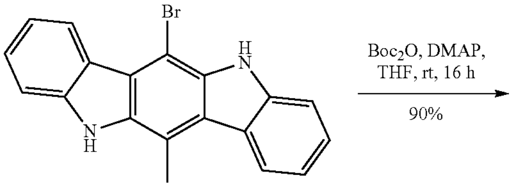

100-3

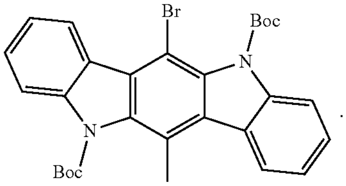

100-4

To a solution of 100-3 (1.05 g, 3.0 mmol) in THF (20 mL) was added $Boc_2O$ (2.16 g, 10.0 mmol) and DMAP (37 mg, 0.3 mmol) at room temperature. The mixture was stirred at room temperature for 16 h under nitrogen. The mixture was concentrated to a crude oil, which was purified by column chromatography on silica gel (petroleum ether/EtOAc=1/30) to give 100-4 (1.48 g, about 90% yield) as a solid.

The synthesis of di-tert-butyl 6-(3-(dimethylamino)prop-1-ynyl)-12-methylindolo[3,2-b]carbazole-5,11-dicarboxylate (100-5):

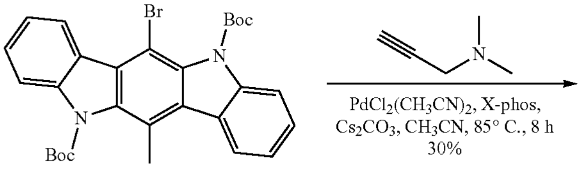

100-4

-continued

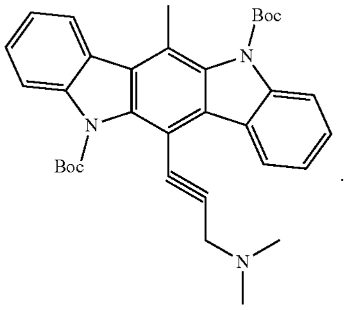

100-5

To a mixture of 100-4 (515 mg, 0.94 mmol) and N,N-dimethylprop-2-yn-1-amine (311 mg, 3.75 mmol) in $CH_3CN$ (10 mL) was added $PdCl_2(CH_3CN)_2$ (26 mg, 0.1 mmol), X-Phos (72 mg, 0.15 mmol), and $Cs_2CO_3$ (919 mg, 2.82 mmol) at room temperature. Then the mixture was heated to 85° C. and stirred for 8 h under nitrogen. The reaction mixture was cooled to room temperature. The mixture was filtered, and washed with EtOAc. The filtrate was concentrated to an oil, which was purified by column chromatography on silica gel (petroleum ether/EtOAc=1/10) to give 100-5 (155 mg, about 30% yield) as a solid. MS Calcd.: 551.3; MS Found: 552.0 $[M+H]^+$.

The synthesis of (Z)-di-tert-butyl 6-(3-(dimethylamino)prop-1-enyl)-12-methylindolo[3,2-b]carbazole-5,11-dicarboxylate (100-6):

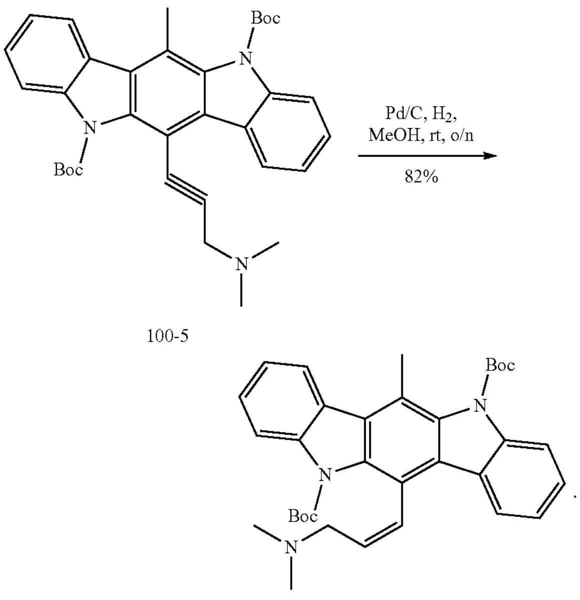

100-5

100-6

To a solution of 100-5 (100 mg, 0.18 mmol) in MeOH (3 mL) was added Pd/C (10 mg, 10%) at room temperature. Then the mixture was stirred at room temperature overnight under hydrogen gas (balloon). The mixture was filtered, and washed with EtOAc and MeOH. The filtrate was concentrated to give 100-6 (82 mg, about 82% yield) as an oil. MS Calcd.: 553.3; MS Found: 554.0 $[M+H]^+$.

The synthesis of (Z)—N,N-dimethyl-3-(12-methyl-5,11-dihydroindolo[3,2-b]carbazol-6-yl)prop-2-en-1-amine (100-7):

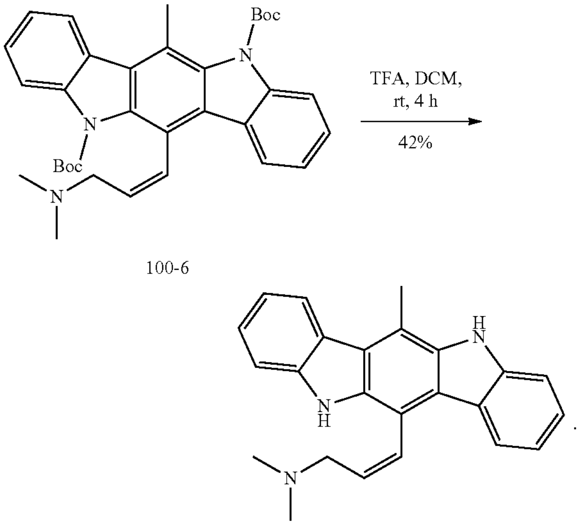

100-6

100-7

To a solution of 100-6 (82 mg, 0.15 mmol) in DCM (3 mL) was added TFA (1 mL) at room temperature. The mixture was stirred at room temperature for 4 h. The reaction mixture was concentrated to a crude oil. The mixture was neutralized with sat. $NaHCO_3$ to pH=8, and then extracted with EtOAc (10 mL×2). The organic layer was then dried with $MgSO_4$ and concentrated under reduced pressure. The crude product was purified by Prep-TLC to give 100-7 (22 mg, about 42% yield) as an oil. MS Calcd.: 353.2; MS Found: 354.1 $[M+H]^+$.

The synthesis of N,N-dimethyl-3-(12-methyl-5,11-dihydroindolo[3,2-b]carbazol-6-yl)propan-1-amine (SS20308-0100-01):

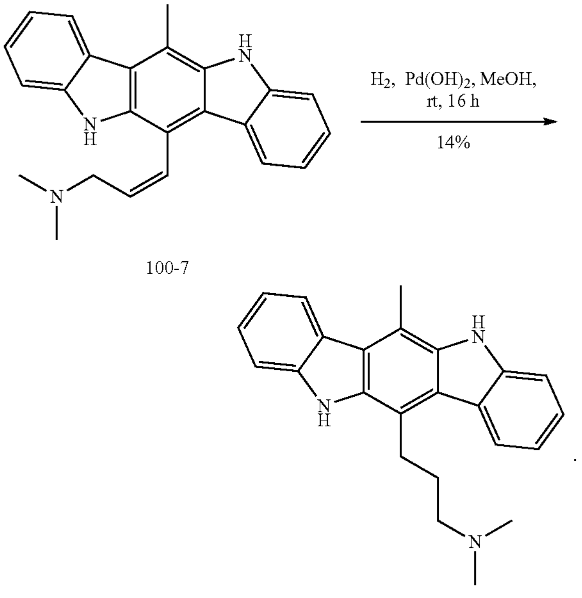

100-7

SS20308-0100-01

To the solution of 100-7 (22 mg, 0.06 mmol) in MeOH (2 mL) was added Pd/C (10%, 5 mg) at room temperature, then the mixture was stirred at room temperature for 16 h under hydrogen gas (balloon). The mixture was filtrated, and washed with EtOAc and MeOH. The filtrate was concentrated to crude oil, which was purified by Prep-TLC to give SS20308-0100-01 (3 mg, 14% yield) as a solid. MS Calcd.: 355.2; MS Found: 356.0 $[M+H]^+$.

$^1H$ NMR (400 MHz, DMSO-$d_6$) δ 11.03 (s, 1H), 10.97 (s, 1H), 8.24 (d, J=8.0, 1H), 8.18 (d, J=8.0 Hz, 1H), 7.54-7.49 (m, 2H), 7.38 (dd, J=7.6, 7.6 Hz, 2H), 7.14 (dd, J=7.6, 7.2 Hz, 2H), 3.47 (t, J=7.4, 2H), 3.01 (s, 3H), 2.40 (t, J=7.0, 2H), 2.21 (s, 6H), 2.00-1.90 (m, 2H).

Example 39

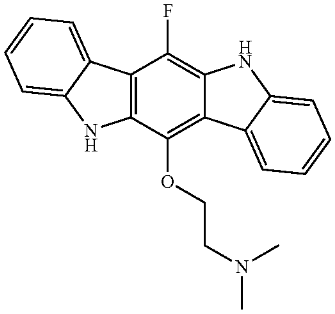

SS20308-0102-01
Chemical Formula: $C_{22}H_{20}FN_3O$
Molecular Weight: 361.42

Example Route for Example 39 (SS20308-0102-01):

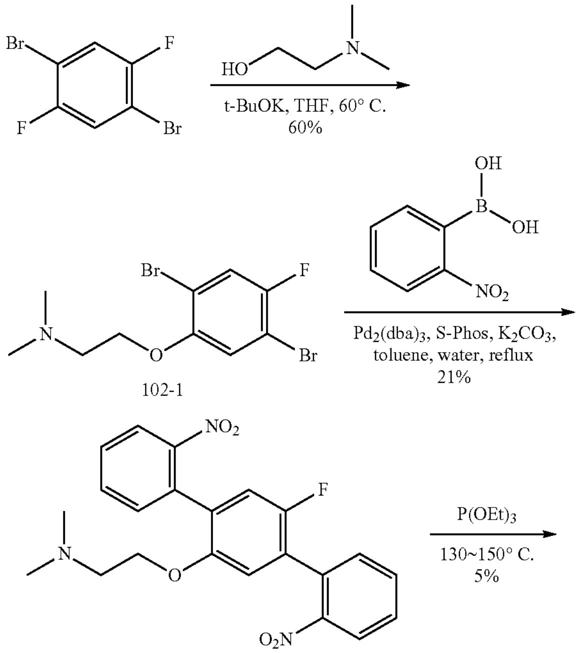

102-1

102-2

-continued

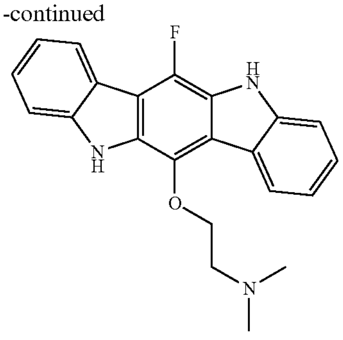

SS20308-0102-01

The synthesis of 2-(2,5-dibromo-4-fluorophenoxy)-N,N-dimethylethanamine (102-1):

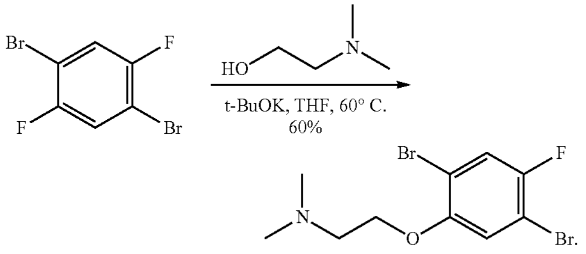

102-1

A mixture of 1,4-dibromo-2,5-difluorobenzene (2.0 g, 7.4 mmol), 2-(dimethylamino)ethanol (989 mg, 11.1 mmol) and t-BuOK (1.7 g, 14.8 mmol) in THF (100 mL) was stirred at 60° C. overnight. After the reaction was complete, the reaction was poured into water (50 mL) and extracted with EtOAc (30 mL×4). The organic layer was washed with water (50 mL), and brine (2×50 mL). The solvent was evaporated to give a solid, which was purified by column chromatography on silica gel (petroleum ether/EtOAc=20/1) to give 102-1 (1.5 g, about 60% yield) as a solid. MS Calcd.: 188.1; MS Found: 189.3 $[M+H]^+$.

The synthesis of (102-2):

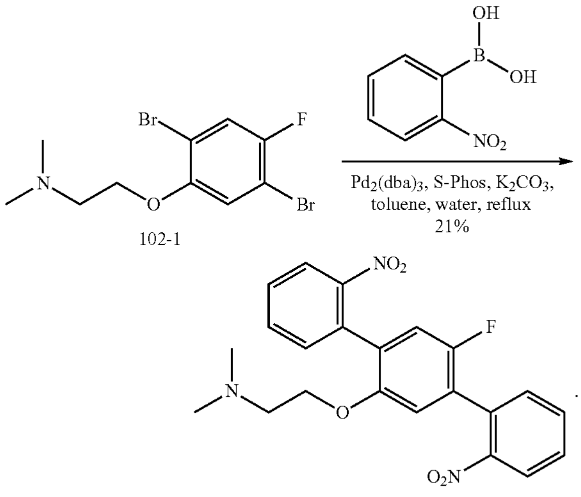

102-1

102-2

A mixture of 102-1 (300 mg, 0.88 mmol), 2-nitrophenylboronic acid (367 mg, 2.2 mmol), $Pd_2(dba)_3$ (32 mg, 0.044 mmol) and S-Phos (36 mg, 0.088 mmol), and $K_2CO_3$ (570 mg, 1.76 mmol) in toluene/water (5/0.5 mL) was stirred at reflux overnight. The reaction mixture was cooled to room temperature and poured into water (50 mL) and extracted with EtOAc (50 mL×3). The organic layer was washed with brine and concentrated. The residue crude product was purified by Prep-HPLC to give 102-2 (80 mg, about 21% yield) as a solid. MS Calcd.: 425.1; MS Found: 426.0 $[M+H]^+$.

The synthesis of 2-(12-fluoro-5,11-dihydroindolo[3,2-b]carbazol-6-yloxy)-N,N-dimethylethanamine (SS20308-0102-01):

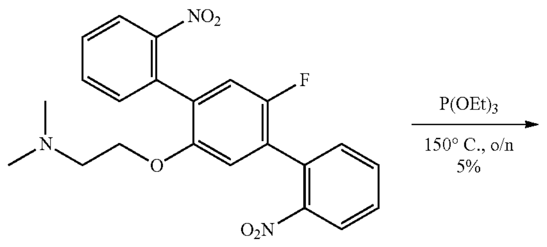

102-2

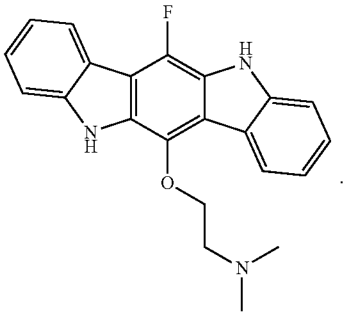

SS20308-0102-01

To a solution of 102-2 (100 mg, 0.24 mmol) in $P(OEt)_3$ (1 mL) was stirred at 150° C. for 18 h. The solution was then concentrated under vacuum to afford a crude product, which was purified by Prep-HPLC twice to give SS20308-0102-01 (4.2 mg, about 5% yield) as a solid. MS Calcd.: 361.2; MS Found: 362.2 $[M+H]^+$.

$^1H$ NMR (400 MHz, DMSO-$d_6$) δ 11.54 (s, 1H), 11.35 (s, 1H), 8.30 (d, J=7.6 Hz, 1H), 8.08 (d, J=7.6 Hz, 1H), 7.50 (d, J=8.0 Hz, 1H), 7.45-7.35 (m, 3H), 7.15-7.11 (m, 2H), 4.31 (t, J=5.6 Hz, 2H), 2.76 (t, J=5.2 Hz, 2H), 2.29 (s, 6H).

Example 40

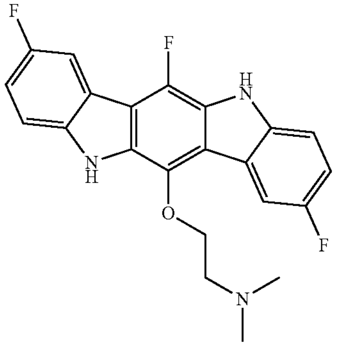

SS20308-0101-01
Chemical Formula: $C_{22}H_{18}F_3N_3O$
Molecular Weight: 397.40

Example Route for Example 40 (SS20308-0101-01):

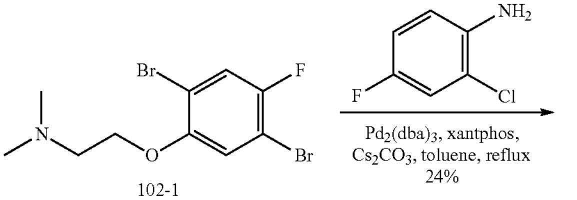

102-1

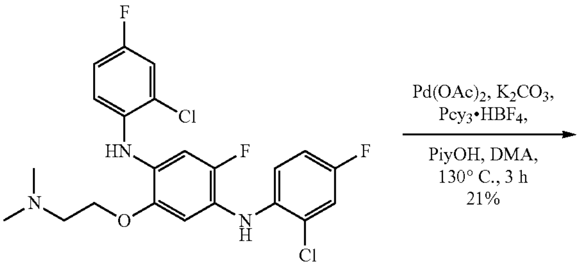

101-1

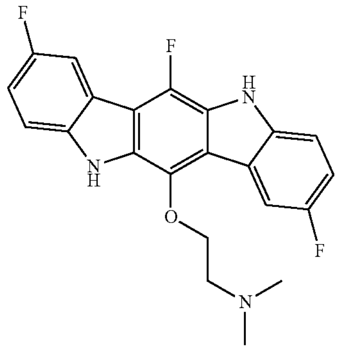

SS20308-0101-01

The synthesis of $N_1$,$N_4$-bis(2-chloro-4-fluorophenyl)-2-(2-(dimethylamino)ethoxy)-5-fluorobenzene-1,4-diamine (101-1):

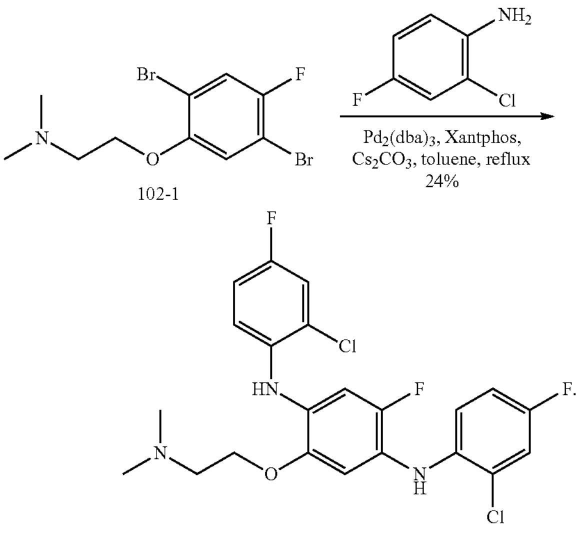

102-1

101-1

A mixture of 102-1 (300 mg, 0.88 mmol), 2-chloro-4-fluoroaniline (140 mg, 0.97 mmol), $Pd_2(dba)_3$ (40 mg, 0.044 mmol) and Xant-Phos (51 mg, 0.088 mmol), and $Cs_2CO_3$ (573 mg, 1.76 mmol) in toluene (10 mL) was stirred at reflux overnight. The reaction mixture was cooled to room temperature and poured into water (50 mL) and extracted with EtOAc (50 mL×3). The organic layer was washed with brine and evaporated. The residue crude product was purified by Prep-TLC (EtOAc) to give 101-1 (100 mg, about 24% yield) as a solid. MS Calcd.: 469.1; MS Found: 470.2 $[M+H]^+$.

The synthesis of N,N-dimethyl-2-(2,8,12-trifluoro-5,11-dihydroindolo[3,2-b]carbazol-6-yloxy) ethanamine (SS20308-101-01):

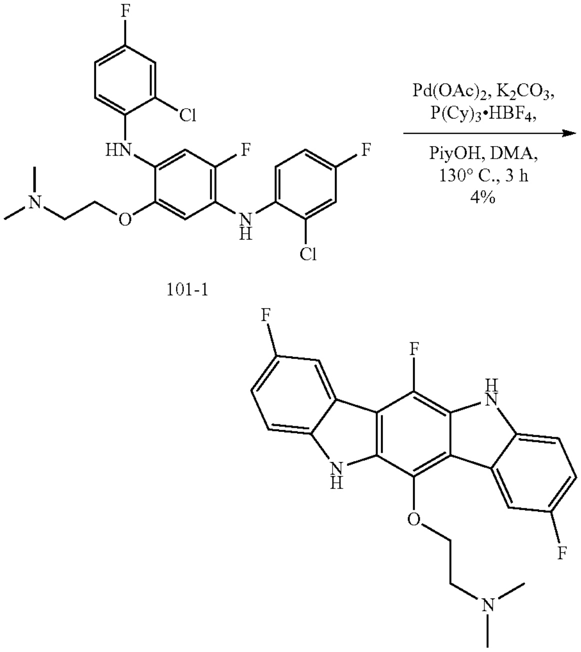

101-1

SS20308-0101-01

A mixture of 101-1 (100 mg, 0.21 mmol), $Pd(OAc)_2$ (24 mg, 0.11 mmol), $P(Cy)_3$.$HBF_4$ (77 mg, 0.21 mmol), PivOH (6 mg, 0.06 mmol) and $K_2CO_3$ (58 mg, 0.42 mmol) in DMA (2 mL) was stirred at 130° C. for 2 h in microwave reactor. The reaction mixture was cooled to room temperature, poured into water (30 mL), and extracted with EtOAc (30 mL×3). The organic layer was washed with brine and evaporated. The residue crude product was purified by Prep-HPLC to give SS20308-101-01 (2.95 mg, about 4% yield) as a solid. MS Calcd.: 397.1; MS Found: 398.0 $[M+H]^+$.

$^1$H NMR (400 MHz, $CDCl_3$) δ 11.66 (brs, 1H), 11.49 (s, 1H), 8.25 (d, J=9.2 Hz, 1H), 7.87 (d, J=8.8 Hz, 1H), 7.58-7.55 (m, 1H), 7.50-7.47 (m, 1H), 7.33 (d, J=9.6 Hz, 2H), 4.37 (s, 2H), 2.81 (s, 2H), 2.36 (s, 6H).

Example 41

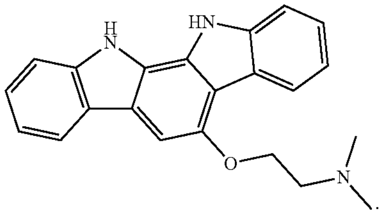

SS20308-0103-01
Chemical Formula: $C_{22}H_{21}N_3O$
Molecular Weight: 343.42

Example Route for Example 41 (SS20308-0103-01):

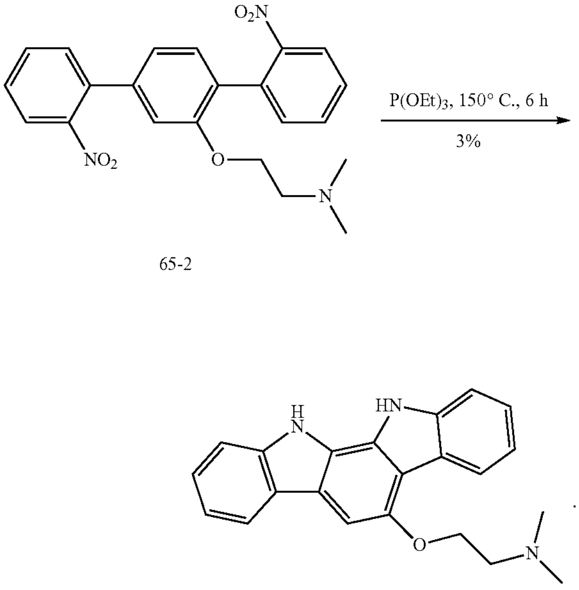

65-2

SS20308-0103-01

The synthesis of 2-(11,12-dihydroindolo[2,3-a]carbazol-5-yloxy)-N,N-dimethylethanamine (SS20308-0103-01):

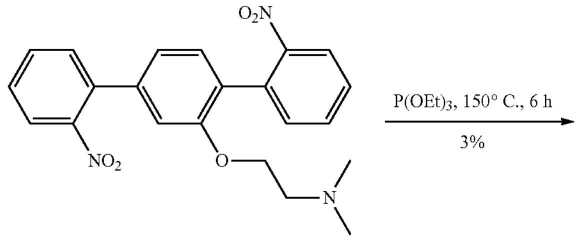

65-2

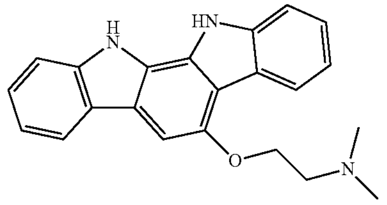

SS20308-0103-01

A solution of 65-2 (100 mg, 0.25 mmol) in $P(OEt)_3$ (2 mL) was stirred at 150° C. for 6 h. After the reaction was completed, the solution was concentrated to a crude product, which was purified by reverse flash column and Prep-TLC twice, Prep-HPLC, to give SS20308-0103-01 (2.5 mg, about 3% yield) as a solid. MS Calcd.: 343.2; MS Found: 344.1 $[M+H]^+$.

$^1H$ NMR (400 MHz, DMSO-$d_6$) δ 11.16 (s, 1H), 10.83 (s, 1H), 8.28 (d, J=8.0 Hz, 1H), 8.12 (d, J=8.0 Hz, 1H), 7.67-7.62 (m, 2H), 7.42 (s, 1H), 7.38-7.32 (m, 2H), 7.22-7.13 (m, 2H), 4.39 (t, J=5.8 Hz, 2H), 2.91 (t, J=5.8 Hz, 2H), 2.35 (s, 6H).

Example 42

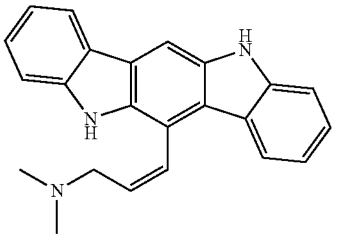

SS20308-0126-01
Chemical Formula: $C_{23}H_{21}N_3$
Molecular Weight: 339.43

Example Route for Example 42 (SS20308-0126-01):

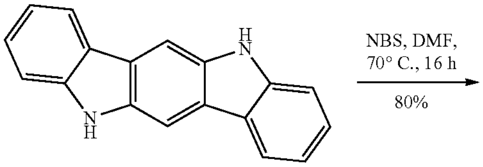

-continued

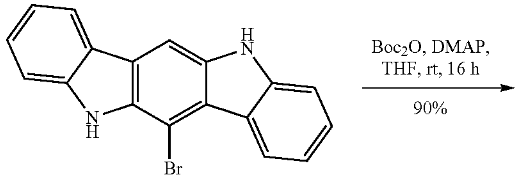

126-1

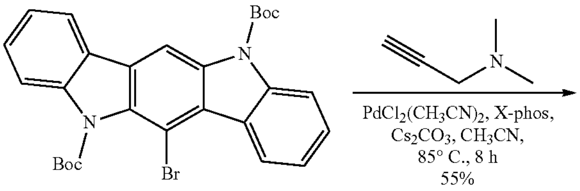

126-2

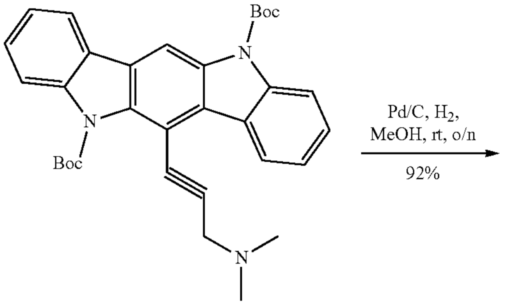

126-3

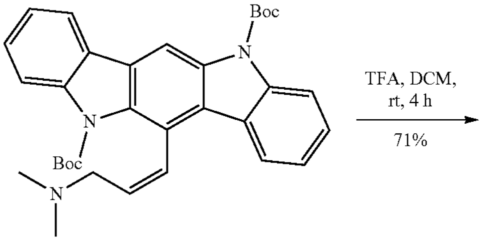

126-4

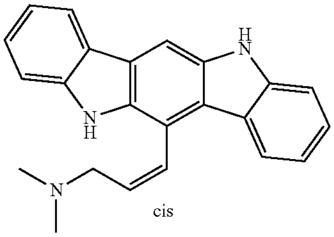

SS20308-0126-01

The synthesis of 6-bromo-5,11-dihydroindolo[3,2-b]carbazole (126-1):

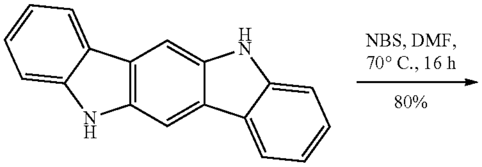

-continued

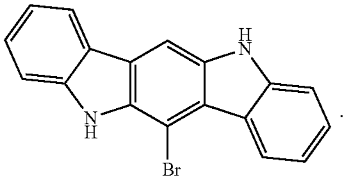

126-1

To a mixture of 5,11-dihydroindolo[3,2-b]carbazole (2.0 g, 7.8 mmol) in DMF (300 mL) was added NBS (1.4 g, 7.8 mmol) at 70° C. The mixture was stirred at 70° C. for 16 h. The mixture was diluted with water (400 mL) and filtered. The solid was washed with water and dried under vacuum to give 126-1 (2.1 g, about 80% yield) as a solid. MS Calcd.: 334.0; MS Found: 333.0 $[M-H]^-$.

The synthesis of di-tert-butyl 6-bromoindolo[3,2-b]carbazole-5,11-dicarboxylate (126-2):

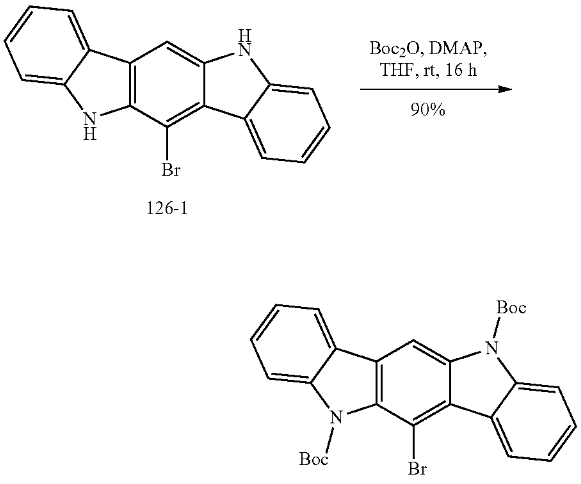

126-1

126-2

To the solution of 126-1 (1.00 g, 3.0 mmol) in THF (20 mL) was added $Boc_2O$ (2.16 g, 10.0 mmol) and DMAP (37 mg, 0.3 mmol) at room temperature. Then the mixture was stirred at room temperature for 16 h under nitrogen. The mixture was concentrated to crude oil, which was purified by column chromatography on silica gel (petroleum ether/EtOAc=1/30) to give 126-2 (1.44 g, about 90% yield) as a solid.

The synthesis of di-tert-butyl 6-(3-(dimethylamino)prop-1-ynyl)indolo[3,2-b]carbazole-5,11-dicarboxylate (126-3):

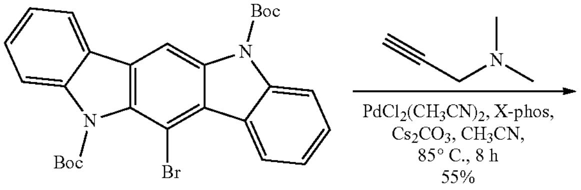

126-2

-continued

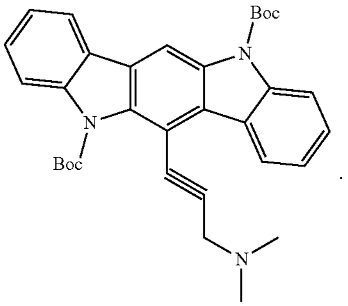

126-3

To a mixture of 126-2 (500 mg, 0.94 mmol) and N,N-dimethylprop-2-yn-1-amine (311 mg, 3.75 mmol) in $CH_3CN$ (10 mL) was added $PdCl_2(CH_3CN)_2$ (26 mg, 0.1 mmol), X-Phos (72 mg, 0.15 mmol), $Cs_2CO_3$ (919 mg, 2.82 mmol) at room temperature. Then the mixture was heated to 85° C. for 8 h under nitrogen. The reaction mixture was cooled to room temperature. The mixture was filtered, and washed with EtOAc. The filtrate was concentrated to an oil, which was purified by column chromatography on silica gel (petroleum ether/EtOAc=1/10) to give 126-3 (278 mg, about 55% yield) as a solid. MS Calcd.: 537.3; MS Found: 538.0 $[M+H]^+$.

The synthesis of 2-(benzyloxy)-6-bromo-4-phenoxyaniline (126-4)

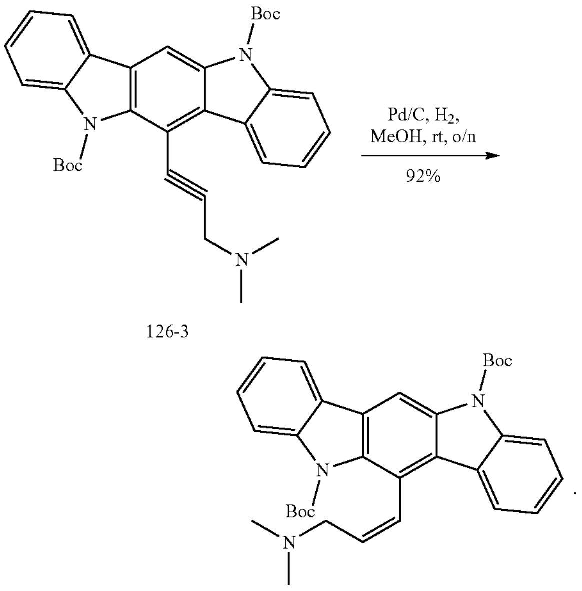

126-3

126-4

To the solution of 126-3 (200 mg, 0.37 mmol) in MeOH (5 mL) was added Pd/C (50 mg, 10%) at room temperature. The mixture was stirred at room temperature overnight under hydrogen gas (balloon). The mixture was filtered, and washed with EtOAc and MeOH. The filtrate was concentrated to oil to give 126-4 (183 mg, about 92% yield) as an oil. MS Calcd.: 539.3; MS Found: 540.1 $[M+H]^+$.

The synthesis of (Z)-3-(5,11-dihydroindolo[3,2-b]carbazol-6-yl)-N,N-dimethylprop-2-en-1-amine (SS20308-0126-01):

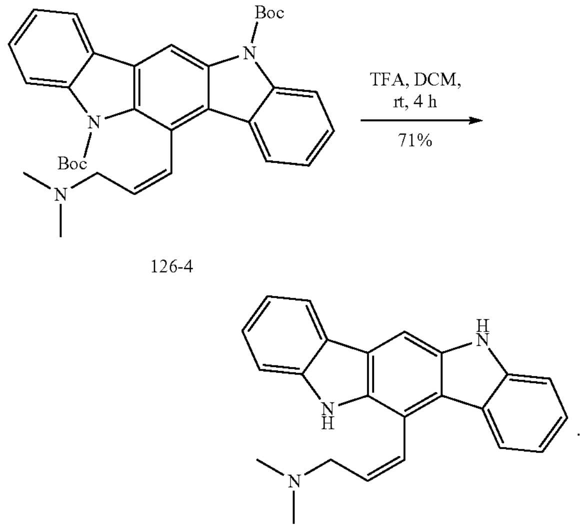

126-4

SS20308-0126-01

To a solution of 126-4 (100 mg, 0.19 mmol) in DCM (3 mL) was added TFA (1 mL) at room temperature. The mixture was stirred at room temperature for 4 h. The reaction mixture was concentrated to a crude oil. The mixture was neutralized by sat. $NaHCO_3$ to pH 8, then extracted by EtOAc (10 mL×2). The organic layer was then dried with $MgSO_4$, filtered, and concentrated under reduced pressure. The crude product was purified by Prep-TLC to give SS20308-0126-01 (46 mg, about 71% yield) as a solid. MS Calcd.: 339.2; MS Found: 340.0 $[M+H]^+$.

$^1H$ NMR (400 MHz, DMSO-$d_6$) δ 11.23 (s, 1H), 11.15 (s, 1H), 8.20 (d, J=7.6, 1H), 8.16 (d, J=8.0 Hz, 1H), 8.09 (s, 1H), 7.51-7.46 (m, 2H), 7.40-7.35 (m, 2H), 7.31 (d, J=11.2 Hz, 1H), 7.16-7.09 (m, 2H), 6.29 (dt, J=11.6, 4.4 Hz, 1H), 2.87 (d, J=7.2, 1H), 2.09 (s, 6H).

Example 43

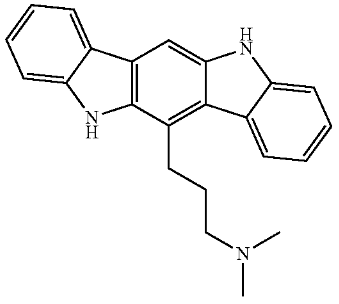

SS20308-0104-01
Chemical Formula: $C_{23}H_{23}N_3$
Molecular Weight: 341.45

Example Route for Example 43 (SS20308-0104-01:

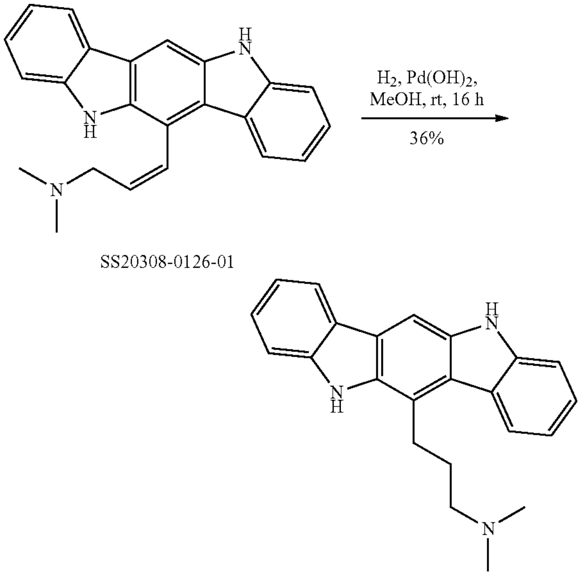

SS20308-0126-01

SS20308-0104-01

The synthesis of 3-(5,11-dihydroindolo[3,2-b]carbazol-6-yl)-N,N-dimethylpropan-1-amine (SS20308-0104-01):

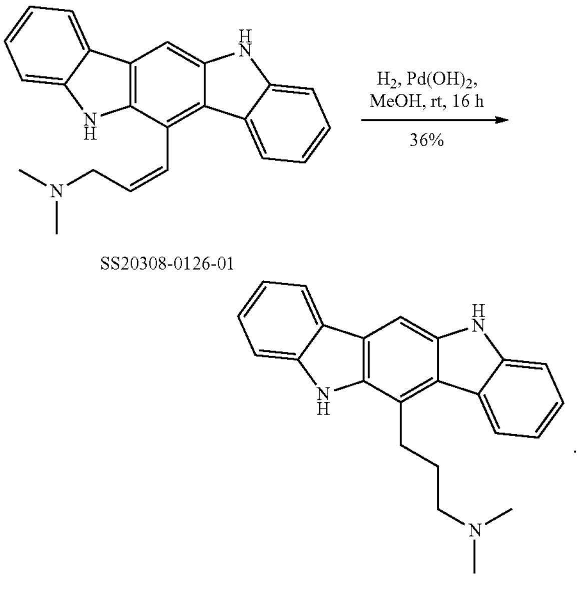

SS20308-0126-01

SS20308-0104-01

To the solution of SS20308-0126-01 (50 mg, 0.15 mmol) in MeOH (2 mL) was added Pd/C (10 mg, 10%) at room temperature. The mixture was stirred at room temperature for 16 h under hydrogen gas (balloon). The mixture was filtered, and washed with EtOAc and MeOH. The filtrate was concentrated to a crude oil, which was purified by Prep-TLC to give SS20308-0104-01 (18 mg, about 36% yield) as a solid. MS Calcd.: 341.2; MS Found: 342.0 $[M+H]^+$.

$^1H$ NMR (400 MHz, DMSO-$d_6$) δ 11.08 (s, 1H), 10.99 (s, 1H), 8.20-8.15 (m, 2H), 7.52-7.46 (m, 2H), 7.40-7.35 (m,

2H), 7.18-7.09 (m, 2H), 3.49 (t, J=7.6, 2H), 2.42 (t, J=7.0, 2H), 2.21 (s, 6H), 2.00-1.94 (m, 2H).
Example 44
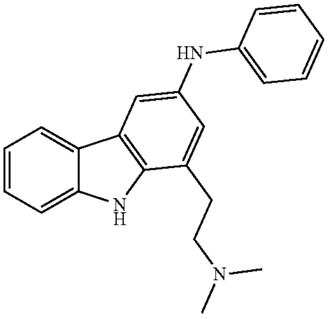
SS20308-0106-01
Chemical Formula: $C_{22}H_{23}N_3$
Molecular Weight: 329.44
Example Route for Example 44 (SS20308-0106-01):
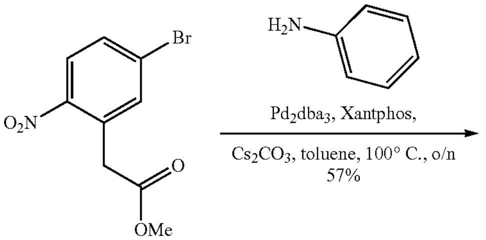
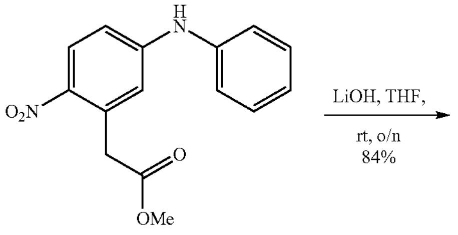
106-1
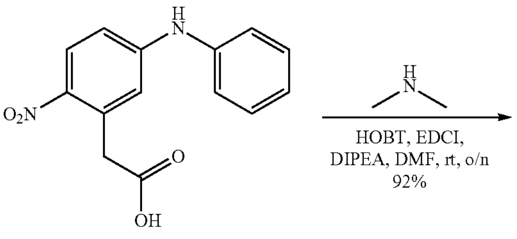
106-2
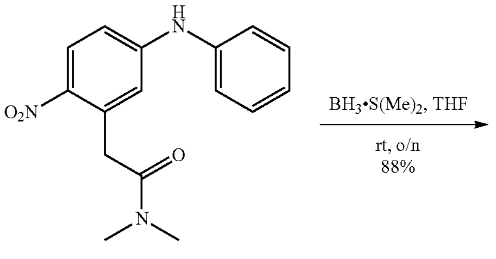
106-3
-continued
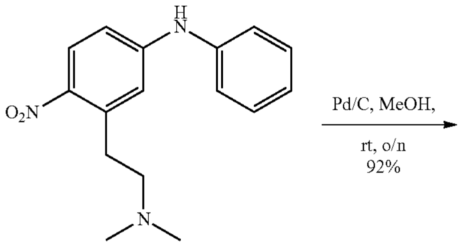
106-4
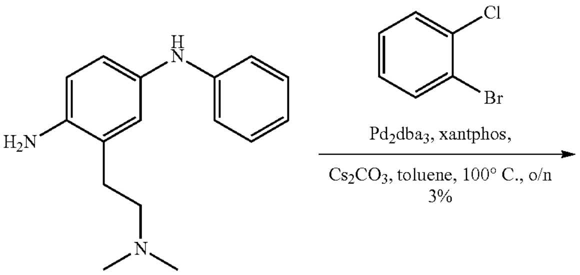
106-5
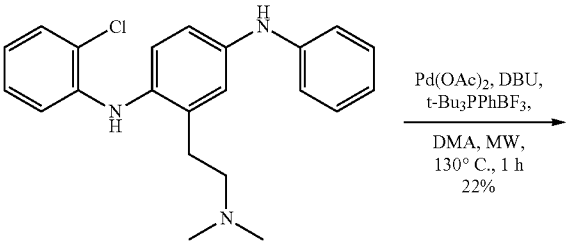
106-6
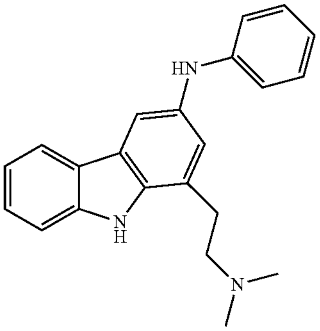
SS20308-0106-01
The synthesis of methyl 2-(2-nitro-5-(phenylamino)phenyl)acetate (106-1):
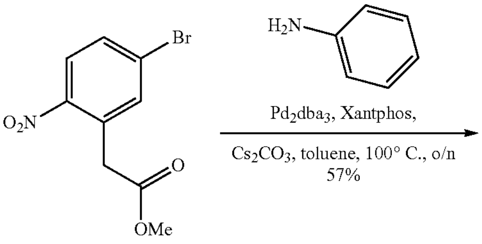

-continued

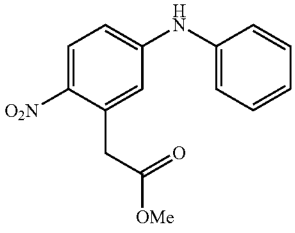

106-1

A mixture of methyl 2-(5-bromo-2-nitrophenyl)acetate (2.00 g, 7.30 mmol), aniline (1.36 g, 14.60 mmol), $Pd_2(dba)_3$ (668 mg, 0.73 mmol), Xantphos (854 mg, 1.46 mmol) and $Cs_2CO_3$ (4.74 g, 14.60 mmol) in toluene (60 mL) was stirred at 100° C. overnight under $N_2$ atmosphere. After cooling to room temperature, the reaction mixture was filtered through celite and concentrated. The residue was purified by column chromatography on silica gel (petroleum ether/EtOAc=5/1) to give 106-1 (1.20 g, about 57% yield) as an oil. MS Calcd.: 286.1; MS Found: 287.4 $[M+H]^+$.

The synthesis of 2-(2-nitro-5-(phenylamino)phenyl)acetic acid (106-2):

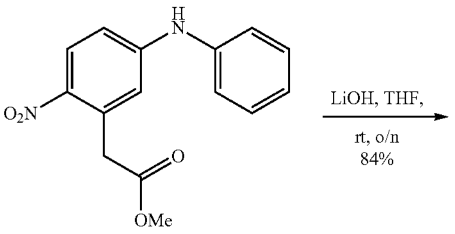

106-1

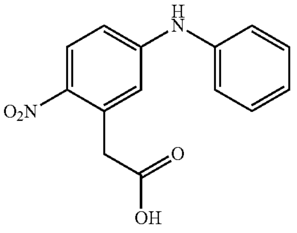

106-2

A mixture of 106-1 (500 mg, 1.75 mmol) and LiOH (147 mg, 3.50 mmol) in THF (30 mL) was stirred at room temperature overnight. Then the reaction mixture was acidified with 1N HCl (aq) till pH 2. The resulting mixture was extracted with EtOAc (80 mL×3). The organic layers were washed with brine, dried over $Na_2SO_4$, filtered, and concentrated to give 106-2 (400 mg, about 84% yield) as an oil. MS Calcd.: 272.1; MS Found: 273.4 $[M+H]^+$.

The synthesis of 2-(2-nitro-5-(phenylamino)phenyl)acetic acid (106-3):

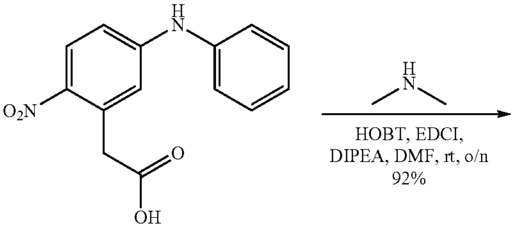

106-2

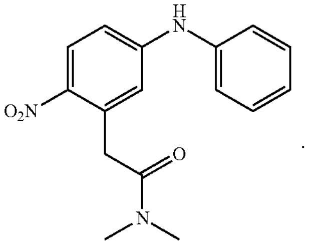

106-3

The mixture of 106-2 (400 mg, 1.47 mmol), dimethylamine (132 mg, 2.94 mmol), HOBT (397 mg, 2.94 mmol), EDCI (564 mg, 2.94 mmol) and DIPEA (379 mg, 2.94 mmol) in DMF (20 mL) was stirred at room temperature overnight. Then the reaction mixture was concentrated and poured into water (100 mL). The resulting mixture was extracted with EtOAc (80 mL×3). The organic layers were washed with brine, dried over $Na_2SO_4$ and concentrated to give 106-3 (405 mg, about 92% yield) as an oil. MS Calcd.: 299.1; MS Found: 300.1 $[M+H]^+$.

The synthesis of 3-(2-(dimethylamino)ethyl)-4-nitro-N-phenylaniline (106-4):

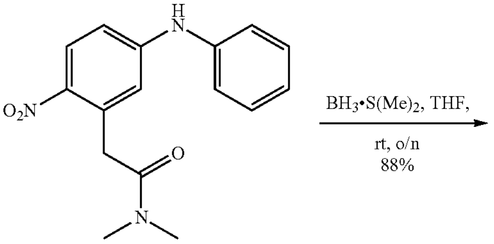

106-3

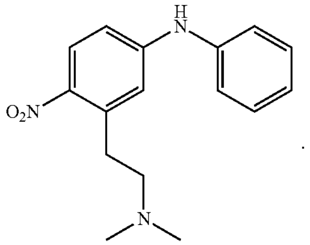

106-4

The mixture of 106-3 (405 mg, 1.35 mmol) and $BH_3$—S$(Me)_2$ (2.7 mL, 2.7 mmol) in THF (5 mL) was stirred at room temperature overnight. Then the reaction mixture was concentrated and dissolved in MeOH. The resulting mixture was acidified with 1N HCl till pH 1 and stirred at 80° C.

overnight. Then the mixture was extracted with EtOAc (50 mL×3). The organic layers were washed with brine, dried over $Na_2SO_4$ and concentrated to give 106-4 (340 mg, about 88% yield) as an oil. MS Calcd.: 285.1; MS Found: 286.2 $[M+H]^+$.

The synthesis of 3-(2-(dimethylamino)ethyl)-$N^1$-phenylbenzene-1,4-diamine (106-5):

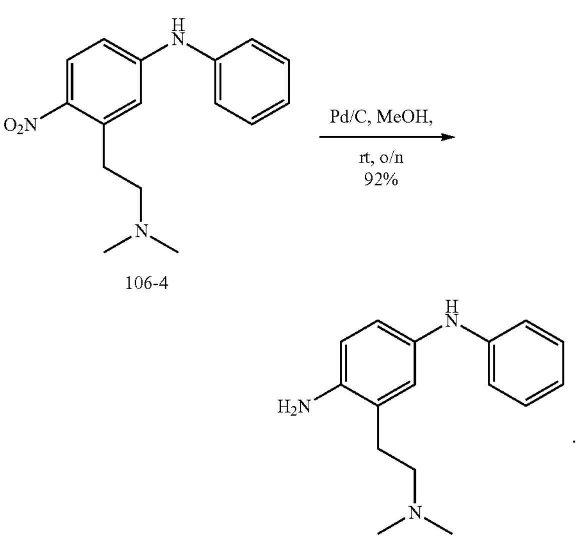

106-4

106-5

The mixture of 106-4 (340 mg, 1.19 mmol) and Pd/C (34 mg, 10%) in MeOH (5 mL) was stirred at room temperature overnight under $N_2$ atmosphere. The reaction mixture was filtered and concentrated to give 106-5 (280 mg, about 92% yield) as an oil. MS Calcd.: 255.2; MS Found: 256.2 $[M+H]^+$.

The synthesis of $N^1$-(2-chlorophenyl)-2-(2-(dimethylamino)ethyl)-N-phenylbenzene-1,4-diamine (106-6):

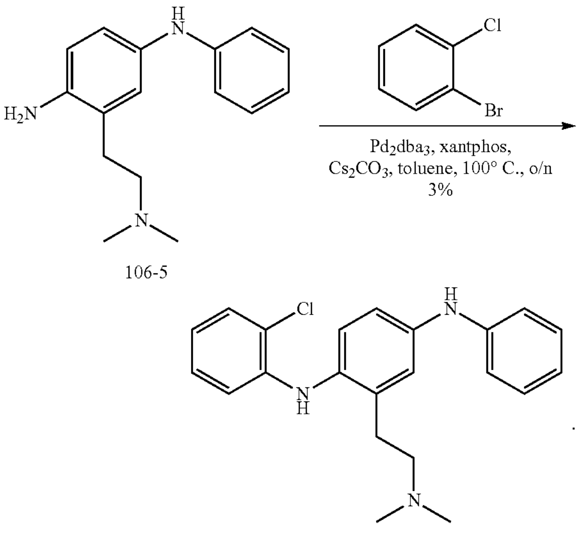

106-5

106-6

The mixture of 106-5 (130 mg, 0.51 mmol), 2-bromochlorobenzene (195 mg, 1.02 mmol), $Pd_2(dba)_3$ (46 mg, 0.05 mmol), Xantphos (57.8 mg, 0.10 mmol) and $Cs_2CO_3$ (332 mg, 1.02 mmol) in toluene (4 mL) was stirred at 100° C. overnight under $N_2$ atmosphere. After cooling to room temperature, the reaction mixture was filtered through celite and concentrated. The residue was purified by column chromatography on silica gel (petroleum ether/EtOAc=1/2) and Prep-HPLC to give 106-6 (6 mg, about 3% yield) as an oil. MS Calcd.: 365.2; MS Found: 366.3 $[M+H]^+$.

$^1H$ NMR (400 MHz, DMSO-d6) δ 8.08 (s, 1H), 7.57 (s, 1H), 7.32 (dd, J=8.0 Hz, 1.2 Hz, 1H), 7.23 (t, J=8.0 Hz, 2H), 7.06-7.02 (m, 5H), 6.96-6.94 (m, 1H), 6.80 (t, J=7.2 Hz, 1H), 6.67-6.63 (m, 1H), 6.56 (dd, J=8.0 Hz, 1.2 Hz, 1H), 2.60 (t, J=6.8 Hz, 2H), 2.44-2.43 (m, 2H), 2.13 (s, 6H).

The synthesis of $N^1$-(2-chlorophenyl)-2-(2-(dimethylamino)ethyl)-N-phenylbenzene-1,4-diamine (SS20308-0106-01):

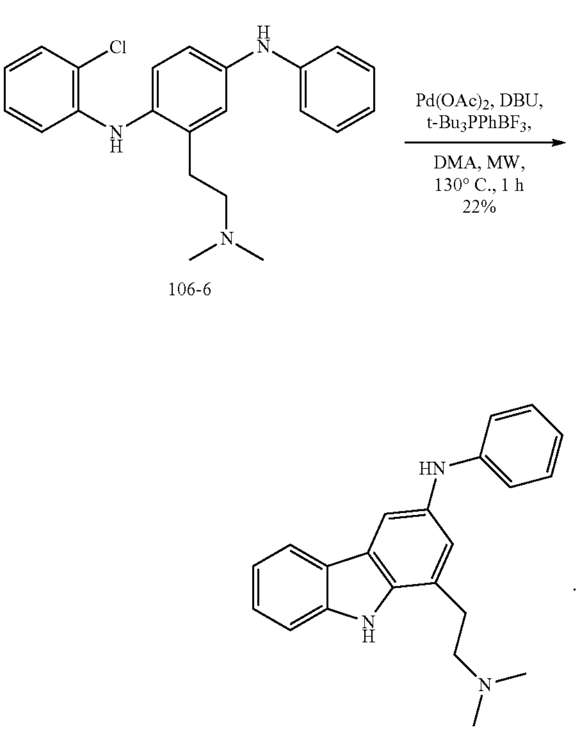

106-6

SS20308-0106-01

The mixture of 106-6 (40 mg, 0.11 mmol), $Pd(OAc)_2$ (5 mg, 0.02 mmol), t-$Bu_3PPhBF_3$ (12 mg, 0.04 mmol) and DBU (34 mg, 0.22 mmol) in DMA (2 mL) was stirred at 130° C. for one hour in a microwave reactor. After cooling to room temperature, the reaction mixture was filtered through celite and concentrated. The residue was purified by column chromatography on silica gel (petroleum ether/EtOAc=1/3) and Prep-HPLC to give SS20308-0106-01 (7.89 mg, about 22% yield) as a solid. MS Calcd.: 329.2; MS Found: 330.0 $[M+H]^+$.

$^1H$ NMR (400 MHz, DMSO-d6) δ 11.10 (s, 1H), 8.02 (d, J=8.0 Hz, 1H), 7.88 (s, 1H). 7.68-6.67 (m, 1H), 7.47 (d, J=8.0 Hz, 1H), 7.36-7.32 (m, 1H), 7.17 (t, J=7.8 Hz, 2H), 7.10-7.05 (m, 2H), 6.97 (d, J=7.6 Hz, 2H), 6.69 (t, J=7.2 Hz, 1H), 3.04 (t, J=7.2 Hz, 2H), 2.62 (t, J=7.2 Hz, 2H), 2.25 (s, 6H).

Example 45
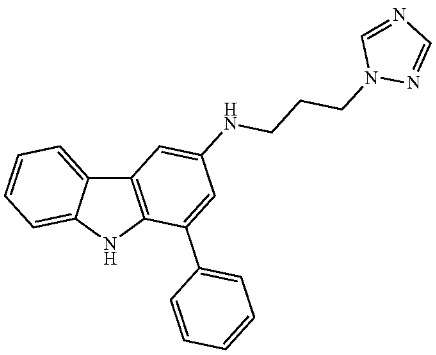
SS20308-0111-01
Chemical Formula: $C_{22}H_{21}N_5$
Molecular Weight: 367.45
Example Route for Example 45 (SS20308-0111-01):
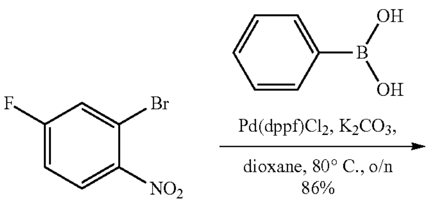
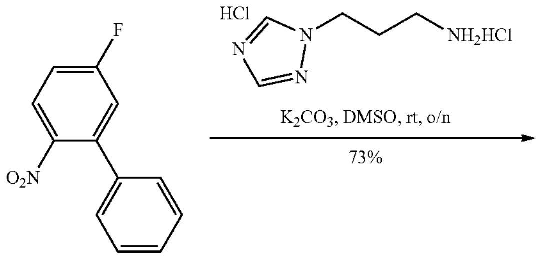
111-1
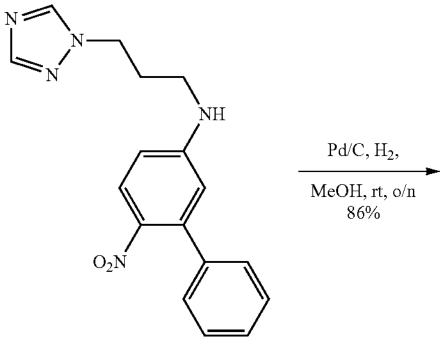
111-2
-continued
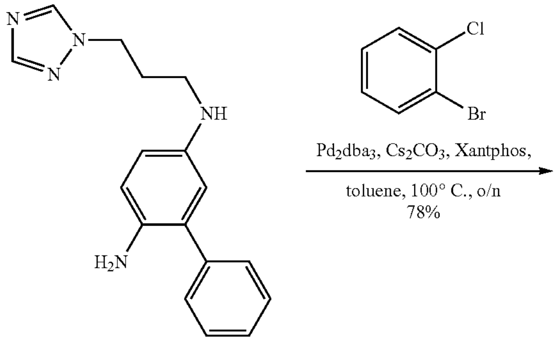
111-3
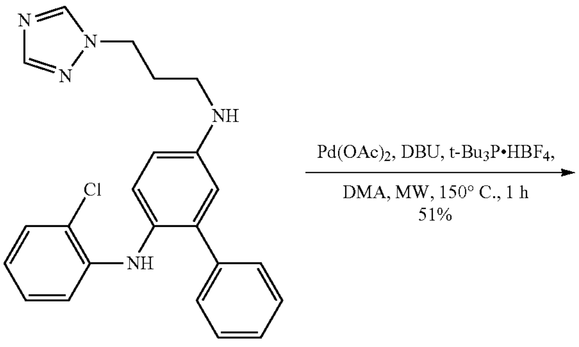
111-4
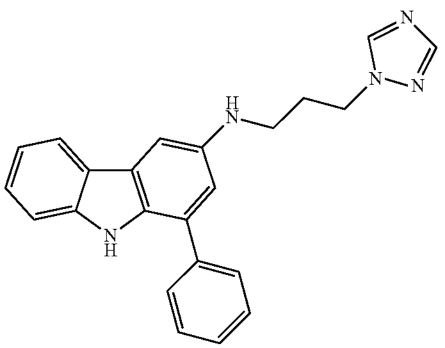
SS20308-0111-01
The synthesis of 5-fluoro-2-nitrobiphenyl (111-1):
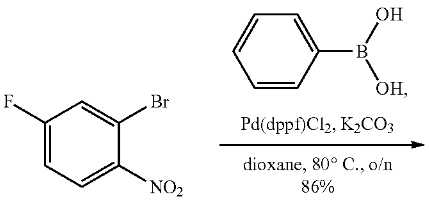

-continued

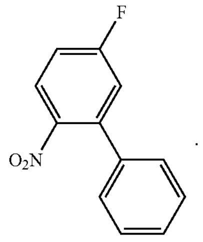

111-1

A solution of 2-bromo-4-fluoro-1-nitrobenzene (2.0 g, 9.09 mmol), phenylboronic acid (2.22 g, 18.18 mmol), Pd(dppf) $Cl_2$—$CH_2Cl_2$ (372 mg, 0.46 mmol), and potassium carbonate (3.14 g, 22.73 mmol,) were suspended in 1,4-dioxane (20 mL) and water (2 mL). The reaction mixture was heated at reflux for overnight and then filtered, rinsing with EtOAc. The filtrate was concentrated and the residue was purified by column chromatography on silica gel (petroleum ether) to give compound 111-1 (1.7 g, about 86% yield) as an oil.

The synthesis of N-(3-(1H-1,2,4-triazol-1-yl)propyl)-6-nitrobiphenyl-3-amine (111-2):

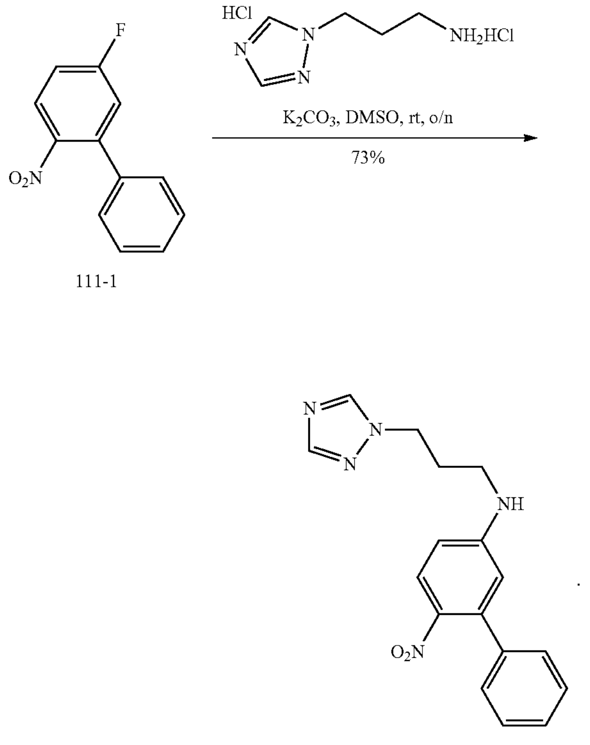

111-1

111-2

A mixture of 111-1 (1.0 g, 4.6 mmol), 3-(1H-1,2,4-triazol-1-yl)propan-1-amine dihydrochloride (917 mg, 4.61 mmol) and potassium carbonate (3.18 g, 23.02 mmol,) were suspended in DMSO (10 mL). After stirring at room temperature for overnight, the mixture was diluted with water (50 mL). The resulting solid was filtered, washed with water, dried, and concentrated to give 111-2 (1.09 g, about 73% yield) as a solid. MS Calcd.:323.1; MS Found: 324.3 $[M+H]^+$.

The synthesis of $N^5$-(3-(1H-1,2,4-triazol-1-yl)propyl)biphenyl-2,5-diamine (111-3):

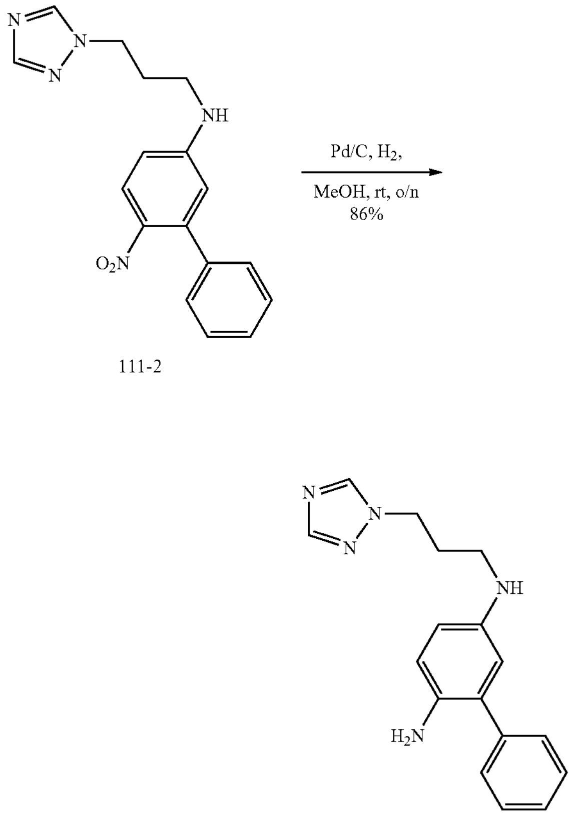

111-2

111-3

A solution of 111-2 (500 mg, 1.55 mmol) and Pd/C (50 mg, 10%) in MeOH (20 mL) was stirred at room temperature for overnight under $H_2$ gas (balloon). Then the reaction mixture was filtered through celite. The filtrate was concentrated to give 111-3 (390 mg, about 86% yield) as an oil. MS Calcd.:293.2; MS Found: 294.0 $[M+H]^+$.

The synthesis of $N^5$-(3-(1H-1,2,4-triazol-1-yl)propyl)-$N^2$-(2-chlorophenyl)biphenyl-2,5-diamine (111-4):

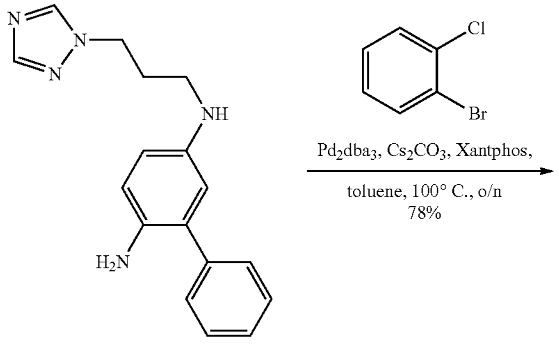

111-3

-continued

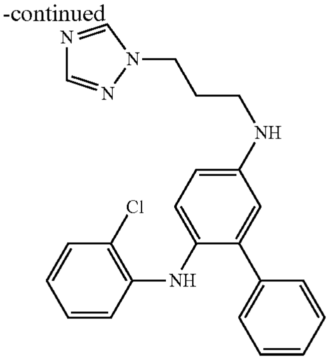

111-4

A mixture of 111-3 (380 mg, 1.30 mmol), 1-bromo-2-chlorobenzene (744 mg, 3.89 mmol), Xantphos (75 mg, 0.13 mmol), $Pd_2(dba)_3$ (60 mg, 0.066 mmol), and anhydrous cesium carbonate (633 mg, 1.94 mmol) was suspended in toluene (20 mL). The reaction mixture was heated to 100° C. for overnight under $N_2$ and then filtered, rinsing with EtOAc. The filtrate was concentrated and purified by column chromatography on silica gel (petroleum ether/EtOAc=5/1 to 3/1 to 1/1) to give 111-4 (409 mg, about 78% yield) as a solid. MS Calcd.: 403.2; MS Found: 404.3 $[M+H]^+$.

The synthesis of N-(3-(1H-1,2,4-triazol-1-yl)propyl)-1-phenyl-9H-carbazol-3-amine (SS20308-0111-01):

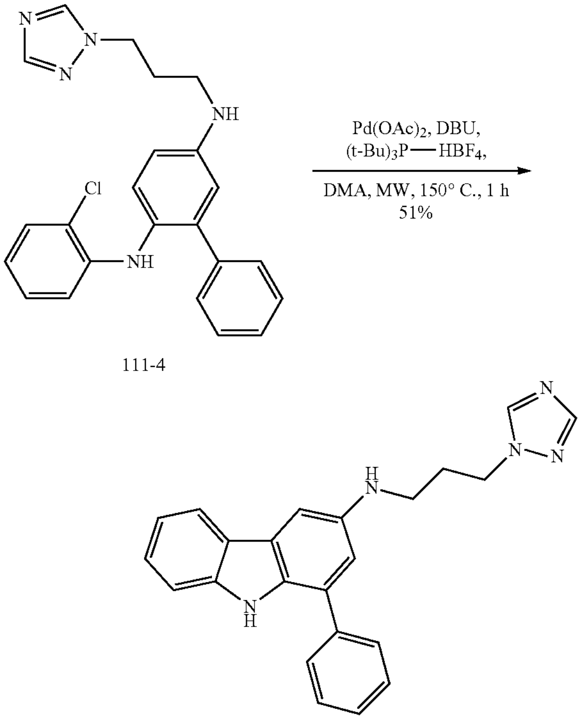

111-4

SS20308-0111-01

A mixture of 111-4 (100 mg, 0.25 mmol), $t\text{-}Bu_3P\text{—}HBF_4$ (64 mg, 0.25 mmol), $Pd(OAc)_2$ (28 mg, 0.12 mmol), and DBU (189 mg, 1.24 mmol) under $N_2$ (g) was stirred and heated to 150° C. for 1 h in a microwave reactor. The reaction mixture was poured into water, and extracted with EtOAc (10 mL×3). The combined organic layers were washed with brine (10 mL×2), dried over sodium sulfate, filtered, and concentrated to dryness. The residue was purified by Prep-TLC and Prep-HPLC to give SS20308-0111-01 (46 mg, about 51% yield) as a solid. MS Calcd.: 367.2; MS Found: 368.3 $[M+H]^+$.

$^1H$ NMR (400 MHz, DMSO-$d_6$) δ 10.60 (brs, 1H), 8.56 (s, 1H), 8.01-7.97 (m, 2H), 7.68 (d, J=7.2 Hz, 2H), 7.56 (dd, J=7.6, 7.6 Hz, 2H), 7.47-7.40 (m, 2H), 7.31-7.25 (m, 1H), 7.20 (d, J=2.0 Hz, 1H), 7.09-7.03 (m, 1H), 6.81 (d, J=2.0 Hz, 1H), 5.39 (t, J=5.8 Hz, 1H), 4.36 (t, J=7.0 Hz, 2H), 3.16-3.09 (m, 2H), 2.19-2.10 (m, 2H).

Example 46

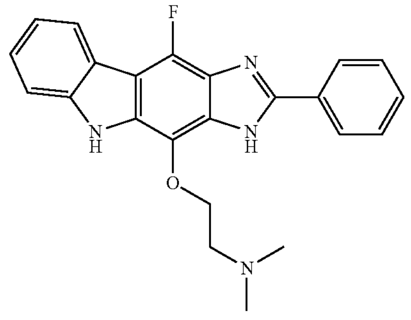

SS20308-0121-01
Chemical Formula: $C_{23}H_{21}FN_4O$
Molecular Weight: 388.44

Example Route for Example 46 (SS20308-0121-01):

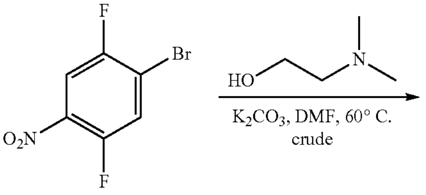

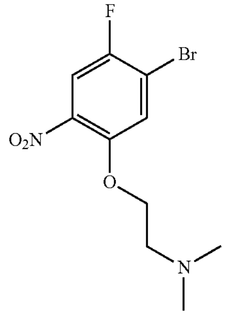

121-1

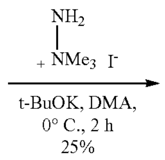

-continued
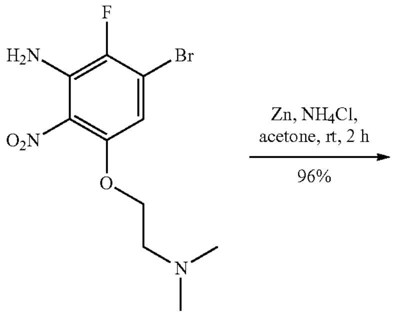
121-2
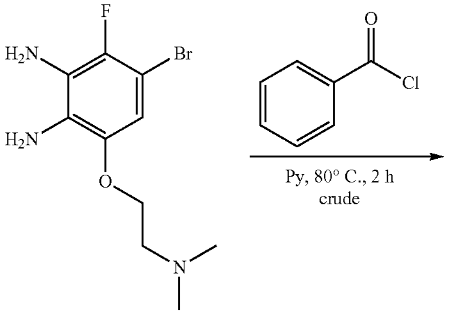
121-3
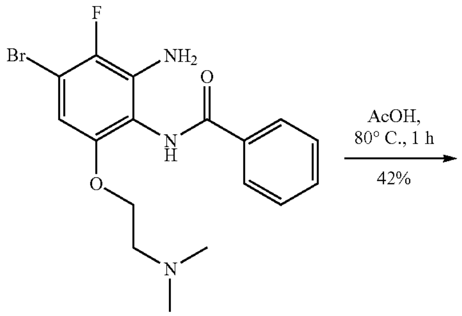
121-4
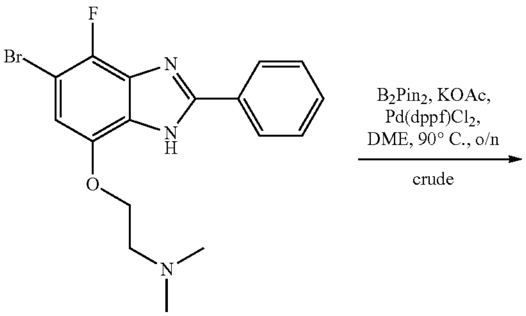
121-5
-continued
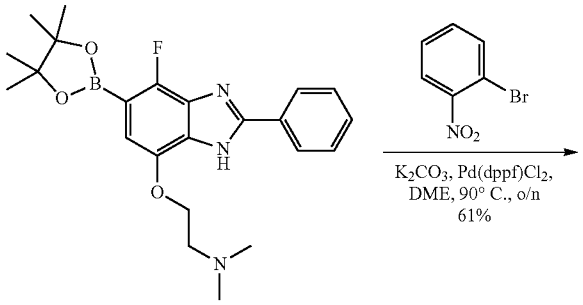
121-6
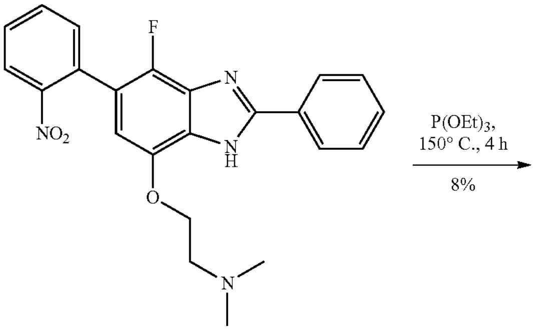
121-7
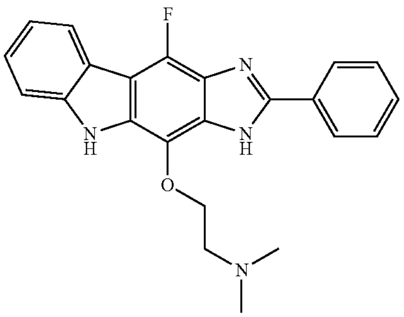
SS20308-0121-01
The synthesis of 2-(5-bromo-4-fluoro-2-nitrophenoxy)-N,N-dimethylethanamine (121-1):
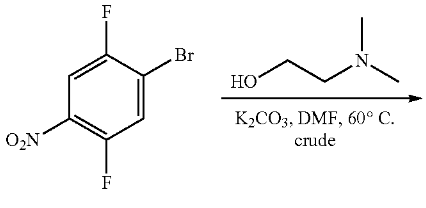

-continued

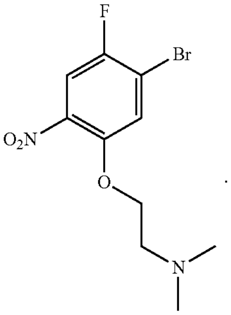

121-1

To a solution of 1-bromo-2,5-difluoro-4-nitrobenzene (15 g, 63.03 mmol) in DMF (60 mL) was added $K_2CO_3$ (17.42 g, 126.06 mmol) and 2-(dimethylamino)ethanol (6.18 g, 69.33 mmol), the mixture was stirred at 60° C. for 24 h. After the reaction was complete, the reaction mixture was poured into water (500 mL) and extracted with EtOAc (400 mL×3). The organic layer was washed brine (2×500 mL), dried over $MgSO_4$, and concentrated under vacuum to afford crude 121-1, which was used in the next step without further purification.

The synthesis of 3-bromo-5-(2-(dimethylamino)ethoxy)-2-fluoro-6-nitroaniline (121-2):

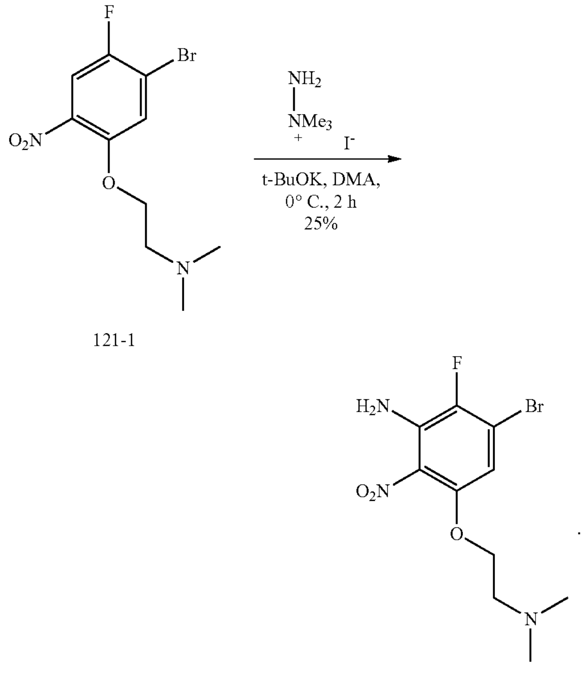

121-1

121-2

To a solution 121-1 (2.30 g, 7.49 mmol) and 1,1,1-trimethylhydrazinium iodide (1.66 g, 8.24 mmol) in DMA (10 mL) was added dropwise over 15 min a solution of t-BuOK (2.02 g, 17.97 mmol) in DMA (5 mL) cooled in an ice-water bath. The mixture was stirred at room temperature for 2 h. Then the reaction was poured into 1N HCl (25 mL), and extracted with EtOAc (50 mL×4). The organic layer was washed with brine (2×50 mL) and the solvent evaporated to give a crude solid, which was purified by column chromatography on silica gel (petroleum ether/EtOAc=1/1) to give 121-2 (600 mg, about 25% yield) as an oil. MS Calcd.: 321.0; MS Found: 322.2 $[M+H]^+$.

The synthesis of 4-bromo-6-(2-(dimethylamino)ethoxy)-3-fluorobenzene-1,2-diamine (121-3):

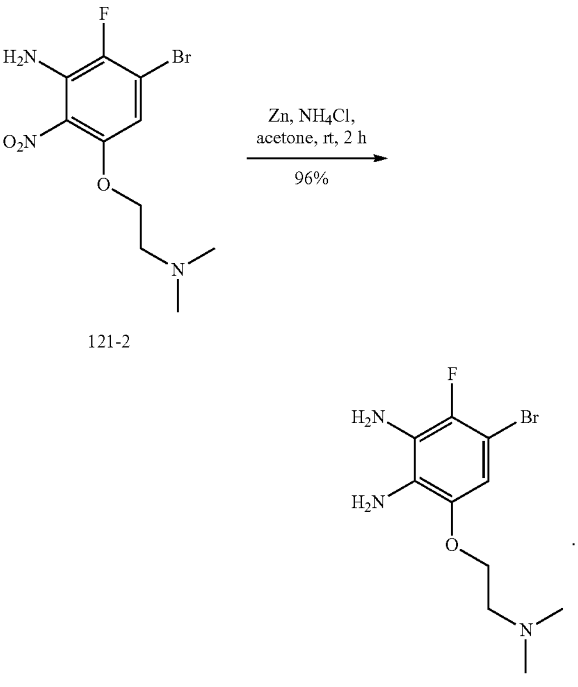

121-2

121-3

To a solution 121-2 (3.00 g, 9.31 mmol) and $NH_4Cl$ (4.98 g, 93.13 mmol) in acetone (50 mL) cooled in an ice-water bath, was added Zn powder (6.09 g, 93.13 mmol). The mixture was stirred at room temperature for 2 h. Then the reaction was poured into 0.5 N HCl (25 mL), and extracted with EtOAc (50 mL×4). The organic layer was washed with brine (2×50 mL) and the solvent evaporated to give oil, which was purified by column chromatography on silica gel (DCM/MeOH=30/1) to give 121-3 (2.60 g, about 96% yield) as an oil. MS Calcd.: 291.0; MS Found: 292.0 $[M+H]^+$.

The synthesis of N-(2-amino-4-bromo-6-(2-(dimethylamino)ethoxy)-3-fluorophenyl)benzamide (121-4):

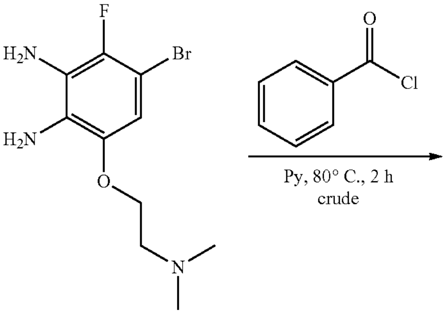

121-3

-continued

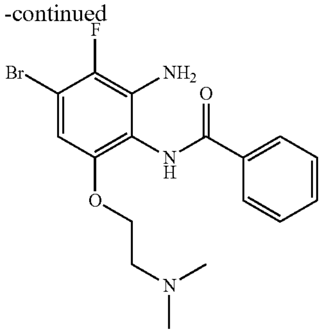

121-4

To a solution of 121-3 (2.60 g, 8.90 mmol) in pyridine (10 mL) was added benzoyl chloride (1.50 g, 10.68 mmol). The mixture was stirred at 80° C. for 2 h. After the reaction was complete, the reaction mixture was poured into water (50 mL) and extracted with EtOAc (50 mL×3). The organic layer was washed with brine (2×50 mL), dried over $MgSO_4$, and concentrated under vacuum to afford 121-4, which was used in the next step without further purification.

The synthesis of 2-(5-bromo-4-fluoro-2-phenyl-1H-benzo[d]imidazol-7-yloxy)-N,N-dimethylethanamine (121-5):

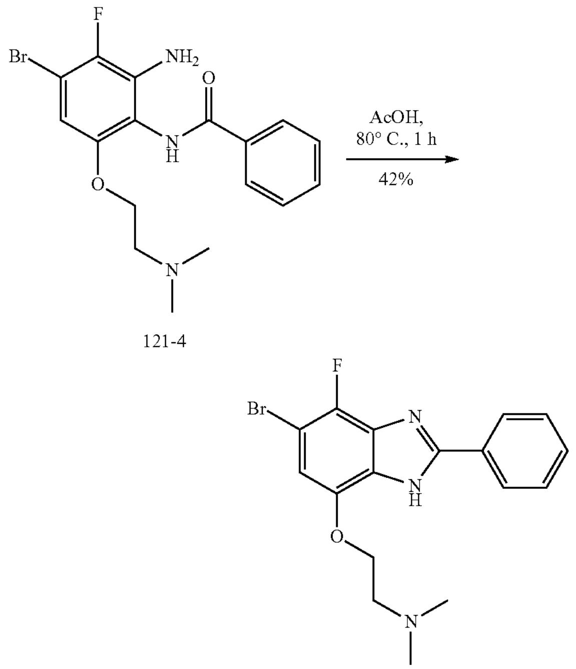

121-4

121-5

A solution of 121-4 (3.00 g, 7.57 mmol) in AcOH (5 mL) was stirred at 80° C. for 1 h. After the reaction was complete, the mixture was poured into water (30 mL), adjusted to pH 8 with $Na_2CO_3$ (aq.), and extracted with ethyl acetate (50 mL×4). The organic layer was washed with brine (2×50 mL) and the solvent evaporated to give a solid, which was purified by column chromatography on silica gel (DCM/MeOH=50/1) to give 121-5 (1.20 g, about 42% yield) as a solid.

The synthesis of 2-(4-fluoro-2-phenyl-5-(4,4,5,5-tetramethyl-1,3,2-dioxaborolan-2-yl)-1H-benzo[d] imidazol-7-yloxy)-N,N-dimethylethanamine (121-6):

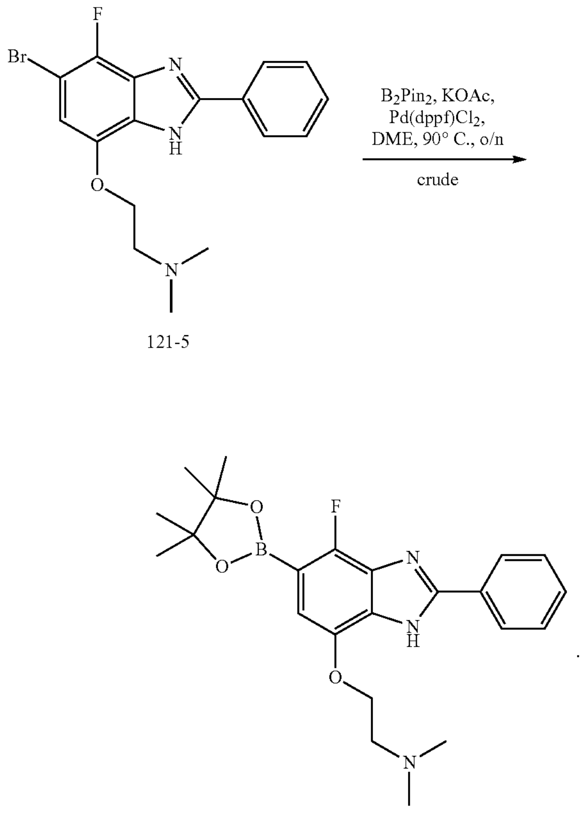

121-5

121-6

A mixture of 121-5 (825 mg, 2.18 mmol), $B_2Pin_2$ (664 mg, 2.62 mmol), $Pd(dppf)Cl_2$ (160 mg, 0.22 mmol), KOAc (428 mg, 4.36 mmol) in DME (20 ml) was stirred at 90° C. under nitrogen atmosphere overnight. After the reaction was complete, the mixture was quenched with water, filtered, and the filtrate was extracted with EtOAc (30 mL×3). The organic layer was separated, dried over $MgSO_4$, and concentrated under vacuum to afford 121-6, which was used in the next step without further purification.

The synthesis of 2-(4-fluoro-5-(2-nitrophenyl)-2-phenyl-1H-benzo[d]imidazol-7-yloxy)-N,N-dimethylethanamine (121-7):

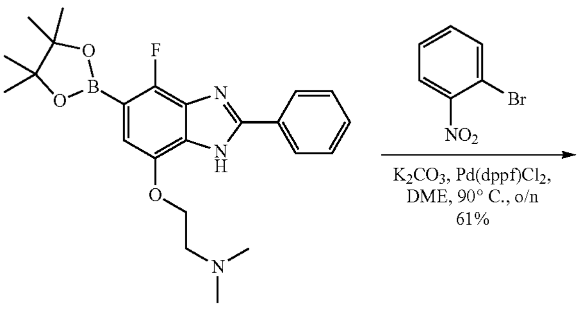

121-6

-continued

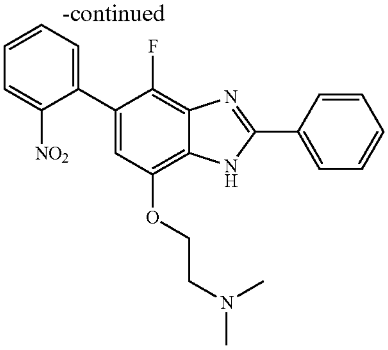

121-7

A mixture of 121-6 (578 mg, 1.36 mmol), 1-bromo-2-nitrobenzene (274 mg, 1.36 mmol), Pd(dppf)$Cl_2$ (100 mg, 0.14 mmol), $K_2CO_3$ (375 mg, 2.72 mmol) in DME (30 ml) was stirred at 90° C. under nitrogen atmosphere overnight. After the reaction was complete, the mixture was quenched with water, filtered, and the filtrate was extracted with EtOAc (50 mL×3). The organic layer was separated, dried over $MgSO_4$, and concentrated under vacuum. The residue was purified by Prep-TLC (EtOAc/petroleum ether=1/1) to give 121-7 (350 mg, about 61% yield) as a solid. MS Calcd.: 420.2; MS Found: 421.2 $[M+H]^+$.

The synthesis of 2-(10-fluoro-2-phenyl-3,5-dihydroimidazo[4,5-b]carbazol-4-yloxy)-N,N-dimethylethanamine (SS20308-0121-01):

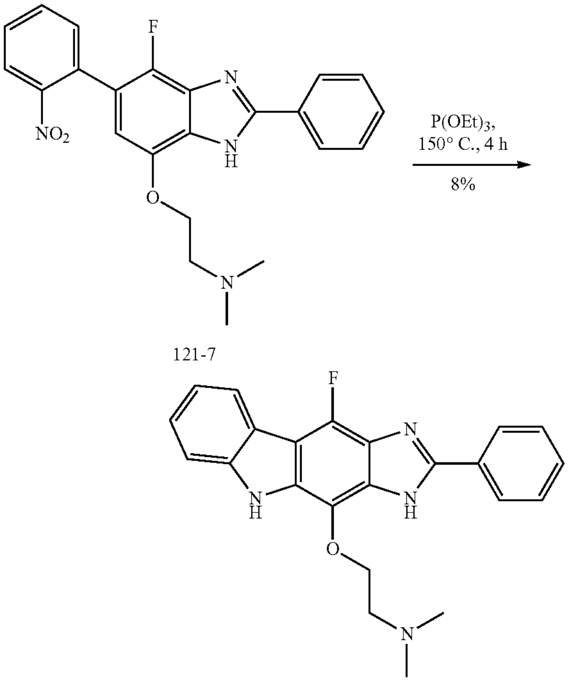

121-7

SS20308-0121-01

A solution of 121-7 (200 mg, 0.48 mmol) in $P(OEt)_3$ (2 mL) was stirred at 150° C. for 4 h. After the reaction was complete, the reaction was concentrated to a crude mixture, which was purified by Prep-HPLC twice to give SS20308-0121-01 (14 mg, about 8% yield) as a solid. MS Calcd.: 388.2; MS Found: 389.0 $[M+H]^+$.

$^1$H NMR (400 MHz, DMSO-$d_6$ and $D_2O$) δ 8.27-8.25 (m, 2H), 8.11 (d, J=7.6 Hz, 1H), 7.62-7.58 (m, 2H), 7.56-7.51 (m, 2H), 7.43 (dd, J=7.6 Hz, 7.2 Hz, 1H), 7.20 (dd, J=7.6 Hz, 7.2 Hz, 1H), 4.77-4.34 (m, 2H), 2.78 (t, J=5.2 Hz, 2H), 2.34 (s, 6H).

Example 47

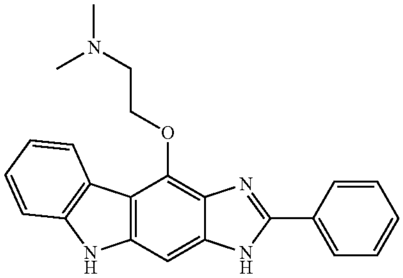

SS20308-0122-01
Chemical Formula: $C_{23}H_{22}N_4O$
Molecular Weight: 370.45

Example Route for Example 47 (SS20308-0122-01):

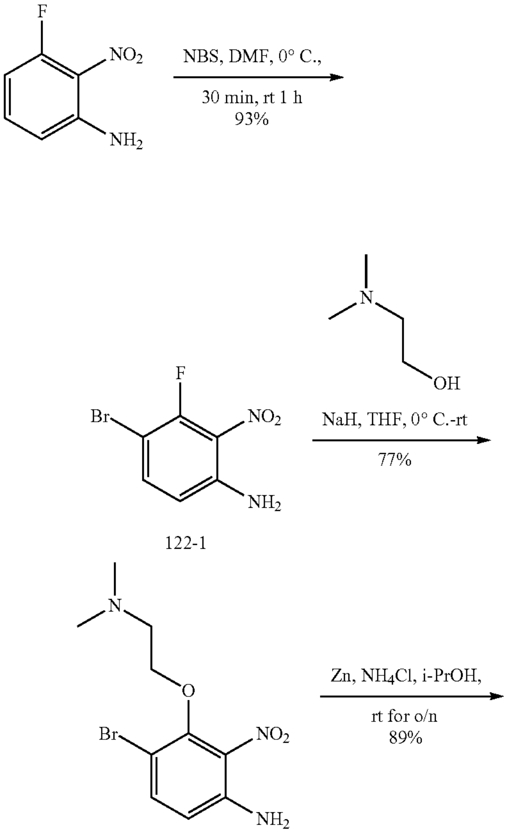

122-1

122-2

-continued

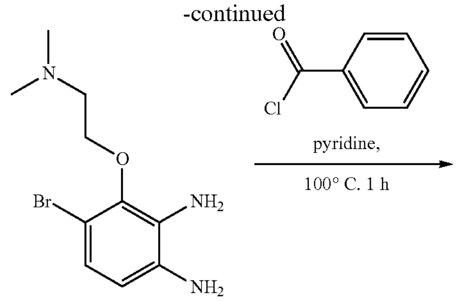

122-3

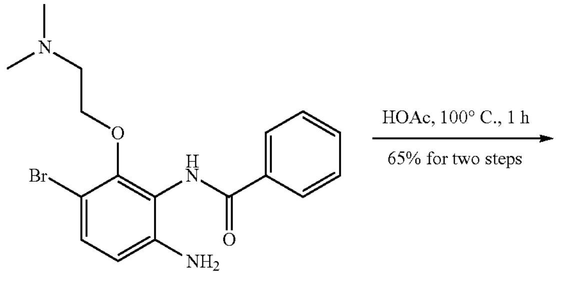

122-4

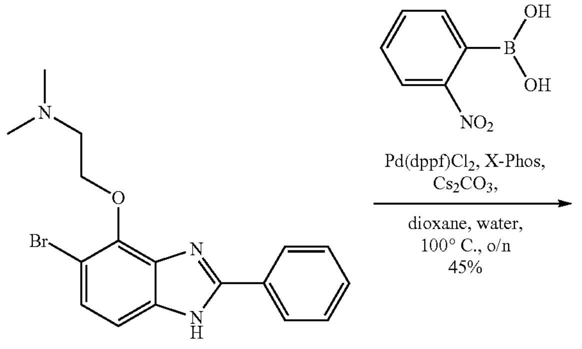

122-5

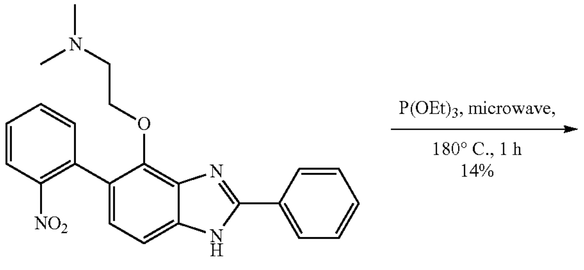

122-6

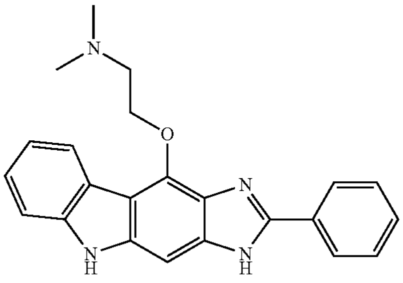

SS20308-0122-01

The synthesis of 4-bromo-3-fluoro-2-nitroaniline (122-1):

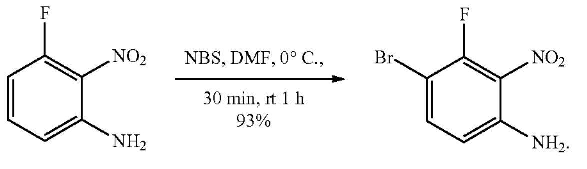

122-1

To a mixture of 3-fluoro-2-nitrobenzenamine (5.0 g, 32.0 mmol) in DMF (25 mL) at 0° C., NBS (5.7 g, 32.0 mmol) was added portionwise. The mixture was stirred at 0° C. for 0.5 h and then warmed to room temperature over 1 h. The mixture was poured into water (100 mL), and the resulting solid was filtered, washed with water, dried, and concentrated to give 122-1 (7.0 g, about 93% yield) as a solid.

The synthesis of 4-bromo-3-(2-(dimethylamino)ethoxy)-2-nitroaniline (122-2):

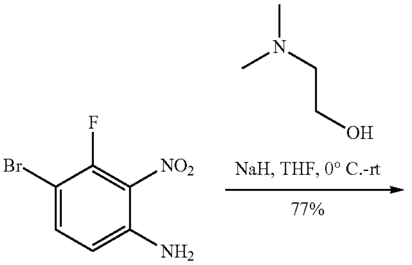

122-1

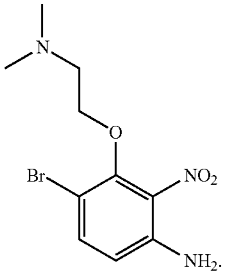

122-2

Sodium hydride (188 mg, 4.70 mmol) was added to a mixture of 2-(dimethylamino)ethanol (835 mg, 9.37 mmol) in THF (20 mL) at 0° C. After stirring for 15 min, compound 122-1 (1.1 g, 4.68 mmol) was added and then the mixture was warmed to room temperature over 1 h. The mixture was diluted with water (80 mL) and extracted with EtOAc (20 mL×3). The combined organic layers were washed with brine (10 mL×2), dried over sodium sulfate, filtered, and concentrated to dryness. The residue was purified by column chromatography on silica gel (petroleum ether/EtOAc=1/1) to give 122-2 (1.1 g, about 77% yield) as a solid. MS Calcd.:303.0; MS Found: 304.0 $[M+H]^+$.

The synthesis of 4-bromo-3-(2-(dimethylamino)ethoxy) benzene-1,2-diamine (122-3):

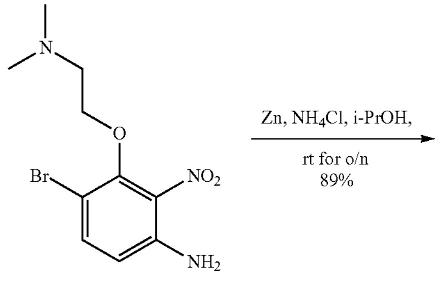

122-2

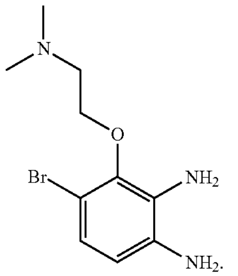

122-3

A mixture of 122-2 (0.9 g, 2.96 mmol), $NH_4Cl$ (317 mg, 5.93 mmol) and zinc powder (5.05 g, 77.75 mmol) in isopropanol (20 mL) was stirred at room temperature for overnight. Then the reaction mixture was filtered through celite. The filtrate was concentrated to give 122-3 (720 mg, about 89% yield) as dark oil. MS Calcd.:273.1; MS Found: 274.0 $[M+H]^+$.

The synthesis of 2-(5-bromo-2-phenyl-1H-benzo[d]imidazol-4-yloxy)-N,N-dimethylethanamine (122-5):

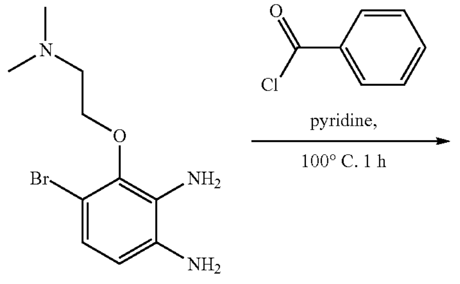

122-3

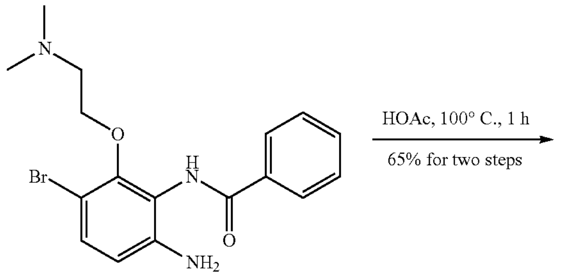

122-4

-continued

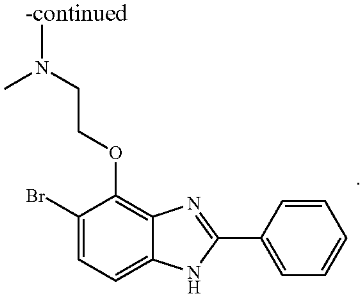

122-5

A solution of 122-3 (750 mg, 2.74 mmol), DMAP (335 mg, 2.74 mmol) and benzoyl chloride (1.73 g, 12.31 mmol) in pyridine (20 mL) was heated at 100° C. for 1 h and then concentrated. The residue 122-4 was dissolved in acetic acid (20 mL) and heated at 100° C. for 1 h. The reaction mixture was concentrated and dissolved in EtOAc, washed with brine, dried over sodium sulfate, and concentrated to dryness. The residue was purified by column chromatography on silica gel (petroleum ether/EtOAc=1/1) to give 122-5 (638 mg, about 65% yield) as a solid. MS Calcd.: 359.1; MS Found: 360.1 $[M+H]^+$.

The synthesis of N,N-dimethyl-2-(5-(2-nitrophenyl)-2-phenyl-1H-benzo[d]imidazol-4-yloxy)ethanamine (122-6):

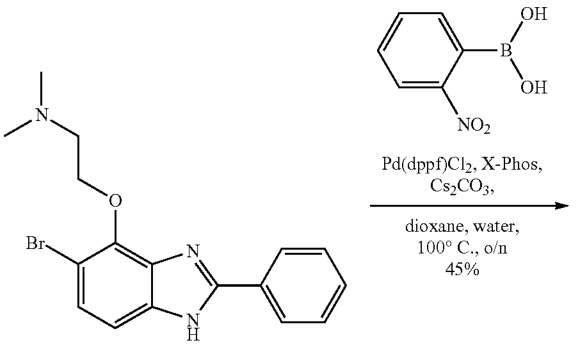

122-5

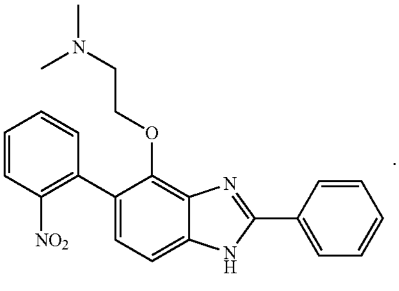

122-6

A solution of 122-5 (650 mg, 1.80 mmol), 2-nitrophenylboronic acid (603 mg, 3.61 mmol,), X-Phos (86 mg, 0.18 mmol), Pd(dppf)$Cl_2$—$CH_2Cl_2$ (74 mg, 0.091 mmol), and cesium carbonate (1.76 g, 5.41 mmol,) were suspended in 1,4-dioxane (20 mL) and water (2 mL). The reaction mixture was heated to reflux for overnight and then filtered, rinsing with EtOAc. The filtrate was concentrated and the residue was purified by column chromatography on silica gel (petroleum ether/EtOAc=5/1 to 3/1 to 1/1) to give compound 122-6 (330 mg, about 45% yield) as a solid. MS Calcd.: 402.2; MS Found: 403.0 $[M+H]^+$.

The synthesis of N,N-dimethyl-2-(2-phenyl-3,5-dihydroimidazo[4,5-b]carbazol-10-yloxy)ethanamine (SS20308-0122-01):

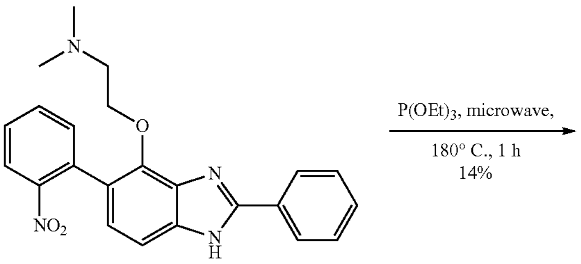

122-6

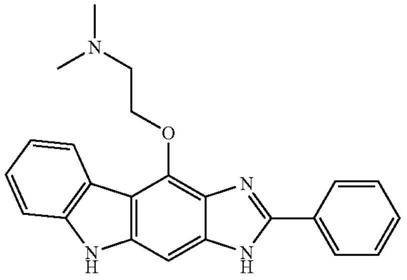

SS20308-0122-01

A solution of 122-6 (100 mg, 0.25 mmol) in $P(OEt)_3$ (5 mL) was stirred at 180° C. for 1 h under microwave irradiation. After the reaction was completed, the reaction mixture was concentrated to a crude mixture, which was purified by reverse phase column chromatography followed by Prep-TLC, and Prep-HPLC to give SS20308-0122-01 (13 mg, about 14% yield) as a solid. MS Calcd.: 370.2; MS Found: 371.2 $[M+H]^+$.

$^1H$ NMR (400 MHz, DMSO-$d_6$) δ 12.70 (brs, 1H), 10.91 (brs, 1H), 8.28 (d, J=7.6 Hz, 1H), 8.18 (d, J=7.6 Hz, 2H), 7.56 (dd, J=7.6, 7.6 Hz, 2H), 7.48 (dd, J=7.2, 7.2 Hz, 1H), 7.37 (d, J=8.0 Hz, 1H), 7.28 (dd, J=7.6, 7.2 Hz, 1H), 7.13-7.04 (m, 2H), 5.25-5.13 (m, 2H), 2.86 (d, J=5.8 Hz, 2H), 2.32 (s, 6H).

Example 48

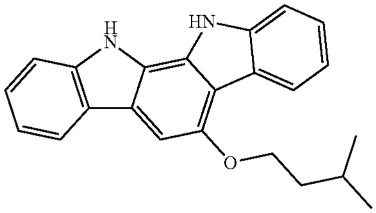

SS20308-0127-01
Chemical Formula: $C_{23}H_{22}N_2O$
Molecular Weight: 342.43

Example Route for Example 48 (SS20308-0127-01):

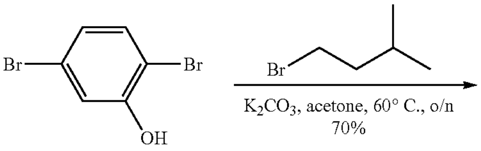

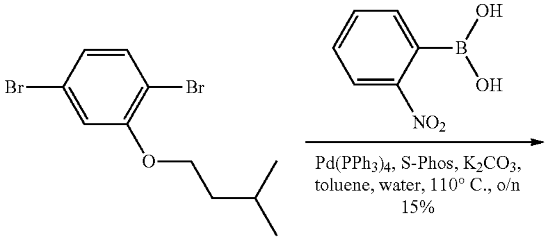

127-1

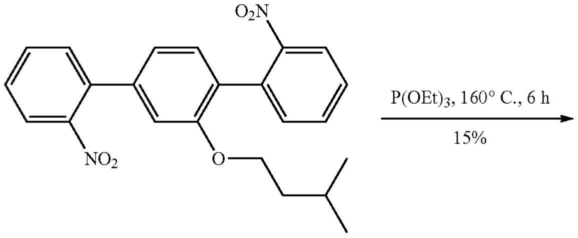

127-2

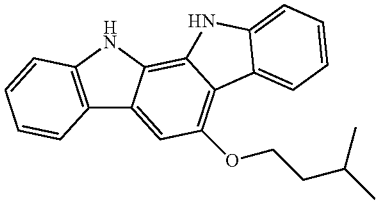

SS20308-0127-01

The synthesis of 1,4-dibromo-2-(isopentyloxy)benzene (127-1):

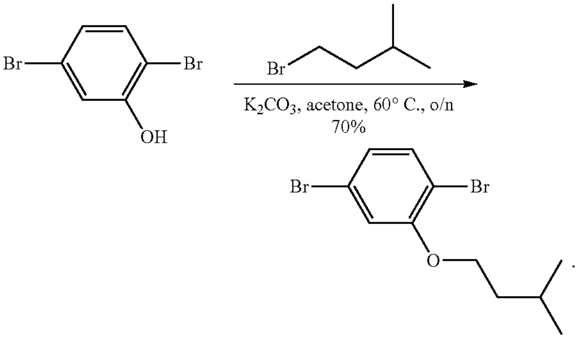

127-1

To a solution of 2,5-dibromophenol (2.0 g, 8.1 mmol) and 1-bromo-3-methylbutane (2.0 g, 8.1 mmol) in acetone (20 mL) was added $K_2CO_3$ (950 mg, 12.1 mmol). The reaction mixture was stirred at 60° C. overnight. The mixture was quenched with water (50 mL), extracted with EtOAc, dried over sodium sulfate, filtered, and concentrated. The crude residue was purified by column chromatography on silica gel (petroleum ether) to give 127-1 (0.9 g, about 70% yield) as a colorless oil.

The synthesis of 5-bromo-N-(2-chloroethyl)biphenyl-2-amine (127-2):

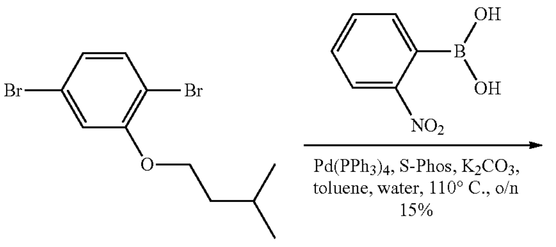

127-1

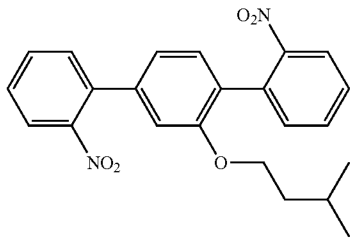

127-2

To a solution of 127-1 (800 mg, 2.5 mmol) in toluene/water (10/1, 30 mL) was added 2-nitrophenylboronic acid (912 mg, 5.5 mmol), $Pd(PPh_3)_4$ (300 mg, 0.3 mmol), S-Phos (201 mg, 0.5 mmol) and $K_2CO_3$ (1.4 g, 9.9 mmol), then the reaction mixture was stirred at 110° C. overnight. The reaction mixture was cooled to room temperature and filtered through celite. The filtrate was diluted with water (40 mL) and then extracted with EtOAc (20 mL×3). The organic layer was washed with brine and concentrated to dryness. The residue was purified by purified by column chromatography on silica gel (petroleum ether/EtOAc=10/1 to 4/1) to give 127-2 (150 mg, about 15% yield) as a solid. MS Calcd.: 406.2; MS Found: 429.0 $[M+Na]^+$.

The synthesis of 5-(isopentyloxy)-11,12-dihydroindolo[2,3-a]carbazole (SS20308-0127-01):

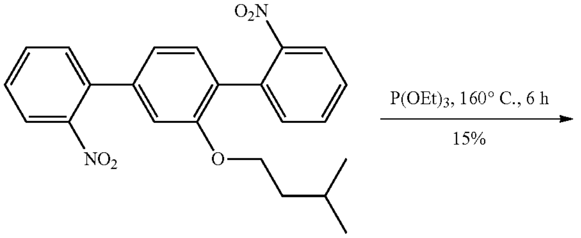

127-2

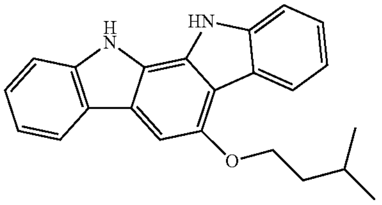

SS20308-0127-01

A solution of 127-2 (80 mg, 0.2 mmol) in $P(OEt)_3$ (1.5 mL) was stirred at 160° C. for 6 hours. The mixture was concentrated to a crude residue, which was purified by Prep-HPLC followed by Prep-TLC (petroleum ether/EtOAc=3/1) to give SS20308-0127-01 (10 mg, about 15% yield). MS Calcd.: 342.2; MS Found: 343.1 $[M+H]^+$.

$^1H$ NMR (400 MHz, DMSO-$d_6$) δ 11.12 (s, 1H), 10.79 (s, 1H), 8.24 (d, J=7.6 Hz, 1H), 8.12 (d, J=7.6 Hz, 1H), 7.67-7.63 (m, 2H), 7.42 (s, 1H), 7.37-7.32 (m, 2H), 7.22-7.14 (m, 2H), 4.33 (t, J=6.8 Hz, 2H), 2.04-1.99 (m, 1H), 1.92-1.87 (m, 2H), 1.05 (d, J=9.2 Hz, 6H).

Example 49

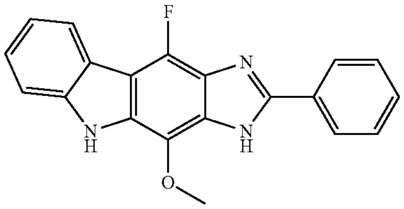

SS20308-0137-01
Chemical Formula: $C_{20}H_{14}FN_3O$
Molecular Weight: 331.34

Example Route for Example 49 SS20308-0137-01:

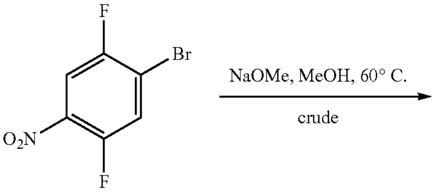

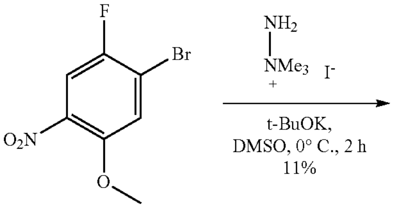

137-1

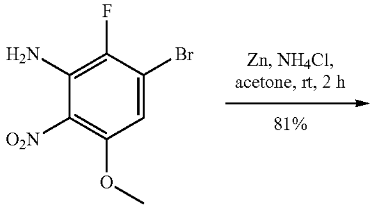

137-2

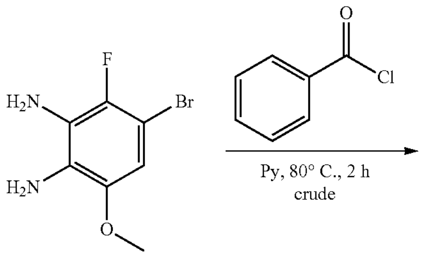

137-3

-continued

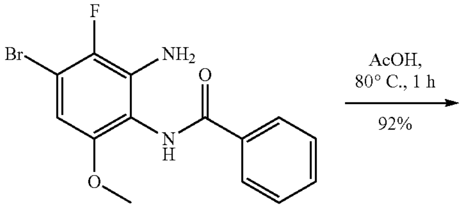

137-4

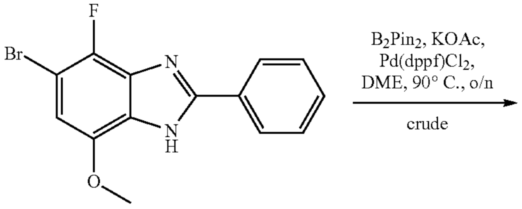

137-5

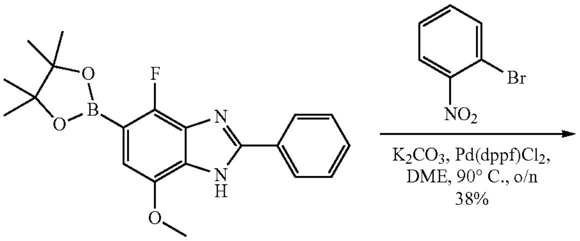

137-6

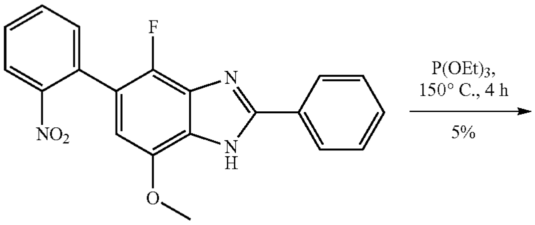

137-7

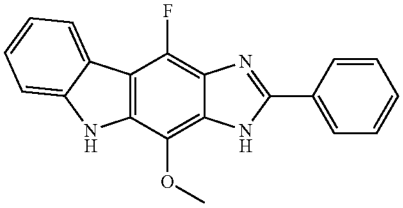

SS20308-0137-01

The synthesis of 1-bromo-2-fluoro-5-methoxy-4-nitrobenzene (137-1):

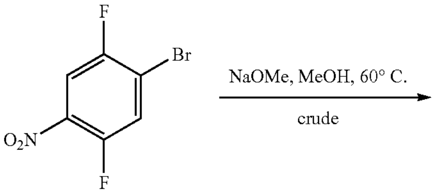

-continued

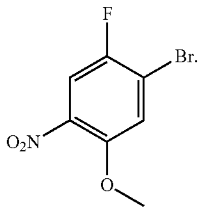

137-1

To a solution of 1-bromo-2,5-difluoro-4-nitrobenzene (15 g, 63.03 mmol) in MeOH (200 mL) was added NaOMe (3.75 g, 69.33 mmol). The mixture was stirred at 60° C. for 5 h. After the reaction was complete, the reaction mixture was poured into water (500 mL) and extracted with EtOAc (400 mL×3). The organic layer was washed with brine (2×500 mL), dried over $MgSO_4$, and concentrated under vacuum to afford 137-1, which was used in the next step without further purification.

The synthesis of 3-bromo-2-fluoro-5-methoxy-6-nitroaniline (137-2):

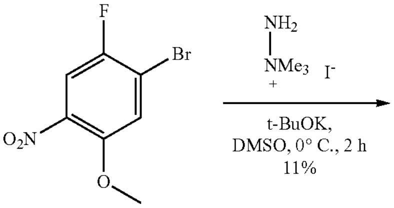

137-1

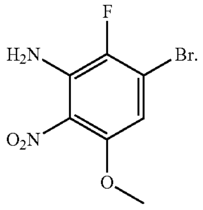

137-2

To a solution 137-1 (2.50 g, 10.00 mmol) and 1,1,1-trimethylhydrazinium iodide (2.22 g, 11.00 mmol) in DMSO (8 mL) was added dropwise over 15 min, a solution of t-BuOK (2.69 g, 24.00 mmol) in DMSO (5 mL) cooled in an ice-water bath. The mixture was stirred at room temperature for 2 h. Then the reaction was poured into 1N HCl (25 mL), and extracted with EtOAc (50 mL×4). The organic layer was washed with brine (2×50 mL) and the solvent evaporated to give a crude solid, which was purified by column chromatography on silica gel (petroleum ether/EtOAc=5/1) to give 137-2 (300 mg, about 11% yield) as a solid. MS Calcd.: 264.0; MS Found: 265.0 $[M+H]^+$.

The synthesis of 4-bromo-3-fluoro-6-methoxybenzene-1, 2-diamine (137-3):

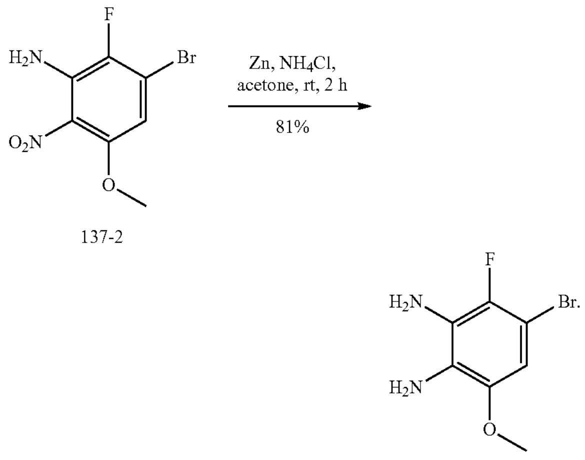

137-2

137-3

To a solution of 137-2 (3.50 g, 13.21 mmol) and $NH_4Cl$ (4.24 g, 79.23 mmol) in acetone (50 mL) was added Zn powder (2.59 g, 39.62 mmol) cooled in an ice-water bath. And the mixture was stirred at room temperature for 2 h. Then the reaction was poured into 0.5 N HCl (25 mL), and extracted with EtOAc (50 mL×4). The organic layer was washed with brine (2×50 mL) and the solvent evaporated to give a solid, which was purified by column chromatography on silica gel (petroleum ether/EtOAc=2/1) to give 137-3 (2.50 g, 81% yield) as a solid. MS Calcd.: 234.0; MS Found: 235.0 $[M+H]^+$.

The synthesis of N-(2-amino-4-bromo-3-fluoro-6-methoxyphenyl)benzamide (137-4):

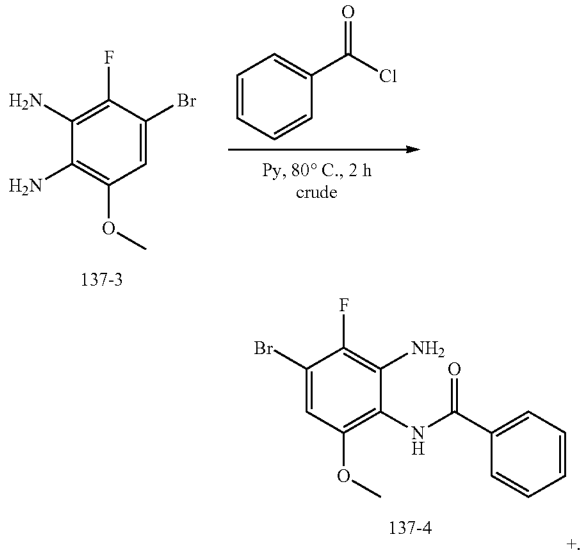

137-3

137-4

+.

To a solution of 137-3 (2.40 g, 10.21 mmol) in pyridine (10 mL) was added benzoyl chloride (1.44 g, 10.21 mmol). The mixture was stirred at 80° C. for 2 h. After the reaction was complete, the reaction mixture was poured into water (50 mL) and extracted with EtOAc (50 mL×3). The organic layer was washed with brine (2×50 mL), dried over $MgSO_4$, and concentrated under vacuum, which was used in the next step without further purification.

The synthesis of 5-bromo-4-fluoro-7-methoxy-2-phenyl-1H-benzo[d]imidazole (137-5):

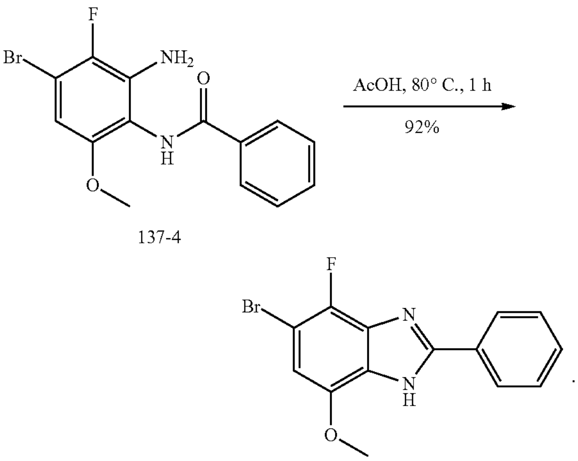

137-4

137-5

A solution of 137-4 (3.20 g, 9.44 mmol) in AcOH (5 mL) was stirred at 80° C. for 1 h. After the reaction was complete, the mixture was poured into water (30 mL) and adjusted pH 8 with $Na_2CO_3$ (aq.), and extracted with ethyl acetate (50 mL×4). The organic layer was washed with brine (2×50 mL) and the solvent was evaporated to give a crude solid, which was purified by column chromatography on silica gel (petroleum ether/EtOAc=2/1) to give 137-5 (2.80 g, about 92% yield) as a solid. MS Calcd.: 320.0; MS Found: 321.0 $[M+H]^+$.

The synthesis of 4-fluoro-7-methoxy-2-phenyl-5-(4,4,5,5-tetramethyl-1,3,2-dioxaborolan-2-yl)-1H-benzo[d]imidazole (137-6):

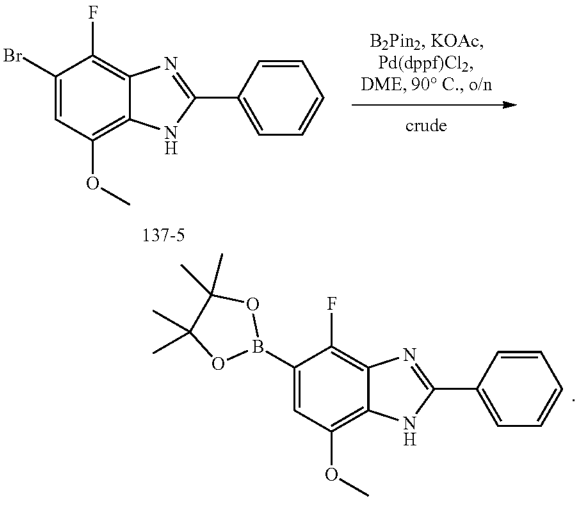

137-5

137-6

A mixture of 137-5 (700 mg, 2.18 mmol), $B_2Pin_2$ (664 mg, 2.62 mmol), $Pd(dppf)Cl_2$ (160 mg, 0.22 mmol), and KOAc (428 mg, 4.36 mmol) in DME (20 ml) was stirred at 90° C.

under nitrogen atmosphere overnight. After the reaction was complete, the mixture was quenched with water. The insoluble material was removed by filtration, and the filtrate was extracted with EtOAc (30 mL×3). The organic layer was separated, dried over $MgSO_4$, and concentrated under vacuum give 137-6, which was used in the next step without further purification.

The synthesis of 4-fluoro-7-methoxy-5-(2-nitrophenyl)-2-phenyl-1H-benzo[d]imidazole (137-7):

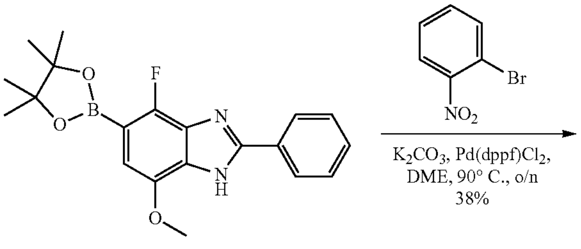

137-6

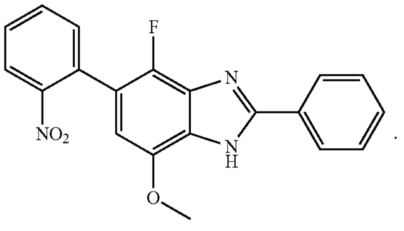

137-7

A mixture of 137-6 (500 mg, 1.36 mmol), 1-bromo-2-nitrobenzene (274 mg, 1.36 mmol), $Pd(dppf)Cl_2$ (100 mg, 0.14 mmol), $K_2CO_3$ (375 mg, 2.72 mmol) in DME (30 ml) was stirred at 90° C. under nitrogen atmosphere overnight. After the reaction was complete, the mixture was quenched with water. The insoluble material was removed by filtration, and the filtrate was extracted with EtOAc (50 mL×3). The organic layer was separated, dried over $MgSO_4$, and concentrated under vacuum. The residue was purified by Prep-TLC (EtOAc/petroleum ether=1/2) to give 137-7 (185 mg, about 38% yield) as a solid. MS Calcd.: 363.1; MS Found: 364.0 $[M+H]^+$.

The synthesis of 10-fluoro-4-methoxy-2-phenyl-3,5-dihydroimidazo[4,5-b]carbazole (SS20308-0137-01):

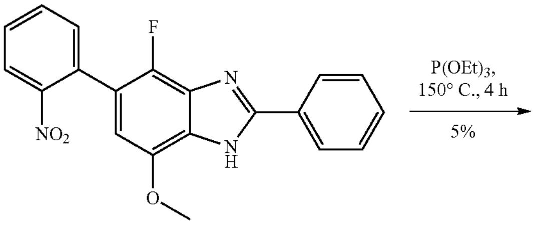

137-7

-continued

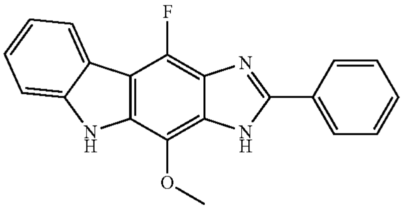

SS20308-0137-01

A solution of 137-7 (100 mg, 0.28 mmol) in $P(OEt)_3$ (2 mL) was stirred at 150° C. for 4 h. After the reaction was complete, the reaction mixture was concentrated to a crude residue, which was purified by Prep-HPLC twice to give SS20308-0137-01 (5 mg, about 5% yield) as a solid. MS Calcd.: 331.1; MS Found: 332.0 $[M+H]^+$.

$^1H$ NMR (400 MHz, DMSO-$d_6$) δ 13.19+13.02 (s, 1H), 11.33+11.19 (s, 1H), 8.33-8.30 (m, 2H), 8.10-8.08 (m, 1H), 7.60-7.51 (m, 3H), 7.49-7.45 (m, 1H), 7.42-7.39 (m, 1H), 7.20-7.16 (m, 1H), 4.39+4.08 (s, 3H).

Example 50

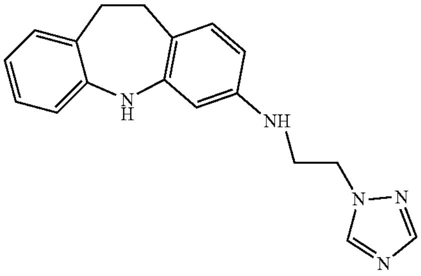

SS20308-0224-01
Chemical Formula: $C_{18}H_{19}N_5$
Molecular Weight: 305.38

Example Route for Example 50 (SS20308-0224-01):

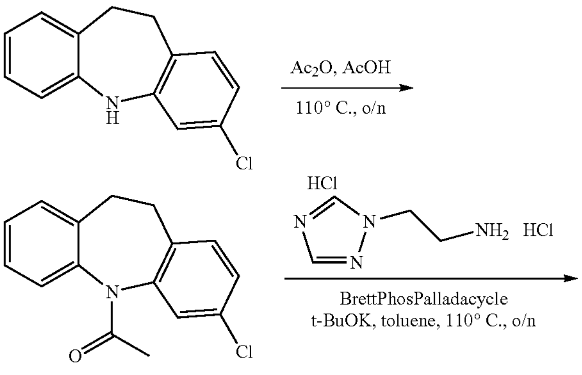

224-1

-continued

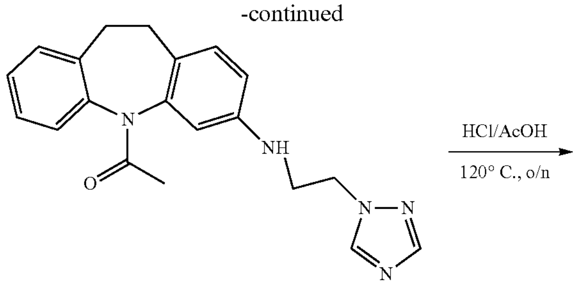

224-2

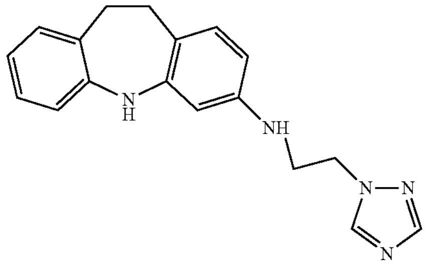

SS20308-0224-01

The synthesis of 1-(3-chloro-10,11-dihydro-5H-dibenzo[b,f]azepin-5-yl)ethanone (224-1):

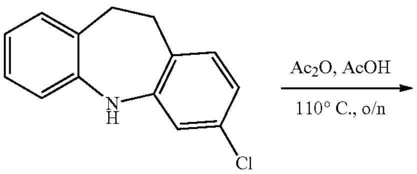

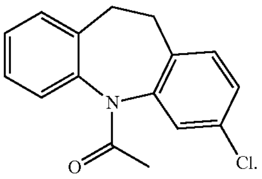

224-1

A solution of 3-chloroiminodibenzyl (2.29 g, 9.97 mmol) in $Ac_2O$ (15 mL) and AcOH (15 mL) was stirred at 110° C. overnight. Then the mixture was poured into water, and basicified with $Na_2CO_3$ (aq.) to pH 7-8. The mixture was extracted with EtOAc, and the combined organic layers were washed with brine, and dried over $Na_2SO_4$. After filtration and concentration, the residue was purified by column chromatography on silica gel (petroleum ether/EtOAc=6/1) to give 224-1 (2.45 g, about 90% yield) as a solid. MS Calcd.: 271.7; MS Found: 272.0 $[M+H]^+$.

The synthesis of 1-(3-(2-(1H-1,2,4-triazol-1-yl)ethylamino)-10,11-dihydro-5H-dibenzo[b,f]azepin-5-yl) ethanone (224-2):

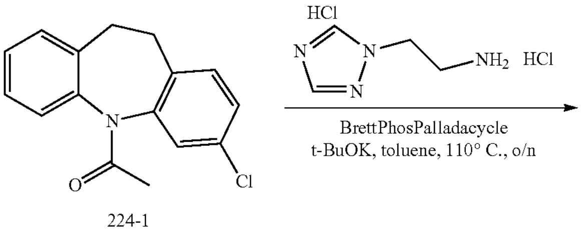

224-1

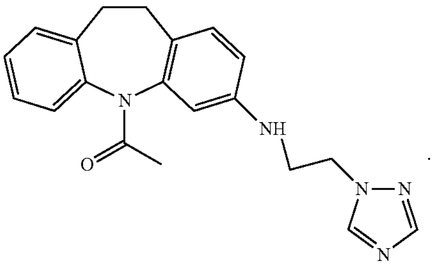

224-2

To a solution of 224-1 (500 mg, 1.84 mmol) in toluene (10 mL) was added 1H-1,2,4-triazole-1-ethanamine, hydrochloride (1:2) (510 mg, 2.76 mmol), t-BuOK (1.24 g, 11.04 mmol), and BrettPhosPalladacycle (143 mg, 0.18 mmol). The mixture was stirred at 110° C. overnight. After cooling to room temperature, the mixture was poured into water and extracted with EtOAc (10 mL×3). The combined organic layers were washed with brine, dried over $Na_2SO_4$, filtered and concentrated to dryness to give 224-2 (500 mg, about 78% yield) as a solid. MS Calcd.: 347.4; MS Found: 348.1 $[M+H]^+$.

The synthesis of N-(2-(1H-1,2,4-triazol-1-yl)ethyl)-10,11-dihydro-5H-dibenzo[b,f]azepin-3-amine (SS20308-0224-01):

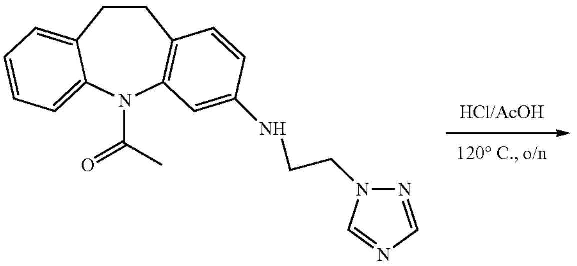

224-2

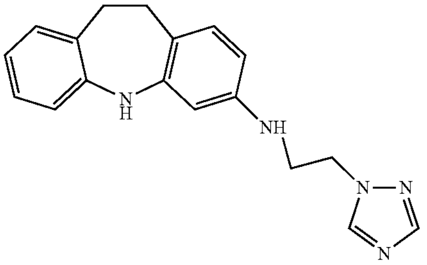

SS20308-0224-01

A solution of 224-2 (210 mg, 0.60 mmol) in HCl (2 mL) and AcOH (2 mL) was stirred at 120° C. overnight. Then the mixture was poured into water, basicified with $Na_2CO_3$ (aq.) to pH 7-8, and extracted with EtOAc. The combined organic layers were washed with brine, dried over $Na_2SO_4$, filtered and concentrated. The residue was purified by Prep-HPLC to give SS20308-0224-01 (65 mg, about 35% yield) as a solid. MS Calcd.: 305.4; MS Found: 306.3 $[M+H]^+$.

$^1H$ NMR (400 MHz, DMSO-$d_6$) δ 8.48 (s, 1H), 8.03 (s, 1H), 7.99 (s, 1H), 7.01-6.91 (m, 3H), 6.70 (d, J=8.4 Hz, 1H), 6.61 (td, J=7.2 Hz, 1.2 Hz, 1H), 6.21 (d, J=2.4 Hz, 1H), 5.97 (dd, J=8.2 Hz, 2.2 Hz, 1H), 5.46 (t, J=6.0 Hz, 1H), 4.33 (t, J=6.2 Hz, 2H), 3.42 (q, J=6.0 Hz, 2H), 2.89 (t, J=4.4 Hz, 2H), 2.81 (t, J=4.2 Hz, 2H).

Example 51

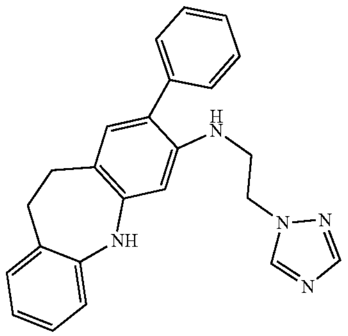

SS20308-0152-01
Chemical Formula: $C_{24}H_{23}N_5$
Molecular Weight: 381.47

Example Route for Example 51 (SS20308-0152-01):

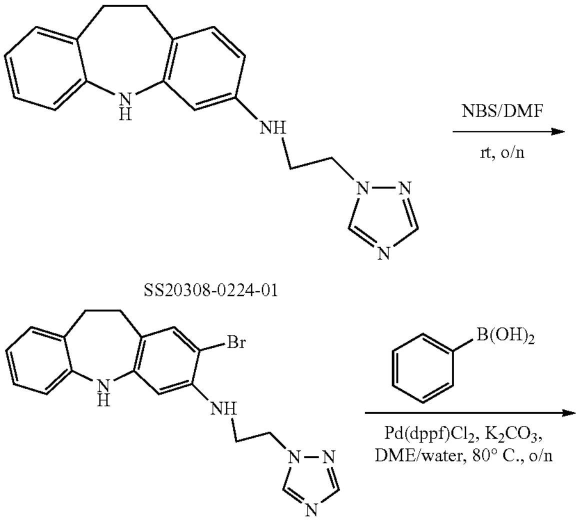

152-1

-continued

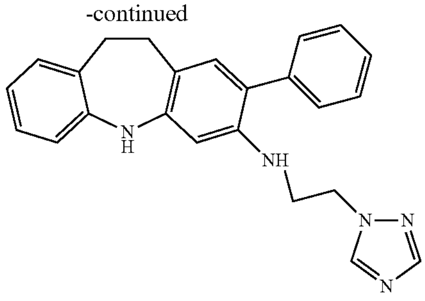

SS20308-0152-01

The synthesis of N-(2-(1H-1,2,4-triazol-1-yl)ethyl)-2-bromo-10,11-dihydro-5H-dibenzo[b,f]azepin-3-amine (152-1):

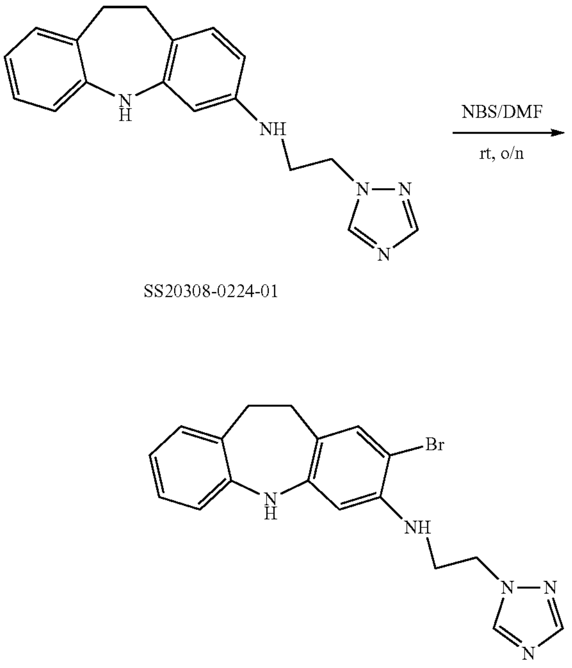

152-1

To a solution of SS20308-0224-01 (650 mg, 2.13 mmol) in DMF (10 mL) was added NBS (379 mg, 2.13 mmol). The mixture was stirred at room temperature overnight. The mixture was poured into water and extracted with EtOAc (10 mL×3). The combined organic layers were washed with brine, dried over $Na_2SO_4$, filtered and concentrated. The residue was purified by column chromatography on silica gel (DCM/MeOH=25/1) to give 152-1 (750 mg, about 92% yield) as an oil. MS Calcd.: 383.1; MS Found: 384.0 $[M+H]^+$.

$^1H$ NMR (400 MHz, DMSO-$d_6$) δ 8.52 (s, 1H), 8.25 (s, 1H), 8.02 (s, 1H), 7.05-7.04 (m, 2H), 6.98 (d, J=7.6 Hz, 1H), 6.92 (d, J=7.6 Hz, 1H), 6.66 (t, J=7.2 Hz, 1H), 6.41 (s, 1H), 5.01 (t, J=5.8 Hz, 1H), 4.45 (t, J=6.2 Hz, 2H), 3.50 (q, J=5.8 Hz, 2H), 2.91-2.89 (m, 2H), 2.83-2.81 (m, 2H).

The synthesis of N-(2-(1H-1,2,4-triazol-1-yl)ethyl)-2-phenyl-10,11-dihydro-5H-dibenzo[b,f]azepin-3-amine (SS20308-0152-01):

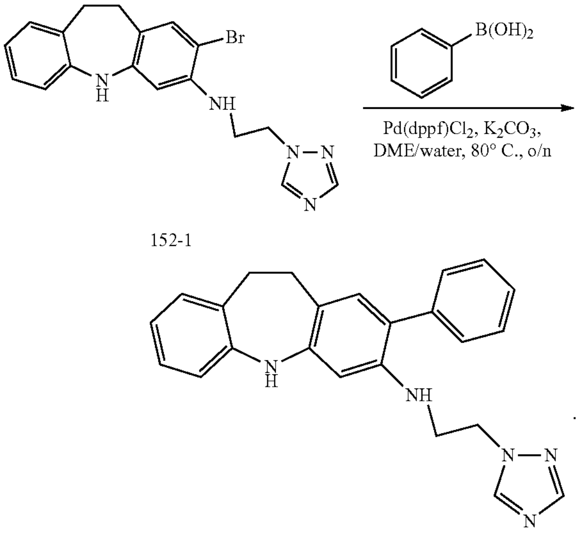

152-1

SS20308-0152-01

A solution of 152-1 (100 mg, 0.26 mmol), phenylboronic acid (48 mg, 0.39 mmol), $Pd(dppf)Cl_2$ (16 mg, 0.02 mmol), and $K_2CO_3$ (108 mg, 0.78 mmol) were suspended in DME (6 mL) and water (2 mL). The reaction mixture was heated at 80° C. for overnight under nitrogen atmosphere. The mixture was poured into water, and extracted with EtOAc (10 mL×2). The combined organic layers were washed with brine, dried over $Na_2SO_4$, filtered, and concentrated. The residue was purified by Prep-HPLC to give SS20308-0152-01 (10 mg, about 10% yield) as a solid. MS Calcd.: 381.2; MS Found: 382.3 $[M+H]^+$.

$^1H$ NMR (400 MHz, DMSO-$d_6$) δ 8.48 (s, 1H), 8.23 (s, 1H), 7.98 (s, 1H), 7.38-7.35 (m, 2H), 7.28-7.21 (m, 3H), 7.05-6.93 (m, 3H), 6.66-6.63 (m, 2H), 6.40 (s, 1H), 4.55 (t, J=5.6 Hz, 1H), 4.41 (t, J=5.8 Hz, 2H), 3.46-3.43 (m, 2H), 2.94-2.92 (m, 2H), 2.88-2.86 (m, 2H).

Example 52

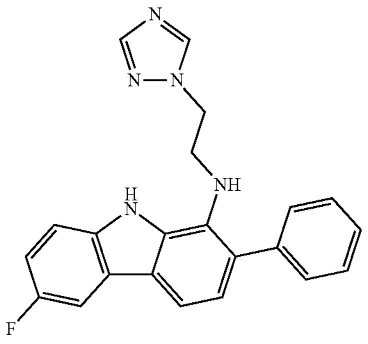

SS20308-0154-01
Chemical Formula: $C_{22}H_{18}FN_5$
Molecular Weight: 371.41

Example Route for Example 52 (SS20308-0154-01):

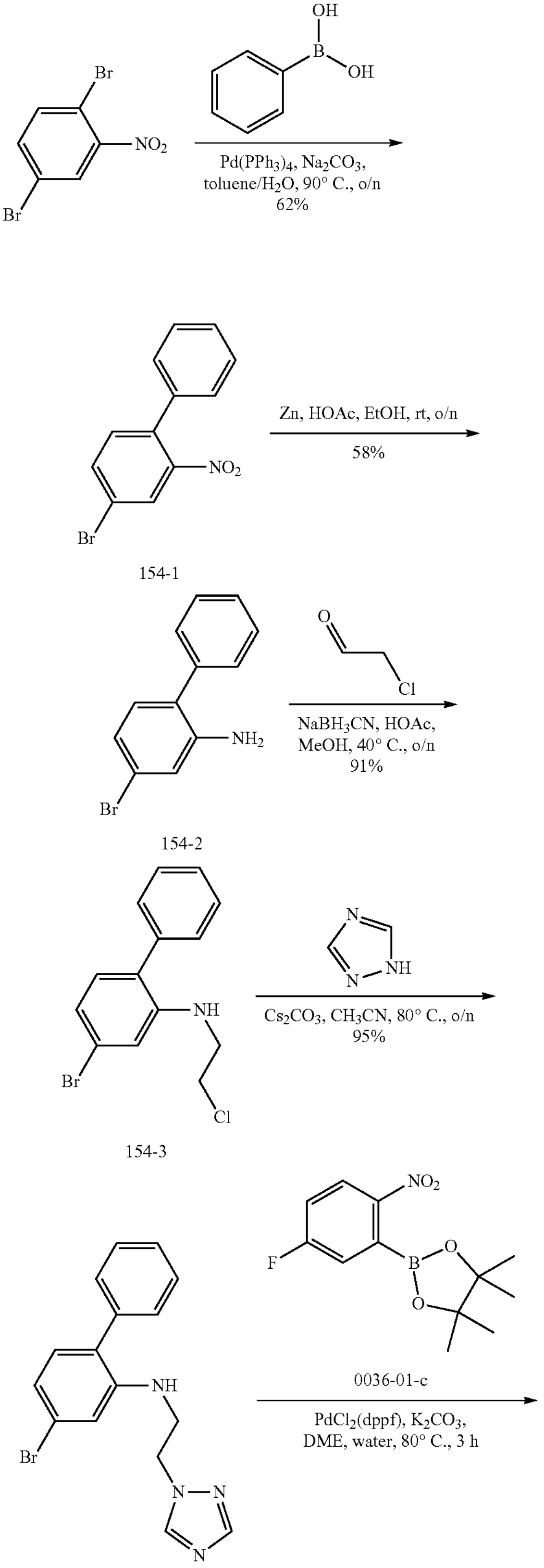

154-1

154-2

154-3

154-4

-continued

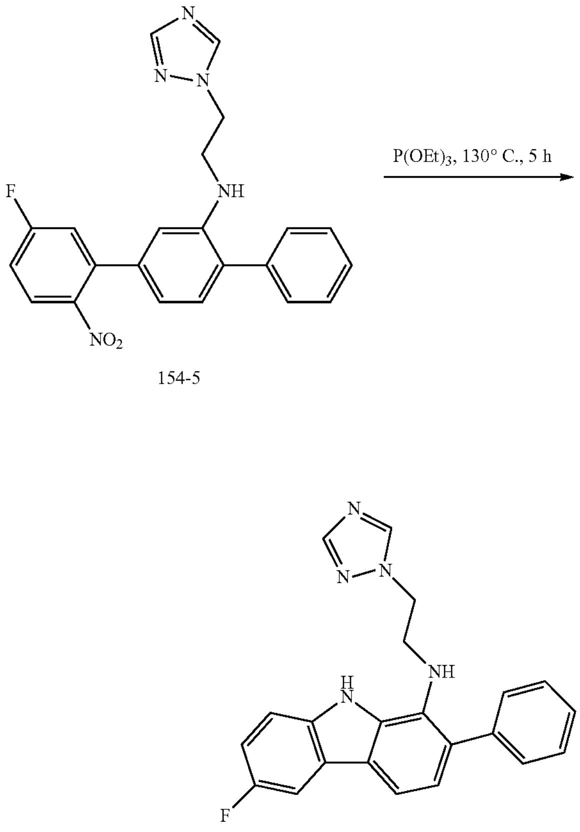

154-5

SS20308-0154-01

The synthesis of 4-bromo-2-nitrobiphenyl (154-1):

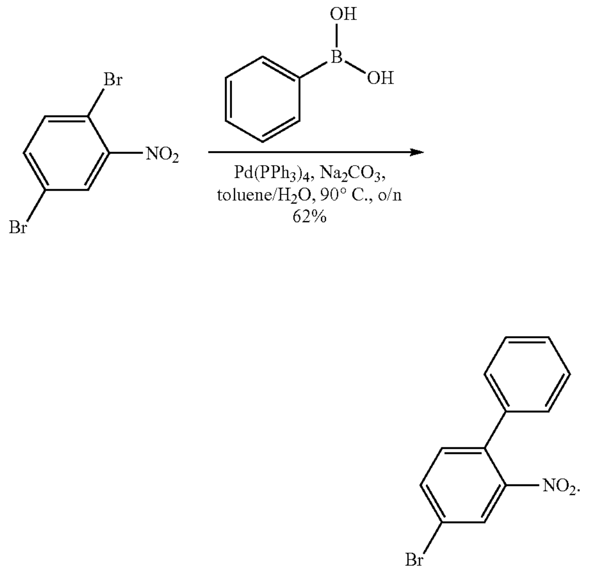

154-1

A mixture of 2,5-dibromonitrobenzene (6.00 g, 21.36 mmol), phenylboronic acid (2.60 g, 21.36 mmol), $Pd(PPh_3)_4$ (1.23 g, 1.07 mmol) and $Na_2CO_3$ (7.90 g, 74.76 mmol) in toluene/$H_2O$ (60 mL, 5/1) was stirred at 90° C. overnight under $N_2$ atmosphere. After cooling to room temperature, the reaction mixture was poured into water and extracted with EtOAc (60 mL×3). The organic layers were washed with brine, dried over $Na_2SO_4$, filtered, and concentrated. The residue was purified by column chromatography on silica gel (petroleum ether) to give 154-1 (3.70 g, about 62% yield) as an oil.

$^1$H NMR (400 MHz, $CDCl_3$) δ 8.00 (d, J=2.0 Hz, 1H), 7.75 (dd, J=8.4 Hz, 2.0 Hz, 1H), 7.45-7.40 (m, 3H), 7.33 (d, J=8.4 Hz, 1H), 7.31-7.27 (m, 2H).

The synthesis of 4-bromobiphenyl-2-amine (154-2):

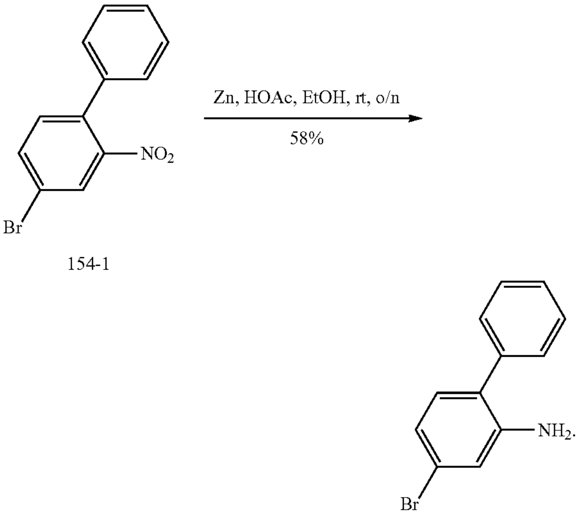

154-1

154-2

The mixture of 154-1 (3.70 g, 13.30 mmol), Zn powder (8.70 g, 133.00 mmol) and HOAc (3.5 mL) in EtOH (35 mL) was stirred at room temperature overnight. Then the reaction mixture was concentrated and poured into water. The mixture was basicified with 40% NaOH to pH 10. The resulting mixture was filtered through celite and washed with MeOH. The filtrate was extracted with EtOAc (50 mL×3). The organic layers were washed with brine, dried over $Na_2SO_4$ and concentrated. The residue was purified by column chromatography on silica gel (petroleum ether/EtOAc=20/1) to give 154-2 (1.90 g, about 58% yield) as an oil. MS Calcd.: 247.0; MS Found: 248.1 $[M+H]^+$.

The synthesis of 4-bromo-N-(2-chloroethyl)biphenyl-2-amine (154-3):

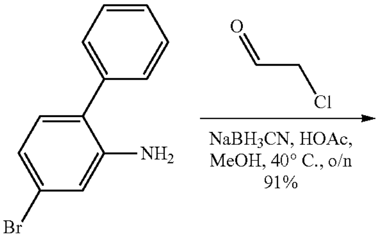

154-2

-continued

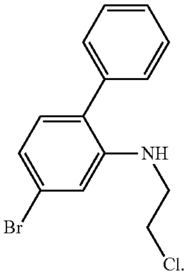

154-3

To a solution of 154-2 (1.75 g, 7.05 mmol) in MeOH (20 mL) was added chloroacetaldehyde (2.77 g, 14.11 mmol, 40%), AcOH (846 mg, 14.11 mmol), and $NaBH_3CN$ (887 mg, 14.11 mmol). The reaction mixture was stirred at 40° C. overnight. Then the reaction mixture was poured into water and basicified with 1N NaOH to pH 10. The mixture was extracted with EtOAc (50 mL×3). The organic layers were washed with brine, dried over $Na_2SO_4$ and concentrated. The residue was purified by column chromatography on silica gel (petroleum ether/EtOAc=20/1) to give 154-3 (2.00 g, about 91% yield) as an oil. MS Calcd.: 309.0; MS Found: 309.8 $[M+H]^+$.

The synthesis of N-(2-(1H-1,2,4-triazol-1-yl)ethyl)-4-bromobiphenyl-2-amine (154-4):

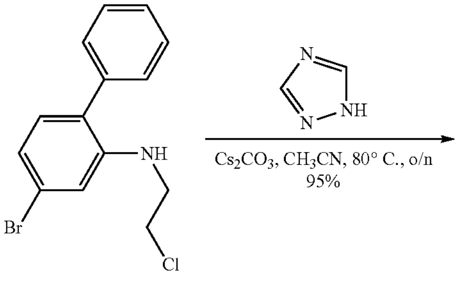

154-3

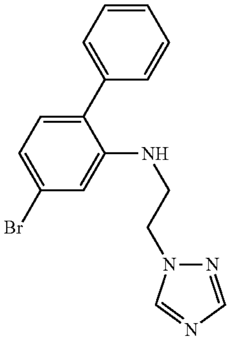

154-4

A mixture of 154-3 (2.00 g, 6.44 mmol), 1,2,4-triazole (677 mg, 9.66 mmol) and $Cs_2CO_3$ (4.20 g, 12.88 mmol) in $CH_3CN$ (40 mL) was stirred at 80° C. overnight. The reaction mixture was then cooled to room temperature and filtered through celite and concentrated. The residue was purified by column chromatography on silica gel (petroleum ether/EtOAc=2/1) to give 154-4 (2.10 g, 95% yield) as an oil. MS Calcd.: 342.1; MS Found: 342.8 $[M+H]^+$.

The synthesis of N-(2-(1H-1,2,4-triazol-1-yl)ethyl)-5"-fluoro-2"-nitro-[1,1':4',1"-terphenyl]-2'-amine (154-5):

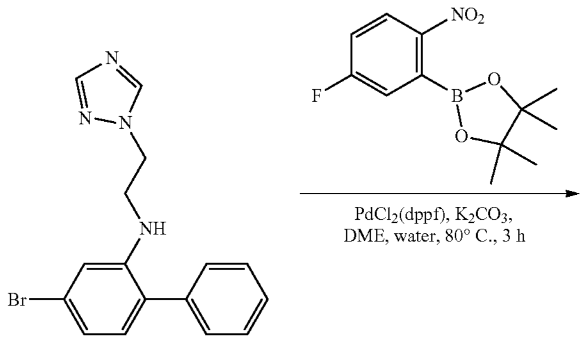

154-4

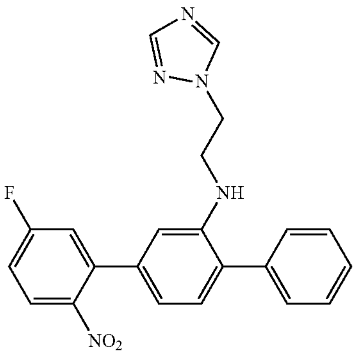

154-5

To a solution of compound 154-4 (200 mg, 0.58 mmol) in DME/water (10 mL, 5/1) was added 2-(5-fluoro-2-nitrophenyl)-4,4,5,5-tetramethyl-1,3,2-dioxaborolane (234.23 mg, 0.88 mmol), $PdCl_2(dppf)$ (42.78 mg, 58.47 umol) and $K_2CO_3$ (240.49 mg, 1.74 mmol). This mixture was heat to 80° C. for 3 h. After the consumption of starting material (by LCMS), then the reaction mixture was filtered and concentrated. The residue was purified by Prep-TLC (petroleum ether/EtOAc=1/1) to give 154-5 (180 mg, about 77% yield) as a solid.

The synthesis of N-(2-(1H-1,2,4-triazol-1-yl)ethyl)-6-fluoro-2-phenyl-9H-carbazol-1-amine (SS20308-0154-01):

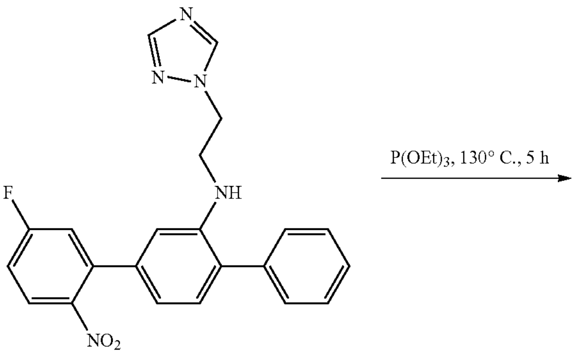

154-5

-continued

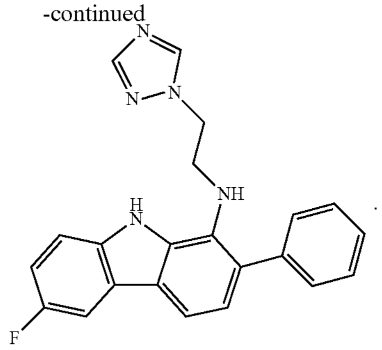

SS20308-0154-01

A solution of 154-5 (100 mg, 0.97 mmol) was stirred in $P(OEt)_3$ (3 mL). The reaction mixture was heated to 130° C. for 5 h. The reaction mixture was concentrated to a crude residue, which was purified by Prep-TLC (petroleum ether/EtOAc=1/1) to give SS20308-0154-01 (5 mg, about 6% yield) as a solid. MS Calcd.: 371.2; MS Found: 372.0 $[M+H]^+$.

$^1H$ NMR (400 MHz, $CD_3OD$) δ 8.07 (s, 1H), 7.89 (s, 1H), 7.70-7.75 (m, 2H), 7.49 (q, J=4.4 Hz 1H), 7.35-7.46 (m, 5H), 7.16 (m, J=2.4 Hz, 1H), 7.01 (d, J=8.0 Hz, 1H), 4.25 (t, J=6.0 Hz, 2H), 3.57 (t, J=5.6 Hz, 2H).

Example 53

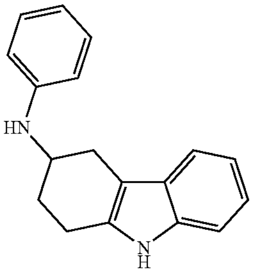

SS20308-0158-01
Chemical Formula: $C_{18}H_{18}N_2$
Molecular Weight: 262.35

Example Route for Example 53 (SS20308-0158-01):

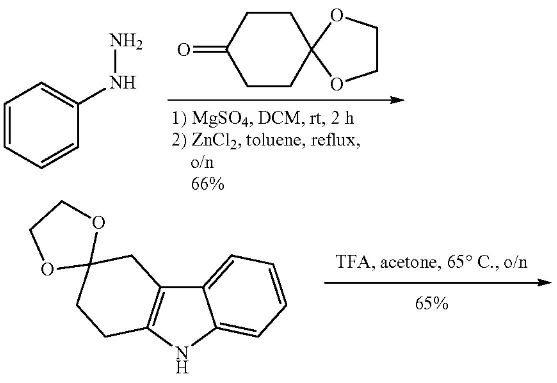

158-1

-continued

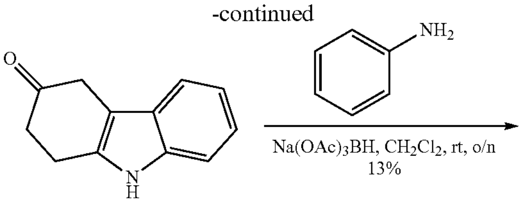

158-2

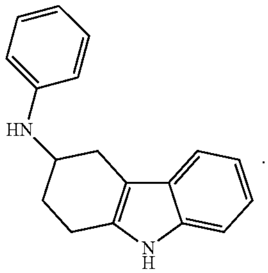

SS20308-0158-01

The synthesis of 1,2,4,9-tetrahydrospiro[carbazole-3,2'-[1,3]dioxolane] (158-1):

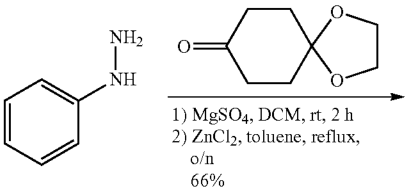

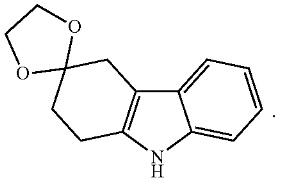

158-1

To a solution of phenyl hydrazine (2.2 g, 19.97 mmol) and in DCM (30 mL) was added $MgSO_4$ (12.0 g, 99.87 mmol), then stirred at room temperature for 2 h. The reaction mixture was filtered through celite. The filtrate was concentrated, azeotrophed with toluene several times to yield a toluene solution (30 mL). To this solution was added 1,4-dioxaspiro[4.5]decan-8-one (3.1 g, 19.97 mmol), and $ZnCl_2$ (2.7 g, 19.97 mmol). The mixture was heated to reflux and stirred overnight. The reaction mixture was purified by column chromatography on silica gel (petroleum ether/EtOAc=20/1 to 8/1) to give 158-1 (3.0 g, about 66% yield) as a solid.

The synthesis of 4,9-dihydro-1H-carbazol-3(2H)-one (158-2):

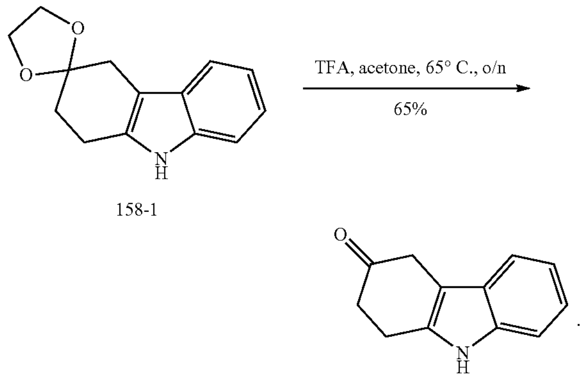

158-1

158-2

To a solution of 158-1 (229 mg, 1.00 mmol) and in acetone (10 mL) was added TFA (239 mg, 2.10 mmol), and then stirred at 65° C. overnight. The mixture was purified by Prep-TLC (DCM) to give 158-2 (120 mg, 65% yield) as a solid.

The synthesis of N-phenyl-2,3,4,9-tetrahydro-1H-carbazol-3-amine (SS20308-0158-01):

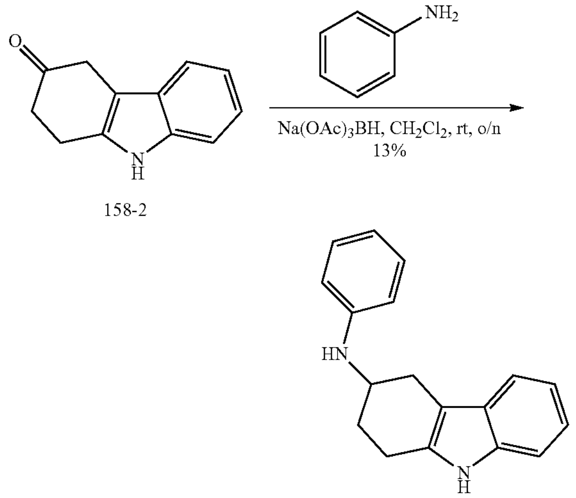

158-2

SS20308-0158-01

To a solution of 158-2 (79 mg, 0.43 mmol) in DCM (10 mL) was added aniline (60 mg, 0.64 mmol) and $Na(OAc)_3BH$ (271 mg, 1.28 mmol). The reaction mixture was stirred at room temperature overnight. The mixture was diluted with water (30 mL) and then extracted with EtOAc (20 mL×3). The organic layer was washed with brine and concentrated to dryness. The residue was purified by Prep-HPLC to give SS20308-0158-01 (14 mg, about 13% yield) as a solid. MS Calcd.: 262.1; MS Found: 263.3 $[M+H]^+$.

$^1$H NMR (400 MHz, DMSO-$d_6$) δ 11.40 (s, 1H), 7.32 (d, J=7.6 Hz, 1H), 7.24 (d, J=8.0 Hz, 1H), 7.09-7.05 (m, 2H), 7.00-6.97 (m, 1H), 6.93-6.89 (m, 1H), 6.67-6.65 (m, 2H), 6.51 (t, J=7.2 Hz, 1H), 5.60 (d, J=8.0 Hz, 1H), 3.75-3.73 (m, 1H), 3.30-3.27 (m, 1H), 3.07-3.02 (m, 1H), 2.87-2.84 (m, 2H), 2.18-2.15 (m, 1H), 1.77-1.73 (m, 1H).

Example 54

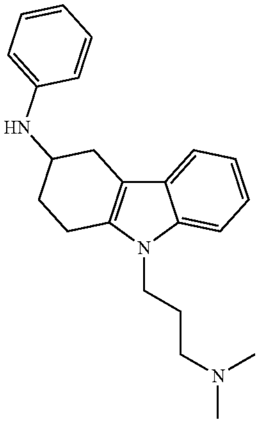

SS20308-0159-01
Chemical Formula: $C_{23}H_{29}N_3$
Molecular Weight: 347.50

Example Route for Example 54 (SS20308-0159-01):

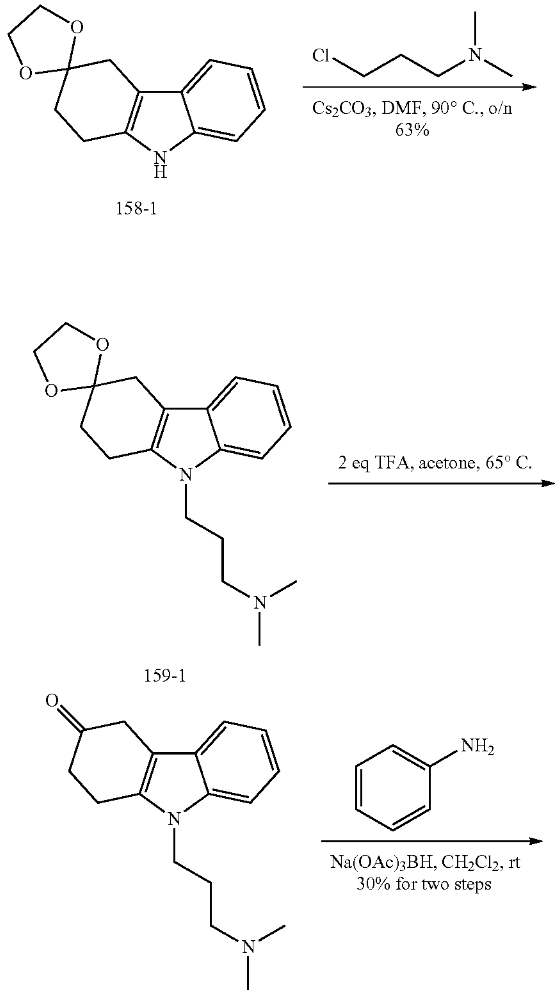

158-1

159-1

159-2

-continued

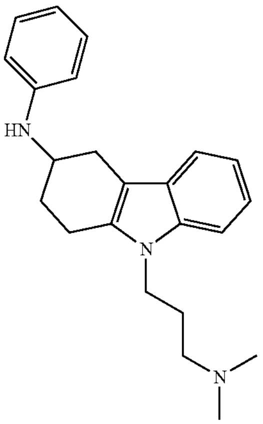

SS20308-0159-01

The synthesis of 3-(1,2-dihydrospiro[carbazole-3,2'-[1,3]dioxolane]-9(4H)-yl)-N,N-dimethylpropan-1-amine (159-1):

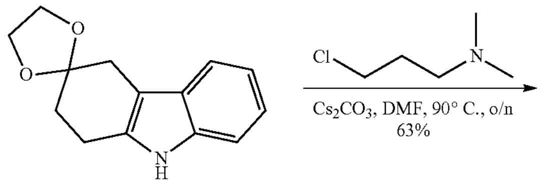

158-1

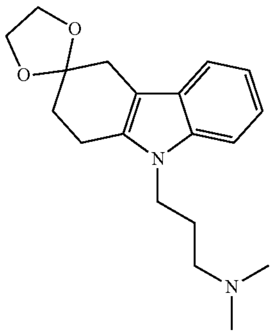

159-1

To a solution of 158-1 (1.2 g, 5.02 mmol) in DMF (20 mL) was added 3-chloro-N,N-dimethyl-1-propanamine (915 mg, 7.52 mmol) and $Cs_2CO_3$ (4.9 g, 15.05 mmol) and the resulting mixture was stirred at 90° C. overnight. The mixture was diluted with water (30 mL) and then extracted with EtOAc (20 mL×3). The organic layer was washed with brine and concentrated to dryness to give 159-1 (1.0 g, about 63% yield) as an oil. MS Calcd.: 314.2; MS Found: 315.1 $[M+H]^+$.

The synthesis of 9-(3-(dimethylamino)propyl)-N-phenyl-2,3,4,9-tetrahydro-1H-carbazol-3-amine (SS20308-0159-01):

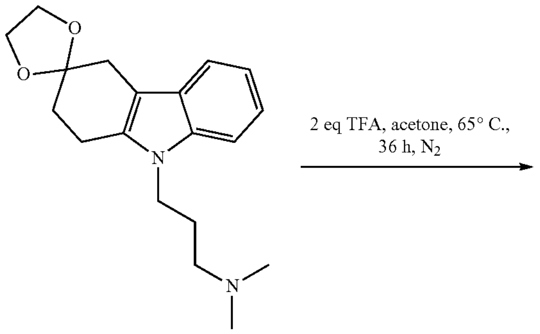

159-1

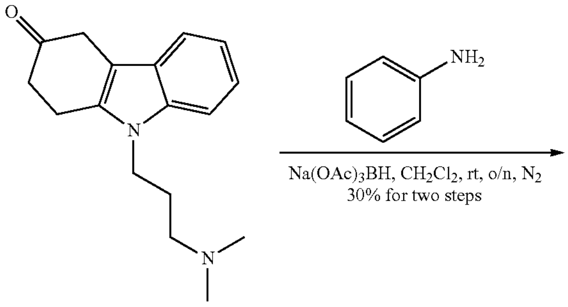

159-2

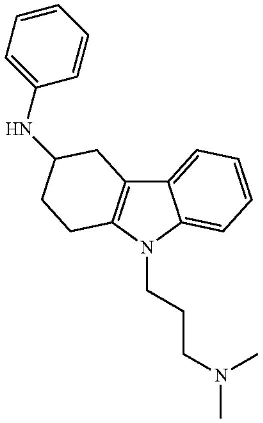

SS20308-0159-01

To a solution of 159-1 (180 mg, 0.57 mmol) in acetone (10 mL) was added TFA (130 mg, 1.14 mmol) and stirred at 65° C. overnight under $N_2$ (g). The mixture was concentrated to dryness and redissolved in DCM (10 mL). To this solution was added aniline (80 mg, 0.86 mmol), and $Na(OAc)_3BH$ (364 mg, 1.72 mmol). The reaction mixture was stirred at room temperature overnight under $N_2$ (g). The mixture was diluted with water (30 mL) and then extracted with EtOAc (20 mL×3). The organic layer was washed with brine and concentrated to dryness. The residue was purified by Prep-HPLC to give SS20308-0159-01 (60 mg, about 30% yield for two steps) as an oil. MS Calcd.: 347.2; MS Found: 348.3 $[M+H]^+$.

$^1H$ NMR (400 MHz, DMSO-$d_6$) δ 7.38-7.35 (m, 2H), 7.09-7.04 (m, 3H), 6.97-6.93 (m, 1H), 6.67-6.65 (m, 2H), 6.51 (t, J=7.2 Hz, 1H), 5.60 (d, J=8.0 Hz, 1H), 4.08 (t, J=7.2 Hz, 2H), 3.74-3.72 (m, 1H), 3.09-3.04 (m, 1H), 2.89-2.85 (m, 2H), 2.56-2.54 (m, 1H), 2.22-2.17 (m, 3H), 2.13 (s, 6H), 1.18-1.76 (m, 3H).

Example 55

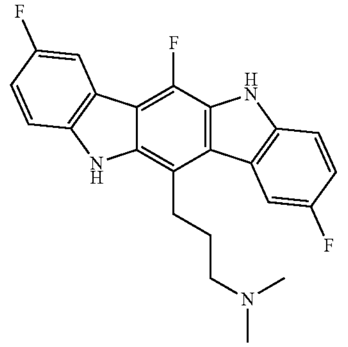

SS20308-0163-01
Chemical Formula: $C_{23}H_{20}F_3N_3$
Molecular Weight: 395.42

Example Route for Example 55 (SS20308-0163-01):

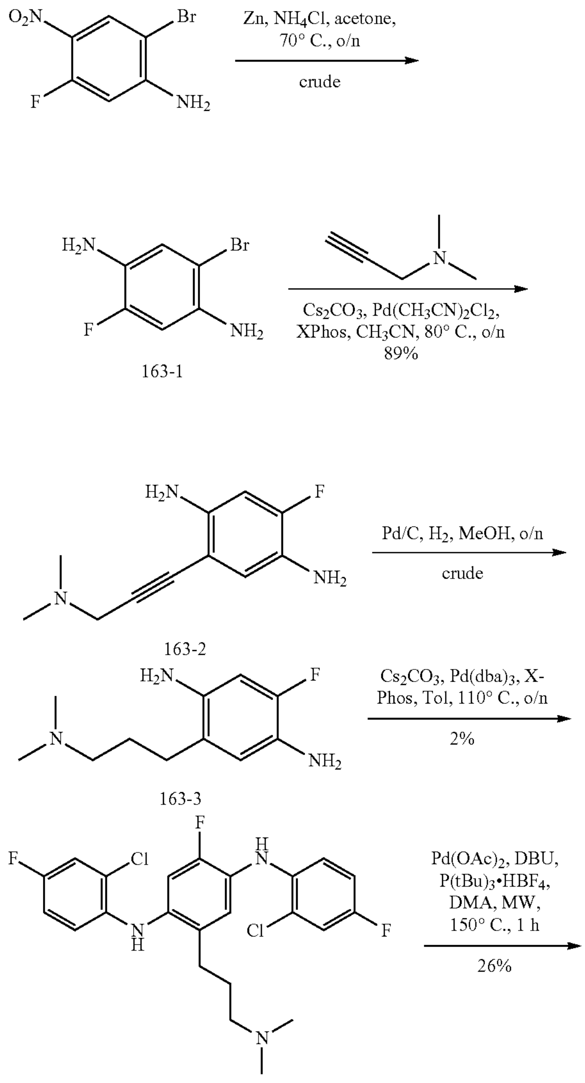

163-1

163-2

163-3

163-4

-continued

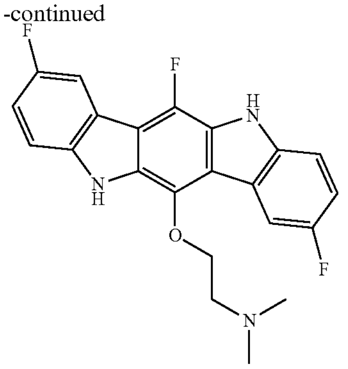

SS20308-0163-01

The synthesis of 2-bromo-5-fluorobenzene-1,4-diamine (163-1):

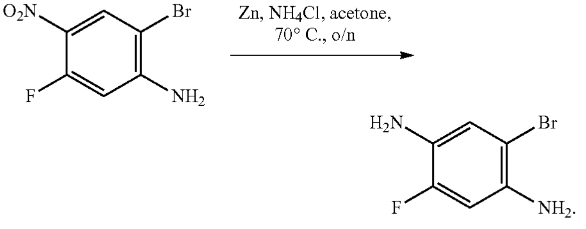

163-1

To a solution of 2-bromo-5-fluoro-4-nitrobenzenamine (300 mg, 1.28 mmol) in acetone (30 mL) was added Zn powder (417 mg, 6.38 mmol) and $NH_4Cl$ (341 mg, 6.38 mmol). The mixture was stirred at 70° C. for 16 h. After the reaction was complete, the insoluble material was removed by filtration. The filtrate was poured into water (50 mL) and extracted with EtOAc (40 mL×3). The organic layer was washed brine (2×50 mL), dried over $MgSO_4$, and concentrated under vacuum to give 163-1, which was used in the next step without further purification.

The synthesis of 2-(3-(dimethylamino)prop-1-ynyl)-5-fluorobenzene-1,4-diamine (163-2):

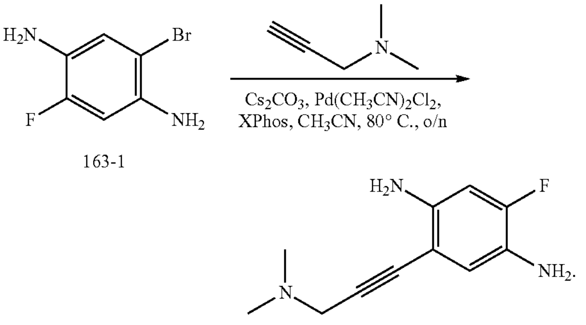

163-1

163-2

A mixture of 163-1 (500 mg, 2.44 mmol), N, N-dimethyl-prop-2-yn-1-amine (2.03 g, 24.39 mmol), $Pd(CH_3CN)_2Cl_2$ (63 mg, 0.24 mmol), $Cs_2CO_3$ (1.59 g, 4.88 mmol) and X-Phos (232 mg, 0.49 mmol) in $CH_3CN$ (20 ml) was stirred at 80° C. under nitrogen atmosphere overnight. After the reaction was complete, the mixture was quenched with water, and the insoluble material was removed by filtration. The filtrate was extracted with EtOAc (30 mL×3). The organic layer was separated, dried over $MgSO_4$, and concentrated under vacuum to give a residue, which was purified by column chromatography on silica gel (petroleum ether/EtOAc=1/1) to give 163-2 (450 mg, about 89% yield) as an oil. MS Calcd.: 207.1; MS Found: 208.1 $[M+H]^+$.

The synthesis of 2-(3-(dimethylamino)propyl)-5-fluorobenzene-1,4-diamine (163-3):

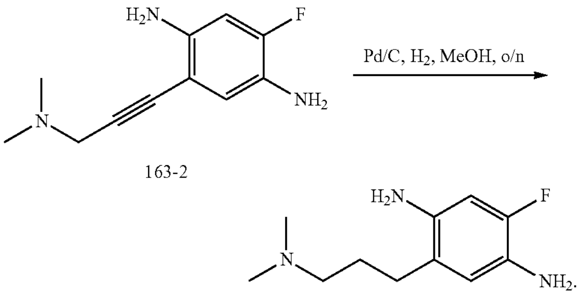

163-2

163-3

To a solution of 163-2 (250 mg, 1.21 mmol) in MeOH (30 mL) was added 10% Pd/C (50 mg), the mixture was stirred at room temperature under hydrogen gas (balloon) for 16 h. After the reaction was complete, the insoluble material was removed by filtration. The filtrate was poured into water (50 mL) and extracted with EtOAc (40 mL×3). The organic layer was washed brine (2×50 mL), dried over $MgSO_4$, and concentrated under vacuum to give 163-3, which was used in the next step without further purification.

The synthesis of $N^1$,$N^4$-bis(2-chloro-4-fluorophenyl)-2-(3-(dimethylamino)propyl)-5-fluorobenzene-1,4-diamine (163-4):

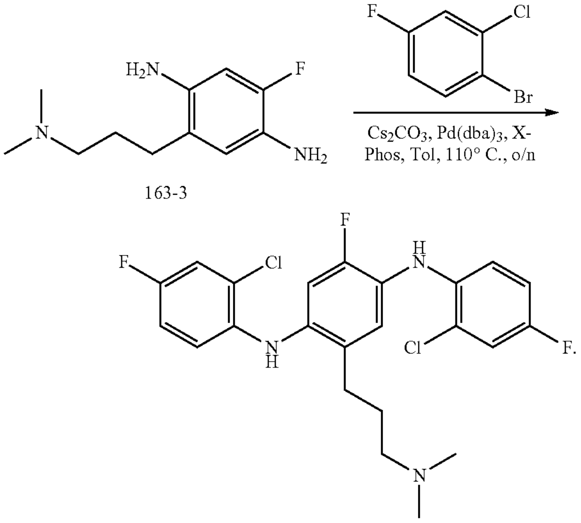

163-3

163-4

A mixture of 163-3 (120 mg, 0.57 mmol), 1-bromo-2-chloro-4-fluorobenzene (357 mg, 1.70 mmol), $Pd_2(dba)_3$ (52 mg, 0.06 mmol), $Cs_2CO_3$ (555 mg, 1.70 mmol) and X-Phos (54 mg, 0.11 mmol) in toluene (10 ml) was stirred at 110° C. under nitrogen atmosphere overnight. After the reaction was complete, the mixture was quenched with water, and the insoluble material was removed by filtration. The filtrate was extracted with EtOAc (30 mL×3). The organic layer was separated, dried over $MgSO_4$, and concentrated under vacuum to give a residue, which was purified by Prep-HPLC to give 163-4 (6 mg, about 2% yield) as an oil. MS Calcd.: 467.1; MS Found: 467.9 $[M+H]^+$.

$^1$H NMR (400 MHz, $CDCl_3$) δ 7.11-6.97 (m, 5H), 6.93-6.88 (m, 1H), 6.82-6.79 (m, 1H), 6.77-6.73 (m, 2H), 5.73 (s, 1H), 2.66-2.60 (m, 4H), 2.56 (s, 6H), 2.00-1.97 (m, 2H).

The synthesis of N,N-dimethyl-3-(2,8,12-trifluoro-5,11-dihydroindolo[3,2-b]carbazol-6-yl)propan-1-amine (SS20308-0163-01):

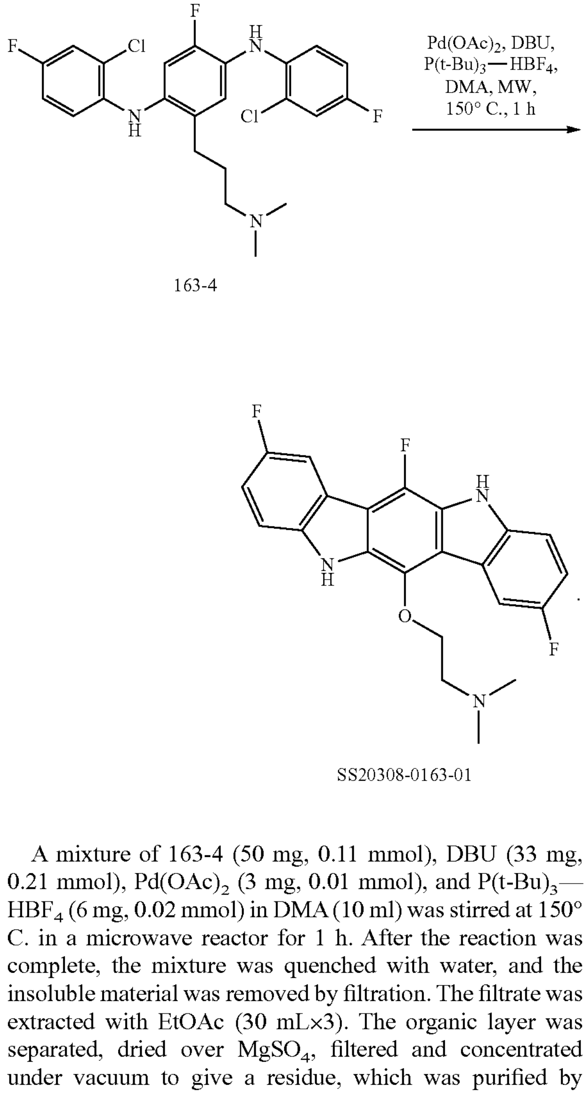

163-4

SS20308-0163-01

A mixture of 163-4 (50 mg, 0.11 mmol), DBU (33 mg, 0.21 mmol), $Pd(OAc)_2$ (3 mg, 0.01 mmol), and $P(t-Bu)_3$—$HBF_4$ (6 mg, 0.02 mmol) in DMA (10 ml) was stirred at 150° C. in a microwave reactor for 1 h. After the reaction was complete, the mixture was quenched with water, and the insoluble material was removed by filtration. The filtrate was extracted with EtOAc (30 mL×3). The organic layer was separated, dried over $MgSO_4$, filtered and concentrated under vacuum to give a residue, which was purified by Prep-HPLC to give SS20308-0163-01 (11 mg, about 26% yield) as a solid. MS Calcd.: 395.1; MS Found: 396.0 $[M+H]^+$.

$^1$H NMR (400 MHz, DMSO-$d_6$) δ 11.49 (s, 1H), 11.33 (s, 1H), 8.02 (dd, J=10.4 Hz, 2.4 Hz, 1H), 7.87 (dd, J=8.8 Hz, 2.4 Hz, 1H), 7.56-7.49 (m, 2H), 7.34-7.29 (m, 2H), 3.44 (t, J=7.2 Hz, 2H), 2.41 (t, J=6.4 Hz, 2H), 2.23 (s, 6H), 1.94-1.87 (m, 2H).

Example 56
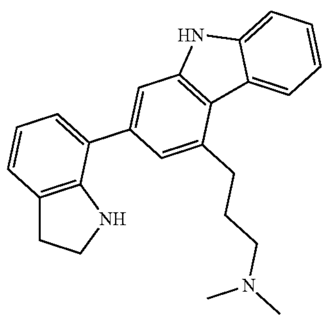
SS20308-0170-01
Chemical Formula: $C_{25}H_{27}N_3$
Molecular Weight: 369.50
Example Route for Example 56 (SS20308-0170-01):
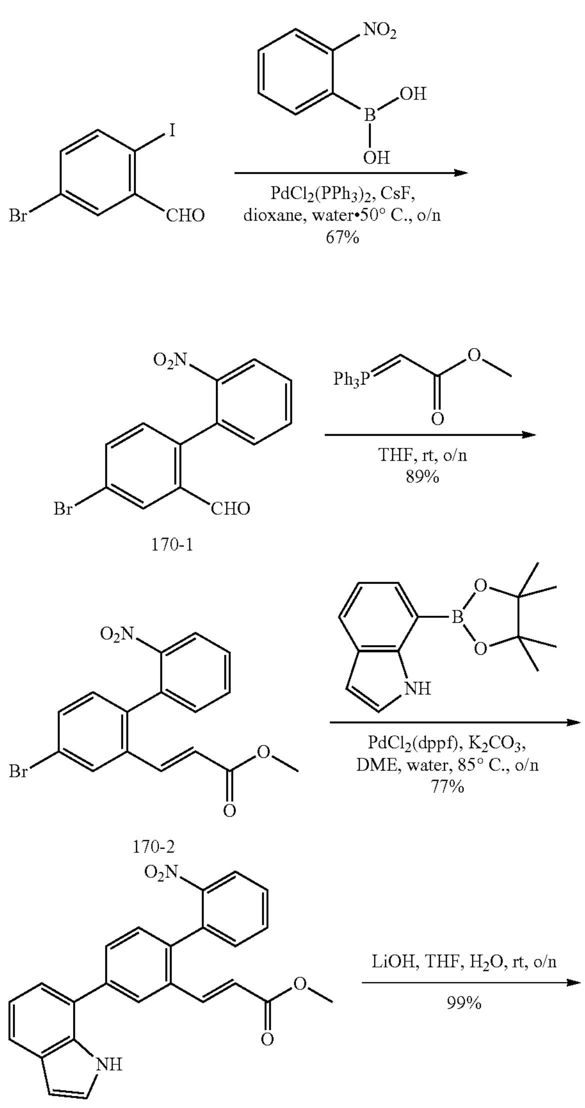
170-1
170-2
170-3
-continued
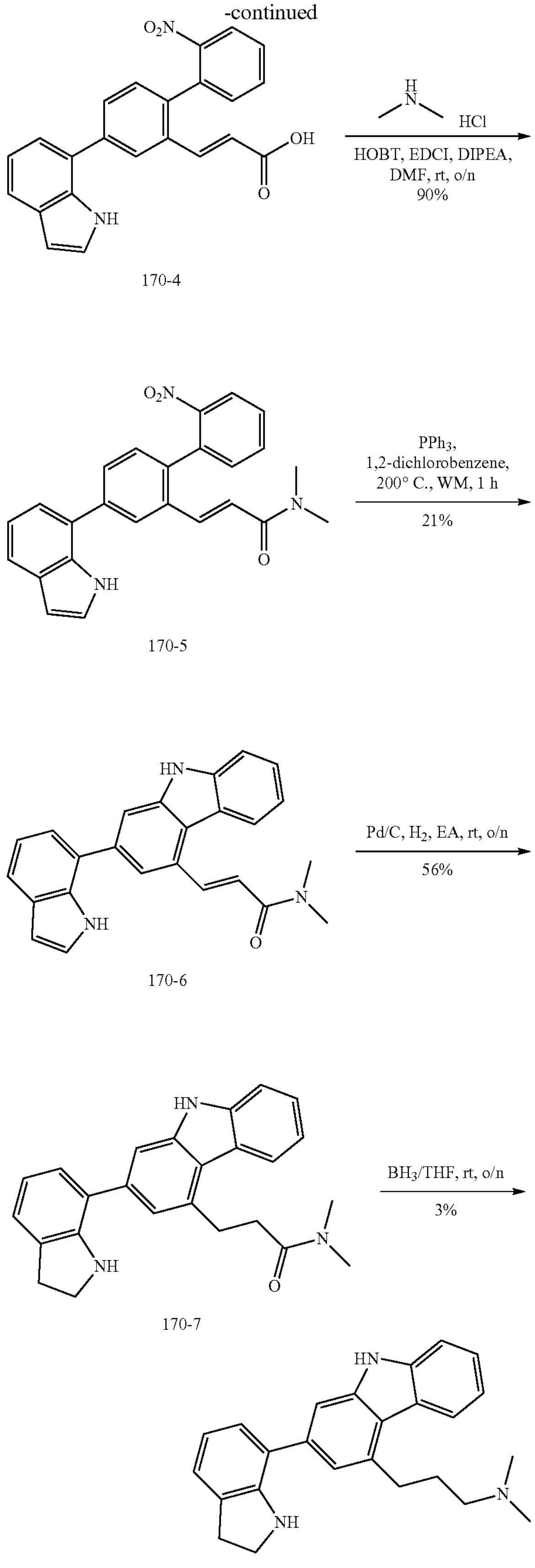
170-4
170-5
170-6
170-7
SS20308-0170-01

The synthesis of 4-bromo-2'-nitrobiphenyl-2-carbaldehyde (170-1):

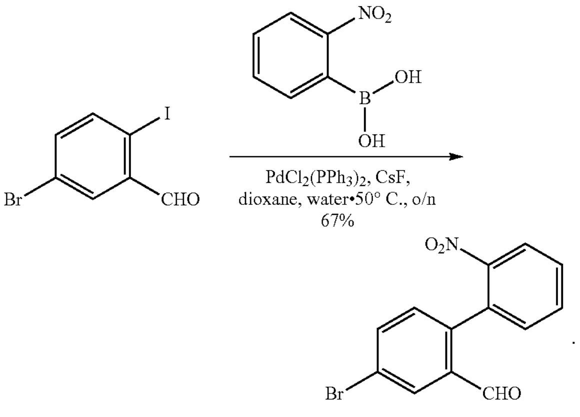

170-1

To a solution of 5-bromo-2-iodobenzaldehyde (620 mg, 1.99 mmol) in 1,4-dioxane/water (10/4 mL) was added CsF (909 mg, 5.98 mmol), $PdCl_2(PPh_3)_2$ (30 mg, 0.04 mmol) and 2-nitrophenylboronic acid (333 mg, 1.99 mmol). This mixture was stirred at 50° C. overnight. The reaction mixture was diluted with water and extracted with EtOAc (3×20 mL). The organic layer was washed with brine and concentrated to dryness to give crude residue, which was purified by column chromatography on silica gel (petroleum ether/EtOAc=10/1 to 8/1) to give 170-1 (410 mg, about 67% yield) as an oil. MS Calcd.: 305.0; MS Found: 323.2 $[M+H]^+$.

The synthesis of (E)-methyl 3-(4-bromo-2'-nitrobiphenyl-2-yl)acrylate (170-2):

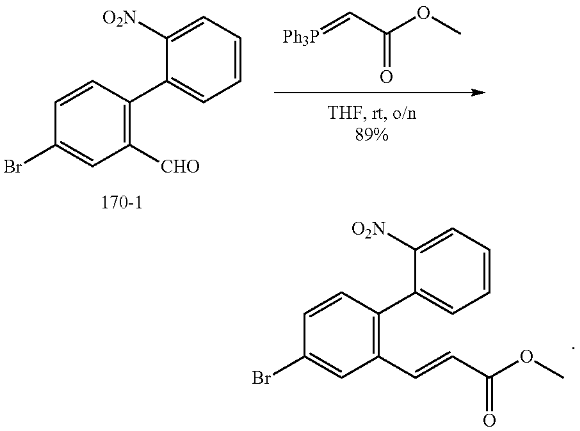

170-1

170-2

To a solution of 170-1 (410 mg, 1.34 mmol) in THF (20 mL) was methyl (triphenylphosphoranylidene) acetate (582 mg, 1.74 mmol) and stirred at room temperature overnight. The reaction mixture was diluted with water and extracted with EtOAc (3×20 mL). The organic layer was washed with brine and concentrated to dryness to give a crude, which was purified by column chromatography on silica gel (petroleum ether/EtOAc=8/1-6/1) to give 170-2 (430 mg, about 89% yield) as a solid. MS Calcd.: 361.0; MS Found: 379.2 $[M+NH_4]^+$.

The synthesis of (E)-methyl 3-(4-(1-indol-7-yl)-2'-nitrobiphenyl-2-yl)acrylate (170-3):

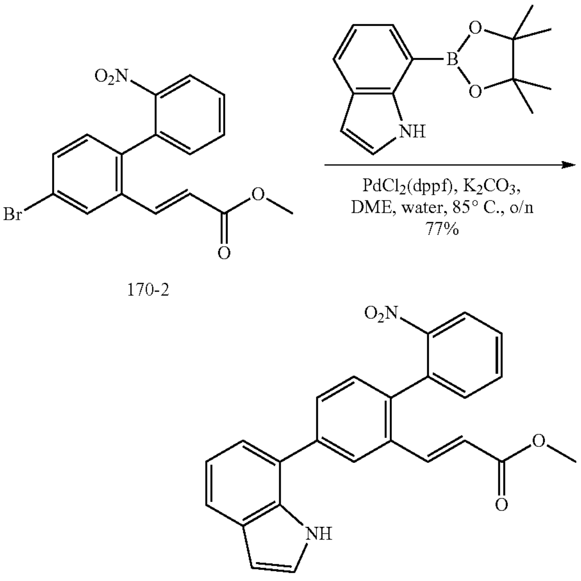

170-2

170-3

To a solution of 170-2 (657 mg, 1.81 mmol) in DME/water (20/2 mL) was added $K_2CO_3$ (501 mg, 3.63 mmol), $PdCl_2$(dppf) (13 mg, 0.02 mmol) and 7-(4,4,5,5-tetramethyl-1,3,2-dioxaborolan-2-yl)-1H-indole (661 mg, 2.72 mmol), The resulting mixture was stirred at 85° C. overnight. The reaction mixture was diluted with water and extracted with EtOAc (3×20 mL). The organic layer was washed with brine and concentrated to dryness to give crude residue, which was purified by column chromatography on silica gel (petroleum ether/EtOAc=6/1 to 5/1) to give 170-3 (560 mg, about 77% yield) as a solid. MS Calcd.: 398.1; MS Found: 399.3 $[M+H]^+$.

The synthesis of (E)-3-(4-(1H-indol-7-yl)-2'-nitrobiphenyl-2-yl)acrylic acid (170-4):

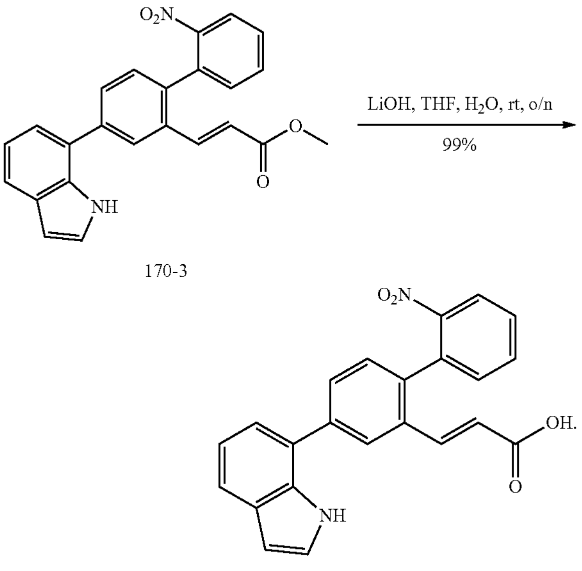

170-3

170-4

To a solution of 170-3 (2.6 g, 6.53 mmol) in THF/$H_2O$ (32/2 mL) was added LiOH (312 mg, 13.05 mmol) and stirred at room temperature overnight. The mixture was diluted with water, adjusted to pH 7 with HCl (1 N) and extracted with EtOAc (3×50 mL). The organic layer was washed with brine and concentrated to dryness to give 170-4 (2.5 g, about 99% yield) as a solid. MS Calcd.: 384.1; MS Found: 385.1 $[M+H]^+$.

The synthesis of ((E)-3-(4-(1H-indol-7-yl)-2'-nitrobiphenyl-2-yl)-N,N-dimethylacrylamide (170-5):

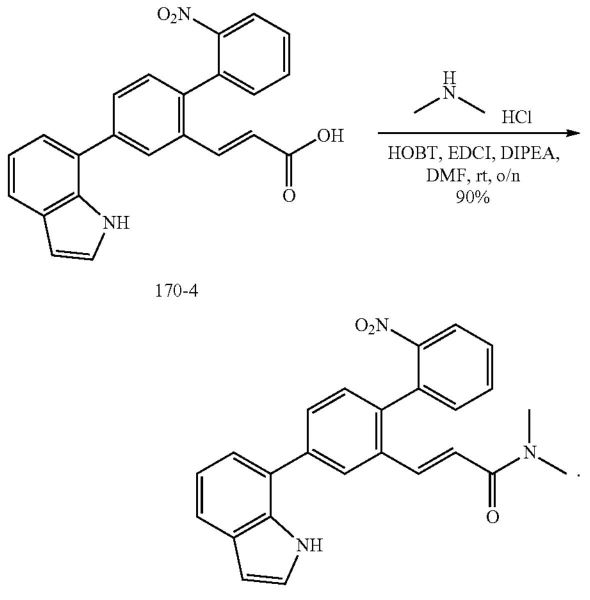

170-4

170-5

To a solution of 170-4 (2.6 g, 6.76 mmol) in DMF (30 mL) was added HOBT (1.4 g, 10.15 mmol), EDCI (1.9 g, 10.15 mmol), DIPEA (3.5 g, 27.08 mmol) and dimethylamine hydrochloride (822 mg, 10.15 mmol). This mixture was stirred at room temperature overnight. The reaction mixture was diluted with water and extracted with EtOAc (3×50 mL). The organic layer was washed with brine and concentrated to dryness to give a crude solid, which was filtered and washed with EtOAc to give 170-5 (2.5 g, about 90% yield) as a solid. MS Calcd.: 411.2; MS Found: 412.1 $[M+H]^+$.

The synthesis of (E)-3-(2-(1H-indol-7-yl)-9H-carbazol-4-yl)-N,N-dimethylacrylamide (170-6):

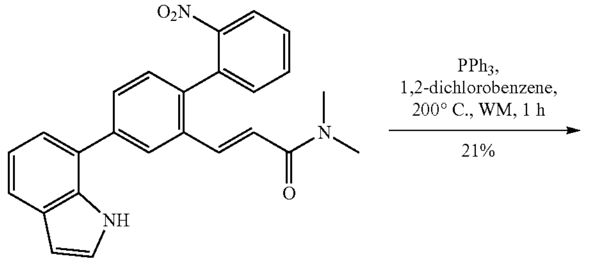

170-5

-continued

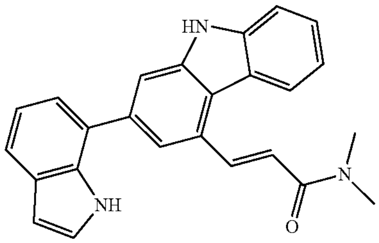

170-6

To a solution of 170-5 (411 mg, 1.00 mmol) in 1,2-dichlorobenzene (4 mL) was added $PPh_3$ (550 mg, 2.10 mmol) and stirred at 200° C. for 1 h in a microwave reactor. After cooling to room temperature, the mixture was concentrated and purified by column chromatography on silica gel (DCM/MeOH=100/1 to 30/1) to give 170-6 (80 mg, about 21% yield) as a solid. MS Calcd.: 379.2; MS Found: 380.4 $[M+H]^+$.

The synthesis of 3-(2-(indolin-7-yl)-9H-carbazol-4-yl)-N,N-dimethylpropanamide (170-7):

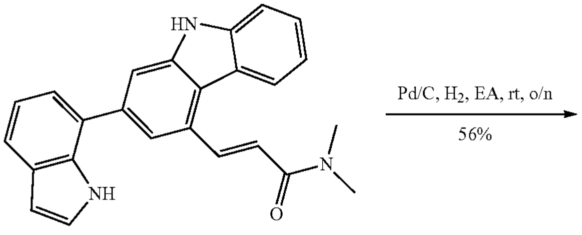

170-6

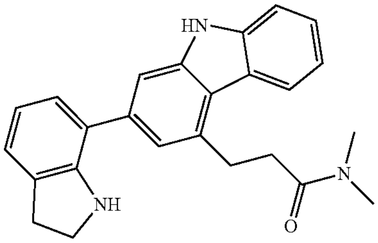

170-7

To a solution of 170-6 (80 mg, 0.21 mmol) in EtOAc (15 mL) was added 10% Pd/C (10 mg) and the mixture was stirred under $H_2$ (g) (balloon) at room temperature overnight. The mixture was filtered through a pad of celite, washed with EtOAc, and concentrated. The crude residue was purified by Prep-TLC (EtOAc) to give 170-7 (45 mg, about 56% yield) as a solid. MS Calcd.:383.2; MS Found: 384.3 $[M+H]^+$.

The synthesis of 3-(2-(indolin-7-yl)-9H-carbazol-4-yl)-N,N-dimethylpropan-1-amine (SS20308-0170-01):

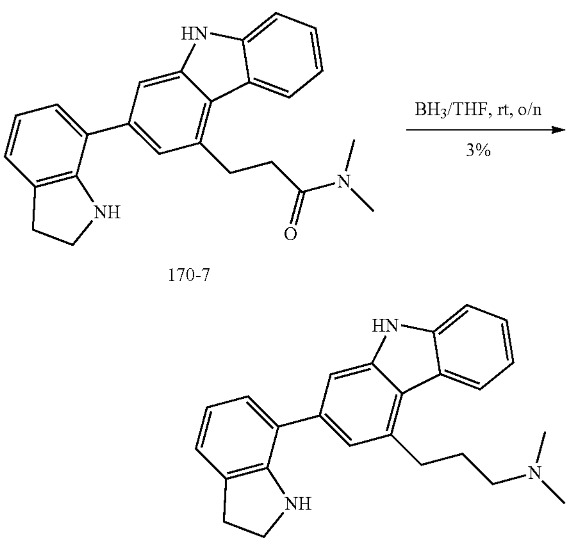

170-7

SS20308-0170-01

To a solution of 170-7 (30 mg, 0.08 mmol) in THF (3 mL) was added $BH_3$/THF (1N, 2 mL) and stirred at room temperature overnight. To this mixture was added MeOH (3 mL). The solution was adjusted to pH 1 with HCl (3 N) and stirred at 60° C. overnight. Then the mixture was diluted with water, adjusted to pH 7 with $NaHCO_3$ (3 N) and extracted with EtOAc (3×20 mL). The organic layer was washed with brine and concentrated to dryness to give the residue, which was purified by Prep-HPLC to give SS20308-0170-01 (1 mg, about 3% yield) as a solid. MS Calcd.: 369.2; MS Found: 370.3 $[M+H]^+$.

$^1H$ NMR (400 MHz, DMSO-$d_6$) δ 11.02 (s, 1H), 8.08 (d, J=8.4 Hz, 1H), 7.80 (s, 1H), 7.68 (d, J=8.4 Hz, 1H), 7.56-7.54 (m, 2H), 7.32 (s, 1H), 7.20-7.18 (m, 1H), 7.14-7.12 (m, 1H), 6.53 (s, 1H), 6.16 (s, 1H), 3.57-3.56 (m, 2H), 3.16-3.15 (m, 4H), 2.20 (s, 6H), 1.79-1.74 (m, 4H).

Example 57

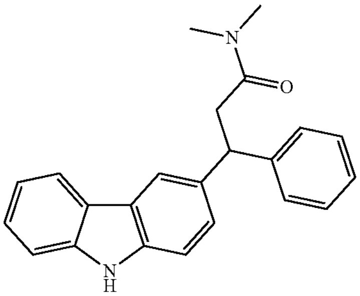

SS20308-0222-01
Chemical Formula: $C_{23}H_{22}N_2O$
Molecular Weight: 342.43

Example Route for Example 57 (SS20308-0222-01):

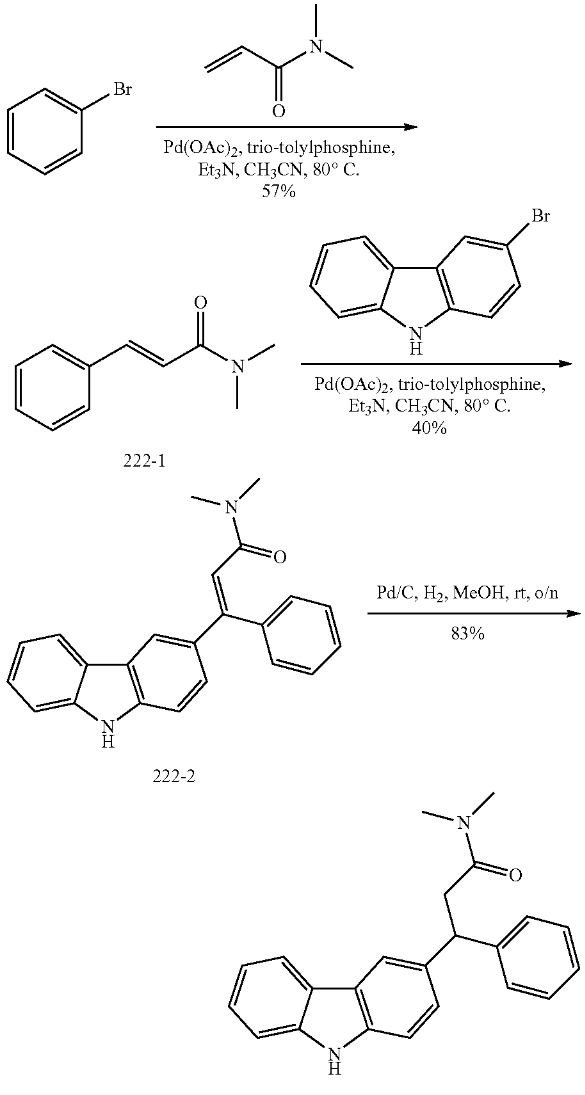

222-1

222-2

SS20308-0222-01

The synthesis of N,N-dimethylcinnamamide (222-1):

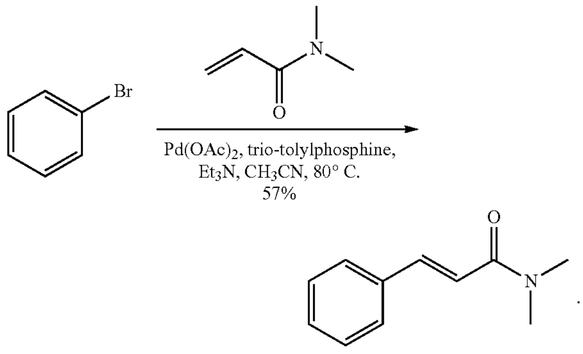

222-1

A solution of bromobenzene (1.0 g, 6.37 mmol), N,N-dimethylcinnamamide (947 mg, 9.55 mmol,), trio-tolylphosphine (110 mg, 0.23 mmol), $Pd(OAc)_2$ (72 mg, 0.32 mmol), and $Et_3N$ (1.61 g, 15.92 mmol,) were suspended in $CH_3CN$ (20 mL). The reaction mixture was heated at reflux for overnight under $N_{2\ (g)}$. The mixture was filtered and rinsed with EtOAc. The filtrate was concentrated and the residue was purified by column chromatography on silica gel (petroleum ether/EtOAc=5/1 to 3/1 to 1/1) to give compound 222-1 (0.64 g, about 57% yield) as a solid. MS Calcd.: 175.1; MS Found: 176.3 $[M+H]^+$.

The synthesis of (E)-3-(9H-carbazol-3-yl)-N,N-dimethyl-3-phenylacrylamide (222-2):

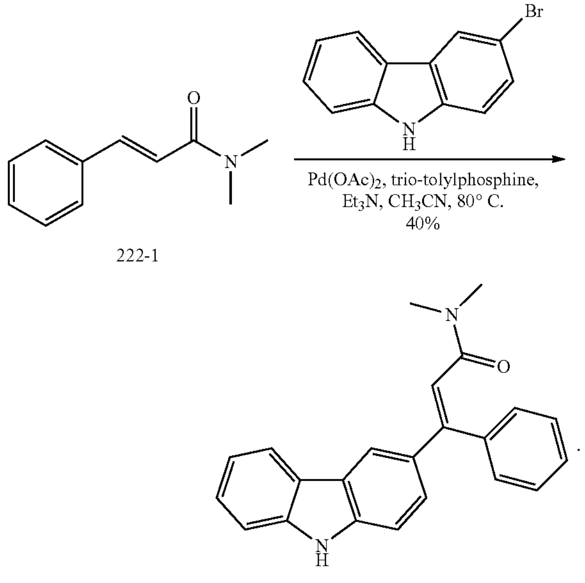

222-1

222-2

A solution of 222-1 (0.59 g, 3.37 mmol), 3-bromocarbazole (1.66 g, 6.73 mmol,), trio-tolylphosphine (410 mg, 1.35 mmol), $Pd(OAc)_2$ (76 mg, 0.34 mmol), and $Et_3N$ (0.852 g, 8.42 mmol,) were suspended in $CH_3CN$ (20 mL). The reaction mixture was heated at reflux for overnight under $N_2$ (g). The mixture was filtered and rinsed with EtOAc. The filtrate was concentrated and the residue was purified by column chromatography on silica gel (petroleum ether/EtOAc=10/1 to 100% EtOAc) to give compound 222-2 (0.46 g, about 40% yield) as a solid. MS Calcd.: 340.2; MS Found: 341.2 $[M+H]^+$.

The synthesis of 3-(9H-carbazol-3-yl)-N,N-dimethyl-3-phenylpropanamide (SS20308-0222-01):

-continued

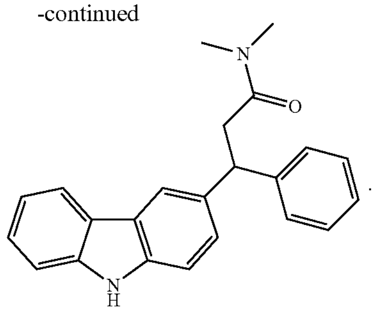

SS20308-0222-01

A solution of 222-2 (455 mg, 1.34 mmol) and 10% Pd/C (50 mg) in MeOH (20 mL) was stirred at room temperature for overnight under $H_{2(g)}$ (balloon). The reaction mixture was filtered through celite. The filtrate was concentrated to give SS20308-0222-01 (380 mg, 83% yield) as a solid. MS Calcd.: 342.2; MS Found: 343.3 $[M+H]^+$.

$^1H$ NMR (400 MHz, DMSO-$d_6$) δ 11.11 (s, 1H), 8.10-8.05 (m, 2H), 7.43 (d, J=8.0 Hz, 1H) 7.40-7.30 (m, 5H), 7.27-7.23 (m, 2H), 7.16-7.08 (m, 2H), 4.65 (t, J=7.4 Hz, 1H), 3.19 (d, J=7.6 Hz, 2H), 3.00 (s, 3H), 2.72 (s, 3H).

Example 58

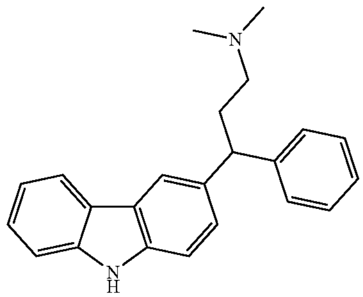

SS20308-0183-01
Chemical Formula: $C_{23}H_{24}N_2$
Molecular Weight: 328.45

Example Route for Example 58 (SS20308-0183-01):

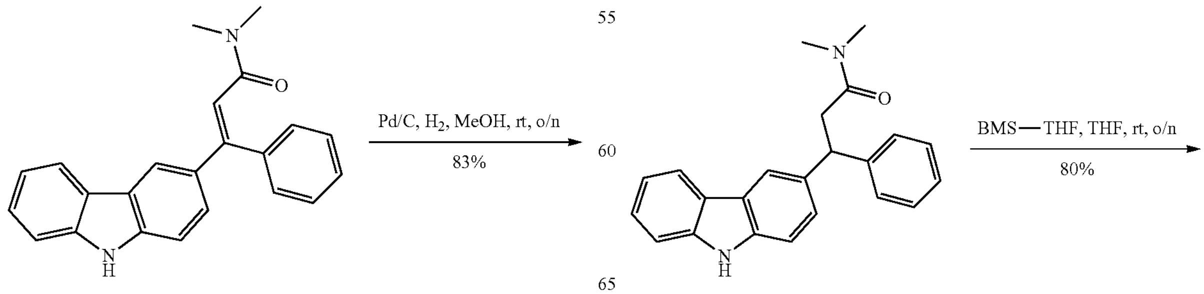

222-2

SS20308-0222-01

-continued

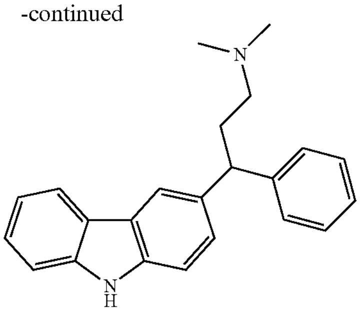

SS20308-0183-01

The synthesis of 3-(9H-carbazol-3-yl)-N,N-dimethyl-3-phenylpropan-1-amino (SS20308-0183-01):

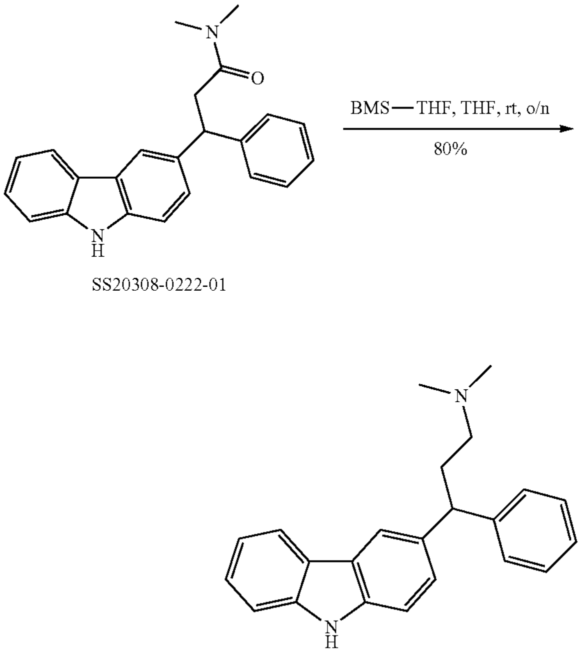

SS20308-0222-01

SS20308-0183-01

To a solution of SS20308-0222-01 (200 mg, 0.58 mmol) in THF (10 mL) was added borane-methyl sulfide complex (1.5 mL, 2M in THF) slowly. The reaction mixture was stirred at room temperature for overnight. The reaction was quenched with MeOH and acidified with 1N HCl to pH 1. Then the reaction mixture was heated to 60° C. and stirred for overnight. After cooling to room temperature, the reaction mixture was basicified with sat. $NaHCO_3$ solution, and extracted with EtOAc (20 mL×3). The combined organic layers were washed with water and brine, dried over $Na_2SO_4$, filtered, and concentrated. The residue was purified by Prep-TLC (DCM/MeOH=10/1) to give SS20308-0183-01 (153 mg, about 80% yield) as a solid. MS Calcd.: 328.2; MS Found: 329.3 $[M+H]^+$.

$^1H$ NMR (400 MHz, DMSO-$d_6$) δ 11.12 (s, 1H), 8.09 (d, J=7.6 Hz, 1H), 8.06 (s, 1H), 7.43 (d, J=8.0 Hz, 1H) 7.39-7.28 (m, 5H), 7.27 (dd, J=7.6 Hz, 2H), 7.16-7.10 (m, 2H), 4.14 (t, J=7.8 Hz, 1H), 2.31-2.19 (m, 2H), 2.13 (t, J=7.6 Hz, 2H), 2.10 (s, 6H).

Example 59

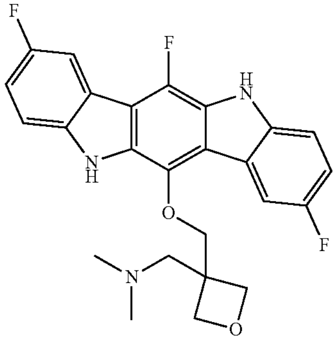

SS20308-0185-01
Chemical Formula: $C_{25}H_{22}F_3N_3O_2$
Molecular Weight: 453.46

Example Route for Example 59 (SS20308-0185-01):

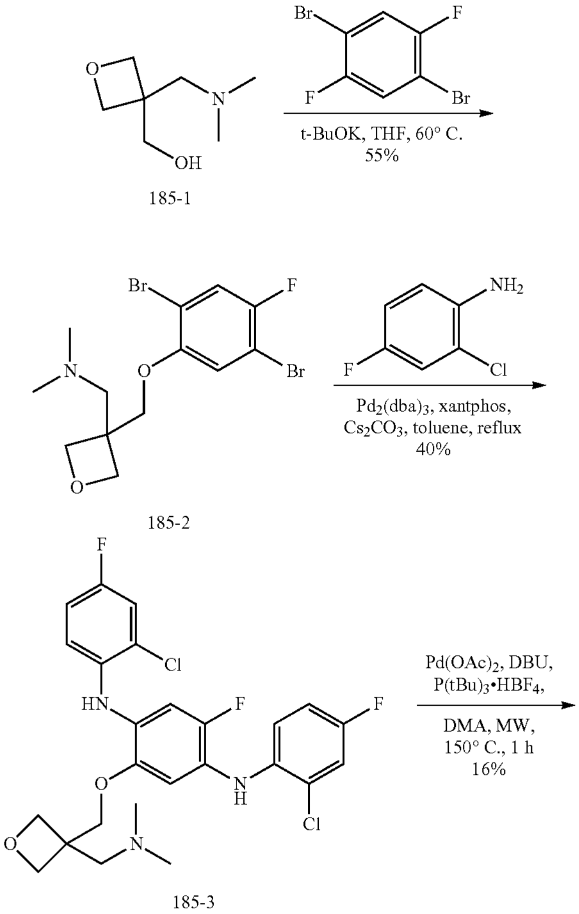

185-1

185-2

185-3

-continued

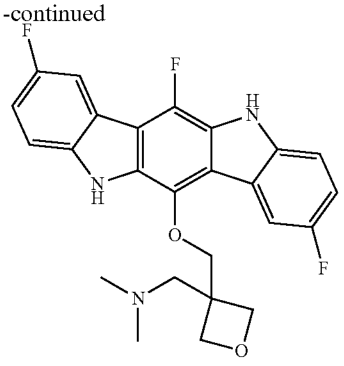

SS20308-0185-01

The synthesis of (3-((dimethylamino)methyl)oxetan-3-yl) methanol (185-1):

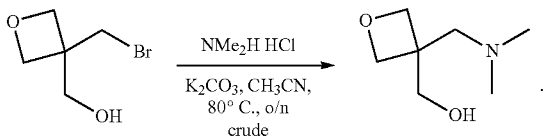

185-1

To a solution of [3-(bromomethyl)oxetan-3-yl]methanol (600 mg, 3.31 mmol) in $CH_3CN$ (30 mL) was added $K_2CO_3$ (1.83 g, 13.26 mmol) and dimethylamine hydrochloride (541 mg, 6.63 mmol). The mixture was stirred at 80° C. for 16 h. After the reaction was complete, the insoluble material was removed by filtration. The filtrate was concentrated under vacuum to give 185-1, which was used in the next step without further purification.

The synthesis of 1-(3-((2,5-dibromo-4-fluorophenoxy) methyl)oxetan-3-yl)-N,N-dimethylmethanamine (185-2):

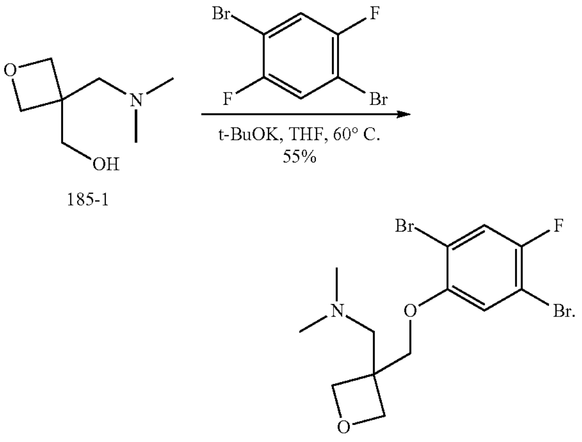

185-1

185-2

To a solution of 185-1 (200 mg, 1.38 mmol) in THF (30 mL) was added t-BuOK (309 mg, 2.75 mmol) and 1,4-dibromo-2,5-difluorobenzene (375 mg, 1.38 mmol). The mixture was stirred at 60° C. for 16 h. After the reaction was complete, the mixture was quenched with water. The insoluble material was removed by filtration, and the filtrate was extracted with EtOAc (30 mL×3). The organic layer was separated, dried over $MgSO_4$, and concentrated under vacuum. The crude residue was purified by column chromatography on silica gel (petroleum ether/EtOAc=1/1) to give 185-2 (300 mg, about 55% yield) as an oil. MS Calcd.: 395.0; MS Found: 396.0 $[M+H]^+$.

The synthesis of $N^1$,$N^4$-bis(2-chloro-4-fluorophenyl)-2-((3-((dimethylamino)methyl)oxetan-3-yl) methoxy)-5-fluorobenzene-1,4-diamine (185-3):

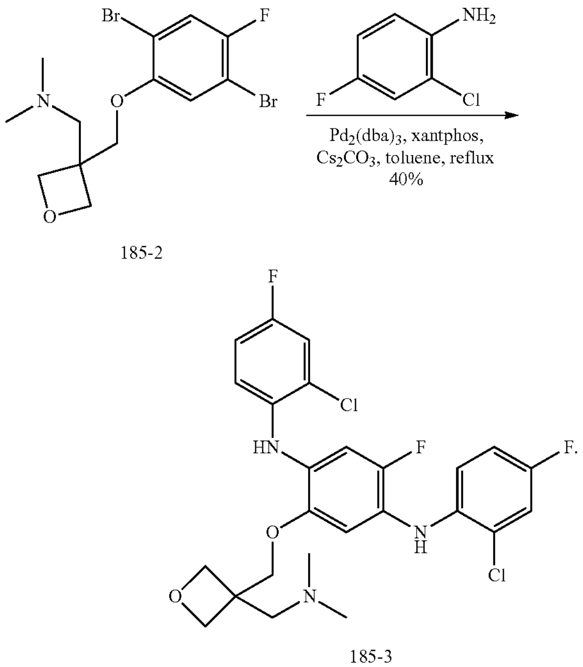

185-2

185-3

A mixture of 185-2 (226 mg, 0.57 mmol), 2-chloro-4-fluoroaniline (166 mg, 1.70 mmol), $Pd_2(dba)_3$ (52 mg, 0.06 mmol), $Cs_2CO_3$ (555 mg, 1.70 mmol) and Xantphos (54 mg, 0.11 mmol) in toluene (10 ml) was stirred at 110° C. under nitrogen atmosphere overnight. After the reaction was complete, the mixture was quenched with water, and filtered. The filtrate was extracted with EtOAc (30 mL×3). The organic layer was separated, dried over $MgSO_4$, and concentrated under vacuum. The crude residue was purified by Prep-HPLC to give 185-3 (120 mg, about 40% yield) as an oil. MS Calcd.: 525.1; MS Found: 526.1 $[M+H]^+$.

The synthesis of N,N-dimethyl-1-(3-((2,8,12-trifluoro-5,11-dihydroindolo[3,2-b]carbazol-6-yloxy) methyl)oxetan-3-yl)methanamine (SS20308-0185-01):

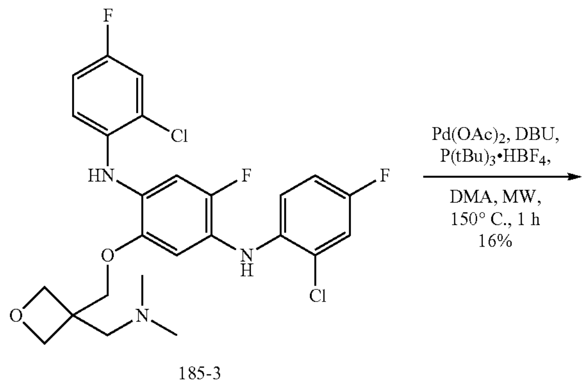

185-3

-continued

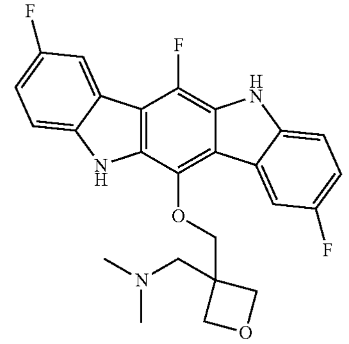

SS20308-0185-01

A mixture of 185-3 (58 mg, 0.11 mmol), DBU (33 mg, 0.21 mmol), $Pd(OAc)_2$ (3 mg, 0.01 mmol), $P(tBu)_3.HBF_4$ (6 mg, 0.02 mmol) in DMA (10 ml) was stirred at 150° C. under microwave irradiation for 1 h. After the reaction was complete, the mixture was quenched with water and filtered. The filtrate was extracted with EtOAc (30 mL×3). The organic layer was separated, dried over $MgSO_4$, filtered, and concentrated under vacuum. The crude residue was purified by Prep-HPLC to give SS20308-0185-01 (8 mg, about 16% yield) as a solid. MS Calcd.: 453.2; MS Found: 454.2 $[M+H]^+$.

$^1$H NMR (400 MHz, DMSO-$d_6$) δ 12.42 (s, 1H), 11.53 (s, 1H), 8.03 (dd, J=9.2 Hz, 2.4 Hz, 1H), 7.89 (dd, J=8.8 Hz, 2.4 Hz, 1H), 7.60 (dd, J=8.8 Hz, 4.4 Hz, 1H), 7.50 (dd, J=8.8 Hz, 4.4 Hz, 1H), 7.37-7.30 (m, 2H), 4.68-4.63 (m, 6H), 3.07 (s, 2H), 2.39 (s, 6H).

Example 60

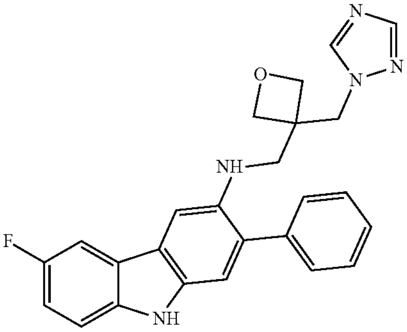

SS20308-0186-01
Chemical Formula: $C_{25}H_{22}FN_5O$
Molecular Weight: 427.47

Example Route for Example 60 (SS20308-00186-01):

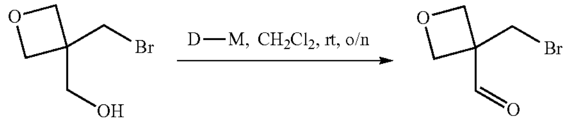

186-1

-continued

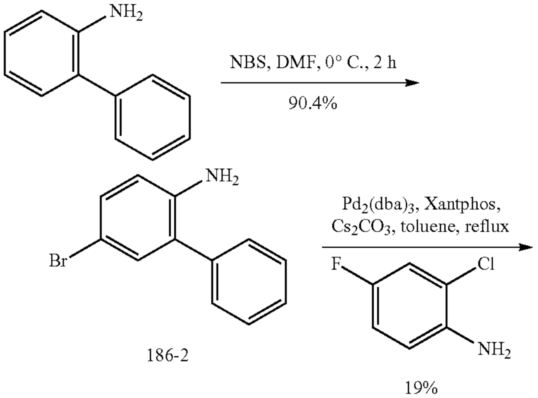

186-2

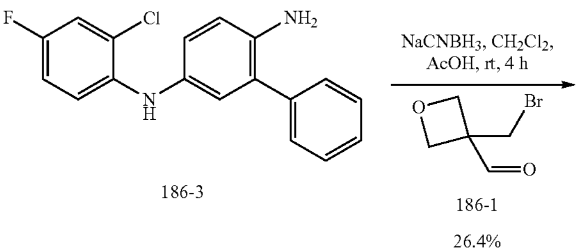

186-3

186-1

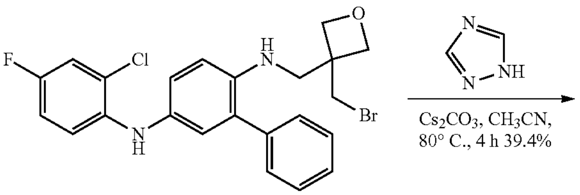

186-4

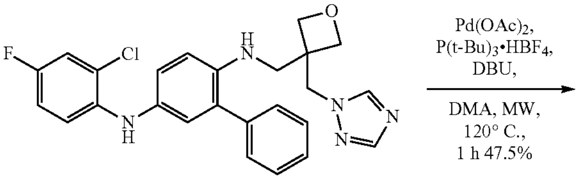

186-5

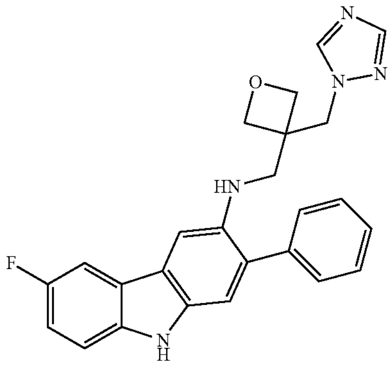

SS20308-0186-01

The synthesis of 3-(bromomethyl)oxetane-3-carbaldehyde (186-1):

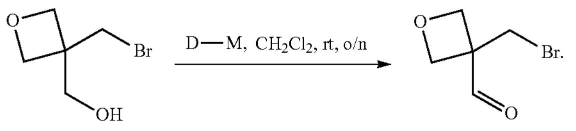

186-1

A mixture of [3-(bromomethyl)oxetan-3-yl]methanol (1 g, 5.4 mmol) and Dess-Martin periodinane (4.6 g, 11.1 mmol) in DCM (20 ml) was stirred overnight. After the reaction was complete, the mixture was quenched with water, and filtered. This crude DCM solution of 186-1 was used in the next step directly without further purification.

The synthesis of 5-bromobiphenyl-2-amine (186-2):

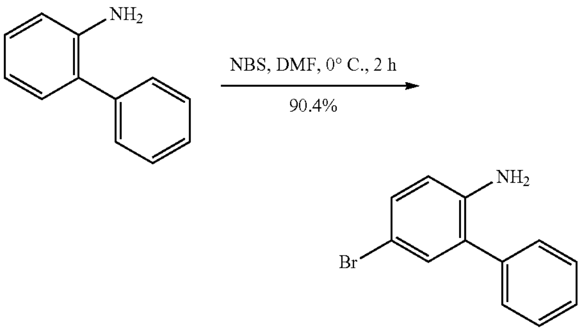

186-2

To a solution of 2-aminobiphenyl (10 g, 59.1 mmol) in DMF (30 mL) was added NBS (10.4 g, 59 mmol,) at 0° C., and stirred for 2 hours. After the reaction was complete, the reaction mixture was added to water, and filtered to give 186-2 (13 g, about 90% yield) as a solid. MS Calcd.: 247.7; MS Found: 248.7[M+H]$^+$.

The synthesis of N5-(2-chloro-4-fluorophenyl)biphenyl-2,5-diamine (186-3):

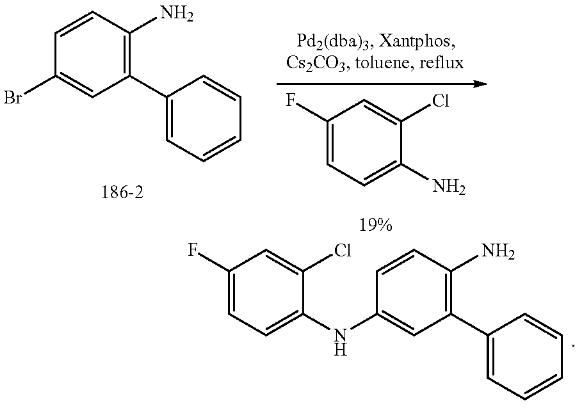

186-3

A mixture of 186-2 (3 g, 12 mmol), 2-chloro-4-fluoroaniline (2 g, 14.4 mmol), $Cs_2CO_3$ (7.8 g, 24 mmol), $Pd_2(dba)_3$ (549 mg, 0.6 mmol) and XantPhos (751 mg, 1.3 mmol) in toluene (20 ml) was stirred at 110° C. under nitrogen atmosphere overnight. After the reaction was complete, the mixture was quenched with water, and filtered. The filtrate was extracted with EtOAc (20 mL×3). The organic layer was separated, dried over $MgSO_4$, filtered, and concentrated. The residue was purified by column chromatography on silica gel (petroleum ether/EtOAc=10/1) to give 186-3 (700 mg, about 19% yield) as an oil. MS Calcd.: 312.7; MS Found: 313.7[M+H]$^+$.

The synthesis of $N^2$-((3-(bromomethyl)oxetan-3-yl)methyl)-$N^5$-(2-chloro-4-fluorophenyl)biphenyl-2,5-diamine (186-4):

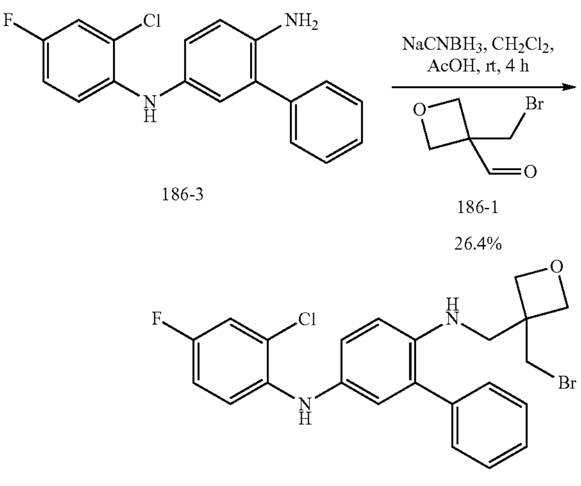

186-4

A solution of 186-3 (700 mg, 2.24 mmol) and 186-1 (482 mg, 2.69 mmol) in DCM (10 mL) was stirred at 0° C. for 0.5 h. To this mixture was added $NaCNBH_3$ (278 mg, 4.48 mmol) and stirred for 4 h. After the reaction was completed, the residue was purified by column chromatography on silica gel (petroleum ether/EtOAc=10/1) to give 186-4 (280 mg, about 26% yield) as an oil. MS Calcd.:474.0; MS Found: 475.0 [M+H]$^+$.

The synthesis of $N^2$-((3-((1H-1,2,4-triazol-1-yl)methyl)oxetan-3-yl)methyl)-$N^5$-(2-chloro-4-fluorophenyl)biphenyl-2,5-diamine (1865):

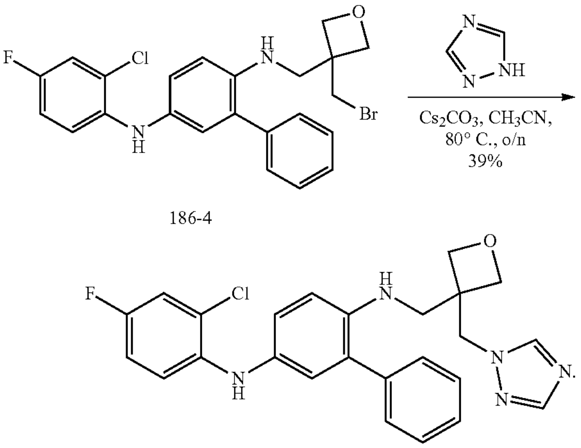

186-5

A mixture of 186-4 (280 mg, 0.59 mmol) and 1H-1,2,4-triazole (100 mg, 1.1 mmol) in ACN (10 mL) was added $Cs_2CO_3$ (400 mg, 1.2 mmol), and stirred at 80° C. overnight. The reaction mixture was quenched with $H_2O$, and extracted with EtOAc (50 mL×3). The organic layers were washed with water and brine, dried over $MgSO_4$ and concentrated. The residue was purified by column chromatography on silica gel (petroleum ether/EtOAc=1/1) give 185-5 (110 mg, about 39% yield) as an oil. MS Calcd.:463.1; MS Found: 464.0 $[M+H]^+$.

The synthesis of N-((3-((1H-1,2,4-triazol-1-yl)methyl) oxetan-3-yl)methyl)-6-fluoro-2-phenyl-9H-carbazol-3-amine (SS20308-0186-01):

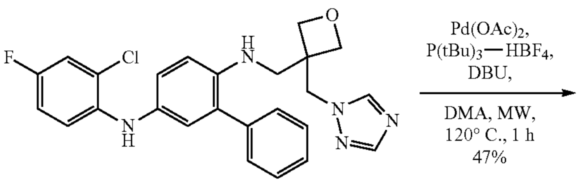

186-5

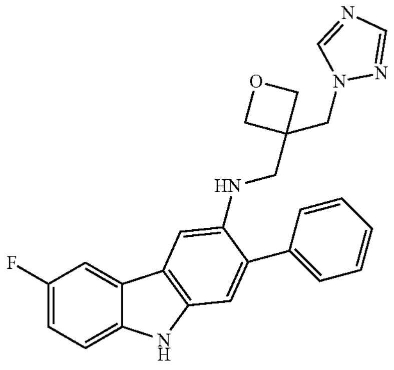

SS20308-0186-01

To a solution of 186-5 (110 mg, 0.2 mmol) in DMA was added $Pd(OAc)_2$ (5 mg, 0.02 mmol), $P(t\text{-}Bu)_3$—$HBF_4$ (10 mg, 0.03 mmol) and DBU (20 mg, 0.1 mmol). The mixture was stirred under microwave irradiation at 120° C. for 1 h. After the reaction was complete, the reaction mixture was quenched with $H_2O$, and extracted with ethyl acetate (50 mL×3). After concentration, the residue was purified by column chromatography on silica gel (petroleum ether/EtOAc=1/1) to give SS20308-0186-01 (48 mg, about 47% yield) as an oil. MS Calcd.: 427.0; MS Found: 428.0 $[M+H]^+$.

$^1H$ NMR (400 MHz, DMSO-$d_6$) δ 10.90 (s, 1H), 8.55 (s, 1H), 7.97 (s, 1H), 7.91-7.89 (m, 1H), 7.53-7.50 (m, 4H), 7.40-7.38 (s, 2H), 7.34 (s, 1H), 7.17 (s, 2H), 4.56 (s, 2H), 4.49 (d, J=6.4 Hz, 2H), 4.40 (d, J=6.0 Hz, 3H), 3.28-3.26 (m, 2H).

Example 61

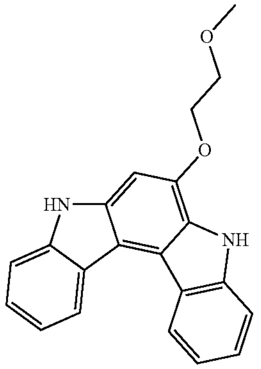

SS20308-0196-01
Chemical Formula: $C_{21}H_{18}N_2O_2$
Molecular Weight: 330.38

Example Route for Example 61 (SS20308-0196-01):

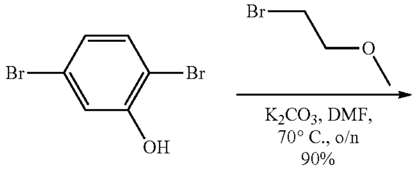

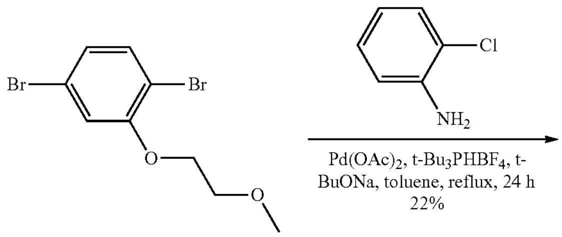

196-1

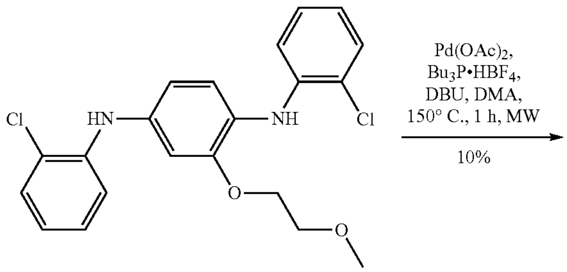

196-2

-continued

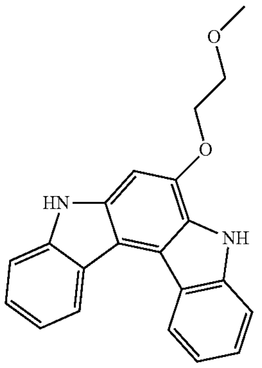

SS20308-0196-01

The synthesis of 1,4-dibromo-2-(2-methoxyethoxy)benzene (196-1):

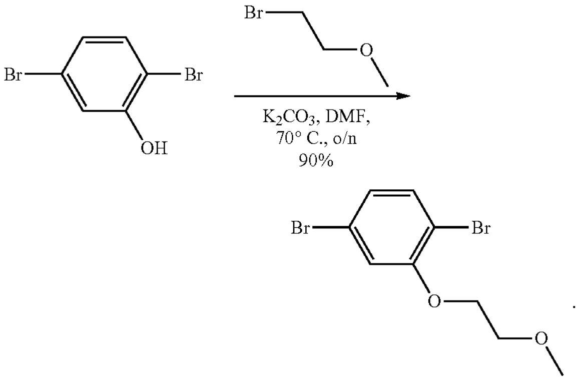

196-1

To a solution of 2,5-dibromophenol (2.0 g, 7.9 mmol) in DMF (30 mL) was added $K_2CO_3$ (2.2 g, 15.8 mmol) and 1-bromo-2-methoxyethane (1.2 g, 8.7 mmol) at room temperature. The reaction mixture was heated to 70° C. overnight. The mixture was cooled to room temperature, diluted with water (50 mL), and extracted with EtOAc (50 mL×3). The combined organic extracts were dried with $MgSO_4$, filtered, and concentrated under reduced pressure to give 196-1 (2.2 g, about 90% yield) as an oil.

The synthesis of N1,N4-bis(2-chlorophenyl)-2-(2-methoxyethoxy)benzene-1,4-diamine (196-2):

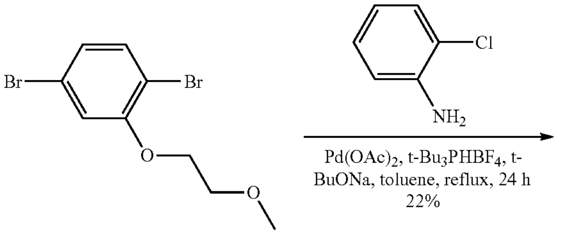

196-1

-continued

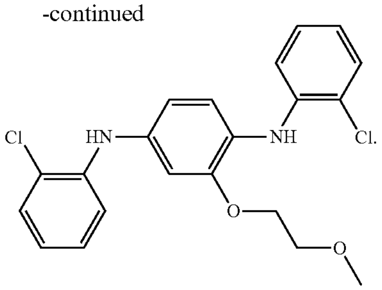

196-2

To a mixture of 196-1 (600 mg, 1.94 mmol) and 2-chloroaniline (615 mg, 4.84 mmol) in toluene (10 mL) was added $Pd(OAc)_2$ (52 mg, 0.20 mmol), $(t\text{-}Bu)_3P$—$HBF_4$ (87 mg, 0.30 mmol), and t-BuONa (541 mg, 5.64 mmol) at room temperature. The mixture was heated to reflux for 8 h under nitrogen. The reaction mixture was cooled to room temperature, filtered, and washed with EtOAc. The filtrate was concentrated to an oil, which was purified by column chromatography on silica gel (petroleum ether/EtOAc=1/3) to give 196-2 (170 mg, about 22% yield) as an oil. MS Calcd.: 402.09; MS Found: 403.3 $[M+H]^+$.

The synthesis of 6-(2-methoxyethoxy)-5,8-dihydroindolo[2,3-c]carbazole (SS20308-0196-01):

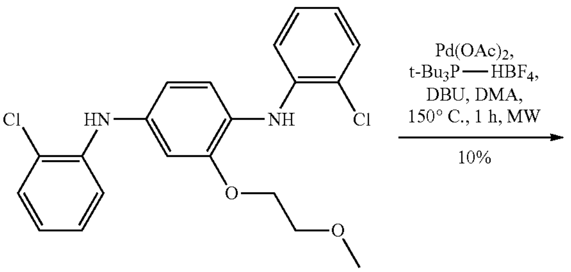

196-2

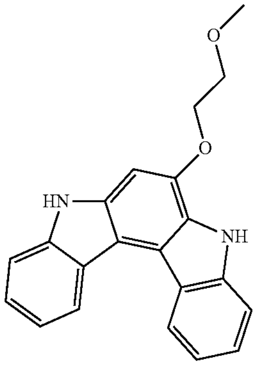

SS20308-0196-01

A mixture of 196-2 (100 mg, 0.25 mmol) and Pd $(OAc)_2$ (7 mg, 0.03 mmol), t-$Bu_3P$—$HBF_4$ (15 mg, 0.05 mmol), DBU (46 mg, 0.3 mmol) in DMA (2 mL) was heated to 150° C. for 1 h in a microwave reactor. The reaction mixture was cooled to room temperature, filtered, and washed with EtOAc. The filtrate was concentrated to an oil, which was purified by Prep-TLC and Prep-HPLC to give SS20308-0196-01 (8 mg, about 10% yield) as a solid. MS Calcd.: 330.1; MS Found: 331.3 $[M+H]^+$.

$^1$H NMR (400 MHz, DMSO-$d_6$) δ 11.33 (m, 2H), 8.67 (d, J=8.0, 1H), 8.59 (d, J=8.0 Hz, 1H), 7.66 (d, J=8.0 Hz, 1H), 7.55 (d, J=7.6 Hz, 1H), 7.42 (dd, J=7.6, 7.6 Hz, 1H), 7.36-7.23 (m, 3H), 7.19 (s, 1H), 4.47-4.43 (m, 2H), 3.91-3.87 (m, 2H), 3.41 (s, 3H).

Example 62

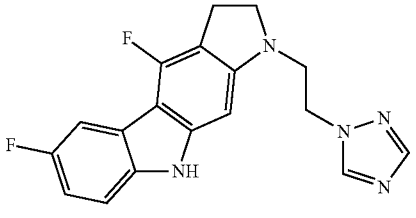

SS20308-0207-01
Chemical Formula: $C_{18}H_{15}F_2N_5$
Molecular Weight: 339.34

Example Route for Example 62 (SS20308-0207-01):

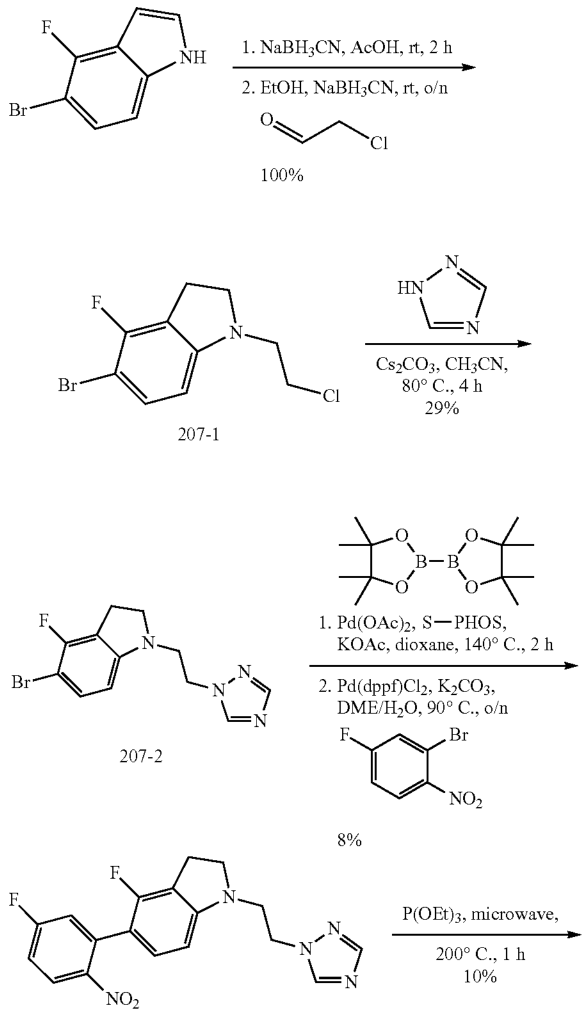

207-1
207-2
207-3

-continued

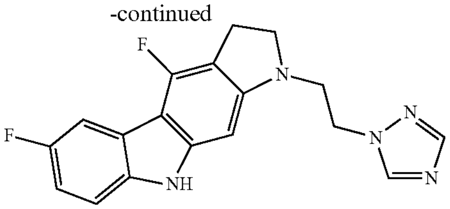

SS20308-0207-01

The synthesis of 5-bromo-1-(2-chloroethyl)-4-fluoroindoline (207-1):

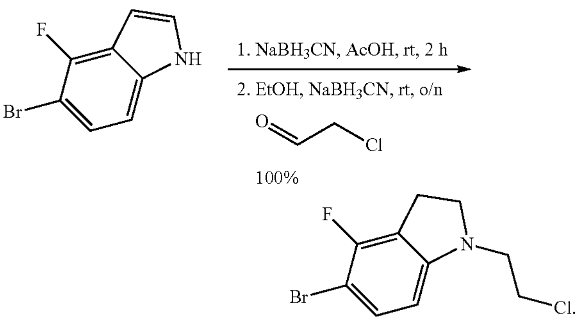

207-1

A mixture of 5-bromo-4-fluoro-1H-indole (3.0 g, 14.0 mmol) and $NaBH_3CN$ (1.77 g, 28.0 mmol) in AcOH (30 mL) was stirred at room temperature for 2 hours. To the reaction mixture was added EtOH (60 mL), $NaBH_3CN$ (1.77 g, 28.0 mmol) and chloroacetaldehyde (5.50 g, 28.0 mmol, 40%) and stirred at room temperature overnight. The reaction mixture was poured into water and basicified with 1N NaOH to pH 10. The mixture was extracted with EtOAc (30 mL×3). The organic layers were washed with brine, dried over $Na_2SO_4$, filtered, and concentrated to give 207-1 (7.0 g, about 100% yield, crude) as an oil. MS Calcd.: 277.0; MS Found: 278.0 $[M+H]^+$.

The synthesis of 1-(2-(1H-1,2,4-triazol-1-yl)ethyl)-5-bromo-4-fluoroindoline (207-2):

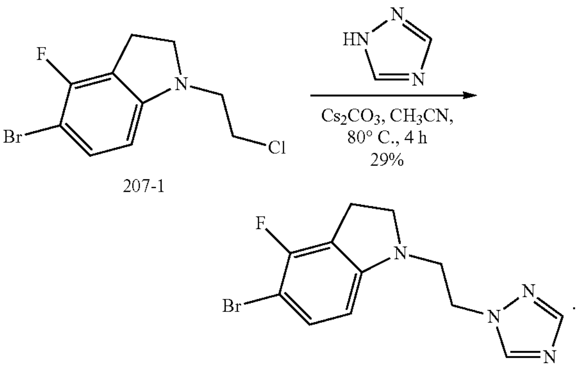

207-1

207-2

A mixture of 207-1 (7.0 g, 25.1 mmol), 1H-1,2,4-triazole (3.45 g, 50.2 mmol) and $Cs_2CO_3$ (16.3 g, 50.2 mmol) in $CH_3CN$ (150 mL) was stirred at 80° C. overnight. The reaction mixture was then cooled to room temperature and filtered through celite and concentrated. The residue was purified by column chromatography on silica gel (petroleum ether/EtOAc=1/1) to give 207-2 (2.25 g, about 29% yield) as a solid. MS Calcd.: 310.0; MS Found: 311.0 [M+H]+.

The synthesis of 1-(2-(1H-1,2,4-triazol-1-yl)ethyl)-4-fluoro-5-(5-fluoro-2-nitrophenyl)indoline (207-3):

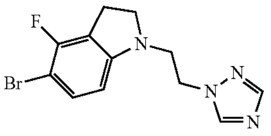

207-2

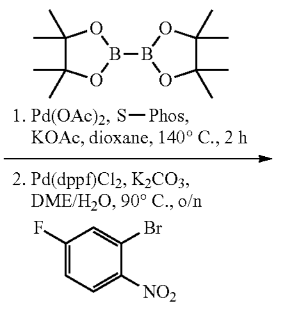

8%

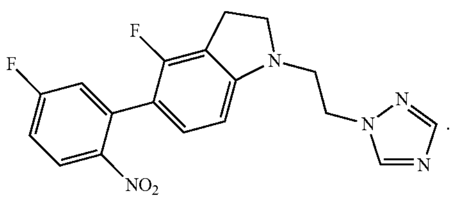

207-3

A mixture of 207-2 (1.50 g, 4.82 mmol), bis(pinacolato) diboron (1.47 g, 5.80 mmol), $Pd(OAc)_2$ (130 mg, 0.580 mmol), S-Phos (476 mg, 1.16 mmol) and AcOK (1.89 g, 19.3 mmol) in 1,4-dioxane (15 mL) were stirred at 140° C. for 2 hours in a microwave reactor. The mixture was filtered through celite and concentrated. Then the crude residue, 2-bromo-4-fluoro-1-nitrobenzene (1.06 g, 4.82 mmol), $Pd(dppf)Cl_2$ (415 mg, 0.580 mmol) and $K_2CO_3$ (1.33 g, 9.64 mmol) in $DME/H_2O$ (22 mL, 10/1) were stirred at 90° C. overnight under $N_2$ (g) atmosphere. The resulting mixture was filtered through celite and washed with MeOH. The filtrate was extracted with EtOAc (80 mL×3). The organic layers were washed with brine, dried over $Na_2SO_4$, filtered, and concentrated. The residue was purified by column chromatography on silica gel (petroleum ether/EtOAc=1/1) to give 207-3 (150 mg, about 8% yield) as an oil. MS Calcd.: 371.1; MS Found: 372.1 [M+H]+.

The synthesis of 1-(2-(1H-1,2,4-triazol-1-yl)ethyl)-4,6-difluoro-1,2,3,9-tetrahydropyrrolo[2,3-b]carbazole (SS20308-0207-01):

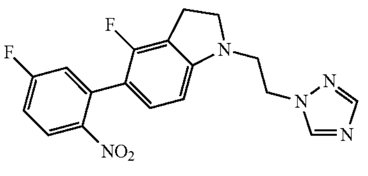

207-3

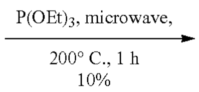

-continued

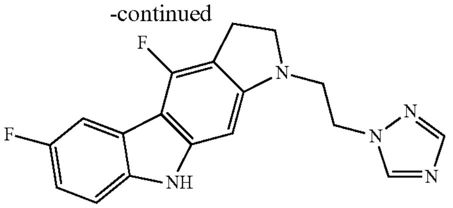

SS20308-0207-01

A mixture of 207-3 (150 mg, 0.40 mmol) in $P(OEt)_3$ (2 mL) was stirred at 200° C. for an hour in a microwave reactor. The reaction mixture concentrated to a residue, which was purified by Prep-HPLC to give SS20308-207-01 (13.6 mg, about 10% yield) as a solid. MS Calcd.: 339.1; MS Found: 340.3 [M+H]+.

$^1H$ NMR (400 MHz, DMSO-$d_6$) δ 11.09 (s, 1H), 8.54 (s, 1H), 7.99 (s, 1H), 7.47-7.43 (m, 1H), 7.33-7.28 (m, 2H), 7.06-7.00 (m, 1H), 6.12 (s, 1H), 4.45 (t, J=6.0 Hz, 2H), 3.62 (t, J=5.8 Hz, 2H), 3.48 (t, J=8.2 Hz, 2H), 3.02 (t, J=8.2 Hz, 2H).

Example 63

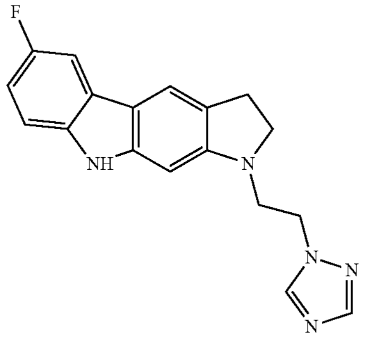

SS20308-0208-01
Chemical Formula: $C_{18}H_{16}FN_5$
Molecular Weight: 321.35

Example 64

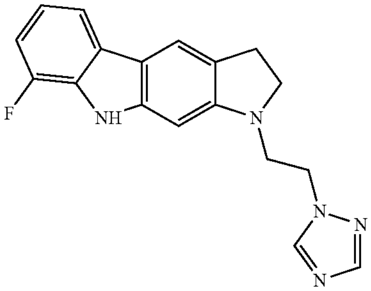

SS20308-0243-01
Chemical Formula: $C_{18}H_{16}FN_5$
Molecular Weight: 321.35

Example Route for Example 63 (SS20308-0208-01) and Example 64 (SS20308-0243-01):

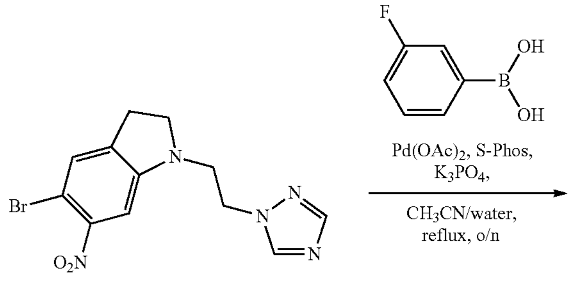

180-3

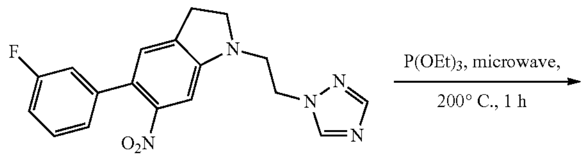

208-1

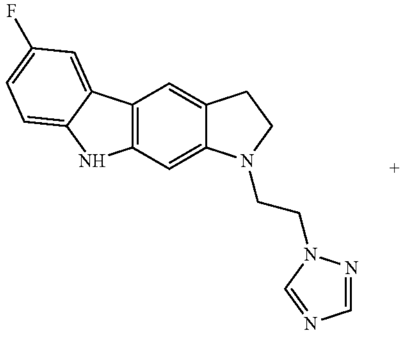

SS20308-0208-01

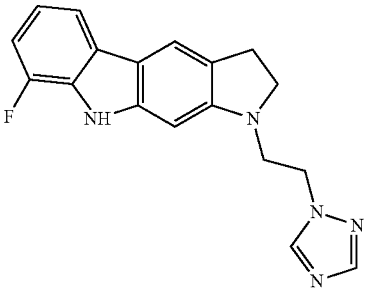

SS20308-0243-01

The synthesis of 1-(2-(1H-1,2,4-triazol-1-yl)ethyl)-5-(3-fluorophenyl)-6-nitroindoline (208-1):

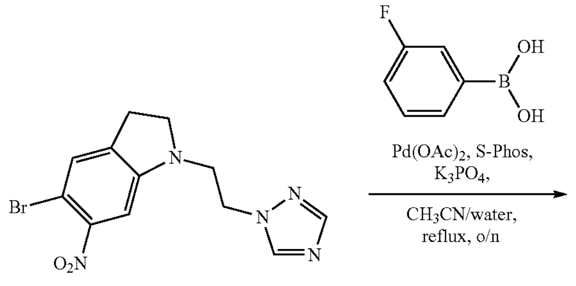

180-3

-continued

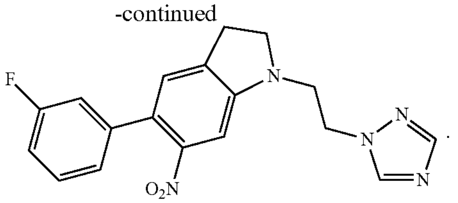

208-1

A solution of 180-3 (300 mg, 0.88 mmol), 3-fluorophenylboronic acid (186 mg, 1.33 mmol), S-Phos (32 mg, 0.08 mmol), $Pd(OAc)_2$ (20 mg, 0.08 mmol), and $K_3PO_4$ (470 mg, 2.22 mmol) were suspended in $CH_3CN$ (6 mL) and water (2 mL). The reaction mixture was heated at reflux for overnight under nitrogen atmosphere. The mixture was poured into water, and the water layer was extracted with EtOAc (10 mL×2). The combined organic layers were washed with brine, dried over $Na_2SO_4$, filtered and concentrated. The residue was purified by Prep-TLC (DCM/MeOH=20/1) to give 208-1 (236 mg, about 75% yield) as an oil. MS Calcd.: 353.4; MS Found: 354.1 $[M+H]^+$.

The synthesis of 1-(2-(1H-1,2,4-triazol-1-yl)ethyl)-6-fluoro-1,2,3,9-tetrahydropyrrolo[2,3-b]carbazole (SS20308-0208-01) and 1-(2-(1H-1,2,4-triazol-1-yl)ethyl)-8-fluoro-1,2,3,9-tetrahydropyrrolo[2,3-b]car bazole (SS20308-0243-01):

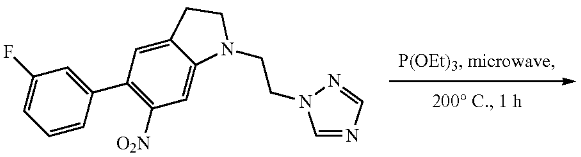

208-1

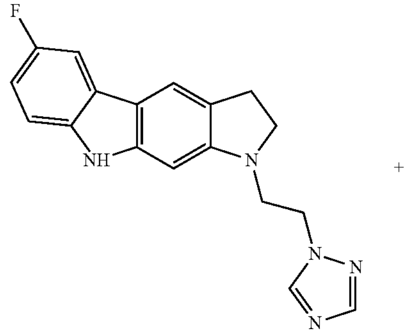

SS20308-0208-01

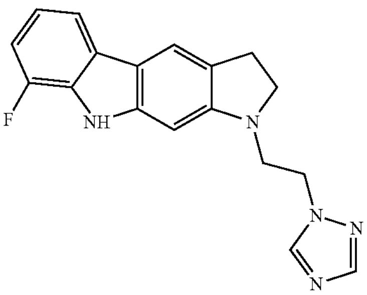

SS20308-0243-01

A solution of 208-1 (230 mg, 0.65 mmol) in $P(OEt)_3$ (2 mL) was stirred in a microwave reactor at 200° C. for 1 h. After the reaction was completed, the mixture was concentrated to a crude residue, which was purified by reverse phase column chromatography, Prep-TLC (petroleum ether/acetone=1/1) and Prep-HPLC to give SS20308-0208-01 (4.6 mg, about 2% yield) as a solid and SS20308-0243-01 (4.7 mg, about 2% yield) as a solid.

SS20308-0208-01: MS Calcd.: 321.4; MS Found: 322.3 $[M+H]^+$. $^1H$ NMR (400 MHz, DMSO-$d_6$) δ 10.81 (s, 1H), 8.55 (s, 1H), 7.99 (s, 1H), 7.65-7.61 (m, 2H), 7.28-7.24 (m, 1H), 6.95 (td, J=9.0 Hz 2.2 Hz, 1H), 6.32 (s, 1H), 4.46 (t, J=5.8 Hz, 2H), 3.59 (t, J=5.8 Hz, 2H), 3.40 (t, J=8.0 Hz, 2H), 2.98 (t, J=8.0 Hz, 2H).

SS20308-0243-01: MS Calcd.: 321.4; MS Found: 322.2 $[M+H]^+$. $^1H$ NMR (400 MHz, DMSO-$d_6$) δ 11.20 (s, 1H), 8.55 (s, 1H), 8.00 (s, 1H), 7.67-7.64 (m, 2H), 7.00-6.96 (m, 2H), 6.33 (s, 1H), 4.47 (t, J=6.0 Hz, 2H), 3.59 (t, J=6.0 Hz, 2H), 3.41 (t, J=8.2 Hz, 2H), 2.99 (t, J=8.0 Hz, 2H).

Example 65

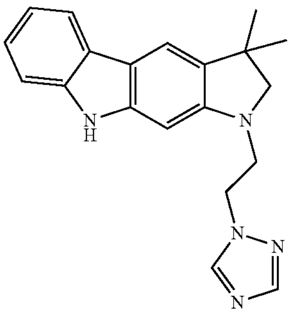

SS20308-0209-01
Chemical Formula: $C_{20}H_{21}N_5$
Molecular Weight: 331.42

Example Route for Example 65 (SS20308-0209-01):

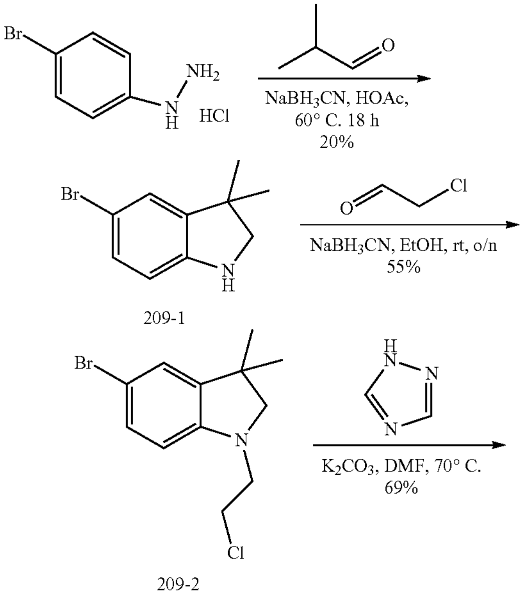

-continued

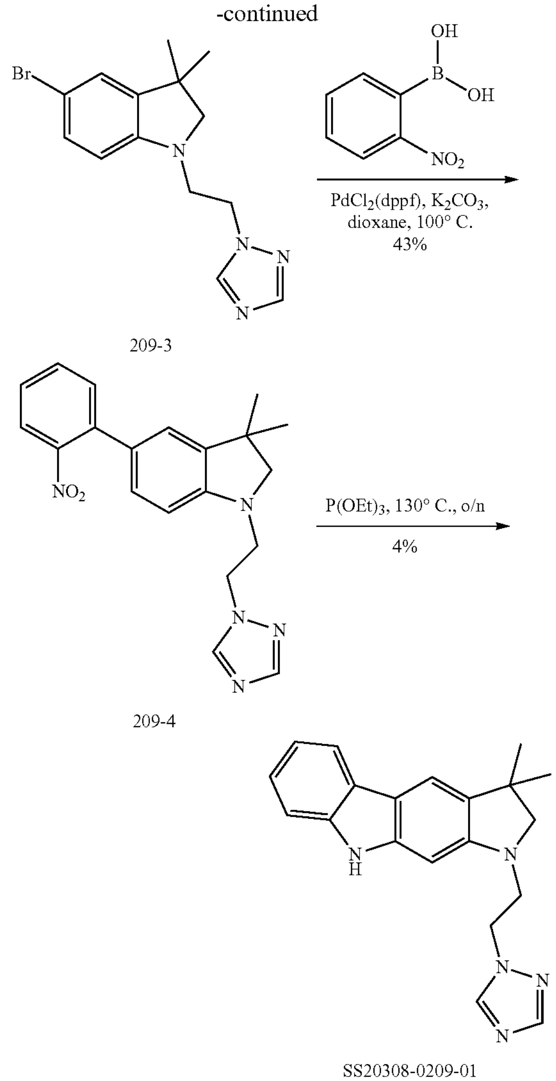

The synthesis of 5-bromo-3,3-dimethylindoline (209-1):

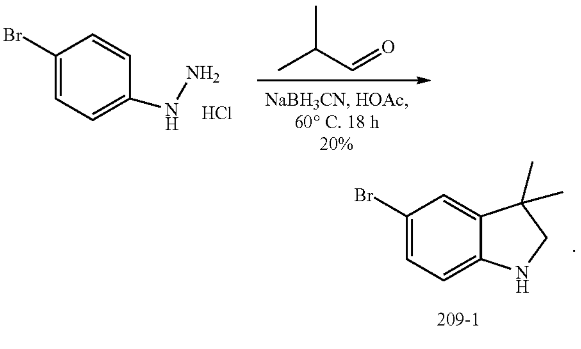

A mixture of 4-bromophenylhydrazine hydrochloride (10 g, 45 mmol), isobutyraldehyde (3.2 g, 45 mol) and $NaBH_3CN$ (2.9 g, 45 mmol) in AcOH (200 mL) was stirred at 60° C. for 18 h. After the reaction was complete, the reaction mixture was concentrated, quenched with water (100 mL), and extracted with EtOAc (100 mL×3). The combined layers were dried over $Na_2SO_4$, filtered, and concentrated under vacuum. The residue was purified by column chromatography on silica gel (petroleum ether/EtOAc=5/1) to give 209-1 (2 g, about 20% yield) as an oil. MS Calcd.: 225.0; MS Found: 226.2 [M+H]$^+$.

The synthesis of 5-bromo-1-(2-chloroethyl)-3,3-dimethylindoline (209-2):

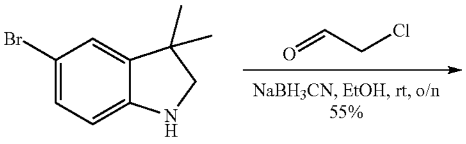

209-1

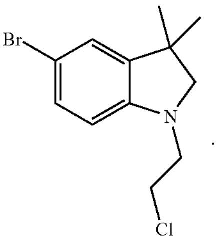

209-2

A mixture of 209-1 (1 g, 4.4 mmol), 2-chloroacetaldehyde (1 g, 13.2 mol) and $NaBH_3CN$ (286 mg, 4.4 mmol) in EtOH (20 mL) was stirred at rt overnight. After the reaction was complete, the reaction mixture was concentrated, quenched with water (50 mL), and extracted with EtOAc (50 mL×3). The combined organic layers were dried over $Na_2SO_4$, filtered, and concentrated under vacuum. The residue was purified by column chromatography on silica gel (petroleum ether/EtOAc=5/1) to give 209-2 (700 mg, about 55% yield) as a solid. MS Calcd.: 287.0; MS Found: 288.2 [M+H]$^+$.

The synthesis of 1-(2-(1H-1,2,4-triazol-1-yl)ethyl)-5-bromo-3,3-dimethylindoline (209-3):

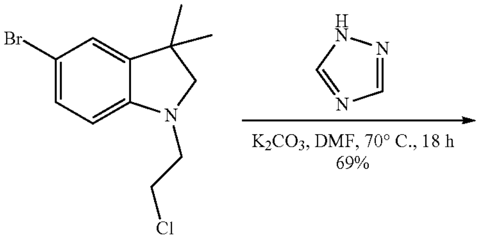

209-2

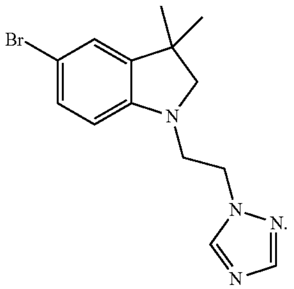

209-3

A mixture of 1H-1,2,4-triazole (331 mg, 4.8 mmol), 209-2 (700 mg, 2.4 mmol) and $K_2CO_3$ (994 mg, 7.2 mmol) in DMF (5 mL) was stirred at 70° C. for 18 h. After the reaction was complete, the reaction mixture was concentrated, diluted with water (10 mL), and extracted with EtOAc (10 mL×3). The combined layers were dried over $Na_2SO_4$ and concentrated under vacuum. The crude product, was purified by column chromatography (petroleum ether/EtOAc=5/1) to give 209-3 (530 mg, about 69% yield) as a solid. MS Calcd.: 320.1; MS Found: 321.2 [M+H]$^+$.

The synthesis of 1-(2-(1H-1,2,4-triazol-1-yl)ethyl)-3,3-dimethyl-5-(2-nitrophenyl)indoline (209-4):

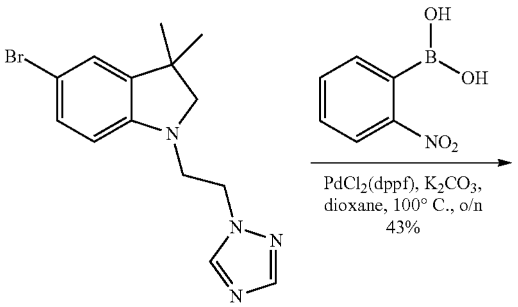

209-3

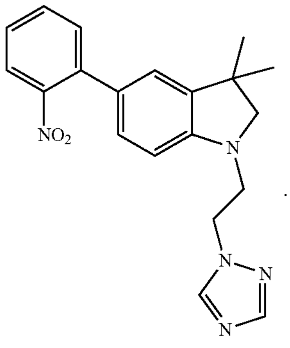

209-4

A mixture of 2-nitrophenylboronic acid (321 mg, 1.9 mmol), 209-3 (150 mg, 1.6 mmol), $PdCl_2$(dppf) (58 mg, 0.08 mmol) and $K_2CO_3$ (1.5 g, 4.8 mmol) in toluene (5 mL) and water (1 mL) was stirred at 100° C. for 18 h. After the reaction was complete, the reaction mixture was filtered, concentrated, diluted with water (20 mL), and extracted with EtOAc (20 mL×3). The combined layers were dried over $Na_2SO_4$, filtered, and concentrated under vacuum. The crude product was purified by column chromatography on silica gel (petroleum ether/EtOAc=5/1) to give 209-4 (250 mg, about 43% yield) as a solid. MS Calcd.: 363.2; MS Found: 364.4 [M+H]$^+$.

The synthesis of 1-(2-(1H-1,2,4-triazol-1-yl)ethyl)-3,3-dimethyl-1,2,3,9-tetrahydropyrrolo[2,3-b] carbazole (SS20308-0209-01):

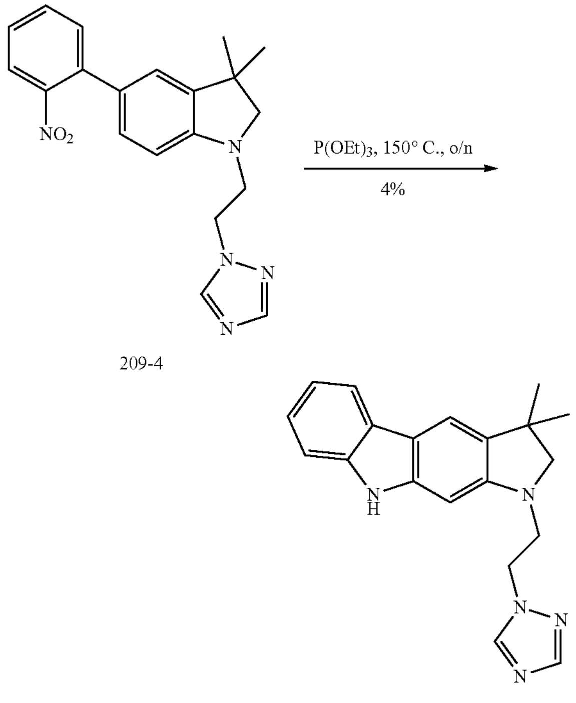

209-4

SS20308-0209-01

To a solution of 209-4 (150 mg, 0.4 mmol) in $P(OEt)_3$ (2 mL) was stirred at 150° C. for 18 h. The mixture was concentrated to a crude residue, which was purified by Prep-HPLC twice to give SS20308-0209-01 (4.2 mg, about 5% yield) as a solid. MS Calcd.: 331.4; MS Found: 332.3 $[M+H]^+$.

$^1$H NMR (400 MHz, DMSO-$d_6$) δ 10.81 (s, 1H), 8.52 (s, 1H), 8.00 (s, 1H), 7.84 (d, J=8.0 Hz, 1H), 7.62 (s, 1H), 7.30 (d, J=7.6 Hz, 1H), 7.14 (t, J=7.6 Hz, 1H), 1H), 7.01 (t, J=7.6 Hz, 1H), 6.33 (s, 1H), 4.47 (t, J=6.0 Hz, 2H), 3.57 (t, J=5.6 Hz, 2H), 3.12 (s, 2H), 1.26 (s, 6H).

Example 66

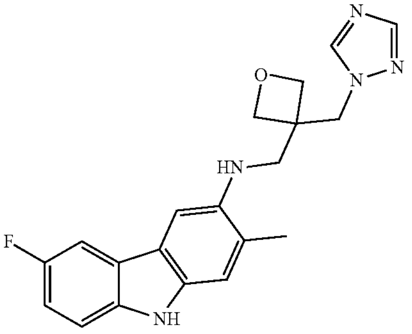

SS20308-0233-01
Chemical Formula: $C_{20}H_{20}FN_5O$
Molecular Weight: 365.40

Example Route for Example 66 (SS20308-0233-01):

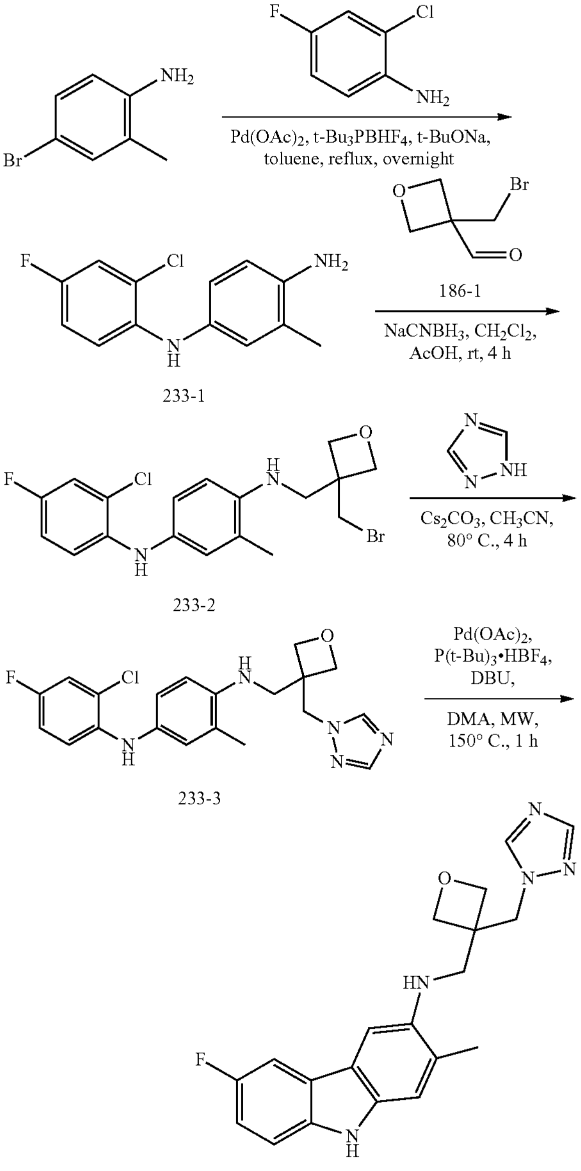

233-1

233-2

233-3

SS20308-0233-01

The synthesis of N1-(2-chloro-4-fluorophenyl)-3-methyl-benzene-1,4-diamine (233-1):

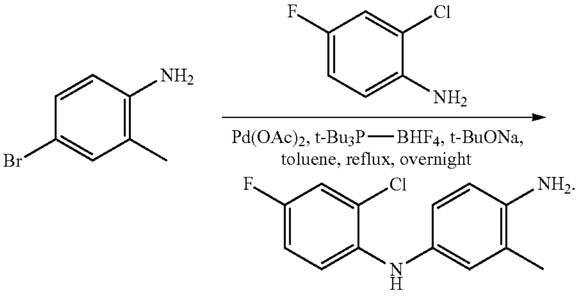

233-1

A mixture of 4-bromo-2-methylaniline (3.0 g, 7.8 mmol), 2-chloro-4-fluoroaniline (2.3 g, 15.6 mmol), $Pd(OAc)_2$ (176 mg, 0.78 mmol), $t\text{-}Bu_3P\text{—}BHF_4$ (339 mg, 1.17 mmol), t-BuONa (2.3 g, 23.4 mmol) in toluene (300 mL) was bubbled with nitrogen for 20 mins. Then the reaction mixture was heated to reflux overnight under nitrogen. The mixture was cooled to room temperature, filtered, and washed with EtOAc. The filtrate was washed with brine and dried over $Na_2SO_4$. After filtration, the organic filtrate was concentrated to an oil, which was purified by column chromatography on silica gel (petroleum ether/EtOAc=1/10) to give 233-1 (750 mg, about 19% yield) as an oil. MS Calcd.: 250.1; MS Found: 251.1 $[M+H]^+$.

The synthesis of N1-((3-(bromomethyl)oxetan-3-yl)methyl)-N4-(2-chloro-4-fluorophenyl)-2-methylbenzene-1,4-diamine (233-2):

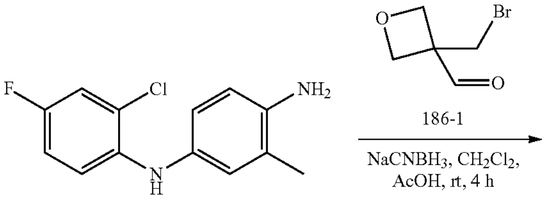

233-1

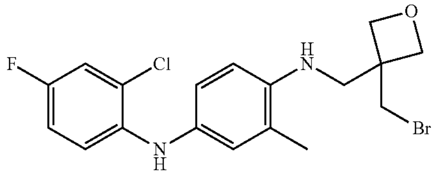

233-2

To a solution of 233-1 (750 mg, 3.0 mmol) in DCM (10 mL) was added 3-(bromomethyl)oxetane-3-carbaldehyde 186-1 (534 mg, 3.0 mmol). $NaCNBH_3$ (189 mg, 3.0 mmol) was then added in several portions, followed by AcOH (0.1 mL). The mixture was stirred at room temperature for 4 h under nitrogen. The mixture was diluted with $H_2O$ and the DCM phase was separated and dried over $Na_2SO_4$. After filtration, the crude product was concentrated to oil, which was purified by column chromatography on silica gel (petroleum ether/EtOAc=1/5) to give 233-2 (400 mg, about 32% yield) as an oil. MS Calcd.: 412.0; MS Found: 413.9 $[M+H]^+$.

The synthesis of N1-((3-((1H-1,2,4-triazol-1-yl)methyl)oxetan-3-yl)methyl)-N4-(2-chloro-4-fluorophenyl)-2-methylbenzene-1,4-diamine (SS20308-0272-01):

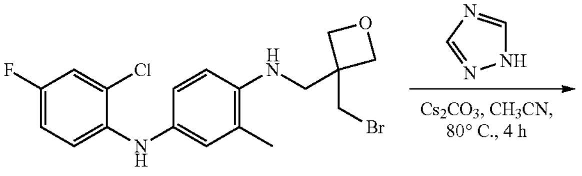

233-2

-continued

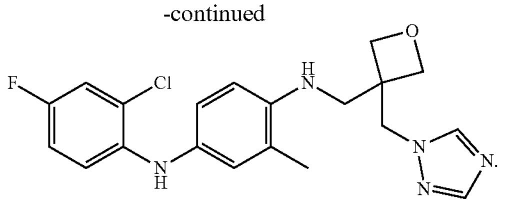

233-3

To a solution of 233-2 (400 mg, 0.97 mmol) in $CH_3CN$ (10 mL) was added 1H-1,2,4-triazole (69 mg, 1 mmol), and $Cs_2CO_3$ (919 mg, 2.82 mmol) at room temperature. The mixture was heated to 80° C. for 4 h under nitrogen. The reaction mixture was cooled to room temperature. The mixture was filtered, and washed with EtOAc. The filtrate was concentrated to an oil, which was purified by reverse phase column chromatography to give 233-3 (200 mg, about 51% yield) as a solid. MS Calcd.: 401.1; MS Found: 402.0 $[M+H]^+$.

$^1H$ NMR (400 MHz, DMSO-$d_6$) δ 8.54 (s, 1H), 8.03 (s, 1H), 7.30 (dd, J=8.4, 3.2 Hz, 1H), 7.00-6.93 (m, 2H), 6.84-6.76 (m, 3H), 6.44 (d, J=8.4 Hz, 1H), 4.73 (t, J=5.8 Hz, 1H), 4.65 (s, 2H), 4.54 (d, J=6.4, 2H), 4.45 (d, J=6.0, 2H), 3.17 (d, J=5.6, 2H), 2.13 (s, 3H).

The synthesis of N-((3-((1H-1,2,4-triazol-1-yl)methyl)oxetan-3-yl)methyl)-6-fluoro-2-methyl-9H-carbazol-3-amine (SS20308-0233-01):

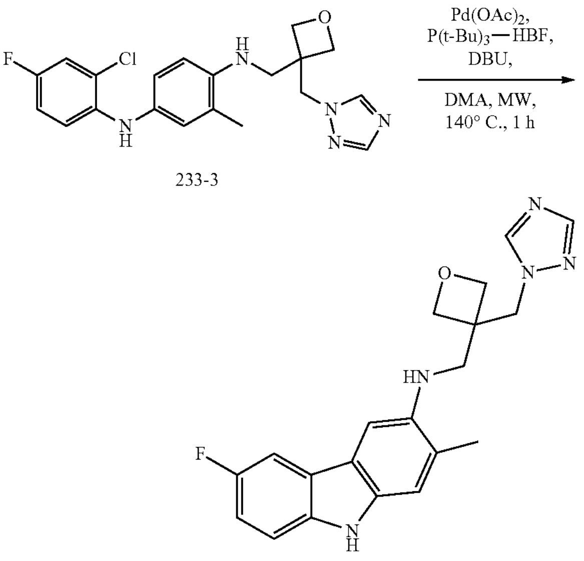

SS20308-0233-01

A mixture of 233-3 (200 mg, 0.5 mmol), $Pd(OAc)_2$ (12 mg, 0.05 mmol), $t\text{-}Bu_3P\text{—}BHF_4$ (22 mg, 0.075 mmol), and DBU (304 mg, 2 mmol) in DMA (3 mL) was bubbled with nitrogen for 20 mins. Then the reaction mixture was heated to 140° C. for 1 h in a microwave reactor. The mixture was cooled to room temperature, filtered, and washed by EtOAc. The filtrate was washed with brine and dried over $Na_2SO_4$. After filtration, the filtrate was concentrated to an oil, which was purified by Prep-TLC and Prep-HPLC to give SS20308-0233-01 (13 mg, about 7% yield) as a solid. MS Calcd.: 365.2; MS Found: 366.4 $[M+H]^+$.

$^1$H NMR (400 MHz, DMSO-$d_6$ and $D_2O$) δ 8.56 (s, 1H), 8.07 (s, 1H), 7.74 (dd, J=9.6, 2.4 Hz, 1H), 7.37 (dd, J=8.8, 4.8 Hz, 1H), 7.22 (s, 1H), 7.15-7.08 (m, 2H), 4.72 (s, 2H), 4.61 (d, J=6.4, 2H), 4.53 (d, J=6.4, 2H), 3.29 (s, 2H), 2.32 (s, 3H).

Example 67

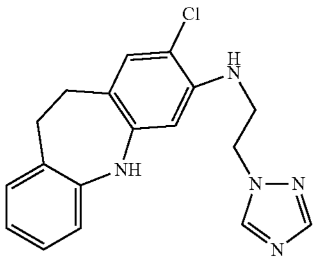

SS20308-0251-01
Chemical Formula: $C_{18}H_{18}ClN_5$
Molecular Weight: 339.82

Example 68

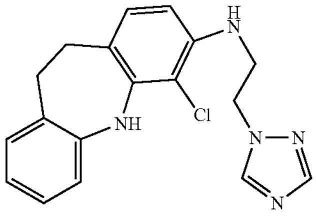

SS20308-0273-01
Chemical Formula: $C_{18}H_{18}ClN_5$
Molecular Weight: 339.82

Example Route for Example 67 (SS20308-0251-01) and Example 68 (SS20308-0273-01):

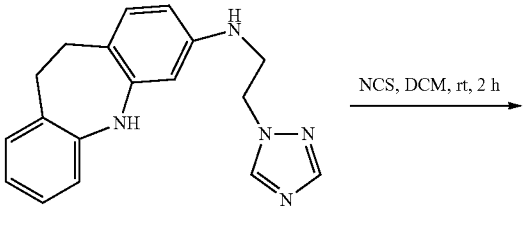

SS20308-0224-01

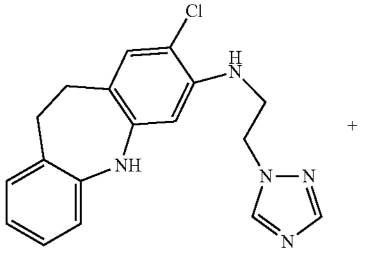

SS20308-0251-01
21%

-continued

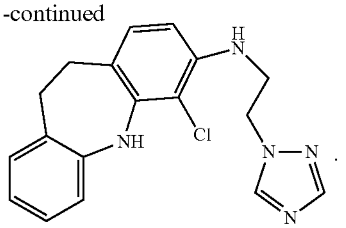

SS20308-0273-01
5%

The synthesis of N-(2-(1H-1,2,4-triazol-1-yl)ethyl)-2-chloro-10,11-dihydro-5H-dibenzo[b,f]azepin-3-amine (SS20308-0251-01) and N-(2-(1H-1,2,4-triazol-1-yl)ethyl)-4-chloro-10,11-dihydro-5H-dibenzo [b,f]azepin-3-amine (SS20308-0273-01):

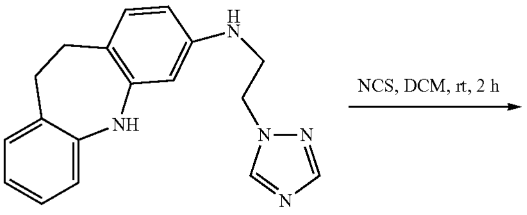

SS20308-0224-01

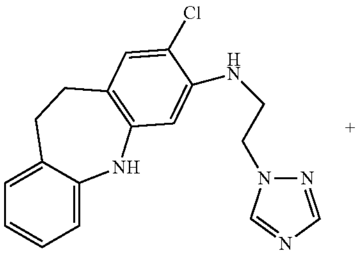

SS20308-0251-01
21%

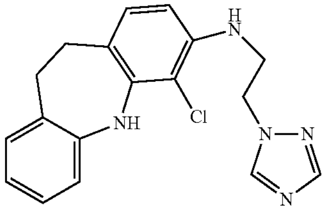

SS20308-0273-01
5%

A mixture of SS20308-0224-01 (50 mg, 0.16 mmol) and NCS (21.86 mg, 0.16 mmol) in DMF (0.5 mL) was stirred at rt for 2 hr. After the reaction was complete, the reaction mixture was quenched with water (10 mL), and extracted with EtOAc (10 mL×3). The combined layers were dried over $Na_2SO_4$ and concentrated under vacuum. The mixture was purified by Prep-HPLC and SFC to give SS20308-0251-01 (13.03 mg, about 21% yield) as a solid, and SS20308-0273-01 (2.64 mg, about 5% yield) as a solid.

SS20308-0251-01: MS Calcd.: 339.82; MS Found: 340.2 $[M+H]^+$. $^1$H NMR (400 MHz, DMSO-$d_6$) δ 8.52 (s, 1H), 8.22 (s, 1H), 8.01 (s, 1H), 7.04-6.97 (m, 2H), 6.91-6.89 (m, 2H), 6.67-6.63 (m, 1H), 6.40 (s, 1H), 5.19 (t, J=6.0 Hz, 1H), 4.44 (t, J=6.0 Hz, 2H), 3.49 (q, J=6.0 Hz, 2H), 2.91-2.89 (m, 2H), 2.83-2.82 (m, 2H).

SS20308-0273-01: MS Calcd.: 339.82; MS Found: 340.2 $[M+H]^+$. $^1H$ NMR (400 MHz, DMSO-$d_6$) δ 8.49 (s, 1H), 7.99 (s, 1H), 7.13-7.10 (m, 2H), 7.07-7.01 (m, 2H), 6.84 (d, J=8.4 Hz, 1H), 6.75-6.71 (m, 1H), 6.21 (d, J=8.0 Hz, 1H), 5.37 (t, J=5.6 Hz, 1H), 4.38 (t, J=6.4 Hz, 2H), 3.53 (q, J=6.0 Hz, 2H), 2.92 (q, J=6.0 Hz, 4H).
Example 69
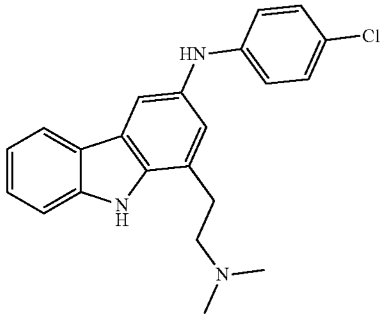
SS20308-0257-01
Chemical Formula: $C_{22}H_{22}ClN_3$
Molecular Weight: 363.88
Example Route for Example 69 (SS20308-0257-01):
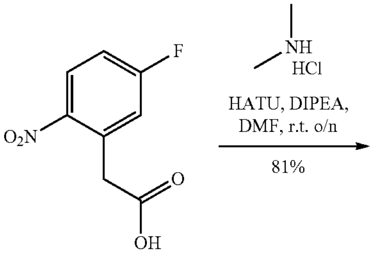
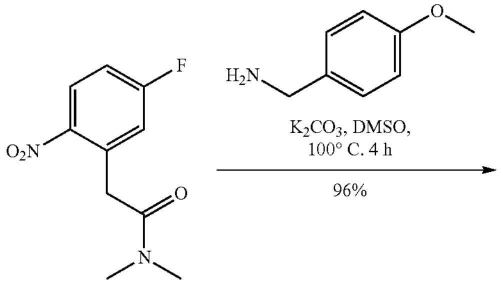
257-1
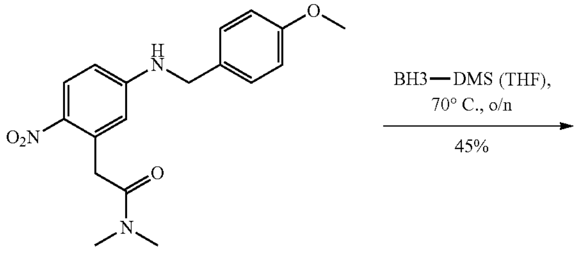
257-2
-continued
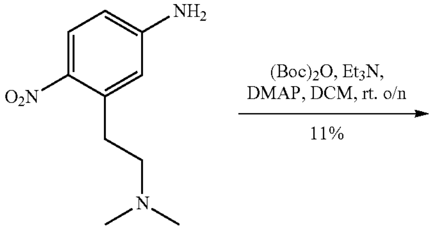
257-3
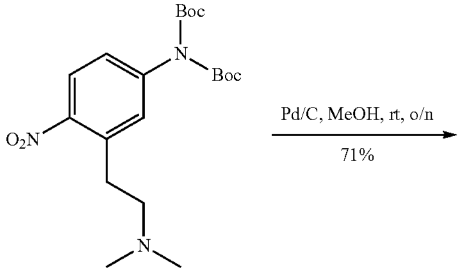
257-4
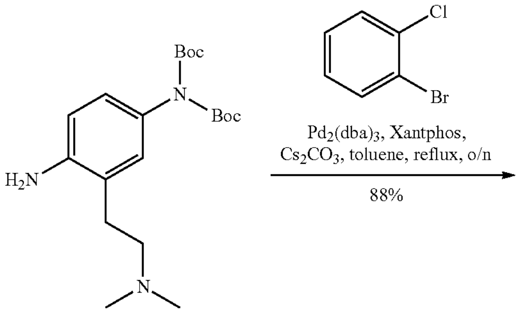
257-5
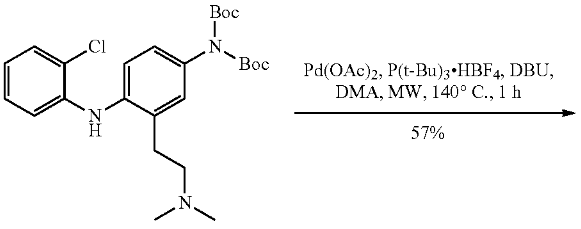
257-6
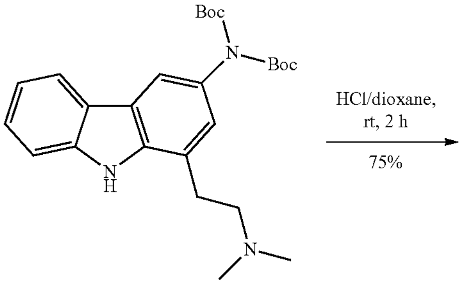
257-7

-continued

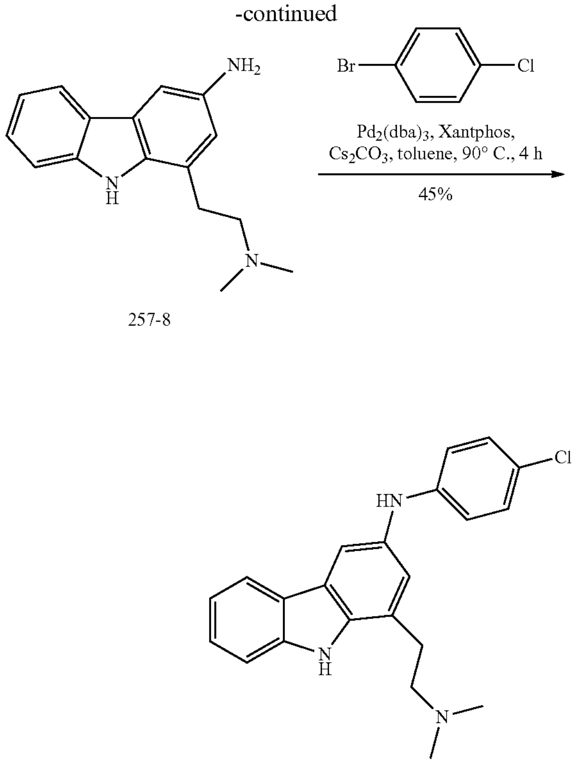

257-8

SS20308-0257-01

The synthesis of 2-(5-fluoro-2-nitrophenyl)-N,N-dimethylacetamide (257-1):

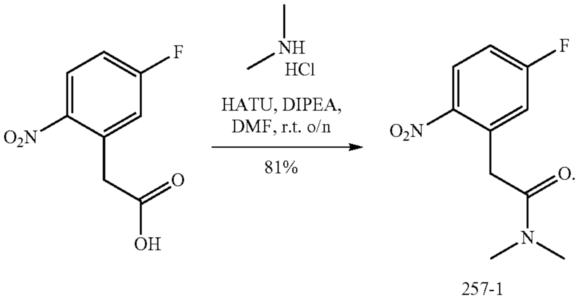

257-1

A mixture of 5-fluoro-2-nitrobenzeneacetic acid (15 g, 75.3 mmol), dimethylamine hydrochloride (12.1 g, 150 mmol), HATU (57.2 g, 150 mmol) and DIPEA (19.4 g, 150 mmol) in DMF (250 mL) was stirred at room temperature for overnight. Then the reaction mixture was concentrated and poured into water (750 mL). The resulting mixture was extracted with EtOAc (500 mL×3), washed with brine, dried over $Na_2SO_4$, and concentrated. The residue were purified by column chromatography on silica gel (petroleum ether/EtOAc=3/1) to give 257-1 (22.5 g, about 81% yield) as an oil. MS Calcd.: 226.1; MS Found: 227.3 $[M+H]^+$.

The synthesis of 2-(5-(4-methoxybenzylamino)-2-nitrophenyl)-N,N-dimethylacetamide (257-2):

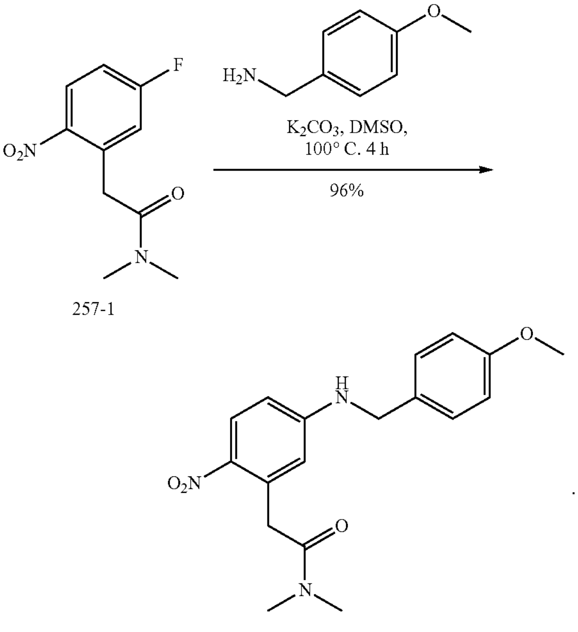

257-1

257-2

The mixture of 257-1 (22.5 g, 61.67 mmol), 4-methoxybenzylamine (9.31 g, 67.84 mmol) and $K_2CO_3$ (17.02 g, 123 mmol) in DMSO (200 mL) were stirred at 100° C. for 4 hours. After cooling to room temperature, the reaction mixture was filtered, diluted with water (600 mL), and extracted with EtOAc (500 mL×4). The organic extracts were washed with brine, dried and concentrated. The residue was purified by recrystallization with EtOH and water to give 257-2 (20.5 g, about 96% yield) as a solid. MS Calcd.: 343.1; MS Found: 344.2 $[M+H]^+$.

The synthesis of 3-(2-(dimethylamino)ethyl)-4-nitroaniline (257-3):

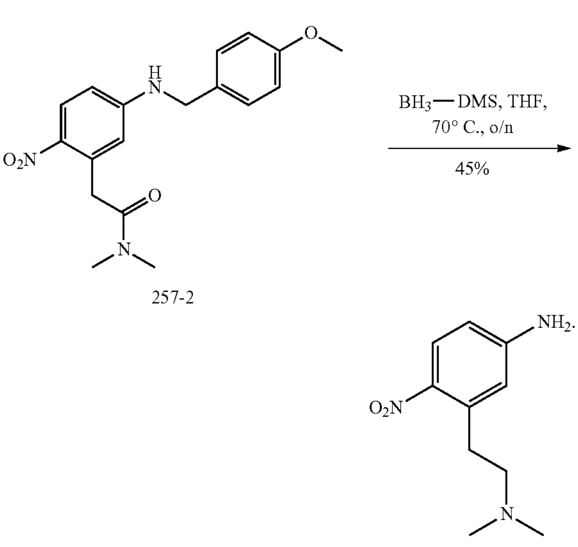

257-2

257-3

A mixture of 257-2 (20 g, 58.25 mmol) in borane-methyl sulfide complex (150 mL, 2M THF) was stirred at 70° C. for overnight. Then the reaction mixture was concentrated and dropped into MeOH. The resulting mixture was acidified with 1N HCl to pH 1 and stirred at 80° C. for overnight. The mixture was basicified with 1N NaOH to pH 10 and extracted with EtOAc (500 mL×3). The organic layers were washed with brine, dried over $Na_2SO_4$ and concentrated. The residue was purified by column chromatography (DCM/MeOH=20/1) to give 257-3 (5.5 g, about 45% yield) as solid. MS Calcd.: 209.1; MS Found: 210.4 $[M+H]^+$.

The synthesis of tert-butyl N-tert-butoxycarbonyl-N-[3-[2-(dimethylamino)ethyl]-4-nitro-phenyl]carbamate (257-4):

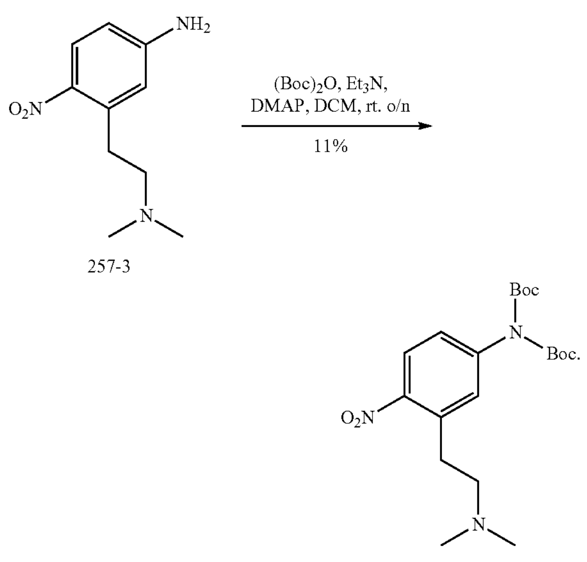

257-3

257-4

To a solution of 257-3 (5.00 g, 23.90 mmol), triethylamine (4.84 g, 47.79 mmol) and $(Boc)_2O$ (18.23 g, 83.63 mmol) in dichloromethane (50 mL) was added DMAP (5.84 g, 47.79 mmol) at room temperature. After stirring for overnight, the reaction mixture was concentrated and the residue was purified by column chromatography on silica gel (petroleum ether/EtOAc=10/1 to 5/1 to 1/1) to give compound 257-4 (1.06 g, about 11% yield) as an oil. MS Calcd.: 409.2; MS Found: 410.2 $[M+H]^+$.

The synthesis of tert-butyl N-[4-amino-3-[2-(dimethylamino)ethyl]phenyl]-N-tert-butoxycarbonyl-carbamate (257-5):

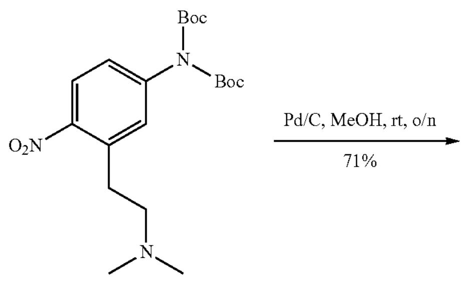

257-4

-continued

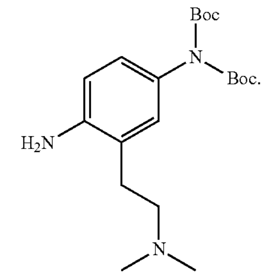

257-5

To a suspension of 257-4 (1.06 g, 2.59 mmol) in methanol (20 mL) was added 10% Pd/C (110 mg) and stirred vigorously under hydrogen gas (balloon) for overnight at room temperature. The solids were removed by filtration through celite, with rinsing with MeOH. The filtrate was concentrated and washed with petroleum ether to give compound 257-5 (700 mg, about 71% yield) as a solid. MS Calcd.: 379.3; MS Found: 380.3 $[M+H]^+$.

The synthesis of tert-butyl N-tert-butoxycarbonyl-N-[4-(2-chloroanilino)-3-[2-(dimethylamino)ethyl]phenyl]carbamate (257-6):

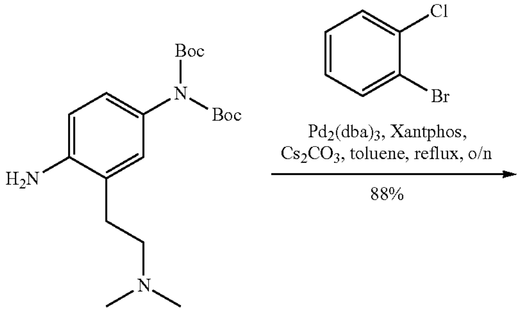

257-5

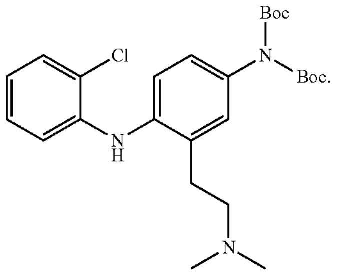

257-6

A mixture of 1-bromo-2-chloro-benzene (605 mg, 3.16 mmol), 257-5 (600 mg, 1.58 mmol), $Pd_2(dba)_3$ (145 mg, 0.16 mmol), Xantphos (183 mg, 0.32 mol) and cesium carbonate (773 mg, 2.37 mmol) in toluene (20 mL) was stirred at 100° C. for 16 hr under $N_2$ (g). The reaction mixture was filtered through celite, and rinsed with EtOAc. The filtrate was concentrated and the residue was purified by column chromatography on silica gel (petroleum ether/EtOAc=10/1 to 5/1 to 3/1 to 1/1) to give compound 257-6 (774 mg, about 88% yield) as an oil. MS Calcd.: 489.2; MS Found: 490.3 $[M+H]^+$.

The synthesis of tert-butyl N-tert-butoxycarbonyl-N-[1-[2-(dimethylamino)ethyl]-9H-carbazol-3-yl]carbamate (257-7):

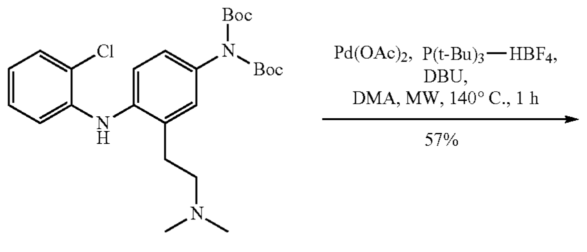

257-6

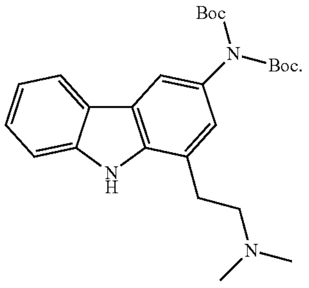

257-7

A mixture of 257-6 (1.1 g, 2.24 mmol), DBU (1.13 g, 4.49 mmol), palladium (II) acetate (101 mg, 0.45 mmol), P(t-Bu)$_3$-HBF$_4$ (261 mg, 0.90 mol) in DMA (10 mL) was heated to 140° C. for 1 hr under microwave irradiation. The reaction mixture was cooled to room temperature, poured into cool water (10 mL), and extracted with EtOAc (10 mL×3). The combined organic layers were washed with brine (10 mL×2), dried over sodium sulfate, and concentrated to dryness. The residue was purified by column chromatography on silica gel (petroleum ether/EtOAc=1/1 to 100% ethyl acetate to DCM/MeOH 50/1 to 20/1 to 10/1) to give compound 257-7 (0.58 g, about 57% yield) as a solid. MS Calcd.: 453.3; MS Found: 454.3 [M+H]$^+$.

The synthesis of 1-(2-(dimethylamino)ethyl)-9H-carbazol-3-amine (257-8):

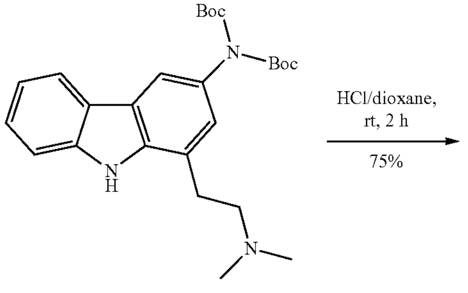

257-7

-continued

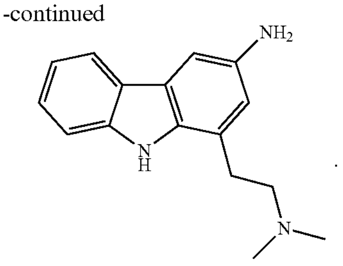

257-8

A mixture of 257-7 (477 mg, 1.05 mmol) in 4 M HCl in dioxane (10 mL) was stirred at room temperature for 2 h. The reaction mixture was concentrated and basicified with 1N NaOH to pH 10. The mixture was extracted with EtOAc (20 mL×3). The organic layers were washed with brine, dried over $Na_2SO_4$ and concentrated to give compound 257-8 (200 mg, about 75% yield) as a solid. MS Calcd.: 253.2; MS Found: 254.2 [M+H]$^+$.

The synthesis of N-(4-chlorophenyl)-1-(2-(dimethylamino)ethyl)-9H-carbazol-3-amine (SS20308-0257-01):

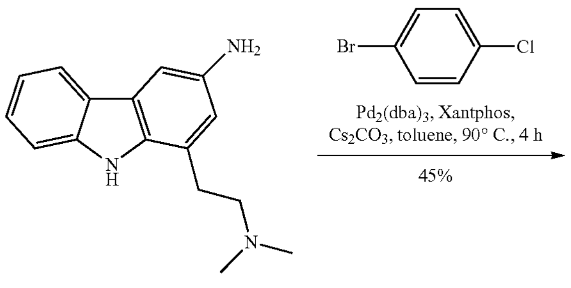

257-8

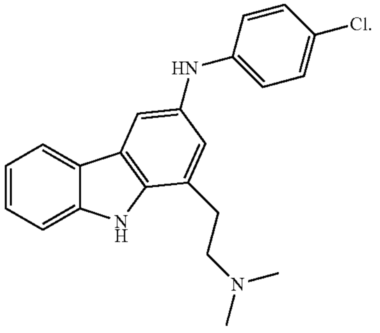

SS20308-0257-01

A mixture of 257-8 (50 mg, 0.20 mmol), 1-bromo-4-chlorobenzene (38 mg, 0.20 mmol), $Pd_2(dba)_3$ (9 mg, 0.01 mmol), Xantphos (12 mg, 0.02 mmol) and cesium carbonate (97 mg, 0.3 mol) in toluene (2 mL) was stirred at 90° C. for 4 hr under $N_{2(g)}$. The reaction mixture was filtered through celite, and rinsed with EtOAc. The filtrate was concentrated and the residue was purified by Prep-TLC (DCM/MeOH=15/1) and reverse phase column chromatography to give compound SS20308-0257-01 (32.6 mg, about 45% yield) as a solid. MS Calcd.: 363.2; MS Found: 364.3 [M+H]$^+$.

$^1$H NMR (400 MHz, DMSO-d$_6$) δ 11.12 (s, 1H), 8.02 (s, 1H), 8.00 (d, J=8.0 Hz, 1H), 7.67 (d, J=1.6 Hz, 1H), 7.45 (d, J=8.0 Hz, 1H), 7.35-7.29 (m, 1H), 7.15 (d, J=8.8 Hz, 2H), 7.07 (dd, J=7.2, 6.8 Hz, 1H), 7.02 (d, J=2.0 Hz, 1H), 6.91 (d, J=8.8 Hz, 2H), 3.01 (t, J=7.6 Hz, 2H), 2.59 (t, J=7.4 Hz, 2H), 2.23 (s, 6H).

Example 70

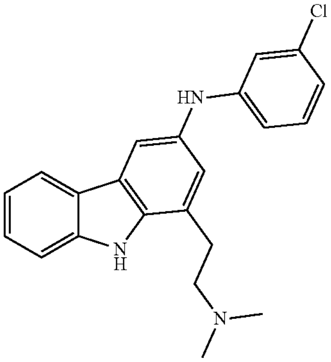

SS20308-0258-01
Chemical Formula: $C_{22}H_{22}ClN_3$
Molecular Weight: 363.88

Example Route for Example 70 (SS20308-0258-01):

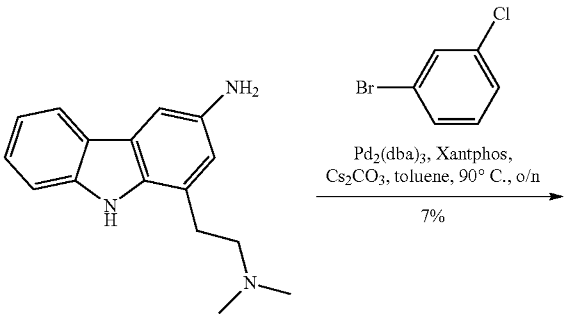

257-8

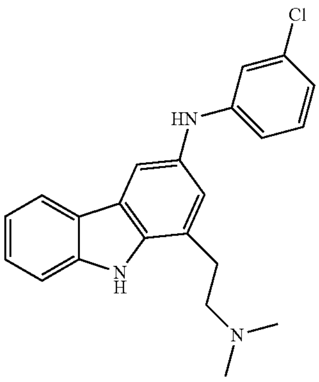

SS20308-0258-01

The synthesis of N-(3-chlorophenyl)-1-(2-(dimethylamino)ethyl)-9H-carbazol-3-amine (SS20308-0258-01):

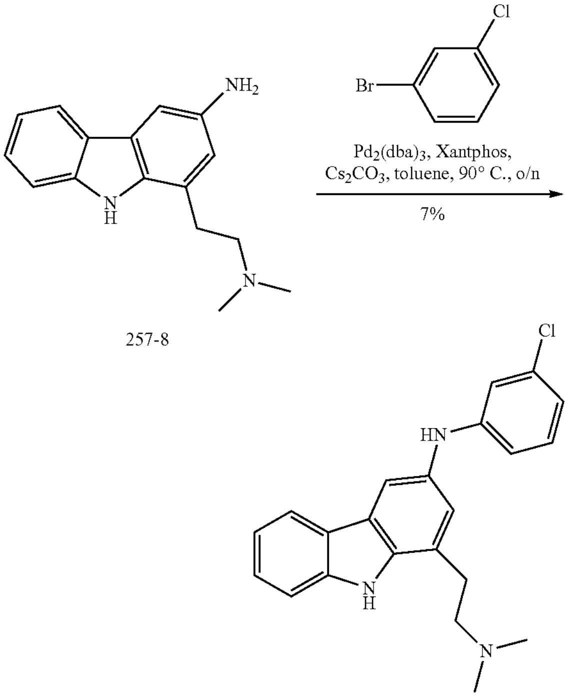

SS20308-0258-01

A mixture of 257-8 (50 mg, 0.20 mmol), 1-bromo-3-chlorobenzene (38 mg, 0.20 mmol), $Pd_2(dba)_3$ (9 mg, 0.01 mmol), Xantphos (12 mg, 0.02 mmol) and cesium carbonate (97 mg, 0.3 mol) in toluene (2 mL) was stirred at 90° C. for overnight under $N_2$ (g). The reaction mixture was filtered through celite, and rinsed with EtOAc. The filtrate was concentrated and the residue was purified by Prep-TLC (DCM/MeOH=10/1) and reverse phase column chromatography to give compound SS20308-0258-01 (5.2 mg, about 7% yield) as a solid. MS Calcd.: 363.2; MS Found: 364.1 $[M+H]^+$.

$^1H$ NMR (400 MHz, DMSO-$d_6$) δ 11.19 (s, 1H), 8.16 (s, 1H), 8.05 (d, J=7.6 Hz, 1H), 7.71 (d, J=2.0 Hz, 1H), 7.49 (d, J=8.4 Hz, 1H), 7.39-7.34 (m, 1H), 7.18-7.09 (m, 2H), 7.07 (d, J=2.0 Hz, 1H), 6.88-6.84 (m, 2H), 6.68-6.65 (m, 1H), 3.06 (t, J=7.4 Hz, 2H), 2.64 (t, J=7.4 Hz, 2H), 2.27 (s, 6H).

Example 71

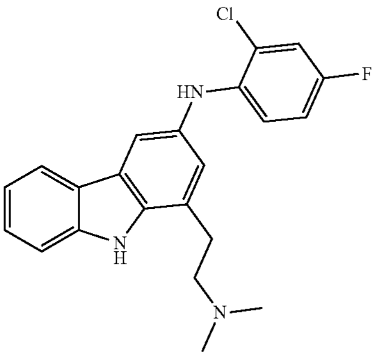

SS20308-0277-01
Chemical Formula: $C_{22}H_{21}ClFN_3$
Molecular Weight: 381.87

Example Route for Example 71 (SS20308-0277-01):

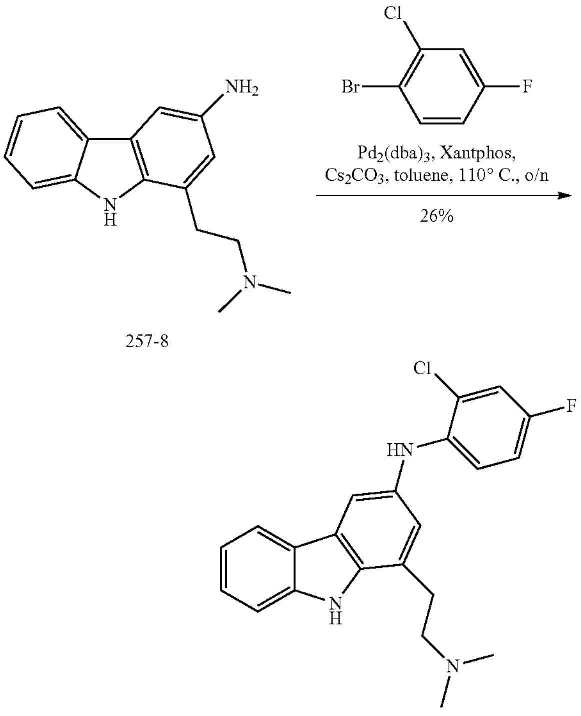

SS20308-0277-01

The synthesis of N-(2-chloro-4-fluorophenyl)-1-(2-(dimethylamino)ethyl)-9H-carbazol-3-amine (SS20308-0277-01):

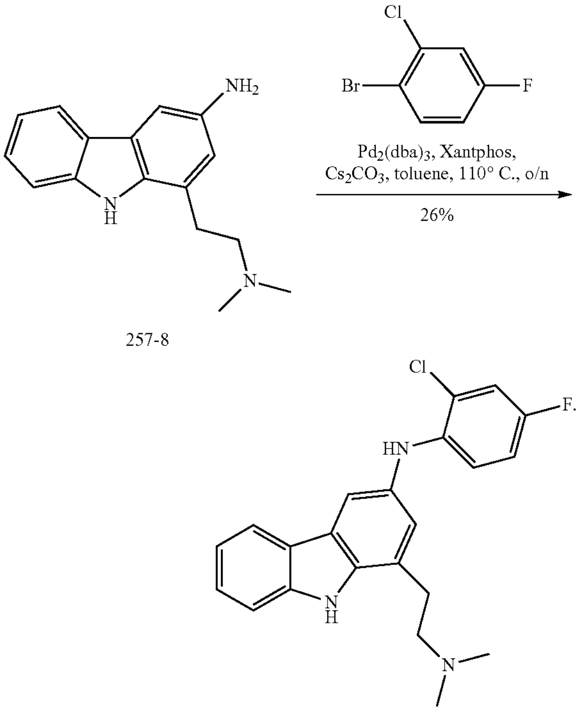

SS20308-0277-01

The mixture of 257-8 (56 mg, 0.22 mmol), 1-bromo-2-chloro-4-fluoro-benzene (92 mg, 0.44 mmol), $Pd_2(dba)_3$ (20 mg, 0.022 mmol), Xantphos (26 mg, 0.044 mmol) and cesium carbonate (108 mg, 0.33 mmol) was stirred at 110° C. for 16 hr under $N_{2(g)}$. The reaction mixture was filtered through celite, and rinsed with EtOAc. The filtrate was concentrated and the residue was purified by Prep-TLC (DCM/MeOH=10/1) to give compound SS20308-0277-01 (22.3 mg, about 26% yield) as a semisolid. MS Calcd.: 381.1; MS Found: 382.3 $[M+H]^+$.

$^1$H NMR (400 MHz, DMSO-$d_6$) δ 11.16 (s, 1H), 7.98 (d, J=7.6 Hz, 1H), 7.66 (d, J=2.0 Hz, 1H), 7.46 (d, J=8.0 Hz, 1H), 7.36-7.29 (m, 3H), 7.10-7.04 (m, 2H), 7.02-6.91 (m, 2H), 3.01 (t, J=7.4 Hz, 2H), 2.59 (t, J=7.6 Hz, 2H), 2.23 (s, 6H).

Example 72

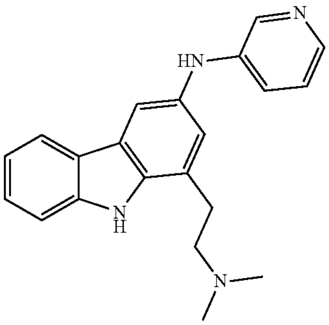

SS20308-0291-01
Chemical Formula: $C_{21}H_{22}N_4$
Molecular Weight: 330.43

Example Route for Example 72 (SS20308-0291-01):

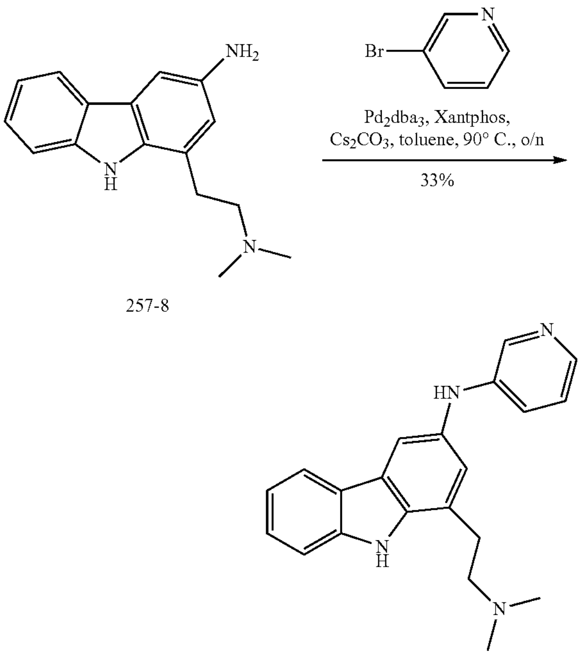

SS20308-0291-01

The synthesis of 1-(2-(dimethylamino)ethyl)-N-(pyridin-3-yl)-9H-carbazol-3-amine (SS20308-0291-01):

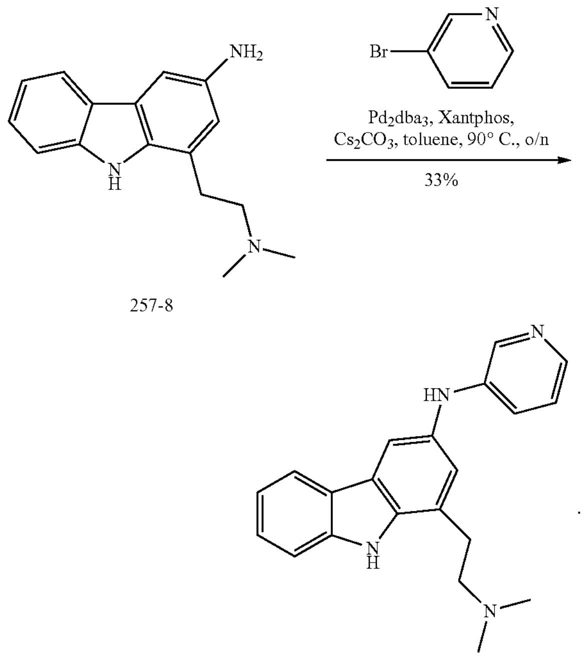

257-8

SS20308-0291-01

The mixture of 257-8 (50 mg, 0.20 mmol), 3-bromopyridine (31 mg, 0.20 mmol), $Pd_2(dba)_3$ (9 mg, 0.01 mmol), Xantphos (12 mg, 0.02 mmol) and cesium carbonate (97 mg, 0.3 mol) in toluene (2 mL) was stirred at 90° C. for 16 hr under $N_{2(g)}$. The reaction mixture was filtered through celite, and rinsed with EtOAc. The filtrate was concentrated and the residue was purified by Prep-TLC (DCM/MeOH=10/1) and reverse phase column chromatography to give compound SS20308-0291-01 (21.4 mg, about 33% yield) as a solid. MS Calcd.: 330.2; MS Found: 331.2 $[M+H]^+$.

$^1H$ NMR (400 MHz, DMSO-$d_6$) δ 11.14 (s, 1H), 8.24 (d, J=2.8 Hz, 1H), 8.09 (s, 1H), 8.02 (d, J=7.6 Hz, 1H), 7.88 (dd, J=8.8, 1.2 Hz, 1H), 7.70 (d, J=2.0 Hz, 1H), 7.45 (d, J=8.0 Hz, 1H), 7.36-7.26 (m, 2H), 7.12 (dd, J=8.4, 3.6 Hz, 1H), 7.10-7.04 (m, 2H), 3.03 (t, J=7.4 Hz, 2H), 2.62 (t, J=7.2 Hz, 2H), 2.25 (s, 6H).

Example 73

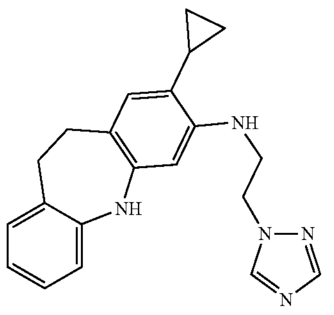

SS20308-0269-01
Chemical Formula: $C_{21}H_{23}N_5$
Molecular Weight: 345.44

Example Route for Example 73 (SS20308-0269-01):

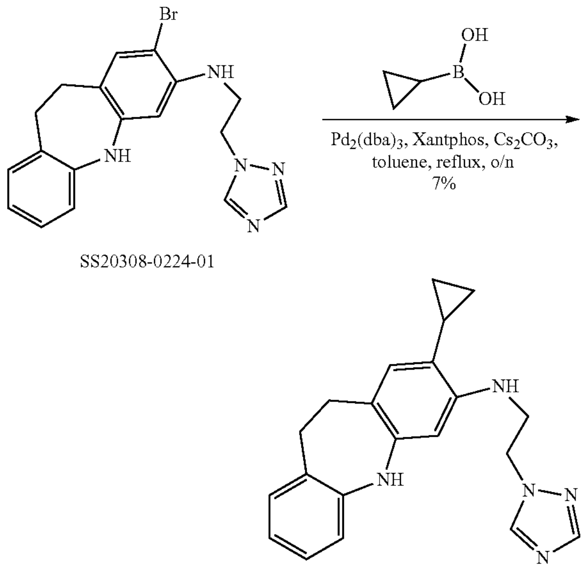

SS20308-0224-01

SS20308-0269-01

The synthesis of N-(2-(1H-1,2,4-triazol-1-yl)ethyl)-2-cyclopropyl-10,11-dihydro-5H-dibenzo[b,f]azepin-3-amine (SS20308-0269-01):

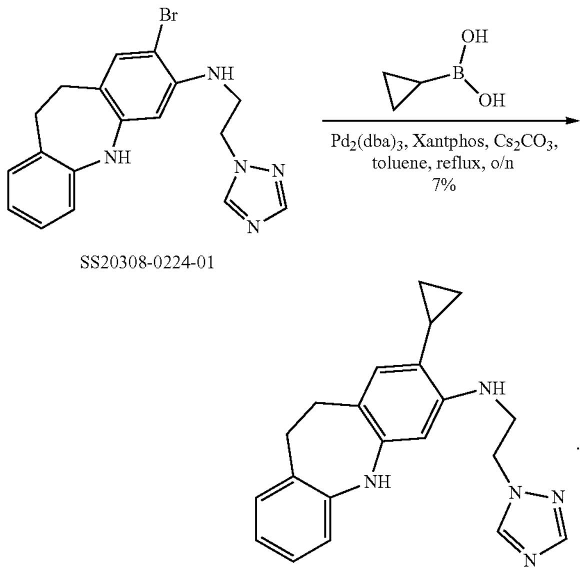

SS20308-0224-01

SS20308-0269-01

A mixture of cyclopropylboronic acid (22.45 mg, 0.26 mmol), SS20308-0224-01 (50 mg, 0.13 mmol), $Pd_2(dba)_3$ (5.95 mg, 0.0065 mmol), Xantphos (6.22 mg, 0.013 mmol) and $Cs_2CO_3$ (85.12 mg, 0.26 mmol) in toluene (0.5 mL) was stirred at 110° C. for 18 hr. The reaction mixture was cooled to room temperature and poured into water (5 mL) and extracted with EtOAc (5 mL×3). The organic layer was washed with brine and concentrated. The crude product was purified by Prep-HPLC to give SS20308-0269-01 (3.29 mg, about 7% yield) as a solid. MS Calcd.: 345.20; MS Found: 345.8 $[M+H]^+$.

$^1$H NMR (400 MHz, MeOD-$d_4$) δ 8.41 (s, 1H), 8.23 (s, 1H), 7.02-6.95 (m, 2H), 6.85 (d, J=7.6 Hz, 1H), 6.71-6.66 (m, 1H), 6.64 (s, 1H), 6.27 (s, 1H), 4.52 (t, J=5.6 Hz, 2H), 3.70 (t, J=6.4 Hz, 2H), 2.99-2.96 (m, 2H), 2.91-2.88 (m, 2H), 1.45-1.41 (m, 1H), 0.78-0.74 (m, 2H), 0.39-0.35 (m, 2H).

Example 74

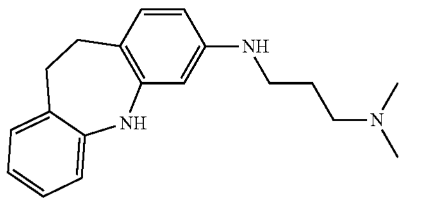

SS20308-0270-01
Chemical Formula: $C_{19}H_{25}N_3$
Molecular Weight: 295.42

Example Route for Example 74 (SS20308-0270-01):

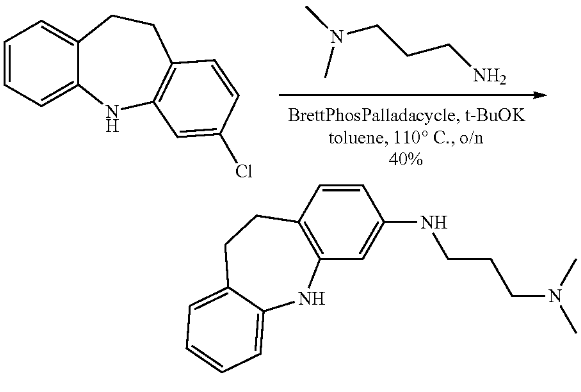

SS20308-0270-01

The synthesis of N[1]-(10,11-dihydro-5H-dibenzo[b,f]azepin-3-yl)-N[3],N[3]-dimethylpropane-1,3-diamine (SS20308-0270-01):

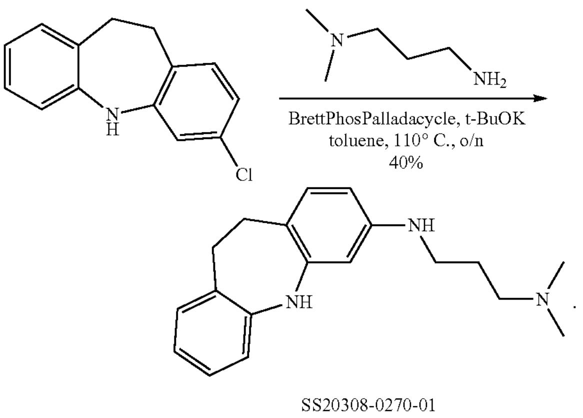

SS20308-0270-01

A mixture of N',N'-dimethylpropane-1,3-diamine (67 mg, 0.65 mmol), 3-chloroiminodibenzyl (100 mg, 0.435 mmol), t-BuOK (146 mg, 1.31 mmol) and Brett-PhosPalladacycle (35 mg, 0.044 mmol) in toluene (2 mL) was stirred at 110° C. overnight. The reaction mixture was cooled to room temperature, poured into water (50 mL) and extracted with EtOAc (30 mL×3). The organic layer was washed with brine and concentrated. The crude product was purified by Prep-HPLC to give SS20308-0270-01 (52.8 mg, 0.176 mmol, about 40% yield) as a solid. MS Calcd.: 345.20; MS Found: 345.8 $[M+H]^+$.

$^1$H NMR (400 MHz, DMSO-$d_6$) δ 8.00 (s, 1H), 7.00-6.91 (m, 3H), 6.67 (d, J=8.0 Hz, 1H), 6.60 (dt, J=7.2, 1.2 Hz, 1H), 6.16 (d, J=2.0 Hz, 1H), 5.96 (dd, J=8.0, 2.4 Hz, 1H), 5.25 (t, J=5.6 Hz, 1H), 2.99-2.44 (m, 2H), 2.90-2.87 (m, 2H), 2.82-2.79 (m, 2H), 2.28 (t, J=6.8 Hz, 2H), 2.13 (s, 6H), 1.68-1.64 (m, 2H).

Example 75

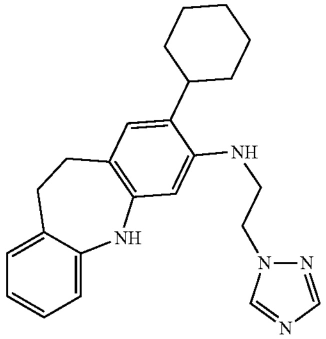

SS20308-0271-01
Chemical Formula: $C_{24}H_{29}N_5$
Molecular Weight: 387.52

Example Route for Example 75 (SS20308-0271-01):

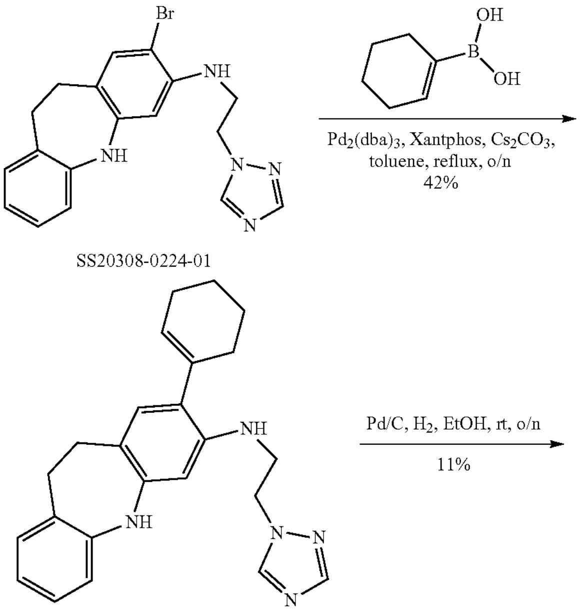

SS20308-0224-01

271-1

-continued

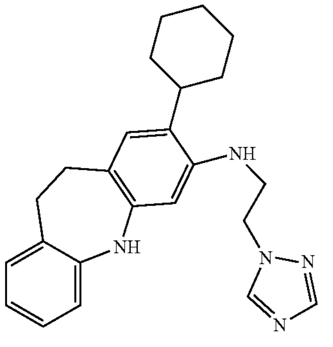

SS20308-0271-01

The synthesis of N-(2-(1H-1,2,4-triazol-1-yl)ethyl)-2-cyclohexenyl-10,11-dihydro-5H-dibenzo[b,f] azepin-3-amine (271-1):

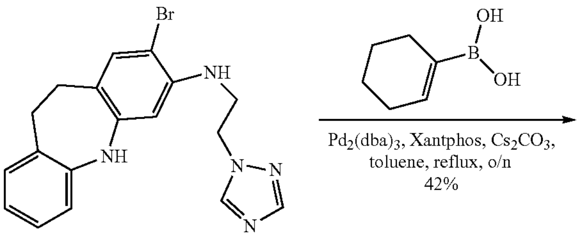

SS20308-0224-01

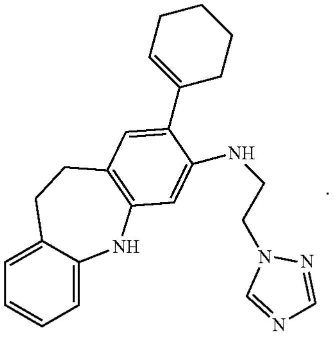

271-1

A mixture of cyclohexen-1-ylboronic acid (65.6 mg, 0.520 mmol), SS20308-0224-01 (100 mg, 0.260 mmol), $Pd_2(dba)_3$ (11.9 mg, 0.013 mmol), Xantphos (12.4 mg, 0.013 mmol) and $Cs_2CO_3$ (169.7 mg, 0.52 mmol) in toluene (2 mL) was stirred at 110° C. for 18 hr. The reaction mixture was cooled to room temperature and poured into water (10 mL) and extracted with EtOAc (10 mL×3). The organic layer was washed with brine and evaporated to crude. It was purified by Prep-TLC (EtOAc/petroleum ether=2/1) to give 271-1 (50 mg, about 42% yield) as a solid.

The synthesis of N-(2-(1H-1,2,4-triazol-1-yl)ethyl)-2-cyclohexyl-10,11-dihydro-5H-dibenzo[b,f]azepin-3-amine (SS20308-0271-01):

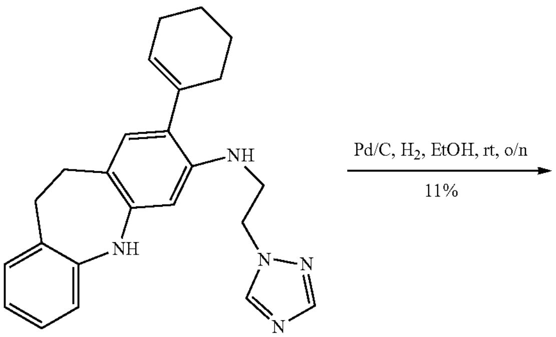

271-1

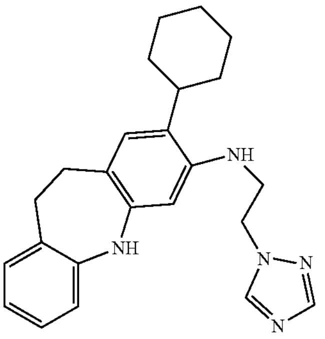

SS20308-0271-01

A mixture of 271-1 (40 mg, 0.10 mmol) and 10% Pd/C (12.6 mg, 0.104 mmol) in MeOH (2 mL) was stirred at rt overnight under $H_2$ (balloon). The mixture was filtered and concentrated. The crude product was purified with Prep-HPLC to give SS20308-0271-01 (4.5 mg, about 11% yield) as a solid. MS Calcd.: 387.52; MS Found: 388.1 $[M+H]^+$.

$^1H$ NMR (400 MHz, DMSO-$d_6$) δ 8.51 (s, 1H), 7.99 (d, J=7.6 Hz, 2H), 6.99-6.87 (m, 2H), 6.88 (d, J=7.6 Hz, 1H), 6.61-6.58 (m, 2H), 6.25 (s, 1H), 4.80-4.80 (m, 1H), 4.45 (t, J=6.0 Hz, 2H), 3.33 (d, J=5.6 Hz, 2H), 2.90-2.88 (m, 2H), 2.83-2.81 (m, 2H), 2.43-2.33 (m, 1H), 1.76-1.70 (m, 2H), 1.68-1.62 (m, 2H), 1.39-1.36 (m, 2H), 1.26-1.18 (m, 4H).

Example 76

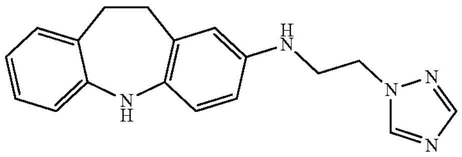

SS20308-0276-01
Chemical Formula: $C_{18}H_{19}N_5$
Molecular Weight: 305.38

Example Route for Example 76 (SS20308-0276-01):

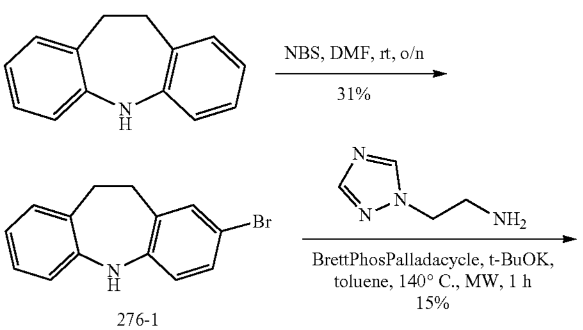

276-1

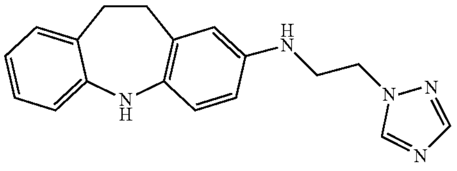

SS20308-0276-01

The synthesis of 2-bromo-10,11-dihydro-5H-dibenzo[b,f]azepine (276-1):

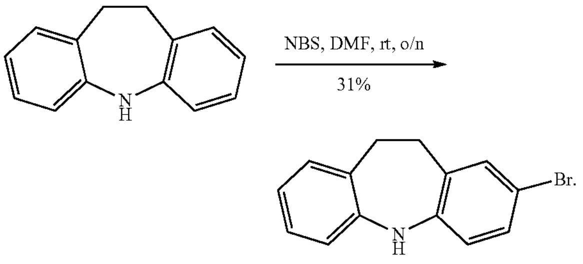

276-1

A mixture of NBS (1.88 g, 10.54 mmol) in 10 ml of DMF was slowly added to a mixture of 10,11-dihydro-5H-dibenz[b,f]azepine (2 g, 10.04 mmol) in 10 ml of DMF. The resultant mixture was stirred at room temperature for overnight. The mixture was diluted with water (60 mL) and extracted with EtOAc (50 mL×3). The organic extracts were dried and concentrated to give the 276-1 (1.82 g, about 31% yield) as an oil. MS Calcd.: 273.0; MS Found: 274.0 $[M+H]^+$.

The synthesis of N-(2-(1H-1,2,4-triazol-1-yl)ethyl)-10,11-dihydro-5H-dibenzo[b,f]azepin-2-amine (SS20308-0276-01):

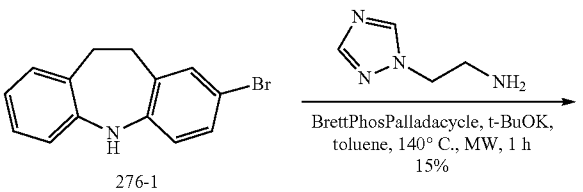

276-1

-continued

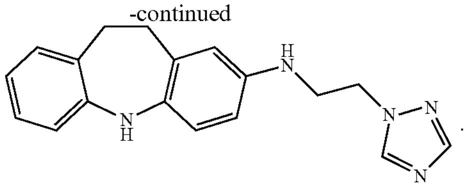

SS20308-0276-01

A mixture of 276-1 (300 mg, 1.09 mmol), 1H-1,2,4-triazole-1-ethanamine (245 mg, 2.19 mmol), BrettPhosPalladacycle (87 mg, 0.11 mmol), and t-BuOK (245 mg, 2.19 mmol) in toluene (5 mL) was stirred at 140° C. for one hour in a microwave reactor. The reaction mixture was then cooled to room temperature, filtered through celite, and concentrated. The residue was purified by Prep-HPLC to give SS20308-0276-01 (50 mg, about 15% yield) as a solid. MS Calcd.: 305.2; MS Found: 306.1 $[M+H]^+$.

$^1H$ NMR (400 MHz, DMSO-$d_6$) δ 8.46 (s, 1H), 7.98 (s, 1H), 7.74 (s, 1H), 6.98-6.90 (m, 2H), 6.83-6.85 (m, 1H), 6.77 (d, J=8.4 Hz, 1H), 6.52-6.57 (m, 1H), 6.32-6.36 (m, 1H), 6.29-6.28 (m, 1H), 5.19 (t, J=6.2 Hz, 1H), 4.30 (t, J=6.2 Hz, 2H), 6.85 (q, J=12.4 Hz, 6.2 Hz, 2H), 2.93-2.90 (m, 2H), 2.86-2.83 (m, 2H).

Example 77

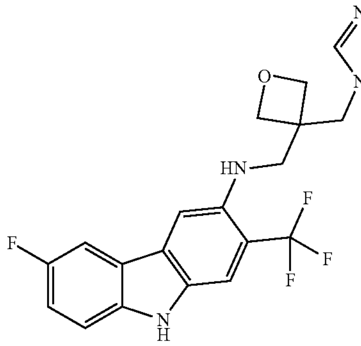

SS20308-0295-01
Chemical Formula: $C_{20}H_{17}F_4N_5O$
Molecular Weight: 419.38

Example Route for Example 77 (SS20308-0295-01):

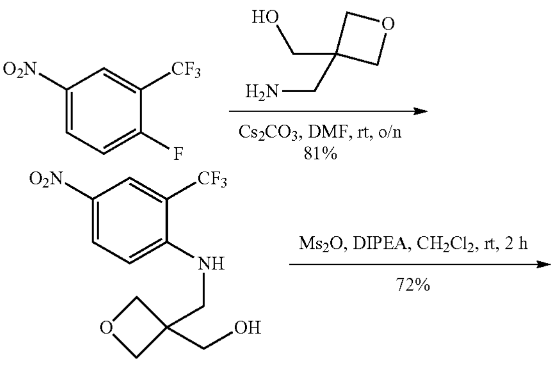

295-1

-continued

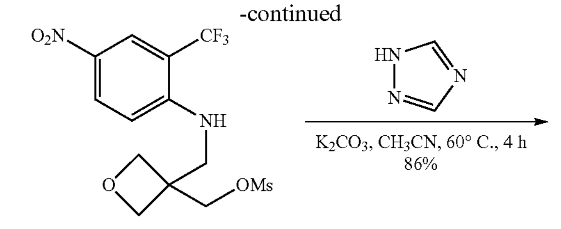

295-2

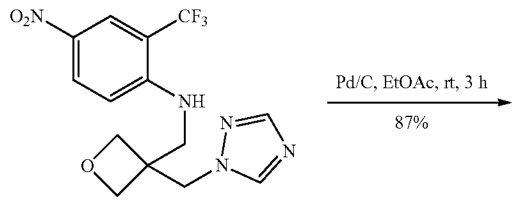

295-3

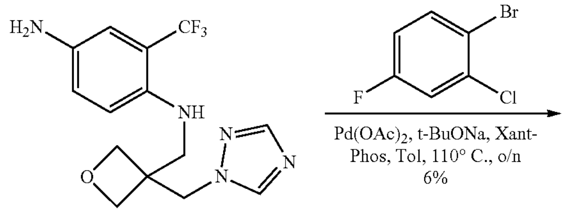

295-4

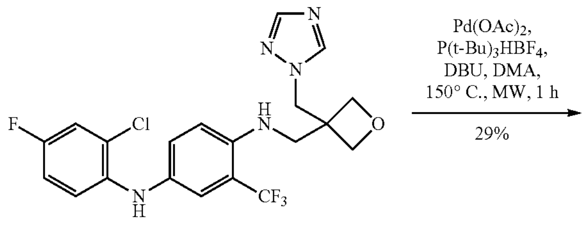

295-5

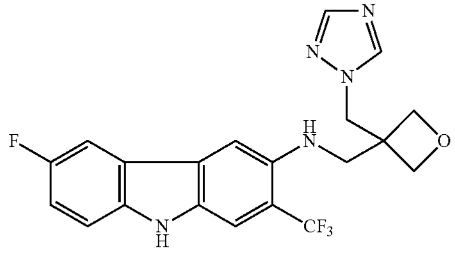

SS20308-0295-01

The synthesis of (3-((4-nitro-2-(trifluoromethyl)phenylamino)methyl)oxetan-3-yl)methanol (295-1):

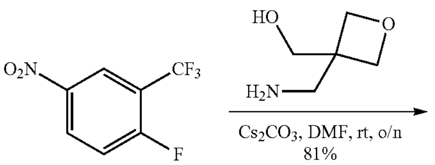

-continued

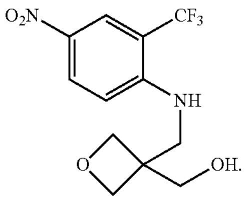

295-1

A mixture of 2-fluoro-5-nitrobenzotrifluoride (1.10 g, 5.26 mmol), (3-(aminomethyl)oxetan-3-yl)methanol (616 mg, 5.26 mmol) and $Cs_2CO_3$ (3.43 g, 10.52 mmol) in DMF (10 ml) was stirred at room temperature under nitrogen atmosphere overnight. After the reaction was complete, the mixture was quenched with water and extracted with EtOAc (50 mL×3). The organic layer was separated, dried over $MgSO_4$, and concentrated under vacuum. The crude product was purified by column chromatography on silica gel (petroleum ether/EtOAc=1/2) to give 295-1 (1.30 g, about 81% yield) as a solid. MS Calcd.: 306.1; MS Found: 307.0 $[M+H]^+$.

The synthesis of (3-((4-nitro-2-(trifluoromethyl)phenylamino)methyl)oxetan-3-yl)methyl methanesulfonate (295-2):

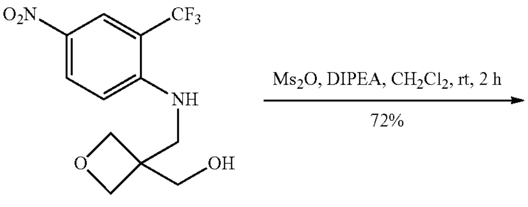

295-1

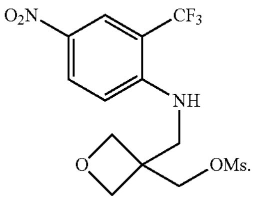

295-2

To a solution of 295-1 (1.10 g, 3.59 mmol) in DCM (20 mL) was added $Ms_2O$ (1.25 g, 7.18 mmol) and DIPEA (928 mg, 7.18 mmol). The mixture was stirred at room temperature for 2 h. After the reaction was complete, it was quenched with water and extracted with DCM (50 mL×3). The organic layer was separated, dried over $MgSO_4$, and concentrated under vacuum. The crude product was purified by column chromatography on silica gel (petroleum ether/EtOAc=1/1) to give 295-2 (1.00 g, about 72% yield) as a solid. MS Calcd.: 384.1; MS Found: 384.8 $[M+H]^+$.

The synthesis of N-((3-((1H-1,2,4-triazol-1-yl)methyl) oxetan-3-yl)methyl)-4-nitro-2-(trifluoromethyl) aniline (295-3):

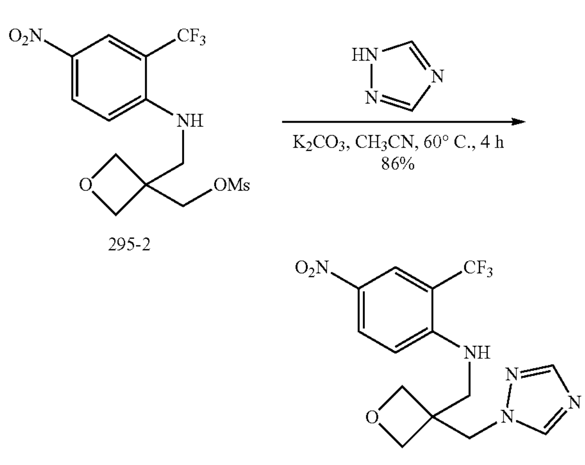

295-2

295-3

To a solution of 295-2 (1.00 g, 2.60 mmol) in $CH_3CN$ (20 mL) was added 1H-1,2,4-triazole (359 mg, 5.20 mmol) and $K_2CO_3$ (719 mg, 5.20 mmol). The mixture was stirred at 60° C. for 4 h. After the reaction was complete, it was quenched with water and extracted with EtOAc (50 mL×3). The organic layer was separated, dried over $MgSO_4$, and concentrated under vacuum. The crude product was purified by column chromatography on silica gel (petroleum ether/EtOAc=1/1) to give 295-3 (0.80 g, about 86% yield) as a solid. MS Calcd.: 357.1; MS Found: 357.8 $[M+H]^+$.

The synthesis of $N^1$-((3-((1H-1,2,4-triazol-1-yl)methyl) oxetan-3-yl)methyl)-2-(trifluoromethyl)benzene-1,4-diamine (295-4):

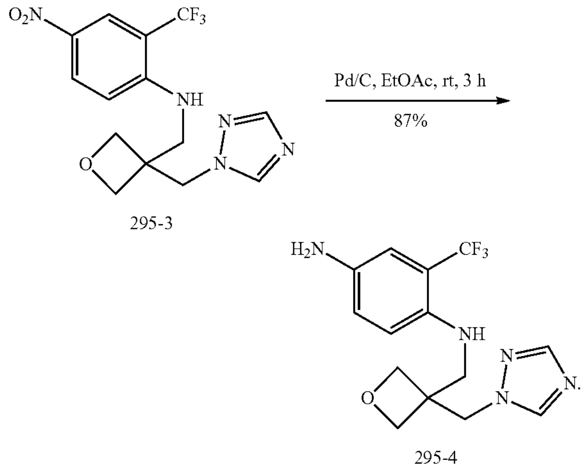

295-3

295-4

To a solution of 295-3 (250 mg, 0.70 mmol) in EtOAc (20 mL) was added 10% Pd/C (35 mg), the mixture was stirred at room temperature under hydrogen gas (balloon) overnight. After the reaction was complete, the reaction mixture was filtered and concentrated under vacuum. The crude product was purified by column chromatography on silica gel (petroleum ether/EtOAc=1/3) to give 295-4 (0.20 g, about 87% yield) as a solid. MS Calcd.: 327.1; MS Found: 328.2 $[M+H]^+$.

The synthesis of $N^1$-((3-((1H-1,2,4-triazol-1-yl)methyl) oxetan-3-yl)methyl)-$N^4$-(2-chloro-4-fluorophenyl)-2-(trifluoromethyl)benzene-1,4-diamine (295-5):

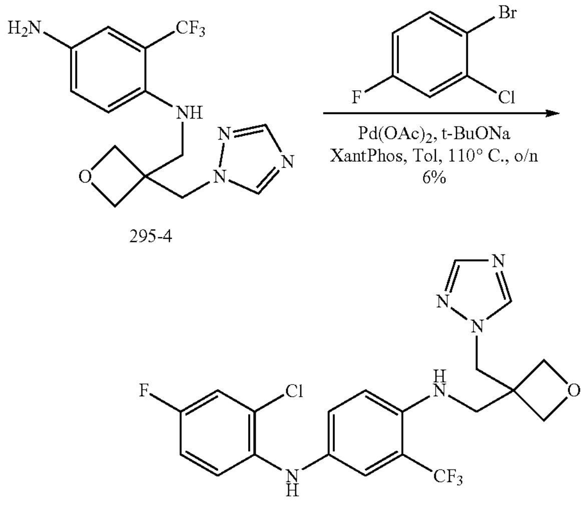

295-4

295-5

A mixture of 295-4 (100 mg, 0.31 mmol), 1-bromo-2-chloro-4-fluorobenzene (128 mg, 0.61 mmol), $Pd(OAc)_2$ (7 mg, 0.03 mmol), Xantphos (35 mg, 0.06 mmol) and t-BuONa (59 mg, 0.61 mmol) in toluene (10 ml) and was stirred at 110° C. under nitrogen atmosphere overnight. After the reaction was complete, the mixture was quenched with water, and filtered. The filtrate was extracted with EtOAc (30 mL×3). The organic layer was separated, dried over $MgSO_4$, and concentrated. The crude product was was purified by Prep-HPLC to give 295-5 (8 mg, about 6% yield) as a light oil. MS Calcd.: 455.1; MS Found: 456.1 $[M+H]^+$. $^1H$ NMR (400 MHz, DMSO-$d_6$) δ 8.56 (s, 1H), 8.01 (s, 1H), 7.36-7.33 (m, 2H), 7.17 (d, J=2.4 Hz, 1H), 7.13 (d, J=8.8 Hz, 1H), 7.04-6.99 (m, 1H), 6.93-6.89 (m, 1H), 6.76 (d, J=9.2 Hz, 1H), 5.28 (t, J=6.0 Hz, 1H), 4.58 (s, 2H), 4.47 (d, J=6.4 Hz, 2H), 4.42 (d, J=6.4 Hz, 2H), 3.26 (d, J=6.0 Hz, 2H).

The synthesis of N-((3-((1H-1,2,4-triazol-1-yl)methyl) oxetan-3-yl)methyl)-6-fluoro-2-(trifluoromethyl)-9H-carbazol-3-amine (SS20308-0295-01):

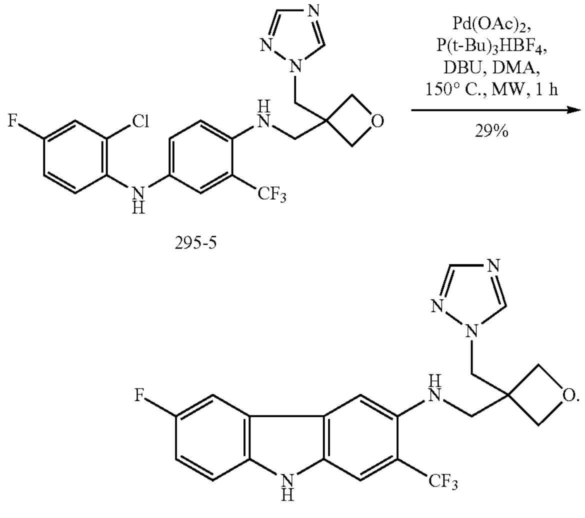

295-5

SS20308-0295-01

A mixture of 295-5 (80 mg, 0.18 mmol), $Pd(OAc)_2$ (20 mg, 0.09 mmol), $P(t\text{-}Bu)_3\text{-}HBF_4$ (51 mg, 0.18 mmol) and DBU (53 mg, 0.35 mmol) in DMA (1 ml) was stirred at 150° C. in a microwave reactor for 1 h. After the reaction was complete, the mixture was quenched with water, and filtered. The filtrate was extracted with EtOAc (30 mL×3). The organic layer was separated, dried over $MgSO_4$, and concentrated under vacuum. The crude product was purified by Prep-HPLC to give SS20308-0295-01 (21 mg, about 29% yield) as a solid. MS Calcd.: 419.1; MS Found: 420.1 $[M+H]^+$.

$^1$H NMR (400 MHz, DMSO-$d_6$) δ 11.12 (s, 1H), 8.57 (s, 1H), 8.05 (s, 1H), 7.97 (dd, J=9.6 Hz, 2.8 Hz, 1H), 7.65 (s, 1H), 7.56 (s, 1H), 7.48 (dd, J=8.8 Hz, 4.4 Hz, 1H), 7.29-7.27 (m, 1H), 4.96 (t, J=6.4 Hz, 1H), 4.67 (s, 2H), 4.56 (d, J=6.4 Hz, 2H), 4.51 (d, J=6.4 Hz, 2H), 3.40 (d, J=6.0 Hz, 2H).

Example 78

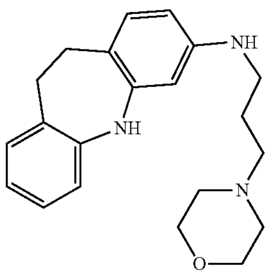

SS20308-0303-01
Chemical Formula: $C_{21}H_{27}N_3O$
Molecular Weight: 337.46

Example Route for Example 78 (SS20308-0303-01):

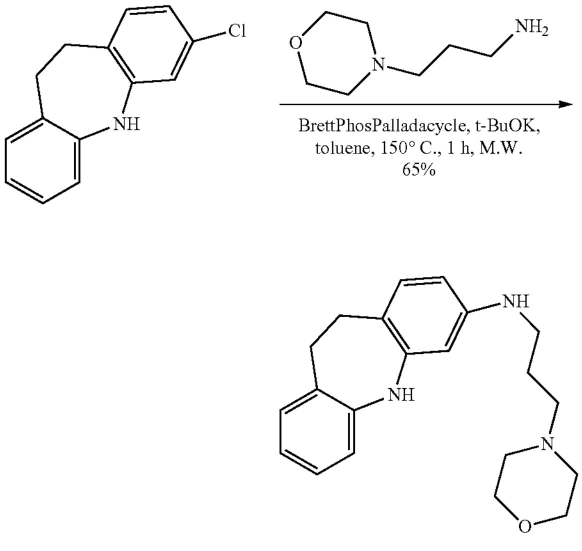

SS20308-0303-01

The synthesis of N-(3-morpholinopropyl)-10,11-dihydro-5H-dibenzo[b,f]azepin-3-amine (SS20308-0303-01):

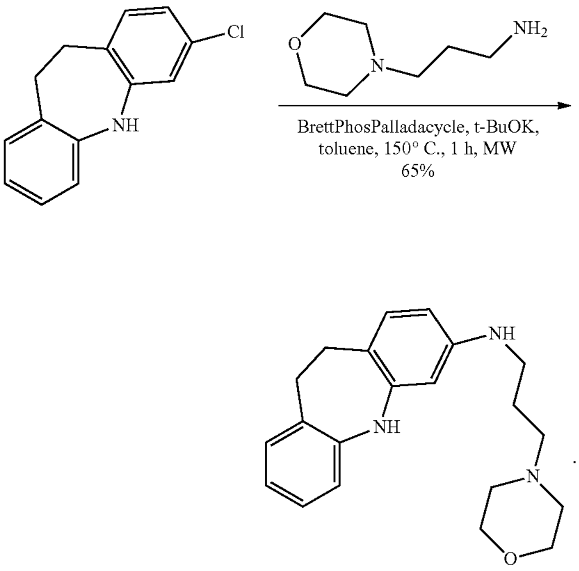

SS20308-0303-01

A mixture of 3-chloroiminodibenzyl (100 mg, 0.43 mmol), 4-(3-aminopropyl)morpholine (94 mg, 0.65 mmol), Brett-PhosPalladacycle (35 mg, 0.043 mmol), and t-BuOK (98 mg, 0.87 mmol) in toluene (2 mL) was stirred at 140° C. for one hour in a microwave reactor. The reaction mixture was then cooled to room temperature, filtered through celite and concentrated. The residue was purified by Prep-HPLC to give SS20308-0303-01 (95 mg, about 65% yield) as a solid. MS Calcd.: 337.2; MS Found: 338.3 $[M+H]^+$.

$^1$H NMR (400 MHz, DMSO-$d_6$) δ 7.97 (s, 1H), 6.99-6.89 (m, 3H), 6.66 (d, J=8.0 Hz, 1H), 6.58 (t, J=7.6 Hz, 1H), 6.15-6.14 (m, 1H), 6.95-6.92 (m, 1H), 5.25 (t, J=5.4 Hz, 1H), 3.57-3.54 (m, 3H), 3.30 (s, 1H), 2.97 (q, J=12.4 Hz, 6.2 Hz, 2H), 2.88-2.85 (m, 2H), 2.80-2.77 (m, 2H), 2.36-2.32 (m, 6H), 1.71-1.63 (m, 2H).

Example 79

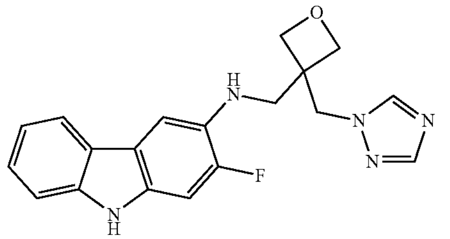

SS20308-0304-01
Chemical Formula: $C_{19}H_{18}FN_5O$
Molecular Weight: 351.38

Example 80

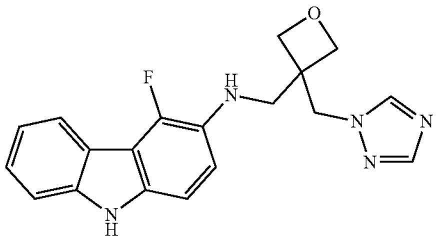

SS20308-0312-01
Chemical Formula: $C_{19}H_{18}FN_5O$
Molecular Weight: 351.38

Example Route for Example 79 (SS20308-0304-01) and Example 80 (SS20308-0312-01):

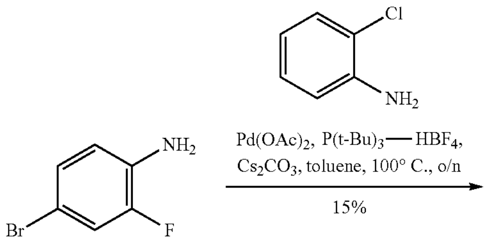

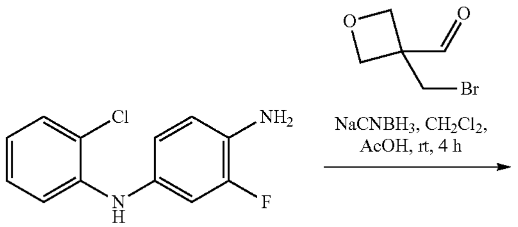

304-1

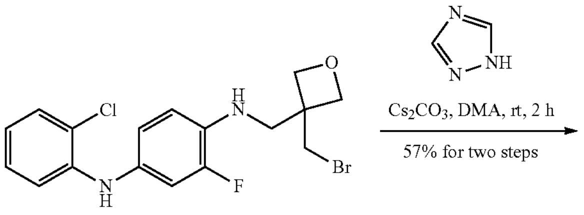

304-2

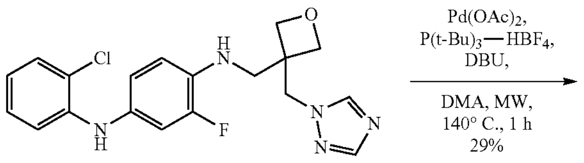

304-3

-continued

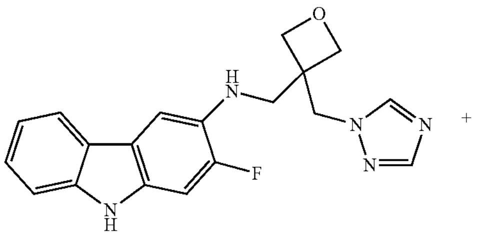

SS20308-0304-01

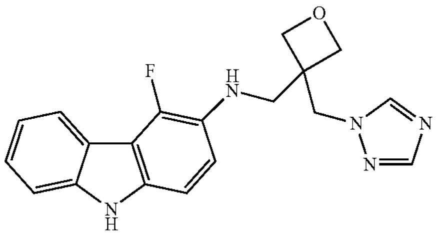

SS20308-0312-01

The synthesis of N[1]-(2-chlorophenyl)-3-fluorobenzene-1,4-diamine (304-1):

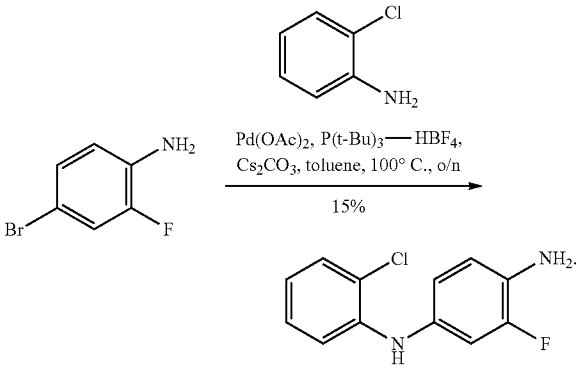

304-1

A mixture of 2-chloroaniline (2.69 g, 21.05 mmol), 4-bromo-2-fluoro-aniline (2.00 g, 10.53 mmol), palladium (II) acetate (118 mg, 0.53 mmol), tri-tert-butylphosphine tetrafluoroborate (304 mg, 1.05 mmol) and cesium carbonate (5.14 g, 15.79 mmol) in toluene (40 mL) was stirred at 100° C. for 16 hr under $N_2$ (g). The reaction mixture was filtered through celite, and rinsed with EtOAc. The filtrate was concentrated and the residue was purified by column chromatography on silica gel (petroleum ether/EtOAc=100/1 to 50/1 to 20/1 to 10/1) to give compound 304-1 (377 mg, about 15% yield) as an oil. MS Calcd.: 236.1; MS Found: 237.1 $[M+H]^+$.

The synthesis of N[1]-((3-(bromomethyl)oxetan-3-yl)methyl)-N-(2-chlorophenyl)-2-fluorobenzene-1,4-diamine (304-2):

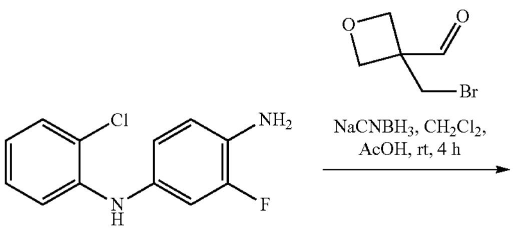

304-1

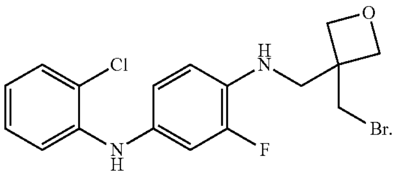

304-2

A solution of 304-1 (377 mg, 1.59 mmol), 3-(bromomethyl)oxetane-3-carbaldehyde (855 mg, 4.78 mmol) and sodium cyanoborohydride (200 mg, 3.19 mmol) in DCM (20 mL) was stirred at room temperature for 2 hr. The reaction mixture was washed with brine, dried over $Na_2SO_4$, filtered, and concentrated. The residue 304-2 was used in the next step directly without further purification. MS Calcd.: 398.0; MS Found: 399.0 $[M+H]^+$.

The synthesis of N[1]-((3-((1H-1,2,4-triazol-1-yl)methyl)oxetan-3-yl)methyl)-N[4]-(2-chlorophenyl)-2-fluorobenzene-1,4-diamine (304-3):

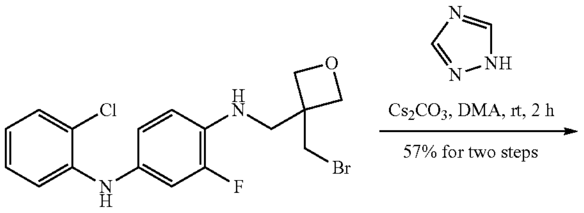

304-2

-continued

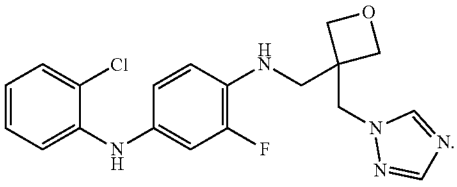

304-3

A mixture of 304-2 (637 mg, 2.50 mmol), 1H-1,2,4-triazole (220 mg, 3.19 mmol) and cesium carbonate (1.04 g, 3.19 mmol) in DMA (5 mL) was stirred at room temperature for 2 h. Then the reaction mixture was poured into cool water (20 mL), and extracted with EtOAc (10 mL×3). The combined organic layers were washed with brine (10 mL×2), dried over sodium sulfate, filtered, and concentrated to dryness. The residue was purified by Prep-TLC (petroleum ether/EtOAc=1/2) to give compound 304-3 (355 mg, about 57% yield for two steps) as an oil. MS Calcd.: 387.1; MS Found: 388.2 $[M+H]^+$.

$^1H$ NMR (400 MHz, DMSO-$d_6$) δ 8.53 (s, 1H), 8.00 (s, 1H), 7.31 (dd, J=7.8, 1.4 Hz, 1H), 7.25 (s, 1H), 7.11-7.05 (m, 1H), 6.92 (dd, J=8.2, 1.4 Hz, 1H), 6.88 (dd, J=13.6, 2.4 Hz, 1H), 6.77 (dd, J=8.6, 2.2 Hz, 1H), 6.74-6.69 (m, 1H), 6.61 (dd, J=9.6, 8.8 Hz, 1H), 5.38 (t, J=6.0 Hz, 1H), 4.60 (s, 2H), 4.50 (d, J=6.4 Hz, 2H), 4.41 (d, J=6.4 Hz, 2H), 3.18 (d, J=6.4 Hz, 2H).

The synthesis of N-((3-((1H-1,2,4-triazol-1-yl)methyl)oxetan-3-yl)methyl)-2-fluoro-9H-carbazol-3-amine (SS20308-0304-01) & N-((3-((1H-1,2,4-triazol-1-yl)methyl)oxetan-3-yl)methyl)-4-fluoro-9H-carbazol-3-amine (SS20308-0312-01):

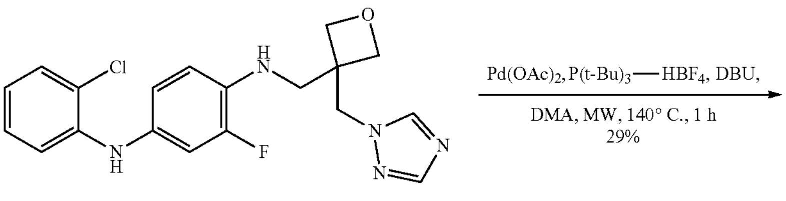

304-3

-continued

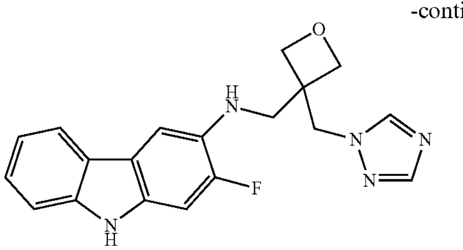

SS20308-0304-01

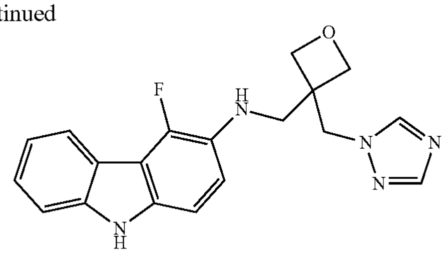

SS20308-0312-01

A mixture of 304-3 (100 mg, 0.26 mmol), DBU (130 mg, 0.52 mmol), palladium (II) acetate (12 mg, 0.052 mmol), and tri-tert-butylphosphine tetrafluoroborate (30 mg, 0.10 mmol) in DMA (2 mL) was heated to 140° C. for 1 hr in a microwave reactor. Then the reaction mixture was cooled down to room temperature, poured into cool water (10 mL), and extracted with ethyl acetate (10 mL×3). The combined organic layers were washed with brine (10 mL×2), dried over sodium sulfate, and concentrated to dryness. The residue was purified by Prep-TLC (100% EtOAc to DCM/MeOH=20/1) to give SS20308-0304-01 (26.1 mg, about 29% yield) as a solid, and SS20308-0312-01 (26.7 mg, about 29% yield) as a solid.

SS20308-0304-01: MS Calcd.: 351.2; MS Found: 352.3 $[M+H]^+$. $^1H$ NMR (400 MHz, DMSO-$d_6$) δ 10.89 (s, 1H), 8.56 (s, 1H), 8.05 (s, 1H), 7.93 (d, J=7.6 Hz, 1H), 7.37 (d, J=8.0 Hz, 1H), 7.27 (d, J=8.4 Hz, 1H), 7.25 (dd, J=7.6, 7.2 Hz, 1H), 7.20 (d, J=12 Hz, 1H), 7.05 (dd, J=7.6, 7.2 Hz, 1H), 5.17 (t, J=6.0 Hz, 1H), 4.67 (s, 2H), 4.55 (d, J=6.0 Hz, 2H), 4.47 (d, J=6.0 Hz, 2H), 3.30 (d, J=6.0 Hz, 2H).

SS20308-0312-01: MS Calcd.: 351.2; MS Found: 352.3 $[M+H]^+$. $^1H$ NMR (400 MHz, DMSO-$d_6$) δ 11.06 (s, 1H), 8.55 (s, 1H), 8.02 (s, 1H), 7.98 (d, J=7.6 Hz, 1H), 7.41 (d, J=8.0 Hz, 1H), 7.35 (dd, J=8.0, 7.2 Hz, 1H), 7.13-7.07 (m, 2H), 6.88 (dd, J=8.8, 8.4 Hz, 1H), 5.05 (t, J=6.0 Hz, 1H), 4.65 (s, 2H), 4.53 (d, J=6.4 Hz, 2H), 4.46 (d, J=6.4 Hz, 2H), 3.25 (d, J=6.8 Hz, 2H).

Example 81

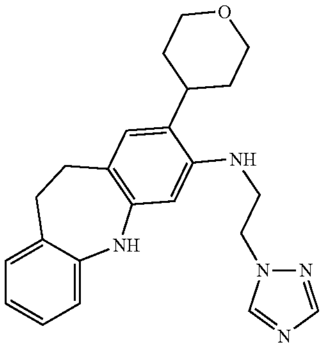

SS20308-0305-01
Chemical Formula: $C_{23}H_{27}N_5O$
Molecular Weight: 389.49

Example Route for Example 81 (SS20308-0305-01):

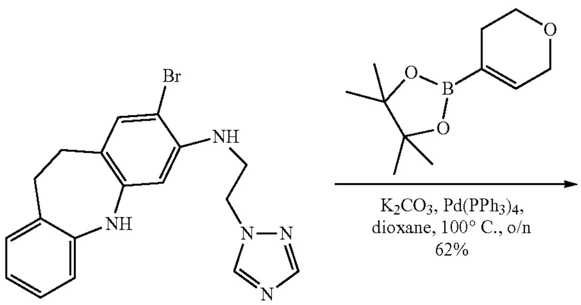

SS20308-0224-01

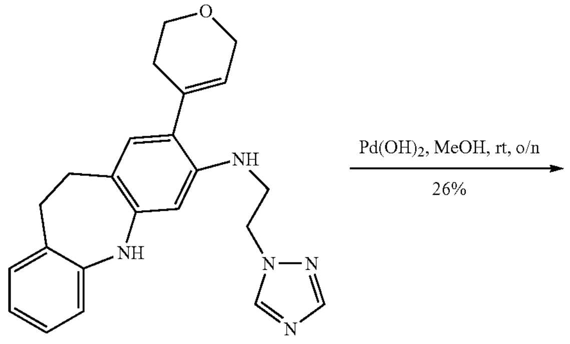

305-1

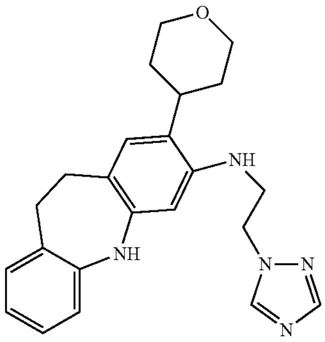

SS20308-0305-01

The synthesis of N-(2-(1H-1,2,4-triazol-1-yl)ethyl)-2-(3,6-dihydro-2H-pyran-4-yl)-10,11-dihydro-5H-dibenzo[b,f]azepin-3-amine (305-1):

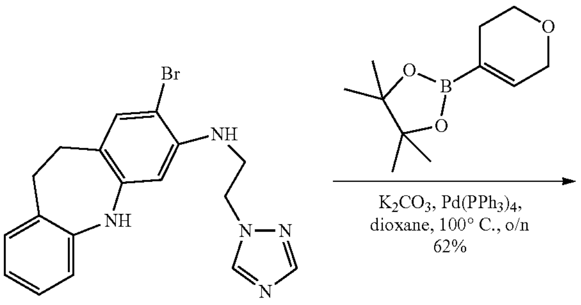

SS20308-0224-01

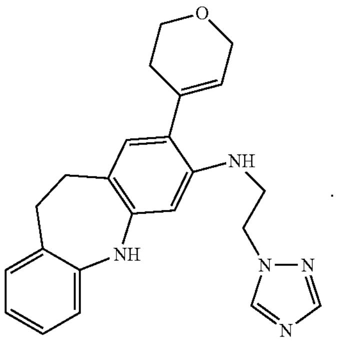

305-1

A mixture of SS20308-0224-01 (160 mg, 0.42 mmol), 2-(3,6-dihydro-2H-pyran-4-yl)-4,4,5,5-tetramethyl-1,3,2-dioxaborolane (175 mg, 0.83 mmol), $Pd(PPh_3)_4$ (48 mg, 0.04 mmol) and $K_2CO_3$ (115 mg, 0.83 mmol) in 1,4-dioxane (10 ml) was stirred at 100° C. under nitrogen atmosphere overnight. After the reaction was complete, the mixture was quenched with water, and extracted with EtOAc (30 mL×3). The organic layers were separated, dried over $MgSO_4$, filtered, and concentrated under vacuum. The crude product was purified by column chromatography on silica gel (petroleum ether/EtOAc=1/1) to give 305-1 (100 mg, about 62% yield) as a solid. MS Calcd.: 387.2; MS Found: 388.0 $[M+H]^+$.

The synthesis of N-(2-(1H-1,2,4-triazol-1-yl)ethyl)-2-(tetrahydro-2H-pyran-4-yl)-10,11-dihydro-5H-dibenzo[b,f]azepin-3-amine (SS20308-0305-01):

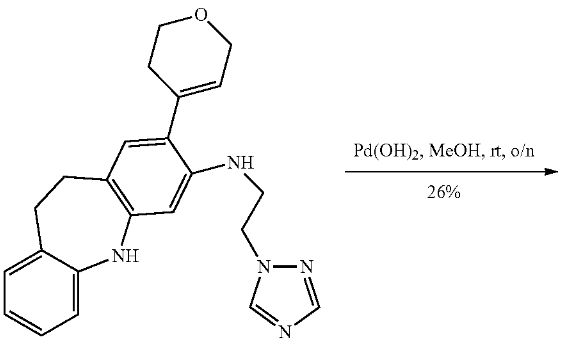

305-1

-continued

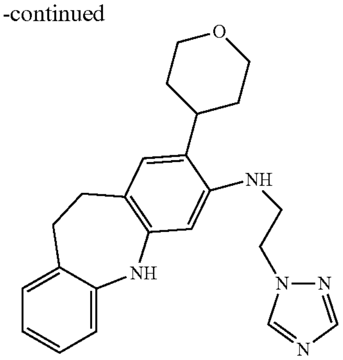

SS20308-0305-01

A mixture of 305-1 (50 mg, 0.13 mmol) and $Pd(OH)_2$ (50 mg) in MeOH (10 ml) and was stirred at room temperature under hydrogen gas (balloon) overnight. After the reaction was complete, the insoluble material was removed by filtration. The organic layer was concentrated under vacuum to give a residue, which was purified by Prep-HPLC to give SS20308-0305-01 (13 mg, about 26% yield) as a solid. MS Calcd.: 389.2; MS Found: 390.0 $[M+H]^+$.

$^1$H NMR (400 MHz, DMSO-$d_6$) δ 8.48 (s, 1H), 7.98 (s, 2H), 6.99-6.94 (m, 2H), 6.87-6.86 (s, 1H), 6.60-6.57 (m, 2H), 6.26 (s, 1H), 4.93 (t, J=5.6 Hz, 1H), 4.42 (t, J=6.4 Hz, 2H), 3.89-3.86 (m, 2H), 3.43-3.38 (m, 4H), 2.89-2.86 (m, 2H), 2.82-2.80 (m, 2H), 2.65-2.64 (m, 1H), 1.54-1.45 (m, 4H).

What is claimed is:

1. A compound of Formula I:

Formula I

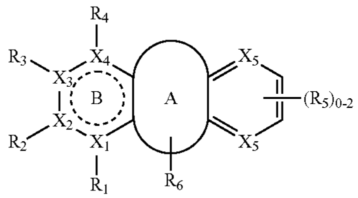

wherein the compound is selected from:

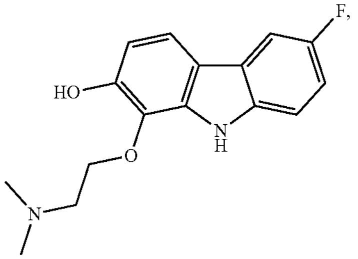

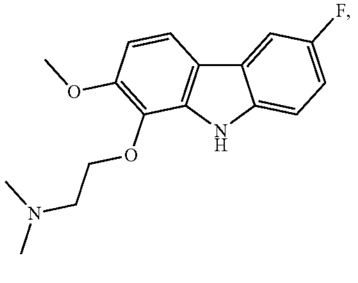

-continued
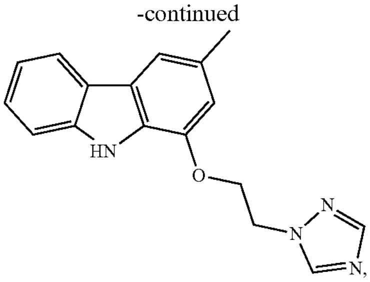
,
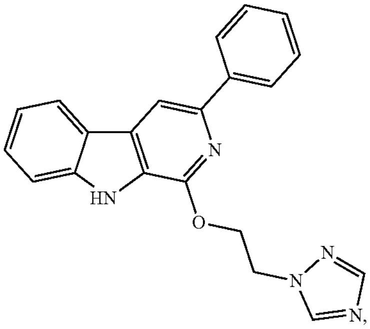
,
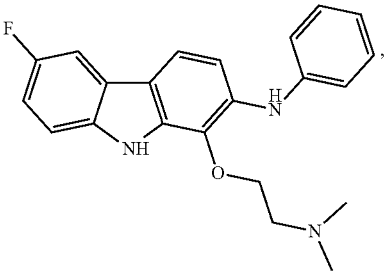
,
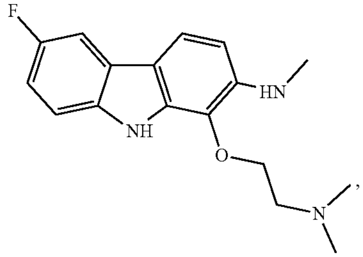
,
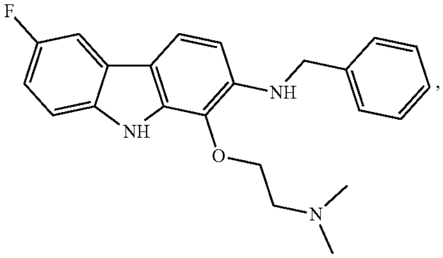
,
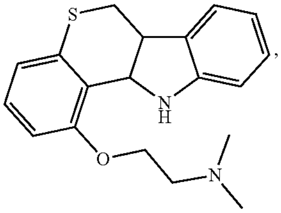
,
-continued
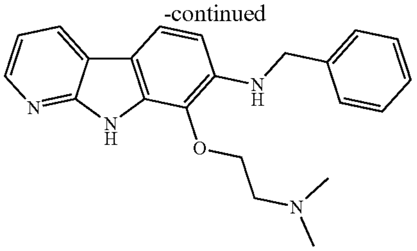
,
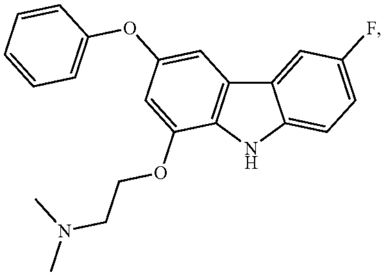
,
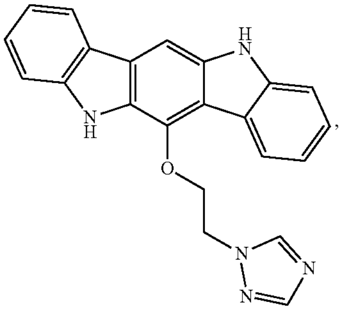
,
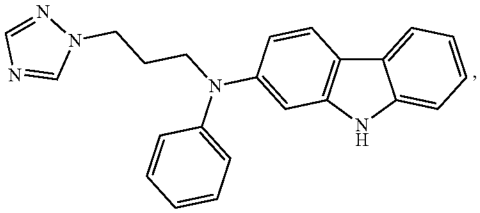
,
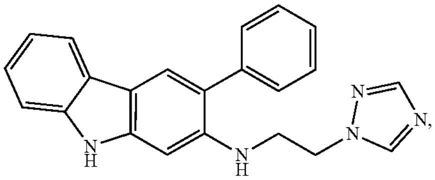
,
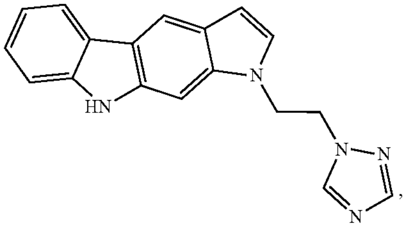
,
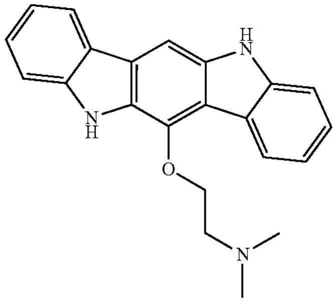
, -continued
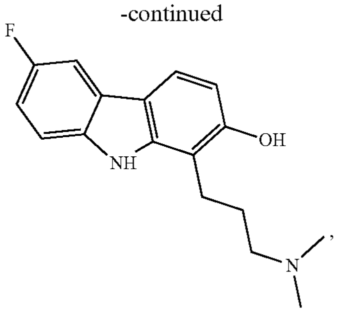
,
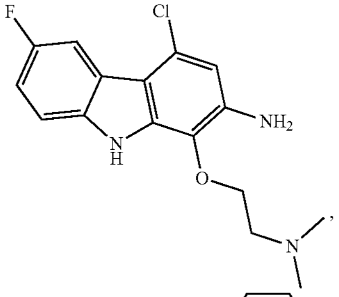
,
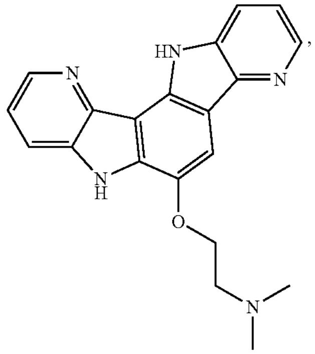
,
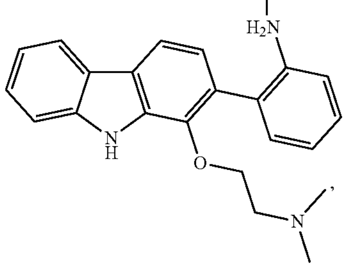
,
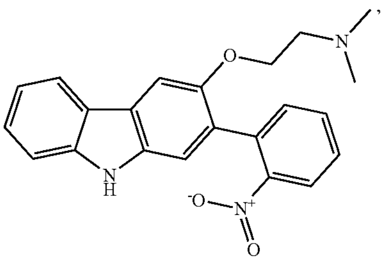
,
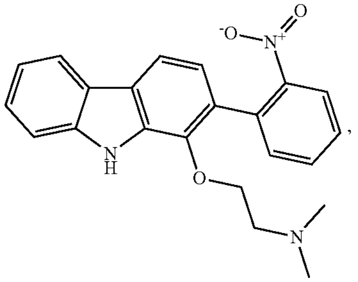
,
-continued
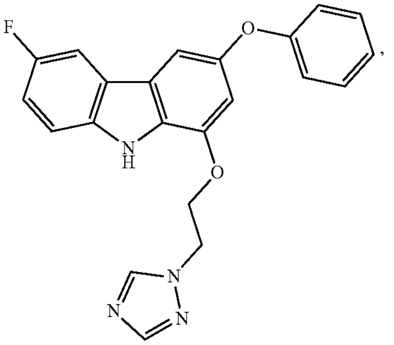
,
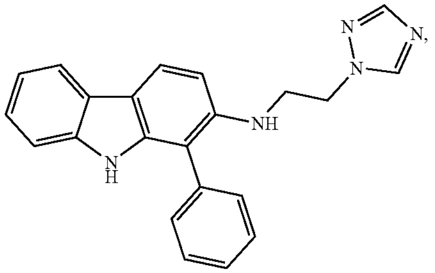
,
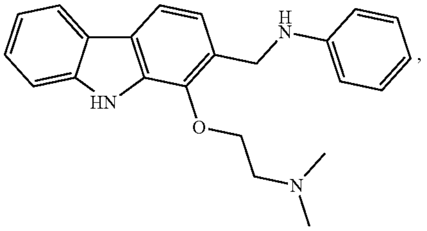
,
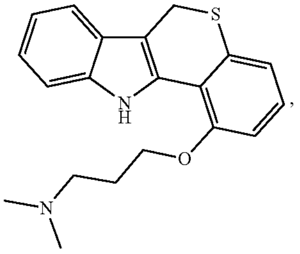
,
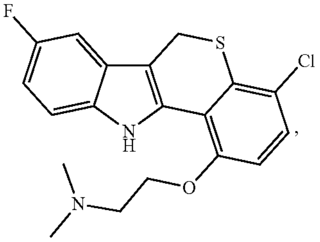
,
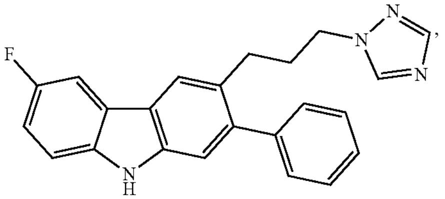
, -continued
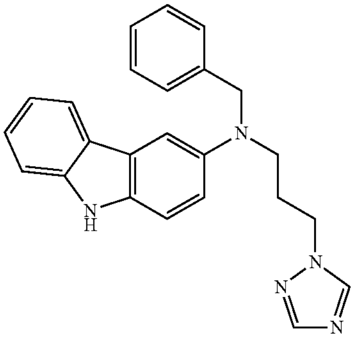
,
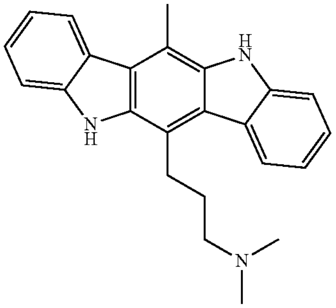
,
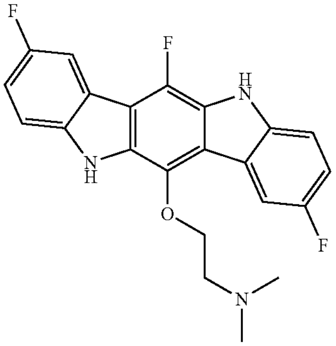
,
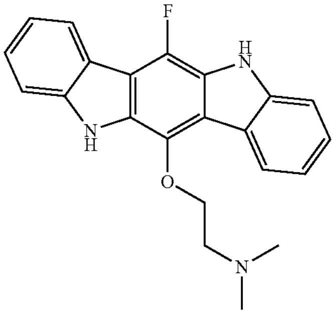
,
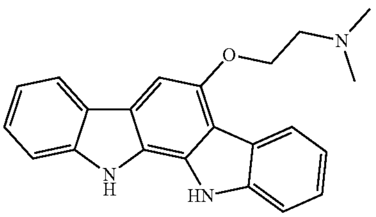
,
-continued
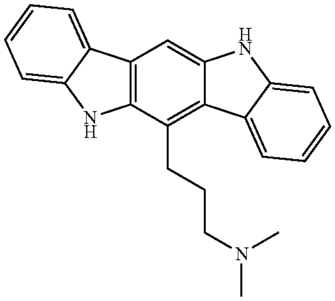
,
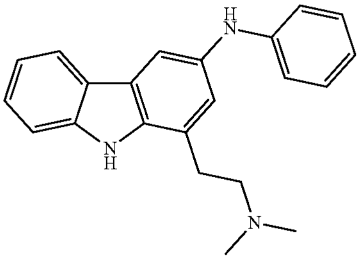
,
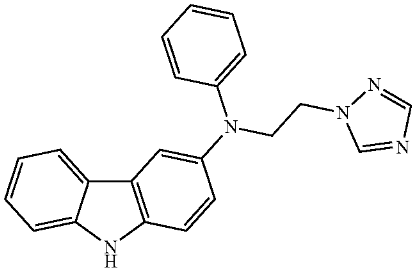
,
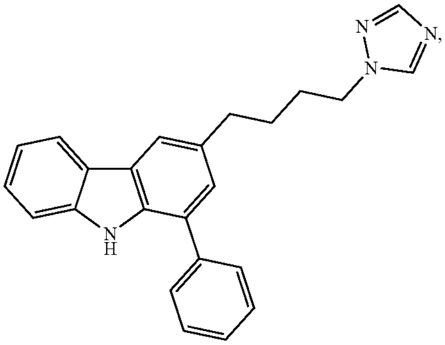
,
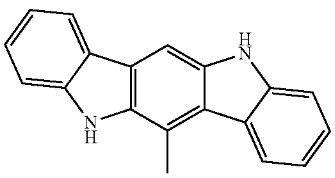
,
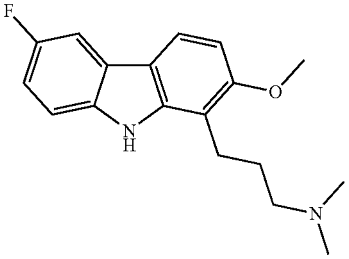
, -continued
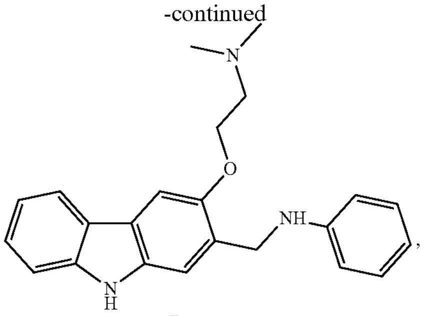
,
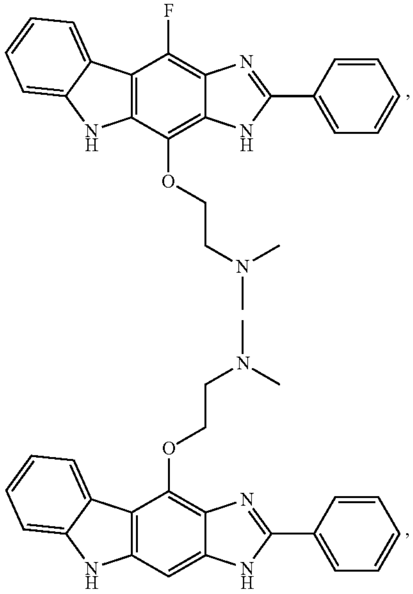
,
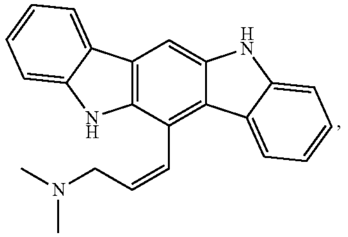
,
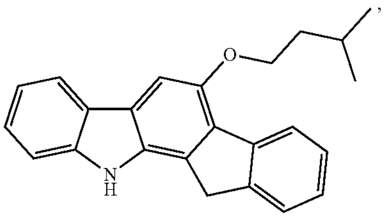
,
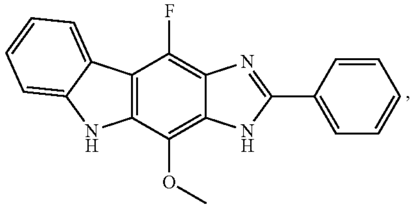
,
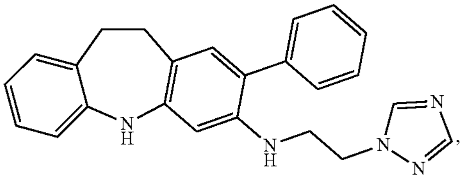
,
-continued
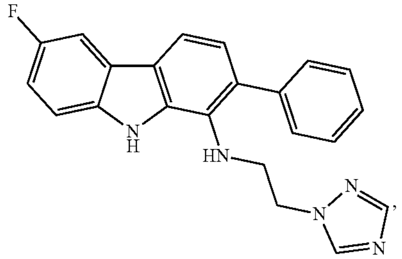
,
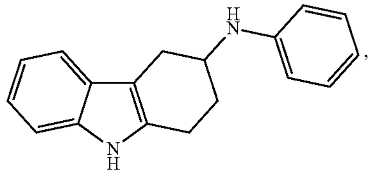
,
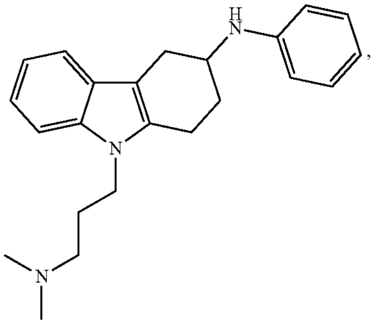
,
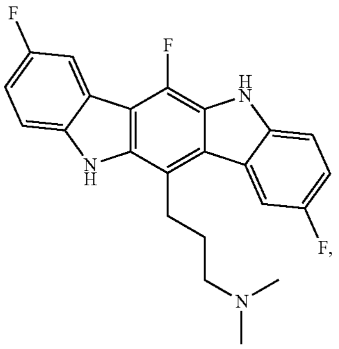
,
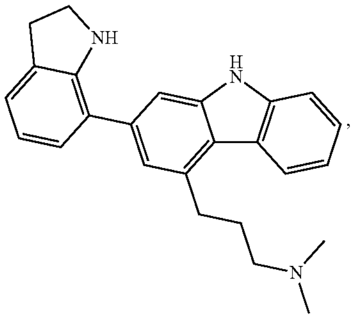
,
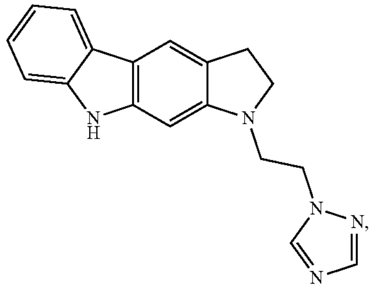
, -continued
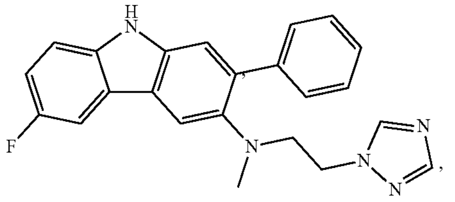
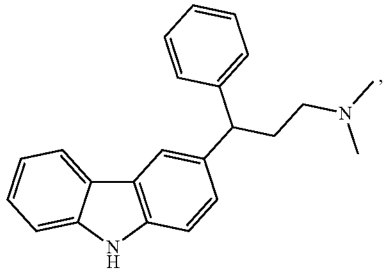
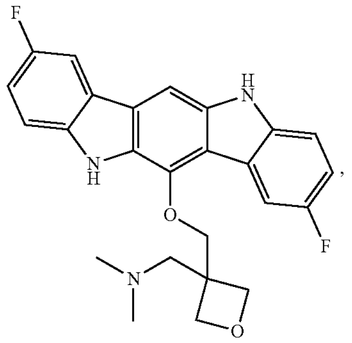
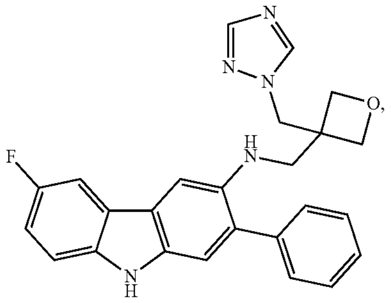
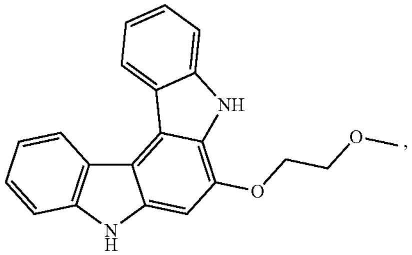
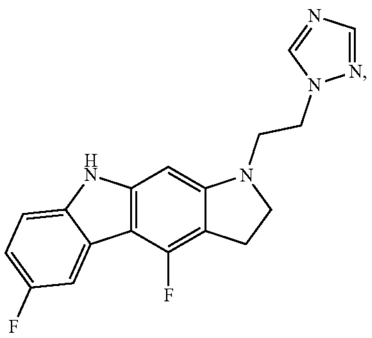
-continued
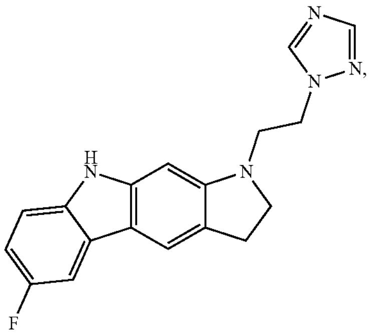
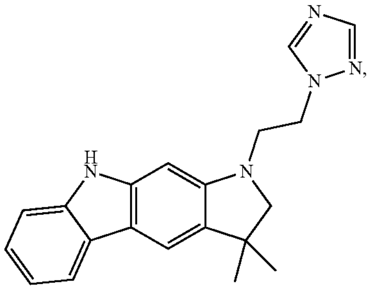
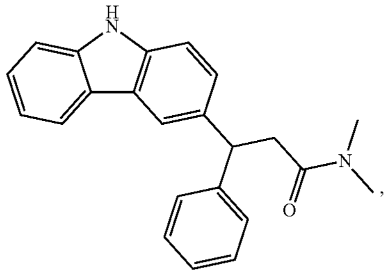
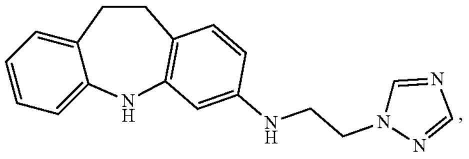
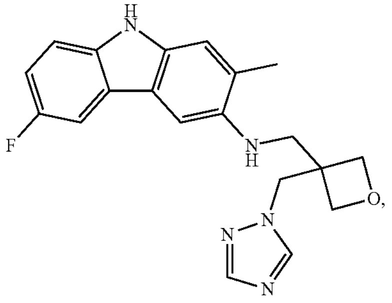
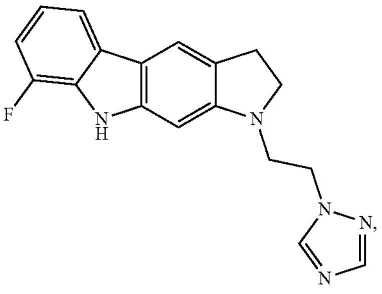

-continued
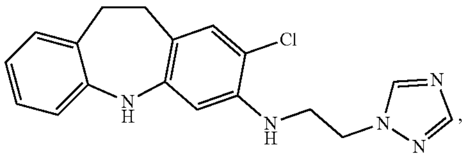
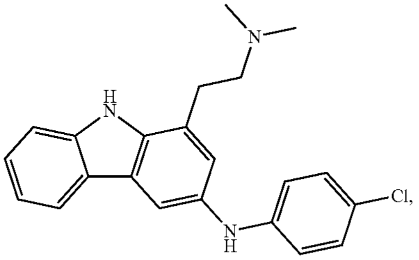
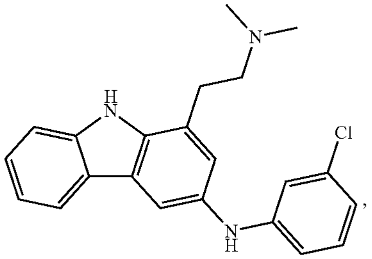
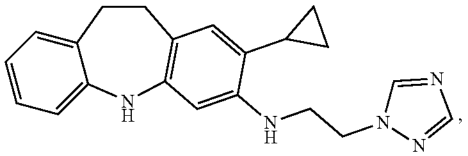
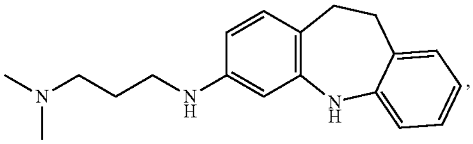
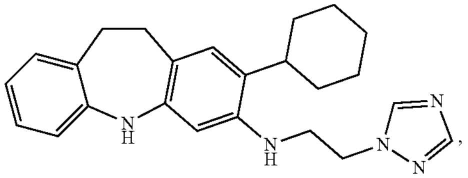
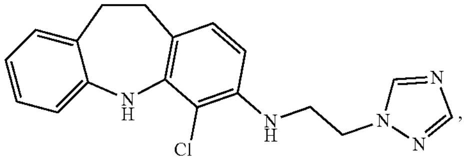
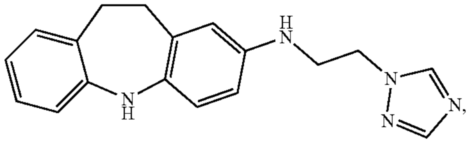
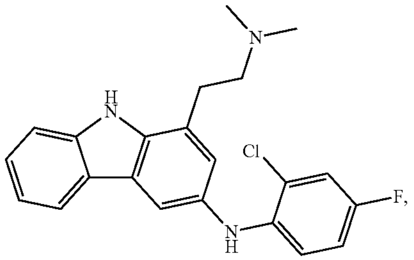
-continued
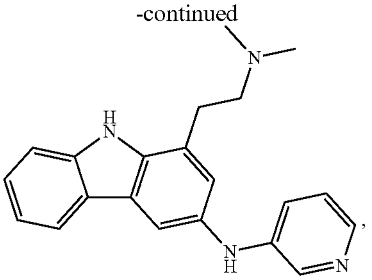
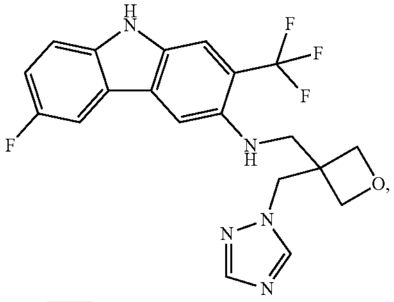
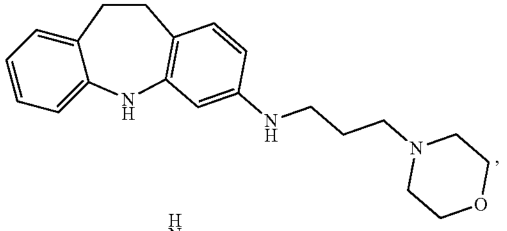
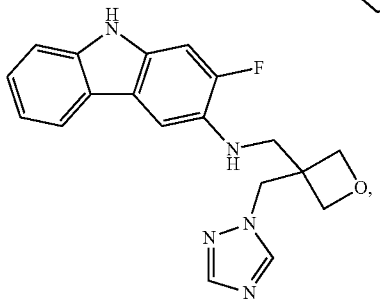
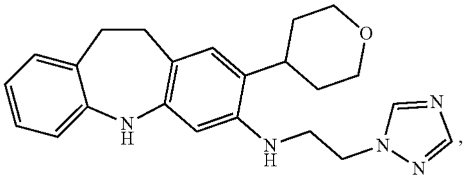
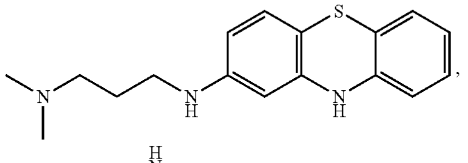
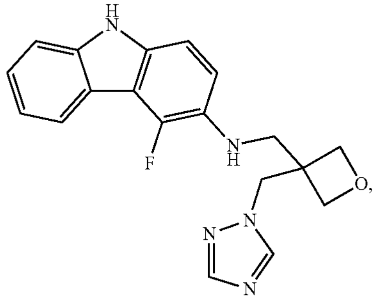
and pharmaceutically acceptable salts thereof.

2. The compound of claim 1, wherein the compound or the pharmaceutically acceptable salts thereof exhibits inhibitory activity against a lipoxygenase.
3. The compound of claim 1, wherein the compound is selected from:
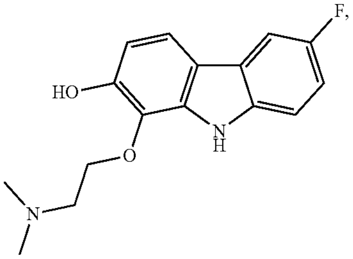
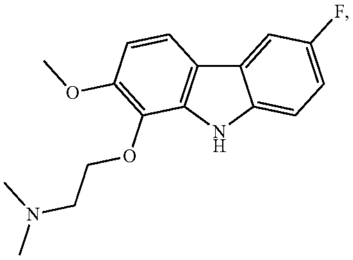
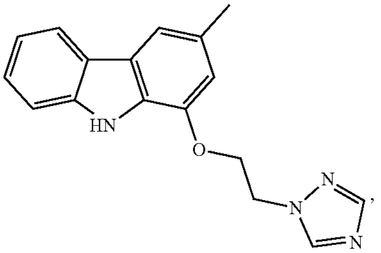
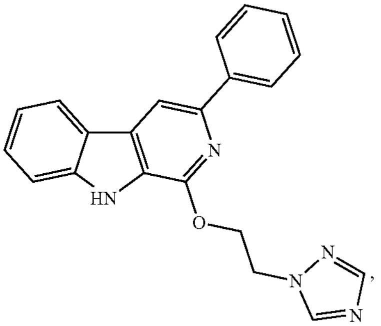
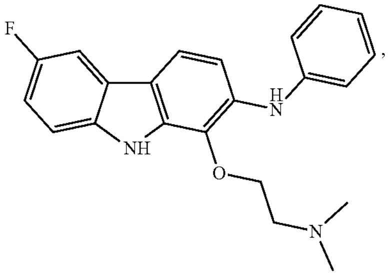
-continued
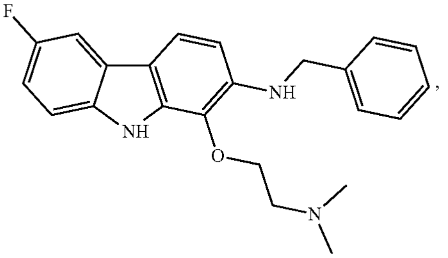
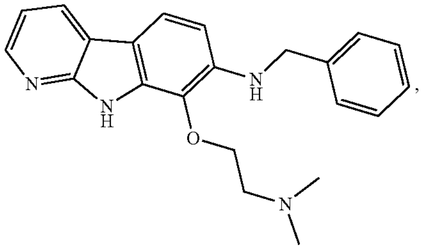
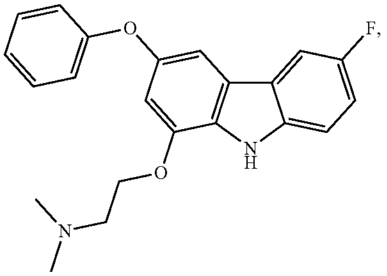
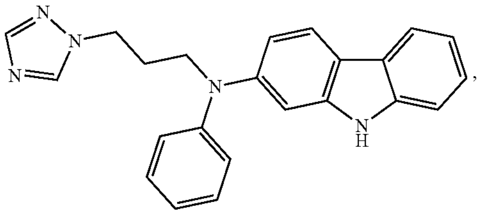
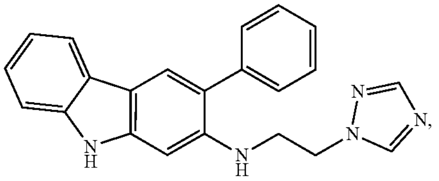
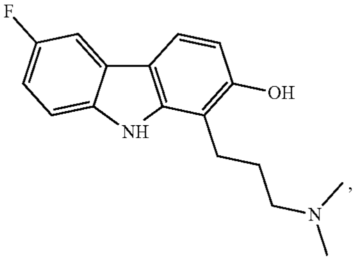
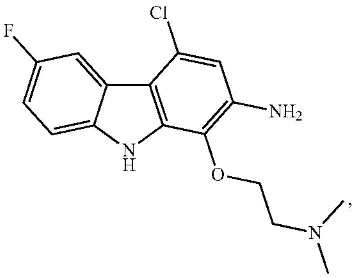

-continued
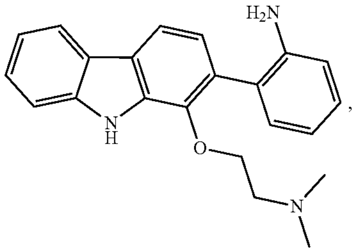
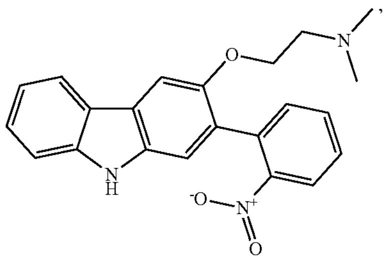
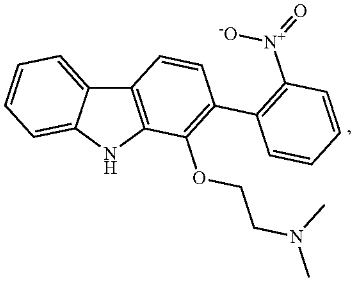
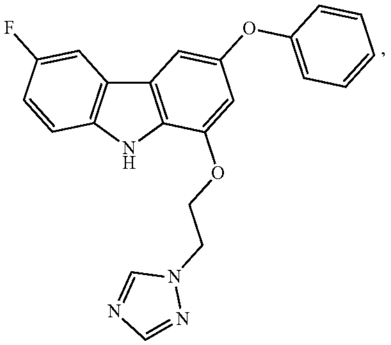
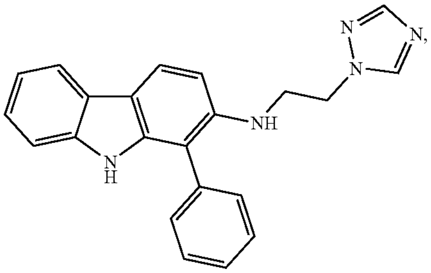
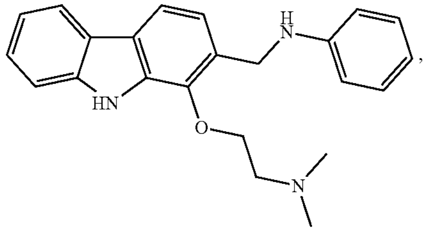
-continued
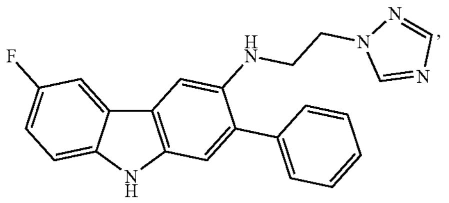
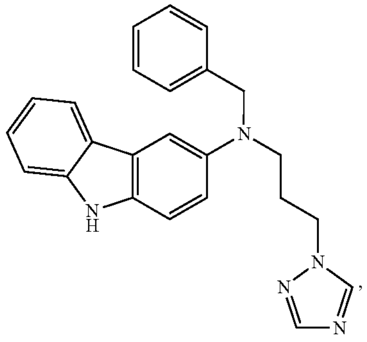
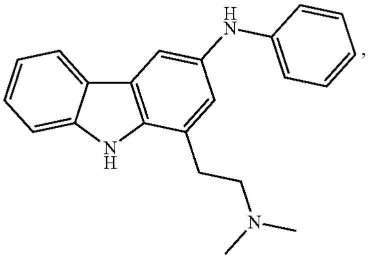 [SMILES: CN(C)CCc1cc(Nc2ccccc2)cc2c1[nH]c1ccccc12]
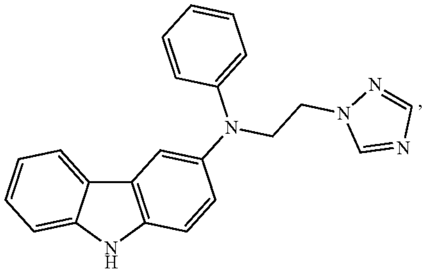
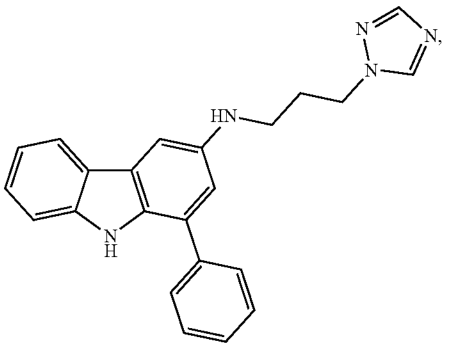
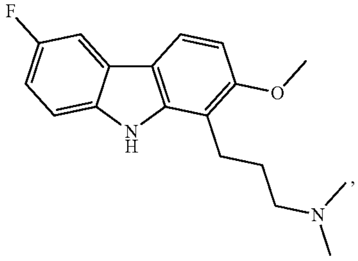

-continued
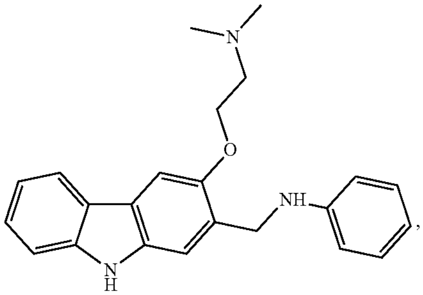
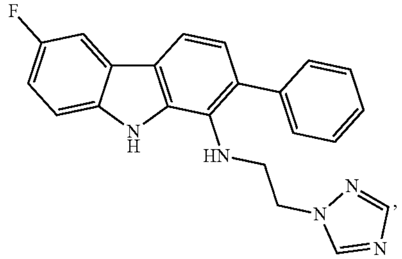
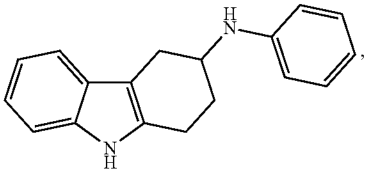
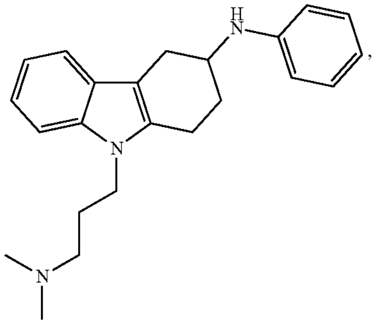
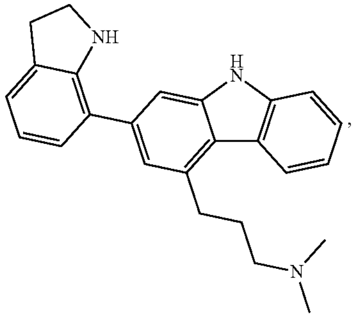
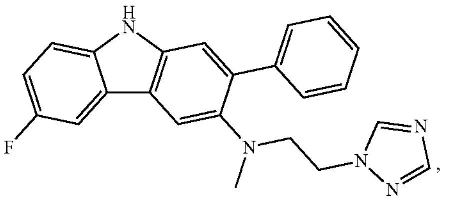
-continued
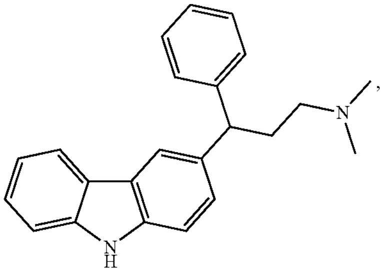
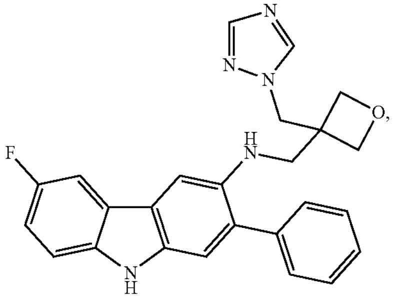
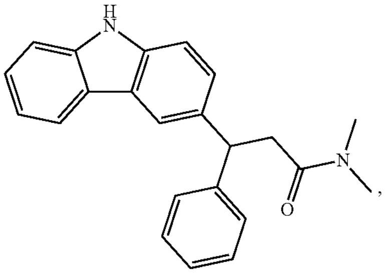 [SMILES: CN(C)C(=O)CC(c1ccccc1)c1ccc2[nH]c3ccccc3c2c1]
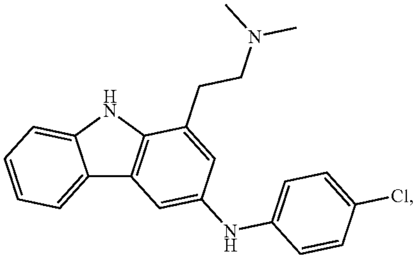
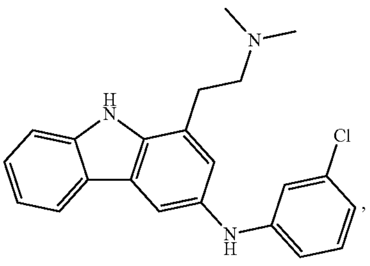
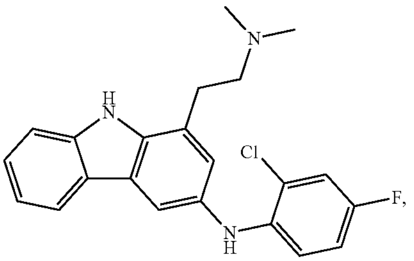

-continued
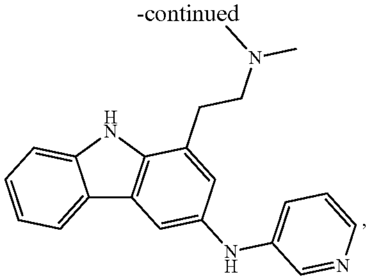
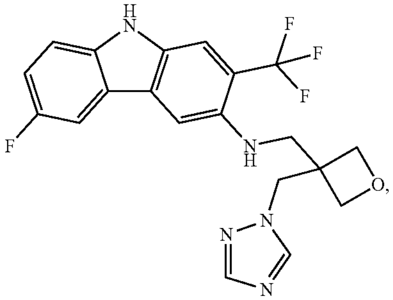
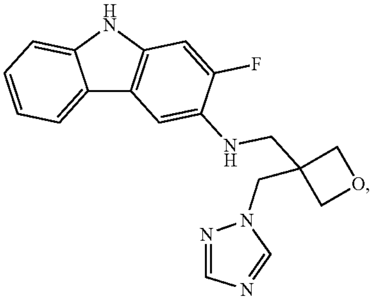
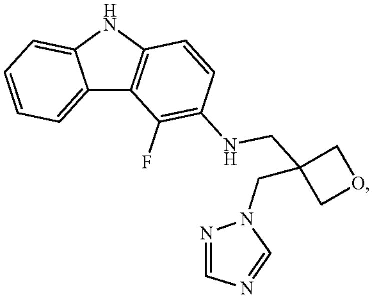 [SMILES: Fc1c(NCC2(Cn3cncn3)COC2)ccc2[nH]c3ccccc3c12]
and pharmaceutically acceptable salts thereof.
4. A compound of Formula IA:
Formula IA
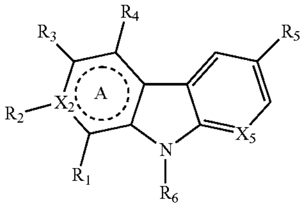
wherein the compound is selected from:
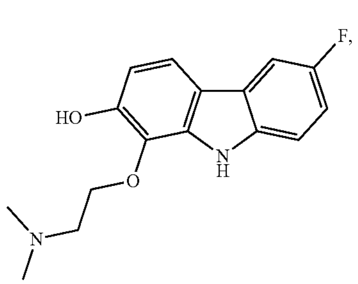
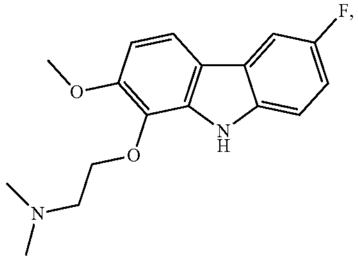
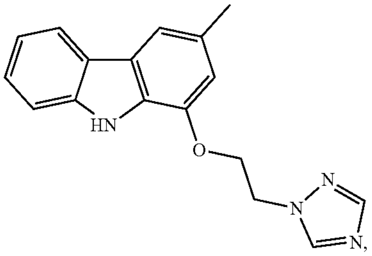
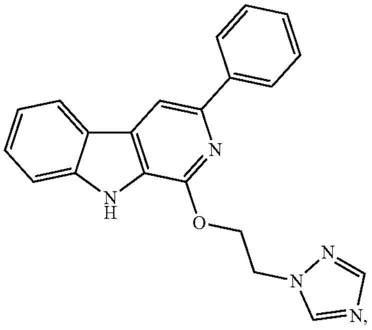
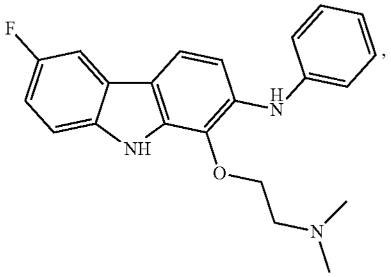
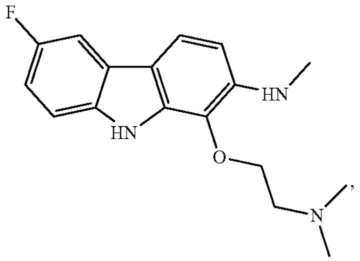

-continued
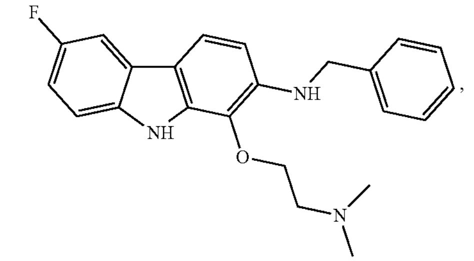
,
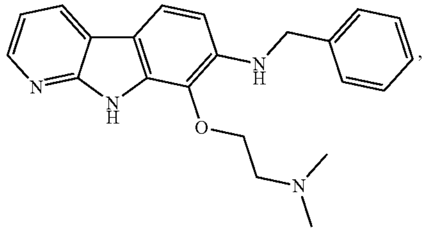
,
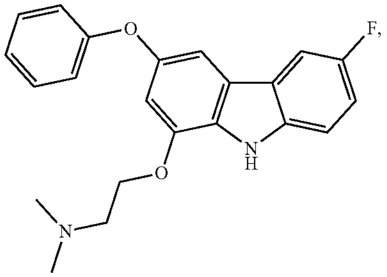
,
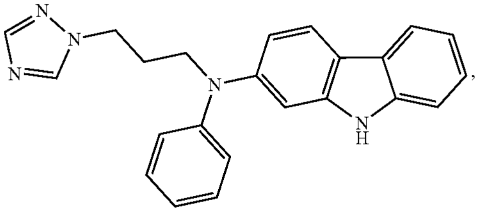
,
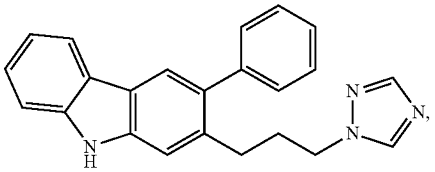
,
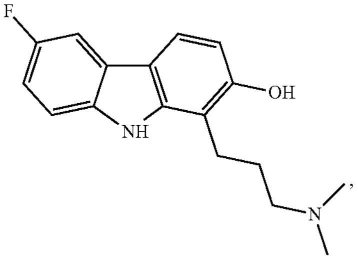
,
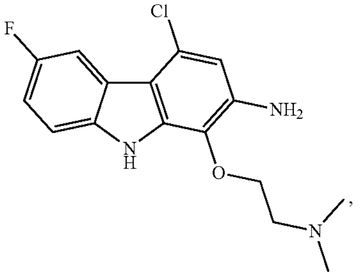
,
-continued
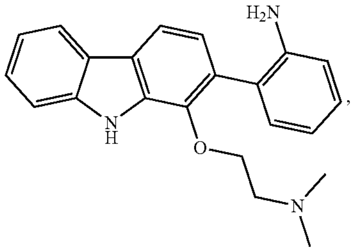
,
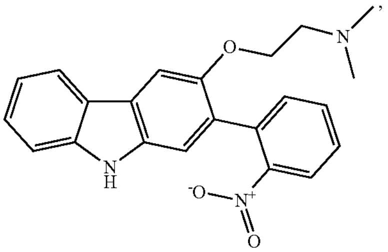
,
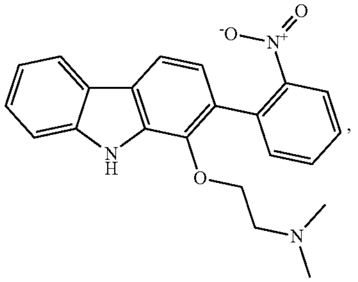
,
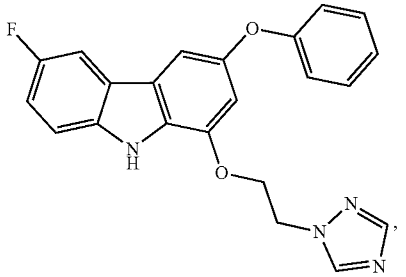
,
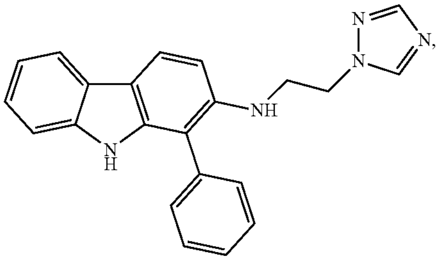
,
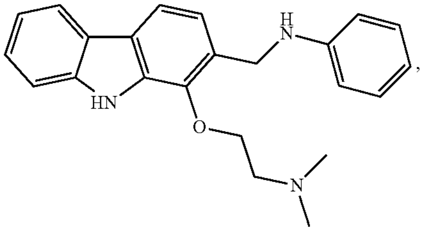
, -continued
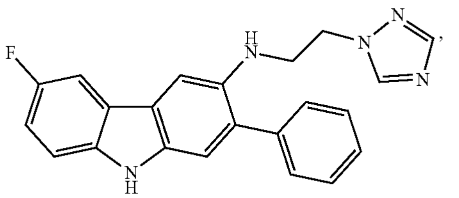
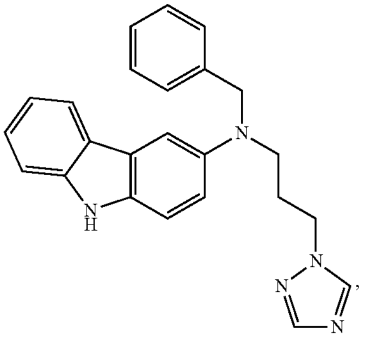
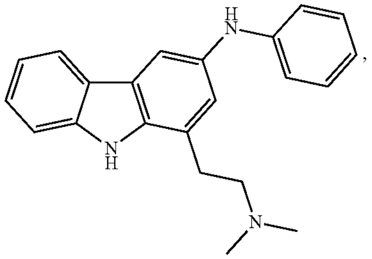
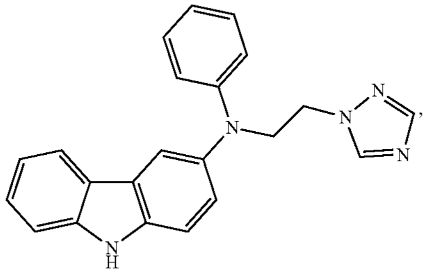
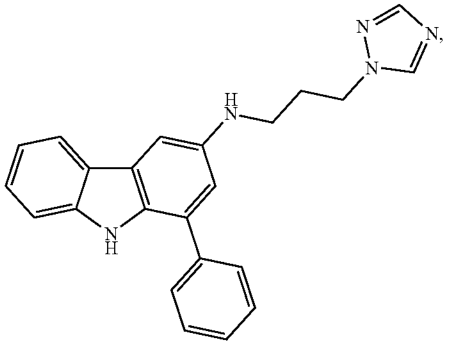
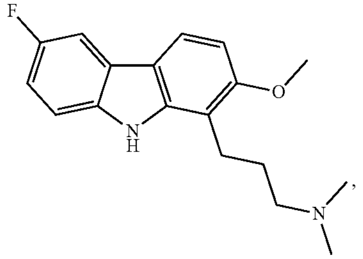
-continued
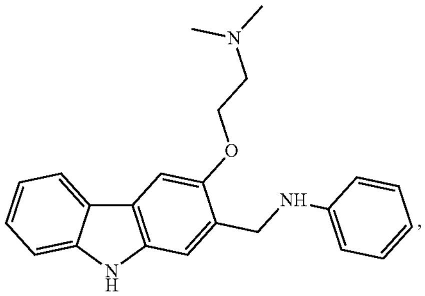
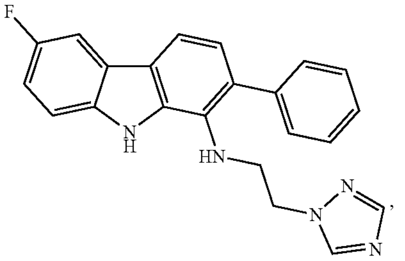
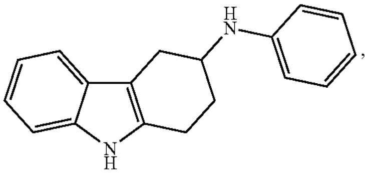
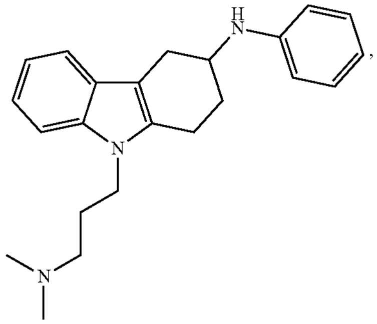
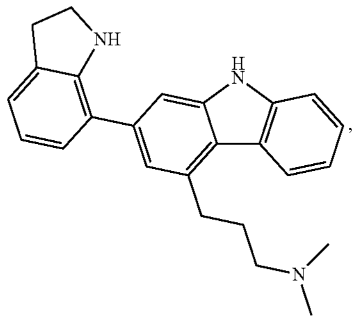
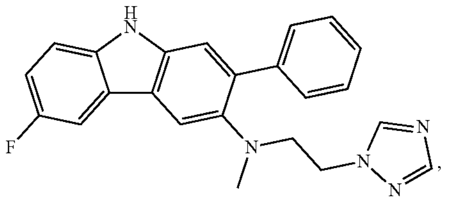

-continued
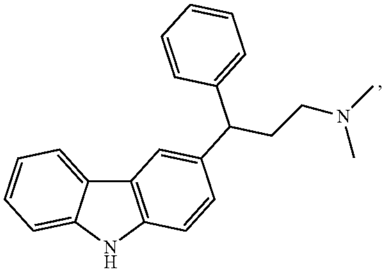
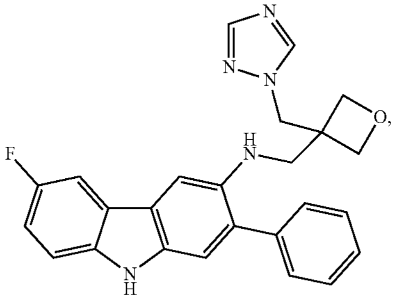
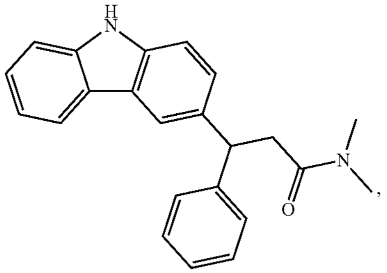
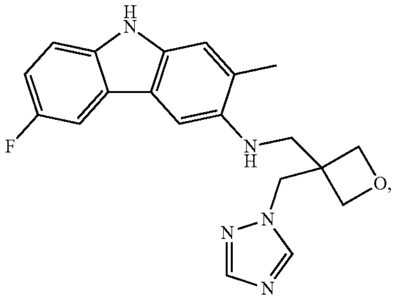
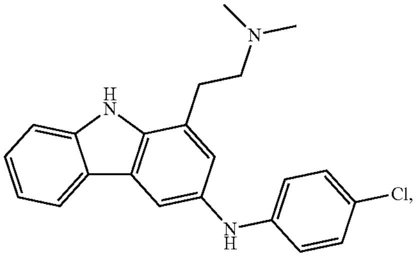
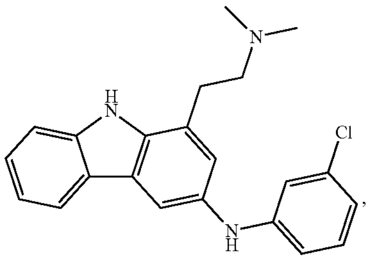
-continued
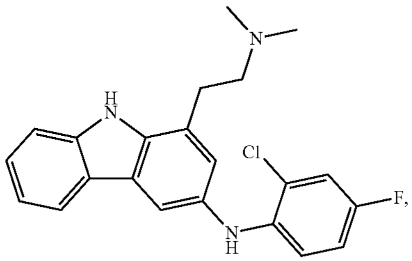
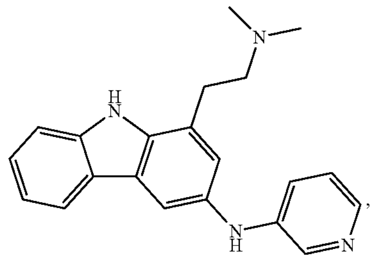
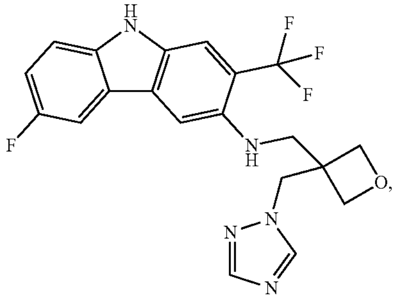
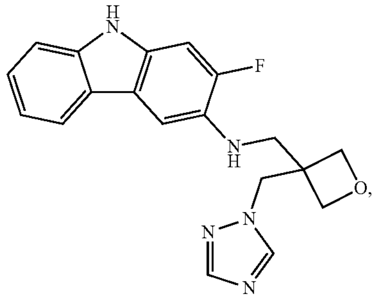
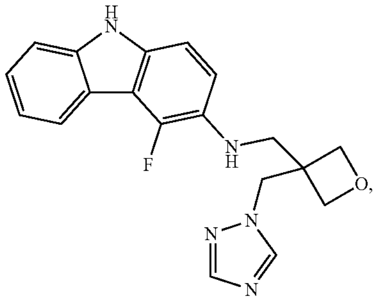
and pharmaceutically acceptable salts thereof.

5. The compound of claim 4, wherein the compound is selected from:
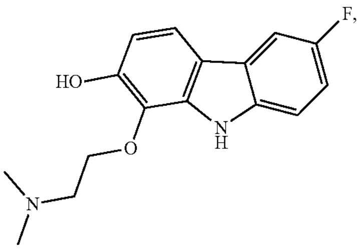
,
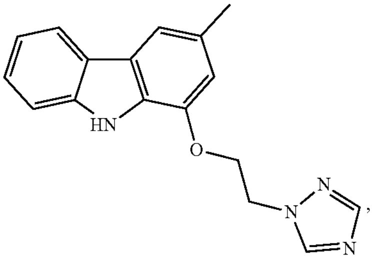
,
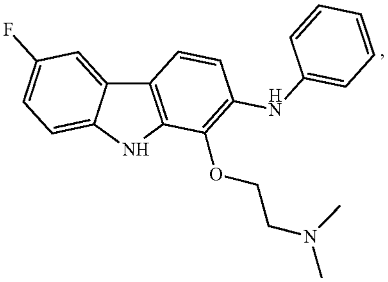
,
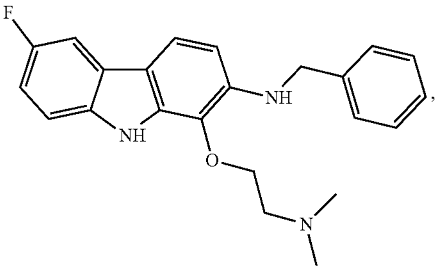
,
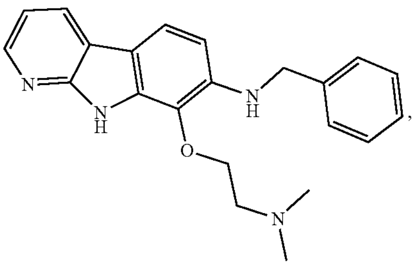
,
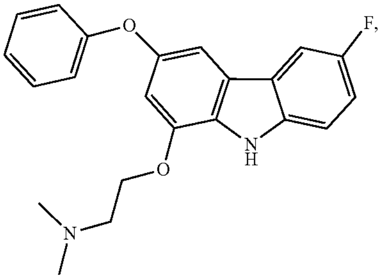
,
-continued
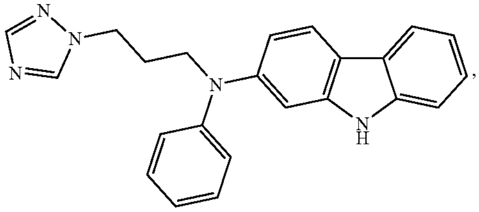
,
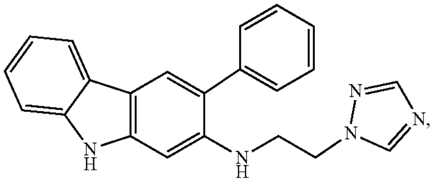
,
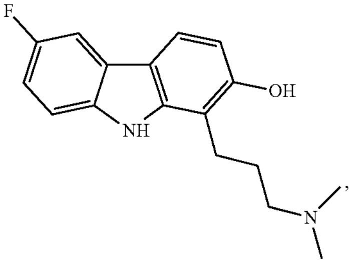
,
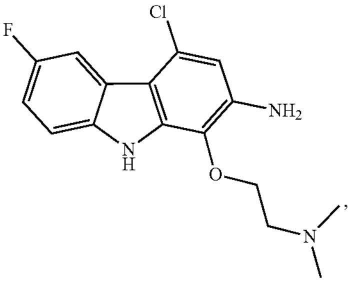
,
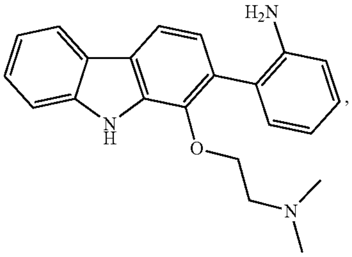
,
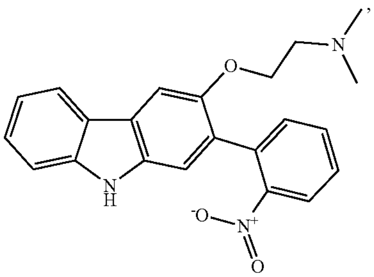
, -continued
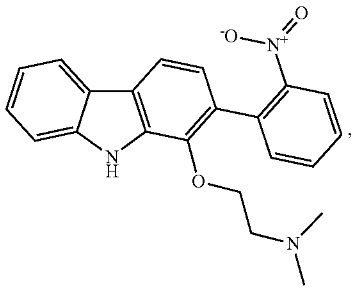
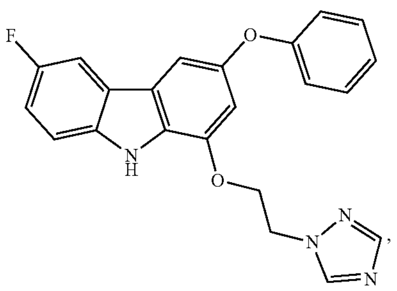
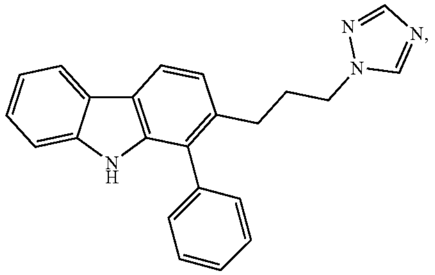
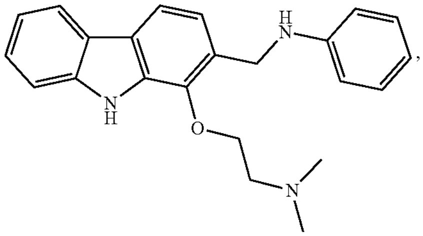
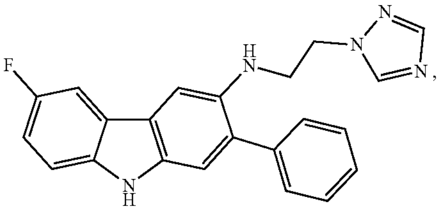
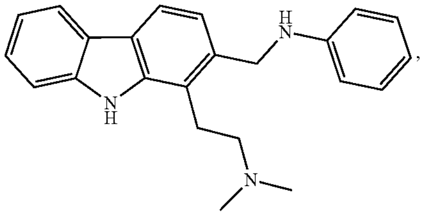
-continued
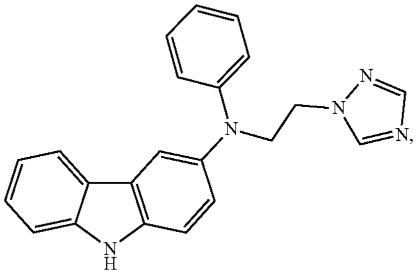
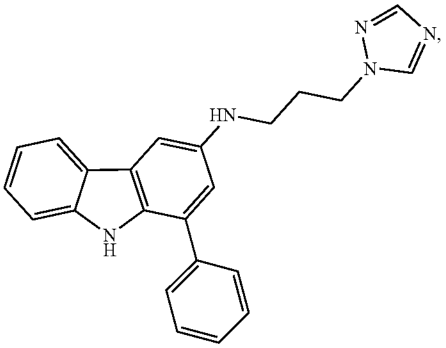
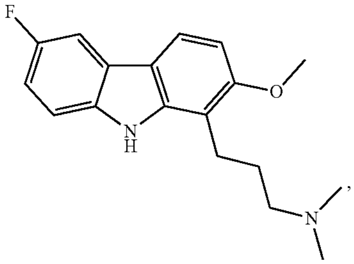
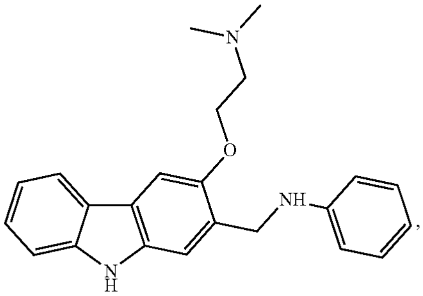
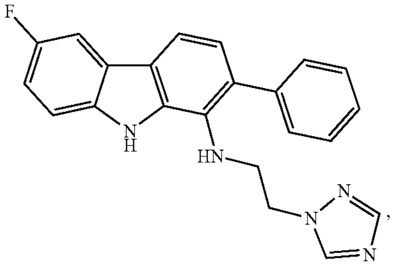
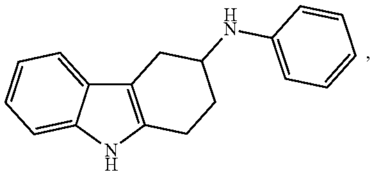

-continued
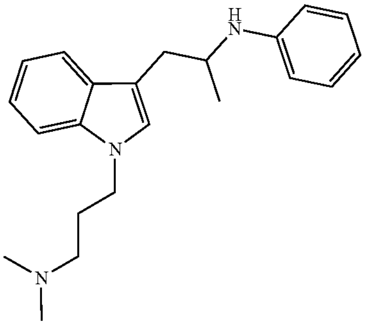
,
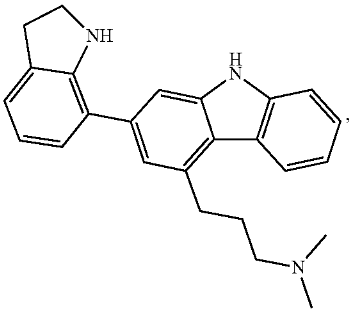
,
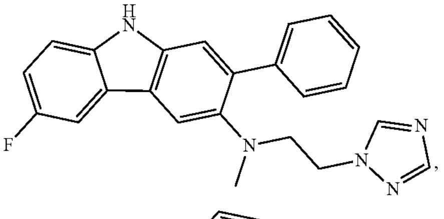
,
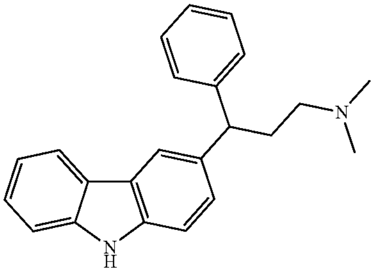
,
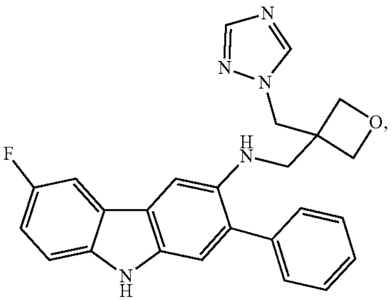
,
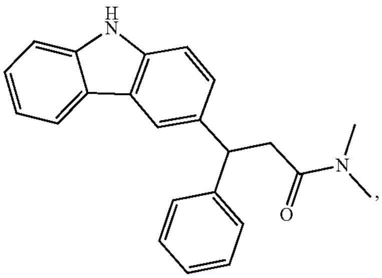
,
-continued
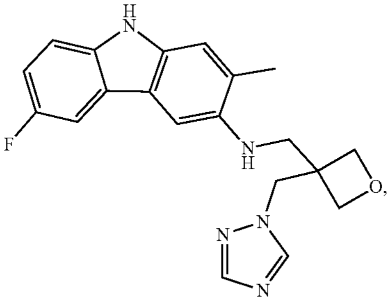
,
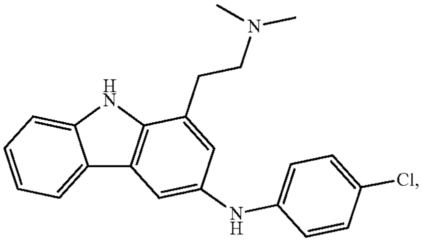
,
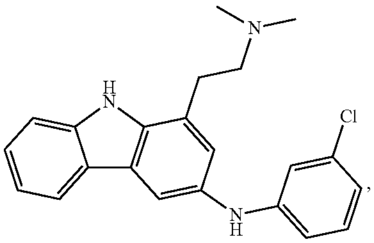
,
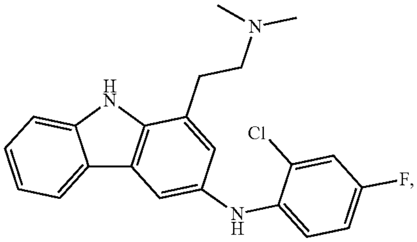
,
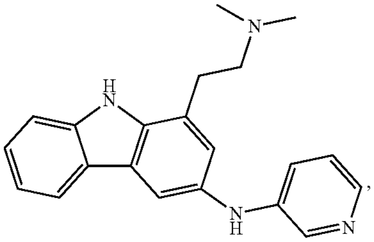
,
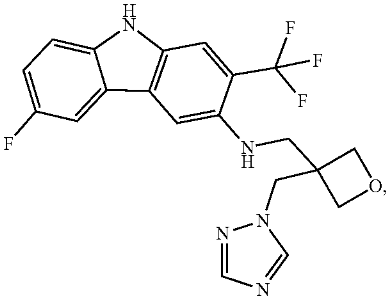
, -continued
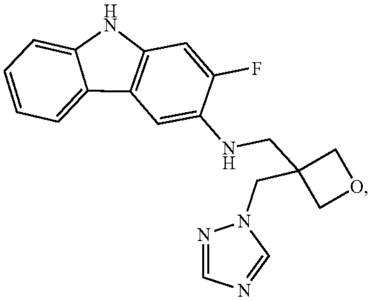
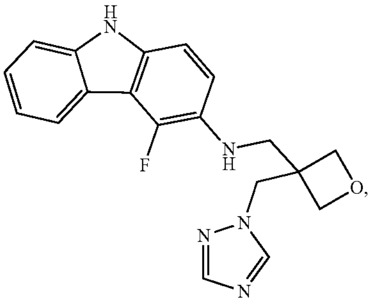
and pharmaceutically acceptable salts thereof.
6. The compound of claim 4, wherein the compound is selected from:
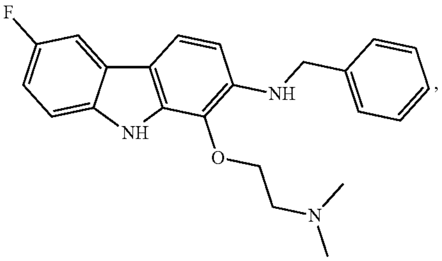
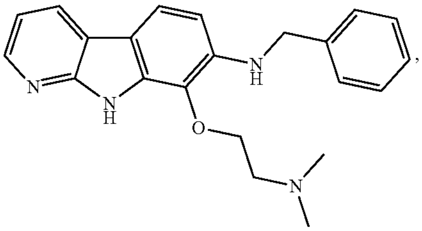
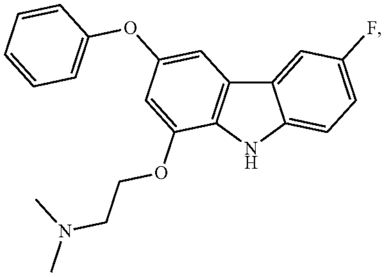
-continued
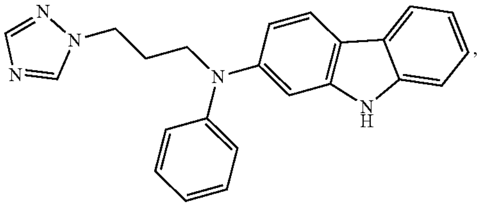
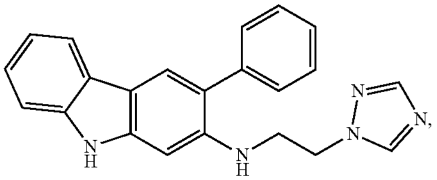
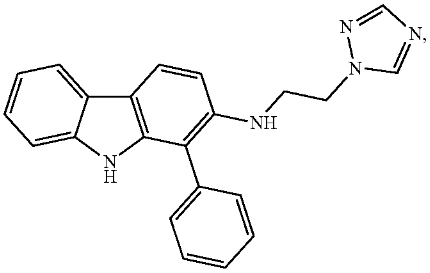
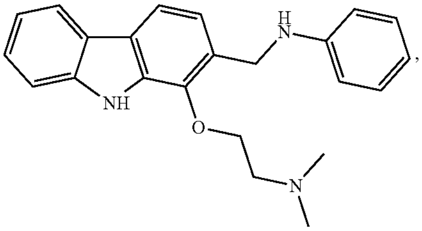
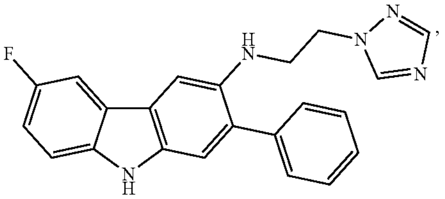
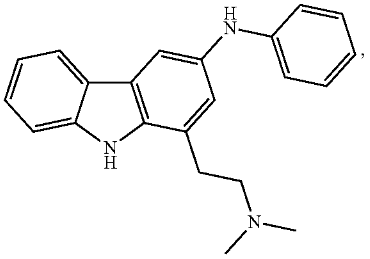
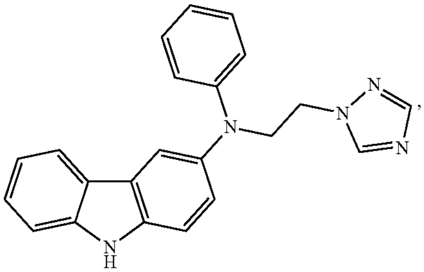

-continued
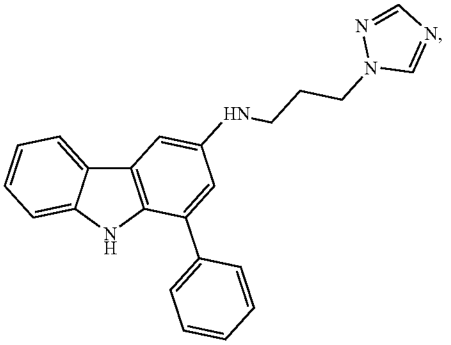
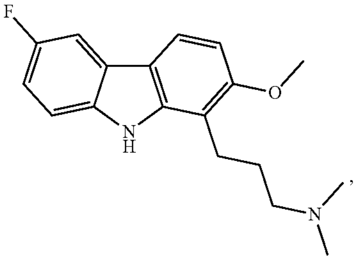
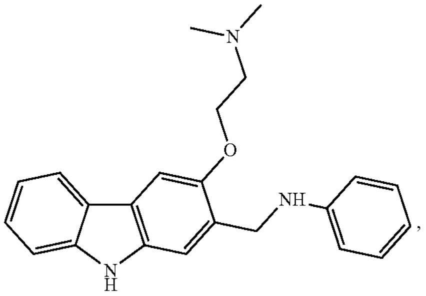
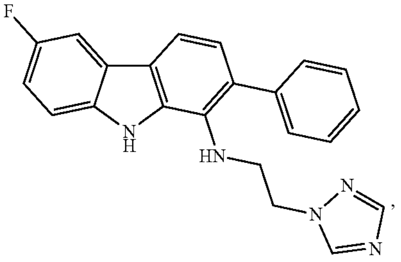
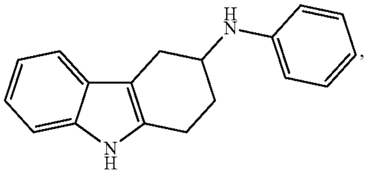
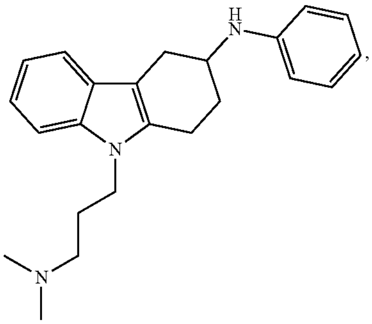
-continued
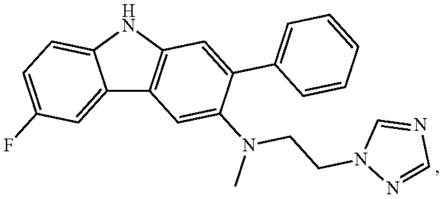
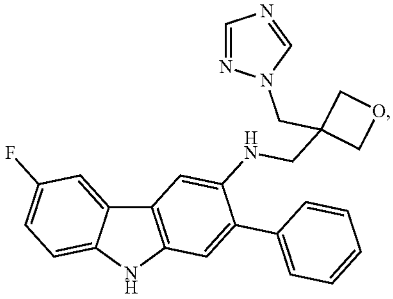
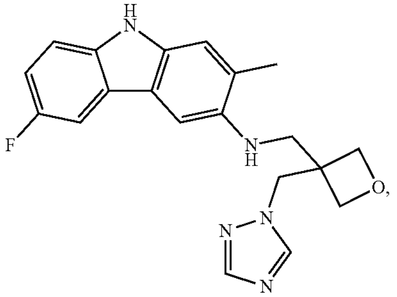
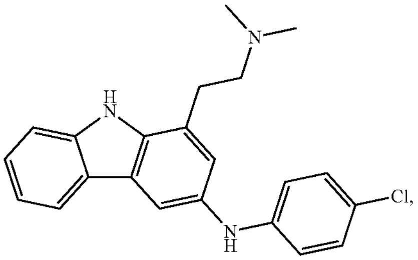
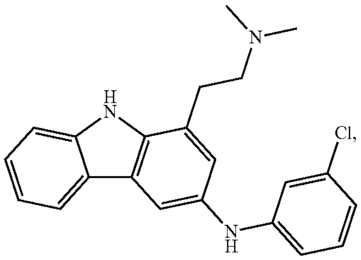
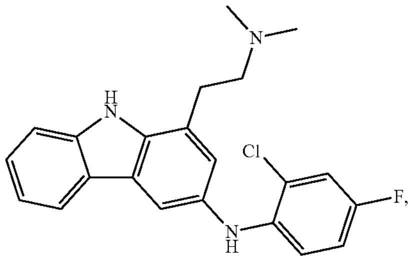

-continued
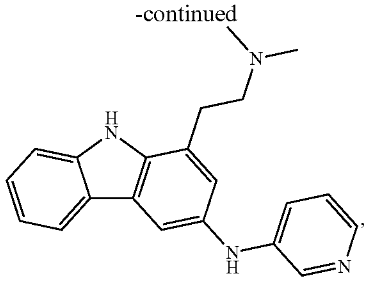
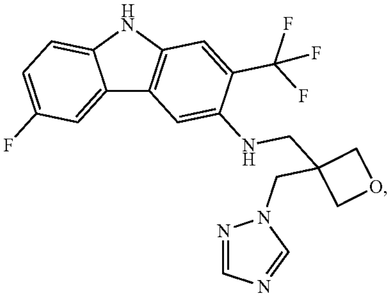
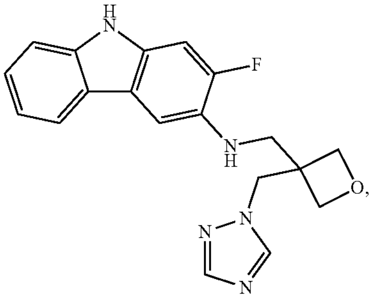
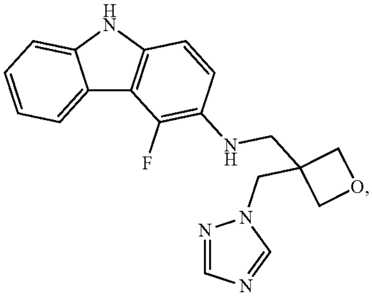
and pharmaceutically acceptable salts thereof.
7. The compound of claim 4, wherein the compound is selected from:
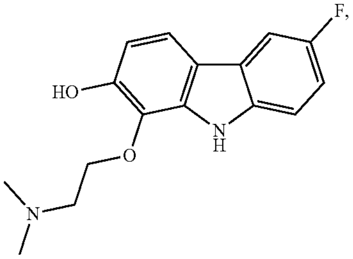
-continued
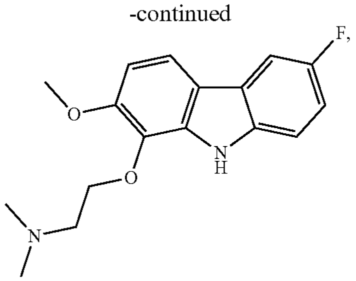
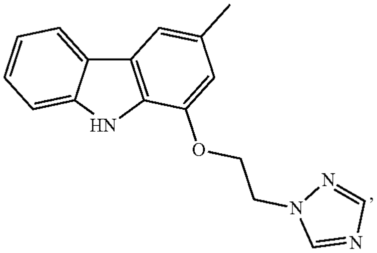
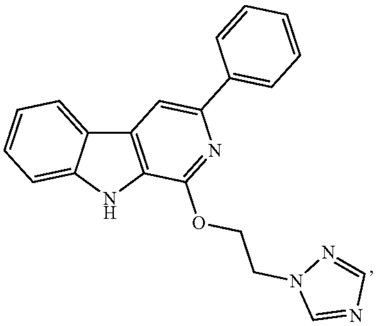
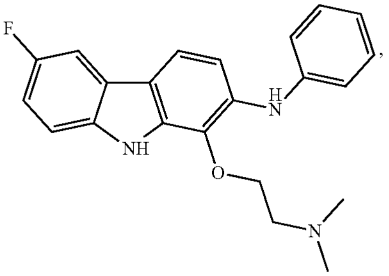
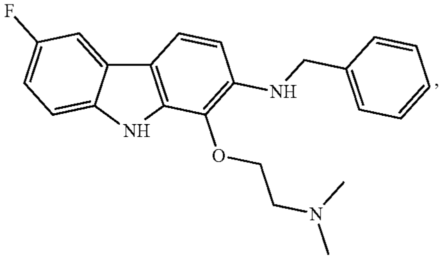
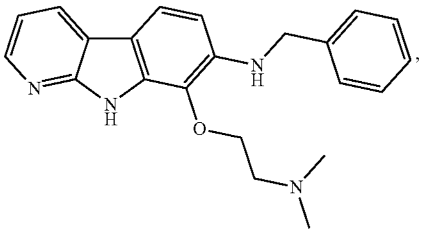

-continued
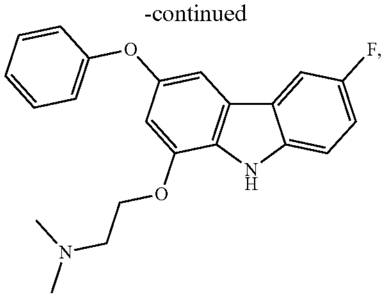
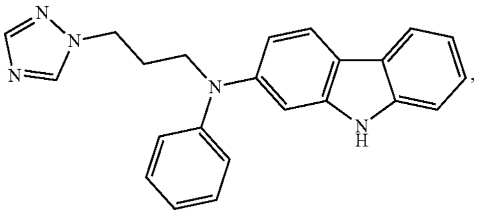
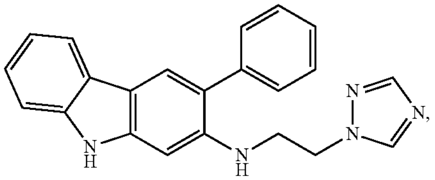
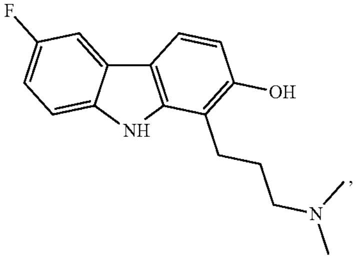
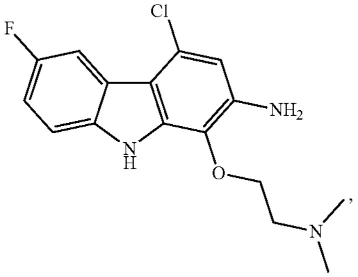
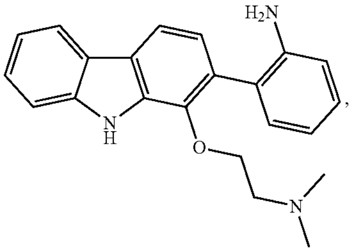
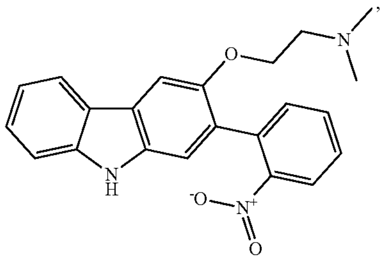
-continued
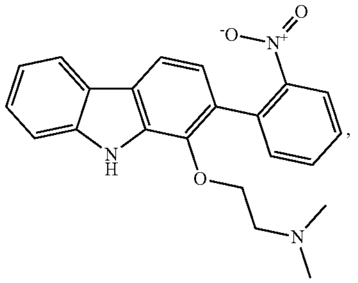
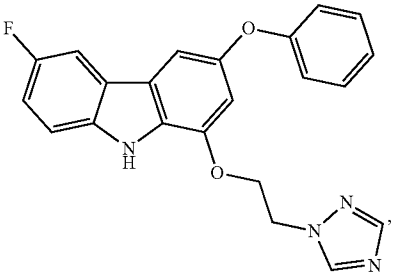
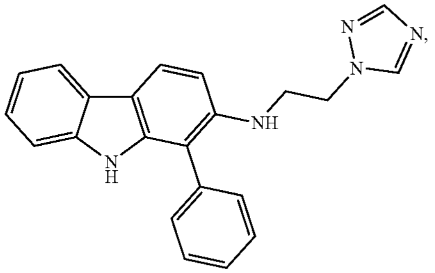
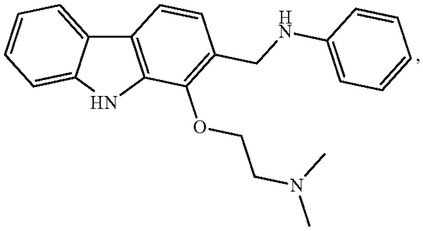
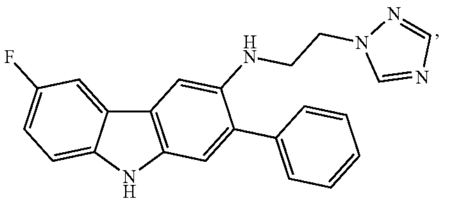
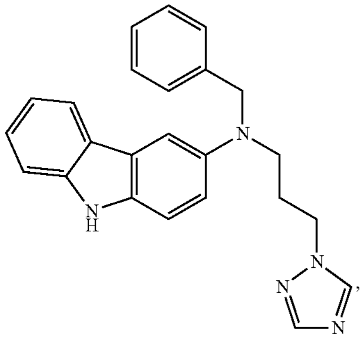

-continued
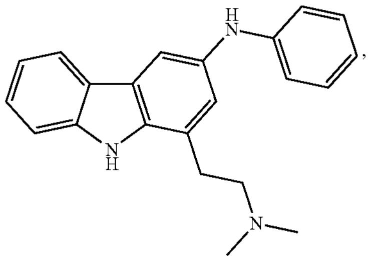
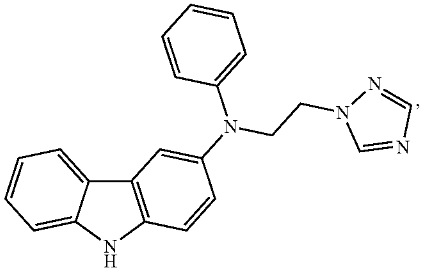
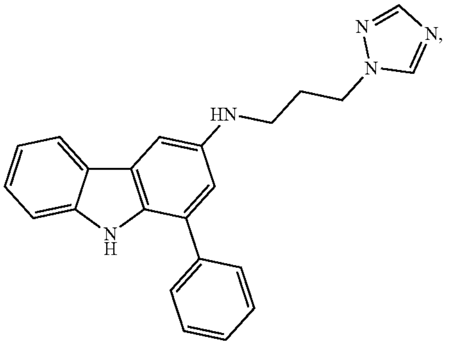
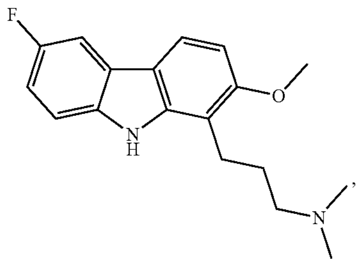
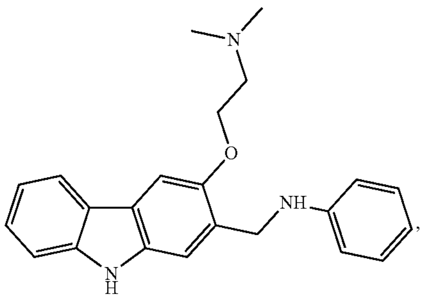
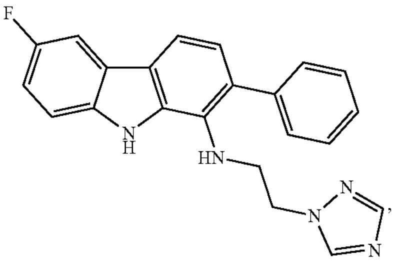
-continued
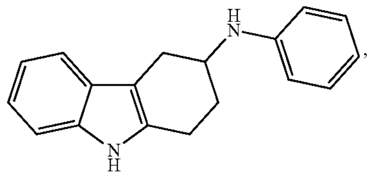
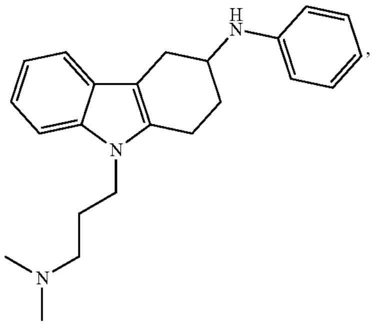
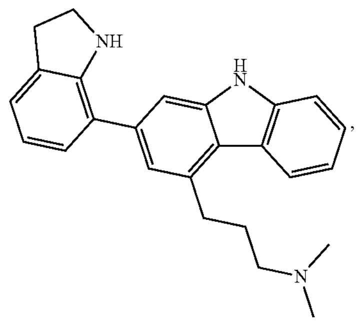
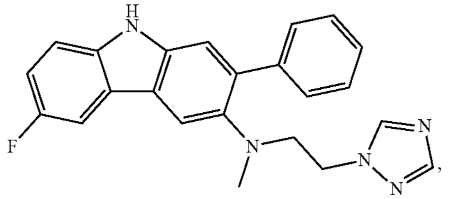
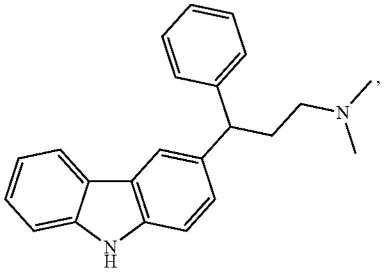
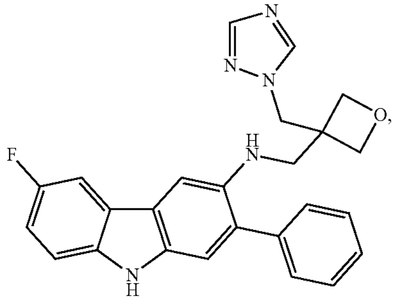

-continued
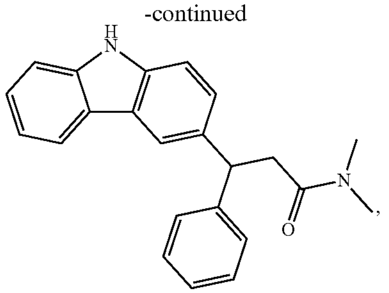
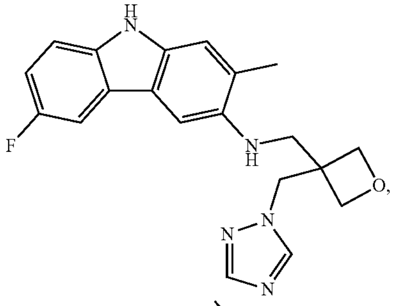
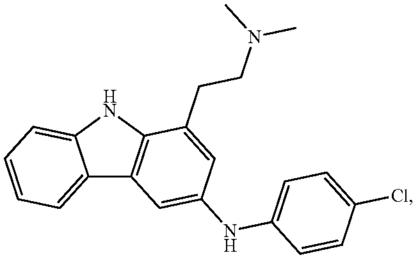
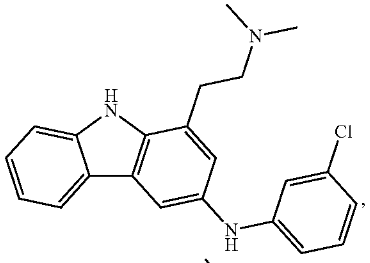
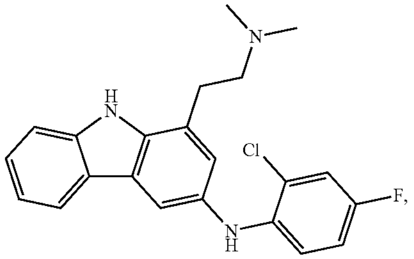
-continued
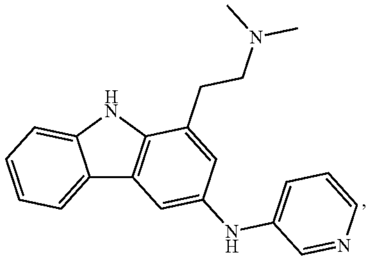
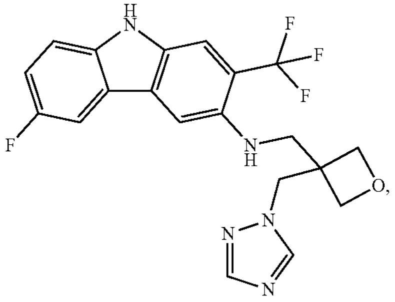
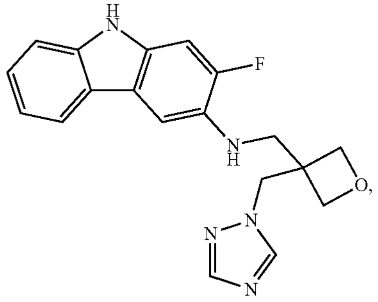
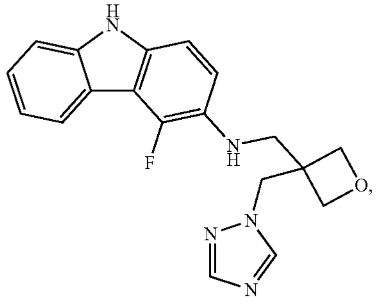
and pharmaceutically acceptable salts thereof.
* * * * *